(12) United States Patent
Tsukamoto et al.

(10) Patent No.: US 9,187,453 B2
(45) Date of Patent: Nov. 17, 2015

(54) HETEROCYCLIC COMPOUND

(71) Applicant: Takeda Pharmaceutical Company Limited, Osaka (JP)

(72) Inventors: Tetsuya Tsukamoto, Kanagawa (JP); Yusuke Ohba, Kanagawa (JP); Takafumi Yukawa, Kanagawa (JP); Hiroyuki Nagamiya, Kanagawa (JP); Taku Kamei, Kanagawa (JP); Norihito Tokunaga, Kanagawa (JP); Morihisa Saitoh, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/388,452

(22) PCT Filed: Mar. 27, 2013

(86) PCT No.: PCT/JP2013/059156
§ 371 (c)(1),
(2) Date: Sep. 26, 2014

(87) PCT Pub. No.: WO2013/146963
PCT Pub. Date: Oct. 3, 2013

(65) Prior Publication Data
US 2015/0094296 A1    Apr. 2, 2015

(30) Foreign Application Priority Data

Mar. 28, 2012  (JP) .................................. 2012-075166

(51) Int. Cl.
| | | |
|---|---|---|
| C07D 401/14 | (2006.01) | |
| C07D 403/14 | (2006.01) | |
| A61K 31/506 | (2006.01) | |
| C07D 403/04 | (2006.01) | |
| C07D 405/14 | (2006.01) | |
| C07D 413/14 | (2006.01) | |
| C07D 401/04 | (2006.01) | |
| C07D 409/14 | (2006.01) | |
| C07D 491/107 | (2006.01) | |

(52) U.S. Cl.
CPC ............ *C07D 403/04* (2013.01); *A61K 31/506* (2013.01); *C07D 401/04* (2013.01); *C07D 401/14* (2013.01); *C07D 403/14* (2013.01); *C07D 405/14* (2013.01); *C07D 409/14* (2013.01); *C07D 413/14* (2013.01); *C07D 491/107* (2013.01)

(58) Field of Classification Search
CPC ............................. C07D 401/14; C07D 403/14
USPC ............... 544/122, 295, 323, 324; 514/235.8, 514/252.19, 275
See application file for complete search history.

(56) References Cited

U.S. PATENT DOCUMENTS

| | | |
|---|---|---|
| 6,200,977 B1 | 3/2001 | Cushing et al. |
| 6,716,831 B1 | 4/2004 | Breault et al. |
| 2001/0018436 A1 | 8/2001 | Cushing et al. |
| 2003/0092721 A1 | 5/2003 | Pitts et al. |
| 2003/0092908 A1 | 5/2003 | Pitts et al. |
| 2003/0100571 A1 | 5/2003 | Vaccaro et al. |
| 2003/0104974 A1 | 6/2003 | Pitts et al. |
| 2003/0130264 A1 | 7/2003 | Jaen |
| 2003/0162802 A1 | 8/2003 | Guo et al. |
| 2003/0191143 A1 | 10/2003 | Pitts et al. |
| 2004/0006068 A1 | 1/2004 | Cushing et al. |
| 2004/0157859 A1 | 8/2004 | Wu et al. |
| 2005/0256144 A1 | 11/2005 | Kath et al. |
| 2006/0116516 A1 | 6/2006 | Pitts et al. |
| 2007/0032493 A1 | 2/2007 | Foley et al. |
| 2008/0255136 A1 | 10/2008 | Wu et al. |
| 2009/0306116 A1 | 12/2009 | Thomas et al. |
| 2010/0137305 A1 | 6/2010 | Binch et al. |
| 2011/0237598 A1 | 9/2011 | Stadtmueller et al. |
| 2011/0288065 A1 | 11/2011 | Fujihara et al. |
| 2011/0288071 A1 | 11/2011 | Stadtmueller et al. |
| 2012/0021434 A1 | 1/2012 | Foley et al. |
| 2013/0131082 A1 | 5/2013 | Fujihara et al. |

FOREIGN PATENT DOCUMENTS

| | | |
|---|---|---|
| JP | 2002/539120 | 11/2002 |
| JP | 2007-537235 | 12/2007 |

(Continued)

OTHER PUBLICATIONS

Radwan et al., Tyrosine Kinase 2 Controls IL-1β Production at the Translational Level, The Journal of Immunology, 185, pp. 3544-3553 (2010).*

(Continued)

*Primary Examiner* — Deepak Rao
(74) *Attorney, Agent, or Firm* — Wenderoth, Lind & Ponack, L.L.P.

(57) ABSTRACT

The present invention provides an agent for the prophylaxis or treatment of autoimmune diseases (e.g., psoriasis, rheumatoid arthritis, inflammatory bowel disease, Sjogren's syndrome, Behcet's disease, multiple sclerosis, systemic lupus erythematosus etc.) and the like, which has a superior Tyk2 inhibitory action.
The present invention relates to a compound represented by the formula

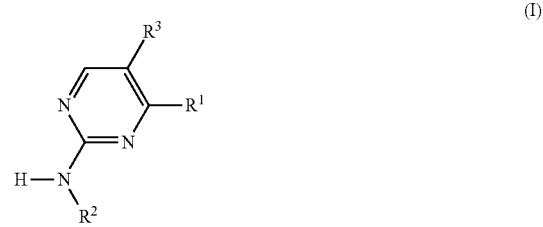

wherein each symbol is as defined in the specification, or a salt thereof.

6 Claims, No Drawings

(56) References Cited

FOREIGN PATENT DOCUMENTS

| JP | 2009-508833 | | 3/2009 |
|----|----|----|----|
| JP | 2010-522194 | | 7/2010 |
| WO | 99/41253 | | 8/1999 |
| WO | 02/064096 | | 8/2002 |
| WO | 02/102313 | | 12/2002 |
| WO | WO 03/026652 | * | 4/2003 |
| WO | 2004/037784 | | 5/2004 |
| WO | 2006/128129 | | 11/2006 |
| WO | 2006/128172 | | 11/2006 |
| WO | 2010/058032 | | 5/2010 |
| WO | 2010/090290 | | 8/2010 |
| WO | 2011/039344 | | 4/2011 |
| WO | WO 2014/147586 | * | 9/2014 |

OTHER PUBLICATIONS

Works et al., Inhibition of TYK2 and JAK1 Ameliorates Imiquimod-Induced Psoriasis-like Dermatitis by Inhibiting IL-22 and the IL-23/IL-17 Axis, The Journal of Immunology, 193, pp. 3278-3287 (2014).*

International Search Report dated May 21, 2013 issued in International (PCT) Application No. PCT/JP2013/059156.

* cited by examiner

HETEROCYCLIC COMPOUND

TECHNICAL FIELD

The present invention relates to a heterocyclic compound having a tyrosine kinase 2 (In the present specification, sometimes to be abbreviated as "Tyk2") inhibitory action, which is useful as an agent for the prophylaxis or treatment of autoimmune diseases (e.g., psoriasis, rheumatoid arthritis, inflammatory bowel disease, Sjogren's syndrome, Behcet's disease, multiple sclerosis, systemic lupus erythematosus etc.) and the like, a pharmaceutical composition containing thereof, and the like.

BACKGROUND OF THE INVENTION

Cytokines are proteins secreted by a cell of the immune system and transduce a signal to a specific cell. Cytokines have various kinds, and many of them are especially associated with immunity and inflammation and also associated with cell growth, differentiation, cell death, wound healing and the like (Curr Opin Cell Biol. 1991 Apr.; 3(2):171-5.).

The janus kinase (JAK) family plays a role in cytokine-dependent regulation of the function of cells associated with growth and immune response. Tyk2 is one of the four kinds of janus kinases (JAK1 (janus kinase 1), JAK2 (janus kinase 2), JAK3 (janus kinase 3) and Tyk2 (tyrosine kinase 2)), and it is known to be involved in signal transduction of cytokines such as IFN (interferon)-α, IFN-β, IL (interleukin)-6, IL-10 family (IL-10, IL-19, IL-20, IL-22, IL-28, IL-29), IL-12, IL-23 and the like (Nature Immunology 10, 356-360 (2009), New York Academy of Science 1246, 34-40 (2011)). These cytokines play an important role in immune response when exist in an appropriate amount. However, excessive production of them is involved in many autoimmune diseases such as psoriasis, rheumatoid arthritis, inflammatory bowel disease, Sjogren's syndrome, Behcet's disease, multiple sclerosis, systemic lupus erythematosus and the like (Journal of Allergy and Clinical Immunology 127, 3,701-721.e70 (2011), Cytokine & Growth Factor Reviews 19, 41-52 (2008), Invest Ophthalmol Vis Sci. 2008 July; 49(7):3058-3064, Ann Rheum Dis. 2010 July; 69(7):1325-1328). For example, Ustekinumab, which is an anti-IL-12/23 monoclonal antibody, has been approved as a therapeutic drug for moderate to severe psoriasis patient in Europe, and furthermore, clinical trials for various diseases in which the IL-12/23 signaling pathway is suggested to be involved are performed. From the foregoing, a Tyk2 inhibitor is a therapeutic drug for various autoimmune diseases such as psoriasis, rheumatoid arthritis, inflammatory bowel disease, Sjogren's syndrome, Behcet's disease, multiple sclerosis, systemic lupus erythematosus and the like (Front Biosci. 2011 Jun. 1; 17:3214-32).

Examples of the compound having a structure similar to the compound described in the present specification include the following compounds.

(1) A compound represented by the following formula:

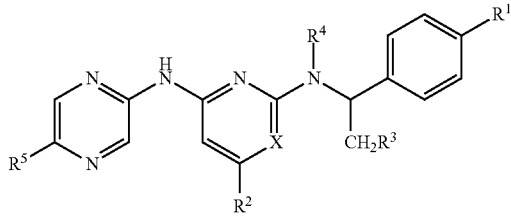

wherein
(I) X is CH or N;
  $R^1$ is halogen;
  $R^2$ is H, halogen, cyano, an optionally substituted nitrogen-containing non-aromatic heterocyclic group or the like;
  $R^3$ is H or alkyl;
  $R^4$ is H or alkyl; and
  $R^5$ is H or alkyl; or
(II) X is —$CR^A$;
  $R^A$ is a group represented by the following formula:

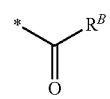

wherein
  * means a binding position; and
  $R^B$ is an optionally substituted amino or the like;
  $R^1$ is halogen;
  $R^2$ is H;
  $R^3$ is H or hydroxy;
  $R^4$ is H or alkyl; and
  $R^5$ is H or alkyl,
which is a JAK2 inhibitor, and is useful for the treatment of inflammatory disease and the like (Patent Document 1).

(2) A compound represented by the following formula:

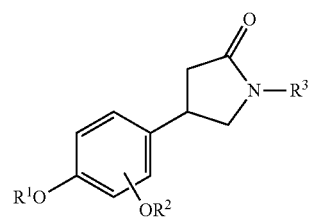

wherein
  $R^1$ is optionally substituted $C_{1-4}$ alkyl or the like;
  $R^2$ is optionally substituted phenyl or the like; and
  $R^3$ is an optionally substituted aromatic heterocyclic group or the like,
which is a HIV transcription inhibitor, and is useful for the treatment of HIV and the like (Patent Document 2).

(3) A compound represented by the following formula:

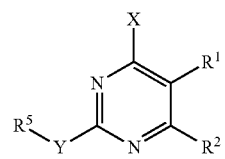

wherein
X is an nitrogen-containing heterocycle or the like;
Y is —$NR^6$— or the like;
$R^1$ and $R^2$ are independently hydrogen, an optionally substituted alkyl group or the like;
$R^5$ is an optionally substituted alkyl group, an optionally fused aryl group or the like; and
$R^6$ is an optionally substituted alkyl group or the like, which is an agent for the prophylaxis or treatment of viral infectious (Patent Documents 3 and 6).

(4) A compound represented by the following formula:

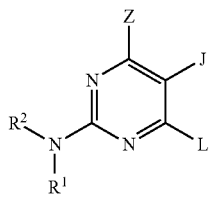

wherein
$R^1$ is a hydrogen atom or an alkyl group;
$R^2$ is an optionally substituted aryl group, an optionally substituted heteroaryl group or the like;
Z is an optionally substituted alkyl group, an optionally substituted aryl group, an optionally substituted heteroaryl group or the like;
J is a hydrogen atom, an optionally substituted alkyl group or the like; and
L is a hydrogen atom, an optionally substituted alkyl group, an optionally substituted aryl group, an optionally substituted heteroaryl group or the like,
which is a PDE inhibitor, and is useful as an agent for the prophylaxis or treatment of inflammatory disease (rheumatoid arthritis, inflammatory bowel disease, multiple sclerosis and the like) and the like (Patent Document 4).

(5) A compound represented by the following formula:

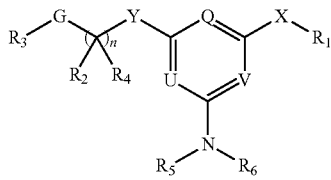

wherein
$R^1$ is

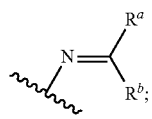

$R^2$, $R^3$, $R^4$, $R^a$ and $R^b$ are independently a hydrogen atom, an optionally substituted alkyl group or the like;
$R^5$ and $R^6$ are independently a nitrogen-containing heterocycle or the like;
X is O, S, $N(R^k)$ or the like;
Y is O, S, $(CHR^g)_m$, $N(R^k)$ or the like;
Q, U and V are independently N or $CR^g$ or the like;
$R^k$ is a hydrogen atom, an optionally substituted alkyl group or the like;
$R^q$ is a hydrogen atom, an optionally substituted alkyl group or the like; and
M is 0, 1, 2, 3 or 4,
which is a c-Rel inhibitor, and is useful as an agent for the prophylaxis or treatment of inflammatory disease (rheumatoid arthritis, psoriatic arthropathy, systemic lupus erythematosus and the like) and the like (Patent Documents 5 and 7).

DOCUMENT LIST

Patent Document

[Patent Document 1] WO 2010/090290
[Patent Document 2] WO 2004/037784
[Patent Document 3] WO 99/41253
[Patent Document 4] WO 02/102313
[Patent Document 5] WO 2006/128172
[Patent Document 6] WO 02/064096
[Patent Document 7] WO 2006/128129

SUMMARY OF THE INVENTION

Problems to be Solved by the Invention

An object of the present invention is to provide an agent for the prophylaxis or treatment of autoimmune diseases (e.g., psoriasis, rheumatoid arthritis, inflammatory bowel disease, Sjogren's syndrome, Behcet's disease, multiple sclerosis, systemic lupus erythematosus etc.) and the like, which has a superior Tyk2 inhibitory action.

Means of Solving the Problems

The present inventors have conducted intensive studies in an attempt to solve the above-mentioned problem and found that compound represented by the following formula (I) has a superior Tyk2 inhibitory action, which resulted in the completion of the present invention.

Accordingly, the present invention provides the following.
[1] A compound represented by the formula (I):

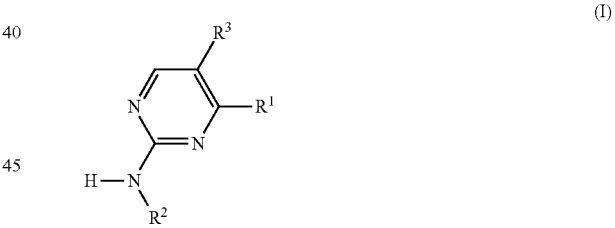

(I)

wherein
$R^1$ is
a group represented by the following formula:

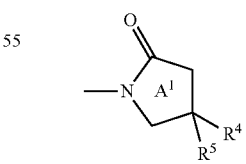

wherein
ring $A^1$ is an optionally further substituted 2-oxopyrrolidine ring;
$R^4$ is a hydrogen atom, a halogen atom, a cyano group, an acyl group, an optionally substituted $C_{1-6}$ alkyl group, an optionally substituted hydroxy group, an optionally substituted amino group, an optionally substituted $C_{3-6}$ cycloalkyl group, or an optionally substituted heterocyclic group; and $R^5$ is a hydrogen atom, a halogen atom, a cyano group, an acyl group, an optionally substituted $C_{1-6}$ alkyl group, an optionally substituted hydroxy group, an optionally substituted amino group, an optionally substituted $C_{3-6}$ cycloalkyl group, or an optionally substituted heterocyclic group, or an optionally substituted 2-oxopiperidino group;

$R^2$ is a hydrogen atom, an optionally substituted $C_{1-6}$ alkyl group, an optionally substituted aromatic ring group, or an acyl group; and $R^3$ is a hydrogen atom, a halogen atom, a cyano group, or an optionally substituted $C_{1-6}$ alkyl group, or a salt thereof (hereinafter sometime to be referred to as "compound (I)").

[2] The compound or salt of the above-mentioned [1], wherein $R^1$ is (A) a group represented by the following formula:

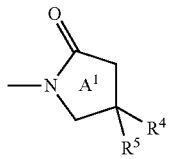

wherein ring $A^1$ is an 2-oxopyrrolidine ring optionally further substituted by 1 to 3 substituents selected from
  (1) a cyano group,
  (2) a carbamoyl group,
  (3) a $C_{1-6}$ alkyl group optionally substituted by 1 to 3 substituents selected from
    (I) a carboxy group,
    (II) a cyano group,
    (III) a halogen atom,
    (IV) a $C_{1-6}$ alkoxy group,
    (V) a $C_{3-6}$ cycloalkyl group,
    (VI) an amino group optionally mono- or di-substituted by substituent(s) selected from
      (i) a $C_{1-6}$ alkyl-carbonyl group, and
      (ii) a $C_{1-6}$ alkoxy-carbonyl group, and
    (VII) a hydroxy group,
  (4) a $C_{3-6}$ cycloalkyl group,
  (5) a 3- to 8-membered monocyclic non-aromatic heterocyclic group optionally substituted by 1 to 3 $C_{1-6}$ alkoxy-carbonyl groups,
  (6) a $C_{1-6}$ alkoxy-carbonyl group, and
  (7) a 5- or 6-membered monocyclic aromatic heterocyclic group optionally substituted by 1 to 3 $C_{1-6}$ alkyl groups;

$R^4$ is a hydrogen atom or a $C_{1-6}$ alkyl group; and $R^5$ is a hydrogen atom; or (B) an 2-oxopiperidino group optionally substituted by 1 to 3 $C_{1-6}$ alkyl groups;

$R^2$ is (1) a 5- or 6-membered monocyclic aromatic heterocyclic group, a $C_{6-14}$ aryl group or a 8- to 12-membered fused aromatic heterocyclic group, each of which is optionally substituted by 1 to 3 substituents selected from
  (a) a cyano group,
  (b) a carboxy group,
  (c) a halogen atom,
  (d) a $C_{1-6}$ alkyl group optionally substituted by 1 to 3 substituents selected from
    (I) a hydroxy group,
    (II) a cyano group,
    (III) a carboxy group,
    (IV) a carbamoyl group optionally mono- or di-substituted by $C_{1-6}$ alkyl group(s) optionally substituted by 1 to 3 substituents selected from
      (i) a $C_{1-6}$ alkoxy group,
      (ii) a hydroxy group,
      (iii) a halogen atom, and
      (iv) a $C_{1-6}$ alkylsulfonyl group,
    (V) an amino group optionally mono- or di-substituted by substituent(s) selected from
      (i) a $C_{1-6}$ alkyl-carbonyl group optionally substituted by 1 to 3 substituents selected from (A) a $C_{1-6}$ alkoxy group and (B) a hydroxy group,
      (ii) a $C_{1-6}$ alkylsulfonyl group,
      (iii) a sulfamoyl group optionally mono- or di-substituted by $C_{1-6}$ alkyl group(s), and
      (iv) a $C_{1-6}$ alkyl group,
    (VI) a $C_{1-6}$ alkoxy-carbonyl group,
    (VII) a $C_{6-14}$ aryl group optionally substituted by 1 to 3 $C_{1-6}$ alkoxy groups,
    (VIII) a 3- to 8-membered monocyclic non-aromatic heterocyclic group,
    (IX) a 3- to 8-membered monocyclic non-aromatic heterocyclylcarbonyl group optionally substituted by 1 to 3 substituents selected from
      (i) a hydroxy group,
      (ii) a carbamoyl group, and
      (iii) a $C_{1-6}$ alkyl group,
    (X) a halogen atom, and
    (XI) a $C_{1-6}$ alkylsulfonyl group,
  (e) a $C_{1-6}$ alkyl-carbonyl group,
  (f) a $C_{1-6}$ alkylsulfonyl group,
  (g) an amino group optionally mono- or di-substituted by substituent(s) selected from
    (I) a $C_{1-6}$ alkyl group,
    (II) a $C_{1-6}$ alkyl-carbonyl group optionally substituted by 1 to 3 $C_{1-6}$ alkoxy groups, and
    (III) a $C_{1-6}$ alkylsulfonyl group,
  (h) a carbamoyl group optionally mono- or di-substituted by substituent(s) selected from
    (I) a $C_{1-6}$ alkyl group optionally substituted by 1 to 3 substituents selected from
      (i) a hydroxy group,
      (ii) a 3- to 8-membered monocyclic non-aromatic heterocyclic group optionally substituted by 1 to 3 $C_{1-6}$ alkyl groups, and
      (iii) a $C_{1-6}$ alkylsulfonyl group,
    (II) a $C_{3-6}$ cycloalkyl group optionally substituted by 1 to 3 substituents selected from
      (i) a cyano group, and
      (ii) a hydroxy group, and
    (III) a 3- to 8-membered monocyclic non-aromatic heterocyclic group,
  (i) a sulfamoyl group optionally mono- or di-substituted by $C_{1-6}$ alkyl group(s),
  (j) a 3- to 8-membered monocyclic non-aromatic heterocyclic group optionally substituted by 1 to 3 substituents selected from
    (I) a $C_{1-6}$ alkyl group optionally substituted by 1 to 3 hydroxy groups, (II) a $C_{1-6}$ alkyl-carbonyl group optionally substituted by 1 to 3 substituents selected from
  (i) a $C_{1-6}$ alkoxy group, and
  (ii) a cyano group,
(III) a $C_{1-6}$ alkoxy-carbonyl group,
(IV) an oxo group,
(V) a $C_{1-6}$ alkylsulfonyl group,
(VI) a carbamoyl group optionally mono- or di-substituted by $C_{1-6}$ alkyl group(s),
(VII) a cyano group,
(VIII) a hydroxy group, and
(IX) a carboxy group,
(k) a $C_{3-6}$ cycloalkyl group optionally substituted by 1 to 3 substituents selected from
  (I) a carbamoyl group optionally mono- or di-substituted by $C_{1-6}$ alkyl group(s),
  (II) a carboxy group, and
  (III) a $C_{1-6}$ alkyl group optionally substituted by 1 to 3 hydroxy groups,
(l) a $C_{1-6}$ alkoxy group optionally substituted by 1 to 3 substituents selected from
  (I) a halogen atom,
  (II) a $C_{1-6}$ alkoxy group, and
  (III) a $C_{3-6}$ cycloalkyl group,
(m) a $C_{1-6}$ alkoxy-carbonyl group,
(n) a 3- to 8-membered monocyclic non-aromatic heterocyclylcarbonyl group optionally substituted by 1 to 3 substituents selected from
  (I) a hydroxy group,
  (II) an oxo group,
  (III) a halogen atom,
  (IV) a $C_{1-6}$ alkoxy group, and
  (V) a $C_{1-6}$ alkyl group,
(o) a $C_{1-6}$ alkylsulfanyl group, and
(p) a 5- or 6-membered monocyclic aromatic heterocyclic group, or
(2) a $C_{1-6}$ alkyl group optionally substituted by 1 to 3 substituents selected from
  (a) a $C_{6-14}$ aryl group optionally substituted by 1 to 3 substituents selected from
    (I) a cyano group,
    (II) a $C_{1-6}$ alkyl group optionally substituted by 1 to 3 of 3- to 8-membered monocyclic non-aromatic heterocyclic groups,
    (III) a $C_{1-6}$ alkoxy group,
    (IV) a halogen atom, and
    (V) a 3- to 8-membered monocyclic non-aromatic heterocyclic group optionally substituted by 1 to 3 $C_{1-6}$ alkyl groups,
  (b) a 5- or 6-membered monocyclic aromatic heterocyclic group optionally substituted by 1 to 3 substituents selected from
    (I) a cyano group,
    (II) a $C_{1-6}$ alkyl group optionally substituted by 1 to 3 of 3- to 8-membered monocyclic non-aromatic heterocyclic groups,
    (III) a $C_{1-6}$ alkoxy group,
    (IV) a halogen atom, and
    (V) a 3- to 8-membered monocyclic non-aromatic heterocyclic group optionally substituted by 1 to 3 $C_{1-6}$ alkyl groups,
  (c) a 8- to 12-membered fused aromatic heterocyclic group optionally substituted by 1 to 3 substituents selected from
    (I) a cyano group,
    (II) a $C_6$ alkyl group optionally substituted by 1 to 3 of 3- to 8-membered monocyclic non-aromatic heterocyclic groups,
    (III) a $C_{1-6}$ alkoxy group,
    (IV) a halogen atom, and
    (V) a 3- to 8-membered monocyclic non-aromatic heterocyclic group optionally substituted by 1 to 3 $C_{1-6}$ alkyl groups, and
  (d) a $C_{3-6}$ cycloalkyl group; and
$R^3$ is a hydrogen atom or a halogen atom.

[3] The compound or salt of the above-mentioned [1], wherein $R^1$ is
(A) a group represented by the following formula:

wherein
$R^{A1}$ and $R^{A2}$ are the same or different and each is
(1) a cyano group,
(2) a carbamoyl group,
(3) a $C_{1-6}$ alkyl group optionally substituted by 1 to 3 substituents selected from
  (I) a carboxy group,
  (II) a cyano group,
  (III) a halogen atom,
  (IV) a $C_{1-6}$ alkoxy group,
  (V) a $C_{3-6}$ cycloalkyl group,
  (VI) an amino group optionally mono- or di-substituted by substituent(s) selected from
    (i) a $C_{1-6}$ alkyl-carbonyl group, and
    (ii) a $C_{1-6}$ alkoxy-carbonyl group, and
  (VII) a hydroxy group,
(4) a $C_{3-6}$ cycloalkyl group,
(5) a 3- to 8-membered monocyclic non-aromatic heterocyclic group optionally substituted by 1 to 3 $C_{1-6}$ alkoxy-carbonyl groups, or
(6) a $C_{1-6}$ alkoxy-carbonyl group;
$R^{A3}$ is a hydrogen atom or a $C_{1-3}$ alkyl group;
$R^{A4}$ is a hydrogen atom;
$R^4$ is a hydrogen atom or a $C_{1-3}$ alkyl group; and
$R^5$ is a hydrogen atom; or
(B) an 2-oxopiperidino group optionally substituted by 1 to 3 $C_{1-6}$ alkyl groups.

[4] The compound or salt of the above-mentioned [1], wherein $R^1$ is
(A) a group represented by the following formula:

wherein
$R^{A1}$ and $R^{A2}$ are the same or different and each is
(1) a cyano group,
(2) a carbamoyl group, (3) a $C_{1-6}$ alkyl group optionally substituted by 1 to 3 substituents selected from
  (I) a carboxy group,
  (II) a cyano group,
  (III) a halogen atom,
  (IV) a $C_{1-6}$ alkoxy group,
  (V) a $C_{3-6}$ cycloalkyl group,
  (VI) an amino group optionally mono- or di-substituted by substituent(s) selected from
    (i) a $C_{1-6}$ alkyl-carbonyl group, and
    (ii) a $C_{1-6}$ alkoxy-carbonyl group, and
  (VII) a hydroxy group,
(4) a $C_{3-6}$ cycloalkyl group,
(5) a 3- to 8-membered monocyclic non-aromatic heterocyclic group optionally substituted by 1 to 3 $C_{1-6}$ alkoxy-carbonyl groups, or
(6) a $C_{1-6}$ alkoxy-carbonyl group;
$R^{43}$ is a hydrogen atom or a $C_{1-3}$ alkyl group;
$R^{44}$ is a hydrogen atom;
$R^{4}$ is a hydrogen atom or a $C_{1-3}$ alkyl group; and
$R^{5}$ is a hydrogen atom.

[5] The compound or salt of the above-mentioned [1], wherein $R^2$ is
(1) a 5- or 6-membered monocyclic aromatic heterocyclic group, a $C_{6-14}$ aryl group or a 8- to 12-membered fused aromatic heterocyclic group, each of which is optionally substituted by 1 to 3 substituents selected from
  (a) a cyano group,
  (b) a carboxy group,
  (c) a halogen atom,
  (d) a $C_{1-6}$ alkyl group optionally substituted by 1 to 3 substituents selected from
    (I) a hydroxy group,
    (II) a cyano group,
    (III) a carboxy group,
    (IV) a carbamoyl group optionally mono- or di-substituted by $C_{1-6}$ alkyl group(s) optionally substituted by 1 to 3 substituents selected from
      (i) a $C_{1-6}$ alkoxy group,
      (ii) a hydroxy group,
      (iii) a halogen atom, and
      (iv) a $C_{1-6}$ alkylsulfonyl group,
    (V) an amino group optionally mono- or di-substituted by substituent(s) selected from
      (i) a $C_{1-6}$ alkyl-carbonyl group optionally substituted by 1 to 3 substituents selected from (A) a $C_{1-6}$ alkoxy group and (B) a hydroxy group,
      (ii) a $C_{1-6}$ alkylsulfonyl group,
      (iii) a sulfamoyl group optionally mono- or di-substituted by $C_{1-6}$ alkyl group(s), and
      (iv) a $C_{1-6}$ alkyl group,
    (VI) a $C_{1-6}$ alkoxy-carbonyl group,
    (VII) a $C_{6-14}$ aryl group optionally substituted by 1 to 3 $C_{1-6}$ alkoxy groups,
    (VIII) a 3- to 8-membered monocyclic non-aromatic heterocyclic group,
    (IX) a 3- to 8-membered monocyclic non-aromatic heterocyclylcarbonyl group optionally substituted by 1 to 3 substituents selected from
      (i) a hydroxy group,
      (ii) a carbamoyl group, and
      (iii) a $C_{1-6}$ alkyl group,
    (X) a halogen atom, and
    (XI) a $C_{1-6}$ alkylsulfonyl group,
  (e) a $C_{1-6}$ alkyl-carbonyl group,
  (f) a $C_{1-6}$ alkylsulfonyl group,
  (g) an amino group optionally mono- or di-substituted by substituent(s) selected from
    (I) a $C_{1-6}$ alkyl group,
    (II) a $C_{1-6}$ alkyl-carbonyl group optionally substituted by 1 to 3 $C_{1-6}$ alkoxy groups, and
    (III) a $C_{1-6}$ alkylsulfonyl group,
  (h) a carbamoyl group optionally mono- or di-substituted by substituent(s) selected from
    (I) a $C_{1-6}$ alkyl group optionally substituted by 1 to 3 substituents selected from
      (i) a hydroxy group,
      (ii) a 3- to 8-membered monocyclic non-aromatic heterocyclic group optionally substituted by 1 to 3 $C_{1-6}$ alkyl groups, and
      (iii) a $C_{1-6}$ alkylsulfonyl group,
    (II) a $C_{3-6}$ cycloalkyl group optionally substituted by 1 to 3 substituents selected from
      (i) a cyano group, and
      (ii) a hydroxy group, and
    (III) a 3- to 8-membered monocyclic non-aromatic heterocyclic group,
  (i) a sulfamoyl group optionally mono- or di-substituted by $C_{1-6}$ alkyl group(s),
  (j) a 3- to 8-membered monocyclic non-aromatic heterocyclic group optionally substituted by 1 to 3 substituents selected from
    (I) a $C_{1-6}$ alkyl group optionally substituted by 1 to 3 hydroxy groups,
    (II) a $C_{1-6}$ alkyl-carbonyl group optionally substituted by 1 to 3 substituents selected from
      (i) a $C_{1-6}$ alkoxy group, and
      (ii) a cyano group,
    (III) a $C_{1-6}$ alkoxy-carbonyl group,
    (IV) an oxo group,
    (V) a $C_{1-6}$ alkylsulfonyl group,
    (VI) a carbamoyl group optionally mono- or di-substituted by $C_{1-6}$ alkyl group(s),
    (VII) a cyano group,
    (VIII) a hydroxy group, and
    (IX) a carboxy group,
  (k) a $C_{3-6}$ cycloalkyl group optionally substituted by 1 to 3 substituents selected from
    (I) a carbamoyl group optionally mono- or di-substituted by $C_{1-6}$ alkyl group(s),
    (II) a carboxy group, and
    (III) a $C_{1-6}$ alkyl group optionally substituted by 1 to 3 hydroxy groups,
  (l) a $C_{1-6}$ alkoxy group optionally substituted by 1 to 3 substituents selected from
    (I) a halogen atom,
    (II) a $C_{1-6}$ alkoxy group, and
    (III) a $C_{3-6}$ cycloalkyl group,
  (m) a $C_{1-6}$ alkoxy-carbonyl group,
  (n) a 3- to 8-membered monocyclic non-aromatic heterocyclylcarbonyl group optionally substituted by 1 to 3 substituents selected from
    (I) a hydroxy group,
    (II) an oxo group,
    (III) a halogen atom,
    (IV) a $C_{1-6}$ alkoxy group, and
    (V) a $C_{1-6}$ alkyl group,
  (o) a $C_{1-6}$ alkylsulfanyl group, and
  (p) a 5- or 6-membered monocyclic aromatic heterocyclic group.

[6] (3S)-3-Cyclopropyl-1-(2-((1-(1-hydroxy-2-methylpropan-2-yl)-1H-pyrazol-4-yl)amino)pyrimidin-4-yl)-2-oxopyrrolidine-3-carbonitrile or a salt thereof.
[7] (3S)-3-Cyclopropyl-1-(2-((1-(1-(hydroxymethyl)cyclopropyl)-1H-pyrazol-4-yl)amino)pyrimidin-4-yl)-2-oxopyrrolidine-3-carbonitrile or a salt thereof.
[8] (3R)-3-Ethyl-1-(2-((4-(4-(hydroxymethyl)tetrahydro-2H-pyran-4-yl)phenyl)amino)pyrimidin-4-yl)-2-oxopyrrolidine-3-carbonitrile or a salt thereof.
[9] A medicament comprising the compound or salt of the above-mentioned [1].
[10] The medicament of the above-mentioned [9], which is a tyrosine kinase 2 inhibitor.
[11] The medicament of the above-mentioned [9], which is an agent for the prophylaxis or treatment of autoimmune diseases.
[12] The medicament of the above-mentioned [11], wherein the autoimmune diseases is psoriasis, rheumatoid arthritis, inflammatory bowel disease, Sjogren's syndrome, Behcet's disease, multiple sclerosis or systemic lupus erythematosus.
[13] The compound or salt of the above-mentioned [1] for use in the prophylaxis or treatment of autoimmune diseases.
[14] The compound or salt of the above-mentioned [13], wherein the autoimmune diseases is psoriasis, rheumatoid arthritis, inflammatory bowel disease, Sjogren's syndrome, Behcet's disease, multiple sclerosis or systemic lupus erythematosus.
[15] A method of inhibiting tyrosine kinase 2 in a mammal, which comprises administering an effective amount of the compound or salt of the above-mentioned [1] to the mammal.
[16] A method for the prophylaxis or treatment of autoimmune diseases, which comprises administering an effective amount of the compound or salt of the above-mentioned [1] to the mammal.
[17] The method of the above-mentioned [16], wherein the autoimmune diseases is psoriasis, rheumatoid arthritis, inflammatory bowel disease, Sjogren's syndrome, Behcet's disease, multiple sclerosis or systemic lupus erythematosus.
[18] Use of the compound or salt of the above-mentioned [1] for the production of an agent for the prophylaxis or treatment of autoimmune diseases.
[19] The use of the above-mentioned [18], wherein the autoimmune diseases is psoriasis, rheumatoid arthritis, inflammatory bowel disease, Sjogren's syndrome, Behcet's disease, multiple sclerosis or systemic lupus erythematosus.

Effect of the Invention

Compound (I) has a superior Tyk2 inhibitory action, which is useful as an agent for the prophylaxis or treatment of autoimmune diseases (e.g., psoriasis, rheumatoid arthritis, inflammatory bowel disease (e.g., Crohn's disease, ulcerative colitis etc.), Sjogren's syndrome, Behcet's disease, multiple sclerosis, systemic lupus erythematosus etc.) and the like.

DETAILED DESCRIPTION OF THE INVENTION

In the present specification, the "halogen atom" means a fluorine atom, a chlorine atom, a bromine atom or iodine atom.

In the present specification, the "$C_{1-3}$ alkyl (group)" means methyl, ethyl, propyl or isopropyl.

In the present specification, the "$C_{1-6}$ alkyl (group)" means, for example, methyl, ethyl, propyl, isopropyl, butyl, isobutyl, sec-butyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl or the like.

In the present specification, the "$C_{1-10}$ alkyl (group)" means, for example, methyl, ethyl, propyl, isopropyl, butyl, isobutyl, sec-butyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl or the like. Among them, a $C_{1-6}$ alkyl group is preferable.

In the present specification, the "$C_{2-6}$ alkenyl (group)" means, for example, vinyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl or the like.

In the present specification, the "$C_{2-10}$ alkenyl (group)" means, for example, vinyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl or the like. Among them, a $C_{2-6}$ alkenyl group is preferable.

In the present specification, the "$C_{2-6}$ alkynyl (group)" means, for example, ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl, 5-hexynyl or the like.

In the present specification, the "$C_{2-10}$ alkynyl (group)" means, for example, ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl, 5-hexynyl, 1-heptynyl, 1-octynyl or the like. Among them, a $C_{2-6}$ alkynyl group is preferable.

In the present specification, the "$C_{1-6}$ alkoxy (group)" means, for example, methoxy, ethoxy, propoxy, isopropoxy, butoxy, isobutoxy, sec-butoxy, tert-butoxy, pentyloxy, isopentyloxy, hexyloxy or the like.

In the present specification, the "$C_{2-6}$ alkenyloxy (group)" means, for example, vinyloxy, 1-propenyloxy, 2-propenyloxy, 2-methyl-1-propenyloxy, 1-butenyloxy, 2-butenyloxy, 3-butenyloxy, 3-methyl-2-butenyloxy, 1-pentenyloxy, 2-pentenyloxy, 3-pentenyloxy, 4-pentenyloxy, 4-methyl-3-pentenyloxy, 1-hexenyloxy, 3-hexenyloxy, 5-hexenyloxy or the like.

In the present specification, the "$C_{2-6}$ alkynyloxy (group)" means, for example, ethynyloxy, 1-propynyloxy, 2-propynyloxy, 1-butynyloxy, 2-butynyloxy, 3-butynyloxy, 1-pentynyloxy, 2-pentynyloxy, 3-pentynyloxy, 4-pentynyloxy, 1,1-dimethylprop-2-yn-1-yloxy, 1-hexynyloxy, 2-hexynyloxy, 3-hexynyloxy, 4-hexynyloxy, 5-hexynyloxy or the like.

In the present specification, the "$C_{1-6}$ alkylenedioxy (group)" means, for example, methylenedioxy, ethylenedioxy or the like.

In the present specification, the "$C_{1-6}$ alkoxy-carbonyl (group)" means, for example, methoxycarbonyl, ethoxycarbonyl, propoxycarbonyl, isopropoxycarbonyl, butoxycarbonyl, isobutoxycarbonyl, tert-butoxycarbonyl or the like.

In the present specification, the "$C_{1-6}$ alkyl-carbonyl (group)" means, for example, acetyl, propanoyl, butanoyl, 2-methylpropanoyl or the like.

In the present specification, the "$C_{3-6}$ cycloalkyl (group)" means, for example, cyclopropyl, cyclobutyl, cyclopentyl and cyclohexyl or the like.

In the present specification, the "$C_{3-6}$ cycloalkyl (group)" means, for example, cyclopropyl, cyclobutyl, cyclopentyl, cyclohexyl, cycloheptyl, cyclooctyl or the like. Among them, a $C_{3-6}$ cycloalkyl group is preferable.

In the present specification, the "$C_{3-10}$ cycloalkyl (group)" means, for example, cyclopropyl, cyclobutyl, cyclopentyl, cyclohexyl, cycloheptyl, cyclooctyl, cyclononyl, cyclodecyl or the like. Among them, a $C_{3-6}$ cycloalkyl group is preferable.

In the present specification, the "$C_{3-8}$ cycloalkenyl (group)" means, for example, cyclopropenyl (e.g., 2-cyclopropen-1-yl), cyclobutenyl (e.g., 2-cyclobuten-1-yl), cyclopentenyl (e.g., 1-cyclopenten-1-yl, 2-cyclopenten-1-yl, 3-cyclopenten-1-yl), cyclohexenyl (e.g., 1-cyclohexen-1-yl, 2-cyclohexen-1-yl, 3-cyclohexen-1-yl) or the like.

In the present specification, the "$C_{3-10}$ cycloalkenyl (group)" means, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 1-cyclohexen-1-yl, 2-cyclohexen-1-yl, 3-cyclohexen-1-yl), cycloheptenyl (e.g., 1-cyclopenten-1-yl, 2-cyclohepten-1-yl, 2-cyclohepten-1-yl), cyclooctenyl (e.g., 1-cyclohepten-1-yl, 2-cyclohepten-1-yl, 3-cyclohepten-1-yl), cyclononenyl (e.g., 1-cyclononen-1-yl, 2-cyclononen-1-yl, 3-cyclononen-1-yl) or the like. Among them, a $C_{3-8}$ cycloalkenyl group is preferable.

In the present specification, the "$C_{4-6}$ cycloalkadienyl (group)" means, for example, 1,3-cyclobutadien-1-yl, 1,3-cyclopentadien-1-yl, 1,4-cyclopentadien-1-yl, 2,4-cyclopentadien-1-yl, 1,3-cyclohexadien-1-yl, 1,4-cyclohexadien-1-yl, 1,5-cyclohexadien-1-yl, 2,4-cyclohexadien-1-yl, 2,5-cyclohexadien-1-yl or the like.

In the present specification, the "$C_{4-10}$ cycloalkadienyl (group)" means, for example, 1,3-cyclobutadien-1-yl, 1,3-cyclopentadien-1-yl, 1,4-cyclopentadien-1-yl, 2,4-cyclopentadien-1-yl, 1,3-cyclohexadien-1-yl, 1,4-cyclohexadien-1-yl, 1,5-cyclohexadien-1-yl, 2,4-cyclohexadien-1-yl, 2,5-cyclohexadien-1-yl, 1,3-cyclooctadien-1-yl, 1,4-cyclooctadien-1-yl, 1,5-cyclooctadien-1-yl, 1,6-cyclooctadien-1-yl, 1,7-cyclooctadien-1-yl, 2,4-cyclooctadien-1-yl, 2,5-cyclooctadien-1-yl, 2,6-cyclooctadien-1-yl, 2,7-cyclooctadien-1-yl, 3,5-cyclooctadien-1-yl, 3,6-cyclooctadien-1-yl or the like. Among them, a $C_{4-6}$ cycloalkadienyl group is preferable.

The above-mentioned $C_{3-10}$ cycloalkyl group, $C_{3-10}$ cycloalkenyl group and $C_{4-10}$ cycloalkadienyl group are each optionally fused with a benzene ring to form a fused ring group, and examples of the fused ring group include indanyl, dihydronaphthyl, tetrahydronaphthyl, fluorenyl and the like.

The above-mentioned $C_{3-10}$ cycloalkyl group, $C_{3-10}$ cycloalkenyl group and $C_{4-10}$ cycloalkadienyl group may be a $C_{7-10}$ bridged hydrocarbon group. Examples of the $C_{7-10}$ bridged hydrocarbon group include bicyclo[2.2.1]heptyl (norbornyl), bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, adamantyl and the like.

In addition, the above-mentioned $C_{1-10}$ cycloalkyl group, $C_{3-10}$ cycloalkenyl group and $C_{4-10}$ cycloalkadienyl group may each form a spiro ring group with a $C_{3-10}$ cycloalkane, a $C_{3-10}$ cycloalkene, a $C_{4-10}$ cycloalkadiene or a non-aromatic heterocycle. Examples of the $C_{3-10}$ cycloalkane, $C_{3-10}$ cycloalkene and $C_{4-10}$ cycloalkadiene include rings corresponding to the above-mentioned $C_{3-10}$ cycloalkyl group, $C_{3-10}$ cycloalkenyl group and $C_{4-10}$ cycloalkadienyl group. Examples of the non-aromatic heterocycle include a ring corresponding to the following non-aromatic heterocyclic group. Examples of the spiro ring group include spiro[4.5]decanyl (e.g., spiro[4.5]decan-8-yl) and the like.

In the present specification, the "$C_{3-6}$ cycloalkyloxy (group)" means, for example, cyclopropyloxy, cyclobutyloxy, cyclopentyloxy, cyclohexyloxy or the like.

In the present specification, the "$C_{3-8}$ cycloalkyloxy (group)" means, for example, cyclopropyloxy, cyclobutyloxy, cyclopentyloxy, cyclohexyloxy, cycloheptyloxy, cyclooctyloxy or the like. Among them, a $C_{3-6}$ cycloalkyloxy group is preferable.

In the present specification, the "$C_{3-8}$ cycloalkenyloxy (group)" means, for example, cyclopropenyloxy (e.g., 2-cyclopropen-1-yloxy), cyclobutenyloxy (e.g., 2-cyclobuten-1-yloxy), cyclopentenyloxy (e.g., 2-cyclopenten-1-yloxy, 3-cyclopenten-1-yloxy), cyclohexenyloxy (e.g., 2-cyclohexen-1-yloxy, 3-cyclohexen-1-yloxy) or the like.

In the present specification, the "$C_{6-14}$ aryl (group)" means, for example, phenyl, 1-naphthyl, 2-naphthyl or the like.

In the present specification, the "$C_{6-14}$ aryloxy (group)" means, for example, phenoxy, 1-naphthyloxy, 2-naphthyloxy or the like.

In the present specification, the "$C_{7-14}$ aralkyl (group)" means, for example, benzyl, phenethyl or the like.

In the present specification, the "$C_{7-14}$ aralkyloxy (group)" means, for example, benzyloxy, phenethyloxy or the like.

In the present specification, the "$C_{8-13}$ arylalkenyl (group)" means, for example, styryl or the like.

In the present specification, the "heterocyclic group" means an aromatic heterocyclic group or a non-aromatic heterocyclic group.

In the present specification, the "aromatic heterocyclic group" means a monocyclic aromatic heterocyclic group or a fused aromatic heterocyclic group.

In the present specification, examples of the "monocyclic aromatic heterocyclic group" include a 5- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom (optionally oxidized) and a nitrogen atom (optionally oxidized), for example, furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., 1H-tetrazol-1-yl, 1H-tetrazol-5-yl), triazinyl (e.g., 1,2,4-triazin-1-yl, 1,2,4-triazin-3-yl) and the like.

In the present specification, examples of the "fused aromatic heterocyclic group" include an 8- to 12-membered fused aromatic heterocyclic group, specifically, a group derived from a fused ring wherein a ring corresponding to the above-mentioned 5- to 7-membered monocyclic aromatic heterocyclic group is fused with a $C_{6-14}$ aromatic hydrocarbon; and a group derived from a fused ring wherein rings corresponding to the above-mentioned 5- to 7-membered monocyclic aromatic heterocyclic groups are fused, for example, quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl, 6-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl, 1H-indazol-5-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl, 2H-imidazo[1,2-a]pyridin-3-yl), thienopyridyl (e.g., thieno[2,3-b]pyridin-3-yl), imidazopyrazinyl (e.g., 1H-imidazo[4,5-b]pyrazin-2-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

In the present specification, the "non-aromatic heterocyclic group" means a monocyclic non-aromatic heterocyclic group or a fused non-aromatic heterocyclic group.

In the present specification, examples of the "monocyclic non-aromatic heterocyclic group" include a 3- to 8-membered (preferably 5- or 6-membered) monocyclic non-aromatic heterocyclic group containing, as a ring-constituting atom besides carbon atoms, 1 to 4 hetero atoms selected from an oxygen atom, a sulfur atom (optionally oxidized) and a nitrogen atom (optionally oxidized), for example, azetidinyl (e.g., 1-azetidinyl, 2-azetidinyl), pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholino), thiomorpholinyl (e.g., thiomorpholino), piperazinyl (e.g., 1-piperazinyl, 2-piperazinyl, 3-piperazinyl), oxazolidinyl (e.g., oxazolidin-2-yl), thiazolidinyl (e.g., thiazolidin-2-yl), dihydrothiopyranyl (e.g., dihydrothiopyran-3-yl, dihydrothiopyran-4-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 2-pyranyl, 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidetetrahydrothiopyranyl (e.g., 1-oxidetetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), oxetanyl (e.g., oxetan-2-yl, oxetan-3-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl), azepanyl (e.g., 1-azepanyl, 2-azepanyl, 3-azepanyl, 4-azepanyl), dihydropyridyl (e.g., dihydropyridin-1-yl, dihydropyridin-2-yl, dihydropyridin-3-yl, dihydropyridin-4-yl), tetrahydropyridyl (e.g., 1,2,3,4-tetrahydropyridin-1-yl, 1,2,3,4-tetrahydropyridin-2-yl, 1,2,3,4-tetrahydropyridin-3-yl, 1,2,3,4-tetrahydropyridin-4-yl), 1,1-dioxidothiomorpholinyl (e.g., 1,1-dioxidothiomorpholino) and the like.

In the present specification, examples of the "fused non-aromatic heterocyclic group" include an 8- to 12-membered fused non-aromatic heterocyclic group, specifically, a group derived from a fused ring wherein a ring corresponding to the above-mentioned 3- to 8-membered monocyclic non-aromatic heterocyclic group is fused with a $C_{6-14}$ aromatic hydrocarbon; a group derived from a fused ring wherein rings corresponding to the above-mentioned 3- to 8-membered monocyclic non-aromatic heterocyclic groups are fused; a group derived from a fused ring wherein a ring corresponding to the above-mentioned 3- to 8-membered monocyclic non-aromatic heterocyclic group is fused with a ring corresponding to the above-mentioned 5- to 7-membered monocyclic aromatic heterocyclic group; and a group wherein the above-mentioned group is partially saturated, for example, dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), tetrahydrobenzofuranyl (e.g., 4,5,6,7-tetrahydro-1-benzofuran-3-yl), dihydrobenzodioxinyl (e.g., 2,3-dihydro-1,4-benzodidioxin-2-yl), dihydrobenzodioxepinyl (e.g., 3,4-dihydro-2H-1,5-benzodioxepin-2-yl), chromenyl (e.g., 4H-chromen-2-yl, 2H-chromen-3-yl), dihydrochromenyl (e.g., 3,4-dihydro-2H-chromen-2-yl), dihydroquinolyl (e.g., 1,2-dihydroquinolin-4-yl), tetrahydroquinolyl (e.g., 1,2,3,4-tetrahydroquinolin-4-yl), dihydroisoquinolyl (e.g., 1,2-dihydroisoquinolin-4-yl), tetrahydroisoquinolyl (e.g., 1,2,3,4-tetrahydroisoquinolin-4-yl), dihydrophthalazinyl (e.g., 1,4-dihydrophthalazin-4-yl) and the like.

In addition, the above-mentioned non-aromatic heterocyclic group may each form a spiro ring group with a $C_{3-10}$ cycloalkane, a $C_{3-10}$ cycloalkene, a $C_{4-10}$ cycloalkadiene or a non-aromatic heterocycle. Examples of the $C_{3-10}$ cycloalkane, $C_{3-10}$ cycloalkene, $C_{4-10}$ cycloalkadiene and non-aromatic heterocycle include rings corresponding to the above-mentioned $C_{3-10}$ cycloalkyl group, $C_{3-10}$ cycloalkenyl group, $C_{4-10}$ cycloalkadienyl group and non-aromatic heterocyclic group. Examples of the spiro ring group include 2-oxa-6-azaspiro[3.3]heptyl (e.g., 2-oxa-6-azaspiro[3.3]heptan-6-yl) and the like.

In the present specification, the "aromatic ring group" means a $C_{6-14}$ aryl group (preferably phenyl) or an aromatic heterocyclic group.

In the present specification, examples of the "$C_{6-14}$ aromatic hydrocarbon" include benzene and naphthalene.

Each symbol of the formula (I) is explained below.

In the formula (I), $R^1$ is a group represented by the following formula:

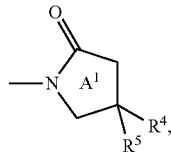

or an optionally substituted 2-oxopiperidino group.

Ring $A^1$ is an optionally further substituted 2-oxopyrrolidine ring.

$R^4$ is a hydrogen atom, a halogen atom, a cyano group, an acyl group, an optionally substituted $C_{1-6}$ alkyl group, an optionally substituted hydroxy group, an optionally substituted amino group, an optionally substituted $C_{3-6}$ cycloalkyl group, or an optionally substituted heterocyclic group.

$R^5$ is a hydrogen atom, a halogen atom, a cyano group, an acyl group, an optionally substituted $C_{1-6}$ alkyl group, an optionally substituted hydroxy group, an optionally substituted amino group, an optionally substituted $C_{3-6}$ cycloalkyl group, or an optionally substituted heterocyclic group.

The "$C_{1-6}$ alkyl group" of the "optionally substituted $C_{1-6}$ alkyl group" for $R^4$ or $R^5$ optionally has 1 to 5 (preferably 1 to 3) substituents at substitutable position(s). Examples of the substituent include substituents selected from the following Substituent Group A. When the number of the substituents is plural, the respective substituents may be the same or different.

Substituent Group A:
(1) a halogen atom;
(2) a cyano group;
(3) a nitro group;
(4) a hydroxy group;
(5) a $C_{3-8}$ cycloalkyl group optionally substituted by 1 to 3 substituents selected from
  (a) a halogen atom,
  (b) a cyano group,
  (c) a $C_{1-6}$ alkyl group optionally substituted by 1 to 3 substituents selected from
    (i) a halogen atom, and
    (ii) a hydroxy group,
  (d) a $C_{1-6}$ alkoxy group optionally substituted by 1 to 3 halogen atoms,
  (e) a carbamoyl group optionally mono- or di-substituted by $C_{1-6}$ alkyl group(s), and
  (f) a carboxy group;
(6) a $C_{6-14}$ aryl group optionally substituted by 1 to 3 substituents selected from
  (a) a halogen atom,
  (b) a cyano group,
  (c) a $C_{1-6}$ alkyl group optionally substituted by 1 to 3 halogen atoms or 3- to 8-membered monocyclic non-aromatic heterocyclic groups,
  (d) a $C_{1-6}$ alkoxy group optionally substituted by 1 to 3 halogen atoms, and
  (e) a 3- to 8-membered monocyclic non-aromatic heterocyclic group optionally substituted by 1 to 3 $C_{1-6}$ alkyl groups;
(7) a $C_{1-6}$ alkoxy group optionally substituted by 1 to 3 substituents selected from
  (a) a halogen atom,
  (b) a cyano group,
  (c) a $C_{3-8}$ cycloalkyl group optionally having 1 to 3 halogen atoms,
  (d) a $C_{3-8}$ cycloalkenyl group optionally having 1 to 3 halogen atoms,
  (e) a $C_{6-14}$ aryl group optionally having 1 to 3 halogen atoms,
  (f) a 5- or 6-membered monocyclic aromatic heterocyclic group, and
  (g) a $C_{1-6}$ alkoxy group;
(8) a $C_{2-6}$ alkenyloxy group (e.g., vinyloxy, propenyloxy, butenyloxy, pentenyloxy, hexenyloxy) optionally having 1 to 3 halogen atoms;
(9) a $C_{2-6}$ alkynyloxy group (e.g., ethynyloxy, propynyloxy, butynyloxy, pentynyloxy, hexynyloxy) optionally having 1 to 3 halogen atoms;
(10) a $C_{3-8}$ cycloalkyloxy group (e.g., cyclopropyloxy, cyclobutyloxy, cyclopentyloxy, cyclohexyloxy) optionally having 1 to 3 halogen atoms;
(11) a $C_{3-8}$ cycloalkenyloxy group (e.g., cyclopropenyloxy, cyclobutenyloxy, cyclopentenyloxy, cyclohexenyloxy) optionally having 1 to 3 halogen atoms;
(12) a $C_{6-14}$ aryloxy group optionally having 1 to 3 halogen atoms;
(13) a $C_{7-14}$ aralkyloxy group optionally having 1 to 3 halogen atoms;
(14) a carbamoyl group optionally mono- or di-substituted by substituent(s) selected from
  (a) a $C_{1-6}$ alkyl group optionally substituted by 1 to 3 substituents selected from
    (i) a hydroxy group,
    (ii) a 3- to 8-membered monocyclic non-aromatic heterocyclic group optionally substituted by 1 to 3 $C_{1-6}$ alkyl groups, and
    (iii) a $C_{1-6}$ alkylsulfonyl group,
  (b) a $C_{3-8}$ cycloalkyl group optionally substituted by 1 to 3 substituents selected from
    (i) a cyano group, and
    (ii) a hydroxy group,
  (c) a $C_{6-14}$ aryl group,
  (d) a $C_{1-6}$ alkoxy group,
  (e) a 5- or 6-membered monocyclic aromatic heterocyclic group,
  (f) a 8- to 12-membered fused aromatic heterocyclic group,
  (g) a 3- to 8-membered monocyclic non-aromatic heterocyclic group, and
  (h) a 8- to 12-membered fused non-aromatic heterocyclic group;
(15) a sulfamoyl group optionally mono- or di-substituted by substituent(s) selected from
  (a) a $C_{1-6}$ alkyl group,
  (b) a $C_{3-8}$ cycloalkyl group,
  (c) a $C_{6-14}$ aryl group,
  (d) a $C_{1-6}$ alkoxy group,
  (e) a 5- or 6-membered monocyclic aromatic heterocyclic group,
  (f) a 8- to 12-membered fused aromatic heterocyclic group,
  (g) a 3- to 8-membered monocyclic non-aromatic heterocyclic group, and
  (h) a 8- to 12-membered fused non-aromatic heterocyclic group;
(16) formyl;
(17) a $C_{1-6}$ alkyl-carbonyl group;
(18) a $C_{2-6}$ alkenyl-carbonyl group (e.g., acryloyl, butenoyl, pentenoyl, hexenoyl, heptenoyl);
(19) a $C_{2-6}$ alkynyl-carbonyl group (e.g., propioloyl, propynylcarbonyl, butynylcarbonyl, pentynylcarbonyl, hexynylcarbonyl);
(20) a $C_{3-8}$ cycloalkyl-carbonyl group (e.g., cyclopropylcarbonyl, cyclobutylcarbonyl, cyclopentylcarbonyl, cyclohexylcarbonyl);
(21) a $C_{3-8}$ cycloalkenyl-carbonyl group (e.g., cyclopropenylcarbonyl, cyclobutenylcarbonyl, cyclopentenylcarbonyl, cyclohexenylcarbonyl);
(22) a $C_{6-14}$ aryl-carbonyl group (e.g., benzoyl, 1-naphthylcarbonyl, 2-naphthylcarbonyl);
(23) a $C_{3-8}$ cycloalkyl-$C_{1-6}$ alkyl-carbonyl group (e.g., cyclopropylacetyl, 3-cyclopropylpropionyl, cyclobutylacetyl, cyclopentylacetyl, cyclohexylacetyl, cyclohexylpropionyl);
(24) a $C_{3-9}$ cycloalkenyl-$C_{1-6}$ alkyl-carbonyl group (e.g., cyclopentenylacetyl, cyclohexenylacetyl, 3-cyclohexenylpropionyl, 3-cyclohexenylpropionyl);
(25) a $C_{7-14}$ aralkyl-carbonyl group (e.g., phenylacetyl, 3-phenylpropionyl);
(26) a 5- or 6-membered monocyclic aromatic heterocyclylcarbonyl group (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyridylcarbonyl, pyrazolylcarbonyl);
(27) a 8- to 12-membered fused aromatic heterocyclylcarbonyl group (e.g., benzofuranylcarbonyl, isobenzofuranylcarbonyl, benzothienylcarbonyl, isobenzothienylcarbonyl, indolylcarbonyl, isoindolylcarbonyl, indazolylcarbonyl, benzimidazolylcarbonyl, benzoxazolylcarbonyl);
(28) a 3- to 8-membered monocyclic non-aromatic heterocyclylcarbonyl group (e.g., oxiranylcarbonyl, azetidinylcarbonyl, oxetanylcarbonyl, thietanylcarbonyl, pyrrolidinylcarbonyl, tetrahydrofurylcarbonyl, thiolanylcarbonyl, piperidylcarbonyl, morpholinylcarbonyl, 2-oxa-6-azaspiro[3.3]heptylcarbonyl, 1,1-dioxidothiomorpholinylcarbonyl) optionally substituted by 1 to 3 substituents selected from
  (a) a hydroxy group,
  (b) an oxo group,
  (c) a halogen atom,
  (d) a $C_{1-6}$ alkoxy group, and
  (e) a $C_{1-6}$ alkyl group;
(29) a 8- to 12-membered fused non-aromatic heterocyclylcarbonyl group (e.g., dihydrobenzofuranyl);
(30) an amino group optionally mono- or di-substituted by substituent(s) selected from
  (a) a $C_{1-6}$ alkyl group optionally substituted by 1 to 3 substituents selected from
    (i) a halogen atom, and
    (ii) a $C_{1-6}$ alkoxy group,
  (b) a $C_{1-6}$ alkyl-carbonyl group optionally having 1 to 3 halogen atoms,
  (c) a $C_{3-8}$ cycloalkyl-carbonyl group,
  (d) a $C_{6-14}$ aryl-carbonyl group optionally having 1 to 3 halogen atoms,
  (e) a 5- or 6-membered monocyclic aromatic heterocyclylcarbonyl group,
  (f) a 8- to 12-membered fused aromatic heterocyclylcarbonyl group,
  (g) a 3- to 8-membered monocyclic non-aromatic heterocyclylcarbonyl group,
  (h) a 8- to 12-membered fused non-aromatic heterocyclylcarbonyl group, and
  (i) a $C_{1-6}$ alkylsulfonyl group;
(31) a sulfanyl group;
(32) a $C_{1-6}$ alkylsulfanyl group (e.g., methylsulfanyl, ethylsulfanyl);
(33) a $C_{2-6}$ alkenylsulfanyl group (e.g., vinylsulfanyl, propenylsulfanyl);
(34) a $C_{2-6}$ alkynylsulfanyl group (e.g., ethynylsulfanyl, propynylsulfanyl);
(35) a $C_{3-8}$ cycloalkylsulfanyl group (e.g., cyclopropylsulfanyl, cyclobutylsulfanyl);
(36) a $C_{3-8}$ cycloalkenylsulfanyl group (e.g., cyclopropenylsulfanyl, cyclobutenylsulfanyl);
(37) a $C_{6-14}$ arylsulfanyl group (e.g., phenylsulfanyl);
(38) a $C_{3-8}$ cycloalkyl-$C_{1-6}$ alkylsulfanyl group (e.g., cyclopropylmethylsulfanyl);
(39) a $C_{3-8}$ cycloalkenyl-$C_{1-6}$ alkylsulfanyl group (e.g., cyclopentenylmethylsulfanyl);
(40) a $C_{1-6}$ alkylsulfinyl group (e.g., methylsulfinyl, ethylsulfinyl);
(41) a $C_{2-6}$ alkenylsulfinyl group (e.g., vinylsulfinyl, propenylsulfinyl);
(42) a $C_{2-6}$ alkynylsulfinyl group (e.g., ethynylsulfinyl, propynylsulfinyl);
(43) a $C_{3-8}$ cycloalkylsulfinyl group (e.g., cyclopropylsulfinyl, cyclobutylsulfinyl);
(44) a $C_{3-8}$ cycloalkenylsulfinyl group (e.g., cyclopropenylsulfinyl, cyclobutenylsulfinyl);
(45) a $C_{6-14}$ arylsulfinyl group (e.g., phenylsulfinyl);
(46) a $C_{3-8}$ cycloalkyl-$C_{1-6}$ alkylsulfinyl group (e.g., cyclopropylmethylsulfinyl);
(47) a $C_{3-8}$ cycloalkenyl-$C_{1-6}$ alkylsulfinyl group (e.g., cyclopentenylmethylsulfinyl);
(48) a $C_{1-6}$ alkylsulfonyl group (e.g., methylsulfonyl, ethylsulfonyl);
(49) a $C_{2-6}$ alkenylsulfonyl group (e.g., vinylsulfonyl, propenylsulfonyl);
(50) a $C_{2-6}$ alkynylsulfonyl group (e.g., ethynylsulfonyl, propynylsulfonyl);
(51) a $C_{3-8}$ cycloalkylsulfonyl group (e.g., cyclopropylsulfonyl, cyclobutylsulfonyl);
(52) a $C_{3-8}$ cycloalkenylsulfonyl group (e.g., cyclopropenylsulfonyl, cyclobutenylsulfonyl);
(53) a $C_{6-14}$ arylsulfonyl group (e.g., phenylsulfonyl);
(54) a $C_{3-8}$ cycloalkyl-$C_{1-6}$ alkylsulfonyl group (e.g., cyclopropylmethylsulfonyl);
(55) a $C_{3-8}$ cycloalkenyl-$C_{1-8}$ alkylsulfonyl group (e.g., cyclopentenylmethylsulfonyl);
(56) a $C_{6-14}$ aryl-$C_{1-6}$ alkylsulfonyl group (e.g., benzylsulfonyl);
(57) a 5- or 6-membered monocyclic aromatic heterocyclylsulfonyl group (e.g., furylsulfonyl, thienylsulfonyl, pyridylsulfonyl);
(58) a 8- to 12-membered fused aromatic heterocyclylsulfonyl group (e.g., benzofuranylsulfonyl, isobenzofuranylsulfonyl);
(59) a 3- to 8-membered monocyclic non-aromatic heterocyclylsulfonyl group (e.g., oxiranylsulfonyl, azetidinylsulfonyl);
(60) a 8- to 12-membered fused non-aromatic heterocyclylsulfonyl group (e.g., dihydrobenzofuranylsulfonyl);
(61) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl) optionally substituted by 1 to 3 substituents selected from
  (a) a halogen atom,
  (b) a $C_{1-6}$ alkyl group optionally substituted by 1 to 3 halogen atoms, and
  (c) a $C_{1-6}$ alkoxy group optionally substituted by 1 to 3 halogen atoms;
(62) a 8- to 12-membered fused aromatic heterocyclic group (e.g., benzofuranyl, isobenzofuranyl, benzothienyl, isobenzothienyl, indolyl, isoindolyl, indazolyl, benzimidazolyl, benzoxazolyl) optionally substituted by 1 to 3 substituents selected from
  (a) a halogen atom,
  (b) a $C_{1-6}$ alkyl group optionally substituted by 1 to 3 halogen atoms, and
  (c) a $C_{1-6}$ alkoxy group optionally substituted by 1 to 3 halogen atoms;
(63) a 3- to 8-membered monocyclic non-aromatic heterocyclic group (e.g., oxiranyl, azetidinyl, oxetanyl, thietanyl, pyrrolidinyl, tetrahydrofuryl, thiolanyl, piperidyl, piperazinyl, dihydrooxadiazolyl, thiazolinyl, morpholinyl, tetrahydropyranyl, 1,1-dioxidothiomorpholinyl, imidazolidinyl, 1,1-dioxidetetrahydrothiopyranyl) optionally substituted by 1 to 3 substituents selected from
  (a) a halogen atom,
  (b) a $C_{1-6}$ alkyl group optionally substituted by 1 to 3 substituents selected from
    (i) a halogen atom, and
    (ii) a hydroxy group,
  (c) a $C_{1-6}$ alkoxy group optionally substituted by 1 to 3 halogen atoms,
  (d) a $C_{1-6}$ alkyl-carbonyl group optionally substituted by 1 to 3 substituents selected from
    (i) a $C_{1-6}$ alkoxy group, and
    (ii) a cyano group,
  (e) an oxo group,
  (f) a $C_{1-6}$ alkoxy-carbonyl group,
  (g) a $C_{1-6}$ alkylsulfonyl group, (h) a carbamoyl group optionally mono- or di-substituted by $C_{1-6}$ alkyl group(s),
(i) a cyano group,
(j) a hydroxy group, and
(k) a carboxy group;
(64) a 8- to 12-membered fused non-aromatic heterocyclic group (e.g., dihydrobenzofuranyl) optionally substituted by 1 to 3 substituents selected from
   (a) a halogen atom,
   (b) a $C_{1-6}$ alkyl group optionally substituted by 1 to 3 halogen atoms,
   (c) a $C_{1-6}$ alkoxy group optionally substituted by 1 to 3 halogen atoms, and
   (d) an oxo group;
(65) a 5- or 6-membered monocyclic aromatic heterocyclyloxy group (e.g., furyloxy, thienyloxy, pyrrolyloxy, oxazolyloxy, isoxazolyloxy, thiazolyloxy, isothiazolyloxy, imidazolyloxy, pyridyloxy, pyrazolyloxy);
(66) a 8- to 12-membered fused aromatic heterocyclyloxy group (e.g., benzofuranyloxy, isobenzofuranyloxy, benzothienyloxy, isobenzothienyloxy, indolyloxy, isoindolyloxy, indazolyloxy, benzimidazolyloxy, benzoxazolyloxy);
(67) a 3- to 8-membered monocyclic non-aromatic heterocyclyloxy group (e.g., oxiranyloxy, azetidinyloxy, oxetanyloxy, thietanyloxy, pyrrolidinyloxy, tetrahydrofuryloxy, thiolanyloxy, piperidyloxy);
(68) a 8- to 12-membered fused non-aromatic heterocyclyloxy group (e.g., dihydrobenzofuranyloxy);
(69) a carboxy group;
(70) a $C_{1-6}$ alkoxy-carbonyl group;
(71) a $C_{2-6}$ alkenyloxy-carbonyl group (e.g., vinyloxycarbonyl, propenyloxycarbonyl, butenyloxycarbonyl, pentenyloxycarbonyl, hexenyloxycarbonyl);
(72) a $C_{2-6}$ alkynyloxy-carbonyl group (e.g., ethynyloxycarbonyl, propynyloxycarbonyl, butynyloxycarbonyl, pentynyloxycarbonyl, hexynyloxycarbonyl);
(73) a $C_{3-8}$ cycloalkyloxy-carbonyl group (e.g., cyclopropyloxycarbonyl, cyclobutyloxycarbonyl, cyclopentyloxycarbonyl, cyclohexyloxycarbonyl);
(74) a $C_{3-8}$ cycloalkenyloxy-carbonyl group (e.g., cyclopropenyloxycarbonyl, cyclobutenyloxycarbonyl, cyclopentenyloxycarbonyl, cyclohexenyloxycarbonyl);
(75) a $C_{6-14}$ aryloxy-carbonyl group (e.g., phenoxycarbonyl, 1-naphthyloxycarbonyl, 2-naphthyloxycarbonyl);
(76) a $C_{3-8}$ cycloalkyl-$C_{1-6}$ alkoxy-carbonyl group (e.g., cyclopropylmethyloxycarbonyl, cyclopropylethyloxycarbonyl, cyclobutylmethyloxycarbonyl, cyclopentylmethyloxycarbonyl, cyclohexylmethyloxycarbonyl, cyclohexylethyloxycarbonyl);
(77) a $C_{3-8}$ cycloalkenyl-$C_{1-6}$ alkoxy-carbonyl group (e.g., cyclopentenylmethyloxycarbonyl, cyclohexenylmethyloxycarbonyl, cyclohexenylethyloxycarbonyl, cyclohexenylpropyloxycarbonyl);
(78) a $C_{7-14}$ aralkyloxy-carbonyl group (e.g., benzyloxycarbonyl, phenethyloxycarbonyl);
(79) mono-$C_{1-6}$ alkylthio-carbamoyl group (e.g., methylthiocarbamoyl, ethylthiocarbamoyl, propylthiocarbamoyl);
(80) di-$C_{1-6}$ alkylthio-carbamoyl group (e.g., dimethylthiocarbamoyl, diethylthiocarbamoyl, dipropylthiocarbamoyl);
(81) a $C_{1-6}$ alkyl-carbonyloxy group (e.g., acetyloxy, propanoyloxy, butanoyloxy, 2-methylpropanoyloxy);
(82) an imino group optionally substituted by a hydroxy group; and
(83) a $C_{1-6}$ alkylenedioxy group (e.g., methylenedioxy, ethylenedioxy).

The "$C_{3-6}$ cycloalkyl group" of the "optionally substituted $C_{3-6}$ cycloalkyl group" for $R^4$ or $R^5$ optionally has 1 to 5 (preferably 1 to 3) substituents at substitutable position(s). Examples of the substituent include substituents selected from the following Substituent Group B. When the number of the substituents is plural, the respective substituents may be the same or different.

Substituent Group B:
(1) the above-mentioned Substituent Group A;
(2) a $C_{1-6}$ alkyl group optionally substituted by 1 to 3 substituents selected from
   (a) a halogen atom,
   (b) a cyano group,
   (c) a hydroxy group,
   (d) a $C_{3-8}$ cycloalkyl group optionally substituted by 1 to 3 substituents selected from
      (i) a halogen atom,
      (ii) a cyano group, and
      (iii) a $C_{1-6}$ alkyl group optionally substituted by 1 to 3 halogen atoms,
   (e) a $C_{6-14}$ aryl group optionally substituted by 1 to 3 substituents selected from
      (i) a halogen atom,
      (ii) a cyano group,
      (iii) a $C_{1-6}$ alkoxy group, and
      (iv) a $C_{1-6}$ alkyl group optionally substituted by 1 to 3 halogen atoms,
   (f) a $C_{1-6}$ alkoxy group optionally substituted by 1 to 3 halogen atoms,
   (g) an amino group optionally mono- or di-substituted by substituent(s) selected from
      (i) a $C_{1-6}$ alkyl group,
      (ii) a $C_{1-6}$ alkyl-carbonyl group optionally substituted by 1 to 3 substituents selected from
         (A) a $C_{1-6}$ alkoxy group, and
         (B) a hydroxy group,
      (iii) a $C_{1-6}$ alkoxy-carbonyl group,
      (iv) a $C_{1-6}$ alkylsulfonyl group, and
      (v) a sulfamoyl group optionally mono- or di-substituted by $C_{1-6}$ alkyl group(s),
   (h) a 5- or 6-membered monocyclic aromatic heterocyclic group,
   (i) a 8- to 12-membered fused aromatic heterocyclic group,
   (j) a 3- to 8-membered monocyclic non-aromatic heterocyclic group,
   (k) a 8- to 12-membered fused non-aromatic heterocyclic group,
   (l) a carboxy group,
   (m) a $C_{1-6}$ alkoxy-carbonyl group optionally substituted by 1 to 3 halogen atoms,
   (n) a $C_{1-6}$ alkyl-carbonyl group,
   (o) a carbamoyl group optionally mono- or di-substituted by $C_{1-6}$ alkyl group(s) optionally substituted by 1 to 3 substituents selected from
      (i) a $C_{1-6}$ alkoxy group,
      (ii) a hydroxy group,
      (iii) a halogen atom, and
      (iv) a $C_{1-6}$ alkylsulfonyl group,
   (p) a 3- to 8-membered monocyclic non-aromatic heterocyclylcarbonyl group optionally substituted by 1 to 3 substituents selected from
      (i) a hydroxy group,
      (ii) a carbamoyl group, and
      (iii) a $C_{1-6}$ alkyl group, and
   (q) a $C_{1-6}$ alkylsulfonyl group;
(3) a $C_{2-6}$ alkenyl group optionally substituted by 1 to 3 substituents selected from
   (a) a halogen atom,
   (b) a hydroxy group, (c) a $C_{1-6}$ alkoxy group,
(d) an amino group optionally mono- or di-substituted by a $C_{1-6}$ alkyl,
(e) a carboxy group, and
(f) a $C_{1-6}$ alkoxy-carbonyl group;
(4) a $C_{7-14}$ aralkyl group optionally substituted by 1 to 3 substituents selected from
(a) a halogen atom,
(b) a hydroxy group,
(c) a $C_{1-6}$ alkoxy group, and
(d) a $C_{1-6}$ alkyl group optionally substituted by 1 to 3 halogen atoms; and
(5) an oxo group.

The "heterocyclic group" of the "optionally substituted heterocyclic group" for $R^4$ or $R^5$ optionally has 1 to 5 (preferably 1 to 3) substituents at substitutable position(s). Examples of the substituent include substituents selected from the above-mentioned Substituent Group B. When the number of the substituents is plural, the respective substituents may be the same or different.

Examples of the "optionally substituted hydroxy group" for $R^4$ or $R^5$ include a hydroxy group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-14}$ aralkyl group, a $C_{8-13}$ arylalkenyl group, a $C_{1-6}$ alkyl-carbonyl group, a heterocyclic group and the like, each of which is optionally substituted.

The $C_{1-10}$ alkyl group, $C_{2-10}$ alkenyl group and $C_{1-6}$ alkyl-carbonyl group optionally have 1 to 5 (preferably 1 to 3) substituents at substitutable position(s). Examples of the substituent include substituents selected from the above-mentioned Substituent Group A. When the number of the substituents is plural, the respective substituents may be the same or different.

The $C_{3-10}$ cycloalkyl group, $C_{3-10}$ cycloalkenyl group, a $C_{6-14}$ aryl group, $C_{7-14}$ aralkyl group, $C_{8-13}$ arylalkenyl group and heterocyclic group optionally have 1 to 5 (preferably 1 to 3) substituents at substitutable position(s). Examples of the substituent include substituents selected from the above-mentioned Substituent Group B. When the number of the substituents is plural, the respective substituents may be the same or different.

Examples of the "optionally substituted amino group" for $R^4$ or $R^5$ include an amino group optionally mono- or di-substituted by substituent(s) selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-14}$ aralkyl group, a $C_{8-13}$ arylalkenyl group and a heterocyclic group, each of which is optionally substituted; an acyl group and the like.

The $C_{1-10}$ alkyl group and $C_{2-10}$ alkenyl group optionally have 1 to 5 (preferably 1 to 3) substituents at substitutable position(s). Examples of the substituent include substituents selected from the above-mentioned Substituent Group A. When the number of the substituents is plural, the respective substituents may be the same or different.

The $C_{3-10}$ cycloalkyl group, $C_{3-10}$ cycloalkenyl group, a $C_{6-14}$ aryl group, $C_{7-14}$ aralkyl group, $C_{8-13}$ arylalkenyl group and heterocyclic group optionally have 1 to 5 (preferably 1 to 3) substituents at substitutable position(s). Examples of the substituent include substituents selected from the above-mentioned Substituent Group B. When the number of the substituents is plural, the respective substituents may be the same or different.

Examples of the "acyl group" exemplified as the substituent for the "optionally substituted amino group" include those similar to the below-mentioned "acyl group" for $R^4$ or $R^5$.

Examples of the "acyl group" for $R^4$ or $R^5$ include a group represented by the formula: —$COR^A$, —CO—$OR^A$, —$SO_3R^A$, —$S(O)_2R^A$, $SOR^A$, —CO—$NR^{A'}R^{B'}$, —CS—$NR^{A'}R^{B'}$, —$S(O)_2NR^{A'}R^{B'}$ wherein $R^A$ is a hydrogen atom, an optionally substituted hydrocarbon group or an optionally substituted heterocyclic group, and $R^{A'}$ and $R^{B'}$ are the same or different and each is a hydrogen atom, an optionally substituted hydrocarbon group or an optionally substituted heterocyclic group, or $R^{A'}$ and $R^{B'}$ in combination optionally form, together with the adjacent nitrogen atom, an optionally substituted nitrogen-containing heterocycle, and the like.

Examples of the "hydrocarbon group" of the "optionally substituted hydrocarbon group" for $R^A$, $R^{A'}$ or $R^{B'}$ include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-14}$ aralkyl group, a $C_{8-13}$ arylalkenyl group and the like.

The $C_{1-10}$ alkyl group, $C_{2-10}$ alkenyl group and $C_{2-10}$ alkynyl group, which are exemplified as the above-mentioned "hydrocarbon group", optionally have 1 to 5 (preferably 1 to 3) substituents at substitutable position(s). Examples of the substituent include substituents selected from the above-mentioned Substituent Group A. When the number of the substituents is plural, the respective substituents may be the same or different.

The $C_{3-10}$ cycloalkyl group, $C_{3-10}$ cycloalkenyl group, $C_{4-10}$ cycloalkadienyl group, a $C_{6-14}$ aryl group, $C_{7-14}$ aralkyl group and $C_{8-13}$ arylalkenyl group, which are exemplified as the above-mentioned "hydrocarbon group", optionally have 1 to 5 (preferably 1 to 3) substituents at substitutable position(s). Examples of the substituent include substituents selected from the above-mentioned Substituent Group B. When the number of the substituents is plural, the respective substituents may be the same or different.

The "heterocyclic group" of the "optionally substituted heterocyclic group" for $R^A$, $R^{A'}$ or $R^{B'}$ optionally has 1 to 5 (preferably 1 to 3) substituents at substitutable position(s). Examples of the substituent include substituents selected from the above-mentioned Substituent Group B. When the number of the substituents is plural, the respective substituents may be the same or different.

Examples of the "nitrogen-containing heterocycle" of the "optionally substituted nitrogen-containing heterocycle" formed by $R^{A'}$ and $R^{B'}$ together with the adjacent nitrogen atom include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

The nitrogen-containing heterocycle optionally has 1 to 5 (preferably 1 to 3) substituents at substitutable position(s). Examples of the substituent include substituents selected from the above-mentioned Substituent Group B. When the number of the substituents is plural, the respective substituents may be the same or different.

Preferable examples of the "acyl group" include
(1) a formyl group;
(2) a carboxy group;
(3) a $C_{1-6}$ alkyl-carbonyl group (e.g., acetyl) optionally substituted by 1 to 3 halogen atoms;
(4) a $C_{1-6}$ alkoxy-carbonyl group (e.g., methoxycarbonyl, ethoxycarbonyl, propoxycarbonyl, tert-butoxycarbonyl) optionally substituted by 1 to 3 halogen atoms;

(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group (e.g., benzoyl, 1-naphthoyl, 2-naphthoyl) optionally substituted by 1 to 3 halogen atoms;
(7) a carbamoyl group optionally mono- or di-substituted by substituent(s) selected from
  (a) a $C_{1-6}$ alkyl group optionally substituted by 1 to 3 substituents selected from a halogen atom, a $C_{1-6}$ alkoxy group, a $C_{1-6}$ alkoxy-carbonyl group and a carboxy group, and
  (b) an amino group optionally mono- or di-substituted by $C_{1-6}$ alkoxy-carbonyl group(s);
(8) a $C_{1-6}$ alkylsulfonyl group (e.g., methylsulfonyl, ethylsulfonyl, isopropylsulfonyl) optionally substituted by 1 to 3 halogen atoms;
(9) a $C_{6-14}$ arylsulfonyl group (e.g., benzenesulfonyl);
(10) a sulfamoyl group;
(11) a thiocarbamoyl group;
(12) an aromatic heterocyclylcarbonyl group (e.g., furylcarbonyl, thienylcarbonyl) optionally substituted by 1 to 3 substituents selected from a $C_{1-6}$ alkyl group optionally substituted by 1 to 3 halogen atoms;
(13) a non-aromatic heterocyclylcarbonyl group (e.g., tetrahydrofurylcarbonyl, pyrrolidinocarbonyl) optionally substituted by 1 to 3 substituents selected from a $C_{1-6}$ alkyl group optionally substituted by 1 to 3 halogen atoms; and the like.

The "2-oxopyrrolidine ring" of the "optionally further substituted 2-oxopyrrolidine ring" for ring $A^1$ optionally has 1 to 3 substituents at substitutable position(s). Examples of the substituent include substituents selected from the abovementioned Substituent Group B. When the number of the substituents is plural, the respective substituents may be the same or different.

Ring $A^1$ is preferably an 2-oxopyrrolidine ring optionally further substituted by 1 to 3 substituents selected from
(1) a cyano group,
(2) a carbamoyl group, and
(3) a $C_{1-6}$ alkyl group (e.g., methyl, ethyl, propyl, isopropyl) optionally substituted by 1 to 3 substituents selected from
  (i) a carboxy group,
  (ii) a cyano group,
  (iii) a halogen atom (e.g., a fluorine atom),
  (iv) a $C_{1-6}$ alkoxy group (e.g., methoxy), and
  (v) a $C_{3-6}$ cycloalkyl group (e.g., cyclopropyl).
$R^4$ and $R^5$ are preferably both hydrogen atoms.

In another embodiment, ring $A^1$ is preferably an 2-oxopyrrolidine ring optionally further substituted by 1 to 3 substituents selected from
(1) a cyano group,
(2) a carbamoyl group,
(3) a $C_{1-6}$ alkyl group (e.g., methyl, ethyl, propyl, isopropyl) optionally substituted by 1 to 3 substituents selected from
  (I) a carboxy group,
  (II) a cyano group,
  (III) a halogen atom (e.g., a fluorine atom),
  (IV) a $C_{1-6}$ alkoxy group (e.g., methoxy),
  (V) a $C_{3-6}$ cycloalkyl group (e.g., cyclopropyl),
  (VI) an amino group optionally mono- or di-substituted by substituent(s) selected from
    (i) a $C_{1-6}$ alkyl-carbonyl group (e.g., acetyl), and
    (ii) a $C_{1-6}$ alkoxy-carbonyl group (e.g., tert-butoxycarbonyl), and
  (VII) a hydroxy group,
(4) a $C_{3-6}$ cycloalkyl group (e.g., cyclopropyl, cyclobutyl),
(5) a 3- to 8-membered monocyclic non-aromatic heterocyclic group (e.g., oxetanyl, azetidinyl) optionally substituted by 1 to 3 $C_{1-6}$ alkoxy-carbonyl groups (e.g., tert-butoxycarbonyl), and
(6) a $C_{1-6}$ alkoxy-carbonyl group (e.g., ethoxycarbonyl), and
(7) a 5- or 6-membered monocyclic aromatic heterocyclic group optionally substituted by 1 to 3 $C_{1-6}$ alkyl groups.

$R^4$ is preferably a hydrogen atom or a $C_{1-6}$ alkyl group (e.g., methyl, ethyl), and $R^5$ is a hydrogen atom.

The "2-oxopiperidino group" of the "optionally substituted 2-oxopiperidino group" for $R^1$ optionally has 1 to 3 substituents at substitutable position(s). Examples of the substituent include substituents selected from the above-mentioned Substituent Group B. When the number of the substituents is plural, the respective substituents may be the same or different.

$R^1$ is preferably
a group represented by the following formula:

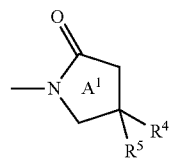

wherein
ring $A^1$ is an optionally further substituted 2-oxopyrrolidine ring; and
$R^4$ and $R^5$ are both hydrogen atoms, or
an optionally substituted 2-oxopiperidino group.

Specifically, $R^1$ is preferably
(A) a group represented by the following formula:

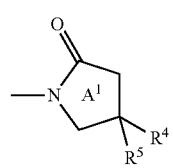

wherein
ring $A^1$ is an 2-oxopyrrolidine ring optionally further substituted by 1 to 3 substituents selected from
  (1) a cyano group,
  (2) a carbamoyl group, and
  (3) a $C_{1-6}$ alkyl group (e.g., methyl, ethyl, propyl, isopropyl) optionally substituted by 1 to 3 substituents selected from
    (i) a carboxy group,
    (ii) a cyano group,
    (iii) a halogen atom (e.g., a fluorine atom),
    (iv) a $C_{1-6}$ alkoxy group (e.g., methoxy), and
    (v) a $C_{3-6}$ cycloalkyl group (e.g., cyclopropyl); and
$R^4$ and $R^5$ are both hydrogen atoms; or
(B) a 2-oxopiperidino group optionally substituted by 1 to 3 $C_{1-6}$ alkyl groups (e.g., methyl).

In another embodiment, $R^1$ is preferably a group represented by the following formula:

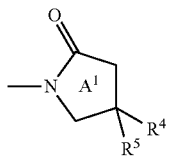

wherein
ring $A^1$ is an optionally further substituted 2-oxopyrrolidine ring;
$R^4$ is a hydrogen atom or a $C_{1-6}$ alkyl group (e.g., methyl, ethyl); and
$R^5$ is a hydrogen atom, or
an optionally substituted 2-oxopiperidino group,
more preferably a group represented by the following formula:

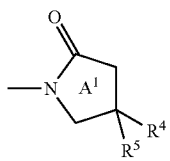

wherein
ring $A^1$ is an optionally further substituted 2-oxopyrrolidine ring;
$R^4$ is a hydrogen atom or a $C_{1-6}$ alkyl group (e.g., methyl, ethyl); and
$R^5$ is a hydrogen atom.

Specifically, $R^1$ is preferably
(A) a group represented by the following formula:

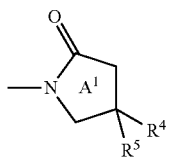

wherein
ring $A^1$ is an 2-oxopyrrolidine ring optionally further substituted by 1 to 3 substituents selected from
(1) a cyano group,
(2) a carbamoyl group,
(3) a $C_{1-6}$ alkyl group (e.g., methyl, ethyl, propyl, isopropyl) optionally substituted by 1 to 3 substituents selected from
  (I) a carboxy group,
  (II) a cyano group,
  (III) a halogen atom (e.g., a fluorine atom),
  (IV) a $C_{1-6}$ alkoxy group (e.g., methoxy),
  (V) a $C_{3-6}$ cycloalkyl group (e.g., cyclopropyl),
  (VI) an amino group optionally mono- or di-substituted by substituent(s) selected from
    (i) a $C_{1-6}$ alkyl-carbonyl group (e.g., acetyl), and
    (ii) a $C_{1-6}$ alkoxy-carbonyl group (e.g., tert-butoxycarbonyl), and
  (VII) a hydroxy group,
(4) a $C_{3-6}$ cycloalkyl group (e.g., cyclopropyl, cyclobutyl),
(5) a 3- to 8-membered monocyclic non-aromatic heterocyclic group (e.g., oxetanyl, azetidinyl) optionally substituted by 1 to 3 $C_{1-6}$ alkoxy-carbonyl groups (e.g., tert-butoxycarbonyl),
(6) a $C_{1-6}$ alkoxy-carbonyl group (e.g., ethoxycarbonyl), and
(7) a 5- or 6-membered monocyclic aromatic heterocyclic group optionally substituted by 1 to 3 $C_{1-6}$ alkyl groups;
$R^4$ is a hydrogen atom or a $C_{1-6}$ alkyl group (e.g., methyl, ethyl); and
$R^5$ is a hydrogen atom; or
(B) a 2-oxopiperidino group optionally substituted by 1 to 3 $C_{1-6}$ alkyl groups (e.g., methyl).

$R^1$ is more preferably
(A) a group represented by the following formula:

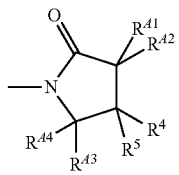

wherein
$R^{A1}$ and $R^{A2}$ are the same or different and each is
(1) a cyano group,
(2) a carbamoyl group,
(3) a $C_{1-6}$ alkyl group (e.g., methyl, ethyl, propyl, isopropyl) optionally substituted by 1 to 3 substituents selected from
  (I) a carboxy group,
  (II) a cyano group,
  (III) a halogen atom (e.g., a fluorine atom),
  (IV) a $C_{1-6}$ alkoxy group (e.g., methoxy),
  (V) a $C_{3-6}$ cycloalkyl group (e.g., cyclopropyl),
  (VI) an amino group optionally mono- or di-substituted by substituent(s) selected from
    (i) a $C_{1-6}$ alkyl-carbonyl group (e.g., acetyl), and
    (ii) a $C_{1-6}$ alkoxy-carbonyl group (e.g., tert-butoxycarbonyl), and
  (VII) a hydroxy group,
(4) a $C_{3-6}$ cycloalkyl group (e.g., cyclopropyl, cyclobutyl),
(5) a 3- to 8-membered monocyclic non-aromatic heterocyclic group (e.g., oxetanyl, azetidinyl) optionally substituted by 1 to 3 $C_{1-6}$ alkoxy-carbonyl groups (e.g., tert-butoxycarbonyl), or
(6) a $C_{1-6}$ alkoxy-carbonyl group (e.g., ethoxycarbonyl);
$R^{A3}$ is a hydrogen atom or a $C_{1-3}$ alkyl group (e.g., methyl, ethyl);
$R^{A4}$ is a hydrogen atom;
$R^4$ is a hydrogen atom or a $C_{1-3}$ alkyl group (e.g., methyl, ethyl); and
$R^5$ is a hydrogen atom; or
(B) an 2-oxopiperidino group optionally substituted by 1 to 3 $C_{1-6}$ alkyl groups.

$R^1$ is still more preferably a group represented by the following formula:

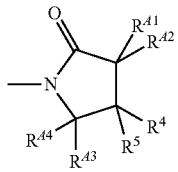

wherein
$R^{A1}$ and $R^{A2}$ are the same or different and each is
(1) a cyano group,
(2) a carbamoyl group,
(3) a $C_{1-6}$ alkyl group (e.g., methyl, ethyl, propyl, isopropyl) optionally substituted by 1 to 3 substituents selected from
  (I) a carboxy group,
  (II) a cyano group,
  (III) a halogen atom (e.g., a fluorine atom),
  (IV) a $C_{1-6}$ alkoxy group (e.g., methoxy),
  (V) a $C_{3-6}$ cycloalkyl group (e.g., cyclopropyl),
  (VI) an amino group optionally mono- or di-substituted by substituent(s) selected from
    (i) a $C_{1-6}$ alkyl-carbonyl group (e.g., acetyl), and
    (ii) a $C_{1-6}$ alkoxy-carbonyl group (e.g., tert-butoxycarbonyl), and
  (VII) a hydroxy group,
(4) a $C_{3-6}$ cycloalkyl group (e.g., cyclopropyl, cyclobutyl),
(5) a 3- to 8-membered monocyclic non-aromatic heterocyclic group (e.g., oxetanyl, azetidinyl) optionally substituted by 1 to 3 $C_{1-6}$ alkoxy-carbonyl groups (e.g., tert-butoxycarbonyl), or
(6) a $C_{1-6}$ alkoxy-carbonyl group (e.g., ethoxycarbonyl);
$R^{A3}$ is a hydrogen atom or a $C_{1-3}$ alkyl group (e.g., methyl, ethyl);
$R^{A4}$ is a hydrogen atom;
$R^4$ is a hydrogen atom or a $C_{1-3}$ alkyl group (e.g., methyl, ethyl); and
$R^5$ is a hydrogen atom.

$R^1$ is particularly preferably a group represented by the following formula:

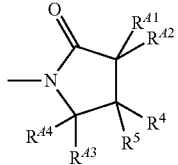

wherein
$R^{A1}$ is
(1) a cyano group,
(2) a $C_{1-6}$ alkyl group (e.g., methyl, ethyl) optionally substituted by 1 to 3 substituents selected from
  (I) an amino group optionally mono- or di-substituted by substituent(s) selected from
    (i) a $C_{1-6}$ alkyl-carbonyl group (e.g., acetyl), and
    (ii) a $C_{1-6}$ alkoxy-carbonyl group (e.g., tert-butoxycarbonyl),
  (II) a hydroxy group, and
  (III) a cyano group, or
(3) a $C_{1-6}$ alkoxy-carbonyl group (e.g., ethoxycarbonyl);

$R^{A2}$ is
(1) a $C_{3-6}$ cycloalkyl group (e.g., cyclopropyl, cyclobutyl),
(2) a $C_{1-6}$ alkyl group (e.g., methyl, ethyl, propyl, isopropyl) optionally substituted by 1 to 3 substituents selected from
  (I) a carboxy group,
  (II) a cyano group,
  (III) a halogen atom (e.g., a fluorine atom),
  (IV) a $C_{1-6}$ alkoxy group (e.g., methoxy),
  (V) a $C_{3-6}$ cycloalkyl group (e.g., cyclopropyl), and
  (VI) a hydroxy group,
(3) a carbamoyl group, or
(4) a 3- to 8-membered monocyclic non-aromatic heterocyclic group (e.g., oxetanyl, azetidinyl) optionally substituted by 1 to 3 $C_{1-6}$ alkoxy-carbonyl groups (e.g., tert-butoxycarbonyl);
$R^{A3}$ is a hydrogen atom or a $C_{1-3}$ alkyl group (e.g., methyl, ethyl);
$R^{A4}$ is a hydrogen atom;
$R^4$ is a hydrogen atom or a $C_{1-3}$ alkyl group (e.g., methyl, ethyl); and
$R^5$ is a hydrogen atom.

In the formula (I), $R^2$ is a hydrogen atom, an optionally substituted $C_{1-6}$ alkyl group, an optionally substituted aromatic ring group, or an acyl group.

The "$C_{1-6}$ alkyl group" of the "optionally substituted $C_{1-6}$ alkyl group" for $R^2$ optionally has 1 to 5 (preferably 1 to 3) substituents at substitutable position(s). Examples of the substituent include substituents selected from the above-mentioned Substituent Group A. When the number of the substituents is plural, the respective substituents may be the same or different.

The "aromatic ring group" of the "optionally substituted aromatic ring group" for $R^2$ is preferably a $C_{6-14}$ aryl group (preferably phenyl) or a 5- or 6-membered monocyclic aromatic heterocyclic group (preferably pyrazolyl, pyridyl, pyrimidinyl, more preferably pyrazolyl).

The "aromatic ring group" of the "optionally substituted aromatic ring group" for $R^2$ optionally have 1 to 5 (preferably 1 to 3) substituents at substitutable position(s). Examples of the substituent include substituents selected from the abovementioned Substituent Group B. When the number of the substituents is plural, the respective substituents may be the same or different.

Examples of the "acyl group" for $R^2$ include those similar to the "acyl group" for $R^4$ or $R^5$.

$R^2$ is preferably an optionally substituted $C_{1-6}$ alkyl group, an optionally substituted aromatic ring group, or an acyl group.

Specifically, $R^2$ is preferably
(1) an aromatic ring group (preferably a $C_{6-14}$ aryl group (preferably phenyl) or a 5- or 6-membered monocyclic aromatic heterocyclic group (preferably pyrazolyl, pyridyl, pyrimidinyl, more preferably pyrazolyl)) optionally substituted by 1 to 5 (preferably 1 to 3) substituents selected from
  (a) a cyano group,
  (b) a carboxy group,
  (c) a halogen atom (e.g., a chlorine atom),
  (d) a $C_{1-6}$ alkyl group (e.g., methyl) optionally substituted by 1 to 3 substituents selected from
    (i) a hydroxy group,
    (ii) a cyano group,
    (iii) a carboxy group,
    (iv) a carbamoyl group optionally mono- or di-substituted by $C_{1-6}$ alkyl group(s) (e.g., methyl),
    (v) an amino group optionally mono- or di-substituted by $C_{1-6}$ alkyl-carbonyl group(s) (e.g., acetyl), (vi) a $C_{1-6}$ alkoxy-carbonyl group (e.g., ethoxycarbonyl, butoxycarbonyl),
(vii) a $C_{6-14}$ aryl group (e.g., phenyl) optionally substituted by 1 to 3 $C_{1-6}$ alkoxy groups (e.g., methoxy), and
(viii) a 3- to 8-membered monocyclic non-aromatic heterocyclic group (e.g., morpholinyl),
(e) a $C_{1-6}$ alkyl-carbonyl group (e.g., acetyl),
(f) a $C_{1-6}$ alkylsulfonyl group (e.g., methylsulfonyl),
(g) an amino group optionally mono- or di-substituted by substituent(s) selected from
(i) a $C_{1-6}$ alkyl group (e.g., methyl), and
(ii) a $C_{1-6}$ alkyl-carbonyl group (e.g., acetyl),
(h) a carbamoyl group optionally mono- or di-substituted by $C_{1-6}$ alkyl group(s) (e.g., methyl, ethyl),
(i) a sulfamoyl group, and
(j) a 3- to 8-membered monocyclic non-aromatic heterocyclic group (e.g., morpholinyl, tetrahydropyranyl, piperidyl, piperazinyl, 1,1-dioxidothiomorpholinyl, dihydrooxadiazolyl) optionally substituted by 1 to 3 substituents selected from
(i) a $C_{1-6}$ alkyl group (e.g., methyl),
(ii) a $C_{1-6}$ alkyl-carbonyl group (e.g., acetyl), and
(iii) an oxo group, or
(2) a $C_{1-6}$ alkyl group (e.g., methyl, ethyl) optionally substituted by 1 to 5 (preferably 1 to 3) substituents selected from
(a) a $C_{6-14}$ aryl group (e.g., phenyl, naphthyl) optionally substituted by 1 to 3 substituents selected from
(i) a cyano group,
(ii) a $C_{1-6}$ alkyl group (e.g., methyl) optionally substituted by 1 to 3 of 3- to 8-membered monocyclic non-aromatic heterocyclic groups (e.g., morpholinyl),
(iii) a $C_{1-6}$ alkoxy group (e.g., methoxy),
(iv) a halogen atom (e.g., a fluorine atom), and
(v) a 3- to 8-membered monocyclic non-aromatic heterocyclic group (e.g., piperazinyl) optionally substituted by 1 to 3 $C_{1-6}$ alkyl groups (e.g., methyl),
(b) a 5- or 6-membered monocyclic aromatic heterocyclic group (e.g., pyridyl, furyl, thienyl),
(c) a 8- to 12-membered fused aromatic heterocyclic group (e.g., benzofuranyl), and
(d) a $C_{3-6}$ cycloalkyl group (e.g., cyclopropyl).

In another embodiment, specifically, $R^2$ is preferably
(1) a 5- or 6-membered monocyclic aromatic heterocyclic group (preferably pyrazolyl, pyridyl, pyrimidinyl, thiazolyl, imidazolyl, thienyl, more preferably pyrazolyl), a $C_{6-14}$ aryl group (preferably phenyl) or a 8- to 12-membered fused aromatic heterocyclic group (preferably indazolyl, benzothiazolyl, indolyl), each of which is optionally substituted by 1 to 3 substituents selected from
(a) a cyano group,
(b) a carboxy group,
(c) a halogen atom (e.g., a chlorine atom, a fluorine atom),
(d) a $C_{1-6}$ alkyl group (e.g., methyl, ethyl, isopropyl, tert-butyl, isobutyl) optionally substituted by 1 to 3 substituents selected from
(I) a hydroxy group,
(II) a cyano group,
(III) a carboxy group,
(IV) a carbamoyl group optionally mono- or di-substituted by $C_{1-6}$ alkyl group(s) (e.g., methyl, ethyl, tert-butyl) optionally substituted by 1 to 3 substituents selected from
(i) a $C_{1-6}$ alkoxy group (e.g., methoxy),
(ii) a hydroxy group,
(iii) a halogen atom (e.g., a fluorine atom), and
(iv) a $C_{1-6}$ alkylsulfonyl group (e.g., methylsulfonyl),
(V) an amino group optionally mono- or di-substituted by substituent(s) selected from
(i) a $C_{1-6}$ alkyl-carbonyl group (e.g., acetyl) optionally substituted by 1 to 3 substituents selected from
(A) a $C_{1-6}$ alkoxy group (e.g., methoxy), and
(B) a hydroxy group,
(ii) a $C_{1-6}$ alkylsulfonyl group (e.g., methylsulfonyl),
(iii) a sulfamoyl group optionally mono- or di-substituted by $C_{1-6}$ alkyl group(s) (e.g., methyl), and
(iv) a $C_{1-6}$ alkyl group (e.g., methyl),
(VI) a $C_{1-6}$ alkoxy-carbonyl group (e.g., ethoxycarbonyl, butoxycarbonyl),
(VII) a $C_{6-14}$ aryl group (e.g., phenyl) optionally substituted by 1 to 3 $C_{1-6}$ alkoxy groups (e.g., methoxy),
(VIII) a 3- to 8-membered monocyclic non-aromatic heterocyclic group (e.g., morpholinyl),
(IX) a 3- to 8-membered monocyclic non-aromatic heterocyclylcarbonyl group (e.g., morpholinylcarbonyl, pyrrolidinylcarbonyl, piperidylcarbonyl, piperazinylcarbonyl) optionally substituted by 1 to 3 substituents selected from
(i) a hydroxy group,
(ii) a carbamoyl group, and
(iii) a $C_{1-6}$ alkyl group (e.g., methyl),
(X) a halogen atom (e.g., a fluorine atom), and
(XI) a $C_{1-6}$ alkylsulfonyl group (e.g., methylsulfonyl),
(e) a $C_{1-6}$ alkyl-carbonyl group (e.g., acetyl),
(f) a $C_{1-6}$ alkylsulfonyl group (e.g., methylsulfonyl),
(g) an amino group optionally mono- or di-substituted by substituent(s) selected from
(I) a $C_{1-6}$ alkyl group (e.g., methyl),
(II) a $C_{1-6}$ alkyl-carbonyl group (e.g., acetyl) optionally substituted by 1 to 3 $C_{1-6}$ alkoxy groups (e.g., methoxy), and
(III) a $C_{1-6}$ alkylsulfonyl group (e.g., methylsulfonyl),
(h) a carbamoyl group optionally mono- or di-substituted by substituent(s) selected from
(I) a $C_{1-6}$ alkyl group (e.g., methyl, ethyl, tert-butyl) optionally substituted by 1 to 3 substituents selected from
(i) a hydroxy group,
(ii) a 3- to 8-membered monocyclic non-aromatic heterocyclic group (e.g., oxetanyl, morpholinyl) optionally substituted by 1 to 3 $C_{1-6}$ alkyl groups (e.g., methyl), and
(iii) a $C_{1-6}$ alkylsulfonyl group (e.g., methylsulfonyl),
(II) a $C_{3-6}$ cycloalkyl group (e.g., cyclopropyl, cyclobutyl, cyclohexyl) optionally substituted by 1 to 3 substituents selected from
(i) a cyano group, and
(ii) a hydroxy group, and
(III) a 3- to 8-membered monocyclic non-aromatic heterocyclic group (e.g., oxetanyl, tetrahydropyranyl),
(i) a sulfamoyl group optionally mono- or di-substituted by $C_{1-6}$ alkyl group(s) (e.g., methyl),
(j) a 3- to 8-membered monocyclic non-aromatic heterocyclic group (e.g., morpholinyl, tetrahydropyranyl, piperidyl, piperazinyl, 1,1-dioxidothiomorpholinyl, dihydrooxadiazolyl, azetidinyl, imidazolidinyl, oxetanyl, pyrrolidinyl, 1,1-dioxidetetrahydrothiopyranyl) optionally substituted by 1 to 3 substituents selected from
(I) a $C_{1-6}$ alkyl group (e.g., methyl) optionally substituted by 1 to 3 hydroxy groups,
(II) a $C_{1-6}$ alkyl-carbonyl group (e.g., acetyl) optionally substituted by 1 to 3 substituents selected from
(i) a $C_{1-6}$ alkoxy group (e.g., methoxy), and
(ii) a cyano group, (III) a $C_{1-6}$ alkoxy-carbonyl group (e.g., tert-butoxycarbonyl),
(IV) an oxo group,
(V) a $C_{1-6}$ alkylsulfonyl group (e.g., methylsulfonyl),
(VI) a carbamoyl group optionally mono- or di-substituted by $C_{1-6}$ alkyl group(s) (e.g., methyl),
(VII) a cyano group,
(VIII) a hydroxy group, and
(IX) a carboxy group,
(k) a $C_{3-6}$ cycloalkyl group (e.g., cyclopropyl, cyclobutyl, cyclopentyl, cyclohexyl) optionally substituted by 1 to 3 substituents selected from
  (I) a carbamoyl group optionally mono- or di-substituted by $C_{1-6}$ alkyl group(s) (e.g., methyl),
  (II) a carboxy group, and
  (III) a $C_{1-6}$ alkyl group (e.g., methyl) optionally substituted by 1 to 3 hydroxy groups,
(l) a $C_{1-6}$ alkoxy group (e.g., methoxy, ethoxy, isopropoxy, isobutoxy) optionally substituted by 1 to 3 substituents selected from
  (I) a halogen atom (e.g., a fluorine atom),
  (II) a $C_{1-6}$ alkoxy group (e.g., methoxy), and
  (III) a $C_{3-6}$ cycloalkyl group (e.g., cyclopropyl),
(m) a $C_{1-6}$ alkoxy-carbonyl group (e.g., tert-butoxycarbonyl),
(n) a 3- to 8-membered monocyclic non-aromatic heterocyclylcarbonyl group (e.g., pyrrolidinylcarbonyl, morpholinylcarbonyl, piperidylcarbonyl, azetidinylcarbonyl, 2-oxa-6-azaspiro[3.3]heptylcarbonyl, 1,1-dioxidothiomorpholinylcarbonyl) optionally substituted by 1 to 3 substituents selected from
  (I) a hydroxy group,
  (II) an oxo group,
  (III) a halogen atom (e.g., a fluorine atom),
  (IV) a $C_{1-6}$ alkoxy group (e.g., methoxy), and
  (V) a $C_{1-6}$ alkyl group (e.g., methyl),
(o) a $C_{1-6}$ alkylsulfanyl group (e.g., methylsulfanyl), and
(p) a 5- or 6-membered monocyclic aromatic heterocyclic group (e.g., tetrazolyl), or
(2) a $C_{1-6}$ alkyl group (e.g., methyl, ethyl) optionally substituted by 1 to 5 (preferably 1 to 3) substituents selected from
  (a) a $C_{6-14}$ aryl group (e.g., phenyl, naphthyl) optionally substituted by 1 to 3 substituents selected from
    (I) a cyano group,
    (II) a $C_{1-6}$ alkyl group (e.g., methyl) optionally substituted by 1 to 3 of 3- to 8-membered monocyclic non-aromatic heterocyclic groups (e.g., morpholinyl),
    (III) a $C_{1-6}$ alkoxy group (e.g., methoxy),
    (IV) a halogen atom (e.g., a fluorine atom), and
    (V) a 3- to 8-membered monocyclic non-aromatic heterocyclic group (e.g., piperazinyl) optionally substituted by 1 to 3 $C_{1-6}$ alkyl groups (e.g., methyl),
  (b) a 5- or 6-membered monocyclic aromatic heterocyclic group (e.g., pyridyl, furyl, thienyl) optionally substituted by 1 to 3 substituents selected from
    (I) a cyano group,
    (II) a $C_{1-6}$ alkyl group (e.g., methyl) optionally substituted by 1 to 3 of 3- to 8-membered monocyclic non-aromatic heterocyclic groups (e.g., morpholinyl),
    (III) a $C_{1-6}$ alkoxy group (e.g., methoxy),
    (IV) a halogen atom (e.g., a fluorine atom), and
    (V) a 3- to 8-membered monocyclic non-aromatic heterocyclic group (e.g., piperazinyl) optionally substituted by 1 to 3 $C_{1-6}$ alkyl groups (e.g., methyl),
  (c) a 8- to 12-membered fused aromatic heterocyclic group (e.g., benzofuranyl) optionally substituted by 1 to 3 substituents selected from
    (I) a cyano group,
    (II) a $C_{1-6}$ alkyl group (e.g., methyl) optionally substituted by 1 to 3 of 3- to 8-membered monocyclic non-aromatic heterocyclic groups (e.g., morpholinyl),
    (III) a $C_{1-6}$ alkoxy group (e.g., methoxy),
    (IV) a halogen atom (e.g., a fluorine atom), and
    (V) a 3- to 8-membered monocyclic non-aromatic heterocyclic group (e.g., piperazinyl) optionally substituted by 1 to 3 $C_{1-6}$ alkyl groups (e.g., methyl), and
(d) a $C_{3-6}$ cycloalkyl group (e.g., cyclopropyl).

$R^2$ is more preferably
(1) a 5- or 6-membered monocyclic aromatic heterocyclic group
(preferably pyrazolyl, pyridyl, pyrimidinyl, thiazolyl, imidazolyl, thienyl, more preferably pyrazolyl), a $C_{6-14}$ aryl group (preferably phenyl) or a 8- to 12-membered fused aromatic heterocyclic group (preferably indazolyl, benzothiazolyl, indolyl), each of which is optionally substituted by 1 to 3 substituents selected from
  (a) a cyano group,
  (b) a carboxy group,
  (c) a halogen atom (e.g., a chlorine atom, a fluorine atom),
  (d) a $C_{1-6}$ alkyl group (e.g., methyl, ethyl, isopropyl, tert-butyl, isobutyl) optionally substituted by 1 to 3 substituents selected from
    (I) a hydroxy group,
    (II) a cyano group,
    (III) a carboxy group,
    (IV) a carbamoyl group optionally mono- or di-substituted by $C_{1-6}$ alkyl group(s) (e.g., methyl, ethyl, tert-butyl) optionally substituted by 1 to 3 substituents selected from
      (i) a $C_{1-6}$ alkoxy group (e.g., methoxy),
      (ii) a hydroxy group,
      (iii) a halogen atom (e.g., a fluorine atom), and
      (iv) a $C_{1-6}$ alkylsulfonyl group (e.g., methylsulfonyl),
    (V) an amino group optionally mono- or di-substituted by substituent(s) selected from
      (i) a $C_{1-6}$ alkyl-carbonyl group (e.g., acetyl) optionally substituted by 1 to 3 substituents selected from
        (A) a $C_{1-6}$ alkoxy group (e.g., methoxy), and
        (B) a hydroxy group,
      (ii) a $C_{1-6}$ alkylsulfonyl group (e.g., methylsulfonyl),
      (iii) a sulfamoyl group optionally mono- or di-substituted by $C_{1-6}$ alkyl group(s) (e.g., methyl), and
      (iv) a $C_{1-6}$ alkyl group (e.g., methyl),
    (VI) a $C_{1-6}$ alkoxy-carbonyl group (e.g., ethoxycarbonyl, butoxycarbonyl),
    (VII) a $C_{6-14}$ aryl group (e.g., phenyl) optionally substituted by 1 to 3 $C_{1-6}$ alkoxy groups (e.g., methoxy),
    (VIII) a 3- to 8-membered monocyclic non-aromatic heterocyclic group (e.g., morpholinyl),
    (IX) a 3- to 8-membered monocyclic non-aromatic heterocyclylcarbonyl group (e.g., morpholinylcarbonyl, pyrrolidinylcarbonyl, piperidylcarbonyl, piperazinylcarbonyl) optionally substituted by 1 to 3 substituents selected from
      (i) a hydroxy group,
      (ii) a carbamoyl group, and
      (iii) a $C_{1-6}$ alkyl group (e.g., methyl),
    (X) a halogen atom (e.g., a fluorine atom), and
    (XI) a $C_{1-6}$ alkylsulfonyl group (e.g., methylsulfonyl),
  (e) a $C_{1-6}$ alkyl-carbonyl group (e.g., acetyl),
  (f) a $C_{1-6}$ alkylsulfonyl group (e.g., methylsulfonyl),
  (g) an amino group optionally mono- or di-substituted by substituent(s) selected from (I) a $C_{1-6}$ alkyl group (e.g., methyl),
(II) a $C_{1-6}$ alkyl-carbonyl group (e.g., acetyl) optionally substituted by 1 to 3 $C_{1-6}$ alkoxy groups (e.g., methoxy), and
(III) a $C_{1-6}$ alkylsulfonyl group (e.g., methylsulfonyl),
(h) a carbamoyl group optionally mono- or di-substituted by substituent(s) selected from
  (I) a $C_{1-6}$ alkyl group (e.g., methyl, ethyl, tert-butyl) optionally substituted by 1 to 3 substituents selected from
    (i) a hydroxy group,
    (ii) a 3- to 8-membered monocyclic non-aromatic heterocyclic group (e.g., oxetanyl, morpholinyl) optionally substituted by 1 to 3 $C_{1-6}$ alkyl groups (e.g., methyl), and
    (iii) a $C_{1-6}$ alkylsulfonyl group (e.g., methylsulfonyl),
  (II) a $C_{3-6}$ cycloalkyl group (e.g., cyclopropyl, cyclobutyl, cyclohexyl) optionally substituted by 1 to 3 substituents selected from
    (i) a cyano group, and
    (ii) a hydroxy group, and
  (III) a 3- to 8-membered monocyclic non-aromatic heterocyclic group (e.g., oxetanyl, tetrahydropyranyl),
(i) a sulfamoyl group optionally mono- or di-substituted by $C_{1-6}$ alkyl group(s) (e.g., methyl),
(j) a 3- to 8-membered monocyclic non-aromatic heterocyclic group (e.g., morpholinyl, tetrahydropyranyl, piperidyl, piperazinyl, 1,1-dioxidothiomorpholinyl, dihydrooxadiazolyl, azetidinyl, imidazolidinyl, oxetanyl, pyrrolidinyl, 1,1-dioxidetetrahydrothiopyranyl) optionally substituted by 1 to 3 substituents selected from
  (I) a $C_{1-6}$ alkyl group (e.g., methyl) optionally substituted by 1 to 3 hydroxy groups,
  (II) a $C_{1-6}$ alkyl-carbonyl group (e.g., acetyl) optionally substituted by 1 to 3 substituents selected from
    (i) a $C_{1-6}$ alkoxy group (e.g., methoxy), and
    (ii) a cyano group,
  (III) a $C_{1-6}$ alkoxy-carbonyl group (e.g., tert-butoxycarbonyl),
  (IV) an oxo group,
  (V) a $C_{1-6}$ alkylsulfonyl group (e.g., methylsulfonyl),
  (VI) a carbamoyl group optionally mono- or di-substituted by $C_{1-6}$ alkyl group(s) (e.g., methyl),
  (VII) a cyano group,
  (VIII) a hydroxy group, and
  (IX) a carboxy group,
(k) a $C_{3-6}$ cycloalkyl group (e.g., cyclopropyl, cyclobutyl, cyclopentyl, cyclohexyl) optionally substituted by 1 to 3 substituents selected from
  (I) a carbamoyl group optionally mono- or di-substituted by $C_{1-6}$ alkyl group(s) (e.g., methyl),
  (II) a carboxy group, and
  (III) a $C_{1-6}$ alkyl group (e.g., methyl) optionally substituted by 1 to 3 hydroxy groups,
(l) a $C_{1-6}$ alkoxy group (e.g., methoxy, ethoxy, isopropoxy, isobutoxy) optionally substituted by 1 to 3 substituents selected from
  (I) a halogen atom (e.g., a fluorine atom),
  (II) a $C_{1-6}$ alkoxy group (e.g., methoxy), and
  (III) a $C_{3-6}$ cycloalkyl group (e.g., cyclopropyl),
(m) a $C_{1-6}$ alkoxy-carbonyl group (e.g., tert-butoxycarbonyl),
(n) a 3- to 8-membered monocyclic non-aromatic heterocyclylcarbonyl group (e.g., pyrrolidinylcarbonyl, morpholinylcarbonyl, piperidylcarbonyl, azetidinylcarbonyl, 2-oxa-6-azaspiro[3.3]heptylcarbonyl, 1,1-dioxidothiomorpholinylcarbonyl) optionally substituted by 1 to 3 substituents selected from
  (I) a hydroxy group,
  (II) an oxo group,
  (III) a halogen atom (e.g., a fluorine atom),
  (IV) a $C_{1-6}$ alkoxy group (e.g., methoxy), and
  (V) a $C_{1-6}$ alkyl group (e.g., methyl),
(o) a $C_{1-6}$ alkylsulfanyl group (e.g., methylsulfanyl), and
(p) a 5- or 6-membered monocyclic aromatic heterocyclic group (e.g., tetrazolyl), or
(2) a $C_{1-6}$ alkyl group (e.g., methyl, ethyl) optionally substituted by 1 to 5 (preferably 1 to 3) substituents selected from
  (a) a $C_{6-14}$ aryl group (e.g., phenyl, naphthyl) optionally substituted by 1 to 3 substituents selected from
    (I) a cyano group,
    (II) a $C_{1-6}$ alkyl group (e.g., methyl) optionally substituted by 1 to 3 of 3- to 8-membered monocyclic non-aromatic heterocyclic groups (e.g., morpholinyl),
    (III) a $C_{1-6}$ alkoxy group (e.g., methoxy),
    (IV) a halogen atom (e.g., a fluorine atom), and
    (V) a 3- to 8-membered monocyclic non-aromatic heterocyclic group (e.g., piperazinyl) optionally substituted by 1 to 3 $C_{1-6}$ alkyl groups (e.g., methyl),
  (b) a 5- or 6-membered monocyclic aromatic heterocyclic group (e.g., pyridyl, furyl, thienyl),
  (c) a 8- to 12-membered fused aromatic heterocyclic group (e.g., benzofuranyl), and
  (d) a $C_{3-6}$ cycloalkyl group (e.g., cyclopropyl).
$R^2$ is still more preferably
(1) a 5- or 6-membered monocyclic aromatic heterocyclic group
(preferably pyrazolyl, pyridyl, pyrimidinyl, thiazolyl, imidazolyl, thienyl, more preferably pyrazolyl), a $C_{6-14}$ aryl group (preferably phenyl) or a 8- to 12-membered fused aromatic heterocyclic group (preferably indazolyl, benzothiazolyl, indolyl), each of which is optionally substituted by 1 to 3 substituents selected from
  (a) a cyano group,
  (b) a carboxy group,
  (c) a halogen atom (e.g., a chlorine atom, a fluorine atom),
  (d) a $C_{1-6}$ alkyl group (e.g., methyl, ethyl, isopropyl, tert-butyl, isobutyl) optionally substituted by 1 to 3 substituents selected from
    (I) a hydroxy group,
    (II) a cyano group,
    (III) a carboxy group,
    (IV) a carbamoyl group optionally mono- or di-substituted by $C_{1-6}$ alkyl group(s) (e.g., methyl, ethyl, tert-butyl) optionally substituted by 1 to 3 substituents selected from
      (i) a $C_{1-6}$ alkoxy group (e.g., methoxy),
      (ii) a hydroxy group,
      (iii) a halogen atom (e.g., a fluorine atom), and
      (iv) a $C_{1-6}$ alkylsulfonyl group (e.g., methylsulfonyl),
    (V) an amino group optionally mono- or di-substituted by substituent(s) selected from
      (i) a $C_{1-6}$ alkyl-carbonyl group (e.g., acetyl) optionally substituted by 1 to 3 substituents selected from
        (A) a $C_{1-6}$ alkoxy group (e.g., methoxy), and
        (B) a hydroxy group,
      (ii) a $C_{1-6}$ alkylsulfonyl group (e.g., methylsulfonyl),
      (iii) a sulfamoyl group optionally mono- or di-substituted by $C_{1-6}$ alkyl group(s) (e.g., methyl), and
      (iv) a $C_{1-6}$ alkyl group (e.g., methyl), (VI) a $C_{1-6}$ alkoxy-carbonyl group (e.g., ethoxycarbonyl, butoxycarbonyl),
(VII) a $C_{6-14}$ aryl group (e.g., phenyl) optionally substituted by 1 to 3 $C_{1-6}$ alkoxy groups (e.g., methoxy),
(VIII) a 3- to 8-membered monocyclic non-aromatic heterocyclic group (e.g., morpholinyl),
(IX) a 3- to 8-membered monocyclic non-aromatic heterocyclylcarbonyl group (e.g., morpholinylcarbonyl, pyrrolidinylcarbonyl, piperidylcarbonyl, piperazinylcarbonyl) optionally substituted by 1 to 3 substituents selected from
  (i) a hydroxy group,
  (ii) a carbamoyl group, and
  (iii) a $C_{1-6}$ alkyl group (e.g., methyl),
(X) a halogen atom (e.g., a fluorine atom), and
(XI) a $C_{1-6}$ alkylsulfonyl group (e.g., methylsulfonyl),
(e) a $C_{1-6}$ alkyl-carbonyl group (e.g., acetyl),
(f) a $C_{1-6}$ alkylsulfonyl group (e.g., methylsulfonyl),
(g) an amino group optionally mono- or di-substituted by substituent(s) selected from
  (I) a $C_{1-6}$ alkyl group (e.g., methyl),
  (II) a $C_{1-6}$ alkyl-carbonyl group (e.g., acetyl) optionally substituted by 1 to 3 $C_{1-6}$ alkoxy groups (e.g., methoxy), and
  (III) a $C_{1-6}$ alkylsulfonyl group (e.g., methylsulfonyl),
(h) a carbamoyl group optionally mono- or di-substituted by substituent(s) selected from
  (I) a $C_{1-6}$ alkyl group (e.g., methyl, ethyl, tert-butyl) optionally substituted by 1 to 3 substituents selected from
    (i) a hydroxy group,
    (ii) a 3- to 8-membered monocyclic non-aromatic heterocyclic group (e.g., oxetanyl, morpholinyl) optionally substituted by 1 to 3 $C_{1-6}$ alkyl groups (e.g., methyl), and
    (iii) a $C_{1-6}$ alkylsulfonyl group (e.g., methylsulfonyl),
  (II) a $C_{3-6}$ cycloalkyl group (e.g., cyclopropyl, cyclobutyl, cyclohexyl) optionally substituted by 1 to 3 substituents selected from
    (i) a cyano group, and
    (ii) a hydroxy group, and
  (III) a 3- to 8-membered monocyclic non-aromatic heterocyclic group (e.g., oxetanyl, tetrahydropyranyl),
(i) a sulfamoyl group optionally mono- or di-substituted by $C_{1-6}$ alkyl group(s) (e.g., methyl),
(j) a 3- to 8-membered monocyclic non-aromatic heterocyclic group (e.g., morpholinyl, tetrahydropyranyl, piperidyl, piperazinyl, 1,1-dioxidothiomorpholinyl, dihydrooxadiazolyl, azetidinyl, imidazolidinyl, oxetanyl, pyrrolidinyl, 1,1-dioxidetetrahydrothiopyranyl) optionally substituted by 1 to 3 substituents selected from
  (I) a $C_{1-6}$ alkyl group (e.g., methyl) optionally substituted by 1 to 3 hydroxy groups,
  (II) a $C_{1-6}$ alkyl-carbonyl group (e.g., acetyl) optionally substituted by 1 to 3 substituents selected from
    (i) a $C_{1-6}$ alkoxy group (e.g., methoxy), and
    (ii) a cyano group,
  (III) a $C_{1-6}$ alkoxy-carbonyl group (e.g., tert-butoxycarbonyl),
  (IV) an oxo group,
  (V) a $C_{1-6}$ alkylsulfonyl group (e.g., methylsulfonyl),
  (VI) a carbamoyl group optionally mono- or di-substituted by $C_{1-6}$ alkyl group(s) (e.g., methyl),
  (VII) a cyano group,
  (VIII) a hydroxy group, and
  (IX) a carboxy group,
  (k) a $C_{3-6}$ cycloalkyl group (e.g., cyclopropyl, cyclobutyl, cyclopentyl, cyclohexyl) optionally substituted by 1 to 3 substituents selected from
    (I) a carbamoyl group optionally mono- or di-substituted by $C_{1-6}$ alkyl group(s) (e.g., methyl),
    (II) a carboxy group, and
    (III) a $C_{1-6}$ alkyl group (e.g., methyl) optionally substituted by 1 to 3 hydroxy groups,
  (l) a $C_{1-6}$ alkoxy group (e.g., methoxy, ethoxy, isopropoxy, isobutoxy) optionally substituted by 1 to 3 substituents selected from
    (I) a halogen atom (e.g., a fluorine atom),
    (II) a $C_{1-6}$ alkoxy group (e.g., methoxy), and
    (III) a $C_{3-6}$ cycloalkyl group (e.g., cyclopropyl),
  (m) a $C_{1-6}$ alkoxy-carbonyl group (e.g., tert-butoxycarbonyl),
  (n) a 3- to 8-membered monocyclic non-aromatic heterocyclylcarbonyl group (e.g., pyrrolidinylcarbonyl, morpholinylcarbonyl, piperidylcarbonyl, azetidinylcarbonyl, 2-oxa-6-azaspiro[3.3]heptylcarbonyl, 1,1-dioxidothiomorpholinylcarbonyl) optionally substituted by 1 to 3 substituents selected from
    (I) a hydroxy group,
    (II) an oxo group,
    (III) a halogen atom (e.g., a fluorine atom),
    (IV) a $C_{1-6}$ alkoxy group (e.g., methoxy), and
    (V) a $C_{1-6}$ alkyl group (e.g., methyl),
  (o) a $C_{1-6}$ alkylsulfanyl group (e.g., methylsulfanyl), and
  (p) a 5- or 6-membered monocyclic aromatic heterocyclic group (e.g., tetrazolyl).

In the formula (I), $R^3$ is a hydrogen atom, a halogen atom, a cyano group, or an optionally substituted $C_{1-6}$ alkyl group.

The "$C_{1-6}$ alkyl group" of the "optionally substituted $C_{1-6}$ alkyl group" for $R^3$ optionally has 1 to 5 (preferably 1 to 3) substituents at substitutable position(s). Examples of the substituent include substituents selected from the above-mentioned Substituent Group A. When the number of the substituents is plural, the respective substituents may be the same or different.

$R^3$ is preferably a hydrogen atom or a halogen atom (e.g., a fluorine atom), particularly preferably a hydrogen atom.

Preferable examples of compound (I) include the following compounds:
[Compound A-1]
Compound (I) wherein
$R^1$ is
a group represented by the

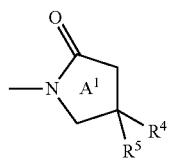

wherein
ring $A^1$ is an optionally further substituted 2-oxopyrrolidine ring; and
$R^4$ and $R^5$ are both hydrogen atoms, or
an optionally substituted 2-oxopiperidino group;
$R^2$ is an optionally substituted $C_{1-6}$ alkyl group, an optionally substituted aromatic ring group, or an acyl group; and
$R^3$ is a hydrogen atom or a halogen atom.

[Compound A-2]
Compound (I) wherein
R¹ is
a group represented by the following formula:

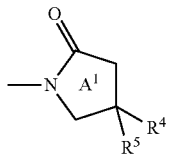

wherein
ring A¹ is an optionally further substituted 2-oxopyrrolidine ring;
R⁴ is a hydrogen atom or a $C_{1-6}$ alkyl group (e.g., methyl, ethyl); and
R⁵ is a hydrogen atom, or
an optionally substituted 2-oxopiperidino group;
R² is an optionally substituted $C_{1-6}$ alkyl group, an optionally substituted aromatic ring group, or an acyl group; and
R³ is a hydrogen atom or a halogen atom.
[Compound B-1]
Compound (I) wherein
R¹ is
(A) a group represented by the following formula:

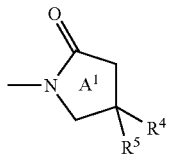

wherein
ring A¹ is an 2-oxopyrrolidine ring optionally further substituted by 1 to 3 substituents selected from
(1) a cyano group,
(2) a carbamoyl group, and
(3) a $C_{1-6}$ alkyl group (e.g., methyl, ethyl, propyl, isopropyl) optionally substituted by 1 to 3 substituents selected from
(i) a carboxy group,
(ii) a cyano group,
(iii) a halogen atom (e.g., a fluorine atom),
(iv) a $C_{1-6}$ alkoxy group (e.g., methoxy), and
(v) a $C_{3-6}$ cycloalkyl group (e.g., cyclopropyl); and
R⁴ and R⁵ are both hydrogen atoms; or
(B) a 2-oxopiperidino group optionally substituted by 1 to 3 $C_{1-6}$ alkyl groups (e.g., methyl);
R² is
(1) an aromatic ring group (preferably a $C_{6-14}$ aryl group (preferably phenyl) or a 5- or 6-membered monocyclic aromatic heterocyclic group (preferably pyrazolyl, pyridyl, pyrimidinyl, more preferably pyrazolyl)) optionally substituted by 1 to 5 (preferably 1 to 3) substituents selected from
(a) a cyano group,
(b) a carboxy group,
(c) a halogen atom (e.g., a chlorine atom),
(d) a $C_{1-6}$ alkyl group (e.g., methyl) optionally substituted by 1 to 3 substituents selected from
(i) a hydroxy group,
(ii) a cyano group,
(iii) a carboxy group,
(iv) a carbamoyl group optionally mono- or di-substituted by $C_{1-6}$ alkyl group(s) (e.g., methyl),
(v) an amino group optionally mono- or di-substituted by $C_{1-6}$ alkyl-carbonyl group(s) (e.g., acetyl),
(vi) a $C_{1-6}$ alkoxy-carbonyl group (e.g., ethoxycarbonyl, butoxycarbonyl),
(vii) a $C_{6-14}$ aryl group (e.g., phenyl) optionally substituted by 1 to 3 $C_{1-6}$ alkoxy groups (e.g., methoxy), and
(viii) a 3- to 8-membered monocyclic non-aromatic heterocyclic group (e.g., morpholinyl),
(e) a $C_{1-6}$ alkyl-carbonyl group (e.g., acetyl),
(f) a $C_{1-6}$ alkylsulfonyl group (e.g., methylsulfonyl),
(g) an amino group optionally mono- or di-substituted by substituent(s) selected from
(i) a $C_{1-6}$ alkyl group (e.g., methyl), and
(ii) a $C_{1-6}$ alkyl-carbonyl group (e.g., acetyl),
(h) a carbamoyl group optionally mono- or di-substituted by $C_{1-6}$ alkyl group(s) (e.g., methyl, ethyl),
(i) a sulfamoyl group, and
(j) a 3- to 8-membered monocyclic non-aromatic heterocyclic group (e.g., morpholinyl, tetrahydropyranyl, piperidyl, piperazinyl, 1,1-dioxidothiomorpholinyl, dihydrooxadiazolyl) optionally substituted by 1 to 3 substituents selected from
(i) a $C_{1-6}$ alkyl group (e.g., methyl),
(ii) a $C_{1-6}$ alkyl-carbonyl group (e.g., acetyl), and
(iii) an oxo group, or
(2) a $C_{1-6}$ alkyl group (e.g., methyl, ethyl) optionally substituted by 1 to 5 (preferably 1 to 3) substituents selected from
(a) a $C_{6-14}$ aryl group (e.g., phenyl, naphthyl) optionally substituted by 1 to 3 substituents selected from
(i) a cyano group,
(ii) a $C_{1-6}$ alkyl group (e.g., methyl) optionally substituted by 1 to 3 of 3- to 8-membered monocyclic non-aromatic heterocyclic groups (e.g., morpholinyl),
(iii) a $C_{1-6}$ alkoxy group (e.g., methoxy),
(iv) a halogen atom (e.g., a fluorine atom), and
(v) a 3- to 8-membered monocyclic non-aromatic heterocyclic group (e.g., piperazinyl) optionally substituted by 1 to 3 $C_{1-6}$ alkyl groups (e.g., methyl),
(b) a 5- or 6-membered monocyclic aromatic heterocyclic group (e.g., pyridyl, furyl, thienyl),
(c) a 8- to 12-membered fused aromatic heterocyclic group (e.g., benzofuranyl), and
(d) a $C_{3-6}$ cycloalkyl group (e.g., cyclopropyl); and
R³ is a hydrogen atom or a halogen atom (e.g., a fluorine atom).
[Compound B-2]
Compound (I) wherein
R¹ is
(A) a group represented by the following formula:

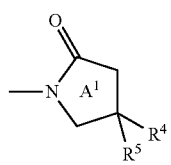

wherein
ring A¹ is an 2-oxopyrrolidine ring optionally further substituted by 1 to 3 substituents selected from
(1) a cyano group,
(2) a carbamoyl group, (3) a $C_{1-6}$ alkyl group (e.g., methyl, ethyl, propyl, isopropyl) optionally substituted by 1 to 3 substituents selected from
  (I) a carboxy group,
  (II) a cyano group,
  (III) a halogen atom (e.g., a fluorine atom),
  (IV) a $C_{1-6}$ alkoxy group (e.g., methoxy),
  (V) a $C_{3-6}$ cycloalkyl group (e.g., cyclopropyl),
  (VI) an amino group optionally mono- or di-substituted by substituent(s) selected from
    (i) a $C_{1-6}$ alkyl-carbonyl group (e.g., acetyl), and
    (ii) a $C_{1-6}$ alkoxy-carbonyl group (e.g., tert-butoxycarbonyl), and
  (VII) a hydroxy group,
(4) a $C_{3-6}$ cycloalkyl group (e.g., cyclopropyl, cyclobutyl),
(5) a 3- to 8-membered monocyclic non-aromatic heterocyclic group (e.g., oxetanyl, azetidinyl) optionally substituted by 1 to 3 $C_{1-6}$ alkoxy-carbonyl groups (e.g., tert-butoxycarbonyl),
(6) a $C_{1-6}$ alkoxy-carbonyl group (e.g., ethoxycarbonyl), and
(7) a 5- or 6-membered monocyclic aromatic heterocyclic group optionally substituted by 1 to 3 $C_{1-6}$ alkyl groups;
$R^4$ is a hydrogen atom or a $C_{1-6}$ alkyl group (e.g., methyl, ethyl); and
$R^5$ is a hydrogen atom; or
(B) a 2-oxopiperidino group optionally substituted by 1 to 3 $C_{1-6}$ alkyl groups (e.g., methyl);
$R^2$ is
(1) a 5- or 6-membered monocyclic aromatic heterocyclic group
(preferably pyrazolyl, pyridyl, pyrimidinyl, thiazolyl, imidazolyl, thienyl, more preferably pyrazolyl), a $C_{6-14}$ aryl group (preferably phenyl) or a 8- to 12-membered fused aromatic heterocyclic group (preferably indazolyl, benzothiazolyl, indolyl), each of which is optionally substituted by 1 to 3 substituents selected from
  (a) a cyano group,
  (b) a carboxy group,
  (c) a halogen atom (e.g., a chlorine atom, a fluorine atom),
  (d) a $C_{1-6}$ alkyl group (e.g., methyl, ethyl, isopropyl, tert-butyl, isobutyl) optionally substituted by 1 to 3 substituents selected from
    (I) a hydroxy group,
    (II) a cyano group,
    (III) a carboxy group,
    (IV) a carbamoyl group optionally mono- or di-substituted by $C_{1-6}$ alkyl group(s) (e.g., methyl, ethyl, tert-butyl) optionally substituted by 1 to 3 substituents selected from
      (i) a $C_{1-6}$ alkoxy group (e.g., methoxy),
      (ii) a hydroxy group,
      (iii) a halogen atom (e.g., a fluorine atom), and
      (iv) a $C_{1-6}$ alkylsulfonyl group (e.g., methylsulfonyl),
    (V) an amino group optionally mono- or di-substituted by substituent(s) selected from
      (i) a $C_{1-6}$ alkyl-carbonyl group (e.g., acetyl) optionally substituted by 1 to 3 substituents selected from
        (A) a $C_{1-6}$ alkoxy group (e.g., methoxy), and
        (B) a hydroxy group,
      (ii) a $C_{1-6}$ alkylsulfonyl group (e.g., methylsulfonyl),
      (iii) a sulfamoyl group optionally mono- or di-substituted by $C_{1-6}$ alkyl group(s) (e.g., methyl), and
      (iv) a $C_{1-6}$ alkyl group (e.g., methyl),
    (VI) a $C_{1-6}$ alkoxy-carbonyl group (e.g., ethoxycarbonyl, butoxycarbonyl),
    (VII) a $C_{6-14}$ aryl group (e.g., phenyl) optionally substituted by 1 to 3 $C_{1-6}$ alkoxy groups (e.g., methoxy),
    (VIII) a 3- to 8-membered monocyclic non-aromatic heterocyclic group (e.g., morpholinyl),
    (IX) a 3- to 8-membered monocyclic non-aromatic heterocyclylcarbonyl group (e.g., morpholinylcarbonyl, pyrrolidinylcarbonyl, piperidylcarbonyl, piperazinylcarbonyl) optionally substituted by 1 to 3 substituents selected from
      (i) a hydroxy group,
      (ii) a carbamoyl group, and
      (iii) a $C_{1-6}$ alkyl group (e.g., methyl),
    (X) a halogen atom (e.g., a fluorine atom), and
    (XI) a $C_{1-6}$ alkylsulfonyl group (e.g., methylsulfonyl),
  (e) a $C_{1-6}$ alkyl-carbonyl group (e.g., acetyl),
  (f) a $C_{1-6}$ alkylsulfonyl group (e.g., methylsulfonyl),
  (g) an amino group optionally mono- or di-substituted by substituent(s) selected from
    (I) a $C_{1-6}$ alkyl group (e.g., methyl),
    (II) a $C_{1-6}$ alkyl-carbonyl group (e.g., acetyl) optionally substituted by 1 to 3 $C_{1-6}$ alkoxy groups (e.g., methoxy), and
    (III) a $C_{1-6}$ alkylsulfonyl group (e.g., methylsulfonyl),
  (h) a carbamoyl group optionally mono- or di-substituted by substituent(s) selected from
    (I) a $C_{1-6}$ alkyl group (e.g., methyl, ethyl, tert-butyl) optionally substituted by 1 to 3 substituents selected from
      (i) a hydroxy group,
      (ii) a 3- to 8-membered monocyclic non-aromatic heterocyclic group (e.g., oxetanyl, morpholinyl) optionally substituted by 1 to 3 $C_{1-6}$ alkyl groups (e.g., methyl), and
      (iii) a $C_{1-6}$ alkylsulfonyl group (e.g., methylsulfonyl),
    (II) a $C_{3-6}$ cycloalkyl group (e.g., cyclopropyl, cyclobutyl, cyclohexyl) optionally substituted by 1 to 3 substituents selected from
      (i) a cyano group, and
      (ii) a hydroxy group, and
    (III) a 3- to 8-membered monocyclic non-aromatic heterocyclic group (e.g., oxetanyl, tetrahydropyranyl),
  (i) a sulfamoyl group optionally mono- or di-substituted by $C_{1-6}$ alkyl group(s) (e.g., methyl),
  (j) a 3- to 8-membered monocyclic non-aromatic heterocyclic group (e.g., morpholinyl, tetrahydropyranyl, piperidyl, piperazinyl, 1,1-dioxidothiomorpholinyl, dihydrooxadiazolyl, azetidinyl, imidazolidinyl, oxetanyl, pyrrolidinyl, 1,1-dioxidetetrahydrothiopyranyl) optionally substituted by 1 to 3 substituents selected from
    (I) a $C_{1-6}$ alkyl group (e.g., methyl) optionally substituted by 1 to 3 hydroxy groups,
    (II) a $C_{1-6}$ alkyl-carbonyl group (e.g., acetyl) optionally substituted by 1 to 3 substituents selected from
      (i) a $C_{1-6}$ alkoxy group (e.g., methoxy), and
      (ii) a cyano group,
    (III) a $C_{1-6}$ alkoxy-carbonyl group (e.g., tert-butoxycarbonyl),
    (IV) an oxo group,
    (V) a $C_{1-6}$ alkylsulfonyl group (e.g., methylsulfonyl),
    (VI) a carbamoyl group optionally mono- or di-substituted by $C_{1-6}$ alkyl group(s) (e.g., methyl),
    (VII) a cyano group,
    (VIII) a hydroxy group, and
    (IX) a carboxy group, (k) a $C_{3-6}$ cycloalkyl group (e.g., cyclopropyl, cyclobutyl, cyclopentyl, cyclohexyl) optionally substituted by 1 to 3 substituents selected from
  (I) a carbamoyl group optionally mono- or di-substituted by $C_{1-6}$ alkyl group(s) (e.g., methyl),
  (II) a carboxy group, and
  (III) a $C_{1-6}$ alkyl group (e.g., methyl) optionally substituted by 1 to 3 hydroxy groups,
(l) a $C_{1-6}$ alkoxy group (e.g., methoxy, ethoxy, isopropoxy, isobutoxy) optionally substituted by 1 to 3 substituents selected from
  (I) a halogen atom (e.g., a fluorine atom),
  (II) a $C_{1-6}$ alkoxy group (e.g., methoxy), and
  (III) a $C_{3-6}$ cycloalkyl group (e.g., cyclopropyl),
(m) a $C_{1-6}$ alkoxy-carbonyl group (e.g., tert-butoxycarbonyl),
(n) a 3- to 8-membered monocyclic non-aromatic heterocyclylcarbonyl group (e.g., pyrrolidinylcarbonyl, morpholinylcarbonyl, piperidylcarbonyl, azetidinylcarbonyl, 2-oxa-6-azaspiro[3.3]heptylcarbonyl, 1,1-dioxidothiomorpholinylcarbonyl) optionally substituted by 1 to 3 substituents selected from
  (I) a hydroxy group,
  (II) an oxo group,
  (III) a halogen atom (e.g., a fluorine atom),
  (IV) a $C_{1-6}$ alkoxy group (e.g., methoxy), and
  (V) a $C_{1-6}$ alkyl group (e.g., methyl),
(o) a $C_{1-6}$ alkylsulfanyl group (e.g., methylsulfanyl), and
(p) a 5- or 6-membered monocyclic aromatic heterocyclic group (e.g., tetrazolyl), or
(2) a $C_{1-6}$ alkyl group (e.g., methyl, ethyl) optionally substituted by 1 to 5 (preferably 1 to 3) substituents selected from
  (a) a $C_{6-14}$ aryl group (e.g., phenyl, naphthyl) optionally substituted by 1 to 3 substituents selected from
    (I) a cyano group,
    (II) a $C_{1-6}$ alkyl group (e.g., methyl) optionally substituted by 1 to 3 of 3- to 8-membered monocyclic non-aromatic heterocyclic groups (e.g., morpholinyl),
    (III) a $C_{1-6}$ alkoxy group (e.g., methoxy),
    (IV) a halogen atom (e.g., a fluorine atom), and
    (V) a 3- to 8-membered monocyclic non-aromatic heterocyclic group (e.g., piperazinyl) optionally substituted by 1 to 3 $C_{1-6}$ alkyl groups (e.g., methyl),
  (b) a 5- or 6-membered monocyclic aromatic heterocyclic group (e.g., pyridyl, furyl, thienyl) optionally substituted by 1 to 3 substituents selected from
    (I) a cyano group,
    (II) a $C_{1-6}$ alkyl group (e.g., methyl) optionally substituted by 1 to 3 of 3- to 8-membered monocyclic non-aromatic heterocyclic groups (e.g., morpholinyl),
    (III) a $C_{1-6}$ alkoxy group (e.g., methoxy),
    (IV) a halogen atom (e.g., a fluorine atom), and
    (V) a 3- to 8-membered monocyclic non-aromatic heterocyclic group (e.g., piperazinyl) optionally substituted by 1 to 3 $C_{1-6}$ alkyl groups (e.g., methyl),
  (c) a 8- to 12-membered fused aromatic heterocyclic group (e.g., benzofuranyl) optionally substituted by 1 to 3 substituents selected from
    (I) a cyano group,
    (II) a $C_{1-6}$ alkyl group (e.g., methyl) optionally substituted by 1 to 3 of 3- to 8-membered monocyclic non-aromatic heterocyclic groups (e.g., morpholinyl),
    (III) a $C_{1-6}$ alkoxy group (e.g., methoxy),
    (IV) a halogen atom (e.g., a fluorine atom), and
    (V) a 3- to 8-membered monocyclic non-aromatic heterocyclic group (e.g., piperazinyl) optionally substituted by 1 to 3 $C_{1-6}$ alkyl groups (e.g., methyl), and
  (d) a $C_{3-6}$ cycloalkyl group (e.g., cyclopropyl); and
$R^3$ is a hydrogen atom or a halogen atom (e.g., a fluorine atom).

[Compound C]
Compound (I) wherein
$R^1$ is
(A) a group represented by the following formula:

wherein
$R^{41}$ and $R^{42}$ are the same or different and each is
(1) a cyano group,
(2) a carbamoyl group,
(3) a $C_{1-6}$ alkyl group (e.g., methyl, ethyl, propyl, isopropyl) optionally substituted by 1 to 3 substituents selected from
  (I) a carboxy group,
  (II) a cyano group,
  (III) a halogen atom (e.g., a fluorine atom),
  (IV) a $C_{1-6}$ alkoxy group (e.g., methoxy),
  (V) a $C_{3-6}$ cycloalkyl group (e.g., cyclopropyl),
  (VI) an amino group optionally mono- or di-substituted by substituent(s) selected from
    (i) a $C_{1-6}$ alkyl-carbonyl group (e.g., acetyl), and
    (ii) a $C_{1-6}$ alkoxy-carbonyl group (e.g., tert-butoxycarbonyl), and
  (VII) a hydroxy group,
(4) a $C_{3-6}$ cycloalkyl group (e.g., cyclopropyl, cyclobutyl),
(5) a 3- to 8-membered monocyclic non-aromatic heterocyclic group (e.g., oxetanyl, azetidinyl) optionally substituted by 1 to 3 $C_{1-6}$ alkoxy-carbonyl groups (e.g., tert-butoxycarbonyl), or
(6) a $C_{1-6}$ alkoxy-carbonyl group (e.g., ethoxycarbonyl);
$R^{43}$ is a hydrogen atom or a $C_{1-3}$ alkyl group (e.g., methyl, ethyl);
$R^{44}$ is a hydrogen atom;
$R^4$ is a hydrogen atom or a $C_{1-3}$ alkyl group (e.g., methyl, ethyl); and
$R^5$ is a hydrogen atom; or
(B) an 2-oxopiperidino group optionally substituted by 1 to 3 $C_{1-6}$ alkyl groups;
$R^2$ is
(1) a 5- or 6-membered monocyclic aromatic heterocyclic group (preferably pyrazolyl, pyridyl, pyrimidinyl, thiazolyl, imidazolyl, thienyl, more preferably pyrazolyl), a $C_{6-14}$ aryl group (preferably phenyl) or a 8- to 12-membered fused aromatic heterocyclic group (preferably indazolyl, benzothiazolyl, indolyl), each of which is optionally substituted by 1 to 3 substituents selected from
  (a) a cyano group,
  (b) a carboxy group,
  (c) a halogen atom (e.g., a chlorine atom, a fluorine atom),
  (d) a $C_{1-6}$ alkyl group (e.g., methyl, ethyl, isopropyl, tert-butyl, isobutyl) optionally substituted by 1 to 3 substituents selected from
    (I) a hydroxy group,
    (II) a cyano group,
    (III) a carboxy group,
    (IV) a carbamoyl group optionally mono- or di-substituted by $C_{1-6}$ alkyl group(s) (e.g., methyl, ethyl, tert-butyl) optionally substituted by 1 to 3 substituents selected from
(i) a $C_{1-6}$ alkoxy group (e.g., methoxy),
(ii) a hydroxy group,
(iii) a halogen atom (e.g., a fluorine atom), and
(iv) a $C_{1-6}$ alkylsulfonyl group (e.g., methylsulfonyl),
(V) an amino group optionally mono- or di-substituted by substituent(s) selected from
  (i) a $C_{1-6}$ alkyl-carbonyl group (e.g., acetyl) optionally substituted by 1 to 3 substituents selected from
    (A) a $C_{1-6}$ alkoxy group (e.g., methoxy), and
    (B) a hydroxy group,
  (ii) a $C_{1-6}$ alkylsulfonyl group (e.g., methylsulfonyl),
  (iii) a sulfamoyl group optionally mono- or di-substituted by $C_{1-6}$ alkyl group(s) (e.g., methyl), and
  (iv) a $C_{1-6}$ alkyl group (e.g., methyl),
(VI) a $C_{1-6}$ alkoxy-carbonyl group (e.g., ethoxycarbonyl, butoxycarbonyl),
(VII) a $C_{6-14}$ aryl group (e.g., phenyl) optionally substituted by 1 to 3 $C_{1-6}$ alkoxy groups (e.g., methoxy),
(VIII) a 3- to 8-membered monocyclic non-aromatic heterocyclic group (e.g., morpholinyl),
(IX) a 3- to 8-membered monocyclic non-aromatic heterocyclylcarbonyl group (e.g., morpholinylcarbonyl, pyrrolidinylcarbonyl, piperidylcarbonyl, piperazinylcarbonyl) optionally substituted by 1 to 3 substituents selected from
  (i) a hydroxy group,
  (ii) a carbamoyl group, and
  (iii) a $C_{1-6}$ alkyl group (e.g., methyl),
(X) a halogen atom (e.g., a fluorine atom), and
(XI) a $C_{1-6}$ alkylsulfonyl group (e.g., methylsulfonyl),
(e) a $C_{1-6}$ alkyl-carbonyl group (e.g., acetyl),
(f) a $C_{1-6}$ alkylsulfonyl group (e.g., methylsulfonyl),
(g) an amino group optionally mono- or di-substituted by substituent(s) selected from
(I) a $C_{1-6}$ alkyl group (e.g., methyl),
(II) a $C_{1-6}$ alkyl-carbonyl group (e.g., acetyl) optionally substituted by 1 to 3 $C_{1-6}$ alkoxy groups (e.g., methoxy), and
(III) a $C_{1-6}$ alkylsulfonyl group (e.g., methylsulfonyl),
(h) a carbamoyl group optionally mono- or di-substituted by substituent(s) selected from
(I) a $C_{1-6}$ alkyl group (e.g., methyl, ethyl, tert-butyl) optionally substituted by 1 to 3 substituents selected from
  (i) a hydroxy group,
  (ii) a 3- to 8-membered monocyclic non-aromatic heterocyclic group (e.g., oxetanyl, morpholinyl) optionally substituted by 1 to 3 $C_{1-6}$ alkyl groups (e.g., methyl), and
  (iii) a $C_{1-6}$ alkylsulfonyl group (e.g., methylsulfonyl),
(II) a $C_{3-6}$ cycloalkyl group (e.g., cyclopropyl, cyclobutyl, cyclohexyl) optionally substituted by 1 to 3 substituents selected from
  (i) a cyano group, and
  (ii) a hydroxy group, and
(III) a 3- to 8-membered monocyclic non-aromatic heterocyclic group (e.g., oxetanyl, tetrahydropyranyl),
(i) a sulfamoyl group optionally mono- or di-substituted by $C_{1-6}$ alkyl group(s) (e.g., methyl),
(j) a 3- to 8-membered monocyclic non-aromatic heterocyclic group (e.g., morpholinyl, tetrahydropyranyl, piperidyl, piperazinyl, 1,1-dioxidothiomorpholinyl, dihydrooxadiazolyl, azetidinyl, imidazolidinyl, oxetanyl, pyrrolidinyl, 1,1-dioxidetetrahydrothiopyranyl) optionally substituted by 1 to 3 substituents selected from
(I) a $C_{1-6}$ alkyl group (e.g., methyl) optionally substituted by 1 to 3 hydroxy groups,
(II) a $C_{1-6}$ alkyl-carbonyl group (e.g., acetyl) optionally substituted by 1 to 3 substituents selected from
  (i) a $C_{1-6}$ alkoxy group (e.g., methoxy), and
  (ii) a cyano group,
(III) a $C_{1-6}$ alkoxy-carbonyl group (e.g., tert-butoxycarbonyl),
(IV) an oxo group,
(V) a $C_{1-6}$ alkylsulfonyl group (e.g., methylsulfonyl),
(VI) a carbamoyl group optionally mono- or di-substituted by $C_{1-6}$ alkyl group(s) (e.g., methyl),
(VII) a cyano group,
(VIII) a hydroxy group, and
(IX) a carboxy group,
(k) a $C_{3-6}$ cycloalkyl group (e.g., cyclopropyl, cyclobutyl, cyclopentyl, cyclohexyl) optionally substituted by 1 to 3 substituents selected from
(I) a carbamoyl group optionally mono- or di-substituted by $C_{1-6}$ alkyl group(s) (e.g., methyl),
(II) a carboxy group, and
(III) a $C_{1-6}$ alkyl group (e.g., methyl) optionally substituted by 1 to 3 hydroxy groups,
(l) a $C_{1-6}$ alkoxy group (e.g., methoxy, ethoxy, isopropoxy, isobutoxy) optionally substituted by 1 to 3 substituents selected from
(I) a halogen atom (e.g., a fluorine atom),
(II) a $C_{1-6}$ alkoxy group (e.g., methoxy), and
(III) a $C_{3-6}$ cycloalkyl group (e.g., cyclopropyl),
(m) a $C_{1-6}$ alkoxy-carbonyl group (e.g., tert-butoxycarbonyl),
(n) a 3- to 8-membered monocyclic non-aromatic heterocyclylcarbonyl group (e.g., pyrrolidinylcarbonyl, morpholinylcarbonyl, piperidylcarbonyl, azetidinylcarbonyl, 2-oxa-6-azaspiro[3.3]heptylcarbonyl, 1,1-dioxidothiomorpholinylcarbonyl) optionally substituted by 1 to 3 substituents selected from
(I) a hydroxy group,
(II) an oxo group,
(III) a halogen atom (e.g., a fluorine atom),
(IV) a $C_{1-6}$ alkoxy group (e.g., methoxy), and
(V) a $C_{1-6}$ alkyl group (e.g., methyl),
(o) a $C_{1-6}$ alkylsulfanyl group (e.g., methylsulfanyl), and
(p) a 5- or 6-membered monocyclic aromatic heterocyclic group (e.g., tetrazolyl); and $R^3$ is a hydrogen atom or a halogen atom (e.g., a fluorine atom).

[Compound D]

Compound (I) wherein
$R^1$ is a group represented by the following formula:

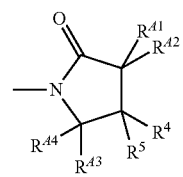

wherein
$R^{41}$ and $R^{42}$ are the same or different and each is
(1) a cyano group,
(2) a carbamoyl group, (3) a $C_{1-6}$ alkyl group (e.g., methyl, ethyl, propyl, isopropyl) optionally substituted by 1 to 3 substituents selected from
  (I) a carboxy group,
  (II) a cyano group,
  (III) a halogen atom (e.g., a fluorine atom),
  (IV) a $C_{1-6}$ alkoxy group (e.g., methoxy),
  (V) a $C_{3-6}$ cycloalkyl group (e.g., cyclopropyl),
  (VI) an amino group optionally mono- or di-substituted by substituent(s) selected from
    (i) a $C_{1-6}$ alkyl-carbonyl group (e.g., acetyl), and
    (ii) a $C_{1-6}$ alkoxy-carbonyl group (e.g., tert-butoxycarbonyl), and
  (VII) a hydroxy group,
(4) a $C_{3-6}$ cycloalkyl group (e.g., cyclopropyl, cyclobutyl),
(5) a 3- to 8-membered monocyclic non-aromatic heterocyclic group (e.g., oxetanyl, azetidinyl) optionally substituted by 1 to 3 $C_{1-6}$ alkoxy-carbonyl groups (e.g., tert-butoxycarbonyl), or
(6) a $C_{1-6}$ alkoxy-carbonyl group (e.g., ethoxycarbonyl);
$R^{43}$ is a hydrogen atom or a $C_{1-3}$ alkyl group (e.g., methyl, ethyl);
$R^{44}$ is a hydrogen atom;
$R^4$ is a hydrogen atom or a $C_{1-3}$ alkyl group (e.g., methyl, ethyl); and
$R^5$ is a hydrogen atom;
$R^2$ is
(l) a 5- or 6-membered monocyclic aromatic heterocyclic group
(preferably pyrazolyl, pyridyl, pyrimidinyl, thiazolyl, imidazolyl, thienyl, more preferably pyrazolyl), a $C_{6-14}$ aryl group (preferably phenyl) or a 8- to 12-membered fused aromatic heterocyclic group (preferably indazolyl, benzothiazolyl, indolyl), each of which is optionally substituted by 1 to 3 substituents selected from
  (a) a cyano group,
  (b) a carboxy group,
  (c) a halogen atom (e.g., a chlorine atom, a fluorine atom),
  (d) a $C_{1-6}$ alkyl group (e.g., methyl, ethyl, isopropyl, tert-butyl, isobutyl) optionally substituted by 1 to 3 substituents selected from
    (I) a hydroxy group,
    (II) a cyano group,
    (III) a carboxy group,
    (IV) a carbamoyl group optionally mono- or di-substituted by $C_{1-6}$ alkyl group(s) (e.g., methyl, ethyl, tert-butyl) optionally substituted by 1 to 3 substituents selected from
      (i) a $C_{1-6}$ alkoxy group (e.g., methoxy),
      (ii) a hydroxy group,
      (iii) a halogen atom (e.g., a fluorine atom), and
      (iv) a $C_{1-6}$ alkylsulfonyl group (e.g., methylsulfonyl),
    (V) an amino group optionally mono- or di-substituted by substituent(s) selected from
      (i) a $C_{1-6}$ alkyl-carbonyl group (e.g., acetyl) optionally substituted by 1 to 3 substituents selected from
        (A) a $C_{1-6}$ alkoxy group (e.g., methoxy), and
        (B) a hydroxy group,
      (ii) a $C_{1-6}$ alkylsulfonyl group (e.g., methylsulfonyl),
      (iii) a sulfamoyl group optionally mono- or di-substituted by $C_{1-6}$ alkyl group(s) (e.g., methyl), and
      (iv) a $C_{1-6}$ alkyl group (e.g., methyl),
    (VI) a $C_{1-6}$ alkoxy-carbonyl group (e.g., ethoxycarbonyl, butoxycarbonyl),
    (VII) a $C_{6-14}$ aryl group (e.g., phenyl) optionally substituted by 1 to 3 $C_{1-6}$ alkoxy groups (e.g., methoxy),
    (VIII) a 3- to 8-membered monocyclic non-aromatic heterocyclic group (e.g., morpholinyl),
    (IX) a 3- to 8-membered monocyclic non-aromatic heterocyclylcarbonyl group (e.g., morpholinylcarbonyl, pyrrolidinylcarbonyl, piperidylcarbonyl, piperazinylcarbonyl) optionally substituted by 1 to 3 substituents selected from
      (i) a hydroxy group,
      (ii) a carbamoyl group, and
      (iii) a $C_{1-6}$ alkyl group (e.g., methyl),
    (X) a halogen atom (e.g., a fluorine atom), and
    (XI) a $C_{1-6}$ alkylsulfonyl group (e.g., methylsulfonyl),
  (e) a $C_{1-6}$ alkyl-carbonyl group (e.g., acetyl),
  (f) a $C_{1-6}$ alkylsulfonyl group (e.g., methylsulfonyl),
  (g) an amino group optionally mono- or di-substituted by substituent(s) selected from
    (I) a $C_{1-6}$ alkyl group (e.g., methyl),
    (II) a $C_{1-6}$ alkyl-carbonyl group (e.g., acetyl) optionally substituted by 1 to 3 $C_{1-6}$ alkoxy groups (e.g., methoxy), and
    (III) a $C_{1-6}$ alkylsulfonyl group (e.g., methylsulfonyl),
  (h) a carbamoyl group optionally mono- or di-substituted by substituent(s) selected from
    (I) a $C_{1-6}$ alkyl group (e.g., methyl, ethyl, tert-butyl) optionally substituted by 1 to 3 substituents selected from
      (i) a hydroxy group,
      (ii) a 3- to 8-membered monocyclic non-aromatic heterocyclic group (e.g., oxetanyl, morpholinyl) optionally substituted by 1 to 3 $C_{1-6}$ alkyl groups (e.g., methyl), and
      (iii) a $C_{1-6}$ alkylsulfonyl group (e.g., methylsulfonyl),
    (II) a $C_{3-6}$ cycloalkyl group (e.g., cyclopropyl, cyclobutyl, cyclohexyl) optionally substituted by 1 to 3 substituents selected from
      (i) a cyano group, and
      (ii) a hydroxy group, and
    (III) a 3- to 8-membered monocyclic non-aromatic heterocyclic group (e.g., oxetanyl, tetrahydropyranyl),
  (i) a sulfamoyl group optionally mono- or di-substituted by $C_{1-6}$ alkyl group(s) (e.g., methyl),
  (j) a 3- to 8-membered monocyclic non-aromatic heterocyclic group (e.g., morpholinyl, tetrahydropyranyl, piperidyl, piperazinyl, 1,1-dioxidothiomorpholinyl, dihydrooxadiazolyl, azetidinyl, imidazolidinyl, oxetanyl, pyrrolidinyl, 1,1-dioxidetetrahydrothiopyranyl) optionally substituted by 1 to 3 substituents selected from
    (I) a $C_{1-6}$ alkyl group (e.g., methyl) optionally substituted by 1 to 3 hydroxy groups,
    (II) a $C_{1-6}$ alkyl-carbonyl group (e.g., acetyl) optionally substituted by 1 to 3 substituents selected from
      (i) a $C_{1-6}$ alkoxy group (e.g., methoxy), and
      (ii) a cyano group,
    (III) a $C_{1-6}$ alkoxy-carbonyl group (e.g., tert-butoxycarbonyl),
    (IV) an oxo group,
    (V) a $C_{1-6}$ alkylsulfonyl group (e.g., methylsulfonyl),
    (VI) a carbamoyl group optionally mono- or di-substituted by $C_{1-6}$ alkyl group(s) (e.g., methyl),
    (VII) a cyano group,
    (VIII) a hydroxy group, and
    (IX) a carboxy group,
  (k) a $C_{3-6}$ cycloalkyl group (e.g., cyclopropyl, cyclobutyl, cyclopentyl, cyclohexyl) optionally substituted by 1 to 3 substituents selected from
    (I) a carbamoyl group optionally mono- or di-substituted by $C_{1-6}$ alkyl group(s) (e.g., methyl), (II) a carboxy group, and
(III) a $C_{1-6}$ alkyl group (e.g., methyl) optionally substituted by 1 to 3 hydroxy groups,
(l) a $C_{1-6}$ alkoxy group (e.g., methoxy, ethoxy, isopropoxy, isobutoxy) optionally substituted by 1 to 3 substituents selected from
    (I) a halogen atom (e.g., a fluorine atom),
    (II) a $C_{1-6}$ alkoxy group (e.g., methoxy), and
    (III) a $C_{3-6}$ cycloalkyl group (e.g., cyclopropyl),
(m) a $C_{1-6}$ alkoxy-carbonyl group (e.g., tert-butoxycarbonyl),
(n) a 3- to 8-membered monocyclic non-aromatic heterocyclylcarbonyl group (e.g., pyrrolidinylcarbonyl, morpholinylcarbonyl, piperidylcarbonyl, azetidinylcarbonyl, 2-oxa-6-azaspiro[3.3]heptylcarbonyl, 1,1-dioxidothiomorpholinylcarbonyl) optionally substituted by 1 to 3 substituents selected from
    (I) a hydroxy group,
    (II) an oxo group,
    (III) a halogen atom (e.g., a fluorine atom),
    (IV) a $C_{1-6}$ alkoxy group (e.g., methoxy), and
    (V) a $C_{1-6}$ alkyl group (e.g., methyl),
(o) a $C_{1-6}$ alkylsulfanyl group (e.g., methylsulfanyl), and
(p) a 5- or 6-membered monocyclic aromatic heterocyclic group (e.g., tetrazolyl); and
$R^3$ is a hydrogen atom or a halogen atom (e.g., a fluorine atom).

[Compound E]
Compound (I) wherein
$R^1$ is a group represented by the following formula:

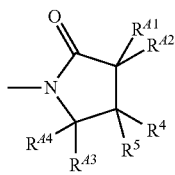

wherein
$R^{41}$ is
(1) a cyano group,
(2) a $C_{1-6}$ alkyl group (e.g., methyl, ethyl) optionally substituted by 1 to 3 substituents selected from
    (I) an amino group optionally mono- or di-substituted by substituent(s) selected from
        (i) a $C_{1-6}$ alkyl-carbonyl group (e.g., acetyl), and
        (ii) a $C_{1-6}$ alkoxy-carbonyl group (e.g., tert-butoxycarbonyl),
    (II) a hydroxy group, and
    (III) a cyano group, or
(3) a $C_{1-6}$ alkoxy-carbonyl group (e.g., ethoxycarbonyl);
$R^{42}$ is
(1) a $C_{3-6}$ cycloalkyl group (e.g., cyclopropyl, cyclobutyl),
(2) a $C_{1-6}$ alkyl group (e.g., methyl, ethyl, propyl, isopropyl) optionally substituted by 1 to 3 substituents selected from
    (I) a carboxy group,
    (II) a cyano group,
    (III) a halogen atom (e.g., a fluorine atom),
    (IV) a $C_{1-6}$ alkoxy group (e.g., methoxy),
    (V) a $C_{3-6}$ cycloalkyl group (e.g., cyclopropyl), and
    (VI) a hydroxy group,
(3) a carbamoyl group, or
(4) a 3- to 8-membered monocyclic non-aromatic heterocyclic group (e.g., oxetanyl, azetidinyl) optionally substituted by 1 to 3 $C_{1-6}$ alkoxy-carbonyl groups (e.g., tert-butoxycarbonyl);
$R^{43}$ is a hydrogen atom or a $C_{1-3}$ alkyl group (e.g., methyl, ethyl);
$R^{44}$ is a hydrogen atom;
$R^4$ is a hydrogen atom or a $C_{1-3}$ alkyl group (e.g., methyl, ethyl); and
$R^5$ is a hydrogen atom;
$R^2$ is
(1) a 5- or 6-membered monocyclic aromatic heterocyclic group (preferably pyrazolyl, pyridyl, pyrimidinyl, thiazolyl, imidazolyl, thienyl, more preferably pyrazolyl), a $C_{6-14}$ aryl group (preferably phenyl) or a 8- to 12-membered fused aromatic heterocyclic group (preferably indazolyl, benzothiazolyl, indolyl), each of which is optionally substituted by 1 to 3 substituents selected from
    (a) a cyano group,
    (b) a carboxy group,
    (c) a halogen atom (e.g., a chlorine atom, a fluorine atom),
    (d) a $C_{1-6}$ alkyl group (e.g., methyl, ethyl, isopropyl, tert-butyl, isobutyl) optionally substituted by 1 to 3 substituents selected from
        (I) a hydroxy group,
        (II) a cyano group,
        (III) a carboxy group,
        (IV) a carbamoyl group optionally mono- or di-substituted by $C_{1-6}$ alkyl group(s) (e.g., methyl, ethyl, tert-butyl) optionally substituted by 1 to 3 substituents selected from
            (i) a $C_{1-6}$ alkoxy group (e.g., methoxy),
            (ii) a hydroxy group,
            (iii) a halogen atom (e.g., a fluorine atom), and
            (iv) a $C_{1-6}$ alkylsulfonyl group (e.g., methylsulfonyl),
        (V) an amino group optionally mono- or di-substituted by substituent(s) selected from
            (i) a $C_{1-6}$ alkyl-carbonyl group (e.g., acetyl) optionally substituted by 1 to 3 substituents selected from
                (A) a $C_{1-6}$ alkoxy group (e.g., methoxy), and
                (B) a hydroxy group,
            (ii) a $C_{1-6}$ alkylsulfonyl group (e.g., methylsulfonyl),
            (iii) a sulfamoyl group optionally mono- or di-substituted by $C_{1-6}$ alkyl group(s) (e.g., methyl), and
            (iv) a $C_{1-6}$ alkyl group (e.g., methyl),
        (VI) a $C_{1-6}$ alkoxy-carbonyl group (e.g., ethoxycarbonyl, butoxycarbonyl),
        (VII) a $C_{6-14}$ aryl group (e.g., phenyl) optionally substituted by 1 to 3 $C_{1-6}$ alkoxy groups (e.g., methoxy),
        (VIII) a 3- to 8-membered monocyclic non-aromatic heterocyclic group (e.g., morpholinyl),
        (IX) a 3- to 8-membered monocyclic non-aromatic heterocyclylcarbonyl group (e.g., morpholinylcarbonyl, pyrrolidinylcarbonyl, piperidylcarbonyl, piperazinylcarbonyl) optionally substituted by 1 to 3 substituents selected from
            (i) a hydroxy group,
            (ii) a carbamoyl group, and
            (iii) a $C_{1-6}$ alkyl group (e.g., methyl),
        (X) a halogen atom (e.g., a fluorine atom), and
        (XI) a $C_{1-6}$ alkylsulfonyl group (e.g., methylsulfonyl),
    (e) a $C_{1-6}$ alkyl-carbonyl group (e.g., acetyl),
    (f) a $C_{1-6}$ alkylsulfonyl group (e.g., methylsulfonyl),
    (g) an amino group optionally mono- or di-substituted by substituent(s) selected from
        (I) a $C_{1-6}$ alkyl group (e.g., methyl),
        (II) a $C_{1-6}$ alkyl-carbonyl group (e.g., acetyl) optionally substituted by 1 to 3 $C_{1-6}$ alkoxy groups (e.g., methoxy), and
        (III) a $C_{1-6}$ alkylsulfonyl group (e.g., methylsulfonyl), (h) a carbamoyl group optionally mono- or di-substituted by substituent(s) selected from
   (I) a $C_{1-6}$ alkyl group (e.g., methyl, ethyl, tert-butyl) optionally substituted by 1 to 3 substituents selected from
      (i) a hydroxy group,
      (ii) a 3- to 8-membered monocyclic non-aromatic heterocyclic group (e.g., oxetanyl, morpholinyl) optionally substituted by 1 to 3 $C_{1-6}$ alkyl groups (e.g., methyl), and
      (iii) a $C_{1-6}$ alkylsulfonyl group (e.g., methylsulfonyl),
   (II) a $C_{3-6}$ cycloalkyl group (e.g., cyclopropyl, cyclobutyl, cyclohexyl) optionally substituted by 1 to 3 substituents selected from
      (i) a cyano group, and
      (ii) a hydroxy group, and
   (III) a 3- to 8-membered monocyclic non-aromatic heterocyclic group (e.g., oxetanyl, tetrahydropyranyl),
(i) a sulfamoyl group optionally mono- or di-substituted by $C_{1-6}$ alkyl group(s) (e.g., methyl),
(j) a 3- to 8-membered monocyclic non-aromatic heterocyclic group (e.g., morpholinyl, tetrahydropyranyl, piperidyl, piperazinyl, 1,1-dioxidothiomorpholinyl, dihydrooxadiazolyl, azetidinyl, imidazolidinyl, oxetanyl, pyrrolidinyl, 1,1-dioxidetetrahydrothiopyranyl) optionally substituted by 1 to 3 substituents selected from
   (I) a $C_{1-6}$ alkyl group (e.g., methyl) optionally substituted by 1 to 3 hydroxy groups,
   (II) a $C_{1-6}$ alkyl-carbonyl group (e.g., acetyl) optionally substituted by 1 to 3 substituents selected from
      (i) a $C_{1-6}$ alkoxy group (e.g., methoxy), and
      (ii) a cyano group,
   (III) a $C_{1-6}$ alkoxy-carbonyl group (e.g., tert-butoxycarbonyl),
   (IV) an oxo group,
   (V) a $C_{1-6}$ alkylsulfonyl group (e.g., methylsulfonyl),
   (VI) a carbamoyl group optionally mono- or di-substituted by $C_{1-6}$ alkyl group(s) (e.g., methyl),
   (VII) a cyano group,
   (VIII) a hydroxy group, and
   (IX) a carboxy group,
(k) a $C_{3-6}$ cycloalkyl group (e.g., cyclopropyl, cyclobutyl, cyclopentyl, cyclohexyl) optionally substituted by 1 to 3 substituents selected from
   (I) a carbamoyl group optionally mono- or di-substituted by $C_{1-6}$ alkyl group(s) (e.g., methyl),
   (II) a carboxy group, and
   (III) a $C_{1-6}$ alkyl group (e.g., methyl) optionally substituted by 1 to 3 hydroxy groups,
(l) a $C_{1-6}$ alkoxy group (e.g., methoxy, ethoxy, isopropoxy, isobutoxy) optionally substituted by 1 to 3 substituents selected from
   (I) a halogen atom (e.g., a fluorine atom),
   (II) a $C_{1-6}$ alkoxy group (e.g., methoxy), and
   (III) a $C_{3-6}$ cycloalkyl group (e.g., cyclopropyl),
(m) a $C_{1-6}$ alkoxy-carbonyl group (e.g., tert-butoxycarbonyl),
(n) a 3- to 8-membered monocyclic non-aromatic heterocyclylcarbonyl group (e.g., pyrrolidinylcarbonyl, morpholinylcarbonyl, piperidylcarbonyl, azetidinylcarbonyl, 2-oxa-6-azaspiro[3.3]heptylcarbonyl, 1,1-dioxidothiomorpholinylcarbonyl) optionally substituted by 1 to 3 substituents selected from
   (I) a hydroxy group,
   (II) an oxo group,
   (III) a halogen atom (e.g., a fluorine atom),
   (IV) a $C_{1-6}$ alkoxy group (e.g., methoxy), and
   (V) a $C_{1-6}$ alkyl group (e.g., methyl),
(o) a $C_{1-6}$ alkylsulfanyl group (e.g., methylsulfanyl), and
(p) a 5- or 6-membered monocyclic aromatic heterocyclic group (e.g., tetrazolyl); and $R^3$ is a hydrogen atom or a halogen atom (e.g., a fluorine atom).

[Compound F]

A compound selected from (3S)-3-cyclopropyl-1-(2-((1-(1-hydroxy-2-methylpropan-2-yl)-1H-pyrazol-4-yl)amino)pyrimidin-4-yl)-2-oxopyrrolidine-3-carbonitrile;

(3S)-3-cyclopropyl-1-(2-((1-(1-(hydroxymethyl)cyclopropyl)-1H-pyrazol-4-yl)amino)pyrimidin-4-yl)-2-oxopyrrolidine-3-carbonitrile; and (3R)-3-ethyl-1-(2-((4-(4-(hydroxymethyl)tetrahydro-2H-pyran-4-yl)phenyl)amino)pyrimidin-4-yl)-2-oxopyrrolidine-3-carbonitrile, and a salt thereof.

When compound (I) is in a form of a salt, examples thereof include metal salts, an ammonium salt, salts with organic base, salts with inorganic acid, salts with organic acid, salts with basic or acidic amino acid, and the like. Preferable examples of the metal salt include alkali metal salts such as sodium salt, potassium salt and the like; alkaline earth metal salts such as calcium salt, magnesium salt, barium salt and the like; an aluminum salt, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Among them, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

[Production Method]

The production method of compound (I) or a salt thereof of the present invention are explained in the followings.

The compound (I) and the raw material compounds can be produced according to a method known per se, for example, method shown in the following scheme and the like. In each step in the following production method, the "room temperature" generally means 10 to 35° C. and, unless otherwise specified, each symbol in the chemical formulas described in the schemes is as defined above. In the compounds in the formulas, each compound includes salts, and examples of such salt include those similar to the salts of compound (I) and the like.

In each reaction, when the raw material compound or intermediate has an amino group, a carboxy group or a hydroxy group as a substituent, these groups may be protected by a protecting group generally used in peptide chemistry and the like. By removing the protecting group as necessary after the reaction, the objective compound can be obtained. The introduction and removal of the protecting group can be performed according to a method known per se, for example, the method described in "Protective Groups in Organic Synthesis, 4th Ed", Wiley-Interscience, Inc. (2006) (Theodora W. Greene, Peter G. M. Wuts).

Examples of the amino-protecting group include a $C_{1-6}$ alkyl group, a $C_{7-14}$ aralkyl group optionally substituted by $C_{1-6}$ alkoxy group(s) (e.g., benzyl, 4-methoxybenzyl), a formyl group, a $C_{1-6}$ alkyl-carbonyl group, a $C_{1-6}$ alkoxy-carbonyl group, a benzoyl group, a 4-fluorobenzoyl group, a $C_{7-14}$ aralkyl-carbonyl group (e.g., benzylcarbonyl etc.), a $C_{7-14}$ aralkyloxy-carbonyl group (e.g., benzyloxycarbonyl, 9-fluorenylmethoxycarbonyl etc.), a trityl group, a phthaloyl group, an N,N-dimethylaminomethylene group, a silyl group optionally substituted by $C_{1-6}$ alkyl group(s) (e.g., trimethylsilyl, triethylsilyl, dimethylphenylsilyl, tert-butyldimethylsilyl, tert-butyldiethylsilyl etc.), a $C_{2-6}$ alkenyl group (e.g., 1-allyl etc.) and the like. These groups are optionally substituted by 1 to 3 substituents selected from a halogen atom, $C_{1-6}$ alkoxy group and a nitro group.

Examples of the carboxyl-protecting group include a $C_{1-6}$ alkyl group, a $C_{7-14}$ aralkyl group (e.g., benzyl etc.), a phenyl group, a trityl group, a silyl group optionally substituted by $C_{1-6}$ alkyl group(s) (e.g., trimethylsilyl, triethylsilyl, dimethylphenylsilyl, tert-butyldimethylsilyl, tert-butyldiethylsilyl etc.), a $C_{2-6}$ alkenyl group (e.g., 1-allyl etc.) and the like.

Examples of the hydroxy-protecting group include a $C_{1-6}$ alkyl group, a phenyl group, a trityl group, a $C_{7-14}$ aralkyl group (e.g., benzyl etc.), a formyl group, a $C_{1-6}$ alkyl-carbonyl group, a benzoyl group, a $C_{7-14}$ aralkyl-carbonyl group (e.g., benzylcarbonyl etc.), a 2-tetrahydropyranyl group, a 2-tetrahydrofuranyl group, a silyl group optionally substituted by $C_{1-6}$ alkyl group(s) (e.g., trimethylsilyl, triethylsilyl, dimethylphenylsilyl, tert-butyldimethylsilyl, tert-butyldiethylsilyl etc.), a $C_{2-6}$ alkenyl group (e.g., 1-allyl etc.) and the like.

These groups are optionally substituted by 1 to 3 substituents selected from a halogen atom, a $C_{1-6}$ alkyl group, a $C_{1-6}$ alkoxy group and a nitro group.

These protecting groups can be removed according to a method known per se, for example, the method described in "Protective Groups in Organic Synthesis, 4$^{th}$ Ed." Wiley-Interscience, Inc. (2006) (Theodora W. Greene, Peter G. M. Wuts) or the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like can be employed.

The compound obtained in each step can be used directly for the next step as the reaction mixture or a crude product, or can be isolated from the reaction mixture according to a conventional means, and can be easily purified according to a separation means such as recrystallized, distillation, chromatography and the like.

Where necessary, the reaction in each step can also be carried out under microwave irradiation using microwave irradiation apparatus (e.g., INITIATOR, manufactured by Biotage, etc.) and the like.

Compound (I) can be produced, for example, according to the following Method A, Method B or a method analogous thereto. The raw material compound in each method may be a commercially available product, or can also be produced according to a method known per se or a method analogous thereto. In each step of the following production methods, the raw material compounds may be in the form of a salt, and examples of such salt include those similar to the salts of compound (I).

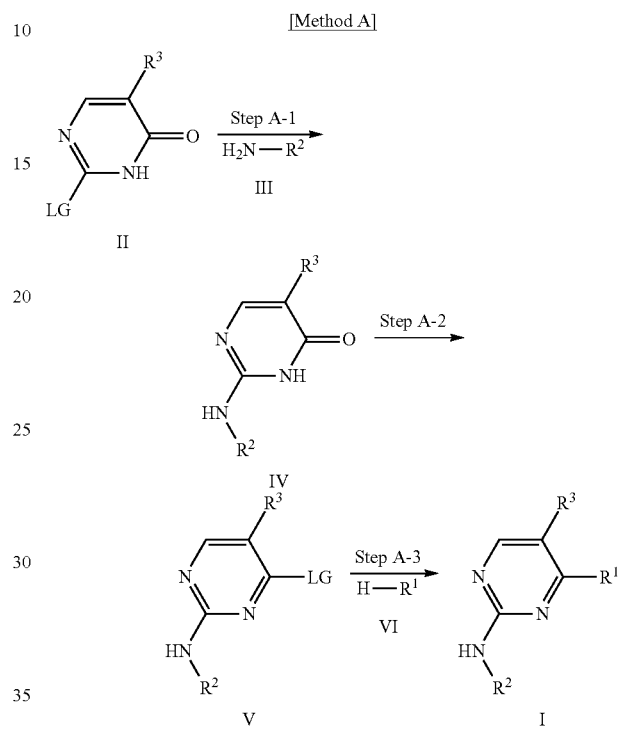

[Method A]

wherein LG is a leaving group, and the other symbols are as defined above.

Examples of the leaving group for LG include halogen atoms (e.g., a chlorine atom, a bromine atom, an iodine atom etc.), optionally substituted sulfonyloxy groups (e.g., $C_{1-6}$ alkylsulfonyloxy groups optionally substituted by 1 to 3 halogen atoms (e.g., a methanesulfonyloxy group, an ethanesulfonyloxy group, a trifluoromethanesulfonyloxy group etc.); $C_{6-14}$ arylsulfonyloxy groups optionally substituted by 1 to 3 $C_{1-6}$ alkyl groups (e.g., a benzenesulfonyloxy group, a p-toluenesulfonyloxy group etc.); $C_{7-14}$ aralkylsulfonyloxy groups (e.g., a benzylsulfonyloxy group etc.) etc.), an [(oxide)phenyl-λ4-sulfanylidene]dimethylammonium group and the like.

In this method, compound (II), compound (III) and compound (VI) used as raw material compounds may be commercially available products, or can also be produced according to a method known per se or a method analogous thereto.

(Step A-1)

This step is a step of reacting compound (II) with compound (III) to convert compound (II) to compound (IV). This step can be performed, where necessary, in the presence of a base, in a solvent that does not adversely influence the reaction.

The amount of compound (III) to be used is about 1-about 100 mol equivalents, particularly preferably about 1-about 10 mol equivalents, relative to compound (II).

Examples of the acid to be used include hydrochloric acid, acetic acid, hydrobromic acid, sulfuric acid, trifluoroacetic acid, trifluoromethanesulfonic acid, hydrogen chloride and the like.

The amount of the acid to be used is about 0.1-about 100 mol equivalents, preferably about 1-about 10 mol equivalents, relative to compound (II).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate etc.), alkali metal hydroxides (e.g., sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali metal disilazides (e.g., lithium disilazide, sodium disilazide, potassium disilazide etc.) and the like. Among them, organic amines (e.g., trimethylamine, triethylamine, N-ethyldiisopropylamine, N-methylmorpholine, 1,8-diazabicyclo[5.4.0]undec-7-ene etc.) are preferable.

The amount of the base to be used is about 0.1-about 100 mol equivalents, preferably about 1-about 10 mol equivalents, relative to compound (II).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane, diethylene glycol dimethyl ether etc.), nitriles (e.g., acetonitrile etc.), aprotic polar solvents (e.g., N,N-dimethylformamide, dimethylsulfoxide, N-methylpyrrolidone, hexamethylphosphoramide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about 0° C.-about 180° C. The reaction time in this step is generally about 0.1 hr-about 100 hr.

The thus-obtained compound (IV) can be isolated and purified by a known separation and purification means, for example, concentration, concentrated under reduced pressure, solvent extraction, crystallization, recrystallization, phase transfer, chromatography and the like. In addition, compound (IV) may be directly used without isolation for the next reaction.

(Step A-2)

This step is a step of reacting compound (IV) with a halogenating agent or a sulfonating agent to convert compound (IV) to compound (V). This step can be performed, where necessary, in a solvent that does not adversely influence the reaction.

Examples of the halogenating agent to be used include phosphorus oxychloride, phosphorus tribromide, phosphorus trichloride and the like. Examples of the sulfonating agent to be used include methanesulfonyl chloride, ethanesulfonyl chloride, benzenesulfonyl chloride, p-toluenesulfonyl chloride, benzylsulfonyl chloride and the like.

The amount of the halogenating agent or sulfonating agent to be used is about 1-about 100 mol equivalents, relative to compound (IV), respectively.

In this reaction, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethylsulfoxide, N-methylpyrrolidone, hexamethylphosphoramide etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (V) can be isolated and purified by a known separation and purification means, for example, concentration, concentrated under reduced pressure, solvent extraction, crystallization, recrystallization, phase transfer, chromatography and the like. In addition, compound (V) may be directly used without isolation for the next reaction.

(Step A-3)

This step is a step of subjecting compound (V) to a coupling reaction with compound (VI) using a transition metal catalyst to convert compound (V) to compound (I).

The reaction using a transition metal catalyst can be carried out according to a method known per se [e.g., Chemical Science, 2011, vol. 2, page 27, and the like], for example, in the presence of a transition metal catalyst and a base, in a solvent that does not adversely influence the reaction.

The amount of compound (VI) to be used is about 1 mol-about 100 mol equivalents, preferably about 1 mol-about 5 mol equivalents, relative to compound (V).

Examples of the transition metal catalyst to be used include palladium catalysts (e.g., palladium(II)acetate, tris(dibenzylideneacetone)dipalladium(0), palladium(II) chloride, tetrakis(triphenylphosphine)palladium(0), (1,1'-bis(diphenylphosphino)ferrocene)dichloropalladium(II)) and the like, nickel catalysts (e.g., nickel chloride etc.) and the like. Where necessary, a ligand (e.g., 4,5-bis(diphenylphosphino)-9,9-dimethylxanthene, 2,2'-bis(diphenylphosphino)-1,1'-binaphthyl, 2,2'-bis(di-p-tolylphosphino)-1,1'-binaphthyl, 2-dicyclohexyl phosphino-2',4',6'-triisopropyl-1,1'-biphenyl, triphenylphosphine, tri-tert-butylphosphine, dicyclohexyl(2', 4',6'-triisopropyl 3,6-dimethoxybiphenyl-2-yl)phosphine etc.) may be added.

While the amount of the transition metal catalyst to be used varies depending on the kinds of the catalyst, it is generally about 0.0001-about 1 mol equivalents, preferably about 0.01-about 0.5 mol equivalents, relative to compound (V). The amount of the ligand to be used is generally about 0.0001-about 4 mol equivalents, preferably about 0.01-about 2 mol equivalents, relative to compound (V).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate etc.), alkali metal hydroxides (e.g., sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali metal disilazides (e.g., lithium disilazide, sodium disilazide, potassium disilazide etc.) and the like. Among them, alkali metal salts (sodium carbonate, potassium carbonate, cesium carbonate etc.) are preferable.

The amount of the base to be used is about 0.1-about 100 mol equivalents, preferably about 1-about 10 mol equivalents, relative to compound (V).

In this reaction, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethylsulfoxide, N-methylpyrrolidone, hexamethylphosphoramide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (I) can be isolated and purified by a known separation and purification means, for example, concentration, concentrated under reduced pressure, solvent extraction, crystallization, recrystallization, phase transfer, chromatography and the like.

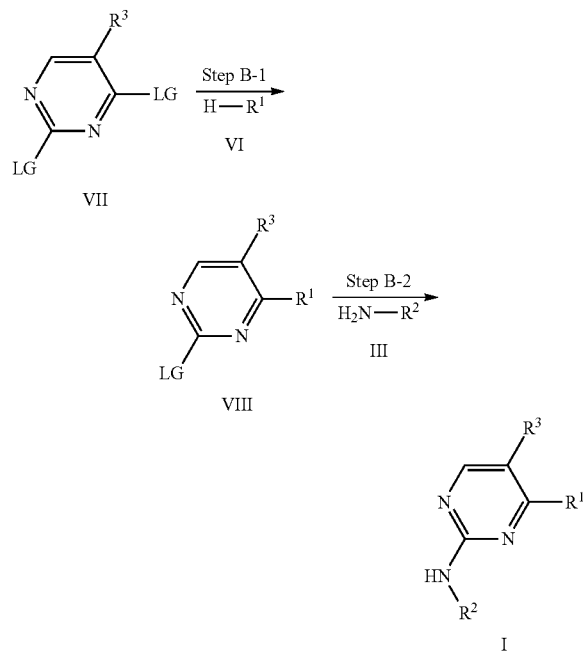

[Method B]

wherein each symbol is as defined above.

In this method, compound (VII), compound (III) and compound (VI) used as raw material compounds may be commercially available products, or can also be produced according to a method known per se or a method analogous thereto.

(Step B-1)

This step is a step of subjecting compound (VII) to a coupling reaction with compound (VI) using a transition metal catalyst to convert compound (VII) to compound (VIII).

The reaction using a transition metal catalyst can be carried out according to a method known per se [e.g., Chemical Science), 2011, vol. 2, page 27, and the like], for example, in the presence of a transition metal catalyst and a base, in a solvent that does not adversely influence the reaction.

The amount of compound (VI) to be used is about 1 mol-about 100 mol equivalents, preferably about 1 mol-about 5 mol equivalents, relative to compound (VII).

Examples of the transition metal catalyst to be used include palladium catalysts (e.g., palladium(II)acetate, tris(dibenzylideneacetone)dipalladium(0), palladium(II) chloride, tetrakis(triphenylphosphine)palladium(0), (1,1'-bis(diphenylphosphino)ferrocene)dichloropalladium (II)) and the like, nickel catalysts (e.g., nickel chloride etc.) and the like. Where necessary, a ligand (e.g., 4,5-bis(diphenylphosphino)-9,9-dimethylxanthene, 2,2'-bis(diphenylphosphino)-1,1'-binaphthyl, 2,2'-bis(di-p-tolylphosphino)-1,1'-binaphthyl, 2-dicyclohexyl phosphino-2',4',6'-triisopropyl-1,1'-biphenyl, triphenylphosphine, tri-tert-butylphosphine, dicyclohexyl(2', 4',6'-triisopropyl-3,6-dimethoxybiphenyl-2-yl)phosphine etc.) may be added.

While the amount of the transition metal catalyst to be used varies depending on the kinds of the catalyst, it is generally about 0.0001-about 1 mol equivalents, preferably about 0.01-about 0.5 mol equivalents, relative to compound (VII). The amount of the ligand to be used is generally about 0.0001-about 4 mol equivalents, preferably about 0.01-about 2 mol equivalents, relative to compound (VII).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate etc.), alkali metal hydroxides (e.g., sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali metal disilazides (e.g., lithium disilazide, sodium disilazide, potassium disilazide etc.) and the like. Among them, alkali metal salts (sodium carbonate, potassium carbonate, cesium carbonate etc.) are preferable.

The amount of the base to be used is about 0.1-about 100 mol equivalents, preferably about 1-about 10 mol equivalents, relative to compound (VII).

In this reaction, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethylsulfoxide, N-methylpyrrolidone, hexamethylphosphoramide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about −10° C.-about 150° C. The reaction time in this step is generally about 0.1 hr-about 100 hr.

The thus-obtained compound (VIII) can be isolated and purified by a known separation and purification means, for example, concentration, concentrated under reduced pressure, solvent extraction, crystallization, recrystallization, phase transfer, chromatography and the like. In addition, compound (VIII) may be directly used without isolation for the next reaction.

(Step B-2)

This step is a step of reacting compound (VIII) with compound (III) to convert compound (VIII) to compound (I). This step can be performed, where necessary, in the presence of an acid or a base, adding a transition metal catalyst, in a solvent that does not adversely influence the reaction.

The amount of compound (III) to be used is about 1-about 100 mol equivalents, particularly preferably about 1-about 10 mol equivalents, relative to compound (VIII).

Examples of the acid to be used include hydrochloric acid, acetic acid, hydrobromic acid, sulfuric acid, trifluoroacetic acid, trifluoromethanesulfonic acid, hydrogen chloride and the like.

The amount of the acid to be used is about 0.1-about 100 mol equivalents, preferably about 1-about 10 mol equivalents, relative to compound (VIII).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate etc.), alkali metal hydroxides (e.g., sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali metal disilazides (e.g., lithium disilazide, sodium disilazide, potassium disilazide etc.) and the like. Among them, organic amines (e.g., trimethylamine, triethylamine, N-ethyldiisopropylamine, N-methylmorpholine, 1,8-diazabicyclo[5.4.0]undec-7-ene etc.) are preferable.

The amount of the base to be used is about 0.1-about 100 mol equivalents, preferably about 1-about 10 mol equivalents, relative to compound (VIII).

Examples of the transition metal catalyst to be used include palladium catalysts (e.g., palladium(II) acetate, tris(dibenzylideneacetone)dipalladium(0), palladium(II) chloride, tetrakis(triphenylphosphine)palladium(0), (1,1'-bis(diphenylphosphino)ferrocene)dichloropalladium (II)) and the like, nickel catalysts (e.g., nickel chloride etc.) and the like. Where necessary, a ligand (e.g., 4,5-bis(diphenylphosphino)-9,9-dimethylxanthene, 2,2'-bis(diphenylphosphino)-1,1'-binaphthyl, 2,2'-bis(di-p-tolylphosphino)-1,1'-binaphthyl, 2-dicyclohexyl phosphino-2',4',6'-triisopropyl-1,1'-biphenyl, triphenylphosphine, tri-tert-butylphosphine, dicyclohexyl(2',4',6'-triisopropyl-3,6-dimethoxybiphenyl-2-yl)phosphine etc.) may be added, or a metal oxide (e.g., copper oxide, silver oxide etc.) may used as a cocatalyst.

While the amount of the transition metal catalyst to be used varies depending on the kinds of the catalyst, it is generally about 0.0001-about 1 mol equivalents, preferably about 0.01-about 0.5 mol equivalents, relative to compound (VIII). The amount of the ligand to be used is generally about 0.0001-about 4 mol equivalents, preferably about 0.01-about 2 mol equivalents, relative to compound (VIII).

In this reaction, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethylsulfoxide, N-methylpyrrolidone, hexamethylphosphoramide etc.), protic polar solvents (e.g., water, methanol, ethanol, 1-propanol, 2-propanol, 1-butanol, 2-methyl-2-propanol etc.) and mixtures thereof.

The reaction temperature in this step is generally about −50-about 200° C., preferably about 0° C.-about 180° C. The reaction time in this step is generally about 0.1 hr-about 100 hr.

The thus-obtained compound (I) can be isolated and purified by a known separation and purification means, for example, concentration, concentrated under reduced pressure, solvent extraction, crystallization, recrystallization, phase transfer, chromatography and the like.

Alternatively, compound (VI) can be produced, for example, according to the following Method C or Method D, or a method analogous thereto. The raw material compounds used in each method may be a commercially available product, or can also be produced according to a method known per se or a method analogous thereto.

Of compound (VI), the compound represented by the formula (VI-A)

VI-A wherein $R^6$ is a cyano group, and $R^7$ is a hydrogen atom or an optionally substituted $C_{1-6}$ alkyl group, and the "$C_{1-6}$ alkyl group" of the "optionally substituted $C_{1-6}$ alkyl group" for $R^7$ optionally has 1 to 5 (preferably 1 to 3) substituents at substitutable position(s), and examples of the substituent include substituents selected from the above-mentioned Substituent Group A, and when the number of the substituents is plural, the respective substituents may be the same or different (hereinafter to be referred to as compound (VI-A)) can be produced according to the following Method C or a method analogous thereto. In each step of the following production methods, the raw material compounds may be in the form of a salt, and examples of such salt include those similar to the salts of compound (I).

[Method C]

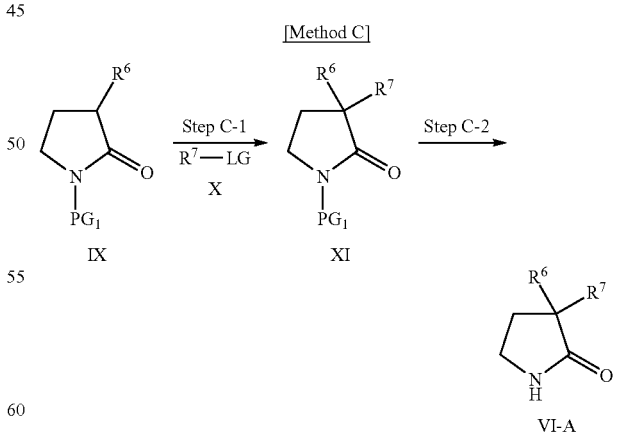

wherein $PG_1$ is an amino-protecting group, and the other symbols are as defined above.

Examples of the "amino-protecting group" for $PG_1$ include a formyl group, $C_{1-6}$ alkyl-carbonyl groups, $C_{1-6}$ alkoxy-carbonyl groups, a benzoyl group, a 4-fluorobenzoyl group, $C_{7-14}$ aralkyl-carbonyl groups (e.g., benzylcarbonyl etc.), $C_{7-4}$ aralkyloxy-carbonyl groups (e.g., benzyloxycarbonyl, 9-fluorenylmethoxycarbonyl etc.) and the like. These group are optionally substituted by 1 to 3 substituents selected from a halogen atom, a $C_{1-6}$ alkoxy group and a nitro group.

In this method, compound (IX) and compound (X) used as raw material compounds may be a commercially available product, or can also be produced according to a method known per se [e.g., Journal Heterocyclic Chemistry, 2005, vol 42, page 543, and the like] or method analogous thereto.

(Step C-1)

This step is a step of reacting compound (IX) with compound (X) to convert compound (IX) to compound (XI).

This step can be performed in the presence of a base, where necessary, in a solvent that does not adversely influence the reaction.

The amount of compound (X) to be used is about 1-about 100 mol equivalents, particularly preferably about 1-about 10 mol equivalents, relative to compound (IX).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate etc.), alkali metal hydroxides (e.g., sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali metal disilazides (e.g., lithium disilazide, sodium disilazide, potassium disilazide etc.), lithium diisopropylamide and the like.

The amount of the base to be used is about 0.1-about 100 mol equivalents, particularly preferably about 1-about 10 mol equivalents, relative to compound (IX).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethylsulfoxide, N-methylpyrrolidone, hexamethylphosphoramide etc.) and mixtures thereof.

The reaction temperature in this step is generally about −80-about 200° C., preferably about −80° C.-about 80° C. The reaction time in this step is generally about 0.1 hr-about 100 hr.

The thus-obtained compound (XI) can be isolated and purified by a known separation and purification means, for example, concentration, concentrated under reduced pressure, solvent extraction, crystallization, recrystallization, phase transfer, chromatography and the like. In addition, compound (XI) may be directly used without isolation for the next reaction.

(Step C-2)

This step is a step of subjecting compound (XI) to a deprotection reaction to convert compound (XI) to compound (VI-A).

This step can be performed, for example, in the presence of an amine (e.g., aqueous ammonia, methylamine, n-octylamine etc.), where necessary, in a solvent that does not adversely influence the reaction.

The amount of the amine to be used is about 0.1-about 100 mol equivalents, particularly preferably about 1-about 10 mol equivalents, relative to compound (XI).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethylsulfoxide, N-methylpyrrolidone, hexamethylphosphoramide etc.) and mixtures thereof.

The reaction temperature in this step is generally about −80-about 200° C., preferably about 0-about 100° C. The reaction time in this step is generally about 0.1 hr-about 100 hr.

The thus-obtained compound (VI-A) can be isolated and purified by a known separation and purification means, for example, concentration, concentrated under reduced pressure, solvent extraction, crystallization, recrystallization, phase transfer, chromatography and the like. In addition, compound (VI-A) may be directly used without isolation for the next reaction.

Of compound (VI), the compound represented by the formula (VI-B)

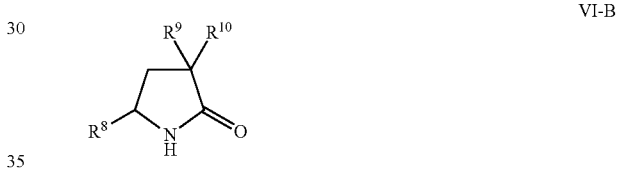

wherein $R^8$, $R^9$ and $R^{10}$ are each independently a hydrogen atom or an optionally substituted $C_{1-6}$ alkyl group, and the "$C_{1-6}$ alkyl group" of the "optionally substituted $C_{1-6}$ alkyl group" for $R^8$, $R^9$ or $R^{10}$ optionally has 1 to 5 (preferably 1 to 3) substituents at substitutable position(s), and examples of the substituent include substituents selected from the above-mentioned Substituent Group A, and when the number of the substituents is plural, the respective substituents may be the same or different (hereinafter to be referred to as compound (VI-B)) can be produced according to the following Method D or a method analogous thereto. In each step of the following production methods, the raw material compounds may be in the form of a salt, and examples of such salt include those similar to the salts of compound (I).

[Method D]

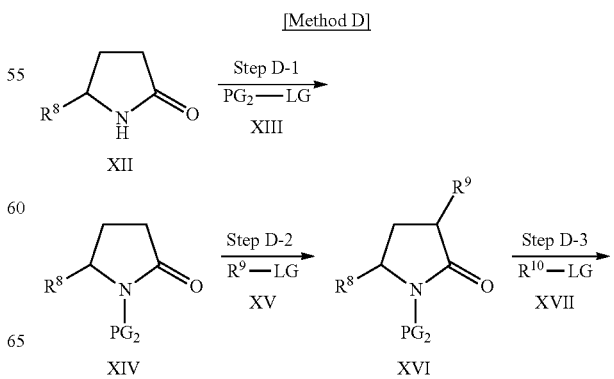

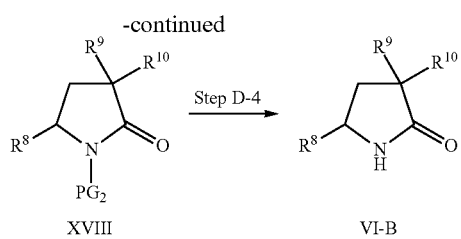

wherein PG$_2$ is an amino-protecting group, and the other symbols are as defined above.

Examples of the "amino-protecting group" for PG$_2$ include C$_{1-6}$ alkyl groups, C$_{7-14}$ aralkyl groups (e.g., benzyl, p-methoxybenzyl) and the like. These groups are optionally substituted by 1 to 3 substituents selected from a halogen atom, a C$_{1-6}$ alkoxy group and a nitro group.

In this method, compound (XII), compound (XIII), compound (XV) and compound (XVII) used as raw material compounds may be commercially available products, or can also be produced according to a method known per se or a method analogous thereto.

(Step D-1)

This step is a step of reacting compound (XII) with compound (XIII) to convert compound (XII) to compound (XIV).

This step can be performed in the presence of a base, where necessary, in a solvent that does not adversely influence the reaction.

The amount of compound (XIII) to be used is about 1-about 100 mol equivalents, particularly preferably about 1-about 10 mol equivalents, relative to compound (XII).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate etc.), alkali metal hydroxides (e.g., sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali metal disilazides (e.g., lithium disilazide, sodium disilazide, potassium disilazide etc.), lithium diisopropylamide and the like.

The amount of the base to be used is about 0.1-about 100 mol equivalents, particularly preferably about 1-about 10 mol equivalents, relative to compound (XII).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethylsulfoxide, N-methylpyrrolidone, hexamethylphosphoramide etc.) and mixtures thereof.

The reaction temperature in this step is generally about −50-about 200° C., preferably about −10° C.-about 100° C. The reaction time in this step is generally about 0.1 hr-about 100 hr.

The thus-obtained compound (XIV) can be isolated and purified by a known separation and purification means, for example, concentration, concentrated under reduced pressure, solvent extraction, crystallization, recrystallization, phase transfer, chromatography and the like. In addition, compound (XIV) may be directly used without isolation for the next reaction.

(Step D-2)

This step is a step of reacting compound (XIV) with compound (XV) to convert compound (XIV) to compound (XVI).

This step can be performed in the presence of a base, where necessary, in a solvent that does not adversely influence the reaction.

The amount of compound (XV) to be used is about 1-about 100 mol equivalents, particularly preferably about 1-about 10 mol equivalents, relative to compound (XIV).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate etc.), alkali metal hydroxides (e.g., sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali metal disilazides (e.g., lithium disilazide, sodium disilazide, potassium disilazide etc.), lithium diisopropylamide and the like.

The amount of the base to be used is about 0.1-about 100 mol equivalents, particularly preferably about 1-about 10 mol equivalents, relative to compound (XIV).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethylsulfoxide, N-methylpyrrolidone, hexamethylphosphoramide etc.) and mixtures thereof.

The reaction temperature in this step is generally about −80-about 200° C., preferably about −80-about 80° C. The reaction time in this step is generally about 0.1 hr-about 100 hr.

The thus-obtained compound (XVI) can be isolated and purified by a known separation and purification means, for example, concentration, concentrated under reduced pressure, solvent extraction, crystallization, recrystallization, phase transfer, chromatography and the like. In addition, compound (XVI) may be directly used without isolation for the next reaction.

(Step D-3)

This step is a step of reacting compound (XVI) with compound (XVII) to convert compound (XVI) to compound (XVIII).

This step can be performed in the presence of a base, where necessary, in a solvent that does not adversely influence the reaction.

The amount of compound (XVII) to be used is about 1-about 100 mol equivalents, particularly preferably about 1-about 10 mol equivalents, relative to compound (XVI).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate etc.), alkali metal hydroxides (e.g., sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali metal disilazides (e.g., lithium disilazide, sodium disilazide, potassium disilazide etc.), lithium diisopropylamide and the like.

The amount of the base to be used is about 0.1-about 100 mol equivalents, particularly preferably about 1-about 10 mol equivalents, relative to compound (XVI).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethylsulfoxide, N-methylpyrrolidone, hexamethylphosphoramide etc.) and mixtures thereof.

The reaction temperature in this step is generally about −80-about 200° C., preferably about −80-80° C. The reaction time in this step is generally about 0.1 hr-about 100 hr.

The thus-obtained compound (XVIII) can be isolated and purified by a known separation and purification means, for example, concentration, concentrated under reduced pressure, solvent extraction, crystallization, recrystallization, phase transfer, chromatography and the like. In addition, compound (XVIII) may be directly used without isolation for the next reaction.

(Step D-4)

This step is a step of subjecting compound (XVIII) to the above-mentioned deprotection reaction to convert compound (XVIII) to compound (VI-B).

This step can be performed, where necessary, in a solvent that does not adversely influence the reaction.

This step can be performed, for example, in the presence of an oxidizing agent (e.g., ammonium hexanitratocerate (IV), 2,3-dichloro-5,6-dicyano-1,4-benzoquinone etc.), in a solvent that does not adversely influence the reaction.

The amount of the oxidizing agent to be used is about 0.1-about 100 mol equivalents, particularly preferably about 1-about 10 mol equivalents, relative to compound (XVIII).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethylsulfoxide, N-methylpyrrolidone, hexamethylphosphoramide etc.), water and mixtures thereof.

The reaction temperature in this step is generally about −80-about 200° C., preferably about −80-about 150° C. The reaction time in this step is generally about 0.1 hr-about 100 hr.

The thus-obtained compound (VI-B) can be isolated and purified by a known separation and purification means, for example, concentration, concentrated under reduced pressure, solvent extraction, crystallization, recrystallization, phase transfer, chromatography and the like. In addition, compound (VI-B) may be directly used without isolation for the next reaction.

Of compound (VI), the compound represented by the formula (VI-C)

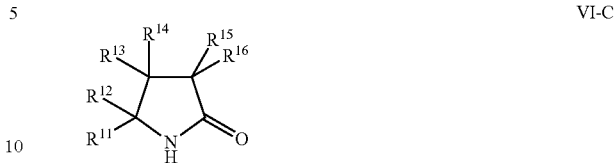

wherein $R^{11}$, $R^{12}$, $R^{13}$ and $R^{14}$ are each independently a hydrogen atom or an optionally substituted $C_{1-6}$ alkyl group, $R^{15}$ is a hydrogen atom, an optionally substituted $C_{1-6}$ alkyl group, an optionally substituted 3- to 8-membered monocyclic non-aromatic heterocyclic group, or a $C_{3-6}$ cycloalkyl group, and $R^{16}$ is a cyano group or a $C_{1-6}$ alkoxycarbonyl group (hereinafter to be referred to as compound (VI-C)) can be produced according to the following Method E or a method analogous thereto. In each step of the following production methods, the raw material compounds may be in the form of a salt, and examples of such salt include those similar to the salts of compound (I).

[Method E]

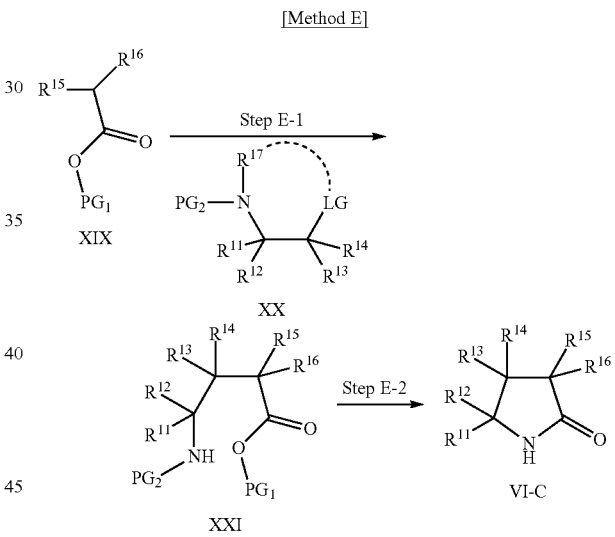

wherein $PG_1$ is the above-mentioned carboxy group-protecting group, $PG_2$ is the above-mentioned amino-protecting group, $R^{17}$ is a hydrogen atom, LG is as defined above, or $R^{17}$ and LG in combination form a heterocycle (e.g., a 2,2-dioxide-1,2,3-oxathiazolidine ring etc.), and the other symbols are as defined above.

Examples of the carboxy-protecting group for $PG_1$ include $C_{1-6}$ alkyl groups, $C_{7-12}$ aralkyl groups (e.g., benzyl etc.), a phenyl group, a trityl group, silyl groups optionally substituted by $C_{1-6}$ alkyl group(s) (e.g., trimethylsilyl, triethylsilyl, tert-butyldimethylsilyl, tert-butyldiethylsilyl etc.), $C_{2-6}$ alkenyl groups (e.g., allyl etc.) and the like. These groups are optionally substituted by 1 to 3 substituents selected from a halogen atom, a $C_{1-6}$ alkoxy group and a nitro group. Examples of the amino-protecting group for $PG_2$ include a formyl group, $C_{1-6}$ alkyl-carbonyl groups, $C_{1-6}$ alkoxy-carbonyl groups (e.g., tert-butoxycarbonyl etc.), a benzoyl group, $C_{7-10}$ aralkyl-carbonyl groups (e.g., benzylcarbonyl etc.), $C_{7-12}$ aralkyloxy-carbonyl groups (e.g., benzyloxycarbonyl etc.) and the like. These groups are optionally substituted by 1 to 3 substituents selected from a halogen atom, a $C_{1-6}$ alkoxy group and a nitro group. In this method, compound (XIX) and compound (XX) used as raw material compounds may be a commercially available product, or can also be produced according to a method known per se or a method analogous thereto.

(Step E-1)

This step is a step of reacting compound (XIX) with compound (XX) to convert compound (XIX) to compound (XXI).

This step can be performed in the presence of a base, where necessary, in the presence of a phase transfer catalysis, in a solvent that does not adversely influence the reaction.

The amount of compound (XX) to be used is 1 to 100 mol equivalents, particularly preferably 1 to 10 mol equivalents, relative to compound (XIX).

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali metal disilazides (e.g., lithium disilazide, sodium disilazide, potassium disilazide etc.) and the like.

The amount of the base to be used is 0.1 to 100 mol equivalents, particularly preferably 1 to 10 mol equivalents, relative to compound (XIX).

Examples of the phase transfer catalysis to be used include quaternized ammonium compounds (e.g., tetramethylammonium fluoride, tetraethylammonium fluoride, tetrabutylammonium fluoride, tetrabutylammonium chloride, tetrabutylammonium bromide, tetrabutylammonium iodide etc.), phosphonium compounds (e.g., tributyl-n-octylphosphonium bromide etc.), pyridinium compounds (e.g., 1-butylpyridinium tetrafluoroborate etc.) and the like.

The amount of the phase transfer catalysis to be used is 0.1 to 100 mol equivalents, particularly preferably 0.1 to 10 mol equivalents, relative to compound (XIX).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethylsulfoxide, hexamethylphosphoramide etc.) and mixtures thereof.

The reaction temperature in this step is generally about −50-200° C., preferably −10-100° C. The reaction time in this step is generally 0.1 hr-100 hr.

The thus-obtained compound (XXI) can be isolated and purified by a known separation and purification means, for example, concentration, concentrated under reduced pressure, solvent extraction, crystallization, recrystallization, phase transfer, chromatography and the like. In addition, compound (XXI) may be directly used without isolation for the next reaction.

(Step E-2)

This step is a step of treating compound (XXI) with a base, or, where necessary, subjecting compound (XXI) to the above-mentioned deprotection reaction (amino-protecting group) and then reacting the resulting compound with a base to convert compound (XXI) to compound (VI-C).

This step can be performed in the presence of a base, in a solvent that does not adversely influence the reaction.

Examples of the base to be used include organic amines (e.g., trimethylamine, triethylamine, N-ethyldiisopropylamine, N-methylmorpholine, 1,8-diazabicyclo[5.4.0]undec-7-ene, pyridine, N,N-dimethylaniline etc.), alkali metal salts (e.g., sodium hydrogen carbonate, potassium hydrogen carbonate, sodium carbonate, potassium carbonate, cesium carbonate, sodium acetate, potassium acetate, sodium phosphate, potassium phosphate, sodium hydroxide, potassium hydroxide etc.), metal hydrides (potassium hydride, sodium hydride etc.), alkali metal alkoxides (sodium methoxide, sodium ethoxide, sodium tert-butoxide, potassium tert-butoxide etc.), alkali metal disilazides (e.g., lithium disilazide, sodium disilazide, potassium disilazide etc.) and the like.

The amount of the base to be used is 0.1 to 100 mol equivalents, particularly preferably 1 to 10 mol equivalents, relative to compound (XXI).

In this step, the solvent is not particularly limited as long as the reaction proceeds. Examples thereof include hydrocarbons (e.g., benzene, toluene, xylene, hexane, heptane etc.), halogenated hydrocarbons (e.g., chloroform, dichloromethane etc.), ethers (e.g., diethyl ether, diisopropyl ether, tert-butyl methyl ether, tetrahydrofuran, 1,4-dioxane, 1,2-dimethoxyethane etc.), nitriles (e.g., acetonitrile etc.), aprotic polar solvents (e.g., N,N-dimethylformamide, dimethylsulfoxide, hexamethylphosphoramide etc.) and mixtures thereof.

The reaction temperature in this step is generally about −50-200° C., preferably −10-100° C. The reaction time in this step is generally 0.1 hr-100 hr.

The thus-obtained compound (VI-C) can be isolated and purified by a known separation and purification means, for example, concentration, concentrated under reduced pressure, solvent extraction, crystallization, recrystallization, phase transfer, chromatography and the like. In addition, compound (VI-C) may be directly used without isolation for the next reaction.

Compound (I) obtained according to the above-mentioned Method A or Method B, compound (IV) and compound (V), obtained according to the above-mentioned Method A, compound (VIII) obtained according to the above-mentioned Method B, compound (VI-A) and compound (XI) obtained according to the above-mentioned Method C, and compound (VI-B), compound (XIV), compound (XVI) and compound (XVIII) obtained according to the above-mentioned Method D can also be modified by subjecting to a known reaction such as condensation reaction (e.g. various acylation reaction, alkylation reaction etc.), oxidation reaction, reduction reaction, dehydration reaction and the like. Such reaction can be carried out according to a known method per se.

The compound (I) obtained according to the above-mentioned Methods can be isolated and purified by a known separation means such as recrystallized, distillation, chromatography and the like.

When compound (I) has an optical isomer, a stereoisomer, a regioisomer or a rotamer, these are also encompassed in compound (I), and can be obtained as a single product according to a synthesis method and separation method known per se (e.g., concentration, solvent extraction, column chromatography, recrystallized etc.). For example, when compound (I) has an optical isomer, the optical isomer resolved from the compound is also encompassed in compound (I).

The optical isomer can be produced according to a method known per se. Specifically, the optical isomer is obtained using an optically active synthetic intermediate or by subjecting the racemic final product to an optical resolution according to a known method.

The method of optical resolution may be a method known per se, such as a fractional recrystallized method, a chiral column method, a diastereomer method etc.

1) Fractional Recrystallized Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallized method, and if desired, a neutralization step to give a free optical isomer.

2) Chiral Column Method

A method wherein a racemate or a salt thereof is applied to a column (a chiral column) for separation of an optical isomer to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine, etc.) as an eluent, solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallized method, a chromatography method etc.) and the like, and is subjected to a chemical treatment such as hydrolysis and the like to separate an optically active reagent moiety, whereby an optical isomer is obtained. For example, when compound (I) contains hydroxy or primary or secondary amino in a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxy group, the compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis.

Compound (I) may be a crystal.

The crystal of compound (I) can be produced according to a crystallization method known per se.

Examples of the crystallization method include crystallization method from a solution, crystallization method from vapor crystallization method from a melt, and the like.

The "crystallization method from a solution" is typically a method of shifting a non-saturated state to supersaturated state by varying factors involved in solubility of compounds (solvent composition, pH, temperature, ionic strength, redox state, etc.) or the amount of solvent. Specific examples thereof include a concentration method, a slow cooling method, a reaction method (a diffusion method, an electrolysis method), a hydrothermal growth method, a flux method and the like. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, etc.), alcohols (e.g., methanol, ethanol, isopropyl alcohol, etc.), water and the like. These solvents are used alone or in a combination of two or more at a suitable ratio (e.g., 1:1 to 1:100 (a volume ratio)). Where necessary, a seed crystal can be used.

The "crystallization method from vapor" is, for example, a vaporization method (a sealed tube method, a gas stream method), a gas phase reaction method, a chemical transportation method and the like.

The "crystallization method from a melt" is, for example, a normal freezing method (a pulling method, a temperature gradient method, a Bridgman method), a zone melting method (a zone leveling method, a floating zone method), a special growth method (a VLS method, a liquid phase epitaxy method) and the like.

Preferable examples of the crystallization method include a method comprising dissolving compound (I) in a suitable solvent (e.g., alcohols such as methanol, ethanol etc.) at about 20° C. to about 120° C., and cooling the obtained solution to a temperature (e.g., about 0 to about 50° C., preferably about 0 to about 20° C.) not higher than the dissolution temperature, and the like.

The thus-obtained crystals of the present invention can be isolated, for example, by filtration and the like.

An analysis method of the obtained crystal is generally a method of crystal analysis by powder X-ray diffraction. As a method of determining crystal orientation, a mechanical method or an optical method and the like can also be used.

The crystal of compound (I) obtained by the above-mentioned production method (hereinafter to be abbreviated as "the crystal of the present invention") has high purity, high quality, and low hygroscopicity, is not denatured even after a long-term preservation under general conditions, and is extremely superior in the stability. In addition, it is also superior in the biological properties (e.g., pharmacokinetics (absorption, distribution, metabolism, excretion), efficacy expression etc.) and is extremely useful as a medicament.

In the present specification, specific optical rotation ([α]D) means a specific optical rotation measured using, for example, polarimeter (JASCO, P-1030 Polarimeter (No. AP-2)) and the like.

In the present specification, the melting point means a melting point measured using, for example, a micro melting point determination apparatus (YANACO, MP-500D), a DSC (differential scanning calorimetry) apparatus (SEIKO, EXSTAR6000) or the like.

Compound (I) may be used as a prodrug. The prodrug of compound (I) means a compound which is converted to compound (I) with a reaction due to an enzyme, gastric acid and the like under the physiological condition in the living body, that is, a compound which is converted to compound (I) by enzymatic oxidation, reduction, hydrolysis and the like; a compound which is converted to compound (I) by hydrolysis and the like due to gastric acid, and the like.

Examples of the prodrug for compound (I) include (1) a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation, tert-butylation, ethoxycarbonylation, tert-butoxycarbonylation, acetylation or cyclopropylcarbonylation, and the like);

(2) a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation, and the like);

(3) a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, and the like) and the like. These compounds can be produced from compound (I) according to a method known per se.

The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, compound (I) and the prodrug of compound (I) are sometimes collectively abbreviated as "the compound of the present invention".

Compound (I) may be a hydrate, a non-hydrate, a solvate or a non-solvate.

Compound (I) also encompasses a compound labeled with an isotope (e.g., $^3H$, $^{14}C$, $^{35}S$, $^{125}I$ etc.) and the like. Compound (I) also encompasses a deuterium conversion form wherein 1H is converted to $^2H(D)$.

Compound (I) also encompasses a tautomer thereof.

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity, solubility and stability etc.). The cocrystal or a salt thereof can be produced according to a cocrystallization a method known per se.

Compound (I) may also be used as a PET tracer.

Since the compound of the present invention has a superior Tyk2 inhibitory action, it is also useful as safe medicaments based on such action.

Since the compound of the present invention has also an IFN-α inhibitory action, IFN-β inhibitory action, IL-6 inhibitory action, IL-10 inhibitory action, IL-19 inhibitory action, IL-20 inhibitory action, IL-22 inhibitory action, IL-28 inhibitory action, IL-29 inhibitory action, IL-12 inhibitory action and/or IL-23 inhibitory action, it is also useful as safe medicaments based on such action.

For example, the medicament of the present invention containing the compound of the present invention can be used for a mammal (e.g., mouse, rat, hamster, rabbit, cat, dog, bovine, sheep, monkey, human etc.) as a prophylactic or therapeutic agent for Tyk2 associated diseases, more specifically, the diseases described in (1)-(4) below.

(1) inflammatory diseases (e.g., acute pancreatitis, chronic pancreatitis, asthma, adult respiratory distress syndrome, chronic obstructive pulmonary disease (COPD), inflammatory bone disease, inflammatory pulmonary disease, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, gastric mucosal injury, meningitis, spondylitis, arthritis, dermatitis, chronic pneumonia, bronchitis, pulmonary infarction, silicosis, pulmonary sarcoidosis etc.), (2) autoimmune diseases (e.g., psoriasis, rheumatoid arthritis, inflammatory bowel disease (e.g., Crohn's disease, ulcerative colitis etc.), Sjogren's syndrome, Behcet's disease, multiple sclerosis, systemic lupus erythematosus, ankylopoietic spondylarthritis, polymyositis, dermatomyositis (DM), polyarteritis nodosa (PN), mixed connective tissue disease (MCTD), scleroderma, profundus lupus erythematosus, chronic thyroiditis, Graves' disease, autoimmune gastritis, type I and type II diabetes, autoimmune hemolytic anemia, autoimmune neutropenia, thrombocytopenia, atopic dermatitis, chronic active hepatitis, myasthenia gravis, graft versus host disease, Addison's disease, abnormal immunoresponse, arthritis, dermatitis, radiodermatitis etc.), (3) osteoarticular degenerative disease (e.g., rheumatoid arthritis, osteoporosis, osteoarthritis etc.), (4) neoplastic diseases [e.g., malignant tumor, angiogenesis glaucoma, infantile hemangioma, multiple myeloma, acute myeloblastic leukemia, chronic sarcoma, multiple myeloma, chronic myelogenous leukemia, metastasis melanoma, Kaposi's sarcoma, vascular proliferation, cachexia, metastasis of the breast cancer, cancer (e.g., colorectal cancer (e.g., familial colorectal cancer, hereditary nonpolyposis colorectal cancer, gastrointestinal stromal tumor etc.), lung cancer (e.g., non-small cell lung cancer, small cell lung cancer, malignant mesothelioma etc.), mesothelioma, pancreatic cancer (e.g., pancreatic duct cancer etc.), gastric cancer (e.g., papillary adenocarcinoma, mucinous adenocarcinoma, adenosquamous carcinoma, etc.), breast cancer (e.g., invasive ductal carcinoma, ductal carcinoma in situ, inflammatory breast cancer etc.), ovarian cancer (e.g., ovarian epithelial carcinoma, extragonadal germ cell tumor, ovarian germ cell tumor, ovarian low malignant potential tumor etc.), prostate cancer (e.g., hormone-dependent prostate cancer, non-hormone dependent prostate cancer etc.), liver cancer (e.g., primary liver cancer, extrahepatic bile duct cancer etc.), thyroid cancer (e.g., medullary thyroid carcinoma etc.), kidney cancer (e.g., renal cell carcinoma, transitional cell carcinoma in kidney and urinary duct etc.), uterine cancer, brain tumor (e.g., pineal astrocytoma, pilocytic astrocytoma, diffuse astrocytoma, anaplastic astrocytoma etc.), melanoma, sarcoma, urinary bladder cancer, hematologic cancer and the like including multiple myeloma, hypophyseal adenoma, glioma, acoustic neurinoma, retinoblastoma, pharyngeal cancer, laryngeal cancer, cancer of the tongue, thymoma, esophagus cancer, duodenal cancer, colorectal cancer, rectal cancer, hepatoma, pancreatic endocrine tumor, bile duct cancer, gallbladder cancer, penile cancer, urinary duct cancer, testis tumor, vulvar cancer, cervix cancer, endometrial cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, acute lymphocytic leukemia, chronic lymphocytic leukemia, adult T cell leukemia, chronic bone marrow proliferative disease, pancreatic endocrine tumor fibrous histiocytoma, leiomyosarcoma, rhabdomyosarcoma, cancer of unknown primary).

The medicament of the present invention can be preferably used as an agent for the prophylaxis or treatment of autoimmune diseases, inflammatory disease, osteoarticular degenerative disease or neoplastic disease, particularly preferably psoriasis, rheumatoid arthritis, inflammatory bowel disease (preferably Crohn's disease or ulcerative colitis), Sjogren's syndrome, Behcet's disease, multiple sclerosis, or systemic lupus erythematosus.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

The medicament of the present invention shows superior pharmacokinetics (e.g., a half-life of the drug in plasma), low toxicity (e.g., HERG inhibition, CYP inhibition, CYP induction), and decreased drug interaction. The compound of the present invention can be directly used as a medicament, or as the medicament of the present invention by producing a pharmaceutical composition by mixing with a pharmaceutically acceptable carrier by a means known per se and generally used in a production method of pharmaceutical preparations. The medicament of the present invention can be orally or parenterally administered safely to mammals (e.g., humans, monkeys, cows, horses, pigs, mice, rats, hamsters, rabbits, cats, dogs, sheep and goats).

A medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal etc.), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, cream, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor and direct administration to the lesion).

The content of the compound of the present invention in the medicament of the present invention is about 0.01 to 100% by weight of the entire medicament. The dose varies depending on administration subject, administration route, disease and the like. For example, for oral administration to patients (body weight about 60 kg) with psoriasis, rheumatoid arthritis, inflammatory bowel disease, Sjogren's syndrome, Behcet's disease, multiple sclerosis or systemic lupus erythematosus, about 0.01 mg/kg body weight-about 500 mg/kg body weight, preferably about 0.1 mg/kg body weight-about 50 mg/kg body weight, more preferably about 1 mg/kg body weight-about 30 mg/kg body weight of an active ingredient (compound (I)) can be administered once to several portions per day.

The pharmaceutically acceptable carrier, which may be used for the production of the medicament of the present invention, may be exemplified by various organic or inorganic carrier materials that are conventionally used as preparation materials, for example, excipient, lubricant, bin ding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidant, colorant, sweetening agent, adsorbing agent, wetting agent and the like can be also used as appropriate in an appropriate amount.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

For the prophylaxis or treatment of various diseases, the compound of the present invention can also be used together with other medicaments. In the following, a medicament to be used when the compound of the present invention is used together with other drug is referred to as "the combination agent of the present invention".

For example, when the compound of the present invention is used as a Tyk2 inhibitor, IFN-α inhibitor, IFN-β inhibitor, IL-6 inhibitor, IL-10 inhibitor, IL-19 inhibitor, IL-20 inhibitor, IL-22 inhibitor, IL-28 inhibitor, IL-29 inhibitor, IL-12 inhibitor and/or IL-23 inhibitor, it can be used together with the following drugs.

(1) non-steroidal anti-inflammatory drug (NSAIDs)
(i) classical NSAIDs alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesylate, camostat mesylate, ulinastatin, colchicine, probenecid, sulfinpyrazone, benzbromarone, allopurinol, sodium aurothiomalate, hyaluronate sodium, sodium salicylate, morphine hydrochloride, salicylic acid, atropine, scopolamine, morphine, pethidine, levorphanol, oxymorphone or a salt thereof and the like.
(ii) cyclooxygenase inhibitor (COX-1 selective inhibitor cox-2 selective inhibitor etc.)
salicylic acid derivatives (e.g., celecoxib, aspirin), etoricoxib, valdecoxib, diclofenac, indomethacin, loxoprofen and the like.
(iii) nitric oxide-releasing NSAIDs.
(iv) JAK inhibitor
tofacitinib, ruxolitinib and the like.
(2) disease-modifying anti-rheumatic drugs (DMARDs)
(i) Gold preparation
auranofin and the like.
(ii) penicillamine
D-penicillamine and the like.
(iii) aminosalicylic acid preparation
sulfasalazine, mesalamine, olsalazine, balsalazide and the like.
(iv) antimalarial drug
chloroquine and the like.
(v) pyrimidine synthesis inhibitor
leflunomide and the like.
(vi) prograf
(3) anti-cytokine drug
(I) protein drug
(i) TNF inhibitor
etanercept, infliximab, adalimumab, certolizumab pegol, golimumab, PASSTNF-α, soluble TNF-α receptor TNF-α binding protein, anti-TNF-α antibody and the like.
(ii) interleukin-1 inhibitor
anakinra (interleukin-1 receptor antagonist), soluble interleukin-1 receptor and the like.
(iii) interleukin-6 inhibitor
tocilizumab (anti-interleukin-6 receptor antibody), anti-interleukin-6 antibody and the like.
(iv) interleukin-10 drug
interleukin-10 and the like.
(v) interleukin-12/23 inhibitor
ustekinumab, briakinumab (anti-interleukin-12/23 antibody) and the like.
(II) non-protein drug
(i) MAPK inhibitor
BMS-582949 and the like.
(ii) gene modulator
inhibitor of molecule involved in signal transduction, such as NF-κ, NF-κB, IKK-1, IKK-2, AP-1 and the like, and the like.
(iii) cytokine production inhibitor
iguratimod, tetomilast and the like.
(iv) TNF-α converting enzyme inhibitor
(v) interleukin-1β converting enzyme inhibitor
VX-765 and the like.
(vi) interleukin-6 antagonist
HMPL-004 and the like.
(vii) interleukin-8 inhibitor
IL-8 antagonist, CXCR1 & CXCR2 antagonist, reparixin and the like.
(viii) chemokine antagonist
CCR9 antagonist (CCX-282, CCX-025), MCP-1 antagonist and the like.
(ix) interleukin-2 receptor antagonist
denileukin, diftitox and the like.
(x) therapeutic vaccines
TNF-α vaccine and the like.
(xi) gene therapy drug
gene therapy drugs aiming at promoting the expression of gene having an anti-inflammatory action such as interleukin-4, interleukin-10, soluble interleukin-1 receptor soluble TNF-α receptor and the like.
(xii) antisense compound
ISIS 104838 and the like.
(4) integrin inhibitor
natalizumab, vedolizumab, AJM300, TRK-170, E-6007 and the like.
(5) immunomodulator (immunosuppressant)
methotrexate, cyclophosphamide, MX-68, atiprimod dihydrochloride, BMS-188667, CKD-461, rimexolone, cyclosporine, tacrolimus, gusperimus, azathiopurine, anti-lymphocyte serum, freeze-dried sulfonated normal immunoglobulin, erythropoietin, colony stimulating factor interleukin, interferon and the like.
(6) steroid
dexamethasone, hexestrol, methimazole, betamethasone, triamcinolone, triamcinolone acetonide, fluocinonide, fluocinolone acetonide, predonisolone, methylpredonisolone, cortisone acetate, hydrocortisone, fluorometholone, beclomethasone dipropionate, estriol and the like.
(7) angiotensin converting enzyme inhibitor
enalapril, captopril, ramipril, lisinopril, cilazapril, perindopril and the like.
(8) angiotensin II receptor antagonist
candesartan, candesartan cilexetil, azilsartan, azilsartan medoxomil, valsartan, irbesartan, olmesartan, eprosartan and the like.
(9) diuretic drug
hydrochlorothiazide, spironolactone, furosemide, indapamide, bendrofluazide, cyclopenthiazide and the like.
(10) cardiotonic drug
digoxin, dobutamine and the like.
(11) β receptor antagonist
carvedilol, metoprolol, atenolol and the like.
(12) Ca sensitizer
$MCC_{1-135}$ and the like.
(13) Ca channel antagonist
nifedipine, diltiazem, verapamil and the like.
(14) anti-platelet drug, anticoagulator
heparin, aspirin, warfarin and the like.
(15) HMG-CoA reductase inhibitor
atorvastatin, simvastatin and the like.
(16) contraceptive
(i) sex hormone or derivatives thereof
gestagen or a derivative thereof (progesterone, 17α-hydroxy progesterone, medroxyprogesterone, medroxyprogesterone acetate, norethisterone, norethisterone enanthate, norethindrone, norethindrone acetate, norethynodrel, levonorgestrel, norgestrel, ethynodiol diacetate, desogestrel, norgestimate, gestodene, progestin, etonogestrel, drospirenone, dienogest, trimegestone, nestorone, chlormadinone acetate, mifepristone, nomegestrol acetate, Org-30659, TX-525, EMM-310525) or a combination agent of a gestagen or a derivative thereof and an estrogen or a derivative thereof (estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethinylestradiol, mestranol) and the like.
(ii) antiestrogen
ormeloxifene, mifepristone, Org-33628 and the like.

(iii) spermatocide
  ushercell and the like.
(17) others
(i) T cell inhibitors
(ii) inosine monophosphate dehydrogenase (IMPDH) inhibitor
  mycophenolate mofetil and the like.
(iii) adhesion molecule inhibitor
  ISIS-2302, selectin inhibitor ELAM-1, VCAM-1, ICAM-1 and the like.
(iv) thalidomide
(v) cathepsin inhibitor
(vi) matrix metalloprotease (MMPs) inhibitor
  V-85546 and the like.
(vii) glucose-6-phosphate dehydrogenase inhibitor
(viii) Dihydroorotate dehydrogenase (DHODH) inhibitor
(ix) phosphodiesterase IV (PDE IV) inhibitor
  roflumilast, CG-1088 and the like.
(x) phospholipase $A_2$ inhibitor
(xi) iNOS inhibitor
  VAS-203 and the like.
(xii) microtubule stimulating drug
  paclitaxel and the like.
(xiii) microtuble inhibitor
  reumacon and the like.
(xiv) MHC class II antagonist
(xv) prostacyclin agonist
  iloprost and the like.
(xvi) CD4 antagonist
  zanolimumab and the like.
(xvii) CD23 antagonist
(xviii) LTB4 receptor antagonist
  DW-1305 and the like.
(xix) 5-lipoxygenase inhibitor
  zileuton and the like.
(xx) cholinesterase inhibitor
  galanthamine and the like.
(xxi) tyrosine kinase inhibitor
  Tyk2 inhibitor (WO2010142752) and the like.
(xxii) cathepsin B inhibitor
(xxiii) adenosine deaminase inhibitor
  pentostatin and the like.
(xxiv) osteogenesis stimulator
(xxv) dipeptidylpeptidase inhibitor
(xxvi) collagen agonist
(xxvii) capsaicin cream
(xxviii) hyaluronic acid derivative
  synvisc (hylan G-F 20), orthovisc and the like.
(xxix) glucosamine sulfate
(xxx) amiprilose
(xxxi) CD-20 inhibitor
  rituximab, ibritumomab, tositumomab, ofatumumab and the like.
(xxxii) BAFF inhibitor
  belimumab, tabalumab, atacicept, A-623 and the like.
(xxxiii) CD52 inhibitor
  alemtuzumab and the like.
(xxxiv) IL-17 inhibitor
  secukinumab (AIN-457), LY-2439821, AMG827 and the like Other concomitant drugs besides the above-mentioned include, for example, antibacterial agent, antifungal agent, antiprotozoal agent, antibiotic, antitussive and expectorant drug, sedative, anesthetic, antiulcer drug, antiarrhythmic agent, hypotensive diuretic drug, anticoagulant, tranquilizer, antipsychotic, antitumor drug, hypolipidemic drug, muscle relaxant, antiepileptic drug, antidepressant, antiallergic drug, cardiac stimulants, therapeutic drug for arrhythmia, vasodilator, vasoconstrictor, hypotensive diuretic, therapeutic drug for diabetes, antinarcotic, vitamin, vitamin derivative, anti-asthmatic, therapeutic agent for pollakisuria/anischuria, antipruritic drug, therapeutic agent for atopic dermatitis, therapeutic agent for allergic rhinitis, hypertensor, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.

(1) Antibacterial agent
(i) sulfa drug
  sulfamethizole, sulfisoxazole, sulfamonomethoxine, sulfamethizole, salazosulfapyridine, silver sulfadiazine and the like.
(ii) quinolone antibacterial agent
  nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin and the like.
(iii) antiphthisic
  isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.
(iv) antiacidfast bacterium drug
  diaphenylsulfone, rifampicin and the like.
(v) antiviral drug
  idoxuridine, acyclovir, vidarabine, gancyclovir and the like.
(vi) anti-HIV agent
  zidovudine, didanosine, zalcitabine, indinavir sulfate ethanolate, ritonavir and the like.
(vii) antispirochetele
(viii) antibiotic
  tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ticarcillin, cephalothin, cephapirin, cephaloridine, cefaclor cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt a salt thereof, griseofulvin, lankacidin-group [Journal of Antibiotics (J. Antibiotics), 38, 877-885(1985)], azole compound [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxyl)phenyl]-3(2H, 4H)-1,2,4-triazolone, fluconazole, itraconazole and the like] and the like.

(2) antifungal agent
(i) polyethylene antibiotic (e.g., amphotericin B, nystatin, trichomycin)
(ii) griseofulvin, pyrrolnitrin and the like
(iii) cytosine metabolism antagonist (e.g., flucytosine)
(iv) imidazole derivative (e.g., econazole, clotrimazole, miconazole nitrate, bifonazole, croconazole)
(v) triazole derivative (e.g., fluconazole, itraconazole)
(vi) thiocarbamic acid derivative (e.g., trinaphthol) and the like.

(3) antiprotozoal agent metronidazole, tinidazole, diethylcarbamazine citrate, quinine hydrochloride, quinine sulfate and the like.

(4) antitussive and expectorant drug ephedrine hydrochloride, noscapine hydrochloride, codeine phosphate, dihydrocodeine phosphate, isoproterenol hydrochloride, methylephedrine hydrochloride, alloclamide, chlophedianol, picoperidamine, cloperastine, protokylol, isoproterenol, salbutamol, terputaline, oxypetebanol, morphine hydrochloride, dextropethorfan hydrobromide, oxycodone hydrochloride, dimorphan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(5) sedative chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(6) anesthetic (6-1) local anesthetic cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine and the like.

(6-2) general anesthetic (i) inhalation anesthetic (e.g., ether, halothane, nitrous oxide, isoflurane, enflurane), (ii) intravenous anesthetic (e.g., ketamine hydrochloride, droperidol, thiopental sodium, thiamylal sodium, pentobarbital) and the like.

(7) antiulcer drug histidine hydrochloride, lansoprazole, metoclopramide, pirenzepine, cimetidine, ranitidine, famotidine, urogastrine, oxethazaine, proglumide, omeprazole, sucralfate, sulpiride, cetraxate, gefarnate, aldioxa, teprenone, prostaglandin and the like.

(8) antiarrhythmic agent (i) sodium channel blocker (e.g., quinidine, procainamide, disopyramide, ajmaline, lidocaine, mexiletine, phenytoin), (ii) β-blocker (e.g., propranolol, alprenolol, bufetolol hydrochloride, oxprenolol, atenolol, acebutolol, metoprolol, bisoprolol, pindolol, carteolol, arotinolol hydrochloride), (iii) potassium channel blocker (e.g., amiodarone), (iv) calcium channel blocker (e.g., verapamil, diltiazem) and the like.

(9) hypotensive diuretic drug hexamethonium bromide, clonidine hydrochloride, hydrochlorothiazide, trichlormethiazide, furosemide, ethacrynic acid, bumetanide, mefruside, azosemide, spironolactone, potassium canrenoate, triamterene, amiloride, acetazolamide, D-mannitol, isosorbide, aminophylline and the like.

(10) anticoagulant heparin sodium, sodium citrate, activated protein C, tissue factor pathway inhibitor antithrombin III, dalteparin sodium, warfarin potassium, argatroban, gabexate, ozagrel sodium, ethyl icosapentate, beraprost sodium, alprostadil, ticlopidine hydrochloride, pentoxifylline, dipyridamole, tisokinase, urokinase, streptokinase and the like.

(11) tranquilizer diazepam, lorazepam, oxazepam, chlordiazepoxide, medazepam, oxazolam, cloxazolam, clotiazepam, bromazepam, etizolam, fludiazepam, hydroxyzine and the like.

(12) antipsychotic chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine and the like.

(13) antitumor drug

6-O-(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, zusulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate and the like.

(14) hypolipidemic drug clofibrate, ethyl 2-chloro-3-[4-(2-methyl-2-phenylpropoxy)phenyl]propionate [Chem. Pharm. Bull, 38, 2792-2796 (1990)], pravastatin, simvastatin, probucol, bezafibrate, clinofibrate, nicomol, cholestyramine, dextran sulfate sodium and the like.

(15) muscle relaxant pridinol, tubocurarine, pancuronium, tolperisone hydrochloride, chlorphenesin carbamate, baclofen, chlormezanone, mephenesin, chlorzoxazone, eperisone, tizanidine and the like.

(16) antiepileptic drug phenytoin, ethosuximide, acetazolamide, chlordiazepoxide, tripetadione, carbamazepine, phenobarbital, primidone, sulthiame, sodium valproate, clonazepam, diazepam, nitrazepam and the like.

(17) antidepressant imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.

(18) antiallergic drug diphenhydramine, chlorpheniramine, tripelennamine, metodilamine, clemizole, diphenylpyraline, methoxyphenamine, sodium cromoglicate, tranilast, repirinast, amlexanox, ibudilast, ketotifen, terfenadine, mequitazine, azelastine hydrochloride, epinastine, ozagrel hydrochloride, pranlukast hydrate, seratrodast and the like.

(19) cardiac stimulants trans-π-oxocamphor terephyllol, aminophylline, etilefrine, dopamine, dobutamine, denopamine, vesinarine, amrinone, pimobendan, ubidecarenone, digitoxin, digoxin, methyldigoxin, lanatoside C, G-strophanthin and the like.

(20) vasodilator oxyfedrine, diltiazem, tolazoline, hexobendine, bamethan, clonidine, methyldopa, guanabenz and the like.

(21) vasoconstrictor dopamine, dobutamine denopamine and the like.

(22) hypotensive diuretic hexamethonium bromide, pentolinium, mecamylamine, ecarazine, clonidine, diltiazem, nifedipine and the like.

(23) therapeutic drug for diabetes tolbutamide, chlorpropamide, acetohexamide, glibenclamide, tolazamide, acarbose, epalrestat, troglitazone, glucagon, glymidine, glipuzide, phenformin, buformin, metformin and the like.

(24) antinarcotic levallorphan, nalorphine, naloxone or a salt thereof and the like.

(25) liposoluble vitamins (i) vitamin A: vitamin $A_1$, vitamin $A_2$ and retinol palmitate
(ii) vitamin D: vitamin $D_1$, $D_2$, $D_3$, $D_4$ and $D_5$
(iii) vitamin E: $\alpha$-tocopherol, $\beta$-tocopherol, $\gamma$-tocopherol, $\delta$-tocopherol, dl-$\alpha$-tocopherol nicotinate
(iv) vitamin K: vitamin $K_1$, $K_2$, $K_3$ and $K_4$
(v) folic acid (vitamin M) and the like.

(26) vitamin derivative various derivatives of vitamins, for example, vitamin $D_3$ derivatives such as 5,6-trans-cholecalciferol, 2,5-hydroxycholecalciferol, 1-$\alpha$-hydroxycholecalciferol and the like, vitamin $D_2$ derivatives such as 5,6-trans-ergocalciferol and the like, and the like.

(27) antiasthmatic isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlkast hydrate, seratrodast, dexamethasone, prednisolone, hydrocortisone, hydrocortisone sodium succinate, beclometasone dipropionate and the like.

(28) therapeutic agent for pollakisuria/anischuria flavoxate hydrochloride and the like.

(29) therapeutic agent for atopic dermatitis sodium cromoglicate and the like.

(30) therapeutic agent for allergic rhinitis sodium cromoglicate, chlorpheniramine maleate, alimemazine tartrate, clemastine fumarate, homochlorcyclizine hydrochloride, fexofenadine, mequitazine and the like.

(31) hypertensor dopamine, dobutamine, denopamine, digitoxin, digoxin, methyldigoxin, lanatoside C, G-strophanthin and the like.

(32) others hydroxycam, diacerein, megestrol acetate, nicergoline, prostaglandins and the like.

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

The dose of the combination agent varies depending on the kind of the compound of the present invention, administration route, symptom, age of patients and the like. For example, for oral administration to patients (body weight about 60 kg) with psoriasis, rheumatoid arthritis, inflammatory bowel disease, Sjogren's syndrome, Behcet's disease, multiple sclerosis or systemic lupus erythematosus, about 0.1 mg/kg body weight-about 50 mg/kg body weight, preferably about 1 mg/kg body weight-30 mg/kg body weight, of compound (I) can be administered once to several portions per day.

The dose of the pharmaceutical composition of the present invention as a sustained-release preparation varies depending on the kind and content of compound (I), dosage form, period of sustained drug release, subject animal of administration (e.g., mammals such as mouse, rat, hamster, guinea pig, rabbit, cat, dog, bovine, horse, swine, sheep, monkey, human etc.), and administration object. For example, for application by parenteral administration, about 0.1 to about 100 mg of compound (I) needs to be released from the administered preparation per 1 week.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times, divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

In Examples, the following abbreviations are used.

BSA: bovine serum albumin
DMSO: dimethyl sulfoxide
DTT: dithiothreitol
EDTA: ethylenediaminetetraacetic acid
EGTA: glycoletherdiaminetetraacetic acid
HEPES: 4-(2-hydroxyethyl)-1-piperazine ethanesulfonic acid
M: mol concentration
SFC: Supercritical fluid chromatography $^1$H NMR (protone nuclear magnetic resonance spectrum) was measured by Fourier-transform type NMR. For the analysis, ACD/SpecManager (trade name) and the like were used. Peaks with very mild protons such as a hydroxy group, an amino group and the like are not described.

MS (mass spectrum) was measured by LC/MS (liquid chromatography mass spectrometer). As ionization method, ESI (Electro Spray Ionization) method or APCI (Atomospheric Pressure Chemical Ionization) method was used. The data indicates those found. Generally, a molecular ion peak is observed. In the case of a salt, a molecular ion peak or fragment ion peak of free form is generally observed.

Example 1

3-ethyl-1-(2-((1-methyl-1H-pyrazol-4-yl)amino)pyrimidin-4-yl)-2-oxopyrrolidine-3-carbonitrile

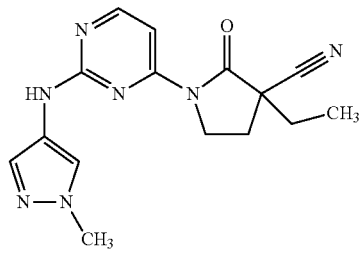 [SMILES: CCC1(C#N)CCN(c2ccnc(Nc3cnn(C)c3)n2)C1=O]

A) 2-(methylsulfanyl)pyrimidin-4 (3H)-one

To 2-thioxo-2,3-dihydropyrimidin-4(1H)-one (21 g) was added dropwise a solution of sodium hydroxide (13 g) in water (120 mL), iodomethane (11.5 mL) was added thereto, and the mixture was stirred overnight at room temperature. To the reaction mixture was added acetic acid (9.5 mL), and the resulting solid was collected by filtration. The obtained solid was washed with cold water to give the title compound (24 g).
$^1$H NMR (300 MHz, DMSO-$d_6$) δ 2.48 (3H, s), 6.09 (1H, d, J=6.4 Hz), 7.87 (1H, d, J=6.8 Hz), 11.83-13.31 (1H, m).

B) 2-((1-methyl-1H-pyrazol-4-yl)amino)pyrimidin-4 (3H)-one

To a solution of 2-(methylsulfanyl)pyrimidin-4(3H)-one (5.2 g) obtained in Step A in diethylene glycol dimethyl ether (50 mL) was added 1-methyl-1H-pyrazol-4-amine (4.1 g), the mixture was stirred overnight at 150° C., and the solvent was evaporated under reduced pressure. The residue was purified by silica gel column chromatography (ethyl acetate/methanol) to give the title compound (5.4 g).
$^1$H NMR (300 MHz, DMSO-$d_6$) δ 3.79 (3H, s), 5.62-5.78 (1H, m), 7.45 (1H, s), 7.63-7.78 (1H, m), 7.89 (1H, s), 8.47-8.75 (1H, m), 10.77 (1H, dd, J=15.5, 8.7 Hz). MS(ESI+): [M+H]$^+$ 192.1.

C) 4-chloro-N-(1-methyl-1H-pyrazol-4-yl)pyrimidin-2-amine

To a solution of 2-((1-methyl-1H-pyrazol-4-yl)amino)pyrimidin-4(3H)-one (3.4 g) obtained in Step B in acetonitrile (35 mL) was added dropwise phosphorus oxychloride (3.2 mL), and the mixture was stirred at 80° C. for 2 hr. The reaction mixture was neutralized with 8M aqueous sodium hydroxide solution, and extracted with ethyl acetate. The organic layer was washed with saturated brine, and dried over anhydrous sodium sulfate, and the solvent was evaporated to give the title compound (3.3 g).
$^1$H NMR (300 MHz, DMSO-$d_6$) δ 3.81 (3H, s), 6.83 (1H, d, J=5.3 Hz), 7.46 (1H, s), 7.85 (1H, s), 8.37 (1H, d, J=5.3 Hz), 9.87 (1H, s).

D) 2-amino-4,5-dihydrofuran-3-carbonitrile

To a solution of malononitrile (6.0 g) and 2-chloroethanol (7.3 g) in methanol (40 mL) was added dropwise a solution of 28% sodium methoxide in methanol (17 mL), and the mixture was stirred at 50° C. for 2 hr. The resulting sodium chloride was removed by filtration through Celite, and the solvent was evaporated under reduced pressure. Ice was added thereto, and the resulting solid was collected by filtration, and washed with cold water to give the title compound (3.5 g).
$^1$H NMR (300 MHz, DMSO-$d_6$) δ 2.59-2.91 (2H, m), 4.17-4.48 (2H, m), 6.93 (2H, brs).

E) N-(3-cyano-4,5-dihydrofuran-2-yl)-4-fluorobenzamide

To a solution of 2-amino-4,5-dihydrofuran-3-carbonitrile (3.5 g) obtained in Step D in pyridine (8 mL) was added dropwise 4-fluorobenzoyl chloride (5.5 g) in an ice bath, and the mixture was stirred at room temperature for 3 hr. The solvent was evaporated under reduced pressure, and to the residue was added dropwise saturated aqueous sodium hydrogen carbonate solution in an ice bath. The resulting solid was collected by filtration, and washed with water to give the title compound (7.1 g).
$^1$H NMR (300 MHz, DMSO-$d_6$) δ 3.00 (2H, t, J=9.2 Hz), 4.53 (2H, t, J=9.2 Hz), 7.37 (2H, t, J=8.9 Hz), 7.88-8.18 (2H, m), 11.16 (1H, s).

F) 1-(4-fluorobenzoyl)-2-oxopyrrolidine-3-carbonitrile

To a solution of N-(3-cyano-4,5-dihydrofuran-2-yl)-4-fluorobenzamide (5.0 g) obtained in Step E in N,N-dimethylformamide (30 mL) was added sodium iodide (6.5 g), and the mixture was stirred at 150° C. for 30 min. The solvent was evaporated under reduced pressure, and to the residue was added ice water. The resulting solid was collected by filtration, and washed with water. The residue was purified by silica gel column chromatography (hexane/ethyl acetate), and the resulting solid was washed with diisopropyl ether to give the title compound (1.3 g).
$^1$H NMR (300 MHz, DMSO-$d_6$) δ 2.28-2.50 (2H, m), 3.74 (1H, td, J=10.6, 6.8 Hz), 3.84-4.04 (1H, m), 4.43 (1H, dd, J=11.3, 8.7 Hz), 7.15-7.39 (2H, m), 7.62-7.86 (2H, m).

G) 3-ethyl-1-(4-fluorobenzoyl)-2-oxopyrrolidine-3-carbonitrile

To a solution of 1-(4-fluorobenzoyl)-2-oxopyrrolidine-3-carbonitrile (1.3 g) obtained in Step F in N,N-dimethylformamide (10 mL) was added sodium hydride (60% in mineral oil, 340 mg) in an ice bath, and the mixture was stirred at the same temperature for 30 min. To the reaction mixture was added dropwise iodoethane (0.90 mL) in an ice bath, and the mixture was stirred at the same temperature for 30 min. To the reaction mixture was added saturated aqueous ammonium chloride solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (1.1 g).
$^1$H NMR (300 MHz, DMSO-$d_6$) δ 1.19 (3H, t, J=7.6 Hz), 1.82 (1H, dq, J=14.3, 7.2 Hz), 2.06-2.33 (2H, m), 2.63 (1H, dt, J=13.3, 6.8 Hz), 4.03 (2H, t, J=6.8 Hz), 7.04-7.20 (2H, m), 7.52-7.84 (2H, m).

H) 3-ethyl-2-oxopyrrolidine-3-carbonitrile

To a solution of 3-ethyl-1-(4-fluorobenzoyl)-2-oxopyrrolidine-3-carbonitrile (1.1 g) obtained in Step G in ethanol (15 mL) was added dropwise 28% aqueous ammonia solution (5 mL), and the mixture was stirred at room temperature for 2 hr. The solvent was evaporated under reduced pressure, and the residue was purified by silica gel column chromatography (hexane/ethyl acetate). The obtained crude crystals were dissolved in diisopropyl ether, and the remaining solid was removed by filtration. The solvent was evaporated under reduced pressure, and the resulting solid was collected by filtration, and washed with diisopropyl ether to give the title compound (82 mg).
$^1$H NMR (300 MHz, CDCl$_3$) δ 1.16 (3H, t, J=7.4 Hz), 1.75 (1H, dq, J=14.2, 7.4 Hz), 1.99-2.31 (2H, m), 2.62 (1H, ddd, J=13.0, 7.9, 4.7 Hz), 3.34-3.46 (1H, m), 3.48-3.62 (1H, m), 5.84 (1H, brs).

I) 3-ethyl-1-(2-((1-methyl-1H-pyrazol-4-yl)amino)pyrimidin-4-yl)-2-oxopyrrolidine-3-carbonitrile To a mixture of 4-chloro-N-(1-methyl-1H-pyrazol-4-yl)pyrimidin-2-amine (110 mg) obtained in Step C, 3-ethyl-2-oxopyrrolidine-3-carbonitrile (82 mg) obtained in Step H, cesium carbonate (350 mg) and 4,5-bis(diphenylphosphino)-9,9-dimethylxanthene (19 mg) in tetrahydrofuran (3 mL) was added tris(dibenzylideneacetone)dipalladium(0) (10 mg), and the mixture was stirred overnight at 90° C. The insoluble substance was removed by filtration through Celite, and the solvent was evaporated under reduced pressure. The residue was purified by silica gel column chromatography (hexane/ethyl acetate), and recrystallized (hexane/ethyl acetate) to give the title compound (87 mg)
$^1$H NMR (300 MHz, DMSO-$d_6$) δ 1.08 (3H, t, J=7.6 Hz), 1.80-2.07 (2H, m), 2.36 (1H, ddd, J=12.7, 7.6, 4.7 Hz), 2.61 (1H, dt, J=12.8, 7.7 Hz), 3.32 (3H, s), 3.93-4.30 (2H, m), 7.45-7.53 (2H, m), 7.81 (1H, brs), 8.35 (1H, d, J=5.7 Hz), 9.52 (1H, brs).
MS(ESI+): [M+H]$^+$ 312.2.

Example 2

3-ethyl-1-(2-((4-(morpholin-4-yl)phenyl)amino)pyrimidin-4-yl)-2-oxopyrrolidine-3-carbonitrile

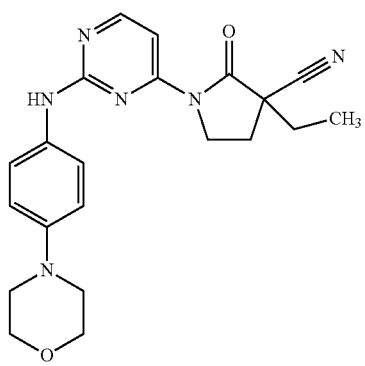 [SMILES: CCC1(C#N)CCN(c2ccnc(Nc3ccc(N4CCOCC4)cc3)n2)C1=O]

A) 1-(2-chloropyrimidin-4-yl)-3-ethyl-2-oxopyrrolidine-3-carbonitrile

To a mixture of 3-ethyl-2-oxopyrrolidine-3-carbonitrile (40 mg) obtained in Step H of Example 1, 2,4-dichloropyrimidine (86 mg), cesium carbonate (190 mg) and 4,5-bis(diphenylphosphino)-9,9-dimethylxanthene (10 mg) in tetrahydrofuran (1 mL) was added tris(dibenzylideneacetone)dipalladium(0) (5 mg), and the mixture was stirred overnight at 100° C. The insoluble substance was removed by filtration through Celite, and the solvent was evaporated under reduced pressure. The residue was purified by silica gel column chromatography (hexane/ethyl acetate) to give the title compound (46 mg).

MS(ESI+): [M+H]$^+$ 251.1.

B) 3-ethyl-1-(2-((4-(morpholin-4-yl)phenyl)amino)pyrimidin-4-yl)-2-oxopyrrolidine-3-carbonitrile A mixture of 1-(2-chloropyrimidin-4-yl)-3-ethyl-2-oxopyrrolidine-3-carbonitrile (42 mg) obtained in Step A, 4-(morpholin-4-yl)aniline (39 mg) and acetic acid (11 μL) in 1-butanol (2 mL) was stirred in a microwave reactor at 160° C. for 1 hr. The reaction mixture was concentrated under reduced pressure, to the residue was added saturated aqueous sodium hydrogen carbonate solution, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate), and recrystallized (hexane/ethyl acetate) to give the title compound (30 mg).

$^1$H NMR (300 MHz, CDCl$_3$) δ 1.20 (3H, t, J=7.6 Hz), 1.83 (1H, dq, J=14.3, 7.2 Hz), 2.08-2.31 (2H, m), 2.52-2.68 (1H, m), 3.07-3.17 (4H, m), 3.83-3.91 (4H, m), 4.05-4.17 (2H, m), 6.86-6.98 (3H, m), 7.44 (2H, d, J=9.1 Hz), 7.68 (1H, d, J=5.7 Hz), 8.32 (1H, d, J=5.7 Hz).

MS(ESI+): [M+H]$^+$ 393.3.

Example 3

(3S)-3-ethyl-1-(2-((4-(morpholin-4-yl)phenyl)amino)pyrimidin-4-yl)-2-oxopyrrolidine-3-carbonitrile

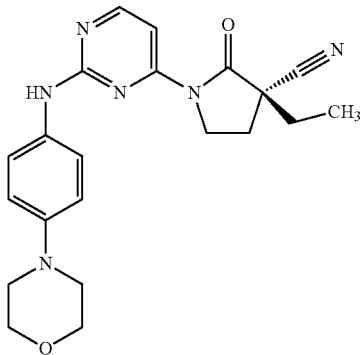 [SMILES: CC[C@@]1(C#N)CCN(c2ccnc(Nc3ccc(N4CCOCC4)cc3)n2)C1=O]

3-Ethyl-1-(2-((4-(morpholin-4-yl)phenyl)amino)pyrimidin-4-yl)-2-oxopyrrolidine-3-carbonitrile (200 mg) obtained in Example 2 was resolved by SFC (column: CHIRALCEL OJH, 20 mmID×250 mmL, manufactured by Daicel Chemical Industries, mobile phase: carbon dioxide/methanol/acetonitrile=660/170/170), and the compound having a shorter retention time was recrystallized (hexane/ethyl acetate) to give the title compound (47 mg).

$^1$H NMR (300 MHz, CDCl$_3$) δ 1.20 (3H, t, J=7.4 Hz), 1.73-1.90 (1H, m), 2.07-2.27 (2H, m), 2.54-2.67 (1H, m), 3.08-3.18 (4H, m), 3.80-3.92 (4H, m), 4.04-4.18 (2H, m), 6.87-6.96 (3H, m), 7.44 (2H, d, J=9.1 Hz), 7.68 (1H, d, J=5.7 Hz), 8.33 (1H, d, J=5.7 Hz).

MS(ESI+): [M+H]$^+$ 393.3.
>99% ee (SFC (column: CHIRALCEL OJH, 4.6 mmID×150 mmL, manufactured by Daicel Chemical Industries, mobile phase: carbon dioxide/methanol/acetonitrile=600/200/200, flow rate: 4 mL/min, retention time: 2.67 min))

Example 4

(3R)-3-ethyl-1-(2-((4-(morpholin-4-yl)phenyl)amino)pyrimidin-4-yl)-2-oxopyrrolidine-3-carbonitrile

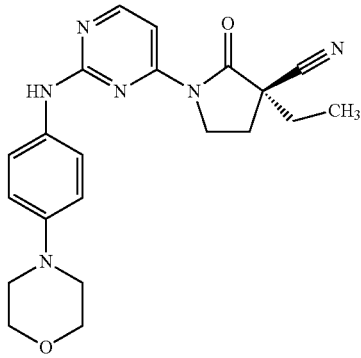 [SMILES: CC[C@]1(C#N)CCN(c2ccnc(Nc3ccc(N4CCOCC4)cc3)n2)C1=O]

3-Ethyl-1-(2-((4-(morpholin-4-yl)phenyl)amino)pyrimidin-4-yl)-2-oxopyrrolidine-3-carbonitrile (200 mg) obtained in Example 2 was resolved by SFC (column: CHIRALCEL OJH, 20 mmID×250 mmL, manufactured by Daicel Chemical Industries, mobile phase: carbon dioxide/methanol/acetonitrile=660/170/170), and the compound having a longer retention time was recrystallized (hexane/ethyl acetate) to give the title compound (58 mg).

$^1$H NMR (300 MHz, CDCl$_3$) δ 1.20 (3H, t, J=7.4 Hz), 1.73-1.90 (1H, m), 2.07-2.30 (2H, m), 2.52-2.68 (1H, m), 3.06-3.18 (4H, m), 3.81-3.91 (4H, m), 4.06-4.16 (2H, m), 6.85-6.96 (3H, m), 7.44 (2H, d, J=9.1 Hz), 7.68 (1H, d, J=5.7 Hz), 8.33 (1H, d, J=5.7 Hz).

MS(ESI+): [M+H]$^+$ 393.3.
>99% ee (SFC (column: CHIRALCEL OJH, 4.6 mmID×150 mmL, manufactured by Daicel Chemical Industries, mobile phase: carbon dioxide/methanol/acetonitrile=600/200/200, flow rate: 4 mL/min, retention time: 3.42 min))

Example 5

3-isopropyl-1-(2-((4-(morpholin-4-yl)phenyl)amino)pyrimidin-4-yl)-2-oxopyrrolidine-3-carbonitrile

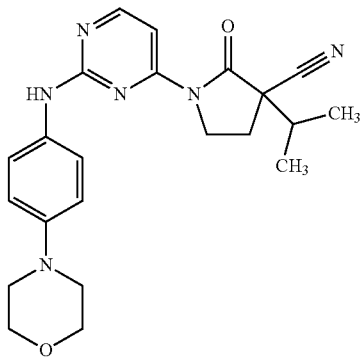 [SMILES: CC(C)C1(C#N)CCN(c2ccnc(Nc3ccc(N4CCOCC4)cc3)n2)C1=O]

A) 1-(4-fluorobenzoyl)-3-isopropyl-2-oxopyrrolidine-3-carbonitrile

To a solution of 1-(4-fluorobenzoyl)-2-oxopyrrolidine-3-carbonitrile (500 mg) obtained in Step F of Example 1 in N,N-dimethylformamide (5 mL) was added sodium hydride (60% in mineral oil, 130 mg) in an ice bath, and the mixture was stirred at the same temperature for 5 min. To the reaction mixture was added 2-iodopropane (1.1 mL) in an ice bath, and the mixture was stirred at 50° C. for 1 hr. To the reaction mixture was added 10% aqueous citric acid solution in an ice bath, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give the title compound (310 mg).

MS(ESI+): [M+H]$^+$ 275.2.

B) 3-isopropyl-2-oxopyrrolidine-3-carbonitrile

To a solution of 1-(4-fluorobenzoyl)-3-isopropyl-2-oxopyrrolidine-3-carbonitrile (280 mg) obtained in Step A in tetrahydrofuran (3 mL) was added n-octylamine (180 μL), and the mixture was stirred overnight at room temperature. To the reaction mixture was added n-octylamine (168 μL) at room temperature, and the mixture was stirred at 50° C. for 5 hr. The reaction mixture was concentrated under reduced pressure, and the residue was purified by silica gel column chromatography (hexane/ethyl acetate) to give the title compound (120 mg).

MS(ESI+): [M+H]$^+$ 152.9.

C) 1-(2-chloropyrimidin-4-yl)-3-isopropyl-2-oxopyrrolidine-3-carbonitrile

To a mixture of 3-isopropyl-2-oxopyrrolidine-3-carbonitrile (120 mg) obtained in Step B, 2,4-dichloropyrimidine (240 mg), cesium carbonate (510 mg) and 4,5-bis(diphenylphosphino)-9,9-dimethylxanthene (27 mg) in tetrahydrofuran (3 mL) was added tris(dibenzylideneacetone)dipalladium(0) (14 mg), and the mixture was stirred overnight at 100° C. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate) to give the title compound (160 mg).

MS(ESI+): [M+H]$^+$ 265.2.

D) 3-isopropyl-1-(2-((4-(morpholin-4-yl)phenyl)amino)pyrimidin-4-yl)-2-oxopyrrolidine-3-carbonitrile A solution of 1-(2-chloropyrimidin-4-yl)-3-isopropyl-2-oxopyrrolidine-3-carbonitrile (100 mg) obtained in Step C, 4-(morpholin-4-yl)aniline (77 mg) and acetic acid (25 jL) in 1-butanol (2 mL) was stirred in a microwave reactor at 160° C. for 1 hr. The reaction mixture was concentrated under reduced pressure, saturated aqueous sodium hydrogen carbonate solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate), and recrystallized (hexane/ethyl acetate) to give the title compound (54 mg).

$^1$H NMR (300 MHz, CDCl$_3$) δ 1.06 (3H, d, J=6.8 Hz), 1.24 (3H, d, J=6.8 Hz), 2.23-2.56 (3H, m), 3.07-3.17 (4H, m), 3.81-3.91 (4H, m), 4.09 (2H, t, J=7.0 Hz), 6.84-6.97 (3H, m), 7.44 (2H, d, J=9.1 Hz), 7.70 (1H, d, J=5.7 Hz), 8.33 (1H, d, J=5.7 Hz). MS(ESI+): [M+H]$^+$ 407.3.

Example 6

(3R)-3-isopropyl-1-(2-((4-(morpholin-4-yl)phenyl)amino)pyrimidin-4-yl)-2-oxopyrrolidine-3-carbonitrile

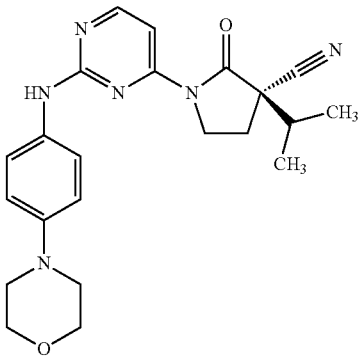 [SMILES: CC(C)[C@@]1(C#N)CCN(c2ccnc(Nc3ccc(N4CCOCC4)cc3)n2)C1=O]

3-Isopropyl-1-(2-((4-(morpholin-4-yl)phenyl)amino)pyrimidin-4-yl)-2-oxopyrrolidine-3-carbonitrile (85 mg) obtained in Example 5 was resolved by SFC (column: CHIRALCEL OJH, 20 mmID×250 mmL, manufactured by Daicel Chemical Industries, mobile phase: carbon dioxide/methanol/acetonitrile=660/170/170), and the compound having a shorter retention time was recrystallized (hexane/ethyl acetate) to give the title compound (13 mg).

$^1$H NMR (300 MHz, CDCl$_3$) δ 1.06 (3H, d, J=6.8 Hz), 1.25 (3H, s), 2.24-2.55 (3H, m), 3.09-3.18 (4H, m), 3.84-3.92 (4H, m), 4.09 (2H, t, J=7.0 Hz), 6.89-6.96 (3H, m), 7.44 (2H, d, J=8.7 Hz), 7.70 (1H, d, J=5.7 Hz), 8.33 (1H, d, J=5.7 Hz).

MS(ESI+): [M+H]$^+$ 407.3.

>99% ee (SFC (column: CHIRALCEL OJH, 4.6 mmID×150 mmL, manufactured by Daicel Chemical Industries, mobile phase: carbon dioxide/methanol/acetonitrile=600/200/200, flow rate: 4 mL/min, retention time: 1.82 min))

Example 7

(3S)-3-isopropyl-1-(2-((4-(morpholin-4-yl)phenyl)amino)pyrimidin-4-yl)-2-oxopyrrolidine-3-carbonitrile

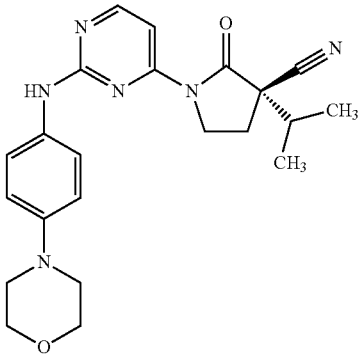 [SMILES: CC(C)[C@]1(C#N)CCN(c2ccnc(Nc3ccc(N4CCOCC4)cc3)n2)C1=O]

3-Isopropyl-1-(2-((4-(morpholin-4-yl)phenyl)amino)pyrimidin-4-yl)-2-oxopyrrolidine-3-carbonitrile (85 mg) obtained in Example 5 was resolved by SFC (column: CHIRALCEL OJH, 20 mmID×250 mmL, manufactured by Daicel Chemical Industries, mobile phase: carbon dioxide/methanol/acetonitrile 660/170/170), and the compound having a longer retention time was recrystallized (hexane/ethyl acetate) to give the title compound (9 mg).

$^1$H NMR (300 MHz, CDCl$_3$) δ 1.06 (3H, d, J=6.8 Hz), 1.24 (3H, d, J=6.8 Hz), 2.23-2.56 (3H, m), 3.08-3.17 (4H, m), 3.82-3.91 (4H, m), 4.09 (2H, t, J=7.0 Hz), 6.87-6.95 (3H, m), 7.44 (2H, d, J=9.1 Hz), 7.70 (1H, d, J=5.7 Hz), 8.33 (1H, d, J=5.7 Hz).

MS(ESI+): [M+H]-407.3.

>99% ee (SFC (column: CHIRALCEL OJH, 4.6 mmID×150 mmL, manufactured by Daicel Chemical Industries, mobile phase: carbon dioxide/methanol/acetonitrile=600/200/200, flow rate: 4 mL/min, retention time: 2.49 min))

Example 8

4-((4-((3R)-3-cyano-3-ethyl-2-oxopyrrolidin-1-yl)pyrimidin-2-yl)amino)-N-methylbenzamide

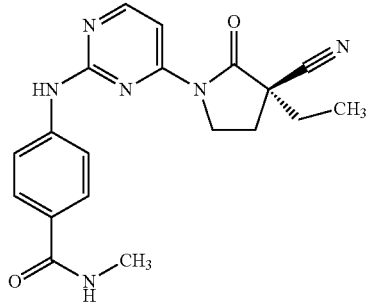 [SMILES: CC[C@]1(C#N)CCN(c2ccnc(Nc3ccc(C(=O)NC)cc3)n2)C1=O]

A) (3R)-1-(2-chloropyrimidin-4-yl)-3-ethyl-2-oxopyrrolidine-3-carbonitrile 1-(2-Chloropyrimidin-4-yl)-3-ethyl-2-oxopyrrolidine-3-carbonitrile (7.8 g) obtained in Step A of Example 2 was resolved by HPLC (column: CHIRALPAK IC, 50 mmID×500 mmL, manufactured by Daicel Chemical Industries, mobile phase: hexane/2-propanol=200/800) to give the title compound (3.5 g) having a shorter retention time.

MS(ESI+): [M+H]$^+$ 251.2.

>99.9% ee (HPLC (column: CHIRALPAK IC, 4.6 mmID×250 mmL, manufactured by Daicel Chemical Industries, mobile phase: hexane/2-propanol=200/800, flow rate: 0.5 mL/min, retention time: 18.5 min))

$[α]_D^{25}$ −2.9 (c 0.39, chloroform)

B) 4-((4-((3R)-3-cyano-3-ethyl-2-oxopyrrolidin-1-yl)pyrimidin-2-yl)amino)-N-methylbenzamide A solution of (3R)-1-(2-chloropyrimidin-4-yl)-3-ethyl-2-oxopyrrolidine-3-carbonitrile (51 mg), 4-amino-N-methylbenzamide (32 mg) and acetic acid (12 μL) in 2-propanol (1 mL) was stirred in a microwave reactor at 150° C. for 1 hr. The reaction mixture was concentrated under reduced pressure, saturated aqueous sodium hydrogen carbonate solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (hexane/ethyl acetate), and recrystallized (hexane/ethyl acetate) to give the title compound (31 mg).

$^1$H NMR (300 MHz, CDCl$_3$) δ 1.15-1.26 (3H, m), 1.77-1.95 (1H, m), 2.10-2.34 (2H, m), 2.59-2.72 (1H, m), 2.96-3.08 (3H, m), 4.15 (2H, t, J=6.6 Hz), 6.11 (1H, brs), 7.29 (1H, brs), 7.61-7.69 (2H, m), 7.73-7.85 (3H, m), 8.35-8.45 (1H, m).

MS(ESI+): [M+H]$^+$ 365.3.

Example 9

4-((4-((3S)-3-cyano-3-isopropyl-2-oxopyrrolidin-1-yl)pyrimidin-2-yl)amino)-N-methylbenzamide hydrochloride

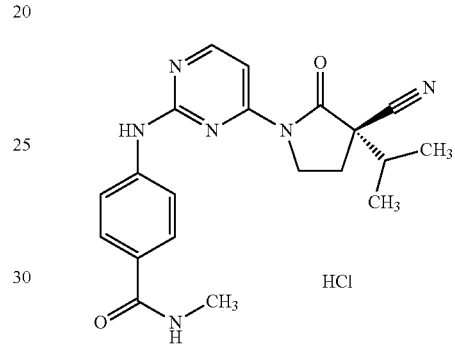

A) (3S)-1-(2-chloropyrimidin-4-yl)-3-isopropyl-2-oxopyrrolidine-3-carbonitrile 1-(2-Chloropyrimidin-4-yl)-3-isopropyl-2-oxopyrrolidine-3-carbonitrile (14.1 g) obtained in Step C of Example 5 was resolved by HPLC (column: CHIRALPAK IC, 50 mmID×500 mmL, manufactured by Daicel Chemical Industries, mobile phase: hexane/2-propanol=200/800) to give the title compound (6.9 g) having a shorter retention time.

MS(ESI+): [M+H]$^+$ 265.2.

>99.9% ee (HPLC (column: CHIRALPAK IC, 4.6 mmID×250 mmL, manufactured by Daicel Chemical Industries, mobile phase: hexane/2-propanol=200/800, flow rate: 0.5 mL/min, retention time: 17.1 min))

$[α_D]^{25}$−31.0 (c 0.41, chloroform)

B) 4-((4-((3S)-3-cyano-3-isopropyl-2-oxopyrrolidin-1-yl) pyrimidin-2-yl)amino)-N-methylbenzamide hydrochloride A solution of (3S)-1-(2-chloropyrimidin-4-yl)-3-isopropyl-2-oxopyrrolidine-3-carbonitrile (55 mg) obtained in Step A, 4-amino-N-methylbenzamide (37 mg) and acetic acid (13 μL) in ethanol (2 mL) was stirred in a microwave reactor at 150° C. for 1 hr, and the solvent was evaporated under reduced pressure. The obtained residue was purified by silica gel column chromatography (NH, hexane/ethyl acetate). To a solution of the residue (87 mg) in ethanol (3 mL) was added 1M hydrochloric acid (230 μL), and the solvent was evaporated under reduced pressure. The residue was recrystallized (diisopropyl ether/ethanol) to give the title compound (65 mg).

¹H NMR (300 MHz, DMSO-d₆) 1.02 (3H, d, J=6.8 Hz), 1.12 (3H, d, J=6.8 Hz), 2.33 (1H, dt, J=13.6, 6.8 Hz), 2.40-2.48 (1H, m), 2.53-2.63 (1H, m), 2.77 (3H, d, J=4.2 Hz), 3.95-4.21 (2H, m), 7.68 (1H, d, J=5.7 Hz), 7.80 (4H, s), 8.28 (1H, d, J=4.2 Hz), 8.49 (1H, d, J=5.7 Hz), 9.98 (1H, s).
MS(ESI+): [M+H]⁺ 379.3.

Example 10

3,3-diethyl-1-(2-((1-methyl-1H-pyrazol-4-yl)amino)pyrimidin-4-yl)pyrrolidin-2-one hydrochloride

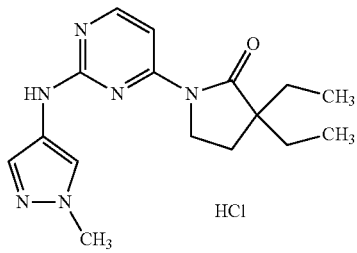 [SMILES: CCC1(CC)CCN(c2ccnc(Nc3cnn(C)c3)n2)C1=O ; Cl]

To a mixture of 4-chloro-N-(1-methyl-1H-pyrazol-4-yl)pyrimidin-2-amine (150 mg) obtained in Step C of Example 1, 3,3-diethylpyrrolidin-2-one (110 mg), cesium carbonate (700 mg) and 2,2'-bis(diphenylphosphino)-1,1'-binaphthyl (90 mg) in tetrahydrofuran (5 mL) was added tris(dibenzylideneacetone)dipalladium(0) (130 mg), and the mixture was stirred in a microwave reactor at 130° C. for 1.5 hr. The insoluble substance was removed by filtration through Celite, and the solvent was evaporated under reduced pressure. The residue was purified by silica gel column chromatography (hexane/ethyl acetate), to a solution of the residue in ethanol (5 mL) was added 12M hydrogen chloride ethanol solution (1 mL), and the mixture was stirred at room temperature for 5 min. The solvent was evaporated under reduced pressure, and the obtained crude crystals were recrystallized (ethanol/ethyl acetate) to give the title compound (76 mg).
MS(ESI+): [M+H]⁺ 315.2.

Example 11

3,3-dimethyl-1-(2-((1-methyl-1H-pyrazol-4-yl)amino)pyrimidin-4-yl)pyrrolidin-2-one hydrochloride

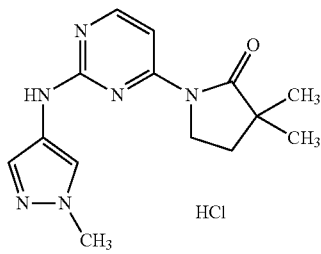 [SMILES: Cn1cc(Nc2nccc(N3CCC(C)(C)C3=O)n2)cn1 ; Cl]

The title compound was obtained from 4-chloro-N-(1-methyl-1H-pyrazol-4-yl)pyrimidin-2-amine obtained in Step C of Example 1 and 3,3-dimethylpyrrolidin-2-one in the same manner as in Example 10.
MS(ESI+): [M+H]⁺ 387.2.

Example 12

1-(2-((1-methyl-H-pyrazol-4-yl)amino)pyrimidin-4-yl)pyrrolidin-2-one

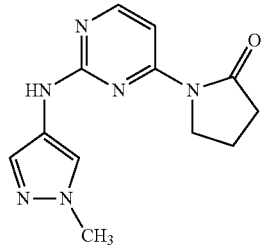 [SMILES: Cn1cc(Nc2nccc(N3CCCC3=O)n2)cn1]

The title compound was obtained from 4-chloro-N-(1-methyl-1H-pyrazol-4-yl)pyrimidin-2-amine obtained in Step C of Example 1 and pyrrolidin-2-one in the same manner as in Example
MS(ESI+): [M+H]⁺ 259.2.

Example 13

3-methyl-1-(2-((1-methyl-1H-pyrazol-4-yl)amino)pyrimidin-4-yl)pyrrolidin-2-one

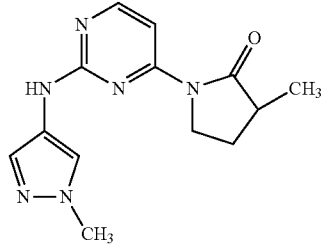 [SMILES: CC1CCN(c2ccnc(Nc3cnn(C)c3)n2)C1=O]

A) 1-(2-chloropyrimidin-4-yl)pyrrolidin-2-one

To a mixture of 2,4-dichloropyrimidine (2.6 g), pyrrolidin-2-one (1.0 g), cesium carbonate (11 g) and 2,2'-bis(diphenylphosphino)-1,1'-binaphthyl (370 mg) in toluene (10 mL) was added tris(dibenzylideneacetone)dipalladium(0) (540 mg), and the mixture was stirred in a microwave reactor at 110° C. for 1.5 hr. The insoluble substance was removed by filtration through Celite, and the solvent was evaporated under reduced pressure. The residue was purified by silica gel column chromatography (hexane/ethyl acetate) to give the title compound (370 mg).
¹H NMR (300 MHz, DMSO-d₆) δ 5 2.00-2.15 (2H, m), 2.63 (2H, t, J=8.1 Hz), 3.82-3.98 (2H, m), 8.27 (1H, d, J=6.0 Hz), 8.58 (1H, d, J=6.0 Hz).

B) 1-(2-chloropyrimidin-4-yl)-3-methylpyrrolidin-2-one

To a solution of diisopropylamine (0.79 mL) in tetrahydrofuran (5 mL) was added dropwise n-butyllithium (1.6 M hexane solution, 3.5 mL) at −78° C. under nitrogen atmosphere, and the mixture was warmed to 0° C., and stirred for 30 min. The reaction mixture was cooled to −78° C., and 1-(2-chloropyrimidin-4-yl)pyrrolidin-2-one (370 mg) obtained in Step A was added thereto. The reaction mixture was stirred at the same temperature for 1 hr, iodomethane (0.35 mL) was added thereto, and the mixture was stirred overnight while it was allowed to be warmed. To the reaction mixture was added saturated aqueous ammonium chloride solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (38 mg).

$^1$H NMR (300 MHz, CDCl$_3$) δ 1.31 (3H, d, J=7.2 Hz), 1.77 (1H, dq, J=12.8, 9.3 Hz), 2.31-2.50 (1H, m), 2.66-2.85 (1H, m), 3.84 (1H, ddd, J=11.6, 9.3, 7.4 Hz), 4.17 (1H, ddd, J=11.4, 8.8, 2.8 Hz), 8.35 (1H, d, J=5.7 Hz), 8.44 (1H, d, J=6.0 Hz).

MS(ESI+): [M+H]$^+$ 212.1.

C) 3-methyl-1-(2-((1-methyl-1H-pyrazol-4-yl)amino)pyrimidin-4-yl)pyrrolidin-2-one The title compound was obtained from 1-(2-chloropyrimidin-4-yl)-3-methylpyrrolidin-2-one obtained in Step B and 1-methyl-1H-pyrazol-4-amine in the same manner as in Step B of Example 2.

MS(ESI+): [M+H]$^+$ 273.2.

Example 14

3,3-diethyl-1-(2-((4-(morpholin-4-yl)phenyl)amino)pyrimidin-4-yl) pyrrolidin-2-one

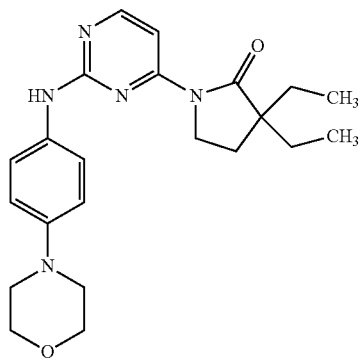 [SMILES: CCC1(CC)CCN(c2ccnc(Nc3ccc(N4CCOCC4)cc3)n2)C1=O]

A) 1-(2-chloropyrimidin-4-yl)-3,3-diethylpyrrolidin-2-one

The title compound was obtained from 2,4-dichloropyrimidine and 3,3-diethylpyrrolidin-2-one in the same manner as in Step A of Example 2.

$^1$H NMR (300 MHz, CDCl$_3$) δ 0.91 (6H, t, J=7.6 Hz), 1.65 (4H, q, J=7.3 Hz), 1.93-2.09 (2H, m), 3.88-4.05 (2H, m), 8.35-8.41 (1H, m), 8.42-8.47 (1H, m).

B) 3,3-diethyl-1-(2-((4-(morpholin-4-yl)phenyl)amino)pyrimidin-4-yl) pyrrolidin-2-one The title compound was obtained from 1-(2-chloropyrimidin-4-yl)-3,3-diethylpyrrolidin-2-one obtained in Step A and 4-(morpholin-4-yl)aniline in the same manner as in Step B of Example 2.

MS(ESI+): [M+H]$^+$ 396.3.

Examples 15 to 28

In Examples 15 to 28, the title compound was obtained from 1-(2-chloropyrimidin-4-yl)-3,3-diethylpyrrolidin-2-one obtained in Step A of Example 14, and aniline, 3-aminobenzenesulfonamide, 3-(methylsulfonyl) aniline, (3-aminophenyl)methanol, 3-(morpholin-4-yl) aniline, 3-aminobenzonitrile, 4-aminobenzenesulfonamide, 3-aminobenzamide, 1-(tetrahydro-2H-pyran-4-yl)-1H-pyrazol-4-amine, 1H-pyrazol-4-amine, 4-(4-methylpiperazin-1-yl) aniline, 4-(piperidin-1-yl)aniline, N,N-dimethylbenzene-1,4-diamine or 1-methyl-1H-pyrazol-3-amine (these compounds can be produced according to a method known per se), each corresponding to the compounds of Examples 15 to 28, in the same manner as in Step B of Example 2. MS in the tables means actual measured value.

TABLE 1-1

| Example Number | IUPAC Name | Structure | Salt | MS |
|---|---|---|---|---|
| 15 | 1-(2-anilino-pyrimidin-4-yl)-3,3-diethyl-pyrrolidin-2-one | 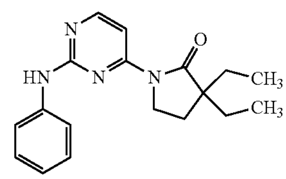 [SMILES: CCC1(CC)CCN(c2ccnc(Nc3ccccc3)n2)C1=O] | Free | 311.2 |
| 16 | 3-((4-(3,3-diethyl-2-oxo-pyrrolidin-1-yl)pyrimidin-2-yl)amino)benzenesulfonamide | 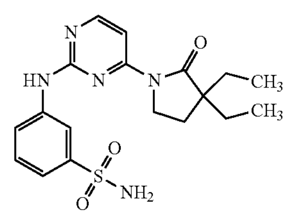 [SMILES: CCC1(CC)CCN(c2ccnc(Nc3cccc(S(N)(=O)=O)c3)n2)C1=O] | Free | 390.3 |
| 17 | 3,3-diethyl-1-(2-((3-(methyl-sulfonyl)phenyl)amino)pyrimidin-4-yl)pyrrolidin-2-one | 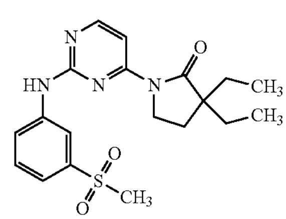 [SMILES: CCC1(CC)CCN(c2ccnc(Nc3cccc(S(C)(=O)=O)c3)n2)C1=O] | Free | 389.3 |
| 18 | 3,3-diethyl-1-(2-((3-(hydroxy-methyl)phenyl)amino)pyrimidin-4-yl)pyrrolidin-2-one | 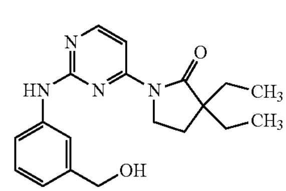 [SMILES: CCC1(CC)CCN(c2ccnc(Nc3cccc(CO)c3)n2)C1=O] | Free | 341.2 |

TABLE 1-1-continued

| Example Number | IUPAC Name | Structure | Salt | MS |
|---|---|---|---|---|
| 19 | 3,3-diethyl-1-(2-((3-(morpholin-4-yl)phenyl)amino)pyrimidin-4-yl)pyrrolidin-2-one | 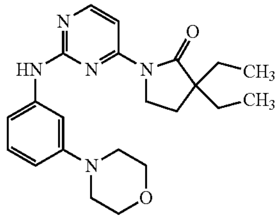 [SMILES: CCC1(CC)CCN(c2ccnc(Nc3cccc(N4CCOCC4)c3)n2)C1=O] | HCl | 396.3 |
| 20 | 3-((4-(3,3-diethyl-2-oxo-pyrrolidin-1-yl)pyrimidin-2-yl)amino)benzonitrile | 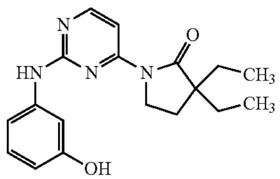 [SMILES: CCC1(CC)CCN(c2ccnc(Nc3cccc(O)c3)n2)C1=O] | Free | 336.3 |
| 21 | 4-((4-(3,3-diethyl-2-oxo-pyrrolidin-1-yl)pyrimidin-2-yl)amino)benzenesulfonamide | 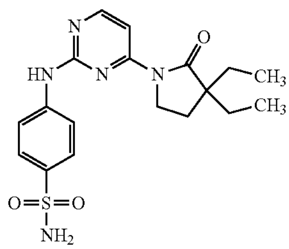 [SMILES: CCC1(CC)CCN(c2ccnc(Nc3ccc(S(N)(=O)=O)cc3)n2)C1=O] | Free | 390.2 |
| 22 | 3-((4-(3,3-diethyl-2-oxo-pyrrolidin-1-yl)pyrimidin-2-yl)amino)benzamide | 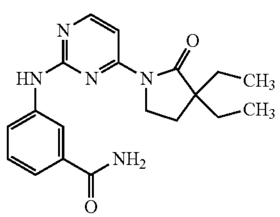 [SMILES: CCC1(CC)CCN(c2ccnc(Nc3cccc(C(N)=O)c3)n2)C1=O] | Free | 354.2 |

TABLE 1-2

| Example Number | IUPAC Name | Structure | Salt | MS |
|---|---|---|---|---|
| 23 | 3,3-diethyl-1-(2-((1-(tetrahydro-2H-pyran-4-yl)-1H-pyrazol-4-yl)amino)pyrimidin-4-yl)pyrrolidin-2-one | | Free | 385.3 |
| 24 | 3,3-diethyl-1-(2-(1H-pyrazol-4-ylamino)pyrimidin-4-yl)pyrrolidin-2-one | | HCl | 301.2 |
| 25 | 3,3-diethyl-1-(2-((4-(4-methyl-piperazin-1-yl)phenyl)amino)pyrimidin-4-yl)pyrrolidin-2-one | 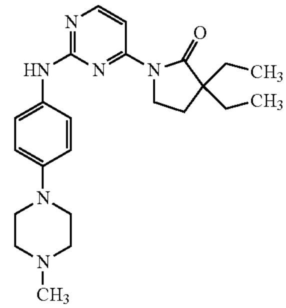 [SMILES: CCC1(CC)CCN(c2ccnc(Nc3ccc(N4CCN(C)CC4)cc3)n2)C1=O] | 2HCl | 409.4 |
| 26 | 3,3-diethyl-1-(2-((4-(piperidin-1-yl)phenyl)amino)pyrimidin-4-yl)pyrrolidin-2-one | 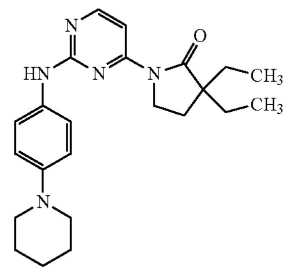 [SMILES: CCC1(CC)CCN(c2ccnc(Nc3ccc(N4CCCCC4)cc3)n2)C1=O] | HCl | 394.4 |
| 27 | 1-(2-((4-(dimethylamino)phenyl)amino)pyrimidin-4-yl)-3,3-diethyl-pyrrolidin-2-one | 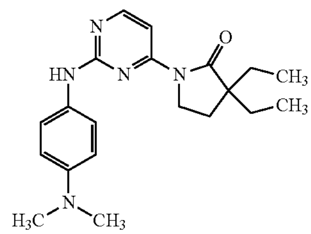 [SMILES: CCC1(CC)CCN(c2ccnc(Nc3ccc(N(C)C)cc3)n2)C1=O] | Free | 354.3 |
| 28 | 3,3-diethyl-1-(2-((1-methyl-1H-pyrazol-3-yl)amino)pyrimidin-4-yl)pyrrolidin-2-one | 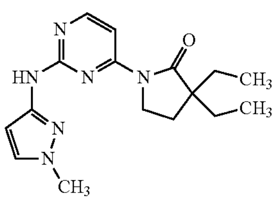 [SMILES: CCC1(CC)CCN(c2ccnc(Nc3ccn(C)n3)n2)C1=O] | Free | 315.2 |

Example 29

1-(5-fluoro-2-((1-methyl-1H-pyrazol-4-yl)amino)pyrimidin-4-yl)-3,3-dimethylpyrrolidin-2-one

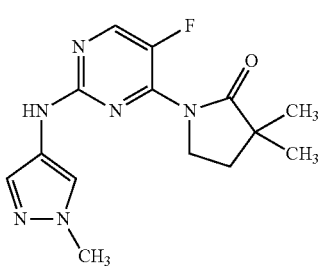 [SMILES: Cn1cc(Nc2ncc(F)c(N3CCC(C)(C)C3=O)n2)cn1]

A) 1-(2-chloro-5-fluoropyrimidin-4-yl)-3,3-dimethylpyrrolidin-2-one

The title compound was obtained from 2,4-dichloro-5-fluoropyrimidine and 3,3-dimethylpyrrolidin-2-one in the same manner as in Step A of Example 2.

$^1$H NMR (300 MHz, CDCl$_3$) δ 1.28 (6H, s), 2.09 (2H, t, J=7.0 Hz), 3.94 (2H, t, J=6.8 Hz), 8.43 (1H, d, J=2.3 Hz).

B) 1-(5-fluoro-2-((1-methyl-1H-pyrazol-4-yl)amino)pyrimidin-4-yl)-3,3-dimethylpyrrolidin-2-one The title compound was obtained from 1-(2-chloro-5-fluoropyrimidin-4-yl)-3,3-dimethylpyrrolidin-2-one obtained in Step A and 1-methyl-1H-pyrazol-4-amine in the same manner as in Step B of Example 2.

MS(ESI+): [M+H]$^+$ 305.2.

Example 30

(3-ethyl-1-(2-((1-methyl-1H-pyrazol-4-yl)amino)pyrimidin-4-yl)-2-oxopyrrolidin-3-yl)acetic acid

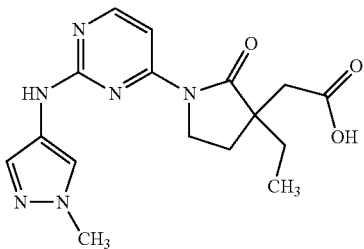 [SMILES: CCC1(CC(=O)O)CCN(c2ccnc(Nc3cnn(C)c3)n2)C1=O]

A) 1-(4-methoxybenzyl)pyrrolidin-2-one

To a solution of pyrrolidin-2-one (15 g) in a mixed solvent of tetrahydrofuran/N,N-dimethylformamide (1/1, 100 mL) was added sodium hydride (60% in mineral oil, 8.5 g) at 0° C. under nitrogen atmosphere, and the mixture was stirred for 30 min. p-Methoxybenzyl chloride (33 g) was added thereto at the same temperature, and the mixture was stirred at room temperature for 5 hr. To the reaction mixture was added water, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (28 g).

$^1$H NMR (300 MHz, CDCl$_3$) δ 1.87-2.09 (2H, m), 2.38-2.50 (2H, m), 3.15-3.34 (2H, m), 3.80 (3H, s), 4.39 (2H, s), 6.81-6.92 (2H, m), 7.17 (2H, d, J=8.7 Hz).

B) 3-ethyl-1-(4-methoxybenzyl)pyrrolidin-2-one

To a solution of diisopropylamine (4.1 mL) in tetrahydrofuran (25 mL) was added dropwise n-butyllithium (1.6 M hexane solution, 18 mL) at −78° C. under nitrogen atmosphere, and the mixture was warmed to 0° C., and stirred for 30 min. The reaction mixture was cooled to −78° C., a solution of 1-(4-methoxybenzyl)pyrrolidin-2-one (5.0 g) obtained in Step A in tetrahydrofuran (25 mL) was added thereto, and the mixture was stirred at the same temperature for 1 hr. Iodoethane (2.9 mL) was added thereto, and the mixture was stirred overnight while it was allowed to be warmed. To the reaction mixture was added saturated aqueous ammonium chloride solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (2.8 g).

$^1$H NMR (300 MHz, CDCl$_3$) δ 0.96 (3H, t, J=7.4 Hz), 1.35-1.52 (1H, m), 1.55-1.72 (1H, m), 1.81-2.00 (1H, m), 2.06-2.26 (1H, m), 2.39 (1H, qd, J=8.7, 4.2 Hz), 3.05-3.30 (2H, m), 3.79 (3H, s), 4.27-4.51 (2H, m), 6.73-6.95 (2H, m), 7.11-7.22 (2H, m).

C) ethyl(3-ethyl-1-(4-methoxybenzyl)-2-oxopyrrolidin-3-yl)acetate

To a solution of diisopropylamine (3.4 mL) in tetrahydrofuran (10 mL) was added dropwise n-butyllithium (1.6 M hexane solution, 15 mL) at −78° C. under nitrogen atmosphere, and the mixture was warmed to 0° C., and stirred for 30 min. The reaction mixture was cooled to −78° C., a solution of 3-ethyl-1-(4-methoxybenzyl)pyrrolidin-2-one (2.8 g) obtained in Step B in tetrahydrofuran (10 mL) was added thereto, and the mixture was stirred at the same temperature for 1 hr. Ethyl bromoacetate (4.0 mL) was added thereto, and the mixture was stirred overnight while it was allowed to be warmed. To the reaction mixture was added saturated aqueous ammonium chloride solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (1.5 g).

$^1$H NMR (300 MHz, CDCl$_3$) δ 0.87 (3H, t, J=7.4 Hz), 1.23 (3H, t, J=7.2 Hz), 1.48-1.72 (2H, m), 1.83-2.19 (2H, m), 2.42-2.59 (1H, m), 2.60-2.76 (1H, m), 3.04-3.25 (2H, m), 3.80 (3H, s), 4.10 (2H, q, J=7.1 Hz), 4.31 (1H, d, J=14.4 Hz), 4.45-4.61 (1H, m), 6.85 (2H, d, J=8.3 Hz), 7.19 (2H, d, J=8.7 Hz).

D) ethyl(3-ethyl-2-oxopyrrolidin-3-yl)acetate

To a solution of ethyl(3-ethyl-1-(4-methoxybenzyl)-2-oxopyrrolidin-3-yl)acetate (1.5 g) obtained in Step C in a mixed solvent of acetonitrile/water (3/1, 8 mL) was added ammonium hexanitratocerate(IV) (5.2 g), and the mixture was stirred at room temperature for 30 min. To the reaction mixture was added potassium carbonate, the solid was removed by filtration through Celite, and the solvent was evaporated under reduced pressure. The residue was purified by silica gel column chromatography (hexane/ethyl acetate) to give the title compound (900 mg).

$^1$H NMR (300 MHz, DMSO-d$_6$) δ 0.82 (3H, t, J=7.4 Hz), 1.17 (3H, td, J=7.2, 2.6 Hz), 1.44 (2H, qd, J=7.5, 1.7 Hz), 1.86-1.97 (1H, m), 2.03-2.19 (1H, m), 2.40 (2H, s), 3.13 (2H, t, J=7.2 Hz), 4.03 (2H, q, J=7.2 Hz), 7.58 (1H, brs).

E) ethyl(3-ethyl-1-(2-((1-methyl-1H-pyrazol-4-yl)amino)pyrimidin-4-yl)-2-oxopyrrolidin-3-yl)acetate The title compound was obtained from ethyl(3-ethyl-2-oxopyrrolidin-3-yl)acetate obtained in Step D and 4-chloro- N-(1-methyl-1H-pyrazol-4-yl)pyrimidin-2-amine obtained in Step C of Example 1 in the same manner as in Step I of Example 1.

MS(ESI+): [M+H]$^+$ 373.3.

F) (3-ethyl-1-(2-((1-methyl-1H-pyrazol-4-yl)amino)pyrimidin-4-yl)-2-oxopyrrolidin-3-yl) acetic acid To a solution of ethyl(3-ethyl-1-(2-((1-methyl-1H-pyrazol-4-yl)amino)pyrimidin-4-yl)-2-oxopyrrolidin-3-yl)acetate (270 mg) obtained in Step E in ethanol (5 mL) was added dropwise 2M aqueous sodium hydroxide solution (1.4 mL), and the mixture was stirred overnight at room temperature. To the reaction mixture was added water, and the mixture was washed with diethyl ether. The aqueous layer was neutralized with 2M hydrochloric acid, and extracted with ethyl acetate. The obtained organic layer was washed with saturated brine, and dried over anhydrous magnesium sulfate, and the solvent was evaporated under reduced pressure. The residue was recrystallized (ethyl acetate) to give the title compound (100 mg).

MS(ESI+): [M+H]$^+$ 345.2.

Example 31

(3-ethyl-1-(2-((1-methyl-1H-pyrazol-4-yl)amino)pyrimidin-4-yl)-2-oxopyrrolidin-3-yl)acetonitrile

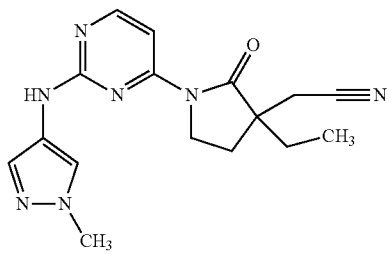 [SMILES: CCC1(CC#N)CCN(c2ccnc(Nc3cnn(C)c3)n2)C1=O]

To a solution of (3-ethyl-1-(2-((1-methyl-H-pyrazol-4-yl)amino)pyrimidin-4-yl)-2-oxopyrrolidin-3-yl)acetic acid (100 mg) obtained in Example 30 and 1-hydroxybenzotriazole ammonium salt (88 mg) in N,N-dimethylformamide (5 mL) was added 1-ethyl-3-(3-dimethylaminopropyl)carbodiimide hydrochloride (110 mg), and the mixture was stirred overnight at room temperature. To the reaction mixture was added water, and the mixture was extracted with ethyl acetate. The obtained organic layer was washed with water and saturated brine, and dried over anhydrous magnesium sulfate, and the solvent was evaporated under reduced pressure. To a solution of the residue and pyridine (70 mg) in tetrahydrofuran (5 mL) was added trifluoroacetic anhydride (0.12 mL), and the mixture was stirred at 70° C. for 30 min. The reaction mixture was neutralized with saturated aqueous sodium hydrogen carbonate solution, and extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate), and recrystallized (hexane/ethyl acetate) to give the title compound (17 mg).

MS(ESI+): [M+H]$^+$ 326.2.

Example 32

3,3-diethyl-5-methyl-1-(2-((4-(morpholin-4-yl)phenyl)amino)pyrimidin-4-yl)pyrrolidin-2-one

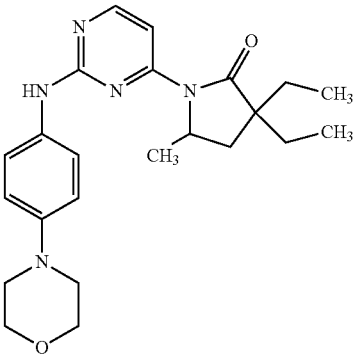 [SMILES: CCC1(CC)CC(C)N(c2ccnc(Nc3ccc(N4CCOCC4)cc3)n2)C1=O]

A) 1-(4-methoxybenzyl)-5-methylpyrrolidin-2-one

The title compound was obtained from 4-methoxybenzyl chloride and 5-methylpyrrolidin-2-one in the same manner as in Step A of Example 30.

$^1$H NMR (300 MHz, CDCl$_3$) δ 1.16 (3H, d, J=6.0 Hz), 1.58 (1H, dddd, J=12.7, 9.6, 7.1, 6.0 Hz), 2.07-2.21 (1H, m), 2.28-2.59 (2H, m), 3.40-3.64 (1H, m), 3.79 (3H, s), 3.91 (1H, d, J=14.7 Hz), 4.91 (1H, d, J=14.7 Hz), 6.79-6.93 (2H, m), 7.17 (2H, d, J=8.7 Hz).

B) 3-ethyl-1-(4-methoxybenzyl)-5-methylpyrrolidin-2-one

To a solution of 1-(4-methoxybenzyl)-5-methylpyrrolidin-2-one (3.0 g) obtained in Step A in tetrahydrofuran (25 mL) was added sodium bis(trimethylsilyl)amide (1.9M tetrahydrofuran solution, 11 mL) at −78° C. under nitrogen atmosphere, and the mixture was stirred at the same temperature for 1 hr. Iodoethane (2.2 mL) was added thereto, and the mixture was stirred overnight while it was allowed to be warmed. To the reaction mixture was added saturated aqueous ammonium chloride solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (2.5 g).

MS(ESI+): [M+H]$^+$ 248.2.

C) 3,3-diethyl-1-(4-methoxybenzyl)-5-methylpyrrolidin-2-one

To a solution of diisopropylamine (2.1 g) in tetrahydrofuran (20 mL) was added dropwise n-butyllithium (1.6 M hexane solution, 13 mL) at −78° C. under nitrogen atmosphere, and the mixture was warmed to 0° C., and stirred for 30 min. The reaction mixture was cooled to −78° C., a solution of 3-ethyl-1-(4-methoxybenzyl)-5-methylpyrrolidin-2-one (2.5 g) obtained in Step B in tetrahydrofuran (10 mL) was added thereto, and the mixture was stirred at the same temperature for 1 hr. Iodoethane (2.5 mL) was added thereto, and the mixture was stirred overnight while it was allowed to be warmed. To the reaction mixture was added saturated aqueous ammonium chloride solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (1.3 g).

$^1$H NMR (300 MHz, CDCl$_3$) δ 0.75-0.98 (6H, m), 1.16 (3H, d, J=6.4 Hz), 1.37-1.70 (5H, m), 1.95 (1H, dd, J=13.2, 7.9 Hz), 3.25-3.50 (1H, m), 3.79 (3H, s), 3.89 (1H, d, J=14.7 Hz), 4.94 (1H, d, J=14.7 Hz), 6.75-6.93 (2H, m), 7.17 (2H, d, J=8.7 Hz).

D) 3,3-diethyl-5-methylpyrrolidin-2-one

The title compound was obtained from 3,3-diethyl-1-(4-methoxybenzyl)-5-methylpyrrolidin-2-one obtained in Step C in the same manner as in Step D of Example 30.

$^1$H NMR (300 MHz, CDCl$_3$) δ 0.90 (6H, dt, J=10.2, 7.6 Hz), 1.21 (3H, d, J=6.0 Hz), 1.42-1.63 (5H, m), 2.05-2.17 (1H, m), 3.57-3.78 (1H, m), 5.53 (1H, brs).

E) 1-(2-chloropyrimidin-4-yl)-3,3-diethyl-5-methylpyrrolidin-2-one

The title compound was obtained from 2,4-dichloropyrimidine and 3,3-diethyl-5-methylpyrrolidin-2-one obtained in Step D in the same manner as in Step A of Example 2.

$^1$H NMR (300 MHz, CDCl$_3$) δ 0.85 (3H, t, J=7.6 Hz), 0.95 (3H, t, J=7.6 Hz), 1.45 (3H, d, J=6.0 Hz), 1.56-1.75 (5H, m), 2.23 (1H, dd, J=13.6, 8.7 Hz), 4.59 (1H, dquin, J=8.7, 6.2 Hz), 8.26 (1H, d, J=6.0 Hz), 8.45 (1H, d, J=5.7 Hz).

F) 3,3-diethyl-5-methyl-1-(2-((4-(morpholin-4-yl)phenyl)amino)pyrimidin-4-yl) pyrrolidin-2-one The title compound was obtained from 1-(2-chloropyrimidin-4-yl)-3,3-diethyl-5-methylpyrrolidin-2-one and 4-(morpholin-4-yl)aniline obtained in Step E in the same manner as in Step B of Example 2.

MS(ESI+): [M+H]$^+$ 410.3.

Example 33

3,3-diethyl-5-methyl-1-(2-((1-methyl-1H-pyrazol-4-yl)amino)pyrimidin-4-yl)pyrrolidin-2-one hydrochloride

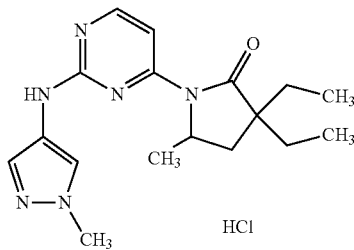 [SMILES: CCC1(CC)CC(C)N(c2ccnc(Nc3cnn(C)c3)n2)C1=O ; Cl]

The title compound was obtained from 1-(2-chloropyrimidin-4-yl)-3,3-diethyl-5-methylpyrrolidin-2-one obtained in Step E of Example 32 and 1-methyl-1H-pyrazol-4-amine in the same manner as in Step B of Example 2.

MS(ESI+): [M+H]$^+$ 329.3.

Example 34

3-ethyl-1-(2-((4-(morpholin-4-yl)phenyl)amino)pyrimidin-4-yl)-2-oxopyrrolidine-3-carboxamide

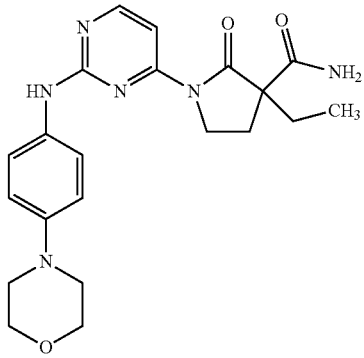 [SMILES: CCC1(C(N)=O)CCN(c2ccnc(Nc3ccc(N4CCOCC4)cc3)n2)C1=O]

To a solution of 3-ethyl-1-(2-((4-(morpholin-4-yl)phenyl)amino)pyrimidin-4-yl)-2-oxopyrrolidine-3-carbonitrile (36 mg) obtained in Example 2 in dimethylsulfoxide (1 mL) were added a solution of 30% aqueous hydrogen peroxide (28 μL) and 2M aqueous potassium carbonate (0.14 mL), and the mixture was stirred overnight at room temperature. Water was added thereto in an ice bath, and the precipitated solid was collected by filtration. The obtained crude crystals were recrystallized (diisopropyl ether/ethanol) to give the title compound (13 mg).

MS(ESI+): [M+H]$^+$ 411.3.

Example 35

1-(2-((4-(morpholin-4-yl)phenyl)amino)pyrimidin-4-yl)-2-oxo-3-(trifluoromethyl)pyrrolidine-3-carbonitrile

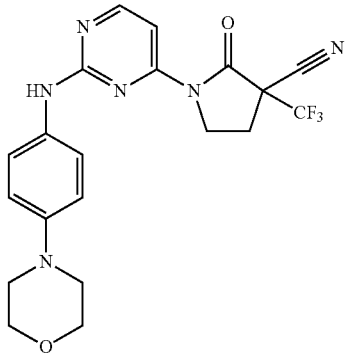 [SMILES: N#CC1(C(F)(F)F)CCN(c2ccnc(Nc3ccc(N4CCOCC4)cc3)n2)C1=O]

A) 1-(4-fluorobenzoyl)-2-oxo-3-(trifluoromethyl)pyrrolidine-3-carbonitrile

To a solution of 1-(4-fluorobenzoyl)-2-oxopyrrolidine-3-carbonitrile (300 mg) obtained in Step F of Example 1 in tetrahydrofuran (3 mL) was added dropwise 1,8-diazabicyclo[5.4.0]undec-7-ene (0.23 mL) at 0° C. under nitrogen atmosphere. The reaction mixture was stirred at room temperature for 20 min, [(oxide)phenyl(trifluoromethyl)-λ4-sulfanylidene]dimethylammonium tetrafluoroborate (630 mg) was added thereto, and the mixture was stirred at room temperature for 1 hr. The solvent was evaporated under reduced pressure, and the residue was purified by silica gel column chromatography (hexane/ethyl acetate) to give the title compound (190 mg).

$^1$H NMR (300 MHz, CDCl$_3$) δ 2.74-2.92 (2H, m), 3.95-4.33 (2H, m), 7.15 (2H, t, J=8.5 Hz), 7.67 (2H, dd, J=8.9, 5.1 Hz).

B) 2-oxo-3-(trifluoromethyl)pyrrolidine-3-carbonitrile

The title compound was obtained from 1-(4-fluorobenzoyl)-2-oxo-3-(trifluoromethyl)pyrrolidine-3-carbonitrile obtained in Step A in the same manner as in Step B of Example 5.

$^1$H NMR (300 MHz, CDCl$_3$) δ2.79 (2H, dt, J=9.6, 3.7 Hz), 3.36-3.79 (2H, m), 5.98 (1H, brs).

C) 1-(2-chloropyrimidin-4-yl)-2-oxo-3-(trifluoromethyl) pyrrolidine-3-carbonitrile The title compound was obtained from 2,4-dichloropyrimidine and 2-oxo-3-(trifluoromethyl)pyrrolidine-3-carbonitrile obtained in Step B in the same manner as in Step A of Example 2.

$^1$H NMR (300 MHz, DMSO-d$_6$) δ 2.78-2.93 (1H, m), 2.95-3.10 (1H, m), 3.99-4.25 (2H, m), 8.21 (1H, d, J=6.0 Hz), 8.78 (1H, d, J=5.7 Hz).

D) 1-(2-((4-(morpholin-4-yl)phenyl)amino)pyrimidin-4-yl)-2-oxo-3-(trifluoromethyl)pyrrolidine-3-carbonitrile The title compound was obtained from 1-(2-chloropyrimidin-4-yl)-2-oxo-3-(trifluoromethyl) pyrrolidine-3-carbonitrile obtained in Step C and 4-(morpholin-4-yl)aniline in the same manner as in Step B of Example 2.

MS(ESI+): [M+H]$^+$ 433.3.

Example 36

1-(2-((4-(morpholin-4-yl)phenyl)amino)pyrimidin-4-yl)-2-oxo-3-propylpyrrolidine-3-carbonitrile

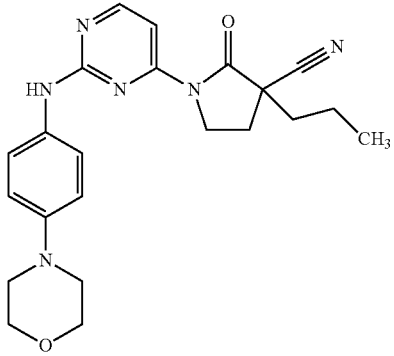 [SMILES: CCCC1(C#N)CCN(c2ccnc(Nc3ccc(N4CCOCC4)cc3)n2)C1=O]

A) 1-(4-fluorobenzoyl)-2-oxo-3-propylpyrrolidine-3-carbonitrile

The title compound was obtained from 1-(4-fluorobenzoyl)-2-oxopyrrolidine-3-carbonitrile obtained in Step F of Example 1 and 1-iodopropane in the same manner as in Step G of Example 1.

$^1$H NMR (300 MHz, CDCl$_3$) δ1.03 (3H, t, J=7.0 Hz), 1.43-1.52 (1H, m), 1.61-1.79 (2H, m), 1.94-2.10 (1H, m), 2.25 (1H, dt, J=13.3, 7.3 Hz), 2.57-2.70 (1H, m), 4.03 (2H, t, J=6.8 Hz), 7.04-7.18 (2H, m), 7.59-7.69 (2H, m).

B) 2-oxo-3-propylpyrrolidine-3-carbonitrile

The title compound was obtained from 1-(4-fluorobenzoyl)-2-oxo-3-propylpyrrolidine-3-carbonitrile obtained in Step A in the same manner as in Step B of Example 5.

$^1$H NMR (300 MHz, CDCl$_3$) δ 1.02 (3H, t, J=7.0 Hz), 1.39-1.63 (2H, m), 1.64-1.76 (1H, m), 1.93-2.03 (1H, m), 2.15-2.29 (1H, m), 2.62 (1H, ddd, J=13.0, 7.7, 4.9 Hz), 3.35-3.46 (1H, m), 3.47-3.58 (1H, m), 6.75 (1H, brs).

C) 1-(2-chloropyrimidin-4-yl)-2-oxo-3-propylpyrrolidine-3-carbonitrile

The title compound was obtained from 2,4-dichloropyrimidine and 2-oxo-3-propylpyrrolidine-3-carbonitrile obtained in Step B in the same manner as in Step A of Example 2.

MS(ESI+): [M+H]$^+$ 265.0.

D) 1-(2-((4-(morpholin-4-yl)phenyl)amino)pyrimidin-4-yl)-2-oxo-3-propylpyrrolidine-3-carbonitrile The title compound was obtained from 1-(2-chloropyrimidin-4-yl)-2-oxo-3-propylpyrrolidine-3-carbonitrile obtained in Step C and 4-(morpholin-4-yl)aniline in the same manner as in Step B of Example 2.

MS(ESI+): [M+H]$^+$ 407.4.

Example 37

1-(2-((1-methyl-1H-pyrazol-4-yl)amino)pyrimidin-4-yl)-2-oxo-3-propylpyrrolidine-3-carbonitrile

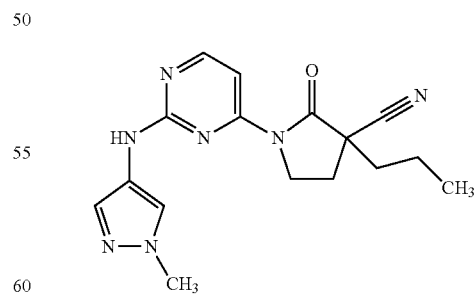

The title compound was obtained from 1-(2-chloropyrimidin-4-yl)-2-oxo-3-propylpyrrolidine-3-carbonitrile obtained in Step C of Example 36 and 1-methyl-1H-pyrazol-4-amine in the same manner as in Step B of Example 2.

MS(ESI+): [M+H]$^+$ 326.2.

Example 38

1-(2-((4-(morpholin-4-yl)phenyl)amino)pyrimidin-4-yl)-2-oxo-3-(2,2,2-trifluoroethyl)pyrrolidine-3-carbonitrile

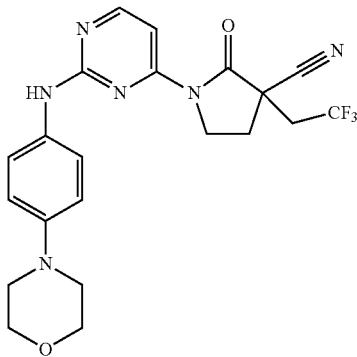 [SMILES: N#CC1(CC(F)(F)F)CCN(c2ccnc(Nc3ccc(N4CCOCC4)cc3)n2)C1=O]

A) 1-(4-fluorobenzoyl)-2-oxo-3-(2,2,2-trifluoroethyl)pyrrolidine-3-carbonitrile The title compound was obtained from 1-(4-fluorobenzoyl)-2-oxopyrrolidine-3-carbonitrile obtained in Step F of Example 1 and 2,2,2-trifluoroethyl trifluoromethanesulfonate in the same manner as in Step A of Example 5.
$^1$H NMR (300 MHz, CDCl$_3$) δ 2.34-2.50 (1H, m), 2.50-2.65 (1H, m), 2.82 (1H, dd, J=13.8, 5.5 Hz), 3.01 (1H, dq, J=15.8, 10.1 Hz), 4.03-4.16 (1H, m), 4.17-4.32 (1H, m), 7.09-7.19 (2H, m), 7.61-7.68 (2H, m).

B) 2-oxo-3-(2,2,2-trifluoroethyl)pyrrolidine-3-carbonitrile

The title compound was obtained from 1-(4-fluorobenzoyl)-2-oxo-3-(2,2,2-trifluoroethyl)pyrrolidine-3-carbonitrile obtained in Step A in the same manner as in Step B of Example 5.
$^1$H NMR (300 MHz, CDCl$_3$) δ 2.29-2.49 (2H, m), 2.71-2.86 (1H, m), 3.05 (1H, dq, J=15.5, 10.3 Hz), 3.40-3.55 (1H, m), 3.59-3.72 (1H, m), 5.98 (1H, brs).

C) 1-(2-chloropyrimidin-4-yl)-2-oxo-3-(2,2,2-trifluoroethyl)pyrrolidine-3-carbonitrile The title compound was obtained from 2,4-dichloropyrimidine and 2-oxo-3-(2,2,2-trifluoroethyl)pyrrolidine-3-carbonitrile obtained in Step B in the same manner as in Step A of Example 2.
$^1$H NMR (300 MHz, CDCl$_3$) δ 2.32-2.48 (1H, m), 2.49-2.64 (1H, m), 2.77-2.95 (1H, m), 3.13 (1H, dq, J=15.5, 10.2 Hz), 4.08-4.20 (1H, m), 4.43 (1H, d, J=1.9 Hz), 8.24 (1H, d, J=5.7 Hz), 8.59 (1H, d, J=5.7 Hz).

D) 1-(2-((4-(morpholin-4-yl)phenyl)amino)pyrimidin-4-yl)-2-oxo-3-(2,2,2-trifluoroethyl)pyrrolidine-3-carbonitrile The title compound was obtained from 1-(2-chloropyrimidin-4-yl)-2-oxo-3-(2,2,2-trifluoroethyl)pyrrolidine-3-carbonitrile obtained in Step C and 4-(morpholin-4-yl)aniline in the same manner as in Step B of Example 2.
MS(ESI+): [M+H]$^+$ 407.4.

Example 39

3-(cyclopropylmethyl)-1-(2-((4-(morpholin-4-yl)phenyl)amino)pyrimidin-4-yl)-2-oxopyrrolidine-3-carbonitrile

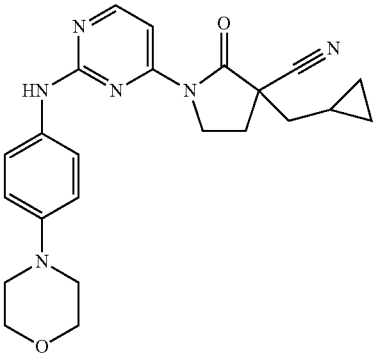 [SMILES: N#CC1(CC2CC2)CCN(c2ccnc(Nc3ccc(N4CCOCC4)cc3)n2)C1=O]

A) 3-(cyclopropylmethyl)-1-(4-fluorobenzoyl)-2-oxopyrrolidine-3-carbonitrile The title compound was obtained from 1-(4-fluorobenzoyl)-2-oxopyrrolidine-3-carbonitrile obtained in Step F of Example 1 and (iodomethyl)cyclopropane in the same manner as in Step G of Example 1.
$^1$H NMR (300 MHz, CDCl$_3$) δ 0.18-0.38 (2H, m), 0.56-0.71 (2H, m), 0.81-0.98 (1H, m), 1.71 (1H, dd, J=14.0, 7.2 Hz), 2.04 (1H, dd, J=14.0, 6.8 Hz), 2.45 (1H, dt, J=13.3, 7.3 Hz), 2.70 (1H, dt, J=13.2, 6.6 Hz), 4.05 (2H, t, J=6.8 Hz), 7.12 (2H, t, J=8.7 Hz), 7.65 (2H, dd, J=8.7, 5.3 Hz).

B) 3-(cyclopropylmethyl)-2-oxopyrrolidine-3-carbonitrile

The title compound was obtained from 3-(cyclopropylmethyl)-1-(4-fluorobenzoyl)-2-oxopyrrolidine-3-carbonitrile obtained in Step A in the same manner as in Step B of Example 5.
$^1$H NMR (300 MHz, CDCl$_3$) 0.16-0.37 (2H, m), 0.50-0.68 (2H, m), 0.80-0.97 (1H, m), 1.68 (1H, dd, J=14.4, 6.8 Hz), 1.97 (1H, dd, J=14.4, 7.2 Hz), 2.42 (1H, ddd, J=13.5, 7.6, 6.4 Hz), 2.68 (1H, ddd, J=13.1, 8.0, 4.9 Hz), 3.36-3.48 (1H, m), 3.49-3.60 (1H, m), 6.63 (1H, brs).

C) 1-(2-chloropyrimidin-4-yl)-3-(cyclopropylmethyl)-2-oxopyrrolidine-3-carbonitrile The title compound was obtained from 2,4-dichloropyrimidine and 3-(cyclopropylmethyl)-2-oxopyrrolidine-3-carbonitrile obtained in Step B in the same manner as in Step A of Example 2.
MS(ESI+): [M+H]$^+$ 277.2.

D) 3-(cyclopropylmethyl)-1-(2-((4-(morpholin-4-yl)phenyl)amino)pyrimidin-4-yl)-2-oxopyrrolidine-3-carbonitrile The title compound was obtained from 1-(2-chloropyrimidin-4-yl)-3-(cyclopropylmethyl)-2-oxopyrrolidine-3-carbonitrile obtained in Step C and 4-(morpholin-4-yl)aniline in the same manner as in Step B of Example 2.
MS(ESI+): [M+H]⁺ 419.4.

Example 40

3-(methoxymethyl)-1-(2-((4-(morpholin-4-yl)phenyl)amino)pyrimidin-4-yl)-2-oxopyrrolidine-3-carbonitrile

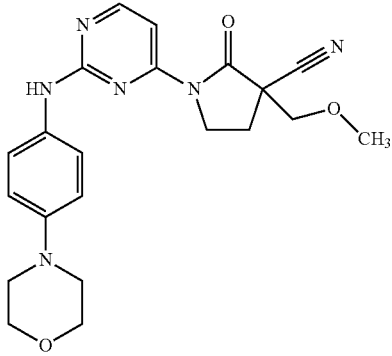 [SMILES: COCC1(C#N)CCN(c2ccnc(Nc3ccc(N4CCOCC4)cc3)n2)C1=O]

A) 1-(4-fluorobenzoyl)-3-(methoxymethyl)-2-oxopyrrolidine-3-carbonitrile

The title compound was obtained from 1-(4-fluorobenzoyl)-2-oxopyrrolidine-3-carbonitrile obtained in Step F of Example 1 and chloromethyl methyl ether in the same manner as in Step G of Example 1.
¹H NMR (300 MHz, CDCl₃) δ 2.54-2.67 (2H, m), 3.44 (3H, s), 3.72 (1H, d, J=9.1 Hz), 3.87 (1H, d, J=9.1 Hz), 4.01 (2H, t, J=7.2 Hz), 7.05-7.17 (2H, m), 7.60-7.71 (2H, m).

B) 3-(methoxymethyl)-2-oxopyrrolidine-3-carbonitrile

The title compound was obtained from 1-(4-fluorobenzoyl)-3-(methoxymethyl)-2-oxopyrrolidine-3-carbonitrile obtained in Step A in the same manner as in Step B of Example 5.
¹H NMR (300 MHz, CDCl₃) δ 2.47-2.68 (2H, m), 3.33-3.60 (5H, m), 3.75 (2H, q, J=9.2 Hz), 6.27 (1H, brs).

C) 1-(2-chloropyrimidin-4-yl)-3-(methoxymethyl)-2-oxopyrrolidine-3-carbonitrile

The title compound was obtained from 2,4-dichloropyrimidine and 3-(methoxymethyl)-2-oxopyrrolidine-3-carbonitrile obtained in Step B in the same manner as in Step A of Example 2.
MS(ESI+): [M+H]⁺ 267.1.

D) 3-(methoxymethyl)-1-(2-((4-(morpholin-4-yl)phenyl)amino)pyrimidin-4-yl)-2-oxopyrrolidine-3-carbonitrile The title compound was obtained from 1-(2-chloropyrimidin-4-yl)-3-(methoxymethyl)-2-oxopyrrolidine-3-carbonitrile obtained in Step C and 4-(morpholin-4-yl)aniline in the same manner as in Step B of Example 2.
MS(ESI+): [M+H]⁺ 409.3.

Example 41

3-methyl-1-(2-((4-(morpholin-4-yl)phenyl)amino)pyrimidin-4-yl)-2-oxopyrrolidine-3-carbonitrile

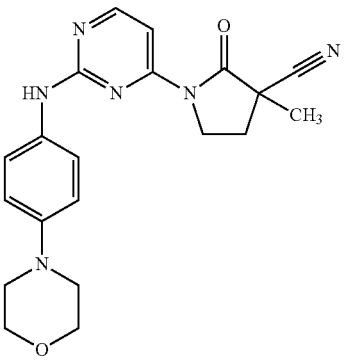 [SMILES: CC1(C#N)CCN(c2ccnc(Nc3ccc(N4CCOCC4)cc3)n2)C1=O]

A) 1-(4-fluorobenzoyl)-3-methyl-2-oxopyrrolidine-3-carbonitrile

The title compound was obtained from 1-(4-fluorobenzoyl)-2-oxopyrrolidine-3-carbonitrile obtained in Step F of Example 1 and iodomethane in the same manner as in Step G of Example 1.
¹H NMR (300 MHz, CDCl₃) δ 1.66 (3H, s), 2.22 (1H, dt, J=13.0, 7.5 Hz), 2.71 (1H, dt, J=13.2, 6.6 Hz), 4.05 (2H, t, J=7.0 Hz), 7.07-7.18 (2H, m), 7.60-7.70 (2H, m).

B) 3-methyl-2-oxopyrrolidine-3-carbonitrile

The title compound was obtained from 1-(4-fluorobenzoyl)-3-methyl-2-oxopyrrolidine-3-carbonitrile obtained in Step A in the same manner as in Step B of Example 5.
¹H NMR (300 MHz, CDCl₃) δ 1.61 (3H, s), 2.12-2.27 (1H, m), 2.70 (1H, ddd, J=12.9, 7.6, 5.1 Hz), 3.37-3.48 (1H, m), 3.49-3.61 (1H, m), 6.50 (1H, brs).

C) 1-(2-chloropyrimidin-4-yl)-3-methyl-2-oxopyrrolidine-3-carbonitrile

The title compound was obtained from 2,4-dichloropyrimidine and 3-methyl-2-oxopyrrolidine-3-carbonitrile obtained in Step B in the same manner as in Step A of Example 2.
MS(ESI+): [M+H]⁺ 237.1.

D) 3-methyl-1-(2-((4-(morpholin-4-yl)phenyl)amino)pyrimidin-4-yl)-2-oxopyrrolidine-3-carbonitrile The title compound was obtained from 1-(2-chloropyrimidin-4-yl)-3-methyl-2-oxopyrrolidine-3-carbonitrile obtained in Step C and 4-(morpholin-4-yl)aniline in the same manner as in Step B of Example 2.
MS(ESI+): [M+H]⁺ 379.3.

Examples 42 to 47

In Examples 42 to 47, the title compound was obtained from 1-(2-chloropyrimidin-4-yl)-3-ethyl-2-oxopyrrolidine- 3-carbonitrile obtained in Step A of Example 2, and (4-amino-1H-pyrazol-1-yl)acetonitrile, 1-(tetrahydro-2H-pyran-4-yl)-1H-pyrazol-4-amine, butyl(4-amino-1H-pyrazol-1-yl)acetate, 1-(4-methoxybenzyl)-1H-pyrazol-4-amine, (4-amino-1H-pyrazol-1-yl)acetic acid or ethyl(4-amino-1H-pyrazol-1-yl)acetate (these compounds can be produced according to a method known per se), each corresponding to the compounds of Examples 42 to 47, in the same manner as in Step B of Example 2 or a method analogous thereto. MS in the tables means actual measured value.

TABLE 2

| Example Number | IUPAC Name | Structure | Salt | MS |
|---|---|---|---|---|
| 42 | 1-(2-((1-(cyanomethyl)-1H-pyrazol-4-yl)amino)pyrimidin-4-yl)-3-ethyl-2-oxopyrrolidine-3-carbonitrile | 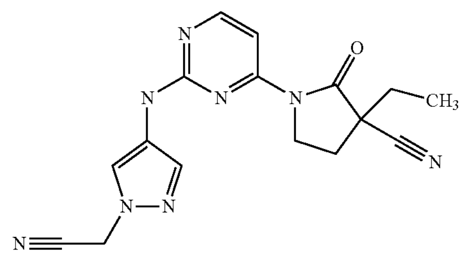 [SMILES: CCC1(C#N)CCN(c2ccnc(Nc3cnn(CC#N)c3)n2)C1=O] | HCl | 337.2 |
| 43 | 3-ethyl-2-oxo-1-(2-((1-(tetrahydro-2H-pyran-4-yl)-1H-pyrazol-4-yl)amino)pyrimidin-4-yl)pyrrolidine-3-carbonitrile | 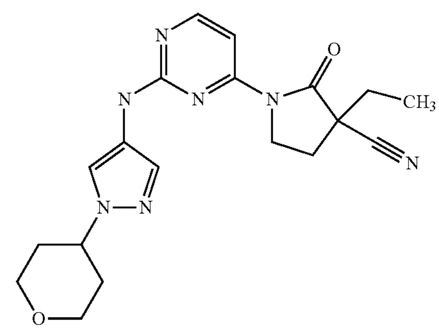 [SMILES: CCC1(C#N)CCN(c2ccnc(Nc3cnn(C4CCOCC4)c3)n2)C1=O] | Free | 382.3 |
| 44 | butyl (4-((4-(3-cyano-3-ethyl-2-oxopyrrolidin-1-yl)pyrimidin-2-yl)amino)-1H-pyrazol-1-yl)acetate | 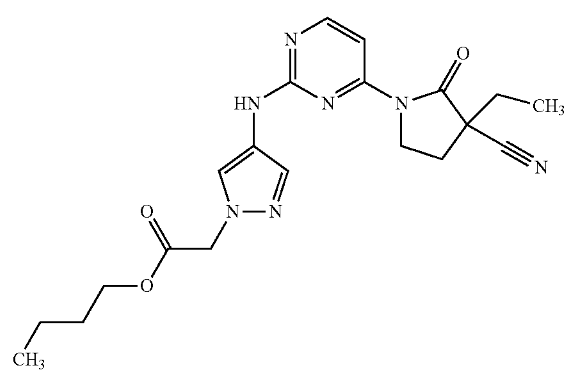 [SMILES: CCCCOC(=O)Cn1cc(Nc2nccc(N3CCC(C#N)(CC)C3=O)n2)cn1] | HCl | 412.3 |
| 45 | 3-ethyl-1-(2-((1-(4-methoxybenzyl)-1H-pyrazol-4-yl)amino)pyrimidin-4-yl)-2-oxopyrrolidine-3-carbonitrile | 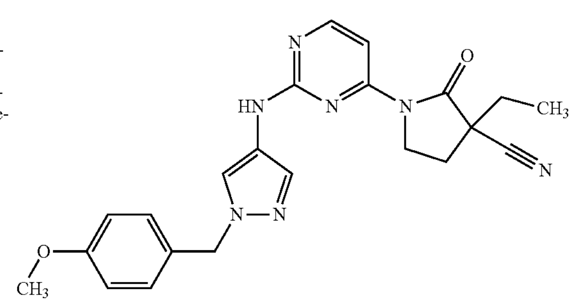 | Free | 418.3 |

TABLE 2-continued

| Example Number | IUPAC Name | Structure | Salt | MS |
|---|---|---|---|---|
| 46 | (4-((4-(3-cyano-3-ethyl-2-oxopyrrolidin-1-yl)pyrimidin-2-yl)amino)-1H-pyrazol-1-yl)acetic acid | 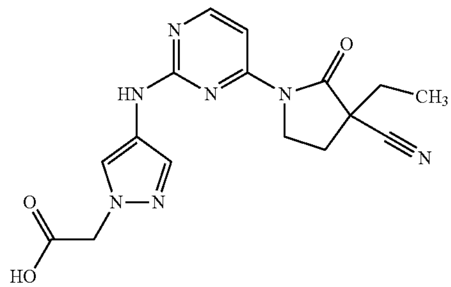 [SMILES: CCC1(C#N)CCN(c2ccnc(Nc3cnn(CC(=O)O)c3)n2)C1=O] | HCl | 356.2 |
| 47 | ethyl (4-((4-(3-cyano-3-ethyl-2-oxopyrrolidin-1-yl)pyrimidin-2-yl)amino)-1H-pyrazol-1-yl)acetate | 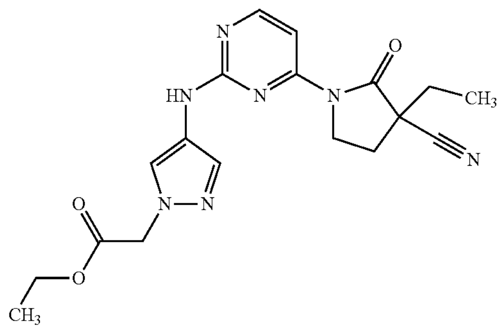 [SMILES: CCOC(=O)Cn1cc(Nc2nccc(N3CCC(C#N)(CC)C3=O)n2)cn1] | HCl | 384.3 |

Examples 48 to 55

In Examples 48 to 55, the title compound was obtained from 1-(2-chloropyrimidin-4-yl)-3-ethyl-2-oxopyrrolidine-3-carbonitrile obtained in Step A of Example 2, and ethyl(4-aminophenyl)acetate, N-(4-aminophenyl)acetamide, 4-aminobenzamide, 4-amino-N-methylbenzamide, 4-amino-N,N-dimethylbenzamide, 4-aminobenzoic acid, 1-(4-aminophenyl)ethanone or 4-(1,1-dioxidethiomorpholin-4-yl)aniline (these compounds can be produced according to a method known per se), each corresponding to the compounds of Examples 48 to 55, in the same manner as in Step B of Example 2 or a method analogous thereto. MS in the tables means actual measured value.

TABLE 3

| Example Number | IUPAC Name | Structure | Salt | MS |
|---|---|---|---|---|
| 48 | ethyl (4-((4-(3-cyano-3-ethyl-2-oxo-pyrrolidin-1-yl)pyrimidin-2-yl)amino)phenyl)acetate | | HCl | 394.3 |
| 49 | N-(4-((4-(3-cyano-3-ethyl-2-oxo-pyrrolidin-1-yl)pyrimidin-2-yl)amino)phenyl)acetamide | 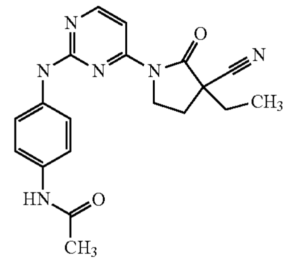 [SMILES: CCC1(C#N)CCN(c2ccnc(Nc3ccc(NC(C)=O)cc3)n2)C1=O] | Free | 365.3 |
| 50 | 4-((4-(3-cyano-3-ethyl-2-oxo-pyrrolidin-1-yl)pyrimidin-2-yl)amino)benzamide | 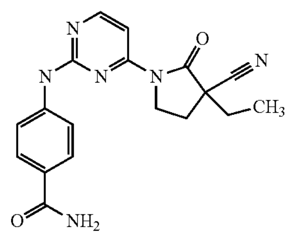 [SMILES: CCC1(C#N)CCN(c2ccnc(Nc3ccc(C(N)=O)cc3)n2)C1=O] | Free | 351.3 |
| 51 | 4-((4-(3-cyano-3-ethyl-2-oxo-pyrrolidin-1-yl)pyrimidin-2-yl)amino)-N-methyl-benzamide | 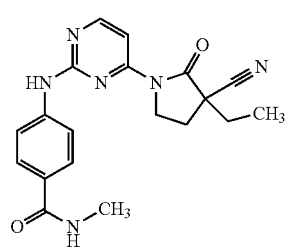 [SMILES: CCC1(C#N)CCN(c2ccnc(Nc3ccc(C(=O)NC)cc3)n2)C1=O] | Free | 365.3 |

TABLE 3-continued

| Example Number | IUPAC Name | Structure | Salt | MS |
|---|---|---|---|---|
| 52 | 4-((4-(3-cyano-3-ethyl-2-oxo-pyrrolidin-1-yl)pyrimidin-2-yl)amino)-N,N-dimethyl-banzamide | 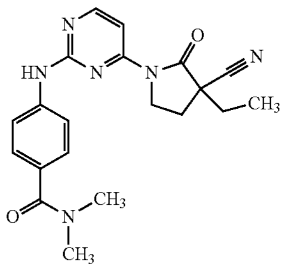 [SMILES: CCC1(C#N)CCN(c2ccnc(Nc3ccc(C(=O)N(C)C)cc3)n2)C1=O] | Free | 379.3 |
| 53 | 4-((4-(3-cyano-3-ethyl-2-oxo-pyrrolidin-1-yl)pyrimidin-2-yl)amino) benzoic acid | 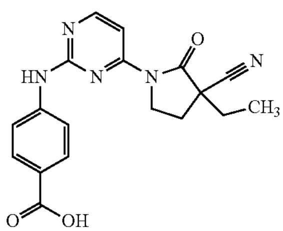 [SMILES: CCC1(C#N)CCN(c2ccnc(Nc3ccc(C(=O)O)cc3)n2)C1=O] | Free | 352.2 |
| 54 | 1-(2-((4-acetylphenyl)amino)pyrimidin-4-yl)-3-ethyl-2-oxo-pyrrolidine-3-carbonitrile | 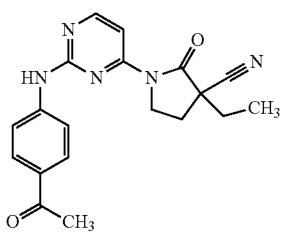 | Free | 350.3 |
| 55 | 1-(2-((4-(1,1-dioxide-thiomorpholin-4-yl)phenyl)amino)pyrimidin-4-yl)-3-ethyl-2-oxo-pyrrolidine-3-carbonitrile | 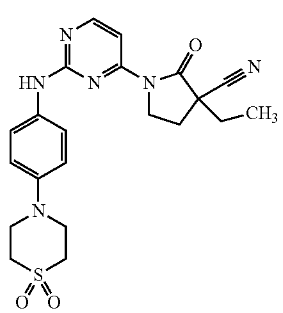 [SMILES: CCC1(C#N)CCN(c2ccnc(Nc3ccc(N4CCS(=O)(=O)CC4)cc3)n2)C1=O] | Free | 441.3 |

Example 56

3-ethyl-2-oxo-1-(2-(pyridin-3-ylamino)pyrimidin-4-yl)pyrrolidine-3-carbonitrile dihydrochloride

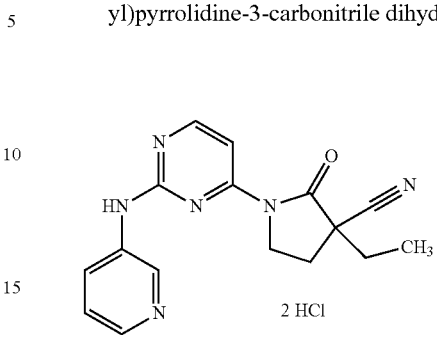

To a mixture of 1-(2-chloropyrimidin-4-yl)-3-ethyl-2-oxopyrrolidine-3-carbonitrile (100 mg) obtained in Step A of Example 2, 3-aminopyridine (45 mg), cesium carbonate (260 mg) and 2,2'-bis(diphenylphosphino)-1,1'-binaphthyl (37 mg) in tetrahydrofuran (2 mL) was added tris(dibenzylideneacetone)dipalladium(0) (37 mg), and the mixture was stirred overnight at 90° C. The insoluble substance was removed by filtration through Celite, and the solvent was evaporated under reduced pressure. The residue was purified by silica gel column chromatography (NH, hexane/ethyl acetate), 4M hydrogen chloride in ethyl acetate (4 mL) was added thereto, and the mixture was stirred at room temperature for 5 min. The solvent was evaporated under reduced pressure, and the residue was recrystallized (ethyl acetate) to give the title compound (49 mg).

MS(ESI+): [M+H]$^+$ 309.2.

Examples 57 and 58

In Examples 57 and 58, the title compound was obtained from 1-(2-chloropyrimidin-4-yl)-3-ethyl-2-oxopyrrolidine-3-carbonitrile obtained in Step A of Example 2, and pyridin-4-amine or 4-(morpholin-4-ylmethyl)aniline (these compounds can be produced according to a method known per se), each corresponding to the compounds of Examples 57 and 58, in the same manner as in Example 56. MS in the tables means actual measured value.

TABLE 4

| Example Number | IUPAC Name | Structure | Salt | MS |
|---|---|---|---|---|
| 57 | 3-ethyl-2-oxo-1-(2-(pyridin-4-ylamino)pyrimidin-4-yl)pyrrolidine-3-carbonitrile | 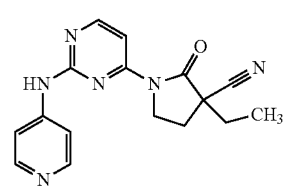 [SMILES: CCC1(C#N)CCN(c2ccnc(Nc3ccncc3)n2)C1=O] | 2HCl | 308.9 |

TABLE 4-continued

| Example Number | IUPAC Name | Structure | Salt | MS |
|---|---|---|---|---|
| 58 | 3-ethyl-1-(2-((4-(morpholin-4-ylmethyl)phenyl)amino)pyrimidin-4-yl)-2-oxopyrrolidine-3-carbonitrile | 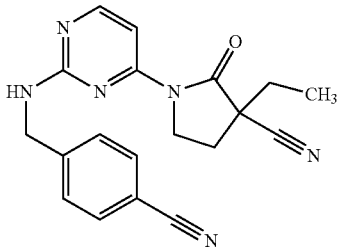 | 2HCl | 407.3 |

Examples 59 and 60

In Examples 59 and 60, the title compound was obtained from 1-(2-chloropyrimidin-4-yl)-3-ethyl-2-oxopyrrolidine-3-carbonitrile obtained in Step A of Example 2, and 2-(morpholin-4-yl)pyrimidin-5-amine or 6-(morpholin-4-yl)pyridin-3-amine (these compounds can be produced according to a method known per se), each corresponding to the compounds of Examples 59 and 60, in the same manner as in Step B of Example 2 or a method analogous thereto. MS in the tables means actual measured value.

TABLE 5

| Example Number | IUPAC Name | Structure | Salt | MS |
|---|---|---|---|---|
| 59 | 3-ethyl-1-(2-((2-(morpholin-4-yl)pyrimidin-5-yl)amino)pyrimidin-4-yl)-2-oxopyrrolidine-3-carbonitrile | 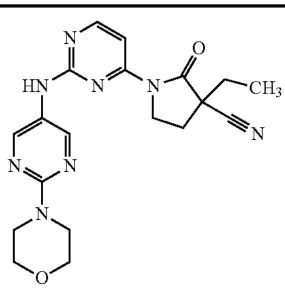 | Free | 395.3 |
| 60 | 3-ethyl-1-(2-((6-(morpholin-4-yl)pyridin-3-yl)amino)pyrimidin-4-yl)-2-oxopyrrolidine-3-carbonitrile | 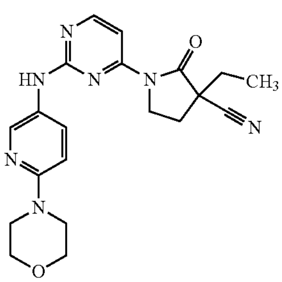 [SMILES: CCC1(C#N)CCN(c2ccnc(Nc3ccc(N4CCOCC4)nc3)n2)C1=O] | Free | 394.3 |

Example 61

1-(2-((4-cyanobenzyl)amino)pyrimidin-4-yl)-3-ethyl-2-oxopyrrolidine-3-carbonitrile To a solution of 1-(2-chloropyrimidin-4-yl)-3-ethyl-2-oxopyrrolidine-3-carbonitrile (20 mg) obtained in Step A of Example 2 and 4-(aminomethyl)benzonitrile hydrochloride (27 mg) in N-methylpyrrolidone (2 mL) was added diisopropylethylamine (0.028 mL), and the mixture was stirred at 60° C. for 3 hr. To the reaction mixture were added ethyl acetate (3 mL) and water (1 mL), and the mixture was stirred for 5 min. The organic layer was filtered through Top-Phase Separation Filter Tube, and the solvent was evaporated at 60° C. The residue was purified by HPLC (C18, mobile phase: acetonitrile/10 mM aqueous ammonium hydrogen carbonate solution), and dried at 60° C. to give the title compound.

MS(ESI+): [M+H]$^+$ 346.9.

Examples 62 to 77

In Examples 62 to 77, the title compound was obtained from 1-(2-chloropyrimidin-4-yl)-3-ethyl-2-oxopyrrolidine-3-carbonitrile obtained in Step A of Example 2, and 3-cyanobenzylamine hydrochloride, benzylamine, 3-methoxybenzylamine, 4-fluorobenzylamine, 4-(4-methylpiperidin-1-yl)benzylamine, 4-(morpholinomethyl)benzylamine, 1-benzofuran-5-ylmethylamine, 2-phenylethylamine, 3-(2-aminoethyl)pyridine, furfurylamine, 2-thiophenemethylamine, 2-naphthalenemethylamine hydrochloride, 4-methoxybenzylamine, 4-(2-aminoethyl)pyridine or cyclopropylmethylamine (these compounds can be produced according to a method known per se), each corresponding to the compounds of Examples 62 to 77, in the same manner as in Example 61. MS in the tables means actual measured value.

TABLE 6-1

| Example Number | IUPAC Name | Structure | Salt | MS |
|---|---|---|---|---|
| 62 | 1-(2-((3-cyanobenzyl)amino)pyrimidin-4-yl)-3-ethyl-2-oxopyrrolidine-3-carbonitrile | 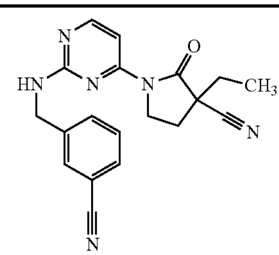 | Free | 347.0 |

TABLE 6-1-continued

| Example Number | IUPAC Name | Structure | Salt | MS |
|---|---|---|---|---|
| 63 | 1-(2-(benzylamino)pyrimidin-4-yl)-3-ethyl-2-oxo-pyrrolidine-3-carbonitrile | 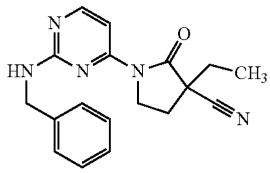 [SMILES: CCC1(C#N)CCN(c2ccnc(NCc3ccccc3)n2)C1=O] | Free | 321.9 |
| 64 | 3-ethyl-1-(2-((3-methoxybenzyl)amino)pyrimidin-4-yl)-2-oxo-pyrrolidine-3-carbonitrile | 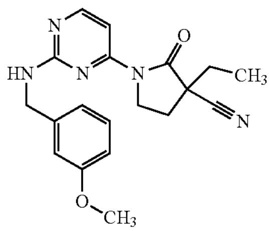 [SMILES: CCC1(C#N)CCN(c2ccnc(NCc3cccc(OC)c3)n2)C1=O] | Free | 352.0 |
| 65 | 3-ethyl-1-(2-((4-fluorobenzyl)amino)pyrimidin-4-yl)-2-oxo-pyrrolidine-3-carbonitrile | 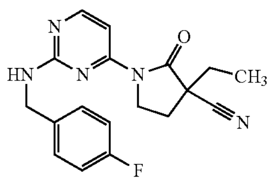 [SMILES: CCC1(C#N)CCN(c2ccnc(NCc3ccc(F)cc3)n2)C1=O] | Free | 339.9 |
| 66 | 3-ethyl-1-(2-((4-(4-methylpiperazin-1-yl)benzyl)amino)pyrimidin-4-yl)-2-oxo-pyrrolidine-3-carbonitrile | 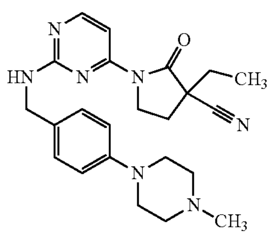 [SMILES: CCC1(C#N)CCN(c2ccnc(NCc3ccc(N4CCN(C)CC4)cc3)n2)C1=O] | Free | 420.1 |
| 67 | 3-ethyl-1-(2-((4-(morpholin-4-ylmethyl)benzyl)amino)pyrimidin-4-yl)-2-oxo-pyrrolidine-3-carbonitrile | 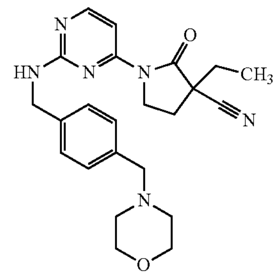 [SMILES: CCC1(C#N)CCN(c2ccnc(NCc3ccc(CN4CCOCC4)cc3)n2)C1=O] | Free | 421.1 |
| 68 | 1-(2-((1-benzofuran-5-ylmethyl)amino)pyrimidin-4-yl)-3-ethyl-2-oxo-pyrrolidine-3-carbonitrile | 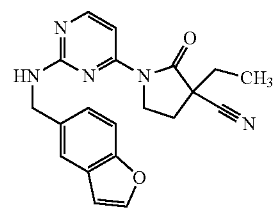 [SMILES: CCC1(C#N)CCN(c2ccnc(NCc3ccc4occc4c3)n2)C1=O] | Free | 362.0 |
| 69 | 3-ethyl-2-oxo-1-(2-((2-phenylethyl)amino)pyrimidin-4-yl)pyrrolidine-3-carbonitrile | 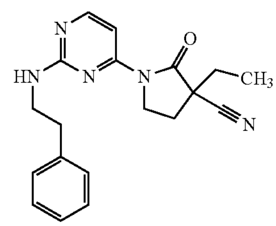 [SMILES: CCC1(C#N)CCN(c2ccnc(NCCc3ccccc3)n2)C1=O] | Free | 335.9 |

TABLE 6-2

| | | | | |
|---|---|---|---|---|
| 70 | 3-ethyl-2-oxo-1-(2-((2-(pyridin-3-yl)ethyl)amino)pyrimidin-4-yl)pyrrolidine-3-carbonitrile | | Free | 337.0 |
| 72 | 3-ethyl-1-(2-((2-furylmethyl)amino)pyrimidin-4-yl)-2-oxopyrrolidine-3carbonitrile | | Free | 311.9 |

TABLE 6-2-continued

| 73 | 3-ethyl-2-oxo-1-(2-((2-thienylmethyl)amino)pyrimidin-4-yl)pyrrolidine-3-carbonitrile | | Free | 327.9 |
|---|---|---|---|---|
| 74 | 3-ethyl-1-(2-((2-naphthylmethyl)amino)pyrimidin-4-yl)-2-oxopyrrolidine-3-carbonitrile | | Free | 372.0 |
| 75 | 3-ethyl-1-(2-((4-methoxybenzyl)amino)pyrimidin-4-yl)-2-oxopyrrolidine-3-carbonitrile | | Free | 361.9 |
| 76 | 3-ethyl-2-oxo-1-(2-((2-(pyridin-4-yl)ethyl)amino)pyrimidin-4-yl)pyrrolidine-3-carbonitrile | | Free | 337.0 |
| 77 | 1-(2-((cyclopropylmethyl)amino)pyrimidin-4-yl)-3-ethyl-2-oxopyrrolidine-3-carbonitrile | | Free | 285.9 |

Examples 78 to 84

In Examples 78 to 84, the title compound was obtained from 1-(2-chloropyrimidin-4-yl)-3-isopropyl-2-oxopyrrolidine-3-carbonitrile obtained in Step C of Example 5, and 2-(4-amino-1H-pyrazol-1-yl)acetamide, 2-(4-amino-1H-pyrazol-1-yl)-N-methylacetamide, 2-(4-amino-1H-pyrazol-1-yl)-N,N-dimethylacetamide, 4-aminobenzamide, 4-amino-N-methylbenzamide, 1-(tetrahydro-2H-pyran-4-yl)-1H-pyrazol-4-amine or N-(4-aminobenzyl)acetamide (these compounds can be produced according to a method known per se), each corresponding to the compounds of Examples 78 to 84, in the same manner as in Step B of Example 2 or a method analogous thereto. MS in the tables means actual measured value.

TABLE 7

| Example Number | IUPAC Name | Structure | Salt | MS |
|---|---|---|---|---|
| 78 | 2-(4-((4-(3-cyano-3-isopropyl-2-oxopyrroldin-1-yl)pyrimidin-2-yl)amino)-1H-pyrazol-1-yl)acetamide | 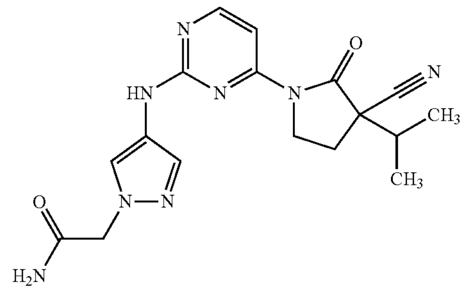 [SMILES: CC(C)C1(C#N)CCN(c2ccnc(Nc3cnn(CC(N)=O)c3)n2)C1=O] | HCl | 369.3 |
| 79 | 2-(4-((4-(3-cyano-3-isopropyl-2-oxopyrrolidin-1-yl)pyrimidin-2-yl)amino)-1H-pyrazol-1-yl)-N-methylacetamide | 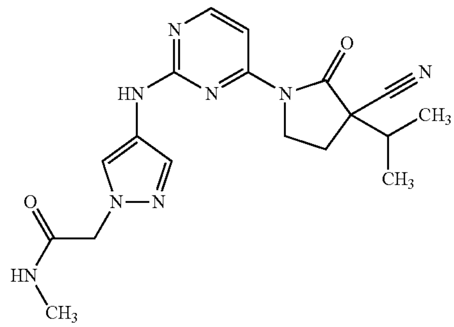 [SMILES: CNC(=O)Cn1cc(Nc2nccc(N3CCC(C#N)(C(C)C)C3=O)n2)cn1] | HCl | 383.3 |
| 80 | 2-(4-((4-(3-cyano-3-isopropyl-2-oxopyrrolidin-1-yl)pyrimidin-2-yl)amino)-1H-pyrazol-1-yl)-N,N-dimethylacetamide | 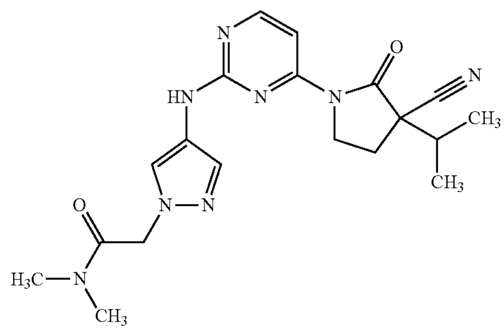 [SMILES: CC(C)C1(C#N)CCN(c2ccnc(Nc3cnn(CC(=O)N(C)C)c3)n2)C1=O] | HCl | 397.3 |
| 81 | 4-((4-(3-cyano-3-isopropyl-2-oxopyrrolidin-1-yl)pyrimidin-2-yl)amino)benzamide | 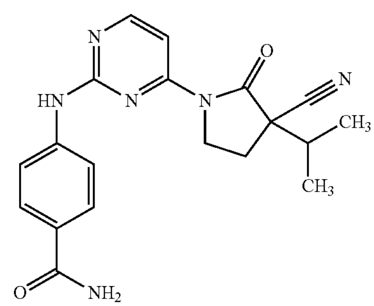 [SMILES: CC(C)C1(C#N)CCN(c2ccnc(Nc3ccc(C(N)=O)cc3)n2)C1=O] | HCl | 365.3 |
| 82 | 4-((4-(3-cyano-3-isopropyl-2-oxopyrrolidin-1-yl)pyrimidin-2-yl)amino)-N-methylbenzamide | 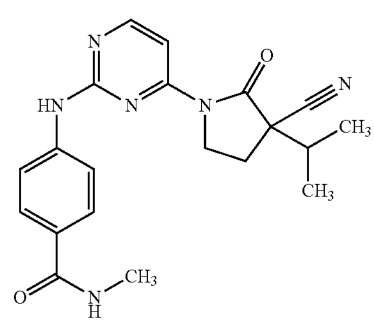 [SMILES: CNC(=O)c1ccc(Nc2nccc(N3CCC(C#N)(C(C)C)C3=O)n2)cc1] | HCl | 379.3 |

TABLE 7-continued

| Example Number | IUPAC Name | Structure | Salt | MS |
|---|---|---|---|---|
| 83 | 3-isopropyl-2-oxo-1-(2-((1-(tetrahydro-2H-pyran-4-yl)-1H-pyrazol-4-yl)amino)pyrimidin-4-yl)pyrrolidine-3-carbonitrile | 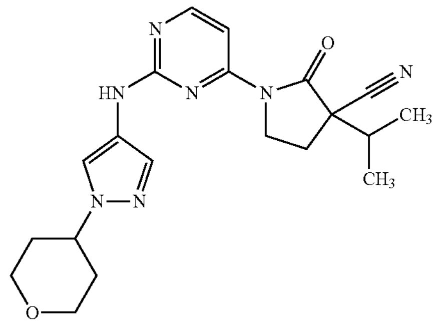 [SMILES: CC(C)C1(C#N)CCN(c2ccnc(Nc3cnn(C4CCOCC4)c3)n2)C1=O] | HCl | 396.3 |
| 84 | N-(4-((4-(3-cyano-3-isopropyl-2-oxopyrrolidin-1-yl)pyrimidin-2-yl)amino)benzyl)acetamide | 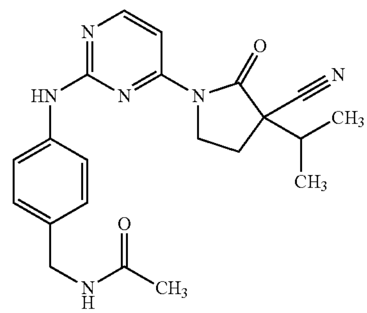 [SMILES: CC(=O)NCc1ccc(Nc2nccc(N3CCC(C#N)(C(C)C)C3=O)n2)cc1] | HCl | 393.3 |

Example 85

2-(4-((4-((3S)-3-cyano-3-isopropyl-2-oxopyrrolidin-1-yl)pyrimidin-2-yl)amino)-1H-pyrazol-1-yl)acetamide hydrochloride

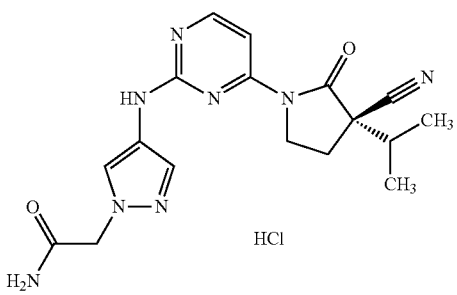 [SMILES: CC(C)[C@]1(C#N)CCN(c2ccnc(Nc3cnn(CC(N)=O)c3)n2)C1=O ; Cl]

A solution Of (3S)-1-(2-chloropyrimidin-4-yl)-3-isopropyl-2-oxopyrrolidine-3-carbonitrile (55 mg) obtained in Step A of Example 9, 2-(4-amino-1H-pyrazol-1-yl)acetamide (35 mg) and acetic acid (13 μL) in ethanol (2 mL) was stirred in a microwave reactor at 150° C. for 1 hr, and the solvent was evaporated under reduced pressure. The obtained residue was purified by silica gel column chromatography (NH, ethyl acetate/methanol). The obtained crude product was subjected to HPLC (C18, mobile phase: water/acetonitrile (containing 0.1% ammonium formate)), to the obtained fraction was added saturated aqueous sodium hydrogen carbonate solution, and the mixture was extracted with ethyl acetate. The extract was dried over anhydrous magnesium sulfate, and concentrated under reduced pressure. To a solution of the residue (17 mg) in ethanol (3 mL) was added 1M hydrochloric acid (57 μL), and the solvent was evaporated under reduced pressure. The residue was recrystallized (diisopropyl ether/ethanol) to give the title compound (13 mg).

$^1$H NMR (300 MHz, DMSO-$d_6$) δ 0.99-1.03 (3H, m), 1.07-1.15 (3H, m), 2.24-2.37 (1H, m), 2.38-2.47 (1H, m), 2.55 (1H, d, J=7.9 Hz), 4.08 (2H, brs), 4.72 (2H, s), 7.23 (1H, brs), 7.39 (1H, brs), 7.49-7.60 (2H, m), 7.87 (1H, brs), 8.37 (1H, d, J=5.7 Hz), 9.61 (1H, brs).

MS(ESI+): [M+H]$^+$ 369.3.

Example 86

2-(4-((4-((3S)-3-cyano-3-isopropyl-2-oxopyrrolidin-1-yl) pyrimidin-2-yl)amino)-1H-pyrazol-1-yl)-N-methylacetamide hydrochloride

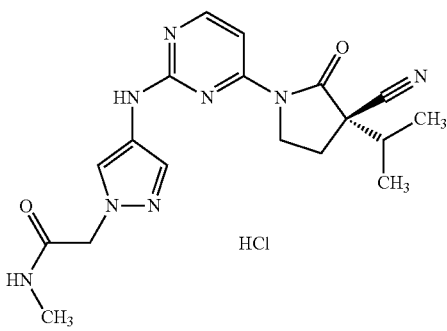 [SMILES: CNC(=O)Cn1cc(Nc2nccc(N3CC[C@@](C#N)(C(C)C)C3=O)n2)cn1 ; Cl]

A solution of (3S)-1-(2-chloropyrimidin-4-yl)-3-isopropyl-2-oxopyrrolidine-3-carbonitrile (55 mg) obtained in Step A of Example 9, 2-(4-amino-1H-pyrazol-1-yl)-N-methylacetamide (38 mg) and acetic acid (13 μL) in ethanol (2 mL) was stirred in a microwave reactor at 150° C. for 1 hr, and the solvent was evaporated under reduced pressure. The obtained residue was purified by silica gel column chromatography (NH, ethyl acetate/methanol). To a solution of the residue (83 mg) in ethanol (3 mL) was added 1M hydrochloric acid (220 μL), and the solvent was evaporated under reduced pressure. The residue was recrystallized (diisopropyl ether/ethanol) to give the title compound (87 mg).

$^1$H NMR (300 MHz, DMSO-$d_6$) δ 0.95-1.05 (3H, m), 1.07-1.16 (3H, m), 2.32 (1H, dt, J=13.6, 6.8 Hz), 2.41-2.46 (1H, m), 2.55 (1H, d, J=7.9 Hz), 2.61 (3H, d, J=4.5 Hz), 4.08 (2H, brs), 4.73 (2H, s), 7.45-7.62 (2H, m), 7.79-7.99 (2H, m), 8.37 (1H, d, J=5.7 Hz), 9.66 (1H, brs).

MS(ESI+): [M+H]$^+$ 383.3.

Example 87

2-(4-((4-((3S)-3-cyano-3-isopropyl-2-oxopyrrolidin-1-yl)pyrimidin-2-yl)amino)-1H-pyrazol-1-yl)-N,N-dimethylacetamide hydrochloride

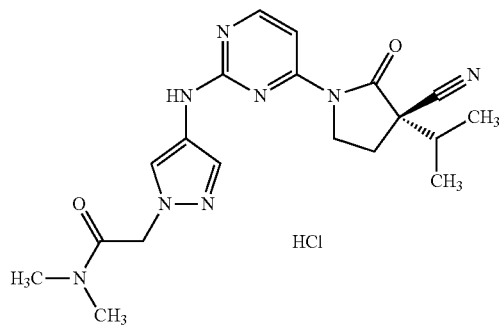 [SMILES: CC(C)[C@]1(C#N)CCN(c2ccnc(Nc3cnn(CC(=O)N(C)C)c3)n2)C1=O ; Cl]

A solution of (3S)-1-(2-chloropyrimidin-4-yl)-3-isopropyl-2-oxopyrrolidine-3-carbonitrile (55 mg) obtained in Step A of Example 9, 2-(4-amino-1H-pyrazol-1-yl)-N,N-dimethylacetamide (42 mg) and acetic acid (13 μL) in ethanol (2 mL) was stirred in a microwave reactor at 150° C. for 1 hr, and the solvent was evaporated under reduced pressure. The obtained residue was purified by silica gel column chromatography (NH, ethyl acetate/methanol). To a solution of the residue (80 mg) in ethanol (3 mL) was added 1M hydrochloric acid (200 μL), and the solvent was evaporated under reduced pressure. The residue was recrystallized (diisopropyl ether/ethanol) to give the title compound (90 mg).

$^1$H NMR (300 MHz, DMSO-$d_6$) δ 0.96-1.05 (3H, m), 1.07-1.15 (3H, m), 2.32 (1H, dt, J=13.6, 6.8 Hz), 2.41-2.46 (1H, m), 2.54-2.60 (1H, m), 2.85 (3H, s), 3.02 (3H, s), 4.04 (2H, brs), 4.98-5.13 (2H, m), 7.46-7.61 (2H, m), 7.68-7.91 (1H, m), 8.37 (1H, d, J=6.0 Hz), 9.68 (1H, brs).

MS(ESI+): [M+H]$^+$ 397.3.

Examples 88 to 97

In Examples 88 to 97, the title compound was obtained from (3S)-1-(2-chloropyrimidin-4-yl)-3-isopropyl-2-oxopyrrolidine-3-carbonitrile obtained in Step A of Example 9, and 4-(4-aminophenyl)morpholin-3-one, 6-((3R)-3-methylmorpholin-4-yl)pyridin-3-amine, N-(3-aminophenyl) acetamide, 6-((3S)-3-methylmorpholin-4-yl)pyridin-3-amine, 4-aminobenzamide, 4-amino-N-methylbenzamide, 2-(4-aminophenyl) acetamide, 2-(4-aminophenyl)-N-methylacetamide, 3-(4-aminophenyl)-1,2,4-oxadiazol-5(4H)-one or 4-(4-aminophenyl)piperazin-2-one (these compounds can be produced according to a method known per se), each corresponding to the compounds of Examples 88 to 97, in the same manner as in Step B of Example 2 or a method analogous thereto. MS in the tables means actual measured value.

TABLE 8-1

| Example Number | IUPAC Name | Structure | Salt | MS |
|---|---|---|---|---|
| 88 | (3S)-3-isopropyl-2-oxo-1-(2-((4-(3-oxomorpholin-4-yl)phenyl)amino)pyrimidin-4-yl)pyrrolidine-3-carbonitrile | 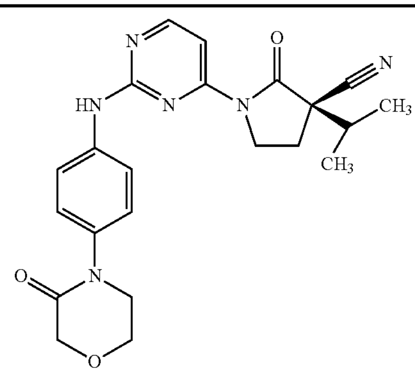 | Free | 421.3 |
| 89 | (3S)-3-isopropyl-1-(2-((6-((3R)-3-methylmorpholin-4-yl)pyridin-3-yl)amino)pyrimidin-4-yl)-2-oxopyrrolidine-3-carbonitrile | 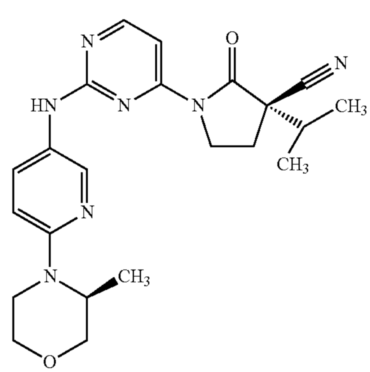 [SMILES: CC(C)[C@]1(C#N)CCN(c2ccnc(Nc3ccc(N4CCOC[C@@H]4C)nc3)n2)C1=O] | HCl | 422.4 |

TABLE 8-1-continued

| Example Number | IUPAC Name | Structure | Salt | MS |
|---|---|---|---|---|
| 90 | N-(3-((4-((3S)-3-cyano-3-isopropyl-2-oxopyrrolidin-1-yl)pyrimidin-2-yl)amino)phenyl)acetamide | 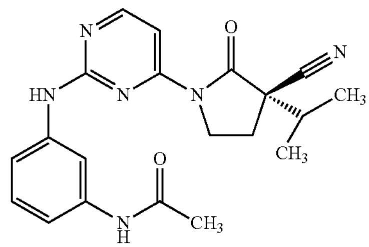 [SMILES: CC(=O)Nc1cccc(Nc2nccc(N3CC[C@@](C#N)(C(C)C)C3=O)n2)c1] | HCl | 379.3 |
| 91 | (3S)-3-isopropyl-1-(2-((6-((3S)-3-methylmorpholin-4-yl)pyridin-3-yl)amino)pyrimidin-4-yl)-2-oxopyrrolidine-3-carbonitrile | 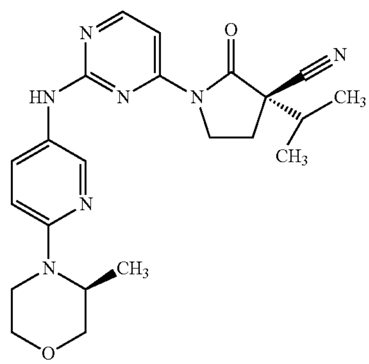 [SMILES: CC(C)[C@]1(C#N)CCN(c2ccnc(Nc3ccc(N4CCOC[C@@H]4C)nc3)n2)C1=O] | HCl | 422.4 |
| 92 | 4-((4-((3S)-3-cyano-3-isopropyl-2-oxopyrrolidin-1-yl)pyrimidin-2-yl)amino)benzamide | 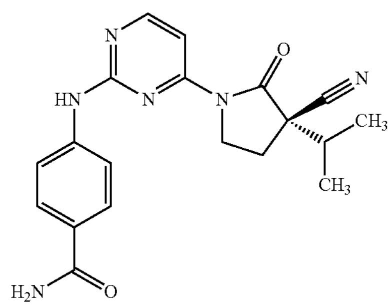 [SMILES: CC(C)[C@]1(C#N)CCN(c2ccnc(Nc3ccc(C(N)=O)cc3)n2)C1=O] | HCl | 365.3 |
| 93 | 4-((4-((3S)-3-cyano-3-isopropyl-2-oxopyrrolidin-1-yl)pyrimidin-2-yl)amino)-N-ethylbenzamide | 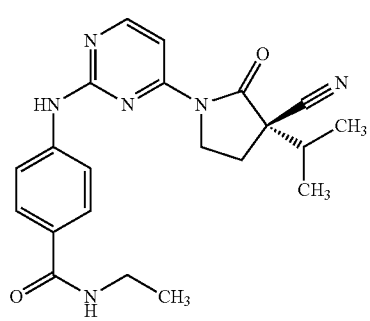 [SMILES: CCNC(=O)c1ccc(Nc2nccc(N3CC[C@@](C#N)(C(C)C)C3=O)n2)cc1] | HCl | 393.3 |
| 94 | 2-(4-((4-((3S)-3-cyano-3-isopropyl-2-oxopyrrolidin-1-yl)pyrimidin-2-yl)amino)phenyl)acetamide | 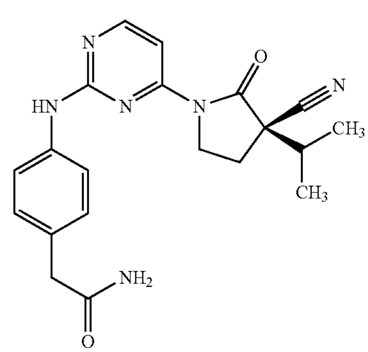 [SMILES: CC(C)[C@]1(C#N)CCN(c2ccnc(Nc3ccc(CC(N)=O)cc3)n2)C1=O] | HCl | 379.3 |

TABLE 8-1-continued

| Example Number | IUPAC Name | Structure | Salt | MS |
|---|---|---|---|---|
| 95 | 2-(4-((4-((3S)-3-cyano-3-isopropyl-2-oxopyrrolidin-1-yl)pyrimidin-2-yl)amino)phenyl)-N-methylacetamide | 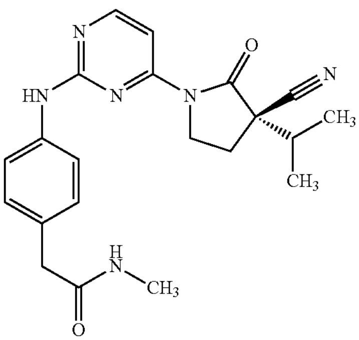 [SMILES: CNC(=O)Cc1ccc(Nc2nccc(N3CC[C@@](C#N)(C(C)C)C3=O)n2)cc1] | HCl | 393.3 |

TABLE 8-2

| | | | | |
|---|---|---|---|---|
| 96 | (3S)-3-isopropyl-2-oxo-1-(2-((4-(5-oxo-4,5-dihydro-1,2,4-oxadiazol-3-yl)phenyl)amino)pyrimidin-4-yl)pyrrolidine-3-carbonitrile | | Free | 406.3 |
| 97 | (3S)-3-isopropyl-2-oxo-1-(2-((4-(3-oxopiperazin-1-yl)phenyl)amino)pyrimidin-4-yl)pyrrolidine-3-carbonitrile | | Free | 420.4 |

Examples 98 to 100

In Examples 98 to 100, the title compound was obtained from (3R)-1-(2-chloropyrimidin-4-yl)-3-ethyl-2-oxopyrrolidine-3-carbonitrile obtained in Step A of Example 8, and N-(4-aminophenyl)-N-methylacetamide, 3-chloro-4-(morpholin-4-yl) aniline or 1-(4-(4-aminophenyl)piperazin-1-yl) ethanone (these compounds can be produced according to a method known per se), each corresponding to the compounds of Examples 98 to 100, in the same manner as in Step B of Example 2 or a method analogous thereto. MS in the tables means actual measured value.

TABLE 9

| Example Number | IUPAC Name | Structure | Salt | MS |
|---|---|---|---|---|
| 98 | N-(4-((4-((3R)-3-cyano-3-ethyl-2-oxopyrrolidin-1-yl)pyrimidin-2-yl)amino)phenyl)-N-methylacetamide | 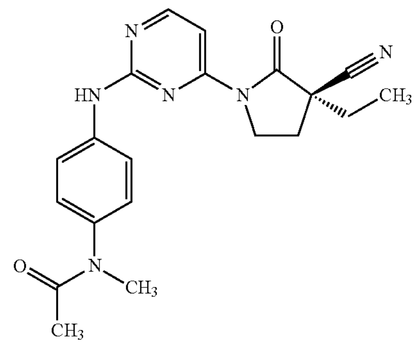 [SMILES: CC[C@]1(C#N)CCN(c2ccnc(Nc3ccc(N(C)C(C)=O)cc3)n2)C1=O] | Free | 370.3 |
| 99 | (3R)-1-(2-((3-chloro-4-(morpholin-4-yl)phenyl)amino)pyrimidin-4-yl)-3-ethyl-2-oxopyrrolidine-3-carbonitrile | 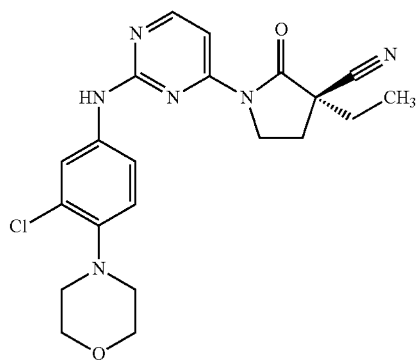 [SMILES: CC[C@]1(C#N)CCN(c2ccnc(Nc3ccc(N4CCOCC4)c(Cl)c3)n2)C1=O] | Free | 427.3 |
| 100 | (3R)-1-(2-((4-(4-acetylpiperazin-1-yl)phenyl)amino)pyrimidin-4-yl)-3-ethyl-2-oxopyrroldine-3-carbonitrile | 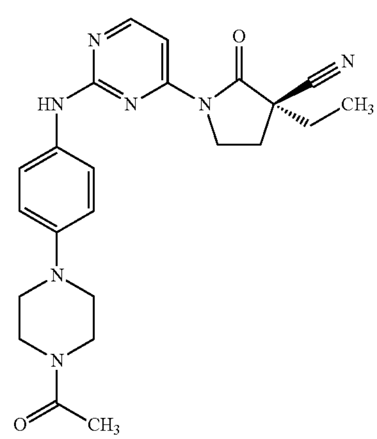 [SMILES: CC[C@]1(C#N)CCN(c2ccnc(Nc3ccc(N4CCN(C(C)=O)CC4)cc3)n2)C1=O] | HCl | 434.4 |

Example 101

3,3-dimethyl-1-(2-((1-methyl-1H-pyrazol-4-yl)amino)pyrimidin-4-yl) piperidin-2-one hydrochloride

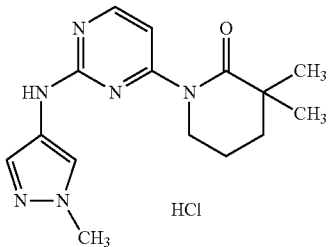 [SMILES: Cn1cc(Nc2nccc(N3CCCC(C)(C)C3=O)n2)cn1 ; Cl]

The title compound was obtained from 4-chloro-N-(1-methyl-1H-pyrazol-4-yl)pyrimidin-2-amine obtained in Step C of Example 1 and 3,3-dimethylpiperidin-2-one in the same manner as in Step I of Example 1.
MS(ESI+): [M+H]$^+$ 301.2.

Example 102

1-(2-((1-methyl-1H-pyrazol-4-yl)amino)pyrimidin-4-yl) piperidin-2-one hydrochloride

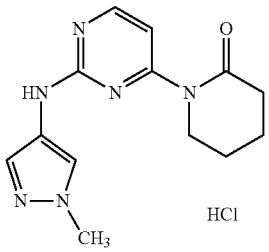 [SMILES: Cn1cc(Nc2nccc(N3CCCCC3=O)n2)cn1 ; Cl]

The title compound was obtained from 4-chloro-N-(1-methyl-1H-pyrazol-4-yl)pyrimidin-2-amine obtained in Step C of Example 1 and piperidin-2-one in the same manner as in Step I of Example 1.
MS(ESI+): [M+H]$^+$ 273.2.

Example 103

(3S)-3-cyclopropyl-1-(2-((1-(1-hydroxy-2-methylpropan-2-yl)-1H-pyrazol-4-yl)amino)pyrimidin-4-yl)-2-oxopyrrolidine-3-carbonitrile

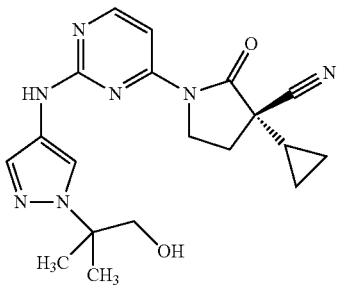 [SMILES: CC(C)(CO)n1cc(Nc2nccc(N3CC[C@@](C#N)(C4CC4)C3=O)n2)cn1]

A) ethyl cyano(cyclopropyl)acetate

To a solution of sodium hydride (60% in mineral oil, 38 g) and diethyl carbonate (97 mL) in toluene (240 mL) was added dropwise a solution of cyclopropylacetonitrile (32 g) in toluene (120 mL) over 40 min with heating under reflux, and the mixture was heated under reflux for additional 2 hr. The mixture was neutralized with acetic acid (120 mL) in an ice bath, water was added thereto, and the mixture was extracted with ethyl acetate. The obtained organic layer was washed with saturated brine, and dried over anhydrous magnesium sulfate, and the solvent was evaporated under reduced pressure. The residue was distilled (boiling point 69-72° C., 4.0 mmHg) to give the title compound (50 g).
$^1$H NMR (400 MHz, CDCl$_3$) δ0.49-0.61 (2H, m), 0.68-0.78 (2H, m), 1.34 (3H, t, J=7.2 Hz), 1.36-1.43 (1H, m), 3.23 (1H, d, J=7.6 Hz), 4.29 (2H, q, J=7.1 Hz).

B) ethyl 4-((tert-butoxycarbonyl)amino)-2-cyano-2-cyclopropylbutanoate

To a solution of ethyl cyano(cyclopropyl)acetate (27 g) obtained in Step A of Example 103 in toluene (400 mL) were added cesium carbonate (88 g), tetrabutylammonium bromide (5.8 g) and tert-butyl 1,2,3-oxathiazolidine-3-carboxylate 2,2-dioxide (40 g), and the mixture was stirred overnight at room temperature. The reaction mixture was neutralized with 0.5 M hydrochloric acid (400 mL), and extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (45 g).
$^1$H NMR (400 MHz, DMSO-d$_6$) δ0.35-0.47 (2H, m), 0.55-0.62 (1H, m), 0.63-0.72 (1H, m), 1.21-1.27 (3H, m), 1.30-1.34 (1H, m), 1.35-1.43 (9H, m), 1.95-2.00 (1H, m), 2.11-2.21 (1H, m), 2.90-3.03 (1H, m), 3.09-3.21 (1H, m), 4.15-4.30 (2H, m), 6.92 (1H, t, J=5.5 Hz).

C) 3-cyclopropyl-2-oxopyrrolidine-3-carbonitrile

To a solution of ethyl 4-((tert-butoxycarbonyl)amino)-2-cyano-2-cyclopropylbutanoate (45 g) obtained in Step B of Example 103 in tetrahydrofuran (1.2 L) was added sodium hydride (60% in mineral oil, 7.3 g) in an ice bath, and the mixture was stirred at room temperature for 2 hr. To the reaction mixture was added saturated aqueous ammonium chloride solution (100 mL), the solvent (tetrahydrofuran) was evaporated under reduced pressure, and the reaction mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (18 g).
$^1$H NMR (400 MHz, DMSO-d$_6$) δ0.40-0.57 (3H, m), 0.59-0.69 (1H, m), 1.31 (1H, m), 2.20 (1H, m), 2.43-2.48 (1H, m), 3.24-3.30 (2H, m), 8.30 (1H, brs).

D) 1-(2-chloropyrimidin-4-yl)-3-cyclopropyl-2-oxopyrrolidine-3-carbonitrile

To a mixture of 3-cyclopropyl-2-oxopyrrolidine-3-carbonitrile (18 g) obtained in Step C of Example 103, 2,4-dichloropyrimidine (17 g), cesium carbonate (76 g) and 4,5-bis(diphenylphosphino)-9,9-dimethylxanthene (4.1 g) in tetrahydrofuran (300 mL) was added tris(dibenzylideneacetone)dipalladium(0) (2.1 g), and the mixture was stirred overnight at 85° C. The insoluble substance was removed by filtration through Celite, and the solvent was evaporated under reduced pressure. The residue was purified by silica gel column chromatography (hexane/ethyl acetate) to give the title compound (23 g).
$^1$H NMR (400 MHz, DMSO-$d_6$) δ0.49-0.59 (2H, m), 0.62-0.74 (2H, m), 1.48-1.60 (1H, m), 2.37 (1H, m), 2.65 (1H, m), 3.95-4.04 (1H, m), 4.05-4.13 (1H, m), 8.24 (1H, d, J=5.9 Hz), 8.70 (1H, d, J=5.6 Hz).
MS(ESI+): [M+H]$^+$ 263.2.

E) (3S)-1-(2-chloropyrimidin-4-yl)-3-cyclopropyl-2-oxopyrrolidine-3-carbonitrile 1-(2-Cloropyrimidin-4-yl)-3-cyclopropyl-2-oxopyrrolidine-3-carbonitrile (23 g) obtained in Step D of Example 103 was resolved by HPLC (column: CHIRALPAK IC, 50 mmID×500 mmL, manufactured by Daicel Chemical Industries, mobile phase: hexane/2-propanol=200/800) to give the title compound (12 g: a shorter retention time).
>99% ee (HPLC (column: CHIRALPAK IC, 4.6 mmID×250 mmL, manufactured by Daicel Chemical Industries, mobile phase: hexane/2-propanol=200/800, flow rate: 0.5 mL/min, retention time: 19.33 min))

F) ethyl 2-methyl-2-(4-nitro-1H-pyrazol-1-yl)propanoate

To a solution of 4-nitro-1H-pyrazole (25 g) in N,N-dimethylformamide (100 mL) was added ethyl 2-bromo-2-methylpropanoate (39 mL), and the mixture was stirred at 80° C. for 2 hr. To the reaction mixture was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (50 g).
$^1$H NMR (400 MHz, CDCl$_3$) δ1.23 (3H, t, J=7.2 Hz), 1.88 (6H, s), 4.20 (2H, q, J=7.1 Hz), 8.11 (1H, s), 8.20-8.51 (1H, m).

G) 2-methyl-2-(4-nitro-1H-pyrazol-1-yl)propan-1-ol

To a solution of ethyl 2-methyl-2-(4-nitro-1H-pyrazol-1-yl)propanoate (45 g) obtained in Step F of Example 103 in tetrahydrofuran (400 mL) was added gradually dropwise diisopropylaluminium hydride in toluene (1.5 M in toluene, 400 mL) while maintaining the internal temperature of −20° C. or less, and the reaction mixture was stirred overnight while it was allowed to be warmed. To the reaction mixture was added aqueous potassium sodium tartrate solution in an ice bath, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (ethyl acetate) to give the crude title compound (36 g).
$^1$H NMR (400 MHz, CDCl$_3$) δ1.60 (6H, s), 2.71 (1H, brs), 3.84 (2H, s), 8.10 (1H, s), 8.28 (1H, d, J=0.5 Hz).

H) 2-(4-amino-1H-pyrazol-1-yl)-2-methylpropan-1-ol

To a solution of the crude 2-methyl-2-(4-nitro-1H-pyrazol-1-yl)propan-1-ol (36 g) obtained in Step G of Example 103 in ethanol (200 mL) was added 10% palladium-carbon (360 mg), and the mixture was stirred overnight at room temperature under hydrogen atmosphere (at normal pressure). The palladium-carbon was removed by filtration through Celite, and the solvent was evaporated under reduced pressure. The residue was purified by silica gel column chromatography (ethyl acetate/methanol), and the obtained solid was washed with diisopropyl ether to give the title compound (15 g).
$^1$H NMR (400 MHz, DMSO-$d_6$) δ1.36 (6H, s), 3.48 (2H, d, J=5.6 Hz), 3.71 (2H, brs), 4.86 (1H, t, J=5.6 Hz), 6.91 (1H, d, J=0.7 Hz), 7.09 (1H, d, J=1.0 Hz).

I) (3S)-3-cyclopropyl-1-(2-((1-(1-hydroxy-2-methylpropan-2-yl)-1H-pyrazol-4-yl)amino)pyrimidin-4-yl)-2-oxopyrrolidine-3-carbonitrile A solution of (3S)-1-(2-chloropyrimidin-4-yl)-3-cyclopropyl-2-oxopyrrolidine-3-carbonitrile (11.5 g) obtained in Step E of Example 103, 2-(4-amino-1H-pyrazol-1-yl)-2-methylpropan-1-ol (7.1 g) obtained in Step H of Example 103 and acetic acid (2.6 mL) in ethanol (200 mL) was stirred in a sealed tube reactor at 150° C. for 1 hr, and the solvent was evaporated under reduced pressure. The reaction mixture was neutralized with saturated aqueous sodium bicarbonate, and extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate), and recrystallized (diisopropyl ether/ethyl acetate) to give the title compound (6.9 g).
$^1$H NMR (400 MHz, DMSO-$d_6$) δ0.43-0.78 (4H, m), 1.45 (6H, s), 1.54 (1H, m), 2.28-2.43 (1H, m), 2.65 (1H, m), 3.56 (2H, d, J=5.6 Hz), 3.90-4.29 (2H, m), 4.97 (1H, t, J=5.5 Hz), 7.48 (1H, d, J=5.6 Hz), 7.54 (1H, s), 7.95 (1H, s), 8.36 (1H, d, J=4.9 Hz), 9.53 (1H, brs).
MS(ESI+): [M+H]$^+$ 382.3.

Example 104

(3S)-3-cyclopropyl-1-(2-(1-(1-hydroxy-2-methylpropan-2-yl)-1H-pyrazol-4-yl)amino)pyrimidin-4-yl)-2-oxopyrrolidine-3-carbonitrile hydrochloride

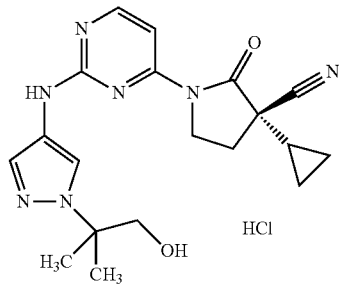 [SMILES: CC(C)(CO)n1cc(Nc2nccc(N3CC[C@@](C#N)(C4CC4)C3=O)n2)cn1 ; Cl]

To a solution of (3S)-3-cyclopropyl-1-(2-((1-(1-hydroxy-2-methylpropan-2-yl)-1H-pyrazol-4-yl)amino)pyrimidin-4-yl)-2-oxopyrrolidine-3-carbonitrile (4.3 g) obtained in Step I of Example 103 in ethanol (80 mL) was added 1 M hydrochloric acid (11 mL), and the mixture was stirred at room temperature for 5 min. The solvent was evaporated under reduced pressure, and the residue was recrystallized (diisopropyl ether/ethanol) to give the title compound (4.1 g).
$^1$H NMR (400 MHz, DMSO-$d_6$) δ0.42-0.84 (4H, m), 1.45 (6H, s), 1.50-1.62 (1H, m), 2.25-2.42 (1H, m), 2.65 (1H, m), 3.92-4.26 (4H, m), 4.44 (2H, brs), 7.50 (1H, d, J=5.9 Hz), 7.55 (1H, s), 7.96 (1H, s), 8.36 (1H, d, J=5.6 Hz), 9.65 (1H, brs).
MS(ESI+): [M+H]$^+$ 382.3.

Example 105

(3R)-3-cyclopropyl-1-(2-((1-(1-hydroxy-2-methyl-propan-2-yl)-1H-pyrazol-4-yl)amino)pyrimidin-4-yl)-2-oxopyrrolidine-3-carbonitrile

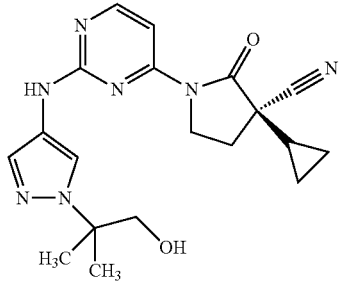 [SMILES: CC(C)(CO)n1cc(Nc2nccc(N3CC[C@](C#N)(C4CC4)C3=O)n2)cn1]

A) (3R)-1-(2-chloropyrimidin-4-yl)-3-cyclopropyl-2-oxopyrrolidine-3-carbonitrile 1-(2-Chloropyrimidin-4-yl)-3-cyclopropyl-2-oxopyrrolidine-3-carbonitrile (23 g) obtained in Step D of Example 103 was resolved by HPLC (column: CHIRALPAK IC, 50 mmID×500 mmL, manufactured by Daicel Chemical Industries, mobile phase: hexane/2-propanol=200/800) to give the title compound (11 g: a longer retention time).
>99% ee (HPLC (column: CHIRALPAK IC, 4.6 mmID×250 mmL, manufactured by Daicel Chemical Industries, mobile phase: hexane/2-propanol=200/800, flow rate: 0.5 mL/min, retention time: 27.06 min))

B) (3R)-3-cyclopropyl-1-(2-((1-(1-hydroxy-2-methylpropan-2-yl)-1H-pyrazol-4-yl)amino)pyrimidin-4-yl)-2-oxopyrrolidine-3-carbonitrile A solution of (3R)-1-(2-chloropyrimidin-4-yl)-3-cyclopropyl-2-oxopyrrolidine-3-carbonitrile (200 mg) obtained in Step A of Example 105, 2-(4-amino-1H-pyrazol-1-yl)-2-methylpropan-1-ol (120 mg) obtained in Step H of Example 103 and acetic acid (48 μL) in ethanol (20 mL) was stirred in a microwave reactor at 150° C. for 1 hr, and the solvent was evaporated under reduced pressure. The reaction mixture was neutralized with saturated aqueous sodium bicarbonate, and extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate), and recrystallized (diisopropyl ether/ethyl acetate) to give the title compound (110 mg).
$^1$H NMR (400 MHz, DMSO-$d_6$) δ0.40-0.87 (4H, m), 1.45 (6H, s), 1.54 (1H, m), 2.29-2.42 (1H, m), 2.57-2.75 (1H, m), 3.56 (2H, d, J=5.6 Hz), 3.95-4.36 (2H, m), 4.98 (1H, t, J=5.4 Hz), 7.48 (1H, d, J=5.6 Hz), 7.54 (1H, s), 7.95 (1H, s), 8.36 (1H, d, J=5.1 Hz), 9.53 (1H, brs).
MS(ESI+): [M+H]$^+$ 382.3.

Example 106

(3S)-3-cyclopropyl-1-(2-((1-(1-hydroxy-2-methyl-propan-2-yl)-($^2$H$_2$)-1H-pyrazol-4-yl)amino)pyrimidin-4-yl)-2-oxopyrrolidine-3-carbonitrile

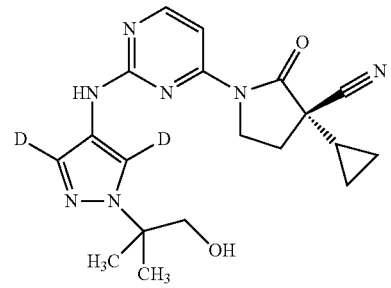 [SMILES: [2H]c1nn(C(C)(C)CO)c([2H])c1Nc1nccc(N2CC[C@@](C#N)(C3CC3)C2=O)n1]

A) 2-(4-amino-($^2$H$_2$)-1H-pyrazol-1-yl)-2-methylpropan-1-ol

To a solution of 2-(4-amino-1H-pyrazol-1-yl)-2-methylpropan-1-ol (350 mg) obtained in Step H of Example 103 in deuterated water (3.0 mL) was added a solution of 4 M hydrogen chloride in ethyl acetate (0.56 mL), the mixture was stirred in a microwave reactor at 180° C. for 1 hr, and the solvent was evaporated under reduced pressure. The residue was purified by silica gel column chromatography (NH, hexane/ethyl acetate) to give the title compound (150 mg).
$^1$H NMR (400 MHz, DMSO-$d_6$) δ1.36 (6H, s), 3.48 (2H, d, J=5.9 Hz), 3.70 (2H, brs), 4.86 (1H, t, J=5.6 Hz).

B) (3S)-3-cyclopropyl-1-(2-((1-(1-hydroxy-2-methylpropan-2-yl)-($^2$H$_2$)-1H-pyrazol-4-yl)amino)pyrimidin-4-yl)-2-oxopyrrolidine-3-carbonitrile The title compound (18 mg) was obtained from (3S)-1-(2-chloropyrimidin-4-yl)-3-cyclopropyl-2-oxopyrrolidine-3-carbonitrile (180 mg) obtained in Step E of Example 103 and 2-(4-amino-($^2$H$_2$)-1H-pyrazol-1-yl)-2-methylpropan-1-ol (150 rag) obtained in Step A of Example 106 in the same manner as in Example 56.
$^1$H NMR (400 MHz, DMSO-$d_6$) δ0.44-0.77 (4H, m), 1.45 (6H, s), 1.49-1.61 (1H, m), 2.30-2.42 (1H, m), 2.59-2.72 (1H, m), 3.56 (2H, d, J=5.4 Hz), 3.95-4.30 (2H, m), 4.97 (1H, t, J=5.4 Hz), 7.48 (1H, d, J=5.6 Hz), 8.36 (1H, d, J=5.4 Hz), 9.52 (1H, brs).
MS(ESI+): [M+H]$^+$ 384.4.

Example 107

(3S)-3-cyclopropyl-1-(2-((1-(1-hydroxy-2-methyl-(1,1-$^2$H$_2$)propan-2-yl)-1H-pyrazol-4-yl)amino)pyrimidin-4-yl)-2-oxopyrrolidine-3-carbonitrile hydrochloride

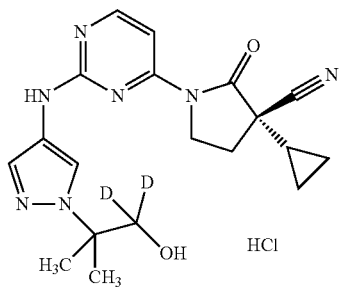 [SMILES: [2H]C([2H])(O)C(C)(C)n1cc(Nc2nccc(N3CC[C@@](C#N)(C4CC4)C3=O)n2)cn1 ; Cl]

A) 2-methyl-2-(4-nitro-(3-²H)-1H-pyrazol-1-yl)-(1,1-²H₂)propan-1-ol

To a solution of deuterated lithium aluminium hydride (2.0 g) in tetrahydrofuran (40 mL) was added a solution of ethyl 2-methyl-2-(4-nitro-1H-pyrazol-1-yl)propanoate (5.0 g) obtained in Step F of Example 103 in tetrahydrofuran (40 mL) at −78° C. under nitrogen atmosphere, and the mixture was stirred for 3 hr while it was allowed to be warmed to 0° C. To the reaction mixture was added sodium sulfate decahydrate in an ice bath, and the mixture was stirred at room temperature for 30 min. The resulting solid was removed by filtration through Celite, and the solvent was evaporated under reduced pressure. The residue was purified by silica gel column chromatography (hexane/ethyl acetate) to give the title compound (260 mg).

$^1$H NMR (400 MHz, CDCl$_3$) δ1.60 (6H, s), 2.61 (1H, s), 8.10 (1H, s).

B) 2-(4-amino-(3-²H)-1H-pyrazol-1-yl)-2-methyl-(1,1-²H₂) propan-1-ol

The title compound (160 mg) was obtained from 2-methyl-2-(4-nitro(3-²H)-1H-pyrazol-1-yl)-(1,1-²H₂)propan-1-ol (260 mg) obtained in Step A of Example 107 in the same manner as in Step H of Example 103.

$^1$H NMR (400 MHz, DMSO-d$_6$) δ1.36 (6H, s), 3.70 (2H, brs), 4.82 (1H, s), 6.90 (1H, s).

C) (3S)-3-cyclopropyl-1-(2-((1-(1-hydroxy-2-methyl-(1,1-²H₂)propan-2-yl)-1H-pyrazol-4-yl)amino)pyrimidin-4-yl)-2-oxopyrrolidine-3-carbonitrile hydrochloride The title compound (150 mg) was obtained from (3S)-1-(2-chloropyrimidin-4-yl)-3-cyclopropyl-2-oxopyrrolidine-3-carbonitrile (200 mg) obtained in Step E of Example 103 and 2-(4-amino(3-²H)-1H-pyrazol-1-yl)-2-methyl-(1,1-²H₂)propan-1-ol (130 mg) obtained in Step B of Example 107 in the same manner as in Step D of Example 109.

$^1$H NMR (400 MHz, DMSO-d$_6$) δ0.43-0.80 (4H, m), 1.45 (6H, s), 1.50-1.67 (1H, m), 2.26-2.42 (1H, m), 2.65 (1H, m), 3.88-4.31 (2H, m), 5.16 (2H, brs), 7.50 (1H, d, J=5.9 Hz), 7.55 (1H, s), 7.96 (1H, s), 8.36 (1H, d, J=5.6 Hz), 9.61 (1H, brs).
MS(ESI+): [M+H]$^+$ 384.3.

Example 108

2-(4-((4-((3S)-3-cyano-3-cyclopropyl-2-oxopyrrolidin-1-yl) pyrimidin-2-yl)amino)-1H-pyrazol-1-yl)-2-methylpropanoic acid hydrochloride

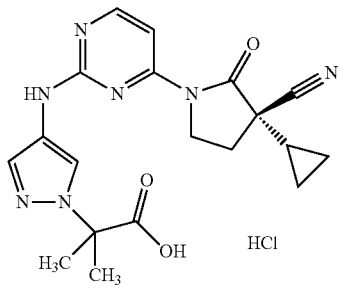 [SMILES: CC(C)(C(=O)O)n1cc(Nc2nccc(N3CC[C@@](C#N)(C4CC4)C3=O)n2)cn1 ; Cl]

A) tert-butyl 2-methyl-2-(4-nitro-1H-pyrazol-1-yl)propanoate

To a solution of 4-nitro-1H-pyrazole (3.0 g) in N,N-dimethylformamide (50 mL) was added tert-butyl 2-bromo-2-methylpropanoate (15 mL), and the mixture was stirred at 80° C. for 3 hr. To the reaction mixture was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (7.0 g).

$^1$H NMR (400 MHz, DMSO-d$_6$) δ1.35 (9H, s), 1.78 (6H, s), 8.33 (1H, s), 9.06 (1H, d, J=0.5 Hz).

B) tert-butyl 2-(4-amino-1H-pyrazol-1-yl)-2-methylpropanoate

The title compound (5.4 g) was obtained from tert-butyl 2-methyl-2-(4-nitro-1H-pyrazol-1-yl)propanoate (7.0 g) obtained in Step A of Example 108 in the same manner as in Step H of Example 103.

$^1$H NMR (400 MHz, DMSO-d$_6$) δ1.33 (9H, s), 1.61 (6H, s), 3.80 (2H, brs), 6.95 (1H, d, J=0.7 Hz), 7.09 (1H, d, J=0.7 Hz).
MS(ESI+): [M−(tBu)+2H]$^+$ 270.2.

C) tert-butyl 2-(4-((4-((3S)-3-cyano-3-cyclopropyl-2-oxopyrrolidin-1-yl) pyrimidin-2-yl)amino)-1H-pyrazol-1-yl)-2-methylpropanoate The title compound (1.5 g) was obtained from (3S)-1-(2-chloropyrimidin-4-yl)-3-cyclopropyl-2-oxopyrrolidine-3-carbonitrile (1.0 g) obtained in Step E of Example 103 and tert-butyl 2-(4-amino-1H-pyrazol-1-yl)-2-methylpropanoate (1.0 g) obtained in Step B of Example 108 in the same manner as in Step I of Example 103.

MS(ESI+): [M+H]$^+$ 452.3.

D) 2-(4-((4-((3S)-3-cyano-3-cyclopropyl-2-oxopyrrolidin-1-yl)pyrimidin-2-yl)amino)-1H-pyrazol-1-yl)-2-methylpropanoic acid hydrochloride To a solution of tert-butyl 2-(4-((4-((3S)-3-cyano-3-cyclopropyl-2-oxopyrrolidin-1-yl)pyrimidin-2-yl)amino)-1H-pyrazol-1-yl)-2-methylpropanoate (1.0 g) obtained in Step C of Example 108 in ethyl acetate (10 mL) was added a solution of 4 M hydrogen chloride in ethyl acetate (10 mL), and the mixture was stirred at room temperature for 3 hr. The solvent was evaporated under reduced pressure, and the residue was recrystallized (diisopropyl ether/ethanol) to give the crude title compound (1.1 g).

The crude title compound (100 mg) was purified by HPLC (C18, mobile phase: water/acetonitrile (containing 10 mM NH$_4$HCO$_3$)), and the solvent was evaporated under reduced pressure. To a solution of the residue (90 mg) in ethanol (3 mL) was added 1M hydrochloric acid (0.23 mL), and the solvent was evaporated under reduced pressure. The residue was recrystallized (diisopropyl ether/ethanol) to give the title compound (55 mg).

MS(ESI+): [M+H]$^+$ 396.3.

Example 109

2-(4-((4-((3S)-3-cyano-3-cyclopropyl-2-oxopyrrolidin-1-yl)pyrimidin-2-yl)amino)-1H-pyrazol-1-yl)-2-methylpropanamide hydrochloride

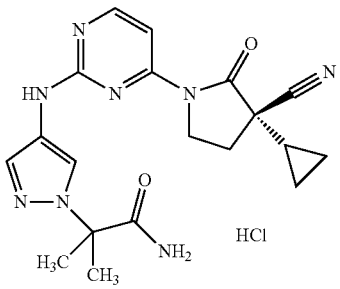 [SMILES: CC(C)(C(N)=O)n1cc(Nc2nccc(N3CC[C@@](C#N)(C4CC4)C3=O)n2)cn1 ; Cl]

A) 2-methyl-2-(4-nitro-H-pyrazol-1-yl)propanoic acid

To a solution of ethyl 2-methyl-2-(4-nitro-1H-pyrazol-1-yl)propanoate (6.0 g) obtained in Step F of Example 103 in ethanol (50 mL) was added dropwise 2 M aqueous sodium hydroxide solution (26 mL), and the mixture was stirred at room temperature for 3 hr. To the reaction mixture was added water, and the mixture was washed with diethyl ether. The obtained aqueous layer was neutralized with 2 M hydrochloric acid, and extracted with ethyl acetate. The obtained organic layer was washed with saturated brine, and dried over anhydrous magnesium sulfate, and the solvent was evaporated under reduced pressure to give the title compound (5.0 g).

$^1$H NMR (300 MHz, DMSO-$d_6$) δ1.79 (6H, s), 8.31 (1H, s), 9.06 (1H, s), 13.40 (1H, brs).

B) 2-methyl-2-(4-nitro-1H-pyrazol-1-yl)propanamide

To a solution of 2-methyl-2-(4-nitro-1H-pyrazol-1-yl)propanoic acid (1.2 g) obtained in Step A of Example 109 in N,N-dimethylformamide (10 mL) were added 1-ethyl-3-(3-dimethylaminopropyl)carbodiimide hydrochloride (1.3 g) and 1-hydroxybenzotriazole ammonia salt (1.4 g), and the mixture was stirred overnight at room temperature. To the reaction mixture was added saturated aqueous sodium hydrogen carbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (NH, ethyl acetate) to give the title compound (1.0 g).

$^1$H NMR (300 MHz, DMSO-$d_6$) δ1.75 (6H, s), 6.89-7.61 (2H, m), 8.29 (1H, s), 8.94 (1H, s).

C) 2-(4-amino-1H-pyrazol-1-yl)-2-methylpropanamide

To a solution of 2-methyl-2-(4-nitro-1H-pyrazol-1-yl)propanamide (1.0 g) obtained in Step B of Example 109 in ethanol (50 mL) was added 10% palladium-carbon (100 mg), and the mixture was stirred at room temperature for 5 hr under hydrogen atmosphere (at normal pressure). The palladium carbon was removed by filtration through Celite, and the solvent was evaporated under reduced pressure. The residue was recrystallized (ethyl acetate/hexane) to give the title compound (760 mg).

$^1$H NMR (300 MHz, DMSO-$d_6$) δ1.60 (6H, s), 3.85 (2H, brs), 6.35 (1H, brs), 7.01 (1H, d, J=0.8 Hz), 7.11 (1H, d, J=0.8 Hz), 7.11 (1H, brs).

D) 2-(4-((4-((3S)-3-cyano-3-cyclopropyl-2-oxopyrrolidin-1-yl)pyrimidin-2-yl)amino)-1H-pyrazol-1-yl)-2-methylpropanamide hydrochloride A solution of (3S)-1-(2-chloropyrimidin-4-yl)-3-cyclopropyl-2-oxopyrrolidine-3-carbonitrile (250 mg) obtained in Step E of Example 103, 2-(4-amino-1H-pyrazol-1-yl)-2-methylpropanamide (160 mg) obtained in Step C of Example 109 and acetic acid (57 μL) in ethanol (3.0 mL) was stirred in a microwave reactor at 150° C. for 1 hr, and the solvent was evaporated under reduced pressure. The reaction mixture was neutralized with saturated aqueous sodium bicarbonate, and extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate).

To a solution of the residue in ethanol (5.0 mL) was added 2 M hydrochloric acid (0.95 mL), the mixture was stirred for 5 min, and the solvent was evaporated under reduced pressure. The residue was recrystallized (ethyl acetate/acetonitrile) to give the title compound (230 mg).

$^1$H NMR (400 MHz, DMSO-$d_6$) δ0.39-0.87 (4H, m), 1.49-1.61 (1H, m), 1.69 (6H, s), 2.27-2.43 (1H, m), 2.65 (1H, m), 3.93-4.36 (2H, m), 4.89 (1H, brs), 6.75 (1H, brs), 7.20 (1H, brs), 7.51 (1H, d, J=5.6 Hz), 7.61 (1H, s), 7.98 (1H, s), 8.38 (1H, d, J=5.9 Hz), 9.63 (1H, brs).

MS(ESI+): [M+H]$^+$395.1.

Example 110

(3S)-3-cyclopropyl-1-(2-((1-(2-methyl-1-(morpholin-4-yl)-1-oxopropan-2-yl)-1H-pyrazol-4-yl)amino)pyrimidin-4-yl)-2-oxopyrrolidine-3-carbonitrile hydrochloride

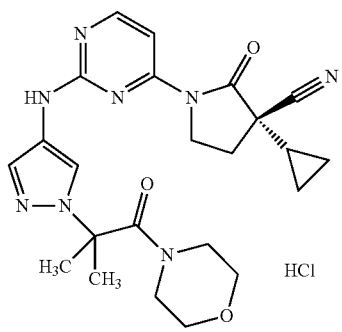 [SMILES: CC(C)(C(=O)N1CCOCC1)n1cc(Nc2nccc(N3CC[C@@](C#N)(C4CC4)C3=O)n2)cn1 ; Cl]

To a solution of 2-(4-((4-((3S)-3-cyano-3-cyclopropyl-2-oxopyrrolidin-1-yl)pyrimidin-2-yl)amino)-1H-pyrazol-1-yl)-2-methylpropanoic acid hydrochloride (80 mg) obtained in Example 108 in N,N-dimethylformamide (2.0 mL) were added 1-ethyl-3-(3-dimethylaminopropyl)carbodiimide (58 mg), 1-hydroxybenzotriazole monohydrate (57 mg), N,N-diisopropylethylamine (97 μL) and morpholine (19 mg), and the mixture was stirred overnight at room temperature. The solvent was evaporated under reduced pressure, and the residue was purified by silica gel column chromatography (NH, hexane/ethyl acetate). To a solution of the residue (87 mg) in ethanol (3.0 mL) was added dropwise 1 M hydrochloric acid (0.19 mL), the mixture was stirred for 5 min, and the solvent was evaporated under reduced pressure. The residue was recrystallized (ethanol/diisopropyl ether) to give the title compound (35 mg).

MS(ESI+): [M+H]$^+$ 465.4.

Examples 111 to 113

In Examples 111 to 113, the title compound was obtained from 2-(4-((4-((3S)-3-cyano-3-cyclopropyl-2-oxopyrrolidin-1-yl)pyrimidin-2-yl)amino)-1H-pyrazol-1-yl)-2-methylpropanoic acid hydrochloride obtained in Example 108 and the amine each corresponding to the compounds of Examples 111 to 113 ((S)-(−)-pyrrolidinol, (R)-(+)-pyrrolidinol and 4-hydroxypiperidine (these compounds can be produced according to a method known per se)), in the same manner as in Example 110 or a method analogous thereto. MS in the tables means actual measured value.

TABLE 10

| Example Number | IUPAC Name | Structure | Salt | MS |
|---|---|---|---|---|
| 111 | (3S)-3-cyclopropyl-1-(2-((1-(1-((3R)-3-hydroxypyrrolidin-1-yl)-2-methyl-1-oxopropan-2-yl)-1H-pyrazol-4-yl)amino)pyrimidin-4-yl)-2-oxopyrrolidine-3-carbonitrile | 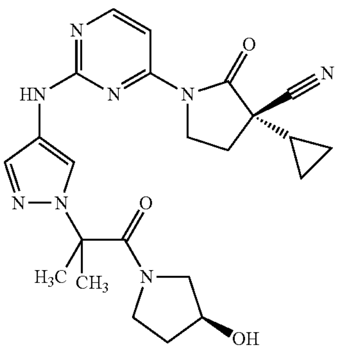 [SMILES: CC(C)(C(=O)N1CC[C@H](O)C1)n1cc(Nc2nccc(N3CC[C@@](C#N)(C4CC4)C3=O)n2)cn1] | HCl | 465.4 |
| 112 | (3S)-3-cyclopropyl-1-(2-((1-(1-((3S)-3-hydroxypyrrolidin-1-yl)-2-methyl-1-oxopropan-2-yl)-1H-pyrazol-4-yl)amino)pyrimidin-4-yl)-2-oxopyrrolidine-3-carbonitrile | 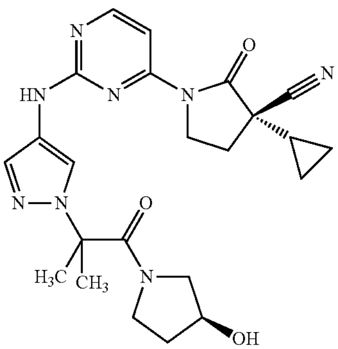 [SMILES: CC(C)(C(=O)N1CC[C@H](O)C1)n1cc(Nc2nccc(N3CC[C@@](C#N)(C4CC4)C3=O)n2)cn1] | HCl | 465.4 |
| 113 | (3S)-3-cyclopropyl-1-(2-((1-(1-(4-hydroxypiperidin-1-yl)-2-methyl-1-oxopropan-2-yl)-1H-pyrazol-4-yl)amino)pyrimidin-4-yl)-2-oxopyrrolidine-3-carbonitrile | 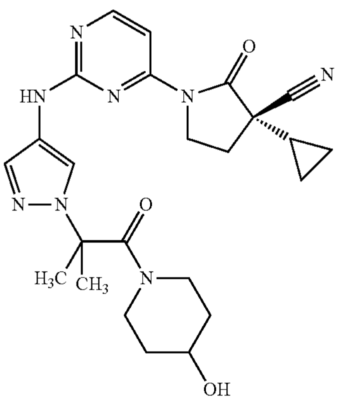 [SMILES: CC(C)(C(=O)N1CCC(O)CC1)n1cc(Nc2nccc(N3CC[C@@](C#N)(C4CC4)C3=O)n2)cn1] | free | 479.2 |

Example 114

(3S)-3-cyclopropyl-1-(2-((1-(2-methyl-1-(methylsulfonyl)propan-2-yl)-1H-pyrazol-4-yl)amino)pyrimidin-4-yl)-2-oxopyrrolidine-3-carbonitrile hydrochloride

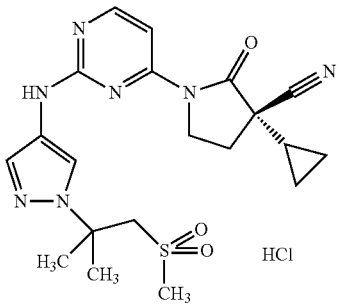 [SMILES: CC(C)(CS(C)(=O)=O)n1cc(Nc2nccc(N3CC[C@@](C#N)(C4CC4)C3=O)n2)cn1 ; Cl]

A) tert-butyl(1-(1-hydroxy-2-methylpropan-2-yl)-1H-pyrazol-4-yl)carbamate

To a solution of 2-(4-amino-1H-pyrazol-1-yl)-2-methylpropan-1-ol (2.1 g) obtained in Step H of Example 103 in tetrahydrofuran (50 mL) were added triethylamine (1.6 g) and di-tert-butyl dicarbonate (3.5 g), and the mixture was stirred at room temperature for 2 hr. To the reaction mixture was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (3.4 g).
$^1$H NMR (400 MHz, DMSO-d$_6$) δ1.40 (6H, s), 1.44 (9H, s), 3.51 (2H, d, J=5.6 Hz), 4.93 (1H, t, J=5.6 Hz), 7.27 (1H, s), 7.66 (1H, s), 9.07 (1H, s).

B) 2-(4-((tert-butoxycarbonyl)amino)-1H-pyrazol-1-yl)-2-methylpropyl methanesulfonate To tert-butyl(1-(1-hydroxy-2-methylpropan-2-yl)-1H-pyrazol-4-yl)carbamate (3.4 g) obtained in Step A of Example 114 were added successively triethylamine (2.4 mL) and methanesulfonyl chloride (1.2 mL) in an ice bath, and the mixture was stirred at room temperature for 2 hr. To the reaction mixture was added water, and the mixture was extracted with ethyl acetate. The obtained organic layer was washed with saturated brine, and dried over anhydrous magnesium sulfate, and the solvent was evaporated under reduced pressure to give the crude title compound (2.2 g).
$^1$H NMR (400 MHz, CDCl$_3$) δ1.50 (9H, s), 1.63 (6H, s), 2.78 (3H, s), 4.41 (2H, s), 6.23 (1H, brs), 7.38 (1H, s), 7.78 (1H, s).

C) tert-butyl(1-(2-methyl-1-(methylsulfonyl)propan-2-yl)-1H-pyrazol-4-yl)carbamate To a solution of the crude 2-(4-((tert-butoxycarbonyl)amino)-1H-pyrazol-1-yl)-2-methylpropyl methanesulfonate (1.1 g) obtained in Step B of Example 114 in N,N-dimethylformamide (10 mL) were added sodium iodide (740 mg) and sodium methanesulfinate (1.0 g), and the mixture was stirred overnight at 140° C. To the reaction mixture was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (250 mg).
MS(ESI+): [M+H]$^+$ 318.3.

D) 1-(2-methyl-1-(methylsulfonyl)propan-2-yl)-1H-pyrazol-4-amine

To tert-butyl(1-(2-methyl-1-(methylsulfonyl)propan-2-yl)-1H-pyrazol-4-yl)carbamate (250 mg) obtained in Step C of Example 114 was added dropwise a solution of 4 M hydrogen chloride in ethyl acetate (4.0 mL), and the mixture was stirred at room temperature for 30 min. The reaction mixture was neutralized with saturated aqueous sodium hydrogen carbonate solution, and extracted with ethyl acetate. The obtained organic layer was washed with saturated brine, and dried over anhydrous magnesium sulfate, and the solvent was evaporated under reduced pressure. The residue was purified by silica gel column chromatography (ethyl acetate/methanol) to give the title compound (23 mg).
$^1$H NMR (400 MHz, DMSO-d$_6$) δ1.64 (6H, s), 2.39 (3H, s), 3.67 (2H, s), 3.86 (2H, brs), 7.02 (1H, d, J=0.7 Hz), 7.17 (1H, d, J=0.7 Hz).

E) (3S)-3-cyclopropyl-1-(2-((1-(2-methyl-1-(methylsulfonyl)propan-2-yl)-1H-pyrazol-4-yl)amino)pyrimidin-4-yl)-2-oxopyrrolidine-3-carbonitrile hydrochloride The title compound (27 mg) was obtained from (3S)-1-(2-chloropyrimidin-4-yl)-3-cyclopropyl-2-oxopyrrolidine-3-carbonitrile (28 mg) obtained in Step E of Example 103 and 1-(2-methyl-1-(methylsulfonyl)propan-2-yl)-1H-pyrazol-4-amine (23 mg) obtained in Step D of Example 114 in the same manner as in Step D of Example 109.
MS(ESI+): [M+H]$^+$ 444.3.

Example 115

(3S)-1-(2-((1-(1-amino-2-methylpropan-2-yl)-1H-pyrazol-4-yl)amino)pyrimidin-4-yl)-3-cyclopropyl-2-oxopyrrolidine-3-carbonitrile dihydrochloride

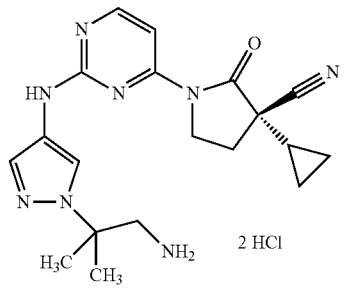 [SMILES: CC(C)(CN)n1cc(Nc2nccc(N3CC[C@@](C#N)(C4CC4)C3=O)n2)cn1 ; "2 HCl"]

A) 2-methyl-2-(4-nitro-1H-pyrazol-1-yl)propyl methanesulfonate

To a solution of 2-methyl-2-(4-nitro-1H-pyrazol-1-yl)propan-1-ol (13 g) obtained in Step G of Example 103 in tetrahydrofuran (100 mL) were added successively dropwise triethylamine (12 mL) and methanesulfonyl chloride (6.3 mL) at 0° C. under nitrogen atmosphere, and the mixture was stirred at room temperature for 2 hr. To the reaction mixture was added water, and the mixture was extracted with ethyl acetate. The obtained organic layer was washed with saturated brine, and dried over anhydrous magnesium sulfate, and the solvent was evaporated under reduced pressure to give the crude title compound (18 g).
$^1$H NMR (400 MHz, CDCl$_3$) δ1.70 (6H, s), 2.90 (3H, s), 4.45 (2H, s), 8.13 (1H, s), 8.27 (1H, s).

B) 1-(1-iodo-2-methylpropan-2-yl)-4-nitro-1H-pyrazole

To a solution of the crude 2-methyl-2-(4-nitro-1H-pyrazol-1-yl)propyl methanesulfonate (18 g) obtained in Step A of Example 115 in N,N-dimethylformamide (150 mL) was added sodium iodide (20 g), and the mixture was stirred overnight at 130° C. To the reaction mixture was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (14 g).
$^1$H NMR (400 MHz, CDCl$_3$) δ1.80 (6H, s), 3.68 (2H, s), 8.13 (1H, s), 8.22 (1H, s).

C) 1-(1-azido-2-methylpropan-2-yl)-4-nitro-1H-pyrazole

To a solution of 1-(1-iodo-2-methylpropan-2-yl)-4-nitro-1H-pyrazole (14 g) obtained in Step B of Example 115 in N,N-dimethylformamide (100 mL) was added sodium azide (4.8 g), and the mixture was stirred overnight at 140° C. To the reaction mixture was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (10 g).
$^1$H NMR (400 MHz, CDCl$_3$) δ1.65 (6H, s), 3.68 (2H, s), 8.13 (1H, s), 8.25 (1H, s).

D) 2-methyl-2-(4-nitro-1H-pyrazol-1-yl)propan-1-amine

To a solution of 1-(1-azido-2-methylpropan-2-yl)-4-nitro-1H-pyrazole (10 g) obtained in Step C of Example 115 in a mixed solvent of tetrahydrofuran/water (v/v=10/1, 88 mL) was added triphenylphosphine (15 g), and the mixture was stirred overnight at room temperature. The solvent was evaporated under reduced pressure, and the residue was purified by silica gel column chromatography (ethyl acetate/methanol) to give the title compound (8.7 g) as a mixture with triphenylphosphine oxide.
MS(ESI+): [M+H]$^+$ 185.3.

E) tert-butyl(2-methyl-2-(4-nitro-1H-pyrazol-1-yl)propyl)carbamate

To a solution of the crude 2-methyl-2-(4-nitro-1H-pyrazol-1-yl)propan-1-amine (8.7 g) obtained in Step D of Example 115 in tetrahydrofuran (100 mL) were added triethylamine (8.6 mL) and di-tert-butyl dicarbonate (13 mL) at 0° C. under nitrogen atmosphere, and the mixture was stirred overnight at room temperature. To the reaction mixture was added 1 M hydrochloric acid, and the mixture was extracted with ethyl acetate. The obtained organic layer was washed with satu-rated brine, and dried over anhydrous magnesium sulfate, and the solvent was evaporated under reduced pressure. The residue was purified by silica gel column chromatography (hexane/ethyl acetate) to give the title compound (3.0 g).
$^1$H NMR (400 MHz, CDCl$_3$) δ1.42 (9H, s), 1.59 (6H, s), 3.58 (2H, d, J=6.8 Hz), 4.74 (1H, brs), 8.10 (1H, s), 8.23 (1H, s).

F) tert-butyl(2-(4-amino-1H-pyrazol-1-yl)-2-methylpropyl)carbamate

The title compound (1.5 g) was obtained from tert-butyl(2-methyl-2-(4-nitro-1H-pyrazol-1-yl)propyl)carbamate (1.9 g) obtained in Step E of Example 115 in the same manner as in Step H of Example 103.
$^1$H NMR (400 MHz, DMSO-d$_6$) δ1.31-1.44 (15H, m), 3.23 (2H, d, J=6.4 Hz), 3.75 (2H, brs), 6.57 (1H, t, J=6.5 Hz), 6.94 (1H, s), 7.08 (1H, s).

G) (3S)-1-(2-((1-(1-amino-2-methylpropan-2-yl)-1H-pyrazol-4-yl)amino)pyrimidin-4-yl)-3-cyclopropyl-2-oxopyrrolidine-3-carbonitrile dihydrochloride The title compound (880 mg) was obtained from (3S)-1-(2-chloropyrimidin-4-yl)-3-cyclopropyl-2-oxopyrrolidine-3-carbonitrile (600 mg) obtained in Step E of Example 103 and tert-butyl(2-(4-amino-1H-pyrazol-1-yl)-2-methylpropyl)carbamate (640 mg) obtained in Step F of Example 115 in the same manner as in Step D of Example 109.
MS(ESI+): [M+H]$^+$381.4.

Example 116

N-(2-(4-((4-((3S)-3-cyano-3-cyclopropyl-2-oxopyrrolidin-1-yl)pyrimidin-2-yl)amino)-1H-pyrazol-1-yl)-2-methylpropyl)-2-methoxyacetamide hydrochloride

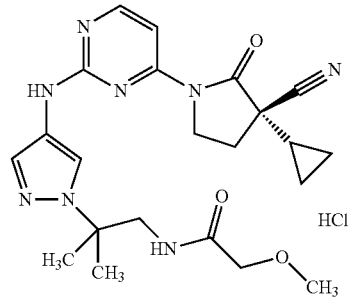 [SMILES: COCC(=O)NCC(C)(C)n1cc(Nc2nccc(N3CC[C@@](C#N)(C4CC4)C3=O)n2)cn1 ; Cl]

To a solution of (3S)-1-(2-((1-(1-amino-2-methylpropan-2-yl)-1H-pyrazol-4-yl)amino)pyrimidin-4-yl)-3-cyclopropyl-2-oxopyrrolidine-3-carbonitrile dihydrochloride (100 mg) obtained in Example 115 in tetrahydrofuran (5 mL) were added successively dropwise triethylamine (0.15 mL) and methoxyacetyl chloride (26 mg) at 0° C. under nitrogen atmosphere, and the mixture was stirred at room temperature for 5 hr. To the reaction mixture was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (ethyl acetate/methanol). To a solution of the residue (89 mg) in ethanol (5.0 mL) was added 1 M hydrochloric acid (0.20 mL), and the mixture was stirred at room temperature for 5 min. The solvent was evaporated under reduced pressure, and the residue was recrystallized (diisopropyl ether/ethyl acetate) to give the title compound (81 mg).

MS(ESI+): [M+H]+ 453.4.

Examples 117 to 121

In Examples 117 to 121, the title compound was obtained from (3S)-1-(2-((1-(1-amino-2-methylpropan-2-yl)-1H-pyrazol-4-yl)amino)pyrimidin-4-yl)-3-cyclopropyl-2-oxopyrrolidine-3-carbonitrile dihydrochloride obtained in Example 115 and the reagent each corresponding to the compounds of Examples 117 to 121 (acetyl chloride, glycol acid, methanesulfonyl chloride, N,N-dimethylsulfamoyl chloride and (tert-butoxycarbonyl)((4-(dimethyliminio)pyridin-1 (4H)-yl)sulfonyl)azanide (these compounds can be produced according to a method known per se)), in the same manner as in Example 116 or a method analogous thereto. MS in the tables means actual measured value.

TABLE 11

| Example Number | IUPAC Name | Structure | Salt | MS |
|---|---|---|---|---|
| 117 | N-(2-(4-((4-((3S)-3-cyano-3-cyclopropyl-2-oxopyrrolidin-1-yl)pyrimidin-2-yl)amino)-1H-pyrazol-1-yl)-2-methylpropyl)acetamide | 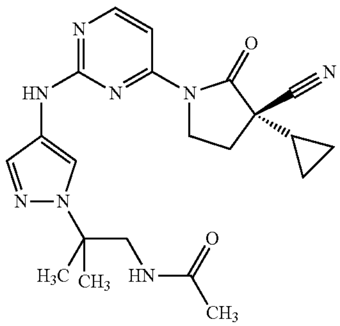 [SMILES: CC(=O)NCC(C)(C)n1cc(Nc2nccc(N3CC[C@@](C#N)(C4CC4)C3=O)n2)cn1] | HCl | 423.4 |
| 118 | N-(2-(4-((4-((3S)-3-cyano-3-cyclopropyl-2-oxopyrrolidin-1-yl)pyrimidin-2-yl)amino)-1H-pyrazol-1-yl)-2-methylpropyl)-2-hydroxyacetamide | 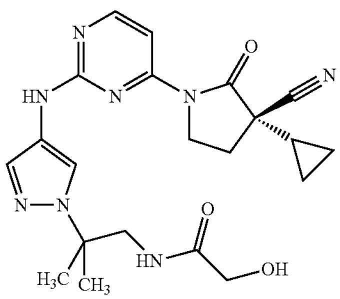 [SMILES: CC(C)(CNC(=O)CO)n1cc(Nc2nccc(N3CC[C@@](C#N)(C4CC4)C3=O)n2)cn1] | HCl | 453.4 |
| 119 | N-(2-(4-((4-((3S)-3-cyano-3-cyclopropyl-2-oxopyrrolidin-1-yl)pyrimidin-2-yl)amino)-1H-pyrazol-1-yl)-2-methylpropyl)methanesulfonamide | 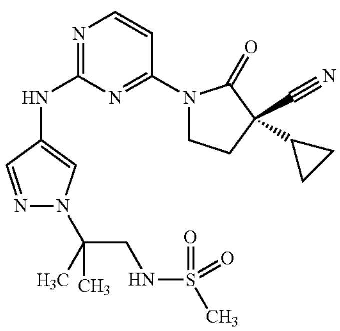 | HCl | 439.3 |
| 120 | N'-(2-(4-((4-((3S)-3-cyano-3-cyclopropyl-2-oxopyrrolidin-1-yl)pyrimidin-2-yl)amino)-1H-pyrazol-1-yl)-2-methylpropyl)-N,N-dimethylsulfonyl diamide | 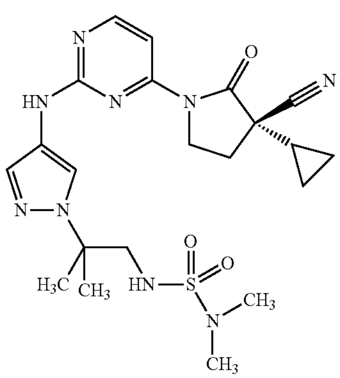 [SMILES: CN(C)S(=O)(=O)NCC(C)(C)n1cc(Nc2nccc(N3CC[C@@](C#N)(C4CC4)C3=O)n2)cn1] | HCl | 459.4 |

TABLE 11-continued

| Example Number | IUPAC Name | Structure | Salt | MS |
|---|---|---|---|---|
| 121 | N-(2-(4-((4-(((3S)-3-cyano-3-cyclopropyl-2-oxopyrrolidin-1-yl)pyrimidin-2-yl)amino)-1H-pyrazol-1-yl)-2-methylpropyl)sulfonyl diamide | 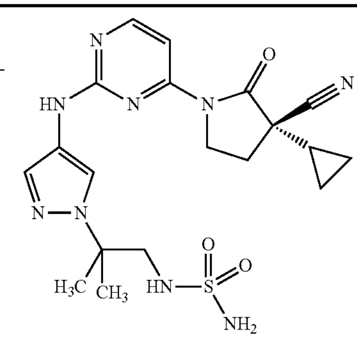 | HCl | 488.4 |

Example 122

(3S)-3-cyclopropyl-1-(2-((1-(2-methyl-1-(methylamino) propan-2-yl)-1H-pyrazol-4-yl)amino)pyrimidin-4-yl)-2-oxopyrrolidine-3-carbonitrile dihydrochloride

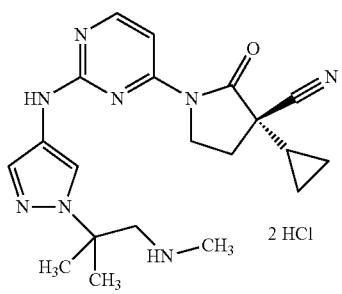 [SMILES: CNCC(C)(C)n1cc(Nc2nccc(N3CC[C@@](C#N)(C4CC4)C3=O)n2)cn1]

A) tert-butyl methyl(2-methyl-2-(4-nitro-1H-pyrazol-1-yl) propyl) carbamate

To a solution of tert-butyl(2-methyl-2-(4-nitro-1H-pyrazol-1-yl)propyl)carbamate (1.1 g) obtained in Step E of Example 115 in N,N-dimethylformamide (10 mL) was added sodium hydride (60% in mineral oil, 160 mg) at 0° C. under nitrogen atmosphere, and the mixture was stirred at room temperature for 30 min. Then, to the reaction mixture was added methyl iodide (640 mg) at room temperature, and the mixture was stirred overnight at room temperature. To the reaction mixture was added 1 M hydrochloric acid, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (1.1 g).

$^1$H NMR (400 MHz, CDCl$_3$) δ1.44 (9H, brs), 1.62 (6H, s), 2.26-2.44 (3H, m), 3.66 (2H, brs), 8.13 (1H, s), 8.22 (1H, s).

B) tert-butyl(2-(4-amino-1H-pyrazol-1-yl)-2-methylpropyl)methylcarbamate

The title compound (1.0 g) was obtained from tert-butyl methyl(2-methyl-2-(4-nitro-1H-pyrazol-1-yl)propyl)carbamate (1.1 g) obtained in Step A of Example 122 in the same manner as in Step H of Example 103.

$^1$H NMR (400 MHz, DMSO-d$_6$) δ1.28-1.52 (15H, m), 2.15 (3H, s), 3.41-3.49 (2H, m), 3.78 (2H, brs), 6.98 (1H, d, J=0.7 Hz), 7.08 (1H, d, J=0.7 Hz).

C) (3S)-3-cyclopropyl-1-(2-((1-(2-methyl-1-(methylamino)propan-2-yl)-1H-pyrazol-4-yl)amino)pyrimidin-4-yl)-2-oxopyrrolidine-3-carbonitrile dihydrochloride The title compound (720 mg) was obtained from (3S)-1-(2-chloropyrimidin-4-yl)-3-cyclopropyl-2-oxopyrrolidine-3-carbonitrile (600 mg) obtained in Step E of Example 103 and tert-butyl(2-(4-amino-1H-pyrazol-1-yl)-2-methylpropyl)methylcarbamate (680 mg) obtained in Step B of Example 122 in the same manner as in Step D of Example 109.

MS(ESI+): [M+H]$^+$ 395.4.

Examples 123 to 126

In Examples 123 to 126, the title compound was obtained from (3S)-3-cyclopropyl-1-(2-((1-(2-methyl-1-(methylamino)propan-2-yl)-1H-pyrazol-4-yl)amino)pyrimidin-4-yl)-2-oxopyrrolidine-3-carbonitrile dihydrochloride obtained in Example 122 and the reagent each corresponding to the compounds of Examples 123 to 126 (glycol acid, acetyl chloride, N,N-dimethylsulfamoyl chloride and (tert-butoxycarbonyl) ((4-(dimethyliminio)pyridin-1(4H)-yl)sulfonyl) azanide (these compounds can be produced according to a method known per se)), in the same manner as in Example 116 or a method analogous thereto. MS in the tables means actual measured value.

TABLE 12

| Example Number | IUPAC Name | Structure | Salt | MS |
|---|---|---|---|---|
| 123 | N-(2-(4-((4-((3S)-3-cyano-3-cyclopropyl-2-oxopyrrolidin-1-yl)pyrimidin-2-yl)amino)-1H-pyrazol-1-yl)-2-methylpropyl)-2-hydroxy-N-methylacetamide | 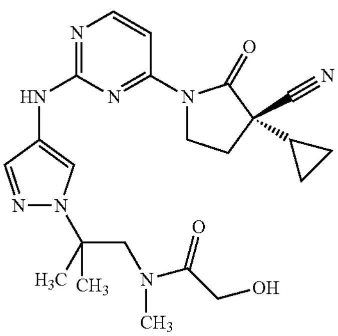 [SMILES: CN(CC(C)(C)n1cc(Nc2nccc(N3CC[C@@](C#N)(C4CC4)C3=O)n2)cn1)C(=O)CO] | HCl | 453.4 |
| 124 | N-(2-(4-((4-((3S)-3-cyano-3-cyclopropyl-2-oxopyrrolidin-1-yl)pyrimidin-2-yl)amino)-1H-pyrazol-1-yl)-2-methylpropyl)-N-methylacetamide | 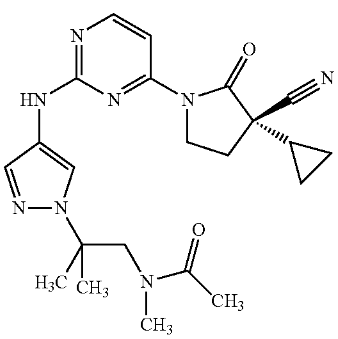 [SMILES: CC(=O)N(C)CC(C)(C)n1cc(Nc2nccc(N3CC[C@@](C#N)(C4CC4)C3=O)n2)cn1] | HCl | 437.4 |
| 125 | N-(2-(4-((4-((3S)-3-cyano-3-cyclopropyl-2-oxopyrrolidin-1-yl)pyrimidin-2-yl)amino)-1H-pyrazol-1-yl)-2-methylpropyl)-N,N',N'-trimethylsulfonyl diamide | 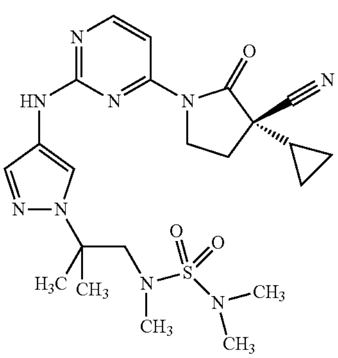 [SMILES: CN(C)S(=O)(=O)N(C)CC(C)(C)n1cc(Nc2nccc(N3CC[C@@](C#N)(C4CC4)C3=O)n2)cn1] | HCl | 502.4 |
| 126 | N-(2-(4-((4-((3S)-3-cyano-3-cyclopropyl-2-oxopyrrolidin-1-yl)pyrimidin-2-yl)amino)-1H-pyrazol-1-yl)-2-methylpropyl)-N-methylsulfonyl diamide | 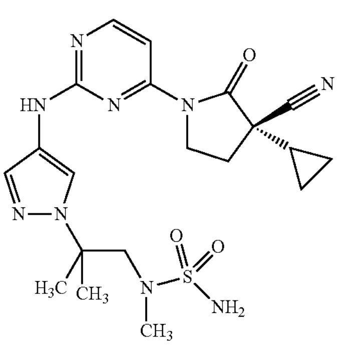 [SMILES: CN(CC(C)(C)n1cc(Nc2nccc(N3CC[C@@](C#N)(C4CC4)C3=O)n2)cn1)S(N)(=O)=O] | HCl | 474.4 |

Example 127

(3S)-3-cyclopropyl-1-(2-((1-(1-(hydroxymethyl)
cyclobutyl)-1H-pyrazol-4-yl)amino)pyrimidin-4-yl)-
2-oxopyrrolidine-3-carbonitrile

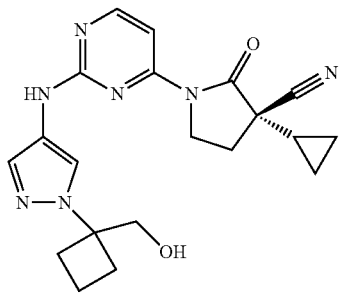 [SMILES: N#C[C@@]1(C2CC2)CCN(c2ccnc(Nc3cnn(C4(CO)CCC4)c3)n2)C1=O]

A) ethyl 1-(4-nitro-1H-pyrazol-1-yl)cyclobutanecarboxylate

To a solution of 4-nitro-1H-pyrazole (8.2 g) in N,N-dimethylacetamide (70 mL) was added sodium hydride (60% in mineral oil, 3.2 g) in an ice bath, and the mixture was stirred at the same temperature for 30 min. To the reaction mixture was added ethyl 1-bromocyclobutanecarboxylate (15 g) in an ice bath, and the mixture was stirred at room temperature for 10 hr. Water was poured into the reaction mixture, and the reaction mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (1.4 g).
MS(ESI+): [M+H]$^+$ 240.9.

B) (1-(4-nitro-1H-pyrazol-1-yl)cyclobutyl)methanol

To a solution of ethyl 1-(4-nitro-1H-pyrazol-1-yl)cyclobutanecarboxylate (500 mg) obtained in Step A of Example 127 in tetrahydrofuran (30 mL) was added lithium tetrahydroborate (68 mg), and the mixture was stirred at room temperature for 3 hr. Water was poured into the reaction mixture, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (410 mg).
MS(ESI+): [M+H]$^{++}$198.8.

C) (1-(4-amino-1H-pyrazol-1-yl)cyclobutyl)methanol

To a solution of (1-(4-nitro-1H-pyrazol-1-yl)cyclobutyl)methanol (480 mg) obtained in Step B of Example 127 in ethanol (30 mL) was added 10% palladium-carbon (100 mg), and the mixture was stirred at room temperature for 10 hr under hydrogen atmosphere (at normal pressures). The palladium-carbon was removed by filtration through Celite, and the solvent was evaporated under reduced pressure to give the title compound (400 mg).
MS(ESI+): [M+H]$^+$ 168.9.

D) (3S)-3-cyclopropyl-1-(2-((1-(1-(hydroxymethyl)cyclobutyl)-1H-pyrazol-4-yl)amino)pyrimidin-4-yl)-2-oxopyrrolidine-3-carbonitrile A solution of (3S)-1-(2-chloropyrimidin-4-yl)-3-cyclopropyl-2-oxopyrrolidine-3-carbonitrile (150 mg) obtained in Step E of Example 103, (1-(4-amino-1H-pyrazol-1-yl)cyclobutyl)methanol (95 mg) obtained in Step C of Example 127 and acetic acid (34 mg) in propan-2-ol (4.0 mL) was stirred in a microwave reactor at 160° C. for 1 hr. The reaction mixture was concentrated under reduced pressure, the residue was poured into saturated aqueous sodium hydrogen carbonate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (NH, hexane/ethyl acetate), and recrystallized (diisopropyl ether/ethyl acetate) to give the title compound (140 mg).
MS(ESI+): [M+H]$^+$ 394.3.

Example 128

(3S)-3-cyclopropyl-1-(2-((1-(1-(hydroxymethyl)cyclopropyl)-1H-pyrazol-4-yl)amino)pyrimidin-4-yl)-2-oxopyrrolidine-3-carbonitrile

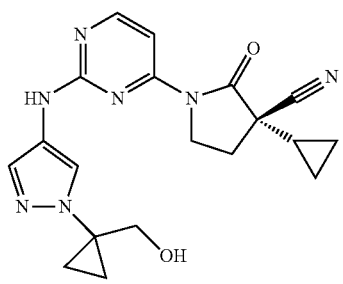 [SMILES: N#C[C@@]1(C2CC2)CCN(c2ccnc(Nc3cnn(C4(CO)CC4)c3)n2)C1=O]

A) methyl 1-(4-nitro-1H-pyrazol-1-yl)cyclopropanecarboxylate

To a solution of 4-nitro-1H-pyrazole (3.0 g) in N,N-dimethylacetamide (30 mL) was added sodium hydride (60% in mineral oil, 1.2 g) in an ice bath, and the mixture was stirred at the same temperature for 30 min. To the reaction mixture was added methyl 2,4-dibromobutanoate (6.9 g) in an ice bath, and the mixture was stirred at room temperature for 10 hr. The reaction mixture was poured into water, and the reaction mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (3.4 g).
$^1$H NMR (400 MHz, CDCl$_3$) δ1.68-1.75 (2H, m), 1.89-1.97 (2H, m), 3.73 (3H, m), 8.08 (1H, s), 8.28 (1H, s).
MS(ESI+): [M+H]$^+$ 211.6.

B) (1-(4-nitro-1H-pyrazol-1-yl)cyclopropyl)methanol

To a solution of methyl 1-(4-nitro-1H-pyrazol-1-yl)cyclopropanecarboxylate (1.0 g) obtained in Step A of Example 128 in tetrahydrofuran (50 mL) was added lithium tetrahydroborate (160 mg), and the mixture was stirred at room temperature for 10 hr. Water was poured into the reaction mixture, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (620 mg).

$^1$H NMR (400 MHz, CDCl$_3$) δ1.16-1.24 (2H, m), 1.33-1.39 (2H, m), 2.05-2.13 (1H, m), 3.82-3.88 (2H, m), 8.09 (1H, brs), 8.30 (1H, brs).

C) (1-(4-amino-1H-pyrazol-1-yl)cyclopropyl)methanol

To a solution of (1-(4-nitro-1H-pyrazol-1-yl)cyclopropyl)methanol (300 mg) obtained in Step B of Example 128 in ethanol (20 mL) was added palladium-activated carbon ethylene diamine complex (Pd: 8.5-11.5%) (100 mg), and the mixture was stirred at room temperature for 5 hr under hydrogen atmosphere (at normal pressures). The palladium-activated carbon ethylene diamine complex was removed by filtration through Celite, and the solvent was evaporated under reduced pressure to give the title compound (250 mg).

$^1$H NMR (400 MHz, CDCl$_3$) δ1.01-1.09 (2H, m), 1.18-1.25 (2H, m), 2.66 (1H, brs), 2.89 (2H, brs), 3.72 (1H, brs), 7.10 (1H, brs), 7.18 (1H, brs).

MS(ESI+): [M+H]$^+$ 154.0.

D) (3S)-3-cyclopropyl-1-(2-((1-(1-(hydroxymethyl)cyclopropyl)-1H-pyrazol-4-yl)amino)pyrimidin-4-yl)-2-oxopyrrolidine-3-carbonitrile To a solution of (3S)-1-(2-chloropyrimidin-4-yl)-3-cyclopropyl-2-oxopyrrolidine-3-carbonitrile (200 mg) obtained in Step E of Example 103, (1-(4-amino-1H-pyrazol-1-yl)cyclopropyl)methanol (120 mg) obtained in Step C of Example 128, cesium carbonate (500 mg) and 2,2'-bis(diphenylphosphino)-1,1'-binaphthyl (71 mg) in tetrahydrofuran (10 mL) was added tris(dibenzylideneacetone)dipalladium(0) (70 mg), and the mixture was stirred at 90° C. for 10 hr under argon atmosphere. The solvent was evaporated under reduced pressure, and the residue was purified by silica gel column chromatography (NH, hexane/ethyl acetate). The obtained crude product was subjected to HPLC (C18, mobile phase: water/acetonitrile (containing 5 mM AcONH$_4$), to the obtained fraction was added saturated aqueous sodium hydrogen carbonate solution, and the mixture was extracted with ethyl acetate. The extract was dried over anhydrous magnesium sulfate, and concentrated under reduced pressure. The residue was recrystallized (ethyl acetate/diisopropyl ether) to give the title compound (71 mg).

$^1$H NMR (400 MHz, DMSO-d$_6$) δ0.43-0.75 (4H, m), 0.94-1.23 (4H, m), 1.42-1.61 (1H, m), 2.28-2.42 (1H, m), 2.61-2.74 (1H, m), 3.54-3.67 (2H, m), 3.92-4.35 (2H, m), 4.87-5.05 (1H, m), 7.28-7.60 (2H, m), 7.93 (1H, s), 8.40 (1H, s), 9.52 (1H, brs).

MS(ESI+): [M+H]$^+$ 380.3.

Example 129

1-(4-((4-((3S)-3-cyano-3-cyclopropyl-2-oxopyrrolidin-1-yl)pyrimidin-2-yl)amino)-1H-pyrazol-1-yl)cyclobutanecarboxamide

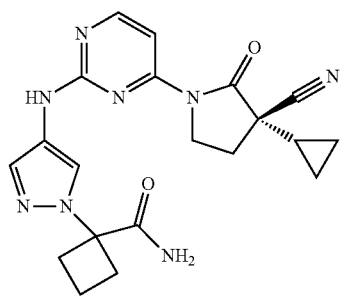 [SMILES: N#C[C@@]1(C2CC2)CCN(c2ccnc(Nc3cnn(C4(C(N)=O)CCC4)c3)n2)C1=O]

A) 1-(4-nitro-1H-pyrazol-1-yl)cyclobutanecarboxamide

A mixture of ethyl 1-(4-nitro-1H-pyrazol-1-yl)cyclobutanecarboxylate (300 mg) obtained in Step A of Example 127 and 8 M ammonia in methanol (15 mL) was stirred at room temperature for 10 hr. The reaction mixture was concentrated under reduced pressure to give the title compound (260 mg).

MS(ESI+): [M+H]$^+$ 210.8.

B) 1-(4-amino-1H-pyrazol-1-yl)cyclobutanecarboxamide

The title compound (220 mg) was obtained from 1-(4-nitro-1H-pyrazol-1-yl)cyclobutanecarboxamide (270 mg) obtained in Step A of Example 129 in the same manner as in Step C of Example 128.

MS(ESI+): [M+H]$^+$ 180.9.

C) 1-(4-((4-((3S)-3-cyano-3-cyclopropyl-2-oxopyrrolidin-1-yl)pyrimidin-2-yl)amino)-1H-pyrazol-1-yl)cyclobutanecarboxamide The title compound (130 mg) was obtained from (3S)-1-(2-chloropyrimidin-4-yl)-3-cyclopropyl-2-oxopyrrolidine-3-carbonitrile (150 mg) obtained in Step E of Example 103 and 1-(4-amino-1H-pyrazol-1-yl)cyclobutanecarboxamide (100 mg) obtained in Step B of Example 129 in the same manner as in Step D of Example 127.

MS(ESI+): [M+H]$^+$ 407.3.

Example 130

1-(4-((4-((3S)-3-cyano-3-cyclopropyl-2-oxopyrrolidin-1-yl)pyrimidin-2-yl)amino)-1H-pyrazol-1-yl)cyclopropanecarboxamide

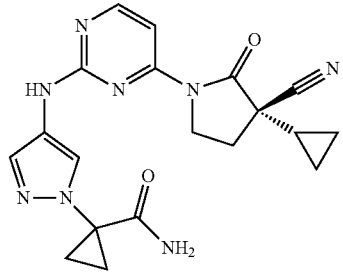 [SMILES: N#C[C@@]1(C2CC2)CCN(c2ccnc(Nc3cnn(C4(C(N)=O)CC4)c3)n2)C1=O]

A)
1-(4-nitro-1H-pyrazol-1-yl)cyclopropanecarboxamide

The title compound (460 mg) was obtained from methyl 1-(4-nitro-1H-pyrazol-1-yl)cyclopropanecarboxylate (500 mg) obtained in Step A of Example 128 in the same manner as in Step A of Example 129.
MS(ESI+): [M+H]$^+$ 196.8.

B)
1-(4-amino-1H-pyrazol-1-yl)cyclopropanecarboxamide

The title compound (370 mg) was obtained from 1-(4-nitro-1H-pyrazol-1-yl)cyclopropanecarboxamide (450 mg) obtained in Step A of Example 130 in the same manner as in Step B of Example 129.
MS(ESI+): [M+H]$^+$ 166.8.

C) 1-(4-((4-((3S)-3-cyano-3-cyclopropyl-2-oxopyrrolidin-1-yl)pyrimidin-2-yl)amino)-1H-pyrazol-1-yl)cyclopropanecarboxamide The title compound (160 mg) was obtained from (3S)-1-(2-chloropyrimidin-4-yl)-3-cyclopropyl-2-oxopyrrolidine-3-carbonitrile (150 mg) obtained in Step E of Example 103 and 1-(4-amino-1H-pyrazol-1-yl)cyclopropanecarboxamide (95 mg) obtained in Step B of Example 130 in the same manner as in Step D of Example 127.
MS(ESI+): [M+H]$^+$ 393.3.

Example 131

(3S)-3-cyclopropyl-1-(2-(1-(1-(methoxyacetyl)azetidin-3-yl)-1H-pyrazol-4-yl)amino)pyrimidin-4-yl)-2-oxopyrrolidine-3-carbonitrile

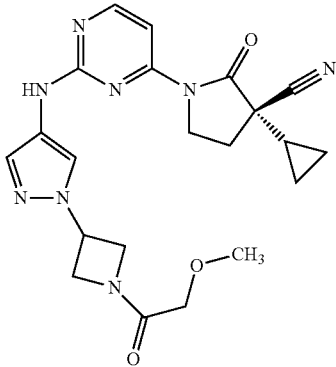 [SMILES: COCC(=O)N1CC(n2cc(Nc3nccc(N4CC[C@@](C#N)(C5CC5)C4=O)n3)cn2)C1]

A) tert-butyl 3-(4-nitro-1H-pyrazol-1-yl)azetidine-1-carboxylate

To a solution of 4-nitro-1H-pyrazole (2.0 g), tert-butyl 3-hydroxyazetidine-1-carboxylate (3.1 g) and triphenylphosphine (5.6 g) in tetrahydrofuran (20 mL) was added di-tert-butyl(E)-diazene-1,2-dicarboxylate (5.3 g) at room temperature, and the mixture was stirred overnight at room temperature. The solvent was evaporated under reduced pressure, and the residue was purified by silica gel column chromatography (hexane/ethyl acetate) to give the title compound (5.3 g).

$^1$H NMR (300 MHz, CDCl$_3$) δ1.47 (9H, s), 4.28-4.37 (2H, m), 4.38-4.47 (2H, m), 5.05 (1H, tt, J=7.9, 5.1 Hz), 8.16 (1H, s), 8.27 (1H, s).

B) tert-butyl 3-(4-amino-1H-pyrazol-1-yl)azetidine-1-carboxylate

To a solution of tert-butyl 3-(4-nitro-1H-pyrazol-1-yl)azetidine-1-carboxylate (5.3 g) obtained in Step B of Example 131 in ethanol (30 mL) was added 5% palladium-carbon (4.2 g), and the mixture was stirred at room temperature for 2 hr under hydrogen atmosphere (at normal pressures). The palladium-carbon was removed by filtration through Celite, the solvent was evaporated under reduced pressure, and the residue was purified by silica gel column chromatography (NH, hexane/ethyl acetate) to give the title compound (2.1 g).
$^1$H NMR (300 MHz, DMSO-d$_6$) δ1.39 (9H, s), 3.89 (2H, s), 3.98-4.08 (2H, m), 4.14-4.26 (2H, m), 4.92-5.06 (1H, m), 7.03 (1H, s), 7.13 (1H, d, J=0.8 Hz).

C) tert-butyl 3-(4-((4-((3S)-3-cyano-3-cyclopropyl-2-oxopyrrolidin-1-yl)pyrimidin-2-yl)amino)-1H-pyrazol-1-yl)azetidine-1-carboxylate To a solution of (3S)-1-(2-chloropyrimidin-4-yl)-3-cyclopropyl-2-oxopyrrolidine-3-carbonitrile (300 mg) obtained in Step E of Example 103, tert-butyl 3-(4-amino-1H-pyrazol-1-yl)azetidine-1-carboxylate (300 mg) obtained in Step B of Example 131, cesium carbonate (740 mg) and 2,2'-bis(diphenylphosphino)-1,1'-binaphthyl (110 mg) in tetrahydrofuran (10 mL) was added tris(dibenzylideneacetone)dipalladium (0) (105 mg), and the mixture was stirred at 90° C. for 10 hr under argon atmosphere. The solvent was evaporated under reduced pressure, and the reaction mixture was poured into water, and extracted with ethyl acetate. The obtained organic layer was washed with saturated brine, and dried over anhydrous magnesium sulfate, and the solvent was evaporated under reduced pressure. The residue was purified by silica gel column chromatography (NH, hexane/ethyl acetate) to give the title compound (310 mg).
MS(ESI+): [M+H]$^+$ 465.4.

D) (3S)-3-cyclopropyl-1-(2-((1-(1-(methoxyacetyl)azetidin-3-yl)-1H-pyrazol-4-yl)amino)pyrimidin-4-yl)-2-oxopyrrolidine-3-carbonitrile To a solution of tert-butyl 3-(4-((4-((3S)-3-cyano-3-cyclopropyl-2-oxopyrrolidin-1-yl)pyrimidin-2-yl)amino)-1H-pyrazol-1-yl)azetidine-1-carboxylate (300 mg) obtained in Step C of Example 131 in ethyl acetate (5 mL) was added a solution of 4 M hydrogen chloride in ethyl acetate (10 mL), and the mixture was stirred at room temperature for 30 min. The solvent was evaporated under reduced pressure, to a suspension of the reaction mixture in tetrahydrofuran (10 mL) were added triethylamine (1.3 g) and methoxyacetyl chloride (77 mg) at room temperature, and the mixture was stirred at room temperature for 3 hr. The solvent was evaporated under reduced pressure, and the reaction mixture was poured into water, and extracted with ethyl acetate. The obtained organic layer was washed with saturated brine, and dried over anhydrous magnesium sulfate, and the solvent was evaporated under reduced pressure. The residue was purified by silica gel column chromatography (NH, ethyl acetate/methanol). The obtained crude product was subjected to HPLC (C18, mobile phase: water/acetonitrile (containing 10 mM NH$_4$HCO$_3$)), and the obtained fraction was concentrated under reduced pressure. The residue was recrystallized (ethyl acetate/diisopropyl ether) to give the title compound (60 mg).
MS(ESI+): [M+H]$^+$ 437.3.

Example 132

2-(4-((4-((3S)-3-cyano-3-cyclopropyl-2-oxopyrrolidin-1-yl)pyrimidin-2-yl)amino)-1H-pyrazol-1-yl)acetamide hydrochloride

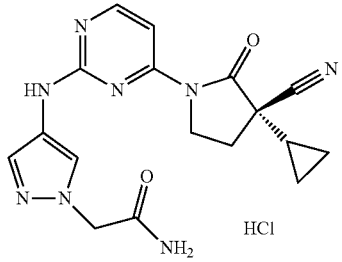 [SMILES: N#C[C@@]1(C2CC2)CCN(c2ccnc(Nc3cnn(CC(N)=O)c3)n2)C1=O ; Cl]

A solution of (3S)-1-(2-chloropyrimidin-4-yl)-3-cyclopropyl-2-oxopyrrolidine-3-carbonitrile (100 mg) obtained in Step E of Example 103, 2-(4-amino-1H-pyrazol-1-yl)acetamide (64 mg) and acetic acid (24 µL) in 2-propanol (3.0 mL) was stirred in a microwave reactor at 160° C. for 1 hr, and the solvent was evaporated under reduced pressure. The obtained residue was purified by silica gel column chromatography (NH, ethyl acetate/methanol).

To a solution of the residue (87 mg) in ethanol (3.0 mL) was added 1M hydrochloric acid (240 µL), and the solvent was evaporated under reduced pressure. The residue was recrystallized (diisopropyl ether/ethanol) to give the title compound (67 mg).

$^1$H NMR (300 MHz, DMSO-d$_6$) δ0.48-0.59 (2H, m), 0.59-0.74 (2H, m), 1.54 (1H, m), 2.30-2.41 (1H, m), 2.65 (1H, m), 3.91-4.30 (2H, m), 4.67-4.80 (2H, m), 7.16-7.31 (1H, m), 7.42 (1H, brs), 7.52-7.61 (2H, m), 7.79-7.99 (1H, m), 8.38 (1H, d, J=5.6 Hz), 9.80 (1H, brs).
MS(ESI+): [M+H]$^+$ 367.3.

Example 133

2-(4-((4-((3R)-3-cyano-3-cyclopropyl-2-oxopyrrolidin-1-yl)pyrimidin-2-yl)amino)-1H-pyrazol-1-yl)-N-methylacetamide hydrochloride

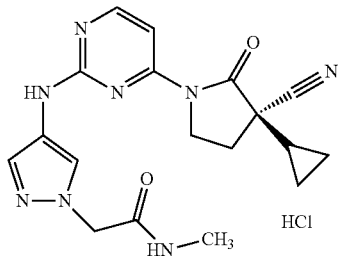 [SMILES: CNC(=O)Cn1cc(Nc2nccc(N3CC[C@](C#N)(C4CC4)C3=O)n2)cn1 ; Cl]

A solution of (3R)-1-(2-chloropyrimidin-4-yl)-3-cyclopropyl-2-oxopyrrolidine-3-carbonitrile (130 mg) obtained in Step A of Example 105, 2-(4-amino-1H-pyrazol-1-yl)-N-methylacetamide (84 mg) and acetic acid (31 µL) in ethanol (3.0 mL) was stirred in a microwave reactor at 160° C. for 1 hr, and the solvent was evaporated under reduced pressure. The obtained residue was purified by silica gel column chromatography (hexane/ethyl acetate). To a solution of the residue (180 mg) in ethanol (5.0 mL) was added 1 M hydrochloric acid (0.50 mL), and the solvent was evaporated under reduced pressure. The residue was recrystallized (diisopropyl ether/ethanol) to give the title compound (120 mg).

$^1$H NMR (300 MHz, DMSO-d$_6$) δ0.41-0.84 (4H, m), 1.43-1.64 (1H, m), 2.15-2.40 (2H, m), 2.61 (3H, d, J=4.5 Hz), 2.65-2.81 (1H, m), 3.97-4.29 (2H, m), 4.73 (2H, s), 7.42-7.59 (2H, m), 7.73-8.09 (2H, m), 8.37 (1H, d, J=5.7 Hz), 9.68 (1H, brs). MS(ESI+): [M+H]$^+$ 381.3.

Example 134

2-(4-((4-((3S)-3-cyano-3-cyclopropyl-2-oxopyrrolidin-1-yl) pyrimidin-2-yl)amino)-1H-pyrazol-1-yl)-N-methylacetamide hydrochloride

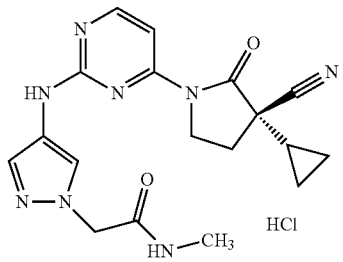 [SMILES: CNC(=O)Cn1cc(Nc2nccc(N3CC[C@@](C#N)(C4CC4)C3=O)n2)cn1 ; Cl]

A solution of (3S)-1-(2-chloropyrimidin-4-yl)-3-cyclopropyl-2-oxopyrrolidine-3-carbonitrile (130 mg) obtained in Step E of Example 103, 2-(4-amino-1H-pyrazol-1-yl)-N-methylacetamide (84 mg) and acetic acid (31 µL) in ethanol (3.0 mL) was stirred in a microwave reactor at 150° C. for 1 hr, and the solvent was evaporated under reduced pressure. The obtained residue was purified by silica gel column chromatography (hexane/ethyl acetate). To a solution of the residue (190 mg) in ethanol (5.0 mL) was added 1 M hydrochloric acid (0.50 mL), and the solvent was evaporated under reduced pressure. The residue was recrystallized (diisopropyl ether/ethanol) to give the title compound (120 mg).

$^1$H NMR (300 MHz, DMSO-d$_6$) δ0.43-0.79 (4H, m), 1.45-1.65 (1H, m), 2.26-2.43 (2H, m), 2.61 (3H, d, J=4.5 Hz), 2.64-2.78 (1H, m), 3.85-4.36 (2H, m), 4.73 (2H, s), 7.44-7.65 (2H, m), 7.80-8.06 (2H, m), 8.37 (1H, d, J=5.7 Hz), 9.67 (1H, brs).
MS(ESI+): [M+H]$^+$ 381.3.

Examples 135 to 137

In Examples 135 to 137, the title compound was obtained from (3S)-1-(2-chloropyrimidin-4-yl)-3-cyclopropyl-2-oxopyrrolidine-3-carbonitrile obtained in Step E of Example 103 and the amine each corresponding to the compounds of Examples 135 to 137 (N-(2-(4-amino-1H-pyrazol-1-yl)ethyl)acetamide, N-(2-(4-amino-1H-pyrazol-1-yl)ethyl)-2-methoxyacetamide and N-(2-(4-amino-1H-pyrazol-1-yl)ethyl)methanesulfonamide (these compounds can be produced according to a method known per se)), in the same manner as in Step I of Example 103 or a method analogous thereto. MS in the tables means actual measured value.

TABLE 13

| Example Number | IUPAC Name | Structure | Salt | MS |
|---|---|---|---|---|
| 135 | N-(2-(4-((4-((3S)-3-cyano-3-cyclopropyl-2-oxopyrrolidin-1-yl)pyrimidin-2-yl)amino)-1H-pyrazol-1-yl)ethyl)acetamide | 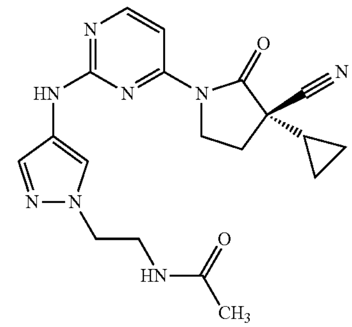 [SMILES: CC(=O)NCCn1cc(Nc2nccc(N3CC[C@@](C#N)(C4CC4)C3=O)n2)cn1] | free | 395.3 |
| 136 | N-(2-(4-((4-((3S)-3-cyano-3-cyclopropyl-2-oxopyrrolidin-1-yl)pyrimidin-2-yl)amino)-1H-pyrazol-1-yl)ethyl)-2-methoxyacetamide | 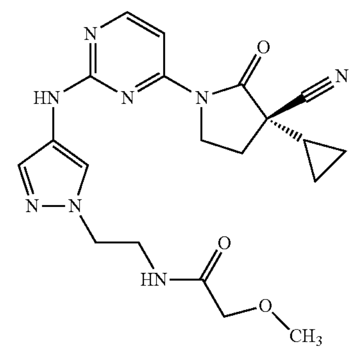 [SMILES: COCC(=O)NCCn1cc(Nc2nccc(N3CC[C@@](C#N)(C4CC4)C3=O)n2)cn1] | HCl | 425.3 |
| 137 | N-(2-(4-((4-((3S)-3-cyano-3-cyclopropyl-2-oxopyrrolidin-1-yl)pyrimidin-2-yl)amino)-1H-pyrazol-1-yl)ethyl)methanesulfonamide | 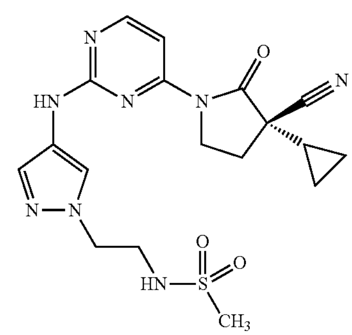 [SMILES: CS(=O)(=O)NCCn1cc(Nc2nccc(N3CC[C@@](C#N)(C4CC4)C3=O)n2)cn1] | free | 431.3 |

Example 138

(3S)-3-cyclopropyl-1-(2-((1-(2-cyanopropan-2-yl)-1H-pyrazol-4-yl)amino)pyrimidin-4-yl)-2-oxopyrrolidine-3-carbonitrile

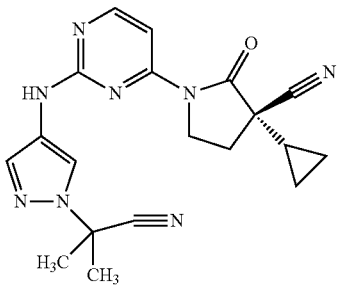 [SMILES: CC(C)(C#N)n1cc(Nc2nccc(N3CC[C@@](C#N)(C4CC4)C3=O)n2)cn1]

To a solution of 2-(4-((4-((3S)-3-cyano-3-cyclopropyl-2-oxopyrrolidin-1-yl)pyrimidin-2-yl)amino)-1H-pyrazol-1-yl)-2-methylpropanamide (250 mg) obtained in the same manner as in Step D of Example 109 in tetrahydrofuran (5.0 mL) were added successively dropwise pyridine (0.15 mL) and 2,2,2-trifluoroacetic anhydride (0.27 mL), and the mixture was stirred at 70° C. for 5 hr. The reaction mixture was neutralized with saturated aqueous sodium bicarbonate, and extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate), and recrystallized (hexane/ethyl acetate) to give the title compound (190 mg).

MS(ESI+): [M+H]$^+$ 377.3.

Example 139 tert-butyl 4-((4-((3S)-3-cyano-3-cyclopropyl-2-oxopyrrolidin-1-yl)pyrimidin-2-yl)amino)-2-ethoxybenzoate

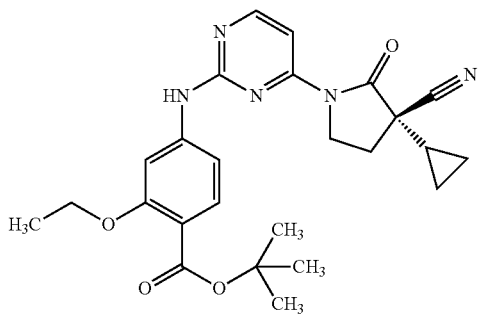 [SMILES: CCOc1cc(Nc2nccc(N3CC[C@@](C#N)(C4CC4)C3=O)n2)ccc1C(=O)OC(C)(C)C]

A) tert-butyl 2-hydroxy-4-nitrobenzoate

To a solution of 2-hydroxy-4-nitrobenzoic acid (5.0 g) in tert-butyl alcohol (100 mL) were added 1-ethyl-3-(3-dimethylaminopropyl)carbodiimide (6.4 g), 1-hydroxybenzotriazole (3.7 g) and triethylamine (7.6 mL), and the mixture was stirred overnight at room temperature. To the reaction mixture was added saturated aqueous sodium hydrogen carbonate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (2.3 g).

$^1$H NMR (400 MHz, DMSO-$d_6$) δ1.57 (9H, s), 7.64-7.80 (2H, m), 7.83-7.97 (1H, m), 11.00 (1H, s).

B) tert-butyl 2-ethoxy-4-nitrobenzoate

To a solution of tert-butyl 2-hydroxy-4-nitrobenzoate (500 mg) obtained in Step A of Example 139 in acetone (5.0 mL) were added potassium carbonate (580 mg) and iodoethane (340 μL), and the mixture was stirred overnight with heating under reflux. To the reaction mixture was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (550 mg).

$^1$H NMR (400 MHz, DMSO-$d_6$) δ1.37 (3H, t, J=7.0 Hz), 1.53 (9H, s), 4.22 (2H, d, J=7.1 Hz), 7.70-7.76 (1H, m), 7.81-7.86 (2H, m).

C) tert-butyl 4-amino-2-ethoxybenzoate

To a solution of tert-butyl 2-ethoxy-4-nitrobenzoate (550 mg) obtained in Step B of Example 139 in ethanol (10 mL) was added 10% palladium-carbon (42 mg), and the mixture was stirred overnight at room temperature under hydrogen atmosphere (at normal pressures). The palladium carbon was removed by filtration through Celite, and the solvent was evaporated under reduced pressure to give the title compound (470 mg).

$^1$H NMR (400 MHz, DMSO-$d_6$) δ 1.32 (3H, t, J=7.0 Hz), 1.46 (9H, s), 3.91 (2H, q, J=7.0 Hz), 5.77 (2H, s), 6.10 (1H, dd, J=8.6, 2.0 Hz), 6.14 (1H, d, J=2.0 Hz), 7.40 (1H, d, J=8.3 Hz).

D) tert-butyl 4-((4-((3S)-3-cyano-3-cyclopropyl-2-oxopyrrolidin-1-yl) pyrimidin-2-yl)amino)-2-ethoxybenzoate To a solution of (3S)-1-(2-chloropyrimidin-4-yl)-3-cyclopropyl-2-oxopyrrolidine-3-carbonitrile (100 mg) obtained in Step E of Example 103, tert-butyl 4-amino-2-ethoxybenzoate (110 mg) obtained in Step C of Example 139, cesium carbonate (250 mg) and 2,2'-bis(diphenylphosphino)-1,1'-binaphthyl (35 mg) in tetrahydrofuran (3.0 mL) was added tris(dibenzylideneacetone)dipalladium(0) (34 mg) under argon atmosphere, and the mixture was stirred overnight at 90° C. The insoluble substance was removed by filtration through Celite, and the solvent was evaporated under reduced pressure. The residue was purified by silica gel column chromatography (hexane/ethyl acetate) to give the title compound (41 mg).

MS(ESI+): [M+H]$^+$ 464.4.

Example 140

4-((4-((3S)-3-cyano-3-cyclopropyl-2-oxopyrrolidin-1-yl)pyrimidin-2-yl)amino)-2-ethoxybenzoic acid hydrochloride

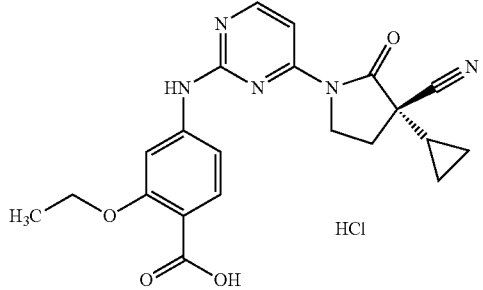 [SMILES: CCOc1cc(Nc2nccc(N3CC[C@@](C#N)(C4CC4)C3=O)n2)ccc1C(=O)O ; Cl]

To a solution of tert-butyl 4-((4-((3S)-3-cyano-3-cyclopropyl-2-oxopyrrolidin-1-yl)pyrimidin-2-yl)amino)-2-ethoxybenzoate (40 mg) obtained in Step D of Example 139 in ethyl acetate (4.0 mL) was added a solution of 4 M hydrogen chloride in ethyl acetate (4.0 mL), the mixture was stirred at room temperature for 2 hr, and the solvent was evaporated under reduced pressure. The residue was washed with ethyl acetate to give the title compound (20 mg).

MS(ESI+): [M+H]$^+$ 408.3.

Example 141 tert-butyl 4-((4-((3S)-3-cyano-3-cyclopropyl-2-oxopyrrolidin-1-yl)pyrimidin-2-yl)amino)-2-isopropoxybenzoate

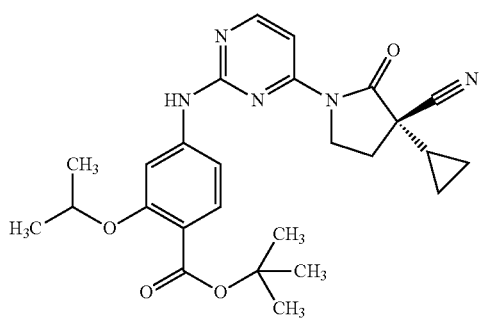 [SMILES: CC(C)Oc1cc(Nc2nccc(N3CC[C@@](C#N)(C4CC4)C3=O)n2)ccc1C(=O)OC(C)(C)C]

169

A) tert-butyl 2-isopropoxy-4-nitrobenzoate

The title compound (600 mg) was obtained from tert-butyl 2-hydroxy-4-nitrobenzoate (500 mg) obtained in Step A of Example 139 and 2-iodopropane (710 mg) in the same manner as in Step B of Example 139.

$^1$H NMR (400 MHz, DMSO-d$_6$) δ 1.31 (6H, d, J=5.9 Hz), 1.48-1.57 (9H, m), 4.87 (1H, dt, J=12.0, 6.0 Hz), 7.69 (1H, s), 7.77-7.82 (1H, m), 7.85 (1H, d, J=2.0 Hz).

B) tert-butyl 4-amino-2-isopropoxybenzoate

The title compound (490 mg) was obtained from tert-butyl 2-isopropoxy-4-nitrobenzoate (550 mg) obtained in Step A of Example 141 in the same manner as in Step C of Example 139.

MS(ESI+): [M+H-(tBu)]$^+$ 196.2.

C) tert-butyl 4-((4-((3S)-3-cyano-3-cyclopropyl-2-oxopyrrolidin-1-yl)pyrimidin-2-yl)amino)-2-isopropoxybenzoate The title compound (46 mg) was obtained from (3S)-1-(2-chloropyrimidin-4-yl)-3-cyclopropyl-2-oxopyrrolidine-3-carbonitrile (100 mg) obtained in Step E of Example 103 and tert-butyl 4-amino-2-isopropoxybenzoate (115 mg) obtained in Step B of Example 141 in the same manner as in Step D of Example 139.

MS(ESI+): [M+H]$^+$ 478.4.

Example 142

4-((4-((3S)-3-cyano-3-cyclopropyl-2-oxopyrrolidin-1-yl)pyrimidin-2-yl)amino)-2-isopropoxybenzoic acid hydrochloride

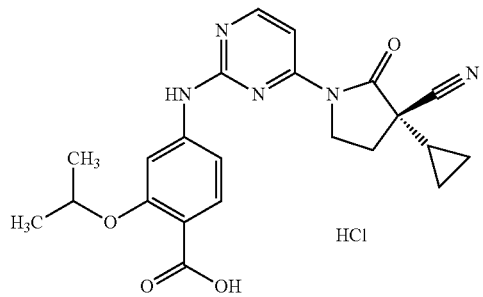 [SMILES: CC(C)Oc1cc(Nc2nccc(N3CC[C@@](C#N)(C4CC4)C3=O)n2)ccc1C(=O)O ; Cl]

The title compound (22 mg) was obtained from tert-butyl 4-((4-((3S)-3-cyano-3-cyclopropyl-2-oxopyrrolidin-1-yl)pyrimidin-2-yl)amino)-2-isopropoxybenzoate (40 mg) obtained in Step C of Example 141 in the same manner as in Example 140.

MS(ESI+): [M+H]$^+$ 422.3.

Example 143

4-((4-((3S)-3-cyano-3-cyclopropyl-2-oxopyrrolidin-1-yl)pyrimidin-2-yl)amino)-2-(2,2,2-trifluoroethoxyl)benzoic acid hydrochloride

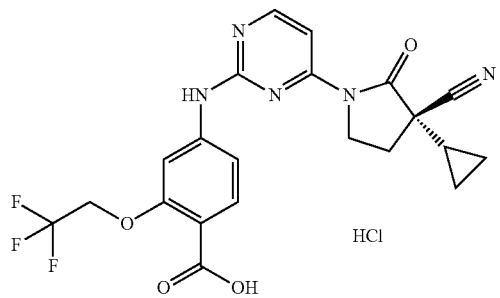 [SMILES: N#C[C@@]1(C2CC2)CCN(c2ccnc(Nc3ccc(C(=O)O)c(OCC(F)(F)F)c3)n2)C1=O ; Cl]

A) tert-butyl 2-fluoro-4-nitrobenzoate

The title compound (4.3 g) was obtained from 2-fluoro-4-nitrobenzoic acid (5.0 g) in the same manner as in Step A of Example 139.

$^1$H NMR (400 MHz, DMSO-d$_6$) δ 1.56 (9H, s), 8.03-8.09 (1H, m), 8.12-8.17 (1H, m), 8.22 (1H, dd, J=10.4, 2.1 Hz).

B) tert-butyl 4-nitro-2-(2,2,2-trifluoroethoxy)benzoate

To a solution of tert-butyl 2-fluoro-4-nitrobenzoate (1.0 g) obtained in Step A of Example 143 in tetrahydrofuran (10 mL) were successively added 2,2,2-trifluoropropan-1-ol (0.53 g) and sodium hydride (60% in mineral oil, 200 mg) in an ice bath, and the mixture was stirred at room temperature for 2 hr. To the reaction mixture was added saturated aqueous sodium hydrogen carbonate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (1.1 g).

$^1$H NMR (400 MHz, DMSO-d$_6$) δ 1.53 (9H, s), 5.04 (2H, q, J=8.7 Hz), 7.82 (1H, d, J=8.3 Hz), 7.96 (1H, dd, J=8.4, 2.1 Hz), 8.02 (1H, d, J=2.2 Hz).

C) tert-butyl 4-amino-2-(2,2,2-trifluoroethoxyl)benzoate

The title compound (1.1 g) was obtained from tert-butyl 4-nitro-2-(2,2,2-trifluoroethoxyl)benzoate (1.1 g) obtained in Step B of Example 143 in the same manner as in Step C of Example 139.

$^1$H NMR (400 MHz, DMSO-d$_6$) δ 1.46 (9H, s), 4.58 (2H, q, J=8.8 Hz), 5.90 (2H, s), 6.17 (1H, d, J=2.0 Hz), 6.23 (1H, dd, J=8.6, 2.0 Hz), 7.45 (1H, d, J=8.6 Hz).

D) tert-butyl 4-((4-((3S)-3-cyano-3-cyclopropyl-2-oxopyrrolidin-1-yl)pyrimidin-2-yl)amino)-2-(2,2,2-trifluoroethoxyl)benzoate The title compound (110 mg) was obtained from (3S)-1-(2-chloropyrimidin-4-yl)-3-cyclopropyl-2-oxopyrrolidine- 3-carbonitrile (100 mg) obtained in Step E of Example 103 and tert-butyl 4-amino-2-(2,2,2-trifluoroethoxyl)benzoate (130 mg) obtained in Step C of Example 143 in the same manner as in Step D of Example 139.

MS(ESI+): [M+H]$^+$ 518.3.

E) 4-((4-((3S)-3-cyano-3-cyclopropyl-2-oxopyrrolidin-1-yl)pyrimidin-2-yl)amino)-2-(2,2,2-trifluoroethoxyl)benzoic acid hydrochloride The title compound (64 mg) was obtained from tert-butyl 4-((4-((3S)-3-cyano-3-cyclopropyl-2-oxopyrrolidin-1-yl)pyrimidin-2-yl)amino)-2-(2,2,2-trifluoroethoxyl)benzoate (110 mg) obtained in Step D of Example 143 in the same manner as in Example 140.

MS(ESI+): [M+H]$^+$ 462.3.

Example 144

4-((4-((3S)-3-cyano-3-cyclopropyl-2-oxopyrrolidin-1-yl)pyrimidin-2-yl)amino)-2-isobutoxybenzoic acid hydrochloride

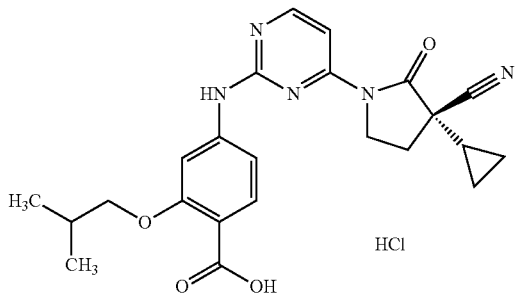 [SMILES: CC(C)COc1cc(Nc2nccc(N3CC[C@@](C#N)(C4CC4)C3=O)n2)ccc1C(=O)O ; Cl]

A) tert-butyl 2-isobutoxy-4-nitrobenzoate

The title compound (280 mg) was obtained from tert-butyl 2-hydroxy-4-nitrobenzoate (500 mg) obtained in Step A of Example 139 and 1-bromo-2-methylpropane (0.34 mL) in the same manner as in Step B of Example 139.

$^1$H NMR (400 MHz, DMSO-d$_6$) δ 1.01 (6H, d, J=6.6 Hz), 1.50-1.57 (9H, m), 1.99-2.15 (1H, m), 3.95 (2H, d, J=6.4 Hz), 7.72 (1H, d, J=8.1 Hz), 7.79-7.86 (2H, m).

B) tert-butyl 4-amino-2-isobutoxybenzoate

The crude title compound (250 mg) was obtained from tert-butyl 2-isobutoxy-4-nitrobenzoate (200 mg) obtained in Step A of Example 144 in the same manner as in Step C of Example 139.

$^1$H NMR (400 MHz, DMSO-d$_6$) δ 1.00 (6H, d, J=6.8 Hz), 1.47 (9H, s), 2.02 (1H, d, J=6.8 Hz), 3.63 (2H, d, J=6.4 Hz), 5.74 (2H, s), 6.09 (1H, dd, J=8.4, 2.1 Hz), 6.14 (1H, d, J=2.0 Hz), 7.39 (1H, d, J=8.6 Hz).

C) tert-butyl 4-((4-((3S)-3-cyano-3-cyclopropyl-2-oxopyrrolidin-1-yl)pyrimidin-2-yl)amino)-2-isobutoxybenzoate The title compound (110 mg) was obtained from (3S)-1-(2-chloropyrimidin-4-yl)-3-cyclopropyl-2-oxopyrrolidine-3-carbonitrile (100 mg) obtained in Step E of Example 103 and the crude tert-butyl 4-amino-2-isobutoxybenzoate (120 mg) obtained in Step B of Example 144 in the same manner as in Step D of Example 139.

MS(ESI+): [M+H]$^+$ 492.4.

D) 4-((4-((3S)-3-cyano-3-cyclopropyl-2-oxopyrrolidin-1-yl)pyrimidin-2-yl)amino)-2-isobutoxybenzoic acid hydrochloride The title compound (90 mg) was obtained from tert-butyl 4-((4-((3S)-3-cyano-3-cyclopropyl-2-oxopyrrolidin-1-yl)pyrimidin-2-yl)amino)-2-isobutoxybenzoate (100 mg) obtained in Step C of Example 144 in the same manner as in Example 140.

MS(ESI+): [M+H]$^+$ 436.3.

Example 145

1-(4-((4-((3S)-3-cyano-3-cyclopropyl-2-oxopyrrolidin-1-yl)pyrimidin-2-yl)amino)phenyl)cyclopropanecarboxylic acid hydrochloride

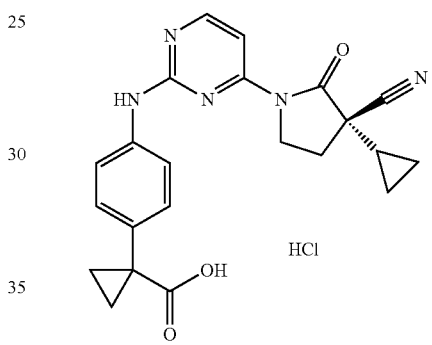

A) ethyl 1-(4-nitrophenyl)cyclopropanecarboxylate

To a solution of ethyl(4-nitrophenyl)acetate (5.0 g) in N,N-dimethylformamide (100 mL) was added sodium hydride (60% in mineral oil, 1.9 g) in an ice bath, and the mixture was stirred at room temperature for 20 min. To the reaction mixture was added 1,2-dibromoethane (4.1 mL) in an ice bath, and the mixture was stirred at the same temperature for 30 min, and the at room temperature for 1 hr. The reaction mixture was colled to 0° C., water was added thereto, and the mixture was extracted with ethyl acetate. The obtained organic layer was washed with saturated brine, and dried over anhydrous sodium sulfate, and the solvent was evaporated under reduced pressure. The residue was purified by silica gel column chromatography (hexane/ethyl acetate) to give the title compound (3.0 g).

$^1$H NMR (400 MHz, DMSO-d$_6$) δ 1.10 (3H, t, J=7.1 Hz), 1.26-1.33 (2H, m), 1.54-1.59 (2H, m), 4.05 (2H, q, J=7.1 Hz), 7.60-7.67 (2H, m), 8.14-8.20 (2H, m).

B) 1-(4-nitrophenyl)cyclopropanecarboxylic acid

To a solution of ethyl 1-(4-nitrophenyl)cyclopropanecarboxylate (3.0 g) obtained in Step A of Example 145 in ethanol (50 mL) was added 1M aqueous sodium hydroxide solution (25 mL), and the mixture was stirred overnight at room temperature. The reaction mixture was concentrated under reduced pressure, and 1M hydrochloric acid was added thereto at 0° C. The resulting solid was collected by filtration to give the title compound (2.5 g).

$^1$H NMR (400 MHz, DMSO-d$_6$) δ1.13-1.34 (2H, m), 1.39-1.67 (2H, m), 7.43-7.71 (2H, m), 7.97-8.27 (2H, m), 12.61 (1H, brs).

C) 1-(4-aminophenyl)cyclopropanecarboxylic acid

To a solution of 1-(4-nitrophenyl)cyclopropanecarboxylic acid (500 mg) obtained in Step B of Example 145 in ethanol (10 mL) was added palladium-activated carbon ethylene diamine complex (Pd 8.5 to 11.5%) (100 mg), and the mixture was stirred overnight at room temperature under hydrogen atmosphere (at normal pressures). The palladium carbon was removed by filtration through Celite, and the solvent was evaporated under reduced pressure to give the title compound (260 mg).

$^1$H NMR (400 MHz, DMSO-d$_6$) δ0.92-1.01 (2H, m), 1.32 (2H, q, J=3.5 Hz), 4.96 (2H, brs), 6.41-6.53 (2H, m), 6.88-6.97 (2H, m).

D) 1-(4-((4-((3S)-3-cyano-3-cyclopropyl-2-oxopyrrolidin-1-yl)pyrimidin-2-yl)amino)phenyl)cyclopropanecarboxylic acid hydrochloride A solution of (3S)-1-(2-chloropyrimidin-4-yl)-3-cyclopropyl-2-oxopyrrolidine-3-carbonitrile (100 mg) obtained in Step E of Example 103, 1-(4-aminophenyl)cyclopropanecarboxylic acid (67 mg) obtained in Step C of Example 145 and acetic acid (30 μL) in 2-propanol (1.5 mL) was stirred in a microwave reactor at 150° C. for 1 hr, and the resulting solid was collected by filtration to give the title compound (130 mg).

MS(ESI+): [M+H]$^+$ 404.3.

Example 146

1-(4-((4-((3S)-3-cyano-3-cyclopropyl-2-oxopyrrolidin-1-yl)pyrimidin-2-yl)amino)phenyl)cyclobutanecarboxylic acid hydrochloride

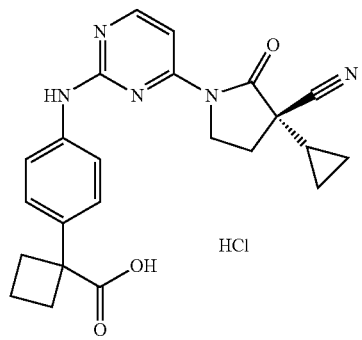 [SMILES: N#C[C@@]1(C2CC2)CCN(c2ccnc(Nc3ccc(C4(C(=O)O)CCC4)cc3)n2)C1=O ; Cl]

A) ethyl 1-(4-nitrophenyl)cyclobutanecarboxylate

The title compound (1.9 g) was obtained from ethyl(4-nitrophenyl)acetate (5.0 g) and 1,3-diiodopropane (5.5 mL) in the same manner as in Step A of Example 145.

$^1$H NMR (400 MHz, DMSO-d$_6$) δ1.06-1.13 (3H, m), 1.79-1.90 (1H, m), 1.95-2.03 (1H, m), 2.45-2.50 (2H, m), 2.73-2.82 (2H, m), 4.06 (2H, q, J=7.1 Hz), 7.48-7.67 (2H, m), 8.16-8.31 (2H, m).

B) 1-(4-nitrophenyl)cyclobutanecarboxylic acid

The title compound (1.4 g) was obtained from ethyl 1-(4-nitrophenyl)cyclobutanecarboxylate (1.9 g) obtained in Step A of Example 146 in the same manner as in Step B of Example 145.

$^1$H NMR (400 MHz, DMSO-d$_6$) δ 1.75-1.88 (1H, m), 2.01 (1H, dquin, J=10.6, 8.5 Hz), 2.40-2.49 (2H, m), 2.70-2.81 (2H, m), 7.50-7.56 (2H, m), 8.17-8.25 (2H, m), 12.70 (1H, brs).

C) 1-(4-aminophenyl)cyclobutanecarboxylic acid

The title compound (550 mg) was obtained from 1-(4-nitrophenyl)cyclobutanecarboxylic acid (1.0 g) obtained in Step B of Example 146 in the same manner as in Step C of Example 139.

$^1$H NMR (400 MHz, DMSO-d$_6$) δ1.64-1.97 (2H, m), 2.20-2.37 (2H, m), 2.56-2.68 (2H, m), 4.97 (2H, brs), 6.44-6.58 (2H, m), 6.88-7.00 (2H, m), 11.94 (1H, brs).

D) 1-(4-((4-((3S)-3-cyano-3-cyclopropyl-2-oxopyrrolidin-1-yl)pyrimidin-2-yl)amino)phenyl)cyclobutanecarboxylic acid hydrochloride The title compound (120 mg) was obtained from (3S)-1-(2-chloropyrimidin-4-yl)-3-cyclopropyl-2-oxopyrrolidine-3-carbonitrile (100 mg) obtained in Step E of Example 103 and 1-(4-aminophenyl)cyclobutanecarboxylic acid (73 mg) obtained in Step C of Example 146 in the same manner as in Step D of Example 145.

MS(ESI+): [M+H]$^+$ 418.3.

Example 147

2-(4-((4-((3S)-3-cyano-3-cyclopropyl-2-oxopyrrolidin-1-yl)pyrimidin-2-yl)amino)phenyl)-2-methylpropanoic acid hydrochloride

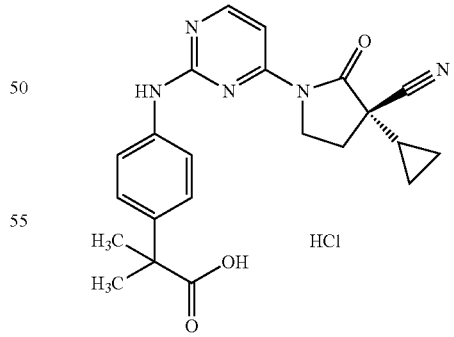

The title compound (110 mg) was obtained from (3S)-1-(2-chloropyrimidin-4-yl)-3-cyclopropyl-2-oxopyrrolidine-3-carbonitrile (100 mg) obtained in Step E of Example 103 and 2-(4-aminophenyl)-2-methylpropanecarboxylic acid (68 mg) in the same manner as in Step D of Example 145.

MS(ESI+): [M+H]$^+$ 406.3.

Example 148

(3S)-1-(2-((4-(2-cyanopropan-2-yl)phenyl)amino)pyrimidin-4-yl)-3-cyclopropyl-2-oxopyrrolidine-3-carbonitrile

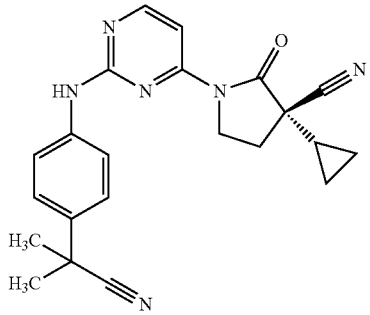 [SMILES: CC(C)(C#N)c1ccc(Nc2nccc(N3CC[C@@](C#N)(C4CC4)C3=O)n2)cc1]

The title compound (110 mg) was obtained from (3S)-1-(2-chloropyrimidin-4-yl)-3-cyclopropyl-2-oxopyrrolidine-3-carbonitrile (150 mg) obtained in Step E of Example 103 and 2-(4-aminophenyl)-2-methylpropanenitrile (91 mg) in the same manner as in Step B of Example 2.

MS(ESI+): [M+H]$^+$ 387.1.

Example 149

2-(4-((4-((3S)-3-cyano-3-cyclopropyl-2-oxopyrrolidin-1-yl) pyrimidin-2-yl)amino)phenyl)-2-methylpropanamide

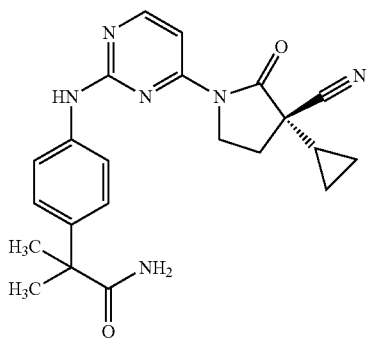 [SMILES: CC(C)(C(N)=O)c1ccc(Nc2nccc(N3CC[C@@](C#N)(C4CC4)C3=O)n2)cc1]

The title compound (40 mg) was obtained from (3S)-1-(2-chloropyrimidin-4-yl)-3-cyclopropyl-2-oxopyrrolidine-3-carbonitrile (61 mg) obtained in Step E of Example 103 and 2-(4-aminophenyl)-2-methylpropanamide (41 mg) in the same manner as in Step B of Example 2.

MS(ESI+): [M+H]$^+$ 405.1.

Example 150

4-(4-((4-((3S)-3-cyano-3-cyclopropyl-2-oxopyrrolidin-1-yl)pyrimidin-2-yl)amino)phenyl)tetrahydro-2H-pyran-4-carboxamide

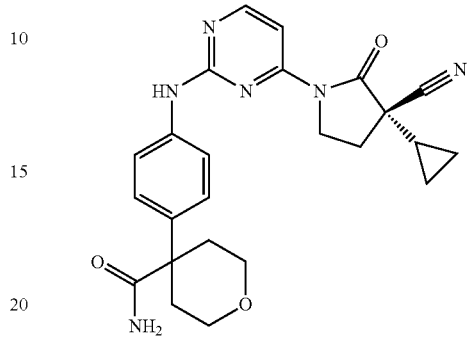

A) 4-(4-bromophenyl)tetrahydro-2H-pyran-4-carbonitrile

To a solution of 2-(4-bromophenyl)acetonitrile (3.9 g) in tetrahydrofuran (50 mL) was added potassium tert-butoxide (4.9 g) in an ice bath, and the mixture was stirred for 1 hr in an ice bath, 1-bromo-2-(2-bromoethoxy)ethane (5.8 g) was added thereto at the same temperature, and the mixture was stirred at room temperature for 10 hr. The solvent was evaporated under reduced pressure, and the residue was purified by silica gel column chromatography (hexane/ethyl acetate) to give the title compound (3.7 g).

$^1$H NMR (400 MHz, CDCl$_3$) δ1.99-2.15 (4H, m), 3.83-3.95 (2H, m), 4.04-4.14 (2H, m), 7.33-7.40 (2H, m), 7.51-7.60 (2H, m).

B) 4-(4-aminophenyl)tetrahydro-2H-pyran-4-carbonitrile

To a solution of 4-(4-bromophenyl)tetrahydro-2H-pyran-4-carbonitrile (1.7 g) obtained in Step A of Example 150, diphenylmethanimine (1.4 g), tris(dibenzylideneacetone)dipalladium(0) (88 mg) and 2,2'-bis(diphenylphosphino)-1,1'-binaphthyl (130 mg) in toluene (50 mL) was added sodium 2-methylpropan-2-olate (920 mg) under nitrogen atmosphere, and the mixture was stirred at 90° C. for 10 hr. The reaction mixture was diluted with ethyl acetate, and the insoluble substance was removed by filtration through Celite. The filtrate was concentrated, and to a solution of the residue in methanol (10 mL) were added hydroxylamine hydrochloride (440 mg) and sodium acetate (530 mg). The mixture was stirred at room temperature for 30 min, and 0.1 M aqueous sodium hydroxide solution and ethyl acetate were added thereto. The solvent was evaporated under reduced pressure, and the reaction mixture was poured into water, and extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (910 mg).

MS(ESI+): [M+H]$^+$ 202.9.

C)
4-(4-aminophenyl)tetrahydro-2H-pyran-4-carboxamide

To a solution of 4-(4-aminophenyl)tetrahydro-2H-pyran-4-carbonitrile (500 mg) obtained in Step B of Example 150 and potassium carbonate (1.0 g) in dimethylsulfoxide (10 mL) was added 30% aqueous hydrogen peroxide (0.65 mL), and the mixture was stirred at room temperature for 10 hr. To the reaction mixture was added saturated aqueous sodium thiosulfate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (ethyl acetate/methanol) to give the title compound (380 mg).

MS(ESI+): [M+H]$^+$ 220.9.

D) 4-(4-((4-((3S)-3-cyano-3-cyclopropyl-2-oxopyrrolidin-1-yl) pyrimidin-2-yl)amino)phenyl)tetrahydro-2H-pyran-4-carboxamide The title compound (41 mg) was obtained from (3S)-1-(2-chloropyrimidin-4-yl)-3-cyclopropyl-2-oxopyrrolidine-3-carbonitrile (100 mg) obtained in Step E of Example 103 and 4-(4-aminophenyl)tetrahydro-2H-pyran-4-carboxamide (84 mg) obtained in Step C of Example 150 in the same manner as in Step B of Example 2.

MS(ESI+): [M+H]$^+$ 447.4.

Example 151

4-(4-((4-((3S)-3-cyano-3-cyclopropyl-2-oxopyrrolidin-1-yl)pyrimidin-2-yl)amino)phenyl)-N-methyltetrahydro-2H-pyran-4-carboxamide

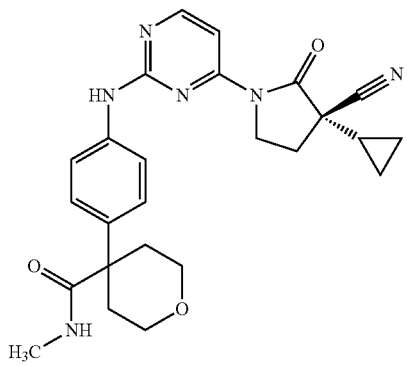 [SMILES: CNC(=O)C1(c2ccc(Nc3nccc(N4CC[C@@](C#N)(C5CC5)C4=O)n3)cc2)CCOCC1]

A) ethyl 4-(4-nitrophenyl)tetrahydro-2H-pyran-4-carboxylate

The title compound (6.6 g) was obtained from ethyl(4-nitrophenyl)acetate (5.0 g) and 2,2'-dibromoethyl ether (6.0 mL) in the same manner as in Step A of Example 145.

$^1$H NMR (400 MHz, CDCl$_3$) δ1.20 (3H, t, J=7.1 Hz), 1.98 (2H, ddd, J=13.4, 11.5, 4.4 Hz), 2.56 (2H, dd, J=13.7, 2.4 Hz), 3.59 (2H, td, J=11.7, 2.1 Hz), 3.96 (2H, dt, J=11.9, 3.6 Hz), 4.17 (2H, q, J=7.2 Hz), 7.48-7.65 (2H, m), 8.21 (2H, d, J=9.0 Hz).

B) 4-(4-nitrophenyl)tetrahydro-2H-pyran-4-carboxylic acid

The title compound (4.0 g) was obtained from ethyl 4-(4-nitrophenyl)tetrahydro-2H-pyran-4-carboxylate (6.6 g) obtained in Step A of Example 151 in the same manner as in Step B of Example 145.

$^1$H NMR (400 MHz, DMSO-d$_6$) δ1.78-2.02 (2H, m), 2.41 (2H, d, J=13.2 Hz), 3.48 (2H, td, J=11.4, 2.0 Hz), 3.82 (2H, dt, J=11.7, 3.7 Hz), 7.69 (2H, d, J=9.3 Hz), 8.07-8.44 (2H, m), 13.02 (1H, s).

C) N-methyl-4-(4-nitrophenyl)tetrahydro-2H-pyran-4-carboxamide

To a solution of 4-(4-nitrophenyl)tetrahydro-2H-pyran-4-carboxylic acid (750 mg) obtained in Step B of Example 151, methanamine hydrochloride (1.0 g) and triethylamine (3.0 g) in a mixed solvent of tetrahydrofuran (20 mL) and N,N-dimethylacetamide (5.0 mL) was added 2-(3H-[1,2,3]triazolo[4,5-b]pyridin-3-yl)-1,1,3,3-tetramethylisouronium hexafluorophosphate(V) (0.86 g), and the mixture was stirred at room temperature for 10 hr. The solvent was evaporated under reduced pressure, and the reaction mixture was poured into water, and extracted with ethyl acetate. The obtained organic layer was washed with saturated aqueous sodium hydrogen carbonate solution, and dried over anhydrous magnesium sulfate, and the solvent was evaporated under reduced pressure. The residue was purified by silica gel column chromatography (NH, hexane/ethyl acetate) to give the title compound (400 mg).

MS(ESI+): [M+H]$^+$ 265.9.

D) 4-(4-aminophenyl)-N-methyltetrahydro-2H-pyran-4-carboxamide

To a solution of N-methyl-4-(4-nitrophenyl)tetrahydro-2H-pyran-4-carboxamide (380 mg) obtained in Step C of Example 151 in ethanol (20 mL) was added 10% palladium-carbon (100 mg), and the mixture was stirred at room temperature for 10 hr under hydrogen atmosphere (at normal pressures). The palladium-carbon was removed by filtration through Celite, and the solvent was evaporated under reduced pressure. The residue was purified by silica gel column chromatography (NH, hexane/ethyl acetate) to give the title compound (330 mg).

MS(ESI+): [M+H]$^+$ 234.9.

E) 4-(4-((4-((3S)-3-cyano-3-cyclopropyl-2-oxopyrrolidin-1-yl)pyrimidin-2-yl)amino)phenyl)-N-methyltetrahydro-2H-pyran-4-carboxamide The title compound (170 mg) was obtained from (3S)-1-(2-chloropyrimidin-4-yl)-3-cyclopropyl-2-oxopyrrolidine-3-carbonitrile (160 mg) obtained in Step E of Example 103 and 4-(4-aminophenyl)-N-methyltetrahydro-2H-pyran-4-carboxamide (140 mg) obtained in Step D of Example 151 in the same manner as in Step B of Example 2.

MS(ESI+): [M+H]$^+$ 461.4.

Example 152

(3S)-3-cyclopropyl-1-(2-((4-(4-(hydroxymethyl)tetrahydro-2H-pyran-4-yl)phenyl)amino)pyrimidin-4-yl)-2-oxopyrrolidine-3-carbonitrile

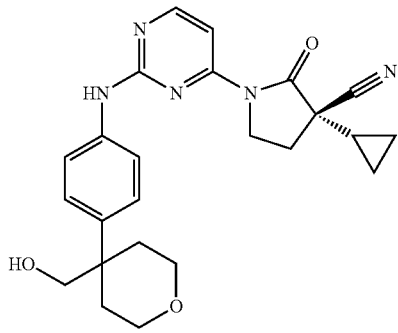 [SMILES: N#C[C@@]1(C2CC2)CCN(c2ccnc(Nc3ccc(C4(CO)CCOCC4)cc3)n2)C1=O]

A) (4-(4-nitrophenyl)tetrahydro-2H-pyran-4-yl)methanol

To a solution of lithium aluminium hydride (300 mg) in tetrahydrofuran (20 mL) was added dropwise a solution of ethyl 4-(4-nitrophenyl)tetrahydro-2H-pyran-4-carboxylate (1.0 g) obtained in Step A of Example 151 in tetrahydrofuran (10 mL) at −78° C., and the mixture was stirred at 0° C. for 1 hr. To the reaction mixture was added sodium sulfate decahydrate, and the mixture was stirred at room temperature for 2 hr. The insoluble substance was removed by filtration through Celite, and the solvent was evaporated under reduced pressure. The residue was purified by silica gel column chromatography (hexane/ethyl acetate) to give the title compound (330 mg).

$^1$H NMR (400 MHz, DMSO-$d_6$) δ1.82-1.94 (2H, m), 1.97-2.08 (2H, m), 3.36 (2H, ddd, J=11.6, 8.9, 2.9 Hz), 3.46 (2H, d, J=5.6 Hz), 3.70 (2H, ddd, J=11.7, 5.6, 3.8 Hz), 4.74 (1H, t, J=5.5 Hz), 7.65 (2H, d, J=9.0 Hz), 8.18 (2H, d, J=9.0 Hz).

B) (4-(4-aminophenyl)tetrahydro-2H-pyran-4-yl)methanol

The title compound (240 mg) was obtained from (4-(4-nitrophenyl)tetrahydro-2H-pyran-4-yl)methanol (330 mg) obtained in Step A of Example 152 in the same manner as in Step D of Example 151.

$^1$H NMR (400 MHz, DMSO-$d_6$) δ1.73-1.92 (4H, m), 3.21 (2H, d, J=5.4 Hz), 3.28-3.36 (2H, m), 3.64 (2H, dt, J=11.4, 4.0 Hz), 4.47 (1H, t, J=5.5 Hz), 4.85 (2H, s), 6.52 (2H, d, J=8.6 Hz), 6.96 (2H, d, J=8.6 Hz).

C) (3S)-3-cyclopropyl-1-(2-((4-(4-(hydroxymethyl)tetrahydro-2H-pyran-4-yl)phenyl)amino)pyrimidin-4-yl)-2-oxopyrrolidine-3-carbonitrile The title compound (95 mg) was obtained from (3S)-1-(2-chloropyrimidin-4-yl)-3-cyclopropyl-2-oxopyrrolidine-3-carbonitrile (100 mg) obtained in Step E of Example 103 and (4-(4-aminophenyl)tetrahydro-2H-pyran-4-yl)methanol (79 mg) obtained in Step B of Example 152 in the same manner as in Step B of Example 2.

MS(ESI+): [M+H]$^+$ 434.4.

Example 153

2-(5-((4-((3S)-3-cyano-3-cyclopropyl-2-oxopyrrolidin-1-yl)pyrimidin-2-yl)amino)pyridin-2-yl)-2-methylpropanamide

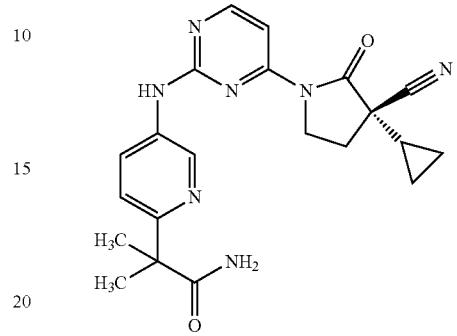

A) tert-butyl ethyl(5-nitropyridin-2-yl)malonate

To a solution of 2-chloro-5-nitropyridine (7.0 g) in N,N-dimethylformamide (100 mL) were successively added sodium hydride (60% in mineral oil, 2.1 g) and tert-butyl ethyl malonate (10 g), and the mixture was stirred overnight at 50° C. To the reaction mixture was added water, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (10 g).

$^1$H NMR (400 MHz, CDCl$_3$) δ1.30 (3H, t, J=7.2 Hz), 1.48 (9H, s), 4.19-4.43 (2H, m), 4.98 (1H, s), 7.76 (1H, dd, J=8.6, 0.5 Hz), 8.50 (1H, dd, J=8.8, 2.7 Hz), 9.38 (1H, d, J=2.4 Hz).

B) ethyl(5-nitropyridin-2-yl)acetate

To tert-butyl ethyl(5-nitropyridin-2-yl)malonate (10 g) obtained in Step A of Example 153 was added a solution of 4 M hydrogen chloride in ethyl acetate (40 mL), and the mixture was stirred overnight at room temperature. The solvent was evaporated under reduced pressure, and diethyl ether (150 mL) and saturated aqueous sodium hydrogen carbonate solution were added thereto. To the reaction mixture was added sodium hydrogen carbonate until bubble generation stopped, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (5.6 g).

$^1$H NMR (400 MHz, CDCl$_3$) δ1.28 (3H, t, J=7.1 Hz), 3.98 (2H, s), 4.21 (2H, q, J=7.1 Hz), 7.54 (1H, d, J=8.6 Hz), 8.46 (1H, dd, J=8.6, 2.7 Hz), 9.38 (1H, d, J=2.4 Hz).

C) ethyl 2-methyl-2-(5-nitropyridin-2-yl)propanoate

To a solution of sodium hydride (60% in mineral oil, 3.2 g) in N,N-dimethylformamide (40 mL) was added a solution of ethyl(5-nitropyridin-2-yl)acetate (5.6 g) obtained in Step B of Example 153 in N,N-dimethylformamide (10 mL) at −20° C. under nitrogen atmosphere, and the mixture was stirred at 0° C. for 1 hr. The reaction mixture was cooled to −20° C. again, iodomethane (5.5 mL) was added thereto, and the mixture was stirred at 0° C. for 5 hr. To the reaction mixture was added saturated aqueous ammonium chloride solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (3.2 g).

$^1$H NMR (400 MHz, CDCl$_3$) δ1.19 (3H, t, J=7.1 Hz), 1.65 (6H, s), 4.16 (2H, q, J=7.1 Hz), 7.50 (1H, dd, J=8.7, 0.6 Hz), 8.44 (1H, dd, J=8.8, 2.7 Hz), 9.36 (1H, dd, J=2.7, 0.5 Hz).

D) ethyl 2-(5-(((benzyloxy)carbonyl)amino)pyridin-2-yl)-2-methylpropanoate

To a solution of ethyl 2-methyl-2-(5-nitropyridin-2-yl)propanoate (3.3 g) obtained in Step C of Example 153 in ethanol (30 mL) was added 10% palladium-carbon (300 mg), and the mixture was stirred overnight at room temperature under hydrogen atmosphere (at normal pressures). The palladium-carbon was removed by filtration through Celite, and the solvent was evaporated under reduced pressure.

To a solution of the residue in tetrahydrofuran (30 mL) were added pyridine (3.3 g) and benzyl chloroformate (4.0 mL), and the mixture was stirred at room temperature for 2 hr in an ice bath. To the reaction mixture was added water, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the title compound (4.7 g).

$^1$H NMR (400 MHz, CDCl$_3$) δ1.17 (3H, t, J=7.1 Hz), 1.58 (6H, s), 4.01-4.27 (2H, m), 5.21 (2H, s), 6.72 (1H, brs), 7.33-7.48 (6H, m), 7.97 (1H, brs), 8.31-8.43 (1H, m).

E) benzyl(6-(1-amino-2-methyl-1-oxopropan-2-yl)pyridin-3-yl)carbamate

To a solution of ethyl 2-(5-(((benzyloxy)carbonyl)amino)pyridin-2-yl)-2-methylpropanoate (4.7 g) obtained in Step D of Example 153 in ethanol (50 mL) was added 2 M aqueous sodium hydroxide solution (30 mL), and the mixture was stirred overnight at room temperature. To the reaction mixture was added water, and the mixture was washed with diethyl ether. The obtained aqueous layer was neutralized with 2 M hydrochloric acid, and extracted with ethyl acetate. The obtained organic layer was washed with saturated brine, and dried over anhydrous magnesium sulfate, and the solvent was evaporated under reduced pressure to give a crude compound (2.42 g).

To a solution of the crude compound (800 mg) in N,N-dimethylacetamide (5.0 mL) were added ammonium chloride (230 mg), diisopropylethylamine (0.74 mL) and O-(benzotriazol-1-yl)-N,N,N',N'-tetramethyluronium hexafluorophosphorate (1.6 g), and the mixture was stirred overnight at room temperature. To the reaction mixture was added saturated aqueous sodium hydrogen carbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the crude title compound (880 mg).

MS(ESI+): [M+H]$^+$ 313.9.

F) 2-(5-aminopyridin-2-yl)-2-methylpropanamide

To a solution of the crude benzyl(6-(1-amino-2-methyl-1-oxopropan-2-yl)pyridin-3-yl)carbamate (880 mg) obtained in Step E of Example 153 in ethanol (30 mL) was added 10% palladium-carbon (90 mg), and the mixture was stirred overnight at room temperature under hydrogen atmosphere (at normal pressures). The palladium-carbon was removed by filtration through Celite, the solvent was evaporated under reduced pressure, and the residue was purified by silica gel column chromatography (ethyl acetate/methanol) to give the title compound (100 mg).

MS(ESI+): [M+H]$^+$ 180.3.

G) 2-(5-((4-((3S)-3-cyano-3-cyclopropyl-2-oxopyrrolidin-1-yl)pyrimidin-2-yl)amino)pyridin-2-yl)-2-methylpropanamide The title compound (30 mg) was obtained from (3S)-1-(2-chloropyrimidin-4-yl)-3-cyclopropyl-2-oxopyrrolidine-3-carbonitrile (70 mg) obtained in Step E of Example 103 and 2-(5-aminopyridin-2-yl)-2-methylpropanamide (48 mg) obtained in Step F of Example 153 in the same manner as in Example 56.

MS(ESI+): [M+H]$^+$ 406.3.

Example 154

2-(5-((4-((3S)-3-cyano-3-cyclopropyl-2-oxopyrrolidin-1-yl)pyrimidin-2-yl)amino)pyridin-2-yl)-N,2-dimethylpropanamide

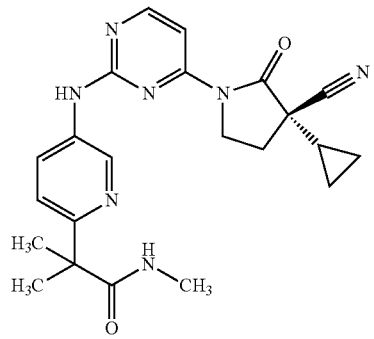 [SMILES: CNC(=O)C(C)(C)c1ccc(Nc2nccc(N3CC[C@@](C#N)(C4CC4)C3=O)n2)cn1]

A) benzyl(6-(2-methyl-1-(methylamino)-1-oxopropan-2-yl)pyridin-3-yl)carbamate

To a solution of ethyl 2-(5-(((benzyloxy)carbonyl)amino)pyridin-2-yl)-2-methylpropanoate (4.7 g) obtained in Step D of Example 153 in ethanol (50 mL) was added 2 M aqueous sodium hydroxide solution 00 (30 mL), and the mixture was stirred overnight at room temperature. To the reaction mixture was added water, and the mixture was washed with diethyl ether. The obtained aqueous layer was neutralized with 2 M hydrochloric acid, and extracted with ethyl acetate. The obtained organic layer was washed with saturated brine, and dried over anhydrous magnesium sulfate, and the solvent was evaporated under reduced pressure to give a crude compound (2.42 g).

To a solution of the crude compound (800 mg) in N,N-dimethylacetamide (5.0 mL) were added methylamine hydrochloride (280 mg), diisopropylethylamine (0.74 mL)

and O-(benzotriazol-1-yl)-N,N,N',N'-tetramethyluronium hexafluorophosphorate (1.6 g), and the mixture was stirred overnight at room temperature. To the reaction mixture was added saturated aqueous sodium hydrogen carbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (hexane/ethyl acetate) to give the crude title compound (1.2 g).

MS(ESI+): [M+H]⁺ 328.3.

B) 2-(5-aminopyridin-2-yl)-N,2-dimethylpropanamide

The title compound (210 mg) was obtained from the crude benzyl(6-(2-methyl-1-(methylamino)-1-oxopropan-2-yl)pyridin-3-yl)carbamate (1.2 g) obtained in Step A of Example 154 in the same manner as in Step F of Example 153.

MS(ESI+): [M+H]⁺ 194.3.

C) 2-(5-((4-((3S)-3-cyano-3-cyclopropyl-2-oxopyrrolidin-1-yl)pyrimidin-2-yl)amino)pyridin-2-yl)-N,2-dimethylpropanamide The title compound (55 mg) was obtained from (3S)-1-(2-chloropyrimidin-4-yl)-3-cyclopropyl-2-oxopyrrolidine-3-carbonitrile (70 mg) obtained in Step E of Example 103 and 2-(5-aminopyridin-2-yl)-N,2-dimethylpropanamide (52 mg) obtained in Step B of Example 154 in the same manner as in Example 56.

MS(ESI+): [M+H]⁺ 420.4.

Example 155

4-((4-((3S)-3-cyano-3-cyclopropyl-2-oxopyrrolidin-1-yl)pyrimidin-2-yl)amino)benzoic acid

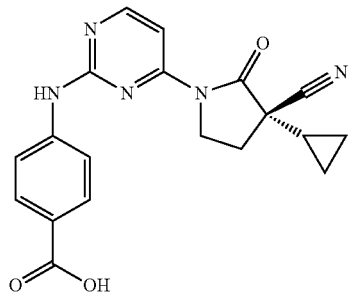 [SMILES: N#C[C@@]1(C2CC2)CCN(c2ccnc(Nc3ccc(C(=O)O)cc3)n2)C1=O]

The title compound (380 mg) was obtained from (3S)-1-(2-chloropyrimidin-4-yl)-3-cyclopropyl-2-oxopyrrolidine-3-carbonitrile (300 mg) obtained in Step E of Example 103 and 4-aminobenzoic acid (160 mg) in the same manner as in Step B of Example 2.

MS(ESI+): [M+H]⁺ 364.3.

Examples 156 to 175

The title compound was obtained from 4-((4-((3S)-3-cyano-3-cyclopropyl-2-oxopyrrolidin-1-yl)pyrimidin-2-yl)amino)benzoic acid obtained in Example 155 and each corresponding amine (these compounds can be produced according to a method known per se), in the same manner as in Example 110.

TABLE 14-1

| Example Number | IUPAC Name | Structure | Salt | MS |
|---|---|---|---|---|
| 156 | (3S)-3-cyclopropyl-1-(2-((4-(morpholin-4-ylcarbonyl)phenyl)amino)pyrimidin-4-yl)-2-oxopyrrolidine-3-carbonitrile | 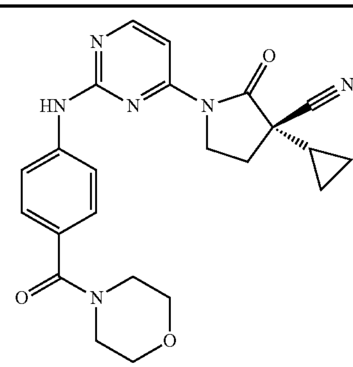 | HCl | 433.3 |
| 157 | (3S)-3-cyclopropyl-1-(2-((4-(((3R)-3-hydroxypyrrolidin-1-yl)carbonyl)phenyl)amino)pyrimidin-4-yl)-2-oxopyrrolidine-3-carbonitrile | 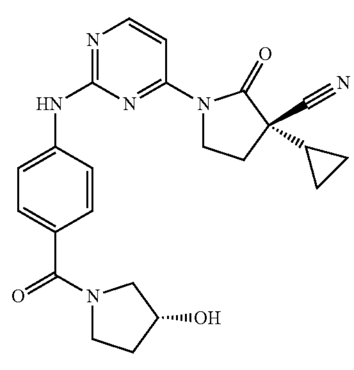 [SMILES: N#C[C@@]1(C2CC2)CCN(c2ccnc(Nc3ccc(C(=O)N4CC[C@@H](O)C4)cc3)n2)C1=O] | Free | 433.3 |

TABLE 14-1-continued

| Example Number | IUPAC Name | Structure | Salt | MS |
|---|---|---|---|---|
| 158 | (3S)-3-cyclopropyl-1-(2-((4-(((3S)-3-hydroxypyrrolidin-1-yl)carbonyl)phenyl)amino)pyrimidin-4-yl)-2-oxopyrrolidine-3-carbonitrile | 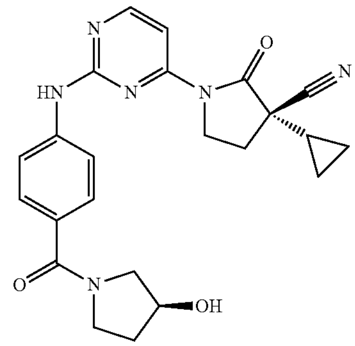 [SMILES: N#C[C@@]1(C2CC2)CCN(c2ccnc(Nc3ccc(C(=O)N4CC[C@H](O)C4)cc3)n2)C1=O] | Free | 433.3 |
| 159 | (3S)-3-cyclopropyl-1-(2-((4-((4-hydroxypiperidin-1-yl)carbonyl)phenyl)amino)pyrimidin-4-yl)-2-oxopyrrolidine-3-carbonitrile | 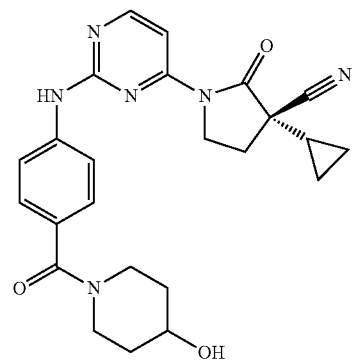 [SMILES: N#C[C@@]1(C2CC2)CCN(c2ccnc(Nc3ccc(C(=O)N4CCC(O)CC4)cc3)n2)C1=O] | Free | 447.1 |
| 160 | 4-((4-((3S)-3-cyano-3-cyclopropyl-2-oxopyrrolidin-1-yl)pyrimidin-2-yl)amino)-N-(2-(methylsulfonyl)ethyl)benzamide | 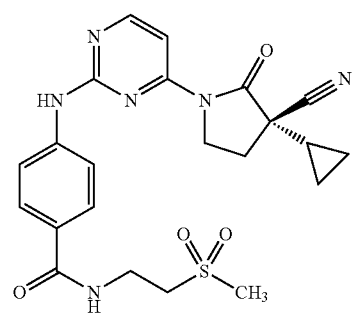 [SMILES: CS(=O)(=O)CCNC(=O)c1ccc(Nc2nccc(N3CC[C@@](C#N)(C4CC4)C3=O)n2)cc1] | Free | 469.3 |
| 161 | (3S)-3-cyclopropyl-1-(2-((4-((3-hydroxyazetidin-1-yl)carbonyl)phenyl)amino)pyrimidin-4-yl)-2-oxopyrrolidine-3-carbonitrile | 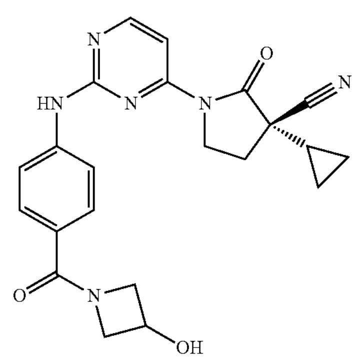 [SMILES: N#C[C@@]1(C2CC2)CCN(c2ccnc(Nc3ccc(C(=O)N4CC(O)C4)cc3)n2)C1=O] | Free | 419.3 |

TABLE 14-1-continued

| Example Number | IUPAC Name | Structure | Salt | MS |
|---|---|---|---|---|
| 162 | (3S)-3-cyclopropyl-2-oxo-1-(2-((4-((3-oxopyrrolidin-1-yl)carbonyl)phenyl)amino)pyrimidin-4-yl)pyrrolidine-3-carbonitrile | 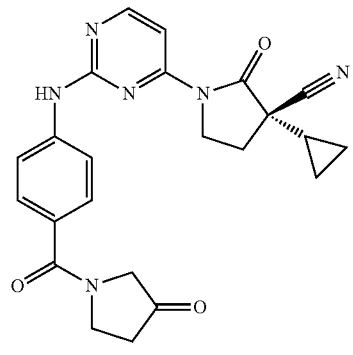 [SMILES: N#C[C@@]1(C2CC2)CCN(c2ccnc(Nc3ccc(C(=O)N4CCC(=O)C4)cc3)n2)C1=O] | Free | 431.3 |
| 163 | (3S)-3-cyclopropyl-1-(2-((4-((3,3-difluoropyrrolidin-1-yl)carbonyl)phenyl)amino)pyrimidin-4-yl)-2-oxopyrrolidine-3-carbonitrile | 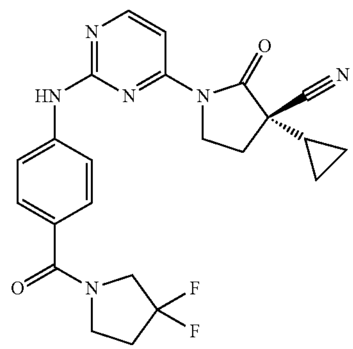 [SMILES: N#C[C@@]1(C2CC2)CCN(c2ccnc(Nc3ccc(C(=O)N4CCC(F)(F)C4)cc3)n2)C1=O] | Free | 453.3 |

TABLE 14-2

| | | | | |
|---|---|---|---|---|
| 164 | (3S)-3-cyclopropyl-1-(2-((4-(2-oxa-6-azaspiro[3.3]hept-6-ylcarbonyl)phenyl)amino)pyrimidin-4-yl)-2-oxopyrrolidine-3-carbonitrile | | Free | 445.3 |
| 165 | (3S)-3-cyclopropyl-1-(2-((4-(1,1-dioxidethiomorpholin-4-yl)carbonyl)phenyl)amino)pyrimidin-4-yl)-2-oxopyrrolidine-3-carbonitrile | | Free | 481.3 |

TABLE 14-2-continued

| 166 | (3S)-3-cyclopropyl-1-(2-((4-(((3S)-3-fluoropyrrolidin-1-yl)carbonyl)phenyl)amino)pyrimidin-4-yl)-2-oxopyrrolidine-3-carbonitrile | 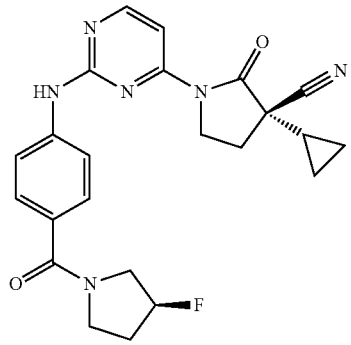 | Free | 435.3 |
| --- | --- | --- | --- | --- |
| 167 | (3S)-3-cyclopropyl-1-(2-((4-(((3R)-3-fluoropyrrolidin-1-yl)carbonyl)phenyl)amino)pyrimidin-4-yl)-2-oxopyrrolidine-3-carbonitrile | 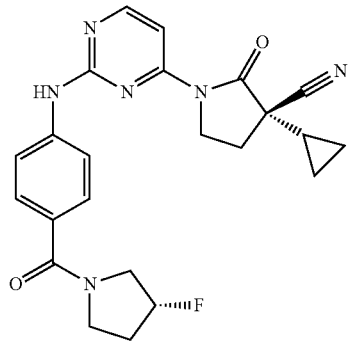 | Free | 435.3 |
| 168 | (3S)-3-cyclopropyl-1-(2-((4-((3-methoxyazetidin-1-yl)carbonyl)phenyl)amino)pyrimidin-4-yl)-2-oxopyrrolidine-3-carbonitrile | 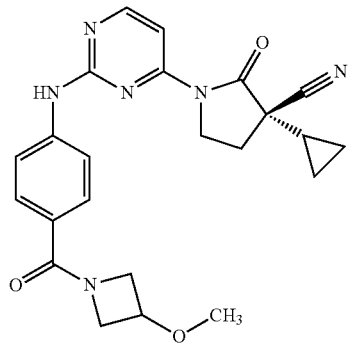 [SMILES: COC1CN(C(=O)c2ccc(Nc3nccc(N4CC[C@@](C#N)(C5CC5)C4=O)n3)cc2)C1] | Free | 433.3 |
| 169 | (3S)-3-cyclopropyl-1-(2-((4-(((3S)-3-hydroxypiperidin-1-yl)carbonyl)phenyl)amino)pyrimidin-4-yl)-2-oxopyrrolidine-3-carbonitrile | 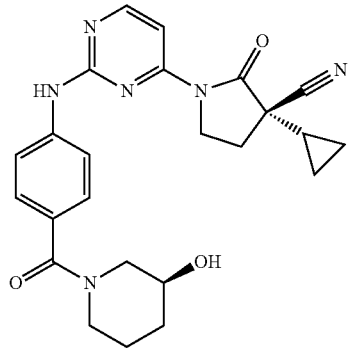 [SMILES: N#C[C@@]1(C2CC2)CCN(c2ccnc(Nc3ccc(C(=O)N4CCC[C@H](O)C4)cc3)n2)C1=O] | Free | 447.4 |

TABLE 14-2-continued

| | | | | |
|---|---|---|---|---|
| 170 | (3S)-3-cyclopropyl-1-(2-((4-(((3R)-3-hydroxypiperidin-1-yl)carbonyl)phenyl)amino)pyrimidin-4-yl)-2-oxopyrrolidine-3-carbonitrile | 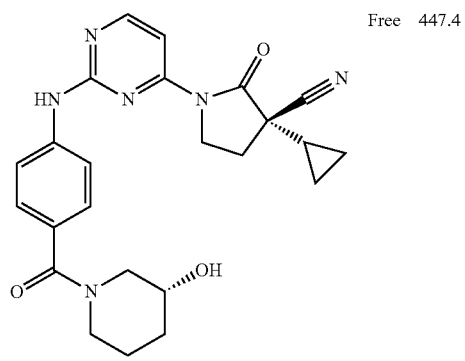 | Free | 447.4 |
| 171 | 4-((4-((3S)-3-cyano-3-cyclopropyl-2-oxopyrrolidin-1-yl)pyrimidin-2-yl)amino)-N-(tetrahydro-2H-pyran-4-yl)benzamide | 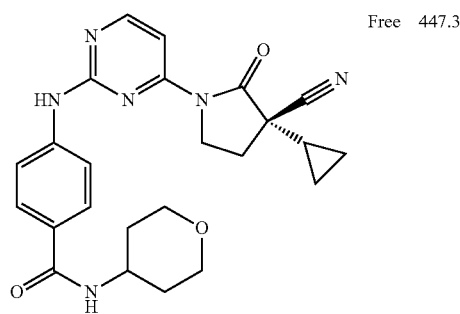 | Free | 447.3 |
| 172 | 4-((4-((3S)-3-cyano-3-cyclopropyl-2-oxopyrrolidin-1-yl)pyrimidin-2-yl)amino)-N-(trans-4-hydroxycyclohexyl)benzamide | 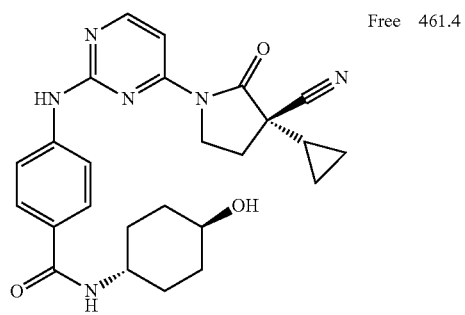 | Free | 461.4 |

TABLE 14-3

| | | | | |
|---|---|---|---|---|
| 173 | (3S)-3-cyclepropyl-1-(2-((4-((3-hydroxy-3-methylpyrrolidin-1-yl)carbonyl)phenyl)amino)pyrimidin-4-yl)-2-oxopyrrolidine-3-carbonitrile | 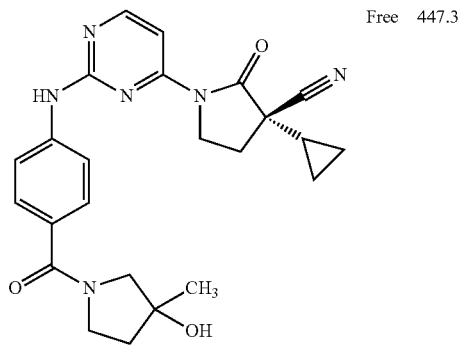 | Free | 447.3 |

TABLE 14-3-continued

| 174 | (3S)-3-cyclepropyl-1-(2-((4-(((3S)-3-methoxypyrrolidin-1-yl)carbonyl)phenyl)amino)pyrimidin-4-yl)-2-oxopyrrolidine-3-carbonitrile | 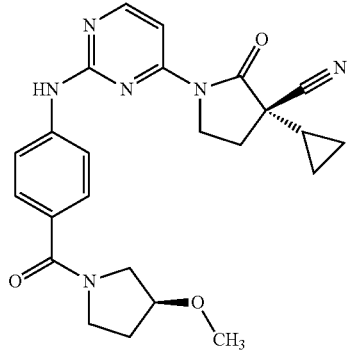 [SMILES: CO[C@H]1CCN(C(=O)c2ccc(Nc3nccc(N4CC[C@@](C#N)(C5CC5)C4=O)n3)cc2)C1] | Free | 447.3 |
| --- | --- | --- | --- | --- |
| 175 | (3S)-3-cyclepropyl-1-(2-((4-(((3R)-3-methoxypyrrolidin-1-yl)carbonyl)phenyl)amino)pyrimidin-4-yl)-2-oxopyrrolidine-3-carbonitrile | 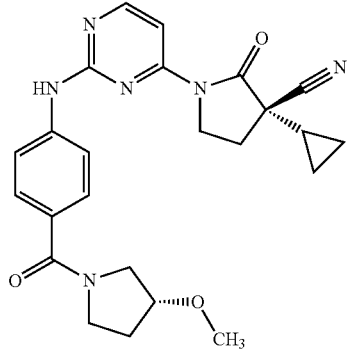 [SMILES: CO[C@@H]1CCN(C(=O)c2ccc(Nc3nccc(N4CC[C@@](C#N)(C5CC5)C4=O)n3)cc2)C1] | Free | 447.3 |

Example 176 to 181

The title compound was obtained from (3R)-1-(2-chloropyrimidin-4-yl)-3-ethyl-2-oxopyrrolidine-3-carbonitrile obtained in Step A of Example 8 and each corresponding amine (these compounds can be produced according to a method known per se), in the same manner as in Step B of Example 2.

TABLE 15

| Example Number | IUPAC Name | Structure | Salt | MS |
| --- | --- | --- | --- | --- |
| 176 | 2-(4-((4-((3R)-3-cyano-3-ethyl-2-oxopyrrolidin-1-yl)pyrimidin-2-yl)amino)-1H-pyrazol-1-yl)acetamide | 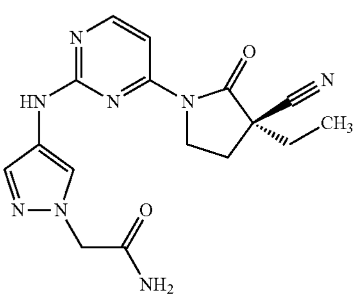 [SMILES: CC[C@]1(C#N)CCN(c2ccnc(Nc3cnn(CC(N)=O)c3)n2)C1=O] | free | 365.3 |
| 177 | 2-(4-((4-((3R)-3-cyano-3-ethyl-2-oxopyrrolidin-1-yl)pyrimidin-2-yl)amino)-1H-pyrazol-1-yl)-N-methylacetamide | 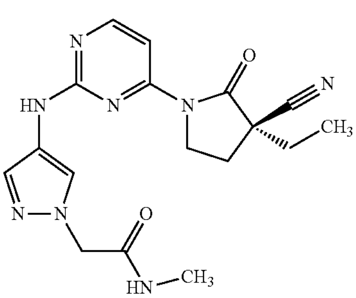 [SMILES: CC[C@]1(C#N)CCN(c2ccnc(Nc3cnn(CC(=O)NC)c3)n2)C1=O] | HCl | 369.3 |

TABLE 15-continued

| Example Number | IUPAC Name | Structure | Salt | MS |
|---|---|---|---|---|
| 178 | 2-(4-((4-((3R)-3-cyano-3-ethyl-2-oxopyrrolidin-1-yl)pyrimidin-2-yl)amino)-1H-pyrazol-1-yl)-N,N-dimethylacetamide | 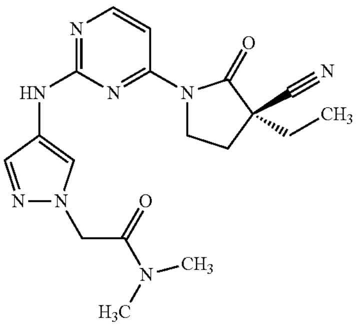 [SMILES: CC[C@]1(C#N)CCN(c2ccnc(Nc3cnn(CC(=O)N(C)C)c3)n2)C1=O] | HCl | 383.3 |
| 179 | (3R)-3-ethyl-1-(2-((1-ethyl-1H-pyrazol-4-yl)amino)pyrimidin-4-yl)-2-oxopyrrolidine-3-carbonitrile | 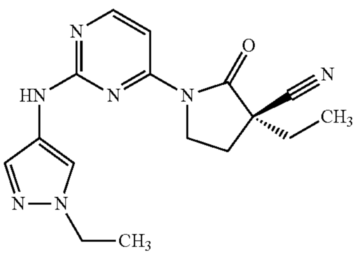 [SMILES: CCn1cc(Nc2nccc(N3CC[C@@](C#N)(CC)C3=O)n2)cn1] | HCl | 326.2 |
| 180 | (3R)-3-ethyl-1-(2-((1-(2-hydroxyethyl)-1H-pyrazol-4-yl)amino)pyrimidin-4-yl)-2-oxopyrrolidine-3-carbonitrile | 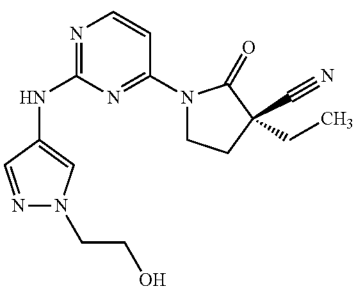 [SMILES: CC[C@]1(C#N)CCN(c2ccnc(Nc3cnn(CCO)c3)n2)C1=O] | HCl | 342.2 |
| 181 | (3R)-1-(2-((1-(1,1-dioxidetetrahydro-2H-thiopyran-4-yl)-1H-pyrazol-4-yl)amino)pyrimidin-4-yl)-3-ethyl-2-oxopyrrolidine-3-carbonitrile | 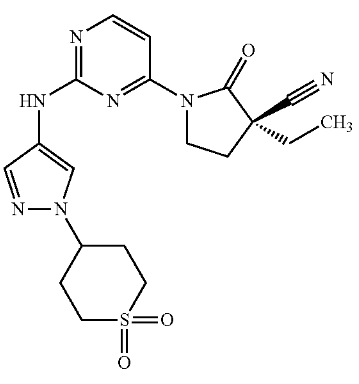 [SMILES: CC[C@]1(C#N)CCN(c2ccnc(Nc3cnn(C4CCS(=O)(=O)CC4)c3)n2)C1=O] | HCl | 430.3 |

Example 182

(3R)-3-ethyl-1-(2-((1-(oxetan-3-yl)-1H-pyrazol-4-yl)amino)pyrimidin-4-yl)-2-oxopyrrolidine-3-carbonitrile

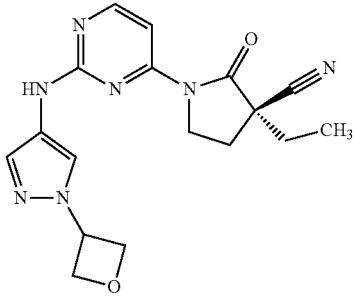 [SMILES: CC[C@]1(C#N)CCN(c2ccnc(Nc3cnn(C4COC4)c3)n2)C1=O]

The title compound (40 mg) was obtained from (3R)-1-(2-chloropyrimidin-4-yl)-3-ethyl-2-oxopyrrolidine-3-carbonitrile (150 mg) obtained in Step A of Example 8 and 1-(oxetan-3-yl)-1H-pyrazol-4-amine (83 mg) in the same manner as in Example 56.

MS(ESI+): [M+H]$^+$ 354.3.

Example 183

(3R)-3-ethyl-1-(2-((1-(1-hydroxy-2-methylpropan-2-yl)-H-pyrazol-4-yl)amino)pyrimidin-4-yl)-2-oxopyrrolidine-3-carbonitrile hydrochloride

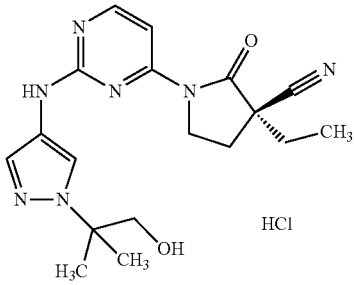 [SMILES: CC[C@]1(C#N)CCN(c2ccnc(Nc3cnn(C(C)(C)CO)c3)n2)C1=O ; Cl]

The title compound (78 mg) was obtained from (3R)-1-(2-chloropyrimidin-4-yl)-3-ethyl-2-oxopyrrolidine-3-carbonitrile (90 mg) obtained in Step A of Example 8 and 2-(4-amino-1H-pyrazol-1-yl)-2-methylpropan-1-ol (56 mg) obtained in Step H of Example 103 in the same manner as in Step B of Example 2.

MS(ESI+): [M+H]$^+$ 370.3.

Example 184 tert-butyl 3-(4-((4-((3R)-3-cyano-3-ethyl-2-oxopyrrolidin-1-yl)pyrimidin-2-yl)amino)-1H-pyrazol-1-yl azetidine-1-carboxylate

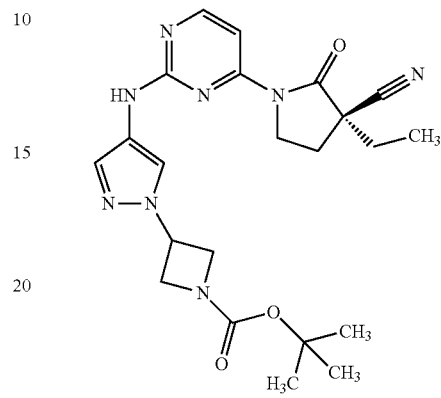

The title compound (450 mg) was obtained from (3R)-1-(2-chloropyrimidin-4-yl)-3-ethyl-2-oxopyrrolidine-3-carbonitrile (500 mg) obtained in Step A of Example 8 and tert-butyl 3-(4-amino-1H-pyrazol-1-yl)azetidine-1-carboxylate (520 mg) obtained in Step B of Example 131 in the same manner as in Example 56.

MS(ESI+): [M+H]$^+$ 453.2.

Example 185

(3R)-1-(2-((1-(azetidin-3-yl)-1H-pyrazol-4-yl)amino)pyrimidin-4-yl)-3-ethyl-2-oxopyrrolidine-3-carbonitrile dihydrochloride

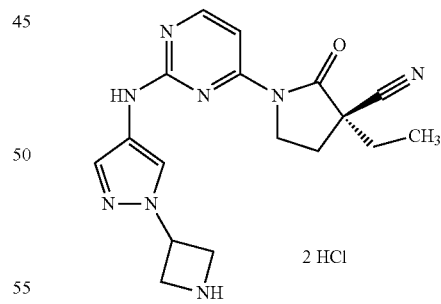

To tert-butyl 3-(4-((4-((3R)-3-cyano-3-ethyl-2-oxopyrrolidin-1-yl)pyrimidin-2-yl)amino)-1H-pyrazol-1-yl)azetidine-1-carboxylate (170 mg) obtained in Example 184 was added a solution of 4 M hydrogen chloride in ethyl acetate (6.0 mL), and the mixture was stirred at room temperature for 30 min. The solvent was evaporated under reduced pressure, and the residue was recrystallized (ethanol/ethyl acetate) to give the title compound (120 mg).

MS(ESI+): [M+H]$^+$ 353.3.

Example 186

(3R)-3-ethyl-1-(2-((1-(1-(methoxyacetyl)azetidin-3-yl)-1H-pyrazol-4-yl)amino)pyrimidin-4-yl)-2-oxopyrrolidine-3-carbonitrile

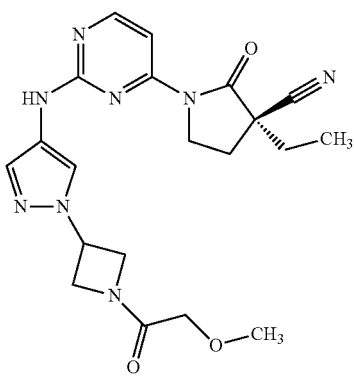 [SMILES: CC[C@]1(C#N)CCN(c2ccnc(Nc3cnn(C4CN(C(=O)COC)C4)c3)n2)C1=O]

To a solution of tert-butyl 3-(4-((4-((3R)-3-cyano-3-ethyl-2-oxopyrrolidin-1-yl)pyrimidin-2-yl)amino)-1H-pyrazol-1-yl)azetidine-1-carboxylate (140 mg) obtained in Example 184 in ethyl acetate (3.0 mL) was added a solution of 4 M hydrogen chloride in ethyl acetate (5.0 mL), and the mixture was stirred at room temperature for 30 min. The solvent was evaporated under reduced pressure, to a suspension of the reaction mixture in tetrahydrofuran (5 mL) were added triethylamine (160 mg) and methoxyacetyl chloride (37 mg) at room temperature, and the mixture was stirred at room temperature for 3 hr. The solvent was evaporated under reduced pressure, and the reaction mixture was poured into water, and extracted with ethyl acetate. The obtained organic layer was washed with saturated brine, and dried over anhydrous magnesium sulfate, and the solvent was evaporated under reduced pressure. The residue was purified by silica gel column chromatography (NH, ethyl acetate/methanol) to give the title compound (110 mg).

MS(ESI+): [M+H]$^+$ 425.2.

Example 187

(3R)-1-(2-((1-(1-(cyanoacetyl)azetidin-3-yl)-1H-pyrazol-4-yl)amino)pyrimidin-4-yl)-3-ethyl-2-oxopyrrolidine-3-carbonitrile

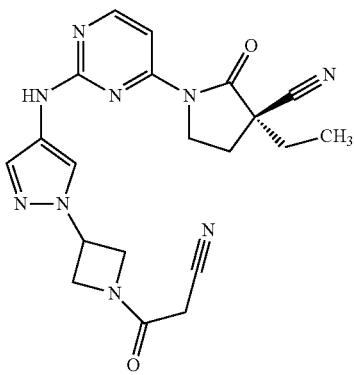 [SMILES: CC[C@]1(C#N)CCN(c2ccnc(Nc3cnn(C4CN(C(=O)CC#N)C4)c3)n2)C1=O]

To a solution of tert-butyl 3-(4-((4-((3R)-3-cyano-3-ethyl-2-oxopyrrolidin-1-yl)pyrimidin-2-yl)amino)-1H-pyrazol-1-yl)azetidine-1-carboxylate (100 mg) obtained in Example 184 in ethyl acetate (3.0 mL) was added a solution of 4 M hydrogen chloride in ethyl acetate (5.0 mL), and the mixture was stirred at room temperature for 30 min. The solvent was evaporated under reduced pressure, to a suspension of the reaction mixture in N,N-dimethylacetamide (3.0 mL) were added triethylamine (220 mg), 2-cyanoacetic acid (20 mg) and O-(7-aza-1H-benzotriazol-1-yl)-N,N,N',N'-tetramethyluronium hexafluorophosphate (170 mg) at room temperature, and the mixture was stirred at room temperature for 10 hr. The solvent was evaporated under reduced pressure, and the reaction mixture was poured into water, and extracted with ethyl acetate. The obtained organic layer was washed with saturated brine, and dried over anhydrous magnesium sulfate, and the solvent was evaporated under reduced pressure to give the title compound (35 mg).

$^1$H NMR (400 MHz, DMSO-d$_6$) δ1.00-1.16 (3H, m), 1.85-2.06 (3H, m), 2.24-2.41 (2H, m), 2.54-2.65 (1H, m), 3.96-4.22 (3H, m), 4.23-4.33 (1H, m), 4.33-4.42 (1H, m), 4.47-4.62 (1H, m), 5.17-5.35 (1H, m), 7.50-7.64 (1H, m), 7.63-7.76 (1H, m), 7.99-8.13 (1H, m), 8.31-8.48 (1H, m), 9.65 (1H, brs).

Example 188

(3R)-3-ethyl-1-(2-((1-(1-(methylsulfonyl) azetidin-3-yl)-1H-pyrazol-4-yl)amino)pyrimidin-4-yl)-2-oxopyrrolidine-3-carbonitrile

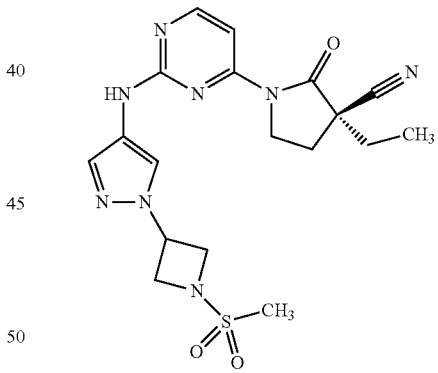

To a suspension of (3R)-1-(2-((1-(azetidin-3-yl)-1H-pyrazol-4-yl)amino)pyrimidin-4-yl)-3-ethyl-2-oxopyrrolidine-3-carbonitrile dihydrochloride (83 mg) obtained in Example 185 in tetrahydrofuran (5 mL) were added triethylamine (30 μL) and methanesulfonyl chloride (33 μL) at room temperature, and the mixture was stirred at room temperature for 2 hr. To the reaction mixture was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (ethyl acetate/hexane), and recrystallized (ethyl acetate/hexane) to give the title compound (16 mg).

MS(ESI+): [M+H]$^+$ 431.3.

Example 189

N-tert-butyl-2-(4-((4-((3R)-3-cyano-3-ethyl-2-oxopyrrolidin-1-yl)pyrimidin-2-yl)amino)-1H-pyrazol-1-yl) acetamide hydrochloride

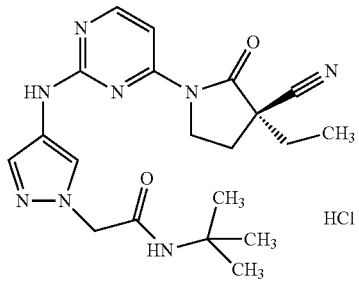 [SMILES: CC[C@]1(C#N)CCN(c2ccnc(Nc3cnn(CC(=O)NC(C)(C)C)c3)n2)C1=O ; Cl]

A) (4-((4-((3R)-3-cyano-3-ethyl-2-oxopyrrolidin-1-yl)pyrimidin-2-yl)amino)-1H-pyrazol-1-yl)acetic acid The title compound (270 mg) was obtained from (3R)-1-(2-chloropyrimidin-4-yl)-3-ethyl-2-oxopyrrolidine-3-carbonitrile (600 mg) obtained in Step A of Example 8 and tert-butyl(4-amino-1H-pyrazol-1-yl)acetate (610 mg) in the same manner as in Step B of Example 2.

MS(ESI+): [M+H]$^+$ 356.0.

B) N-tert-butyl-2-(4-((4-((3R)-3-cyano-3-ethyl-2-oxopyrrolidin-1-yl)pyrimidin-2-yl)amino)-1H-pyrazol-1-yl)acetamide hydrochloride To a solution of (4-((4-((3R)-3-cyano-3-ethyl-2-oxopyrrolidin-1-yl)pyrimidin-2-yl)amino)-1H-pyrazol-1-yl)acetic acid (100 mg) obtained in Step A of Example 189 in N,N-dimethylformamide (3 mL) were added 1-ethyl-3-(3-dimethylaminopropyl)carbodiimide (79 mg), 1-hydroxybenzotriazole monohydrate (78 mg), N,N-diisopropylethylamine (0.13 mL) and 2-methylpropan-2-amine (37 mg), and the mixture was stirred overnight at room temperature. To the reaction mixture was added saturated aqueous sodium hydrogen carbonate solution, and the mixture was extracted with ethyl acetate. The obtained organic layer was washed successively with water and saturated brine, and dried over anhydrous magnesium sulfate, and the solvent was evaporated under reduced pressure. The residue was purified by silica gel column chromatography (ethyl acetate/hexane). To a solution of the obtained residue in ethanol (3 mL) was added 1 M hydrochloric acid (0.19 mL), and the mixture was stirred at room temperature for 10 min. The solvent was evaporated under reduced pressure, and the residue was recrystallized (ethanol/diisopropyl ether) to give the title compound (66 mg)

MS(ESI+): [M+H]$^+$ 411.4.

Examples 190 to 198

The title compound was obtained from (4-((4-((3R)-3-cyano-3-ethyl-2-oxopyrrolidin-1-yl)pyrimidin-2-yl)amino)-1H-pyrazol-1-yl)acetic acid obtained in Step A of Example 189 and the each corresponding amine (these compounds can be produced according to a method known per se), in the same manner as in Step B of Example 189.

TABLE 16

| Example Number | IUPAC Name | Structure | Salt | MS |
|---|---|---|---|---|
| 190 | 2-(4-((4-((3R)-3-cyano-3-ethyl-2-oxopyrrolidin-1-yl)pyrimidin-2-yl)amino)-1H-pyrazol-1-yl)-N-(2,2,2-trifluoroethyl)acetamide | 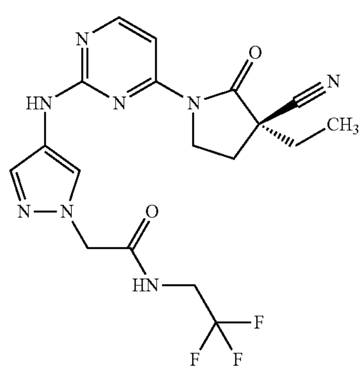 [SMILES: CC[C@]1(C#N)CCN(c2ccnc(Nc3cnn(CC(=O)NCC(F)(F)F)c3)n2)C1=O] | HCl | 437.3 |
| 191 | 2-(4-((4-((3R)-3-cyano-3-ethyl-2-oxopyrrolidin-1-yl)pyrimidin-2-yl)amino)-1H-pyrazol-1-yl)-N-(2-hydroxyethyl)acetamide | 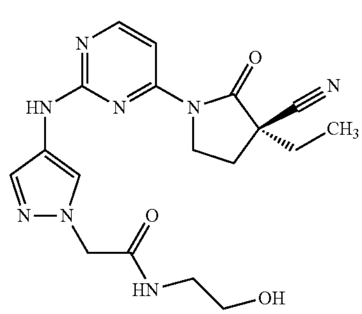 [SMILES: CC[C@]1(C#N)CCN(c2ccnc(Nc3cnn(CC(=O)NCCO)c3)n2)C1=O] | HCl | 399.3 |

TABLE 16-continued

| Example Number | IUPAC Name | Structure | Salt | MS |
|---|---|---|---|---|
| 192 | 2-(4-((4-((3R)-3-cyano-3-ethyl-2-oxopyrrolidin-1-yl)pyrimidin-2-yl)amino)-1H-pyrazol-1-yl)-N-(2-methoxyethyl)acetamide | 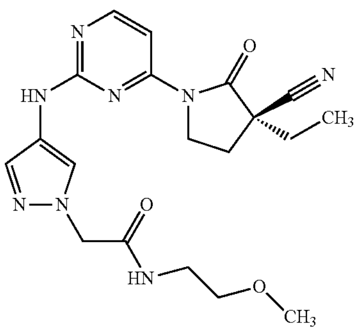 [SMILES: CC[C@]1(C#N)CCN(c2ccnc(Nc3cnn(CC(=O)NCCOC)c3)n2)C1=O] | HCl | 413.3 |
| 193 | (3R)-3-ethyl-1-(2-((1-(2-(morpholin-4-yl)-2-oxoethyl)-1H-pyrazol-4-yl)amino)pyrimidin-4-yl)-2-oxopyrrolidine-3-carbonitrile | 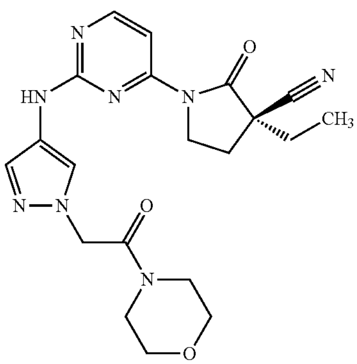 [SMILES: CC[C@]1(C#N)CCN(c2ccnc(Nc3cnn(CC(=O)N4CCOCC4)c3)n2)C1=O] | HCl | 435.3 |
| 194 | (3R)-3-ethyl-1-(2-((1-(2-(4-hydroxypiperidin-1-yl)-2-oxoethyl)-1H-pyrazol-4-yl)amino)pyrimidin-4-yl)-2-oxopyrrolidine-3-carbonitrile | 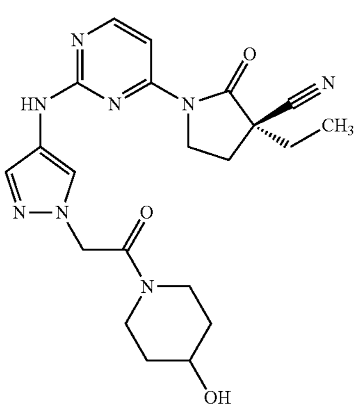 [SMILES: CC[C@]1(C#N)CCN(c2ccnc(Nc3cnn(CC(=O)N4CCC(O)CC4)c3)n2)C1=O] | HCl | 439.3 |
| 195 | 1-((4-((4-((3R)-3-cyano-3-ethyl-2-oxopyrrolidin-1-yl)pyrimidin-2-yl)amino)-1H-pyrazol-1-yl)acetyl)piperidine-4-carboxamide | 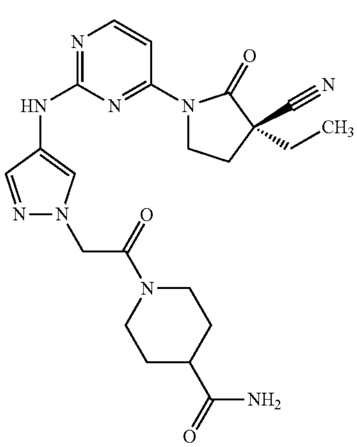 [SMILES: CC[C@]1(C#N)CCN(c2ccnc(Nc3cnn(CC(=O)N4CCC(C(N)=O)CC4)c3)n2)C1=O] | HCl | 466.4 |

TABLE 16-continued

| Example Number | IUPAC Name | Structure | Salt | MS |
|---|---|---|---|---|
| 196 | (3R)-3-ethyl-1-(2-((1-(2-(4-methylpiperazin-1-yl)-2-oxoethyl)-1H-pyrazol-4-yl)amino)pyrimidin-4-yl)-2-oxopyrrolidine-3-carbonitrile | 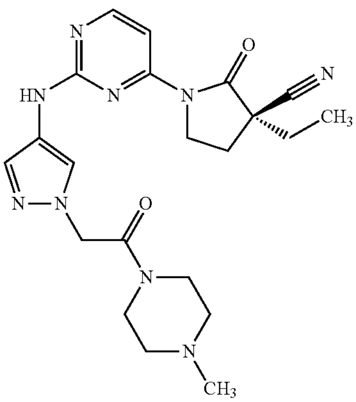 [SMILES: CC[C@]1(C#N)CCN(c2ccnc(Nc3cnn(CC(=O)N4CCN(C)CC4)c3)n2)C1=O] | HCl | 438.4 |
| 197 | 2-(4-((4-((3R)-3-cyano-3-ethyl-2-oxopyrrolidin-1-yl)pyrimidin-2-yl)amino)-1H-pyrazol-1-yl)-N-(2-hydroxyethyl)-N-methylacetamide | 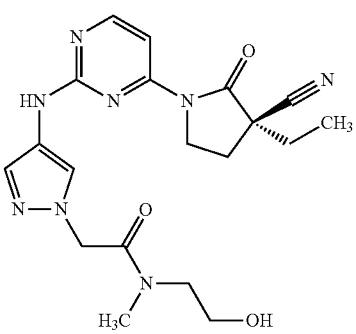 [SMILES: CC[C@]1(C#N)CCN(c2ccnc(Nc3cnn(CC(=O)N(C)CCO)c3)n2)C1=O] | HCl | 413.3 |
| 198 | 2-(4-((4-((3R)-3-cyano-3-ethyl-2-oxopyrrolidin-1-yl)pyrimidin-2-yl)amino)-1H-pyrazol-1-yl)-N-(2-(methylsulfonyl)ethyl)acetamide | 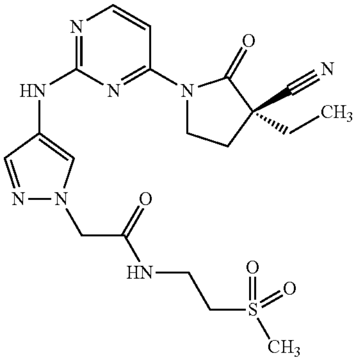 [SMILES: CC[C@]1(C#N)CCN(c2ccnc(Nc3cnn(CC(=O)NCCS(C)(=O)=O)c3)n2)C1=O] | HCl | 461.3 |

Example 199

2-(4-((4-((3R)-3-cyano-3-ethyl-2-oxopyrrolidin-1-yl)pyrimidin-2-yl)amino)-1H-pyrazol-1-yl)-2-methylpropanoic acid hydrochloride

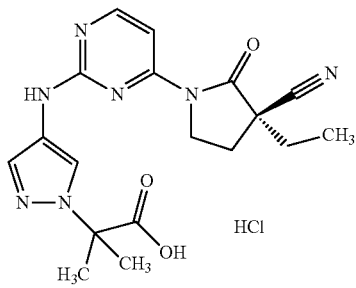 [SMILES: CC[C@]1(C#N)CCN(c2ccnc(Nc3cnn(C(C)(C)C(=O)O)c3)n2)C1=O ; Cl]

A) tert-butyl 2-(4-((4-((3R)-3-cyano-3-ethyl-2-oxopyrrolidin-1-yl)pyrimidin-2-yl)amino)-1H-pyrazol-1-yl)-2-methylpropanoate The title compound (1.6 g) was obtained from (3R)-1-(2-chloropyrimidin-4-yl)-3-ethyl-2-oxopyrrolidine-3-carbonitrile (1.0 g) obtained in Step A of Example 8 and tert-butyl 2-(4-amino-1H-pyrazol-1-yl)-2-methylpropanoate (1.1 g) obtained in Step B of Example 108 in the same manner as in Step B of Example 2.

MS(ESI+): [M+H]$^+$ 440.4.

B) 2-(4-((4-((3R)-3-cyano-3-ethyl-2-oxopyrrolidin-1-yl)pyrimidin-2-yl)amino)-1H-pyrazol-1-yl)-2-methylpropanoic acid hydrochloride To a solution of tert-butyl 2-(4-((4-((3R)-3-cyano-3-ethyl-2-oxopyrrolidin-1-yl)pyrimidin-2-yl)amino)-1H-pyrazol-1-yl)-2-methylpropanoate (1.0 g) obtained in Step A of Example 199 in ethyl acetate (10 mL) was added a solution of 4 M hydrogen chloride in ethyl acetate (10 mL), and the mixture was stirred at room temperature for 3 hr. The solvent was evaporated under reduced pressure, and the residue was recrystallized (ethanol/diisopropyl ether) to give the crude title compound (820 mg). The crude title compound (100 mg) was purified by HPLC (C18, mobile phase: water/acetonitrile (containing 10 mM NH$_4$HCO$_3$)), and the solvent was evaporated under reduced pressure. To a solution of the residue in ethanol (3 mL) was added 1 M hydrochloric acid (0.20 mL), and the mixture was stirred at room temperature for 10 min. The solvent was evaporated under reduced pressure, and the residue was recrystallized (ethanol/diisopropyl ether) to give the title compound (820 mg).

MS(ESI+): [M+H]$^+$ 384.3.

Example 200

(3R)-3-ethyl-1-(2-((1-(2-methyl-1-(morpholin-4-yl)-1-oxopropan-2-yl)-1H-pyrazol-4-yl)amino)pyrimidin-4-yl)-2-oxopyrrolidine-3-carbonitrile hydrochloride

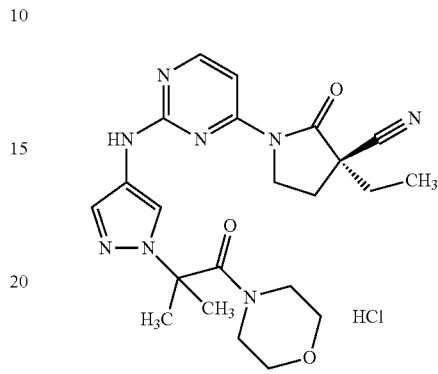

The title compound (25 mg) was obtained from 2-(4-((4-((3R)-3-cyano-3-ethyl-2-oxopyrrolidin-1-yl)pyrimidin-2-yl)amino)-1H-pyrazol-1-yl)-2-methylpropanoic acid hydrochloride (80 mg) obtained in Step B of Example 199 and morpholine (20 mg) in the same manner as in Step B of Example 189.

MS(ESI+): [M+H]$^+$ 453.4.

Example 201

(3R)-1-(2-((1,5-dimethyl-1H-pyrazol-4-yl)amino)pyrimidin-4-yl)-3-ethyl-2-oxopyrrolidine-3-carbonitrile

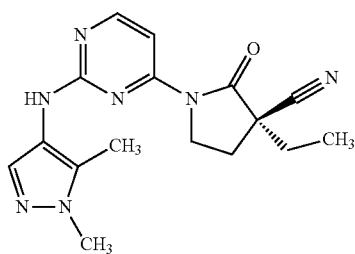 [SMILES: CC[C@]1(C#N)CCN(c2ccnc(Nc3cnn(C)c3C)n2)C1=O]

A solution of (3R)-1-(2-chloropyrimidin-4-yl)-3-ethyl-2-oxopyrrolidine-3-carbonitrile (100 mg) obtained in Step A of Example 8 and 1,5-dimethyl-1H-pyrazol-4-amine dihydrochloride (73 mg) in propan-2-ol (4.0 mL) was stirred in a microwave reactor at 160° C. for 1 hr, and the solvent was evaporated under reduced pressure. The obtained residue was purified by silica gel column chromatography (NH, hexane/ethyl acetate), and recrystallized (diisopropyl ether/ethyl acetate) to give the title compound (90 mg).

MS(ESI+): [M+H]$^+$ 326.0.

Example 202

(3R)-1-(2-((1,3-dimethyl-1H-pyrazol-4-yl)amino)pyrimidin-4-yl)-3-ethyl-2-oxopyrrolidine-3-carbonitrile

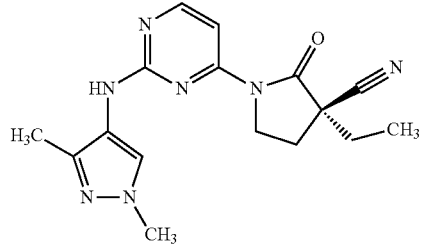 [SMILES: CC[C@]1(C#N)CCN(c2ccnc(Nc3cn(C)nc3C)n2)C1=O]

The title compound (73 mg) was obtained from (3R)-1-(2-chloropyrimidin-4-yl)-3-ethyl-2-oxopyrrolidine-3-carbonitrile (100 mg) obtained in Step A of Example 8 and 1,3-dimethyl-1H-pyrazol-4-amine dihydrochloride in the same manner as in Example 201.

MS(ESI+): [M+H]$^+$ 326.0.

Example 203

1-(4-((4-((3R)-3-cyano-3-ethyl-2-oxopyrrolidin-1-yl)pyrimidin-2-yl)amino)-1H-pyrazol-1-yl)cyclobutanecarboxamide

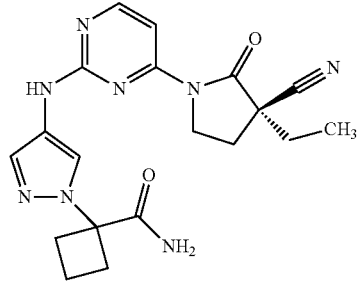 [SMILES: CC[C@]1(C#N)CCN(c2ccnc(Nc3cnn(C4(C(N)=O)CCC4)c3)n2)C1=O]

The title compound (90 mg) was obtained from (3R)-1-(2-chloropyrimidin-4-yl)-3-ethyl-2-oxopyrrolidine-3-carbonitrile (140 mg) obtained in Step A of Example 8 and 1-(4-amino-1H-pyrazol-1-yl)cyclobutanecarboxamide (103 mg) obtained in Step B of Example 129 in the same manner as in Step B of Example 2.

MS(ESI+): [M+H]$^+$ 395.4.

Example 204

1-(4-((4-((3R)-3-cyano-3-ethyl-2-oxopyrrolidin-1-yl)pyrimidin-2-yl)amino)-1H-pyrazol-1-yl)cyclopropanecarboxamide

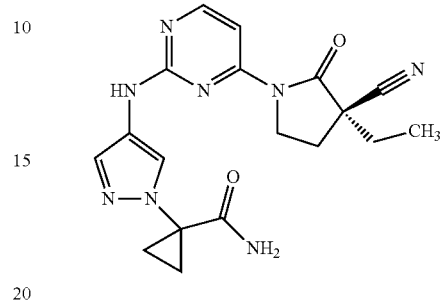

The title compound (140 mg) was obtained from (3R)-1-(2-chloropyrimidin-4-yl)-3-ethyl-2-oxopyrrolidine-3-carbonitrile (150 mg) obtained in Step A of Example 8 and 1-(4-amino-1H-pyrazol-1-yl)cyclopropanecarboxamide (99 mg) obtained in Step B of Example 130 in the same manner as in Step B of Example 2.

MS(ESI+): [M+H]$^+$ 382.3.

Example 205

(3R)-3-ethyl-1-(2-((1-(1-(hydroxymethyl)cyclobutyl)-1H-pyrazol-4-yl)amino)pyrimidin-4-yl)-2-oxopyrrolidine-3-carbonitrile

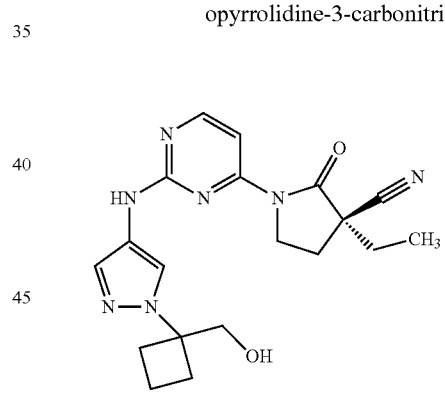

The title compound (64 mg) was obtained from (3R)-1-(2-chloropyrimidin-4-yl)-3-ethyl-2-oxopyrrolidine-3-carbonitrile (150 mg) obtained in Step A of Example 8 and (1-(4-amino-1H-pyrazol-1-yl)cyclobutyl)methanol (100 mg) obtained in Step C of Example 127 in the same manner as in Step B of Example 2.

MS(ESI+): [M+H]$^+$ 382.3.

Examples 206 to 222

The title compound was obtained from (3R)-1-(2-chloropyrimidin-4-yl)-3-ethyl-2-oxopyrrolidine-3-carbonitrile obtained in Step A of Example 8 and each corresponding aniline derivative (these compounds can be produced according to a method known per se), in the same manner as in Step B of Example 2.

TABLE 17-1

| Example Number | IUPAC Name | Structure | Salt | MS |
|---|---|---|---|---|
| 206 | 4-((4-((3R)-3-cyano-3-ethyl-2-oxopyrrolidin-1-yl)pyrimidin-2-yl)amino)-N-methylbenzenesulfonamide | 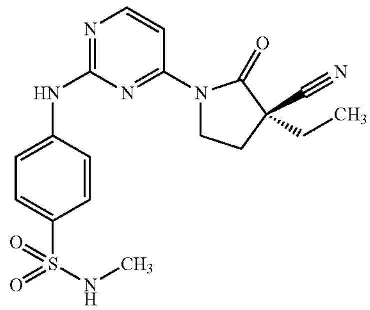 [SMILES: CC[C@]1(C#N)CCN(c2ccnc(Nc3ccc(S(=O)(=O)NC)cc3)n2)C1=O] | Free | 401.3 |
| 207 | (3R)-3-ethyl-2-oxo-1-(2-((4-(2-oxoimidazolidin-1-yl)phenyl)amino)pyrimidin-4-yl)pyrrolidine-3-carbonitrile | 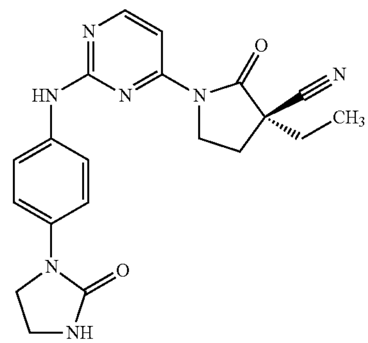 [SMILES: CC[C@]1(C#N)CCN(c2ccnc(Nc3ccc(N4CCNC4=O)cc3)n2)C1=O] | Free | 392.3 |
| 209 | (3-((4-((3R)-3-cyano-3-ethyl-2-oxopyrrolidin-1-yl)pyrimidin-2-yl)amino)phenyl)acetic acid | 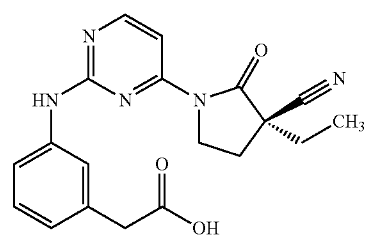 [SMILES: CC[C@]1(C#N)CCN(c2ccnc(Nc3cccc(CC(=O)O)c3)n2)C1=O] | HCl | 366.3 |
| 210 | (3R)-3-ethyl-2-oxo-1-(2-((4-(pyrrolidin-1-ylcarbonyl)phenyl)amino)pyrimidin-4-yl)pyrrolidine-3-carbonitrile | 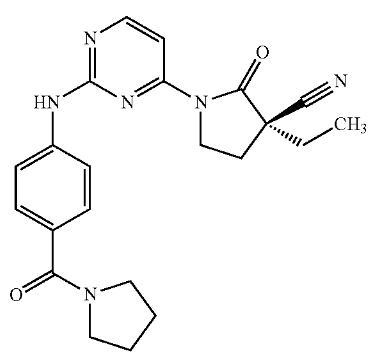 [SMILES: CC[C@]1(C#N)CCN(c2ccnc(Nc3ccc(C(=O)N4CCCC4)cc3)n2)C1=O] | HCl | 405.3 |
| 211 | 4-((4-((3R)-3-cyano-3-ethyl-2-oxopyrrolidin-1-yl)pyrimidin-2-yl)amino)-N-(2-hydroxyethyl)benzamide | 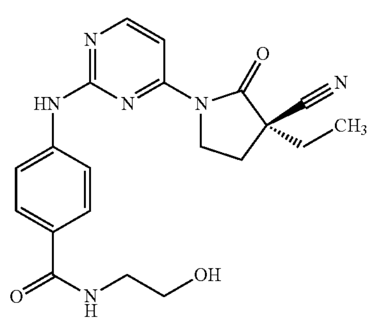 [SMILES: CC[C@]1(C#N)CCN(c2ccnc(Nc3ccc(C(=O)NCCO)cc3)n2)C1=O] | HCl | 395.3 |

TABLE 17-1-continued

| Example Number | IUPAC Name | Structure | Salt | MS |
|---|---|---|---|---|
| 212 | (4-((4-((3R)-3-cyano-3-ethyl-2-oxopyrrolidin-1-yl)pyrimidin-2-yl)amino)phenyl)acetic acid | 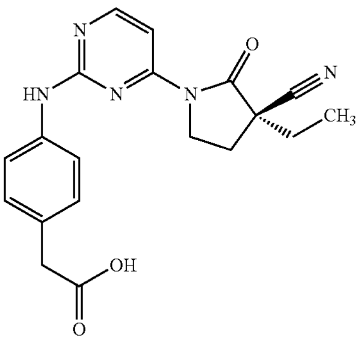 [SMILES: CC[C@]1(C#N)CCN(c2ccnc(Nc3ccc(CC(=O)O)cc3)n2)C1=O] | Free | 366.3 |
| 213 | (3R)-3-ethyl-2-oxo-1-(2-((4-(5-oxo-4,5-dihydro-1,2,4-oxadiazol-3-yl)phenyl)amino)pyrimidin-4-yl)pyrrolidine-3-carbonitrile | 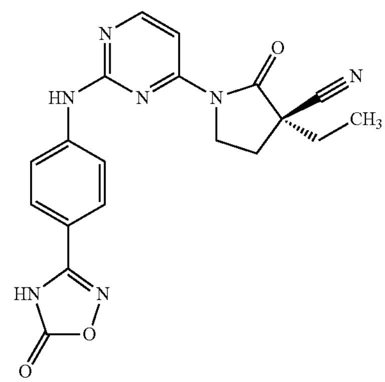 [SMILES: CC[C@]1(C#N)CCN(c2ccnc(Nc3ccc(-c4noc(=O)[nH]4)cc3)n2)C1=O] | Free | 392.3 |
| 214 | N-(3-((4-((3R)-3-cyano-3-ethyl-2-oxopyrrolidin-1-yl)pyrimidin-2-yl)amino)phenyl)-N-methylacetamide | 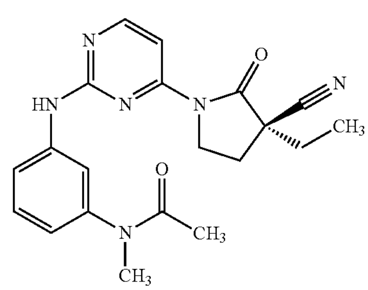 [SMILES: CC[C@]1(C#N)CCN(c2ccnc(Nc3cccc(N(C)C(C)=O)c3)n2)C1=O] | HCl | 379.3 |

TABLE 17-2

| Example Number | IUPAC Name | Structure | Salt | MS |
|---|---|---|---|---|
| 215 | 4-((4-((3R)-3-cyano-3-ethyl-2-oxopyrrolidin-1-yl)pyrimidin-2-yl)amino)-2-methoxybenzamide | 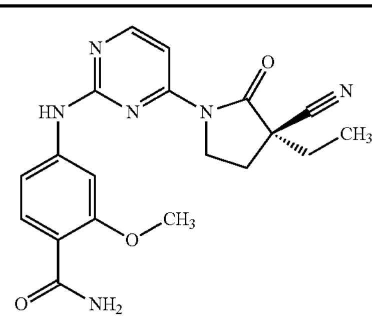 | Free | 381.3 |

TABLE 17-2-continued

| Example Number | IUPAC Name | Structure | Salt | MS |
|---|---|---|---|---|
| 216 | 4-((4-((3R)-3-cyano-3-ethyl-2-oxopyrrolidin-1-yl)pyrimidin-2-yl)amino)-2-methoxy-N-methylbenzamide | 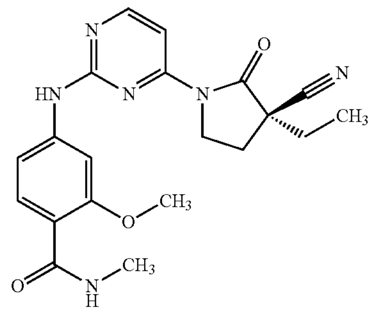 [SMILES: CC[C@]1(C#N)CCN(c2ccnc(Nc3ccc(C(=O)NC)c(OC)c3)n2)C1=O] | Free | 395.3 |
| 217 | N-(3-((4-((3R)-3-cyano-3-ethyl-2-oxopyrrolidin-1-yl)pyrimidin-2-yl)amino)phenyl)-2-methoxyacetamide | 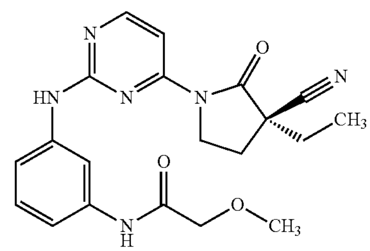 [SMILES: CC[C@]1(C#N)CCN(c2ccnc(Nc3cccc(NC(=O)COC)c3)n2)C1=O] | HCl | 395.3 |
| 218 | tert-butyl 4-(4-((4-((3R)-3-cyano-3-ethyl-2-oxopyrrolidin-1-yl)pyrimidin-2-yl)amino)phenyl)piperazine-1-carboxylate | 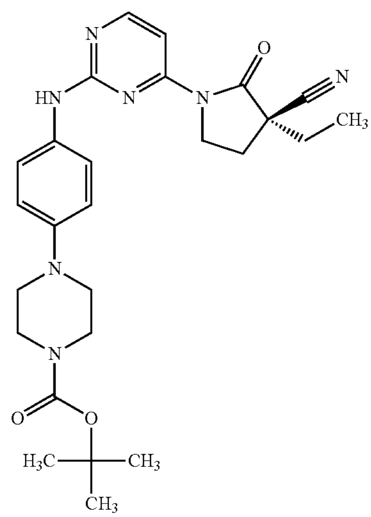 [SMILES: CC[C@]1(C#N)CCN(c2ccnc(Nc3ccc(N4CCN(C(=O)OC(C)(C)C)CC4)cc3)n2)C1=O] | Free | 492.4 |
| 219 | (3R)-3-ethyl-1-(2-((4-(4-methylpiperazin-1-yl)phenyl)amino)pyrimidin-4-yl)-2-oxopyrrolidine-3-carbonitrile | 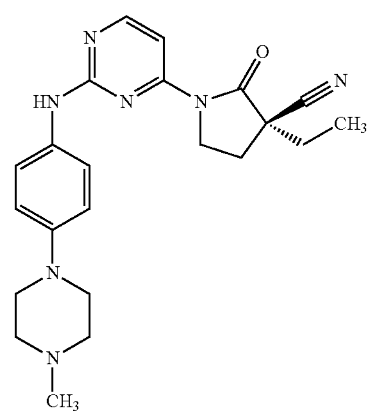 [SMILES: CC[C@]1(C#N)CCN(c2ccnc(Nc3ccc(N4CCN(C)CC4)cc3)n2)C1=O] | Free | 406.3 |

TABLE 17-2-continued

| Example Number | IUPAC Name | Structure | Salt | MS |
|---|---|---|---|---|
| 220 | (3R)-3-ethyl-2-oxo-1-(2-((4-(piperazin-1-yl)phenyl)amino)pyrimidin-4-yl)pyrrolidine-3-carbonitrile | 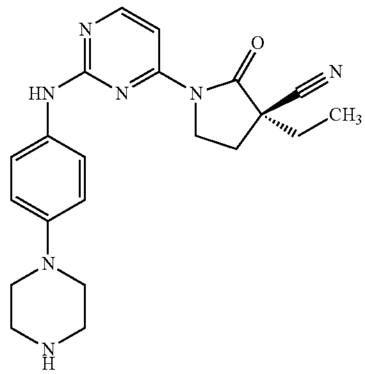 [SMILES: CC[C@]1(C#N)CCN(c2ccnc(Nc3ccc(N4CCNCC4)cc3)n2)C1=O] | Free | 392.4 |
| 222 | N-(3-((4-((3R)-3-cyano-3-ethyl-2-oxopyrrolidin-1-yl)pyrimidin-2-yl)amino)benzyl)acetamide | 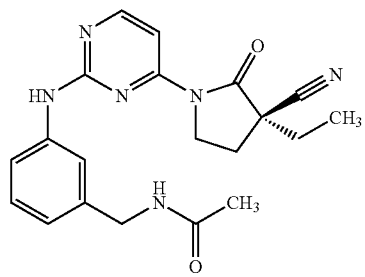 [SMILES: CC[C@]1(C#N)CCN(c2ccnc(Nc3cccc(CNC(C)=O)c3)n2)C1=O] | HCl | 379.3 |

Example 224

N-(3-((4-((3R)-3-cyano-3-ethyl-2-oxopyrrolidin-1-yl) pyrimidin-2-yl)amino)phenyl)methanesulfonamide hydrochloride

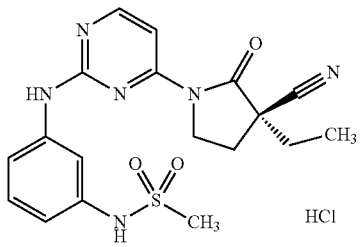 [SMILES: CC[C@]1(C#N)CCN(c2ccnc(Nc3cccc(NS(C)(=O)=O)c3)n2)C1=O ; Cl]

Crude N-(3-((4-((3R)-3-cyano-3-ethyl-2-oxopyrrolidin-1-yl)pyrimidin-2-yl)amino)phenyl)-N-(methylsulfonyl)methanesulfonamide (100 mg) was obtained from (3R)-1-(2-chloropyrimidin-4-yl)-3-ethyl-2-oxopyrrolidine-3-carbonitrile (55 mg) obtained in Step A of Example 8 and N-(3-aminophenyl)-N-(methylsulfonyl)methanesulfonamide (58 mg) in the same manner as in Step B of Example 2.

To a solution of the crude N-(3-((4-((3R)-3-cyano-3-ethyl-2-oxopyrrolidin-1-yl)pyrimidin-2-yl)amino)phenyl)-N-(methylsulfonyl)methanesulfonamide (100 mg) in tetrahydrofuran (3.0 mL) was added 4 M aqueous lithium hydroxide solution (52 μL), and the mixture was stirred at room temperature for 3 hr. To the reaction mixture was added saturated aqueous ammonium chloride solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate). To a solution of the residue in ethanol (3.0 mL) was added 1 N hydrochloric acid (72 μL), and the mixture was stirred at room temperature for 5 min. The solvent was evaporated under reduced pressure, and the residue was recrystallized (ethanol/diisopropyl ether) to give the title compound (12 mg).

MS(ESI+): [M+H]$^+$ 401.3.

Example 225

4-(4-((4-((3R)-3-cyano-3-ethyl-2-oxopyrrolidin-1-yl)pyrimidin-2-yl)amino)phenyl)-N-methylpiperazine-1-carboxamide

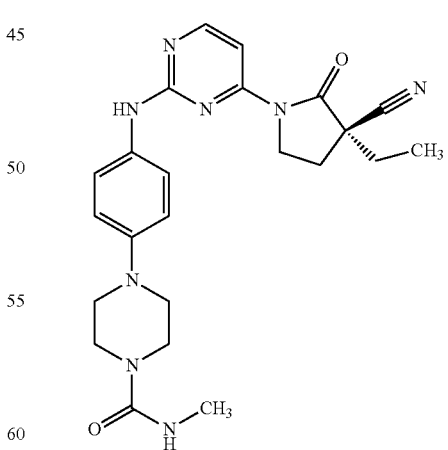

To a solution of 2 M methylamine in tetrahydrofuran (0.28 mL) were added 1,1'-carbonyldiimidazole (91 mg) and tetrahydrofuran (3.0 mL) in an ice bath, and the mixture was stirred at the same temperature for 10 min. To the reaction mixture was added (3R)-3-ethyl-2-oxo-1-(2-((4-(piperazin-1-yl)phenyl)amino)pyrimidin-4-yl)pyrrolidine-3-carbonitrile (200 mg) obtained in Example 220, and the mixture was stirred at 70° C. for 2 hr. To the reaction mixture was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate). To a solution of the obtained purified product (290 mg) in ethanol (3 mL) was added 1 M hydrochloric acid (0.64 mL), and the mixture was stirred at room temperature for 5 min. The solvent was evaporated under reduced pressure, and the residue was recrystallized (ethanol/diisopropyl ether) to give the title compound (220 mg)

MS(ESI+): [M+H]$^+$ 449.4.

Example 226

(3R)-3-ethyl-1-(2-((4-(4-(methylsulfonyl)piperazin-1-yl)phenyl)amino)pyrimidin-4-yl)-2-oxopyrrolidine-3-carbonitrile hydrochloride

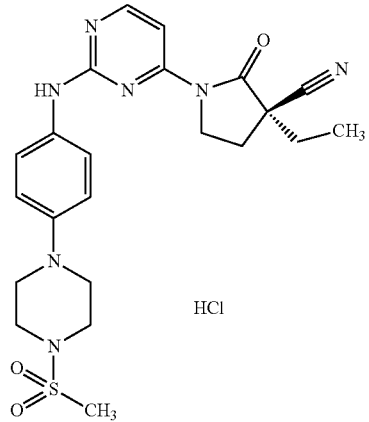 [SMILES: CC[C@]1(C#N)CCN(c2ccnc(Nc3ccc(N4CCN(S(C)(=O)=O)CC4)cc3)n2)C1=O ; Cl]

To a solution of (3R)-3-ethyl-2-oxo-1-(2-((4-(piperazin-1-yl)phenyl)amino)pyrimidin-4-yl)pyrrolidine-3-carbonitrile (100 mg) obtained in Example 220 in tetrahydrofuran (3.0 mL) were added successively dropwise triethylamine (71 µL) and methanesulfonyl chloride (24 µL) in an ice bath, and the mixture was stirred at the same temperature for 3 hr. To the reaction mixture was added saturated aqueous ammonium chloride solution, and the solvent was evaporated under reduced pressure. The residue was purified by silica gel column chromatography (hexane/ethyl acetate), to a solution of the obtained purified product (120 mg) in ethanol (3 mL) was added 1 M hydrochloric acid (0.25 mL), and the mixture was stirred at room temperature for 5 min. The solvent was evaporated under reduced pressure, and the residue was recrystallized (ethanol/diisopropyl ether) to give the title compound (91 mg).

MS(ESI+): [M+H]$^+$ 470.4.

Example 227

(3R)-3-ethyl-1-(2-((4-(4-(methoxyacetyl)piperazin-1-yl)phenyl)amino)pyrimidin-4-yl)-2-oxopyrrolidine-3-carbonitrile hydrochloride

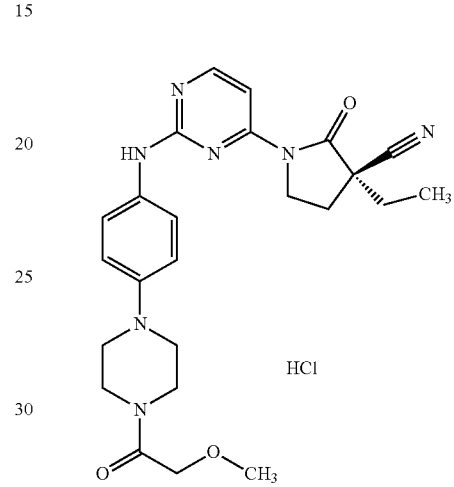

The title compound (85 mg) was obtained from (3R)-3-ethyl-2-oxo-1-(2-((4-(piperazin-1-yl)phenyl)amino)pyrimidin-4-yl)pyrrolidine-3-carbonitrile (100 mg) obtained in Example 220 and methoxyacetyl chloride (28 µL) in the same manner as in Example 226.

MS(ESI+): [M+H]$^+$ 464.4.

Examples 228 to 234

The title compound was obtained from (3R)-1-(2-chloropyrimidin-4-yl)-3-ethyl-2-oxopyrrolidine-3-carbonitrile obtained in Step A of Example 8 and each corresponding aniline derivative (these compounds can be produced according to a method known per se), in the same manner as in Step B of Example 2.

TABLE 18

| Example Number | IUPAC Name | Structure | Salt | MS |
| --- | --- | --- | --- | --- |
| 228 | 4-((4-((3R)-3-cyano-3-ethyl-2-oxopyrrolidin-1-yl)pyrimidin-2-yl)amino)-2-(methylsulfonyl)benzamide | 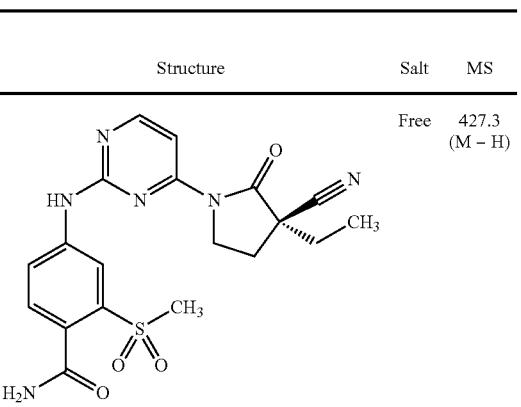 | Free | 427.3 (M − H) |

TABLE 18-continued

| Example Number | IUPAC Name | Structure | Salt | MS |
|---|---|---|---|---|
| 229 | 4-((4-((3R)-3-cyano-3-ethyl-2-oxopyrrolidin-1-yl)pyrimidin-2-yl)amino)-3-fluoro-N-methylbenzamide | 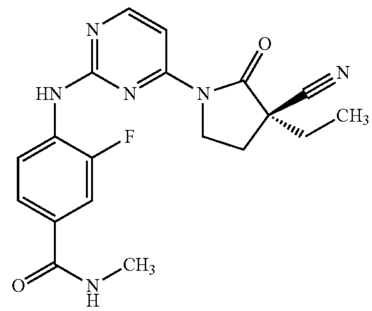 [SMILES: CC[C@]1(C#N)CCN(c2ccnc(Nc3ccc(C(=O)NC)cc3F)n2)C1=O] | Free | 383.1 |
| 230 | 4-((4-((3R)-3-cyano-3-ethyl-2-oxopyrrolidin-1-yl)pyrimidin-2-yl)amino)-2-fluoro-N-methylbenzamide | 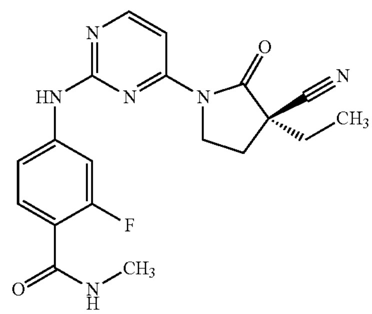 [SMILES: CC[C@]1(C#N)CCN(c2ccnc(Nc3ccc(C(=O)NC)c(F)c3)n2)C1=O] | Free | 383.0 |
| 231 | 4-((4-((3R)-3-cyano-3-ethyl-2-oxopyrrolidin-1-yl)pyrimidin-2-yl)amino)benzoic acid | 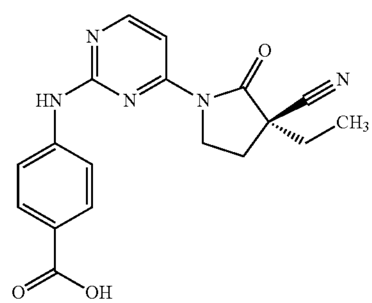 [SMILES: CC[C@]1(C#N)CCN(c2ccnc(Nc3ccc(C(=O)O)cc3)n2)C1=O] | HCl | 352.3 |
| 232 | 1-(4-((4-((3R)-3-cyano-3-ethyl-2-oxopyrrolidin-1-yl)pyrimidin-2-yl)amino)phenyl)cyclopropanecarboxylic acid | 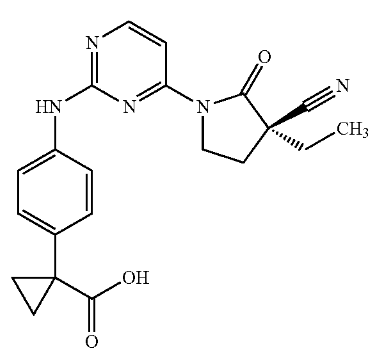 [SMILES: CC[C@]1(C#N)CCN(c2ccnc(Nc3ccc(C4(C(=O)O)CC4)cc3)n2)C1=O] | HCl | 392.3 |

TABLE 18-continued

| Example Number | IUPAC Name | Structure | Salt | MS |
|---|---|---|---|---|
| 233 | 2-(4-((4-((3R)-3-cyano-3-ethyl-2-oxopyrrolidin-1-yl)pyrimidin-2-yl)amino)phenyl)acetamide | 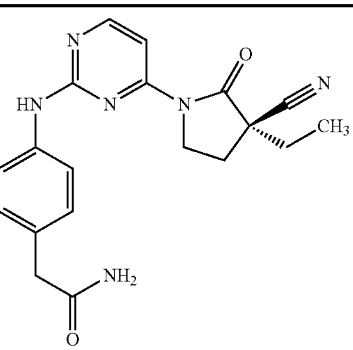 | Free | 365.3 |
| 234 | 2-(4-((4-((3R)-3-cyano-3-ethyl-2-oxopyrrolidin-1-yl)pyrimidin-2-yl)amino)phenyl)-N-methylacetamide | 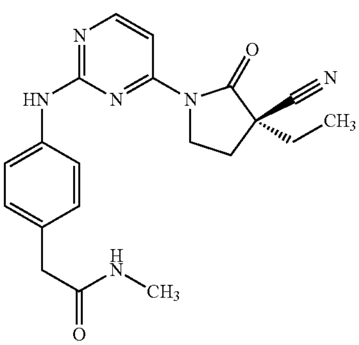 [SMILES: CC[C@]1(C#N)CCN(c2ccnc(Nc3ccc(CC(=O)NC)cc3)n2)C1=O] | Free | 379.3 |

Example 235

N-(1-cyanocyclopropyl)-4-((4-((3R)-3-cyano-3-ethyl-2-oxopyrrolidin-1-yl) pyrimidin-2-yl)amino) benzamide

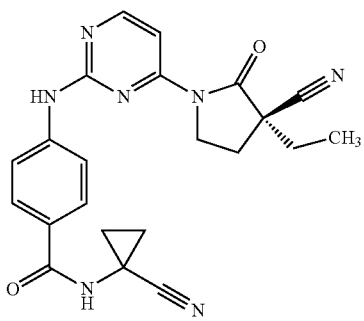 [SMILES: CC[C@]1(C#N)CCN(c2ccnc(Nc3ccc(C(=O)NC4(C#N)CC4)cc3)n2)C1=O]

To a solution of 4-((4-((3R)-3-cyano-3-ethyl-2-oxopyrrolidin-1-yl)pyrimidin-2-yl)amino)benzoic acid (100 mg) obtained in Example 231 in N,N-dimethylformamide (2.0 mL) were added 1-aminocyclopropanecarbonitrile hydrochloride (31 mg), 1-ethyl-3-(3-dimethylaminopropyl)carbodiimide (46 mg), 1-hydroxybenzotriazole (40 mg) and triethylamine (56 µL), and the mixture was stirred overnight at room temperature. To the reaction mixture was added saturated aqueous sodium hydrogen carbonate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (38 mg).

MS(ESI+): [M+H]$^+$ 416.3.

Examples 236 to 247

The title compound was obtained from 4-((4-((3R)-3-cyano-3-ethyl-2-oxopyrrolidin-1-yl)pyrimidin-2-yl)amino) benzoic acid obtained in Example 231 and each corresponding amine (these compounds can be produced according to a method known per se), in the same manner as in Example 235.

TABLE 19-1

| Example Number | IUPAC Name | Structure | Salt | MS |
|---|---|---|---|---|
| 236 | 4-((4-((3R)-3-cyano-3-ethyl-2-oxopyrrolidin-1-yl)pyrimidin-2-yl)amino)-N-(oxetan-3-yl)benzamide | 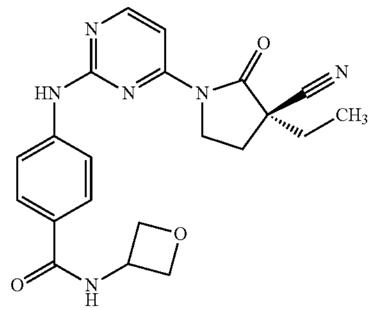 | Free | 407.4 |
| 237 | 4-((4-((3R)-3-cyano-3-ethyl-2-oxopyrrolidin-1-yl)pyrimidin-2-yl)amino)-N-((3-methyloxetan-3-yl)methyl)benzamide | 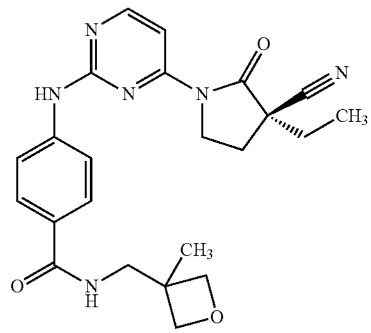 [SMILES: CC[C@]1(C#N)CCN(c2ccnc(Nc3ccc(C(=O)NCC4(C)COC4)cc3)n2)C1=O] | Free | 435.4 |
| 238 | (3R)-3-ethyl-1-(2-((4-(morpholin-4-ylcarbonyl)phenyl)amino)pyrimidin-4-yl)-2-oxopyrrolidine-3-carbonitrile | 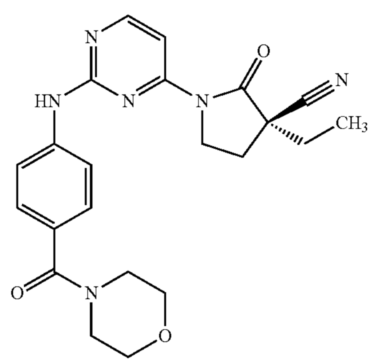 [SMILES: CC[C@]1(C#N)CCN(c2ccnc(Nc3ccc(C(=O)N4CCOCC4)cc3)n2)C1=O] | HCl | 421.3 |
| 239 | (3R)-3-ethyl-1-(2-((4-((4-hydroxypiperidin-1-yl)carbonyl)phenyl)amino)pyrimidin-4-yl)-2-oxopyrrolidine-3-carbonitrile | 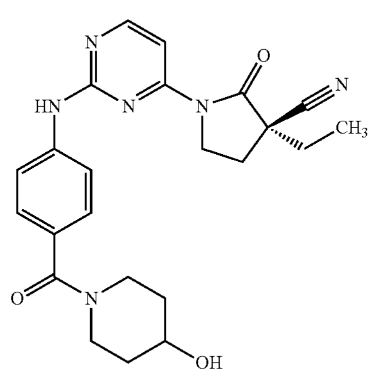 [SMILES: CC[C@]1(C#N)CCN(c2ccnc(Nc3ccc(C(=O)N4CCC(O)CC4)cc3)n2)C1=O] | HCl | 435.3 |

TABLE 19-1-continued

| Example Number | IUPAC Name | Structure | Salt | MS |
|---|---|---|---|---|
| 240 | (3R)-3-ethyl-1-(2-((4-(((3R)-3-hydroxypyrrolidin-1-yl)carbonyl)phenyl)amino)pyrimidin-4-yl)-2-oxopyrrolidine-3-carbonitrile | 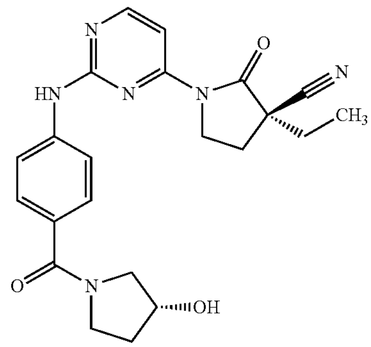 [SMILES: CC[C@]1(C#N)CCN(c2ccnc(Nc3ccc(C(=O)N4CC[C@@H](O)C4)cc3)n2)C1=O] | Free | 419.3 (M − H) |
| 241 | (3R)-3-ethyl-1-(2-((4-(((3S)-3-hydroxypyrrolidin-1-yl)carbonyl)phenyl)amino)pyrimidin-4-yl)-2-oxopyrrolidine-3-carbonitrile | 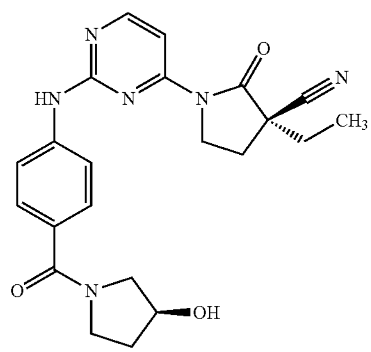 [SMILES: CC[C@]1(C#N)CCN(c2ccnc(Nc3ccc(C(=O)N4CC[C@H](O)C4)cc3)n2)C1=O] | Free | 419.4 (M − H) |
| 242 | 4-((4-((3R)-3-cyano-3-ethyl-2-oxopyrrolidin-1-yl)pyrimidin-2-yl)amino)-N-cyclobutylbenzamide | 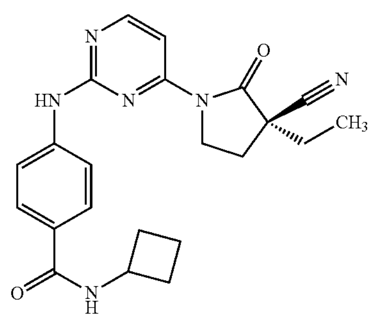 [SMILES: CC[C@]1(C#N)CCN(c2ccnc(Nc3ccc(C(=O)NC4CCC4)cc3)n2)C1=O] | Free | 406.3 |
| 243 | 4-((4-((3R)-3-cyano-3-ethyl-2-oxopyrrolidin-1-yl)pyrimidin-2-yl)amino)-N-methyl-N-(2-(methylsulfonyl)ethyl)benzamide | 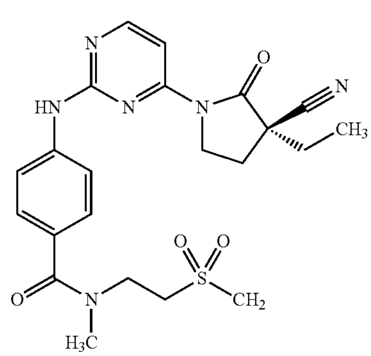 [SMILES: CC[C@]1(C#N)CCN(c2ccnc(Nc3ccc(C(=O)N(C)CCS(C)(=O)=O)cc3)n2)C1=O] | Free | 471.4 |

TABLE 19-2

| Example Number | IUPAC Name | Structure | Salt | MS |
|---|---|---|---|---|
| 244 | 4-((4-((3R)-3-cyano-3-ethyl-2-oxopyrrolidin-1-yl)pyrimidin-2-yl)amino)-N-(2-(methylsulfonyl)ethyl)benzamide | 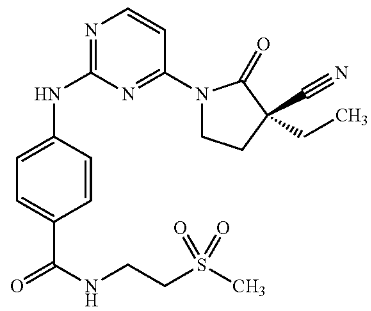 [SMILES: CC[C@]1(C#N)CCN(c2ccnc(Nc3ccc(C(=O)NCCS(C)(=O)=O)cc3)n2)C1=O] | Free | 457.1 |
| 245 | (3R)-4-((4-(3-cyano-3-ethyl-2-oxopyrrolidin-1-yl)pyrimidin-2-yl)amino)-N-(1-hydroxy-2-methylpropan-2-yl)benzamide | 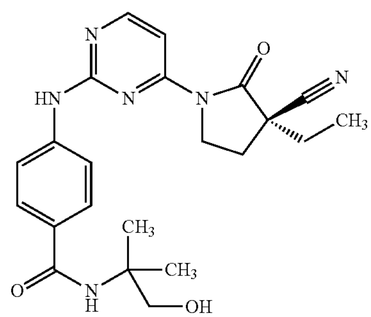 [SMILES: CC[C@]1(C#N)CCN(c2ccnc(Nc3ccc(C(=O)NC(C)(C)CO)cc3)n2)C1=O] | Free | 423.1 |
| 246 | 4-((4-((3R)-3-cyano-3-ethyl-2-oxopyrrolidin-1-yl)pyrimidin-2-yl)amino)-N-(2-methyl-1-(morpholin-4-yl)propan-2-yl)benzamide | 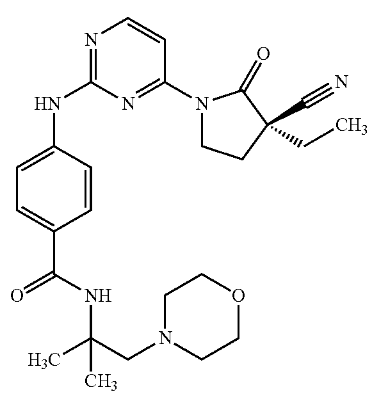 [SMILES: CC[C@]1(C#N)CCN(c2ccnc(Nc3ccc(C(=O)NC(C)(C)CN4CCOCC4)cc3)n2)C1=O] | Free | 492.2 |
| 247 | 4-((4-((3R)-3-cyano-3-ethyl-2-oxopyrrolidin-1-yl)pyrimidin-2-yl)amino)-N-(tetrahydro-2H-pyran-4-yl)benzamide | 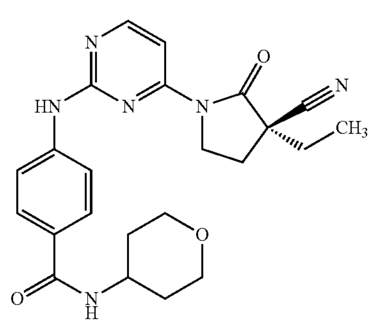 [SMILES: CC[C@]1(C#N)CCN(c2ccnc(Nc3ccc(C(=O)NC4CCOCC4)cc3)n2)C1=O] | Free | 435.3 |

Example 248

(3R)-3-ethyl-1-(2-((4-(4-hydroxytetrahydro-2H-pyran-4-yl)phenyl)amino)pyrimidin-4-yl)-2-oxopyrrolidine-3-carbonitrile

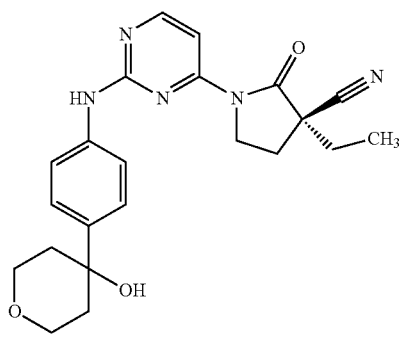 [SMILES: CC[C@]1(C#N)CCN(c2ccnc(Nc3ccc(C4(O)CCOCC4)cc3)n2)C1=O]

A) tert-butyl(4-(4-hydroxytetrahydro-2H-pyran-4-yl)phenyl)carbamate

To a solution of tert-butyl(4-bromophenyl)carbamate (1.5 g) in tetrahydrofuran (30 mL) was added dropwise n-butyllithium (1.6 M hexane solution, 7.2 mL) at −78° C. under nitrogen atmosphere, and the mixture was stirred at the same temperature for 1 hr. Dihydro-2H-pyran-4(3H)-one (0.58 g) was added thereto, and the mixture was stirred overnight while it was allowed to be warmed. To the reaction mixture was added saturated aqueous ammonium chloride solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (590 mg).

$^1$H NMR (400 MHz, CDCl$_3$) δ1.52 (9H, s), 1.65-1.73 (2H, m), 2.09-2.22 (2H, m), 3.82-3.99 (4H, m), 6.48 (1H, br. s), 7.32-7.39 (2H, m), 7.39-7.45 (2H, m).

B) (3R)-3-ethyl-1-(2-((4-(4-hydroxytetrahydro-2H-pyran-4-yl)phenyl)amino)pyrimidin-4-yl)-2-oxopyrrolidine-3-carbonitrile The title compound (53 mg) was obtained from (3R)-1-(2-chloropyrimidin-4-yl)-3-ethyl-2-oxopyrrolidine-3-carbonitrile (80 mg) obtained in Step A of Example 8 and tert-butyl (4-(4-hydroxytetrahydro-2H-pyran-4-yl)phenyl)carbamate (110 mg) obtained in Step A of Example 248 in the same manner as in Step B of Example 2.

$^1$H NMR (400 MHz, DMSO-d$_6$) δ1.02-1.15 (3H, m), 1.84-2.08 (2H, m), 2.28-2.47 (5H, m), 2.56-2.72 (1H, m), 3.76-3.87 (2H, m), 4.01-4.17 (2H, m), 4.19-4.26 (2H, m), 6.17 (1H, s), 7.32-7.47 (2H, m), 7.57-7.64 (1H, m), 7.67-7.79 (2H, m), 8.39-8.49 (1H, m), 9.73 (1H, s).

Example 249

(3R)-1-(2-((4-(4-cyanotetrahydro-2H-pyran-4-yl)phenyl)amino)pyrimidin-4-yl)-3-ethyl-2-oxopyrrolidine-3-carbonitrile

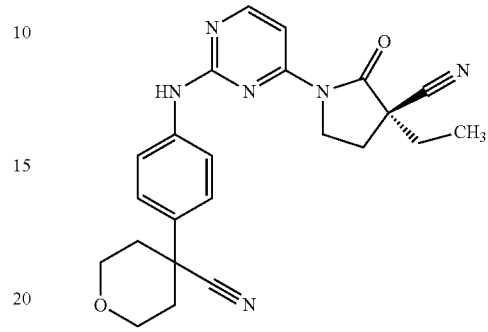

A) 4-(4-bromophenyl)tetrahydro-2H-pyran-4-carbonitrile

To a solution of 2-(4-bromophenyl)acetonitrile (3.9 g) in tetrahydrofuran (50 mL) was added potassium t-butoxide (4.9 g) in an ice bath, and the mixture was stirred for 1 hr in an ice bath. 1-Bromo-2-(2-bromoethoxy)ethane (5.8 g) was added thereto at the same temperature, and the mixture was stirred at room temperature for 10 hr. The solvent was evaporated under reduced pressure, and the residue was purified by silica gel column chromatography (hexane/ethyl acetate) to give the title compound (3.7 g).

$^1$H NMR (400 MHz, CDCl$_3$) δ1.99-2.15 (4H, m), 3.83-3.95 (2H, m), 4.04-4.14 (2H, m), 7.33-7.40 (2H, m), 7.51-7.60 (2H, m).

B) 4-(4-aminophenyl)tetrahydro-2H-pyran-4-carbonitrile

To a solution of 4-(4-bromophenyl)tetrahydro-2H-pyran-4-carbonitrile (1.7 g) obtained in Step A of Example 249, diphenylmethanimine (1.4 g), tris(dibenzylideneacetone)dipalladium(0) (88 mg) and 2,2'-bis(diphenylphosphino)-1,1'-binaphthyl (130 mg) in toluene (50 mL) was added sodium 2-methylpropan-2-olate (921 mg), and the mixture was stirred at 90° C. for 10 hr under nitrogen atmosphere. The reaction mixture was diluted with ethyl acetate, the insoluble substance was removed by filtration through Celite, and the solvent was evaporated under reduced pressure. To a solution of the residue in methanol (10 mL) were added hydroxylamine hydrochloride (440 mg) and sodium acetate (530 mg). The mixture was stirred at room temperature for 30 min, and 0.1 M aqueous sodium hydroxide solution and ethyl acetate were added thereto. The solvent was evaporated under reduced pressure, the reaction mixture was poured into water, and the reaction mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (910 mg).

MS(ESI+): [M+H]$^+$ 202.9.

C) (3R)-1-(2-((4-(4-cyanotetrahydro-2H-pyran-4-yl)phenyl)amino)pyrimidin-4-yl)-3-ethyl-2-oxopyrrolidine-3-carbonitrile The title compound (140 mg) was obtained from (3R)-1-(2-chloropyrimidin-4-yl)-3-ethyl-2-oxopyrrolidine-3-carbonitrile (100 mg) obtained in Step A of Example 8 and 4-(4-aminophenyl)tetrahydro-2H-pyran-4-carbonitrile (81 mg) obtained in Step B of Example 249 in the same manner as in Step B of Example 2.

MS(ESI+): [M+H]$^+$ 417.1.

Example 250

4-((4-((3R)-3-cyano-3-ethyl-2-oxopyrrolidin-1-yl)pyrimidin-2-yl)amino)-2-ethoxybenzoic acid hydrochloride

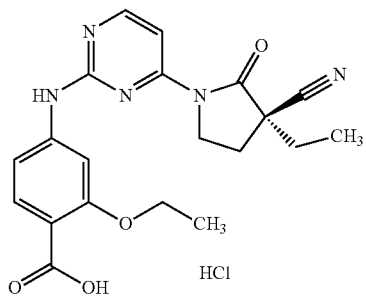 [SMILES: CCOc1cc(Nc2nccc(N3CC[C@@](C#N)(CC)C3=O)n2)ccc1C(=O)O ; Cl]

A) tert-butyl 4-((4-((3R)-3-cyano-3-ethyl-2-oxopyrrolidin-1-yl) pyrimidin-2-yl)amino)-2-ethoxybenzoate The title compound (120 mg) was obtained from (3R)-1-(2-chloropyrimidin-4-yl)-3-ethyl-2-oxopyrrolidine-3-carbonitrile (100 mg) obtained in Step A of Example 8 and tert-butyl 4-amino-2-ethoxybenzoate (110 mg) obtained in Step C of Example 139 in the same manner as in Example 56.

MS(ESI+): [M+H]$^+$ 452.2.

B) 4-((4-((3R)-3-cyano-3-ethyl-2-oxopyrrolidin-1-yl)pyrimidin-2-yl)amino)-2-ethoxybenzoic acid hydrochloride To tert-butyl 4-((4-((3R)-3-cyano-3-ethyl-2-oxopyrrolidin-1-yl)pyrimidin-2-yl)amino)-2-ethoxybenzoate (120 mg) obtained in Step A of Example 250 was added a solution of 4 M hydrogen chloride in ethyl acetate (6.0 mL), and the mixture was stirred at room temperature for 2 hr. The reaction mixture was concentrated under reduced pressure. The residue was washed with ethyl acetate to give the title compound (90 mg).

MS(ESI+): [M+H]$^+$ 396.3.

Example 251

4-((4-((3R)-3-cyano-3-ethyl-2-oxopyrrolidin-1-yl)pyrimidin-2-yl)amino)-2-isopropoxybenzoic acid hydrochloride

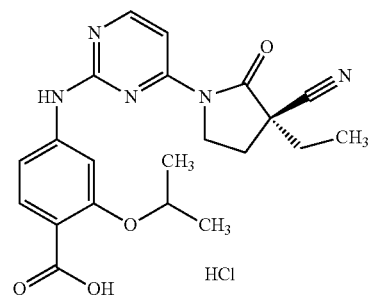 [SMILES: CC[C@]1(C#N)CCN(c2ccnc(Nc3ccc(C(=O)O)c(OC(C)C)c3)n2)C1=O ; Cl]

A) tert-butyl 4-((4-((3R)-3-cyano-3-ethyl-2-oxopyrrolidin-1-yl)pyrimidin-2-yl)amino)-2-isopropoxybenzoate The title compound (99 mg) was obtained from (3R)-1-(2-chloropyrimidin-4-yl)-3-ethyl-2-oxopyrrolidine-3-carbonitrile (100 mg) obtained in Step A of Example 8 and tert-butyl 4-amino-2-isopropoxybenzoate (120 mg) obtained in Step B of Example 141 in the same manner as in Example 56.

MS(ESI+): [M+H]$^+$ 466.4.

B) 4-((4-((3R)-3-cyano-3-ethyl-2-oxopyrrolidin-1-yl)pyrimidin-2-yl)amino)-2-isopropoxybenzoic acid hydrochloride The title compound (78 mg) was obtained from tert-butyl 4-((4-((3R)-3-cyano-3-ethyl-2-oxopyrrolidin-1-yl)pyrimidin-2-yl)amino)-2-isopropoxybenzoate (120 mg) obtained in Step A of Example 251 in the same manner as in Step B of Example 250.

MS(ESI+): [M+H]$^+$ 410.3.

Example 252

1-(4-((4-((3R)-3-cyano-3-ethyl-2-oxopyrrolidin-1-yl)pyrimidin-2-yl)amino)phenyl)cyclopropanecarboxamide

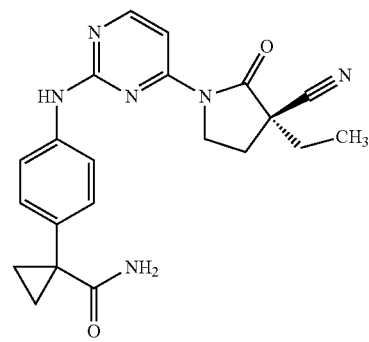 [SMILES: CC[C@]1(C#N)CCN(c2ccnc(Nc3ccc(C4(C(N)=O)CC4)cc3)n2)C1=O]

The title compound (67 mg) was obtained from 1-(4-((4-((3R)-3-cyano-3-ethyl-2-oxopyrrolidin-1-yl)pyrimidin-2-yl)amino)phenyl)cyclopropanecarboxylic acid hydrochloride (90 mg) obtained in Example 232 in the same manner as in Example 235.

MS(ESI+): [M+H]$^+$ 391.3.

Example 253

1-(4-((4-((3R)-3-cyano-3-ethyl-2-oxopyrrolidin-1-yl)pyrimidin-2-yl)amino)phenyl)-N-methylcyclopropanecarboxamide

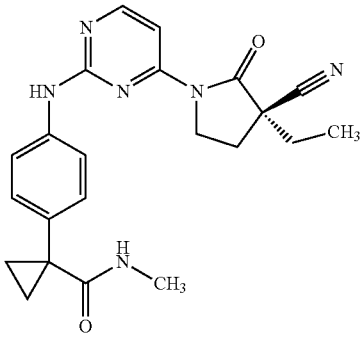 [SMILES: CC[C@]1(C#N)CCN(c2ccnc(Nc3ccc(C4(C(=O)NC)CC4)cc3)n2)C1=O]

The title compound (60 mg) was obtained from 1-(4-((4-((3R)-3-cyano-3-ethyl-2-oxopyrrolidin-1-yl)pyrimidin-2-yl)amino)phenyl)cyclopropanecarboxylic acid hydrochloride (90 mg) obtained in Example 232 and methylamine hydrochloride (18 mg) in the same manner as in Example 235.
MS(ESI+): [M+H]⁺ 405.4.

Example 254

4-((4-((3R)-3-cyano-3-ethyl-2-oxopyrrolidin-1-yl)pyrimidin-2-yl)amino)-2-ethoxybenzamide

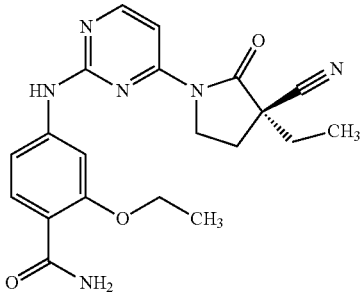 [SMILES: CCOc1cc(Nc2nccc(N3CC[C@@](C#N)(CC)C3=O)n2)ccc1C(N)=O]

The title compound (60 mg) was obtained from (3R)-1-(2-chloropyrimidin-4-yl)-3-ethyl-2-oxopyrrolidine-3-carbonitrile (70 mg) obtained in Step A of Example 8 and 4-amino-2-ethoxybenzamide (60 mg) in the same manner as in Step B of Example 2.
MS(ESI+): [M+H]⁺ 395.3.

Example 255

(3R)-3-ethyl-1-(2-((4-(4-(hydroxymethyl)tetrahydro-2H-pyran-4-yl)phenyl)amino)pyrimidin-4-yl)-2-oxopyrrolidine-3-carbonitrile

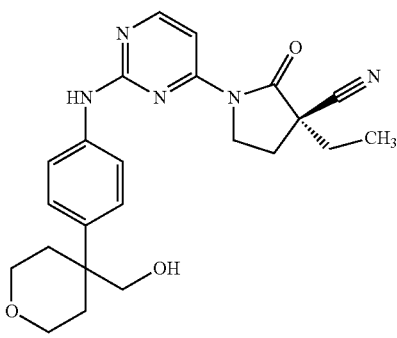 [SMILES: CC[C@]1(C#N)CCN(c2ccnc(Nc3ccc(C4(CO)CCOCC4)cc3)n2)C1=O]

To a solution of (3R)-1-(2-chloropyrimidin-4-yl)-3-ethyl-2-oxopyrrolidine-3-carbonitrile (100 mg) obtained in Step A of Example 8 in ethanol (3.0 mL) were added (4-(4-aminophenyl)tetrahydro-2H-pyran-4-yl)methanol (83 mg) obtained in Step B of Example 152 and acetic acid (25 μL), and the mixture was stirred in a microwave reactor at 150° C. for 1 hr. The reaction mixture was concentrated under reduced pressure, and the residue was purified by silica gel column chromatography (hexane/ethyl acetate), and recrystallized (hexane/ethyl acetate) to give the title compound (100 mg).
¹H NMR (400 MHz, DMSO-d₆) δ 1.08 (3H, t, J=7.5 Hz), 1.77-2.10 (6H, m), 2.29-2.41 (1H, m), 2.56-2.72 (1H, m), 3.34-3.42 (4H, m), 3.62-3.75 (2H, m), 3.98-4.24 (2H, m), 4.54-4.63 (1H, m), 7.26 (2H, d, J=8.8 Hz), 7.59 (1H, d, J=5.6 Hz), 7.69 (2H, d, J=9.0 Hz), 8.41 (1H, d, J=5.6 Hz), 9.62 (1H, s).
MS(ESI+): [M+H]⁺ 422.3.

Example 256

4-(4-((4-((3R)-3-cyano-3-ethyl-2-oxopyrrolidin-1-yl)pyrimidin-2-yl)amino)phenyl)-N-methyltetrahydro-2H-pyran-4-carboxamide

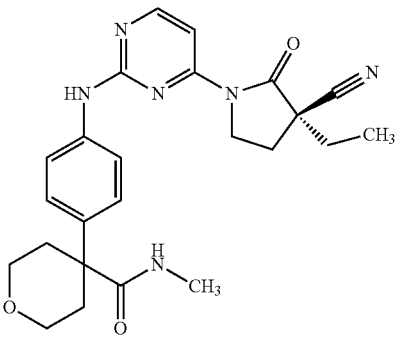 [SMILES: CC[C@]1(C#N)CCN(c2ccnc(Nc3ccc(C4(C(=O)NC)CCOCC4)cc3)n2)C1=O]

The title compound (170 mg) was obtained from (3R)-1-(2-chloropyrimidin-4-yl)-3-ethyl-2-oxopyrrolidine-3-carbonitrile (150 mg) obtained in Step A of Example 8 and 4-(4-aminophenyl)-N-methyltetrahydro-2H-pyran-4-carboxamide (140 mg) obtained in Step D of Example 151 in the same manner as in Step B of Example 2.
MS(ESI+): [M+H]⁺ 449.4.

Example 257

2-(5-((4-(3R)-3-cyano-3-ethyl-2-oxopyrrolidin-1-yl)pyrimidin-2-yl)amino)pyridin-2-yl)-2-methylpropanamide

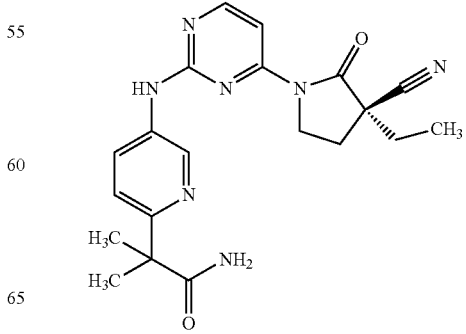

The title compound (25 mg) was obtained from (3R)-1-(2-chloropyrimidin-4-yl)-3-ethyl-2-oxopyrrolidine-3-carbonitrile (70 mg) obtained in Step A of Example 8 and 2-(5-aminopyridin-2-yl)-2-methylpropanamide (50 mg) obtained in Step F of Example 153 in the same manner as in Example 56.

MS(ESI+): [M+H]$^+$ 394.3.

Examples 258 to 265

The title compound was obtained from (3S)-1-(2-chloropyrimidin-4-yl)-3-isopropyl-2-oxopyrrolidine-3-carbonitrile obtained in Step A of Example 9 and each corresponding amine (these compounds can be produced according to a method known per se), in the same manner as in Step B of Example 2. MS in the tables means actual measured value.

TABLE 20

| Example Number | IUPAC Name. | Structure | Salt | MS |
| --- | --- | --- | --- | --- |
| 258 | (4-((4-((3S)-3-cyano-3-isopropyl-2-oxopyrrolidin-1-yl)pyrimidin-2-yl)amino)-1H-pyrazol-1-yl)acetic acid | 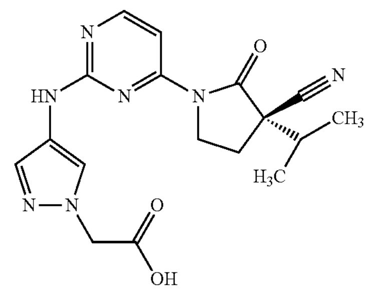 [SMILES: CC(C)[C@]1(C#N)CCN(c2ccnc(Nc3cnn(CC(=O)O)c3)n2)C1=O] | HCl | 370.3 |
| 259 | (3S)-1-(2-((1-ethyl-1H-pyrazol-4-yl)amino)pyrimidin-4-yl)-3-isopropyl-2-oxopyrrolidine-3-carbonitrile | 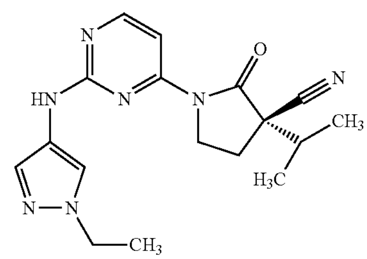 [SMILES: CCn1cc(Nc2nccc(N3CC[C@@](C#N)(C(C)C)C3=O)n2)cn1] | HCl | 340.3 |
| 260 | (3S)-3-isopropyl-2-oxo-1-(2-((1-(2,2,2-trifluoroethyl)-1H-pyrazol-4-yl)amino)pyrimidin-4-yl)pyrrolidine-3-carbonitrile | 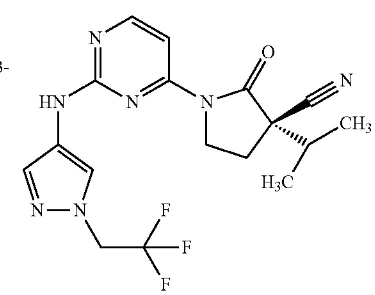 | HCl | 394.3 |
| 261 | (3S)-1-(2-((1-(2-hydroxyethyl)-1H-pyrazol-4-yl)amino)pyrimidin-4-yl)-3-isopropyl-2-oxopyrrolidine-3-carbonitrile | 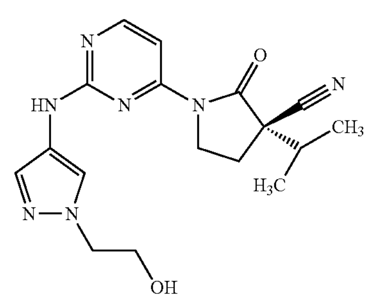 [SMILES: CC(C)[C@]1(C#N)CCN(c2ccnc(Nc3cnn(CCO)c3)n2)C1=O] | HCl | 354.3 |

TABLE 20-continued

| Example Number | IUPAC Name | Structure | Salt | MS |
|---|---|---|---|---|
| 262 | (3S)-3-isopropyl-1-(2-((1-isopropyl-1H-pyrazol-4-yl)amino)pyrimidin-4-yl)-2-oxopyrrolidine-3-carbonitrile | 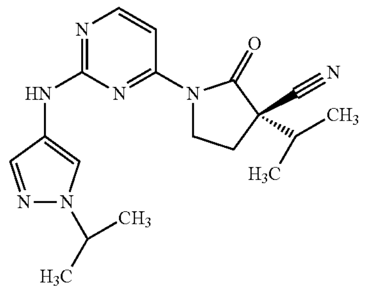 [SMILES: CC(C)n1cc(Nc2nccc(N3CC[C@@](C#N)(C(C)C)C3=O)n2)cn1] | HCl | 342.2 |
| 263 | 3-(4-((4-((3S)-3-cyano-3-isopropyl-2-oxopyrrolidin-1-yl)pyrimidin-2-yl)amino)-1H-pyrazol-1-yl)propanamide | 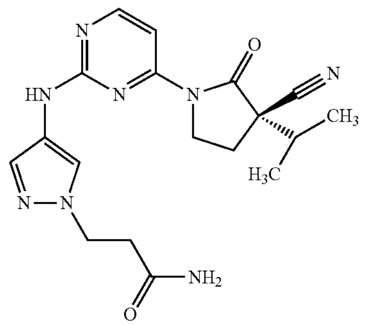 [SMILES: CC(C)[C@]1(C#N)CCN(c2ccnc(Nc3cnn(CCC(N)=O)c3)n2)C1=O] | HCl | 383.3 |
| 264 | 3-(4-((4-((3S)-3-cyano-3-isopropyl-2-oxopyrrolidin-1-yl)pyrimidin-2-yl)amino)-1H-pyrazol-1-yl)-N-methylpropanamide | 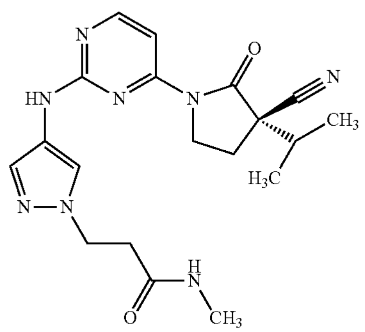 [SMILES: CNC(=O)CCn1cc(Nc2nccc(N3CC[C@@](C#N)(C(C)C)C3=O)n2)cn1] | HCl | 397.3 |
| 265 | 3-(4-((4-((3S)-3-cyano-3-isopropyl-2-oxopyrrolidin-1-yl)pyrimidin-2-yl)amino)-1H-pyrazol-1-yl)-N,N-dimethylpropanamide | 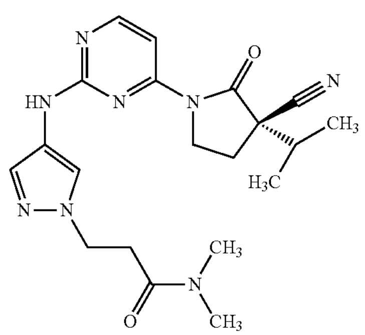 [SMILES: CC(C)[C@]1(C#N)CCN(c2ccnc(Nc3cnn(CCC(=O)N(C)C)c3)n2)C1=O] | HCl | 411.4 |

Examples 266 to 270

The title compound was obtained from (3S)-1-(2-chloropyrimidin-4-yl)-3-isopropyl-2-oxopyrrolidine-3-carbonitrile obtained in Step A of Example 9 and each corresponding amine (these compounds can be produced according to a method known per se), in the same manner as in Example 56. MS in the tables means actual measured value.

TABLE 21

| Example Number | IUPAC Name | Structure | Salt | MS |
|---|---|---|---|---|
| 266 | (3S)-1-(2-((1-(2-hydroxy-2-methylpropyl)-1H-pyrazol-4-yl)amino)pyrimidin-4-yl)-3-isopropyl-2-oxopyrrolidine-3-carbonitrile | 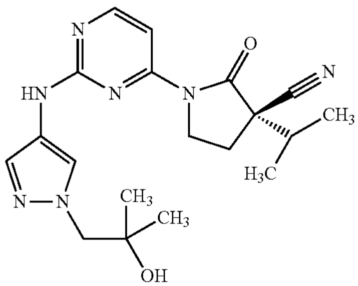 [SMILES: CC(C)[C@]1(C#N)CCN(c2ccnc(Nc3cnn(CC(C)(C)O)c3)n2)C1=O] | HCl | 384.3 |
| 267 | (3S)-1-(2-((1-(difluoromethyl)-1H-pyrazol-4-yl)amino)pyrimidin-4-yl)-3-isopropyl-2-oxopyrrolidine-3-carbonitrile | 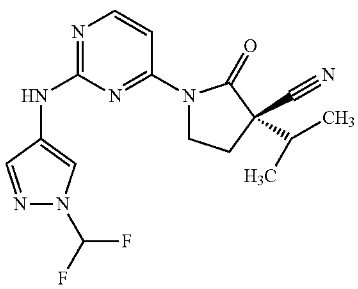 [SMILES: CC(C)[C@]1(C#N)CCN(c2ccnc(Nc3cnn(C(F)F)c3)n2)C1=O] | HCl | 362.3 |
| 268 | 2-(4-((4-((3S)-3-cyano-3-isopropyl-2-oxopyrrolidin-1-yl)pyrimidin-2-yl)amino)-1H-pyrazol-1-yl)-2-methylpropanamide | 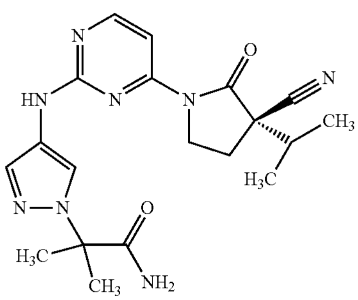 [SMILES: CC(C)[C@]1(C#N)CCN(c2ccnc(Nc3cnn(C(C)(C)C(N)=O)c3)n2)C1=O] | HCl | 397.3 |
| 269 | 2-(4-((4-((3S)-3-cyano-3-isopropyl-2-oxopyrrolidin-1-yl)pyrimidin-2-yl)amino)-1H-pyrazol-1-yl)-N,2-dimethylpropanamide | 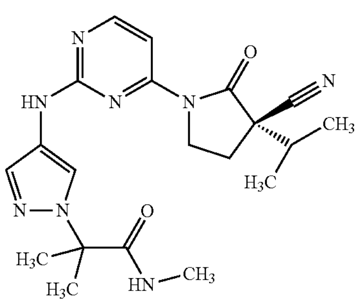 [SMILES: CNC(=O)C(C)(C)n1cc(Nc2nccc(N3CC[C@@](C#N)(C(C)C)C3=O)n2)cn1] | HCl | 411.3 |
| 270 | 2-(4-((4-((3S)-3-cyano-3-isopropyl-2-oxopyrrolidin-1-yl)pyrimidin-2-yl)amino)-1H-pyrazol-1-yl)-N,N,2-trimethylpropanamide | 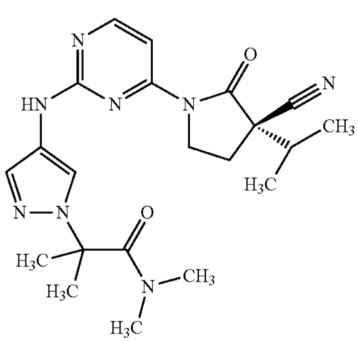 [SMILES: CC(C)[C@]1(C#N)CCN(c2ccnc(Nc3cnn(C(C)(C)C(=O)N(C)C)c3)n2)C1=O] | HCl | 425.4 |

Example 271

(3S)-1-(2-((1-(1-acetylazetidin-3-yl)-1H-pyrazol-4-yl)amino)pyrimidin-4-yl)-3-isopropyl-2-oxopyrrolidine-3-carbonitrile hydrochloride

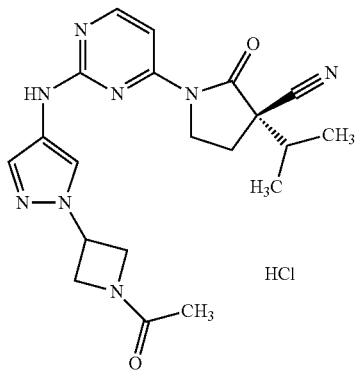 [SMILES: CC(=O)N1CC(n2cc(Nc3nccc(N4CC[C@@](C#N)(C(C)C)C4=O)n3)cn2)C1 ; Cl]

A) tert-butyl 3-(4-((4-((3S)-3-cyano-3-isopropyl-2-oxopyrrolidin-1-yl)pyrimidin-2-yl)amino)-1H-pyrazol-1-yl)azetidine-1-carboxylate To a mixture of (3S)-1-(2-chloropyrimidin-4-yl)-3-isopropyl-2-oxopyrrolidine-3-carbonitrile (200 mg) obtained in Step A of Example 9, tert-butyl 3-(4-amino-1H-pyrazol-1-yl)azetidine-1-carboxylate (97 mg) obtained in Step B of Example 131, cesium carbonate (370 mg) and dicyclohexyl(2',4',6'-triisopopropyl-3,6-dimethoxybiphenyl-2-yl)phosphine (57 mg) in tert-butanol (2.0 mL) was added tris(dibenzylideneacetone)dipalladium(0) (48 mg), and the mixture was stirred at 100° C. for 5 hr. The insoluble substance was removed by filtration through Celite, and the solvent was evaporated under reduced pressure. The residue was purified by silica gel column chromatography (hexane/ethyl acetate) to give the title compound (22 mg).
MS(ESI+): [M+H]$^+$ 467.4.

B) (3S)-1-(2-((1-(1-acetylazetidin-3-yl)-1H-pyrazol-4-yl)amino)pyrimidin-4-yl)-3-isopropyl-2-oxopyrrolidine-3-carbonitrile hydrochloride To tert-butyl 3-(4-((4-((3S)-3-cyano-3-isopropyl-2-oxopyrrolidin-1-yl)pyrimidin-2-yl)amino)-1H-pyrazol-1-yl)azetidine-1-carboxylate (22 mg) obtained in Step A of Example 271 was added a solution of 4 M hydrogen chloride in ethyl acetate (1.0 mL), the mixture was stirred at room temperature for 30 min, and the solvent was evaporated under reduced pressure. To a solution of the residue in tetrahydrofuran (1.0 mL) were added triethylamine (20 μL) and acetic anhydride (5.3 μL), and the mixture was stirred at room temperature for 30 min. To the reaction mixture was added water, and the mixture was extracted with ethyl acetate. The obtained organic layer was washed with saturated brine, and dried over anhydrous sodium sulfate, and the solvent was evaporated under reduced pressure. The residue was purified by silica gel column chromatography (ethyl acetate/methanol).
To a solution of the purified product in ethanol (2.0 mL) was added 1 M hydrochloric acid (36 μL), the mixture was stirred at room temperature for 5 min, and the solvent was evaporated under reduced pressure. The residue was recrystallized (diisopropyl ether/ethanol) to give the title compound (13 mg).
MS(ESI+): [M+H]$^+$ 409.4.

Example 272

(3S)-1-(2-((1-(1-acetylpiperidin-4-yl)-1H-pyrazol-4-yl)amino)pyrimidin-4-yl)-3-isopropyl-2-oxopyrrolidine-3-carbonitrile hydrochloride

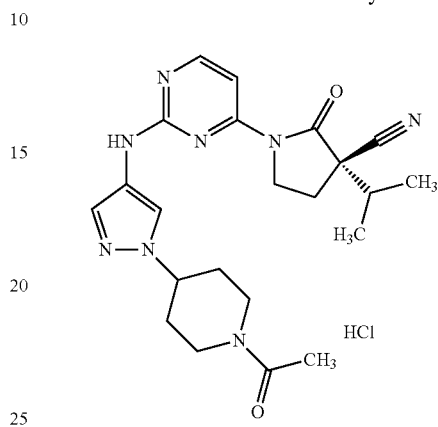

A) tert-butyl 4-(4-((4-((3S)-3-cyano-3-isopropyl-2-oxopyrrolidin-1-yl)pyrimidin-2-yl)amino)-1H-pyrazol-1-yl)piperidine-1-carboxylate The title compound (110 mg) was obtained from (3S)-1-(2-chloropyrimidin-4-yl)-3-isopropyl-2-oxopyrrolidine-3-carbonitrile (140 mg) obtained in Step A of Example 9 and tert-butyl 4-(4-amino-1H-pyrazol-1-yl)piperidine-1-carboxylate (120 mg) in the same manner as in Example 56.
MS(ESI+): [M+H]$^+$ 495.5.

B) (3S)-1-(2-((1-(1-acetylpiperidin-4-yl)-1H-pyrazol-4-yl)amino)pyrimidin-4-yl)-3-isopropyl-2-oxopyrrolidine-3-carbonitrile hydrochloride The title compound (47 mg) was obtained from tert-butyl 4-(4-((4-((3S)-3-cyano-3-isopropyl-2-oxopyrrolidin-1-yl)pyrimidin-2-yl)amino)-1H-pyrazol-1-yl)piperidine-1-carboxylate (110 mg) obtained in Step A of Example 272 in the same manner as in Step B of Example 271.
MS(ESI+): [M+H]$^+$ 437.4.

Example 273

(3S)-1-(2-((1-((3R)-1-acetylpyrrolidin-3-yl)-1H-pyrazol-4-yl)amino)pyrimidin-4-yl)-3-isopropyl-2-oxopyrrolidine-3-carbonitrile hydrochloride

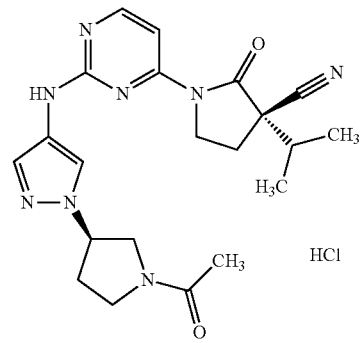 [SMILES: CC(=O)N1CC[C@@H](n2cc(Nc3nccc(N4CC[C@@](C#N)(C(C)C)C4=O)n3)cn2)C1 ; Cl]

245

A) tert-butyl(3R)-3-(4-(4-((4-((3S)-3-cyano-3-isopropyl-2-oxopyrrolidin-1-yl)pyrimidin-2-yl)amino)-1H-pyrazol-1-yl)pyrrolidine-1-carboxylate The title compound (69 mg) was obtained from (3S)-1-(2-chloropyrimidin-4-yl)-3-isopropyl-2-oxopyrrolidine-3-carbonitrile (100 mg) obtained in Step A of Example 9 and tert-butyl(3R)-3-(4-amino-1H-pyrazol-1-yl)pyrrolidine-1-carboxylate (100 mg) in the same manner as in Example 56.
MS(ESI+): [M+H]⁺ 481.5.

B) (3S)-1-(2-((1-((3R)-1-acetylpyrrolidin-3-yl)-1H-pyrazol-4-yl)amino)pyrimidin-4-yl)-3-isopropyl-2-oxopyrrolidine-3-carbonitrile hydrochloride The title compound (47 mg) was obtained from tert-butyl(3R)-3-(4-((4-((3S)-3-cyano-3-isopropyl-2-oxopyrrolidin-1-yl)pyrimidin-2-yl)amino)-1H-pyrazol-1-yl)pyrrolidine-1-carboxylate (69 mg) obtained in Step A of Example 273 in the same manner as in Step B of Example 271.
MS(ESI+): [M+H]⁺ 423.4.

Example 274

(3S)-1-(2-((1-((3S)-1-acetylpyrrolidin-3-yl)-1H-pyrazol-4-yl)amino)pyrimidin-4-yl)-3-isopropyl-2-oxopyrrolidine-3-carbonitrile hydrochloride

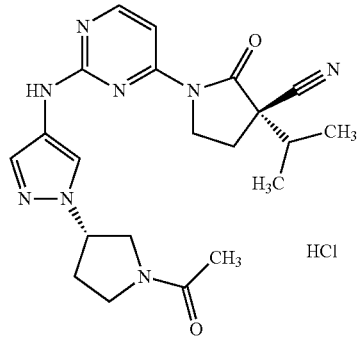 [SMILES: CC(=O)N1CC[C@H](n2cc(Nc3nccc(N4CC[C@@](C#N)(C(C)C)C4=O)n3)cn2)C1 ; Cl]

246

A) tert-butyl(3S)-3-(4-((4-((3S)-3-cyano-3-isopropyl-2-oxopyrrolidin-1-yl)pyrimidin-2-yl)amino)-1H-pyrazol-1-yl) pyrrolidine-1-carboxylate The title compound (70 mg) was obtained from (3S)-1-(2-chloropyrimidin-4-yl)-3-isopropyl-2-oxopyrrolidine-3-carbonitrile (100 mg) obtained in Step A of Example 9 and tert-butyl(3S)-3-(4-amino-1H-pyrazol-1-yl)pyrrolidine-1-carboxylate (100 mg) in the same manner as in Example 56.
MS(ESI+): [M+H]⁺ 481.4.

B) (3S)-1-(2-((1-((3S)-1-acetylpyrrolidin-3-yl)-1H-pyrazol-4-yl)amino)pyrimidin-4-yl)-3-isopropyl-2-oxopyrrolidine-3-carbonitrile hydrochloride The title compound (38 mg) was obtained from tert-butyl (3)-3-(4-((4-((3S)-3-cyano-3-isopropyl-2-oxopyrrolidin-1-yl)pyrimidin-2-yl)amino)-1H-pyrazol-1-yl)pyrrolidine-1-carboxylate (70 mg) obtained in Step A of Example 274 in the same manner as in Step B of Example 271.
MS(ESI+): [M+H]⁺ 423.4.

Examples 275 to 276

The title compound was obtained from (4-((4-((3S)-3-cyano-3-isopropyl-2-oxopyrrolidin-1-yl)pyrimidin-2-yl)amino)-1H-pyrazol-1-yl)acetic acid hydrochloride obtained in Example 258, and morpholine or 4-hydroxypiperidine (these compounds can be produced according to a method known per se), each corresponding to the compounds of Examples 275 and 276, in the same manner as in Example 110.

TABLE 22

| Example Number | IUPAC Name | Structure | Salt | MS |
|---|---|---|---|---|
| 275 | (3S)-3-isopropyl-1-(2-((1-(2-(morpholin-4-yl)-2-oxoethyl)-1H-pyrazol-4-yl)amino)pyrimidin-4-yl)-2-oxopyrrolidine-3-carbonitrile | 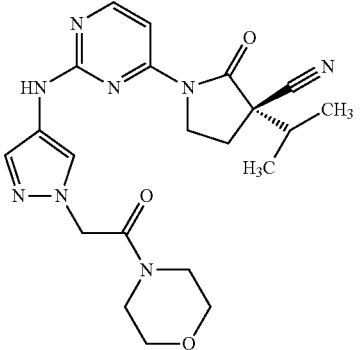 [SMILES: CC(C)[C@]1(C#N)CCN(c2ccnc(Nc3cnn(CC(=O)N4CCOCC4)c3)n2)C1=O] | HCl | 439.4 |

TABLE 22-continued

| Example Number | IUPAC Name | Structure | Salt | MS |
|---|---|---|---|---|
| 276 | (3S)-1-(2-((1-(2-(4-hydroxypiperidin-1-yl)-2-oxoethyl)-1H-pyrazol-4-yl)amino)pyrimidin-4-yl)-3-isopropyl-2-oxopyrrolidine-3-carbonitrile | 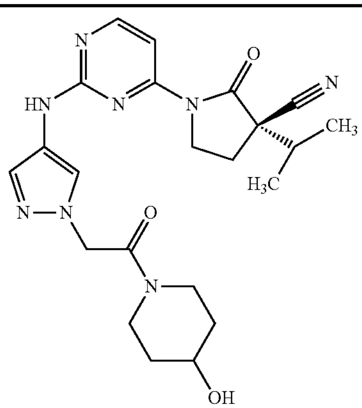 | HCl | 453.4 |

Examples 277-290

The title compound was obtained from (3S)-1-(2-chloropyrimidin-4-yl)-3-isopropyl-2-oxopyrrolidine-3-carbonitrile obtained in Step A of Example 9 and each corresponding amine (these compounds can be produced according to a method known per se), in the same manner as in Step B of Example 2. MS in the tables means actual measured value.

TABLE 23-1

| Example Number | IUPAC Name | Structure | Salt | MS |
|---|---|---|---|---|
| 277 | 4-((4-((3S)-3-cyano-3-isopropyl-2-oxopyrrolidin-1-yl)pyrimidin-2-yl)amino)benzoic acid | 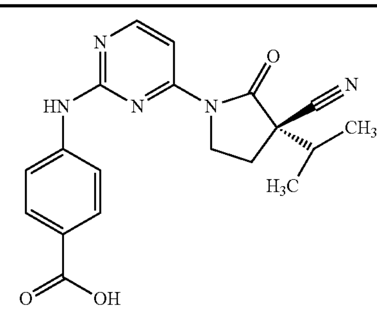 | HCl | 366.3 |
| 278 | ethyl (4-((4-((3S)-3-cyano-3-isopropyl-2-oxopyrrolidin-1-yl)pyrimidin-2-yl)amino)phenyl)acetate | 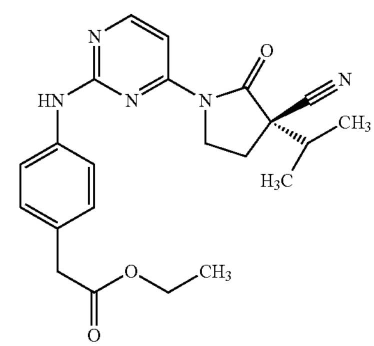 [SMILES: CCOC(=O)Cc1ccc(Nc2nccc(N3CC[C@@](C#N)(C(C)C)C3=O)n2)cc1] | HCl | 408.3 |
| 279 | N-(5-((4-((3S)-3-cyano-3-isopropyl-2-oxopyrrolidin-1-yl)pyrimidin-2-yl)amino)-2-fluorophenyl)acetamide | 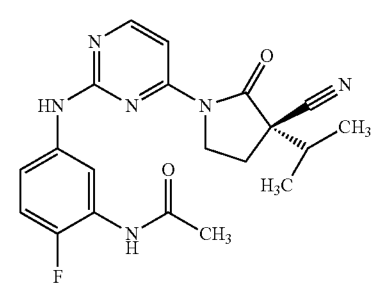 [SMILES: CC(=O)Nc1cc(Nc2nccc(N3CC[C@@](C#N)(C(C)C)C3=O)n2)ccc1F] | HCl | 397.3 |

TABLE 23-1-continued

| Example Number | IUPAC Name | Structure | Salt | MS |
|---|---|---|---|---|
| 280 | 6-((4-((3S)-3-cyano-3-isopropyl-2-oxopyrrolidin-1-yl)pyrimidin-2-yl)amino)-N-methylpyridine-2-carboxamide | 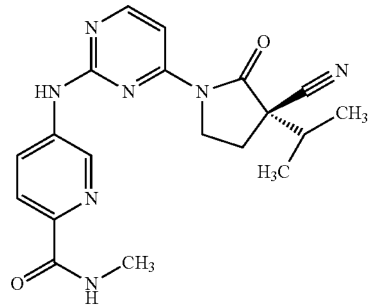 [SMILES: CNC(=O)c1ccc(Nc2nccc(N3CC[C@@](C#N)(C(C)C)C3=O)n2)cn1] | Free | 380.3 |
| 281 | (4-((4-((3S)-3-cyano-3-isopropyl-2-oxopyrrolidin-1-yl)pyrimidin-2-yl)amino)phenyl)acetic acid | 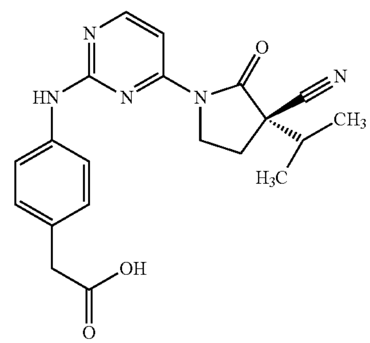 [SMILES: CC(C)[C@]1(C#N)CCN(c2ccnc(Nc3ccc(CC(=O)O)cc3)n2)C1=O] | HCl | 380.3 |
| 282 | (3S)-1-(2-((4-(4-acetylpiperazin-1-yl)phenyl)amino)pyrimidin-4-yl)-3-isopropyl-2-oxopyrrolidin-3-carbonitrile | 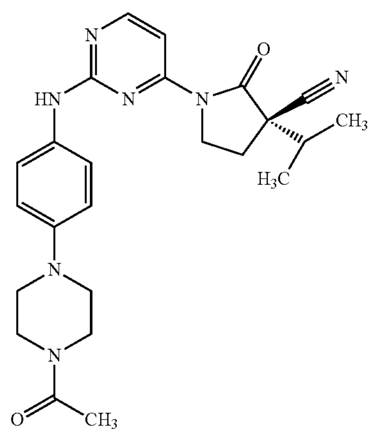 [SMILES: CC(=O)N1CCN(c2ccc(Nc3nccc(N4CC[C@@](C#N)(C(C)C)C4=O)n3)cc2)CC1] | HCl | 448.4 |
| 283 | 2-(3-((4-((3S)-3-cyano-3-isopropyl-2-oxopyrrolidin-1-yl)pyrimidin-2-yl)amino)phenyl)acetamide | 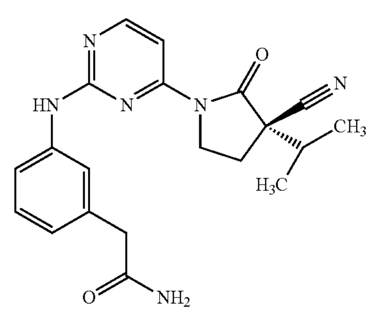 [SMILES: CC(C)[C@]1(C#N)CCN(c2ccnc(Nc3cccc(CC(N)=O)c3)n2)C1=O] | HCl | 379.3 |

TABLE 23-1-continued

| Example Number | IUPAC Name | Structure | Salt | MS |
|---|---|---|---|---|
| 284 | 2-(3-((4-((3S)-3-cyano-3-isopropyl-2-oxopyrrolidin-1-yl)pyrimidin-2-yl)amino)phenyl)-N-methylacetamide | 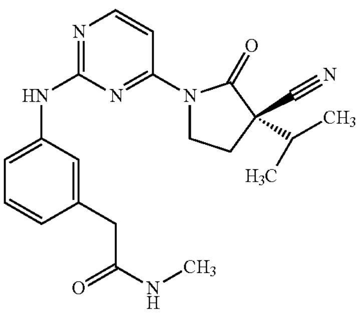 [SMILES: CNC(=O)Cc1cccc(Nc2nccc(N3CC[C@@](C#N)(C(C)C)C3=O)n2)c1] | HCl | 393.3 |

TABLE 23-2

| Example Number | IUPAC Name | Structure | Salt | MS |
|---|---|---|---|---|
| 285 | 2-(3-((4-((3S)-3-cyano-3-isopropyl-2-oxopyrrolidin-1-yl)pyrimidin-2-yl)amino)phenyl)-N,N-dimethylacetamide | 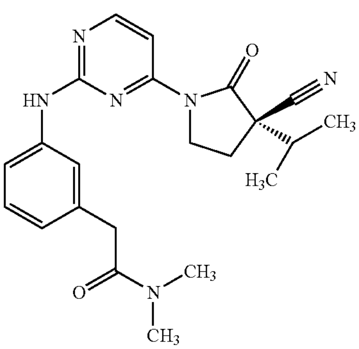 [SMILES: CC(C)[C@]1(C#N)CCN(c2ccnc(Nc3cccc(CC(=O)N(C)C)c3)n2)C1=O] | HCl | 407.3 |
| 287 | N-(5-((4-((3S)-3-cyano-3-isopropyl-2-oxopyrrolidin-1-yl)pyrimidin-2-yl)amino)-2-methoxyphenyl)acetamide | 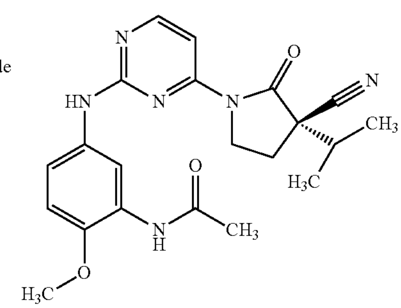 | HCl | 409.3 |
| 289 | (3S)-3-isopropyl-1-(2-((3-methoxy-4-(1H-tetrazol-5-yl)phenyl)amino)pyrimidin-4-yl)-2-oxopyrrolidine-3-carbonitrile | 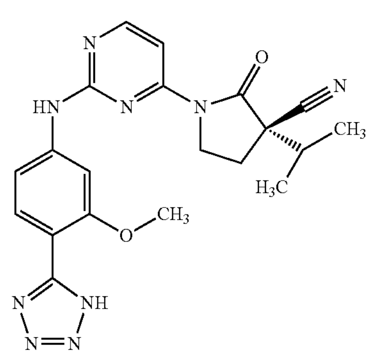 [SMILES: COc1cc(Nc2nccc(N3CC[C@@](C#N)(C(C)C)C3=O)n2)ccc1-c1nnn[nH]1] | HCl | 420.3 |

TABLE 23-2-continued

| Example Number | IUPAC Name | Structure | Salt | MS |
|---|---|---|---|---|
| 290 | 2-(4-((4-((3S)-3-cyano-3-isopropyl-2-oxopyrrolidin-1-yl)pyrimidin-2-yl)amino)phenyl)-2-methylpropanoic acid | 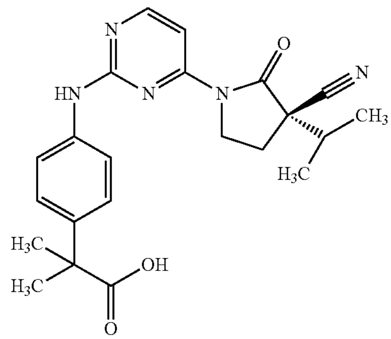 [SMILES: CC(C)[C@]1(C#N)CCN(c2ccnc(Nc3ccc(C(C)(C)C(=O)O)cc3)n2)C1=O] | HCl | 408.3 |

Example 291

4-((4-((3S)-3-cyano-3-isopropyl-2-oxopyrrolidin-1-yl)pyrimidin-2-yl)amino)-2-methoxybenzoic acid hydrochloride

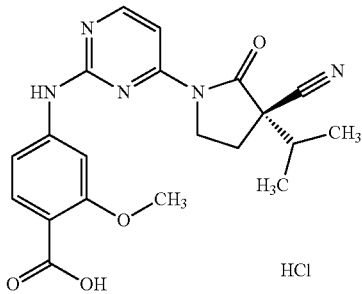 [SMILES: COc1cc(Nc2nccc(N3CC[C@@](C#N)(C(C)C)C3=O)n2)ccc1C(=O)O ; Cl]

The title compound (11 mg) was obtained from (3S)-1-(2-chloropyrimidin-4-yl)-3-isopropyl-2-oxopyrrolidine-3-carbonitrile (100 mg) obtained in Step A of Example 9 and 4-amino-2-methoxybenzoic acid (63 mg) in the same manner as in Example 56.

MS(ESI+): [M+H]$^+$ 396.3.

Example 292

4-((4-((3S)-3-cyano-3-isopropyl-2-oxopyrrolidin-1-yl)pyrimidin-2-yl)amino)-2-(2,2,2-trifluoroethoxyl)benzoic acid hydrochloride

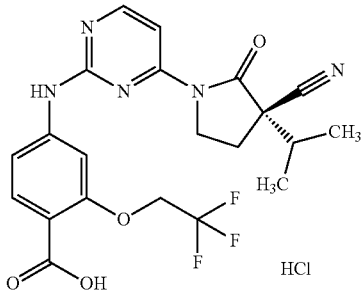 [SMILES: CC(C)[C@]1(C#N)CCN(c2ccnc(Nc3ccc(C(=O)O)c(OCC(F)(F)F)c3)n2)C1=O ; Cl]

A) tert-butyl 4-((4-((3S)-3-cyano-3-isopropyl-2-oxopyrrolidin-1-yl)pyrimidin-2-yl)amino)-2-(2,2,2-trifluoroethoxyl)benzoate The title compound (120 mg) was obtained from (3S)-1-(2-chloropyrimidin-4-yl)-3-isopropyl-2-oxopyrrolidine-3-carbonitrile (100 mg) obtained in Step A of Example 9 and tert-butyl 4-amino-2-(2,2,2-trifluoroethoxyl)benzoate (130 mg) obtained in Step C of Example 143 in the same manner as in Example 56.

MS(ESI+): [M+H]$^+$ 520.4.

B) 4-((4-((3S)-3-cyano-3-isopropyl-2-oxopyrrolidin-1-yl)pyrimidin-2-yl)amino)-2-(2,2,2-trifluoroethoxyl)benzoic acid hydrochloride To tert-butyl 4-((4-((3S)-3-cyano-3-isopropyl-2-oxopyrrolidin-1-yl)pyrimidin-2-yl)amino)-2-(2,2,2-trifluoroethoxyl)benzoate (120 mg) obtained in Step A of Example 292 was added dropwise a solution of 4 M hydrogen chloride in ethyl acetate (6.0 mL), and the mixture was stirred at room temperature for 1 hr. The solvent was evaporated under reduced pressure, and the residue was washed with ethyl acetate to give the title compound (71 mg).

MS(ESI+): [M+H]$^+$ 464.3.

Example 293

4-((4-((3S)-3-cyano-3-isopropyl-2-oxopyrrolidin-1-yl)pyrimidin-2-yl)amino)-2-fluorobenzoic acid hydrochloride

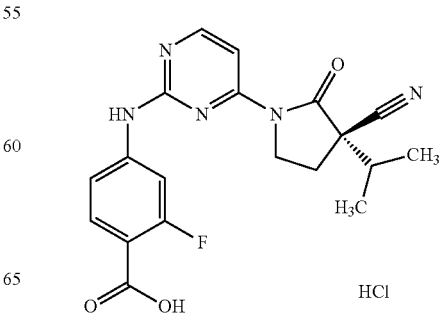

A) tert-butyl 4-amino-2-fluorobenzoate

The title compound (410 mg) was obtained from tert-butyl 2-fluoro-4-nitrobenzoate (500 mg) obtained in Step A of Example 143 in the same manner as in Step C of Example 139.

$^1$H NMR (400 MHz, DMSO-d$_6$) δ 1.48 (9H, s), 6.17 (2H, s), 6.25 (1H, dd, J=14.2, 2.2 Hz), 6.36 (1H, dd, J=8.7, 2.1 Hz), 7.49 (1H, t, J=8.8 Hz).

B) tert-butyl 4-((4-((3S)-3-cyano-3-isopropyl-2-oxopyrrolidin-1-yl)pyrimidin-2-yl)amino)-2-fluorobenzoate The title compound (100 mg) was obtained from (3S)-1-(2-chloropyrimidin-4-yl)-3-isopropyl-2-oxopyrrolidine-3-carbonitrile (100 mg) obtained in Step A of Example 9 and tert-butyl 4-amino-2-fluorobenzoate (100 mg) obtained in Step A of Example 293 in the same manner as in Example 56.

MS(ESI+): [M+H]$^+$ 440.3.

C) 4-((4-((3S)-3-cyano-3-isopropyl-2-oxopyrrolidin-1-yl) pyrimidin-2-yl)amino)-2-fluorobenzoic acid hydrochloride The title compound (64 mg) was obtained from tert-butyl 4-((4-((3S)-3-cyano-3-isopropyl-2-oxopyrrolidin-1-yl) pyrimidin-2-yl)amino)-2-fluorobenzoate (100 mg) obtained in Step B of Example 293 in the same manner as in Step B of Example 292.

MS(ESI+): [M+H]$^+$ 384.3.

Example 294

4-((4-((3S)-3-cyano-3-isopropyl-2-oxopyrrolidin-1-yl)pyrimidin-2-yl)amino)-2-(methylsulfanyl)benzoic acid hydrochloride

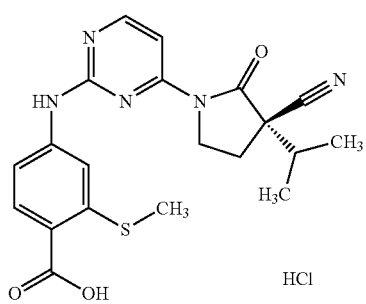 [SMILES: CSc1cc(Nc2nccc(N3CC[C@@](C#N)(C(C)C)C3=O)n2)ccc1C(=O)O ; Cl]

A) tert-butyl 2-(methylsulfanyl)-4-nitrobenzoate

To a solution of 2-(methylsulfanyl)-4-nitrobenzoic acid (1.0 g) in toluene (30 mL) was added dropwise N,N-dimethylformamide di-tert-butylacetal (11 mL), and the mixture was stirred at 100° C. for 10 hr. The solvent was evaporated under reduced pressure, and the residue was purified by silica gel column chromatography (hexane/ethyl acetate) to give the title compound (1.2 g).

$^1$H NMR (400 MHz, CDCl$_3$) δ1.63 (9H, s), 2.54 (3H, s), 7.93 (1H, dd, J=8.6, 2.0 Hz), 8.05 (1H, d, J=8.6 Hz), 8.08 (1H, d, J=2.2 Hz).

B) tert-butyl 4-amino-2-(methylsulfanyl)benzoate

The title compound (940 mg) was obtained from tert-butyl 2-(methylsulfanyl)-4-nitrobenzoate (1.2 g) obtained in Step A of Example 294 in the same manner as in Step C of Example 139.

$^1$H NMR (400 MHz, CDCl$_3$) δ1.58 (9H, s), 2.39 (3H, s), 4.00 (2H, brs), 6.38 (1H, dd, J=8.6, 2.2 Hz), 6.43 (1H, d, J=2.0 Hz), 7.81 (1H, d, J=8.3 Hz).

C) tert-butyl 4-((4-((3S)-3-cyano-3-isopropyl-2-oxopyrrolidin-1-yl)pyrimidin-2-yl)amino)-2-(methylsulfanyl)benzoate The title compound (37 mg) was obtained from (3S)-1-(2-chloropyrimidin-4-yl)-3-isopropyl-2-oxopyrrolidine-3-carbonitrile (100 mg) obtained in Step A of Example 9 and tert-butyl 4-amino-2-(methylsulfanyl)benzoate (100 mg) obtained in Step B of Example 294 in the same manner as in Example 56.

MS(ESI+): [M+H]$^+$ 468.4.

D) 4-((4-((3S)-3-cyano-3-isopropyl-2-oxopyrrolidin-1-yl)pyrimidin-2-yl)amino)-2-(methylsulfanyl)benzoic acid hydrochloride The title compound (22 mg) was obtained from tert-butyl 4-((4-((3S)-3-cyano-3-isopropyl-2-oxopyrrolidin-1-yl)pyrimidin-2-yl)amino)-2-(methylsulfanyl)benzoate (37 mg) obtained in Step C of Example 294 in the same manner as in Step B of Example 292.

MS(ESI+): [M+H]$^+$ 412.3.

Examples 295 to 299

The title compound was obtained from (3S)-1-(2-chloropyrimidin-4-yl)-3-isopropyl-2-oxopyrrolidine-3-carbonitrile obtained in Step A of Example 9 and each corresponding amine (these compounds can be produced according to a method known per se), in the same manner as in Step B of Example 2. MS in the tables means actual measured value.

TABLE 24

| Example Number | IUPAC Name | Structure | Salt | MS |
|---|---|---|---|---|
| 295 | 1-(4-((4-((3S)-3-cyano-3-isopropyl-2-oxopyrrolidin-1-yl)pyrimidin-2-yl)amino)phenyl)cyclopropane-carboxylic acid | 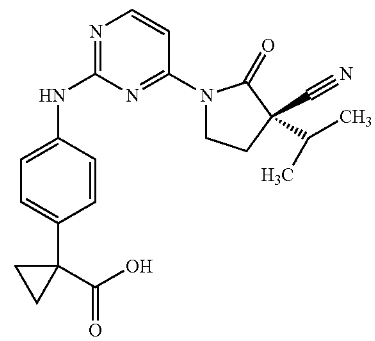 [SMILES: CC(C)[C@]1(C#N)CCN(c2ccnc(Nc3ccc(C4(C(=O)O)CC4)cc3)n2)C1=O] | HCl | 406.3 |
| 296 | 1-(4-((4-((3S)-3-cyano-3-isopropyl-2-oxopyrrolidin-1-yl)pyrimidin-2-yl)amino)phenyl)cyclobutane-carboxylic acid | 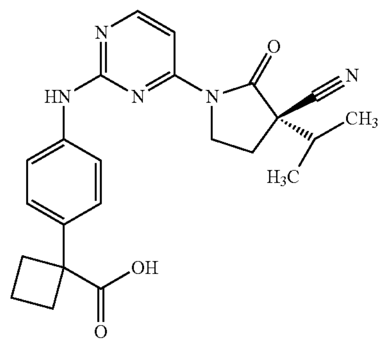 [SMILES: CC(C)[C@]1(C#N)CCN(c2ccnc(Nc3ccc(C4(C(=O)O)CCC4)cc3)n2)C1=O] | HCl | 420.3 |
| 297 | 1-(4-((4-((3S)-3-cyano-3-isopropyl-2-oxopyrrolidin-1-yl)pyrimidin-2-yl)amino)phenyl)cyclopentane-carboxylic acid | 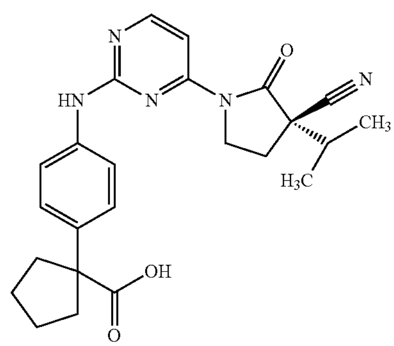 [SMILES: CC(C)[C@]1(C#N)CCN(c2ccnc(Nc3ccc(C4(C(=O)O)CCCC4)cc3)n2)C1=O] | HCl | 434.3 |
| 298 | 1-(4-((4-((3S)-3-cyano-3-isopropyl-2-oxopyrrolidin-1-yl)pyrimidin-2-yl)amino)phenyl)cyclohexane-carboxylic acid | 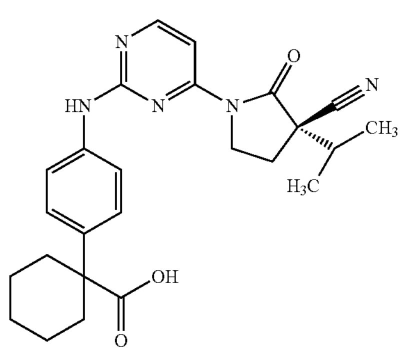 [SMILES: CC(C)[C@]1(C#N)CCN(c2ccnc(Nc3ccc(C4(C(=O)O)CCCCC4)cc3)n2)C1=O] | HCl | 448.4 |

TABLE 24-continued

| Example Number | IUPAC Name | Structure | Salt | MS |
|---|---|---|---|---|
| 299 | tert-butyl 4-(4-((4-((3S)-3-cyano-3-isopropyl-2-oxopyrrolidin-1-yl)pyrimidin-2-yl)amino)phenyl)tetrahydro-2H-pyran-4-carboxylate | 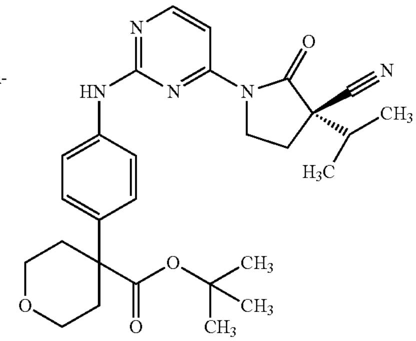 | Free | 506.3 |

Example 300

4-(4-((4-((3S)-3-cyano-3-isopropyl-2-oxopyrrolidin-1-yl) pyrimidin-2-yl)amino)phenyl)tetrahydro-2H-pyran-4-carboxylic acid hydrochloride

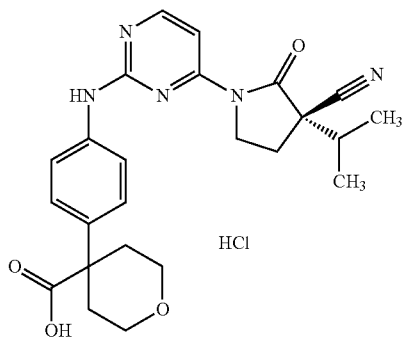 [SMILES: CC(C)[C@]1(C#N)CCN(c2ccnc(Nc3ccc(C4(C(=O)O)CCOCC4)cc3)n2)C1=O ; Cl]

To a suspension of tert-butyl 4-(4-((4-((3S)-3-cyano-3-isopropyl-2-oxopyrrolidin-1-yl)pyrimidin-2-yl)amino)phenyl)tetrahydro-2H-pyran-4-carboxylate (30 mg) obtained in Example 299 in water (5.0 mL) was added 2 M hydrochloric acid (3.0 mL), and the mixture was stirred at 100° C. for 1 hr. The solvent was evaporated under reduced pressure, and the residue was crystallized (diisopropyl ether/ethyl acetate) to give the title compound (7.5 mg).

MS(ESI+): [M+H]$^+$ 450.4.

Example 301

4-((4-((3S)-3-cyano-3-isopropyl-2-oxopyrrolidin-1-yl)pyrimidin-2-yl)amino)-2-cyclopropylbenzoic acid

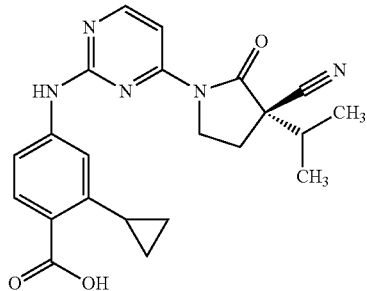 [SMILES: CC(C)[C@]1(C#N)CCN(c2ccnc(Nc3ccc(C(=O)O)c(C4CC4)c3)n2)C1=O]

A) tert-butyl 2-bromo-4-nitrobenzoate

To a solution of 2-bromo-4-nitrobenzoic acid (2.0 g) in tert-butanol (20 mL) were successively added 4-dimethylaminopyridine (1.1 g) and di-tert-butyl dicarbonate (2.1 mL), and the mixture was stirred overnight at room temperature. To the reaction mixture was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (1.5 g).

$^1$H NMR (400 MHz, DMSO-d$_6$) δ1.55-1.60 (9H, m), 7.89 (1H, d, J=8.6 Hz), 8.29 (1H, dd, J=8.6, 2.2 Hz), 8.48 (1H, d, J=2.2 Hz).

B) tert-butyl 2-cyclopropyl-4-nitrobenzoate

To a solution of tert-butyl 2-bromo-4-nitrobenzoate (1.5 g) obtained in Step A of Example 301 in a mixed solvent of toluene-water (v/v=5/1, 18 mL) were successively added cyclopropylboronic acid (1.3 g), tripotassium phosphate (4.7 g), tricyclohexyl phosphine (280 mg) and palladium acetate (110 mg), and the mixture was stirred overnight at 100° C. To the reaction mixture was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (1.3 g).

$^1$H NMR (400 MHz, DMSO-d$_6$) δ0.77-0.83 (2H, m), 1.02-1.10 (2H, m), 1.58 (9H, s), 2.35-2.46 (1H, m), 7.76 (1H, d, J=2.4 Hz), 7.79 (1H, d, J=8.6 Hz), 8.06 (1H, dd, J=8.4, 2.3 Hz).

C) tert-butyl 4-amino-2-cyclopropylbenzoate

To a solution of tert-butyl 2-cyclopropyl-4-nitrobenzoate (500 mg) obtained in Step B of Example 301 in ethanol (5.0 mL) was added 10% palladium-carbon (100 mg), and the mixture was stirred at room temperature for 3 hr under hydrogen atmosphere (at normal pressures). The palladium-carbon was removed by filtration, and the solvent was evaporated under reduced pressure. The residue was purified by silica gel column chromatography (hexane/ethyl acetate) to give the title compound (300 mg).

$^1$H NMR (400 MHz, DMSO-d$_6$) δ0.49-0.57 (2H, m), 0.83-0.92 (2H, m), 1.46-1.54 (9H, m), 2.68 (1H, tt, J=8.5, 5.6 Hz), 5.62 (2H, s), 6.13 (1H, d, J=2.2 Hz), 6.33 (1H, dd, J=8.4, 2.3 Hz), 7.48 (1H, d, J=8.6 Hz).

D) (S)-tert-butyl 4-((4-(3-cyano-3-isopropyl-2-oxopyrrolidin-1-yl)pyrimidin-2-yl)amino)-2-cyclopropylbenzoate The title compound (150 mg) was obtained from (3S)-1-(2-chloropyrimidin-4-yl)-3-isopropyl-2-oxopyrrolidine-3-carbonitrile (100 mg) obtained in Step A of Example 9 and tert-butyl 4-amino-2-cyclopropylbenzoate (88 mg) obtained in Step C of Example 301 in the same manner as in Step B of Example 2.
MS (ESI+). found: 362.3.

E) 4-((4-((3S)-3-cyano-3-isopropyl-2-oxopyrrolidin-1-yl)pyrimidin-2-yl)amino)-2-cyclopropylbenzoic acid The title compound (1.5 mg) was obtained from (S)-tert-butyl 4-((4-(3-cyano-3-isopropyl-2-oxopyrrolidin-1-yl)pyrimidin-2-yl)amino)-2-cyclopropylbenzoate (70 mg) obtained in Step D of Example 301 in the same manner as in Example 300.
MS(ESI+): [M+H]$^+$ 406.3.

Example 302

(3S)-1-(2-((4-cyano-3-ethoxyphenyl)amino)pyrimidin-4-yl)-3-isopropyl-2-oxopyrrolidine-3-carbonitrile

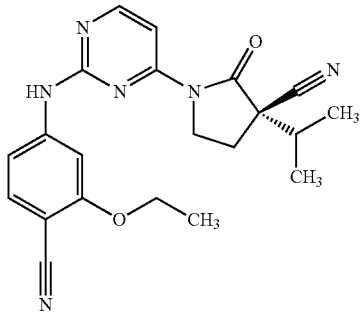 [SMILES: CCOc1cc(Nc2nccc(N3CC[C@@](C#N)(C(C)C)C3=O)n2)ccc1C#N]

The title compound (39 mg) was obtained from (3S)-1-(2-chloropyrimidin-4-yl)-3-isopropyl-2-oxopyrrolidine-3-carbonitrile (70 mg) obtained in Step A of Example 9 and 4-amino-2-ethoxybenzonitrile (64 mg) in the same manner as in Step B of Example 2.
MS(ESI+): [M+H]$^+$ 391.3.

Example 303

4-((4-((3S)-3-cyano-3-isopropyl-2-oxopyrrolidin-1-yl) pyrimidin-2-yl)amino)-2-isobutoxybenzoic acid hydrochloride

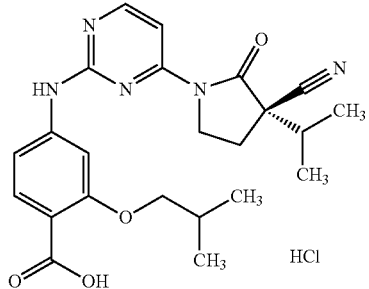 [SMILES: CC(C)COc1cc(Nc2nccc(N3CC[C@@](C#N)(C(C)C)C3=O)n2)ccc1C(=O)O ; Cl]

A) tert-butyl 4-((4-((3S)-3-cyano-3-isopropyl-2-oxopyrrolidin-1-yl)pyrimidin-2-yl)amino)-2-isobutoxybenzoate The title compound (100 mg) was obtained from (3S)-1-(2-chloropyrimidin-4-yl)-3-isopropyl-2-oxopyrrolidine-3-carbonitrile (100 mg) obtained in Step A of Example 9 and tert-butyl 4-amino-2-isobutoxybenzoate (120 mg) obtained in Step B of Example 144 in the same manner as in Example 56.
MS(ESI+): [M+H]$^+$ 494.4.

B) 4-((4-((3S)-3-cyano-3-isopropyl-2-oxopyrrolidin-1-yl)pyrimidin-2-yl)amino)-2-isobutoxybenzoic acid hydrochloride The title compound (62 mg) was obtained from tert-butyl 4-((4-((3S)-3-cyano-3-isopropyl-2-oxopyrrolidin-1-yl)pyrimidin-2-yl)amino)-2-isobutoxybenzoate (100 mg) obtained in Step A of Example 303 in the same manner as in Example 140.
MS(ESI+): [M+H]$^+$ 438.3.

Example 304

4-((4-((3S)-3-cyano-3-isopropyl-2-oxopyrrolidin-1-yl) pyrimidin-2-yl)amino)-2-(cyclopropylmethoxy)benzoic acid hydrochloride

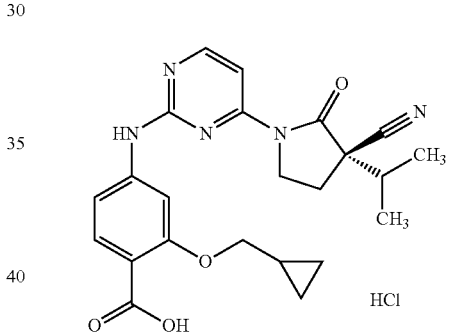

A) tert-butyl 2-(cyclopropylmethoxy)-4-nitrobenzoate

The title compound (600 mg) was obtained from tert-butyl 2-hydroxy-4-nitrobenzoate (500 mg) obtained in Step A of Example 139, (bromomethyl)cyclopropane (0.30 mL) and sodium iodide (470 mg) in the same manner as in Step B of Example 139.
$^1$H NMR (400 MHz, DMSO-d$_6$) δ 0.35-0.40 (2H, m), 0.55-0.62 (2H, m), 1.24 (1H, s), 1.55 (9H, s), 4.02-4.05 (2H, m), 7.72 (1H, d, J 8.3 Hz), 7.77-7.85 (2H, m).

B) tert-butyl 4-amino-2-(cyclopropylmethoxy)benzoate

The title compound (520 mg) was obtained from tert-butyl 2-(cyclopropylmethoxy)-4-nitrobenzoate (600 mg) obtained in Step A of Example 304 in the same manner as in Step C of Example 139.
$^1$H NMR (400 MHz, DMSO-d$_6$) δ 0.33 (2H, dd, J=4.8, 1.6 Hz), 0.52-0.58 (2H, m), 1.37-1.43 (1H, m), 1.47 (9H, s), 3.72 (2H, d, J=6.6 Hz), 5.73 (2H, s), 6.08-6.13 (2H, m), 7.39 (1H, d, J=8.3 Hz).

C) tert-butyl 4-((4-((3S)-3-cyano-3-isopropyl-2-ox-opyrrolidin-1-yl)pyrimidin-2-yl)amino)-2-(cyclopropylmethoxy)benzoate The title compound (150 mg) was obtained from (3S)-1-(2-chloropyrimidin-4-yl)-3-isopropyl-2-oxopyrrolidine-3-carbonitrile (100 mg) obtained in Step A of Example 9 and tert-butyl 4-amino-2-(cyclopropylmethoxy)benzoate (120 mg) obtained in Step B of Example 304 in the same manner as in Example 56.
MS(ESI+): [M+H]$^+$ 492.4.

D) 4-((4-((3S)-3-cyano-3-isopropyl-2-oxopyrrolidin-1-yl)pyrimidin-2-yl)amino)-2-(cyclopropylmethoxy)benzoic acid hydrochloride The title compound (68 mg) was obtained from tert-butyl 4-((4-((3S)-3-cyano-3-isopropyl-2-oxopyrrolidin-1-yl)pyrimidin-2-yl)amino)-2-(cyclopropylmethoxy)benzoate (150 mg) obtained in Step C of Example 304 in the same manner as in Example 140.
MS(ESI+): [M+H]$^+$ 436.3.

Example 305

3-(cyanomethyl)-1-(2-((4-(morpholin-4-yl)phenyl)amino)pyrimidin-4-yl)-2-oxopyrrolidine-3-carbonitrile

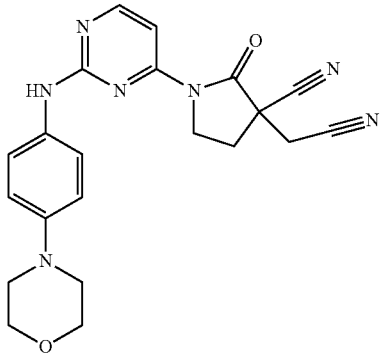 [SMILES: N#CCC1(C#N)CCN(c2ccnc(Nc3ccc(N4CCOCC4)cc3)n2)C1=O]

A) 3-(cyanomethyl)-1-(4-fluorobenzoyl)-2-oxopyrrolidine-3-carbonitrile

The title compound (150 mg) was obtained from 1-(4-fluorobenzoyl)-2-oxopyrrolidine-3-carbonitrile (300 mg) obtained in Step F of Example 1 and chloroacetonitrile (0.12 mL) in the same manner as in Step G of Example 1.
$^1$H NMR (300 MHz, CDCl$_3$) δ 2.54 (1H, ddd, J=13.4, 9.6, 8.3 Hz), 2.84 (1H, ddd, J=13.5, 6.5, 2.6 Hz), 3.10 (2H, d, J=1.1 Hz), 4.06-4.31 (2H, m), 7.04-7.21 (2H, m), 7.60-7.78 (2H, m).

B) 3-(cyanomethyl)-2-oxopyrrolidine-3-carbonitrile

The title compound (72 mg) was obtained from 3-(cyanomethyl)-1-(4-fluorobenzoyl)-2-oxopyrrolidine-3-carbonitrile (150 mg) obtained in Step A of Example 305 in the same manner as in Step B of Example 5.
$^1$H NMR (300 MHz, CDCl$_3$) δ 2.51 (1H, dt, J=13.6, 8.3 Hz), 2.83 (1H, ddd, J=13.6, 6.8, 2.6 Hz), 2.92-3.17 (2H, m), 3.49-3.75 (2H, m), 6.04 (1H, brs).

C) 1-(2-chloropyrimidin-4-yl)-3-(cyanomethyl)-2-oxopyrrolidine-3-carbonitrile

The title compound (53 mg) was obtained from 2,4-dichloropyrimidine (110 mg) and 3-(cyanomethyl)-2-oxopyrrolidine-3-carbonitrile (72 mg) obtained in Step B of Example 305 in the same manner as in Step A of Example 2.
$^1$H NMR (300 MHz, CDCl$_3$) δ 2.44-2.66 (1H, m), 2.89 (1H, ddd, J=13.5, 6.9, 2.6 Hz), 3.03-3.29 (2H, m), 4.19 (1H, ddd, J=12.0, 9.3, 7.0 Hz), 4.37-4.60 (1H, m), 8.26 (1H, d, J=5.7 Hz), 8.61 (1H, d, J=5.7 Hz).

D) 3-(cyanomethyl)-1-(2-((4-(morpholin-4-yl)phenyl)amino)pyrimidin-4-yl)-2-oxopyrrolidine-3-carbonitrile The title compound (20 mg) was obtained from 1-(2-chloropyrimidin-4-yl)-3-(cyanomethyl)-2-oxopyrrolidine-3-carbonitrile (53 mg) obtained in Step C of Example 305 and 4-(morpholin-4-yl)aniline (36 mg) in the same manner as in Step B of Example 2.
MS(ESI+): [M+H]$^+$ 414.3.

Example 306

(3S)-3-cyclopropyl-1-(2-((1-(1-hydroxy-2-methylpropan-2-yl)-1H-imidazol-4-yl)amino)pyrimidin-4-yl)-2-oxopyrrolidine-3-carbonitrile

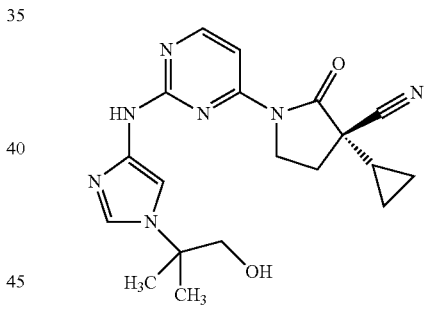

A) ethyl 2-methyl-2-(4-nitro-1H-imidazol-1-yl)propanoate

To a solution of 4-nitro-1H-imidazole (10 g) in N,N-dimethylformamide (150 mL) was added sodium hydride (60% in mineral oil, 4.2 g) in an ice bath, and the mixture was stirred at the same temperature for 20 min. To the reaction mixture was added ethyl 2-bromo-2-methylpropanoate (20 mL) at the same temperature, and the mixture was stirred overnight at 50° C. To the reaction mixture was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (12 g).
$^1$H NMR (400 MHz, DMSO-d$_6$) δ 1.18 (3H, t, J=7.1 Hz), 1.84 (6H, s), 4.16 (2H, q, J=7.1 Hz), 8.09 (1H, d, J=1.5 Hz), 8.60 (1H, d, J=1.5 Hz).

B) 2-methyl-2-(4-nitro-1H-imidazol-1-yl)propan-1-ol

To a solution of lithium aluminium hydride (400 mg) in tetrahydrofuran (50 mL) was added a solution of ethyl 2-methyl-2-(4-nitro-1H-imidazol-1-yl)propanoate (2.0 g) obtained in Step A of Example 306 in tetrahydrofuran (20 mL) in an ice bath, and the mixture was stirred at room temperature for 1 hr. To the reaction mixture were added water and 2M aqueous sodium hydroxide solution, the insoluble substance was removed by filtration through Celite, and the solvent was evaporated under reduced pressure. The residue was purified by silica gel column chromatography (ethyl acetate/methanol) to give the title compound (260 mg).

$^1$H NMR (400 MHz, DMSO-$d_6$) δ 1.50 (6H, s), 3.54 (2H, d, J=5.6 Hz), 5.23 (1H, t, J=5.6 Hz), 7.95 (1H, d, J=1.5 Hz), 8.47 (1H, d, J=1.5 Hz).

C) 2-(4-amino-1H-imidazol-1-yl)-2-methylpropan-1-ol

The title compound (220 mg) was obtained from 2-methyl-2-(4-nitro-1H-imidazol-1-yl)propan-1-ol (250 mg) obtained in Step B of Example 306 in the same manner as in Step H of Example 103.

$^1$H NMR (400 MHz, DMSO-$d_6$) δ 1.30-1.46 (6H, m), 3.41 (2H, d, J=4.9 Hz), 3.98 (2H, s), 5.01 (1H, t, J=5.0 Hz), 6.23 (1H, d, J=1.5 Hz), 7.17 (1H, d, J=1.7 Hz).

D) (3S)-3-cyclopropyl-1-(2-((1-(1-hydroxy-2-methylpropan-2-yl)-1H-imidazol-4-yl)amino)pyrimidin-4-yl)-2-oxopyrrolidine-3-carbonitrile The title compound (10 mg) was obtained from (3S)-1-(2-chloropyrimidin-4-yl)-3-cyclopropyl-2-oxopyrrolidine-3-carbonitrile (150 mg) obtained in Step E of Example 103 and 2-(4-amino-1H-imidazol-1-yl)-2-methylpropan-1-ol (93 mg) obtained in Step C of Example 306 in the same manner as in Step B of Example 2.

MS(ESI+): [M+H]$^+$ 382.3.

Example 307

(3S)-1-(2-((1-(1-hydroxy-2-methylpropan-2-yl)-1H-imidazol-4-yl)amino)pyrimidin-4-yl)-3-isopropyl-2-oxopyrrolidine-3-carbonitrile

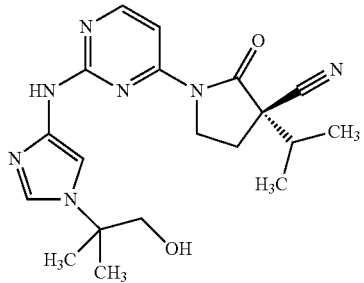 [SMILES: CC(C)[C@]1(C#N)CCN(c2ccnc(Nc3cn(C(C)(C)CO)cn3)n2)C1=O]

The title compound (4.9 mg) was obtained from (3S)-1-(2-chloropyrimidin-4-yl)-3-isopropyl-2-oxopyrrolidine-3-carbonitrile (100 mg) obtained in Step A of Example 9 and 2-(4-amino-1H-imidazol-1-yl)-2-methylpropan-1-ol (65 mg) obtained in Step C of Example 306 in the same manner as in Step B of Example 2.

MS(ESI+): [M+H]$^+$ 384.1.

Example 308

(3R)-3-ethyl-1-(2-((2-methyl-1,3-thiazol-5-yl)amino)pyrimidin-4-yl)-2-oxopyrrolidine-3-carbonitrile hydrochloride

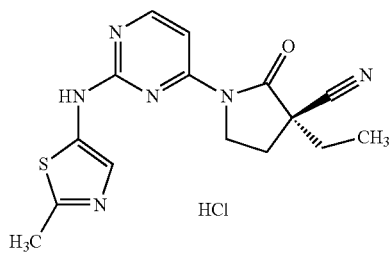 [SMILES: CC[C@]1(C#N)CCN(c2ccnc(Nc3cnc(C)s3)n2)C1=O ; Cl]

To a mixture of (3R)-1-(2-chloropyrimidin-4-yl)-3-ethyl-2-oxopyrrolidine-3-carbonitrile (100 mg) obtained in Step A of Example 8, 2-methyl-1,3-thiazol-5-amine (56 mg), potassium carbonate (110 mg) and dicyclohexyl(2',4',6'-triisopropyl-[1,1'-biphenyl]-2-yl)phosphine (58 mg) in tert-butanol (1.0 mL) was added tris(dibenzylideneacetone)dipalladium (0) (22 mg), and the mixture was stirred for 5 hr with heated under reflux. The insoluble substance was removed by filtration through Celite, and the solvent was evaporated under reduced pressure. The residue was purified by silica gel column chromatography (hexane/ethyl acetate). To a solution of the obtained compound (26 mg) in ethanol (2.0 mL) was added 1 M hydrochloric acid (80 µL), and the mixture was stirred at room temperature for 5 min. The solvent was evaporated under reduced pressure, and the residue was recrystallized (ethanol) to give the title compound (15 mg).

MS(ESI+): [M+H]$^+$ 329.2.

Example 309 tert-butyl 3-(3-cyano-1-(2-((4-(morpholin-4-yl)phenyl)amino)pyrimidin-4-yl)-2-oxopyrrolidin-3-yl)azetidine-1-carboxylate

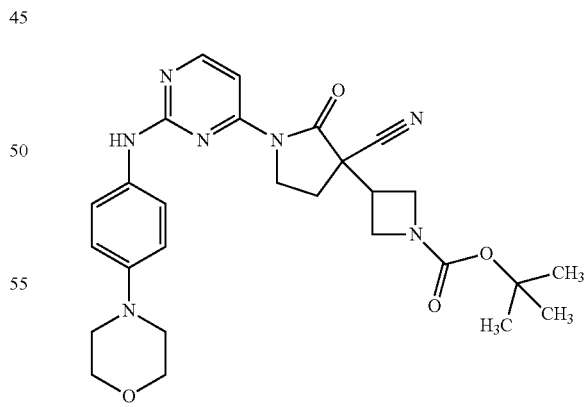

A) tert-butyl 3-(1-cyano-2-ethoxy-2-oxoethyl)azetidine-1-carboxylate

To a solution of tert-butyl 3-oxoazetidine-1-carboxylate (3.4 g), diethyl 2,6-dimethyl-1,4-dihydropyridine-3,5-dicarboxylate (5.0 g) and ethyl cyanoacetate (2.2 g) in dimethylsulfoxide (40 mL) was added L-proline (460 mg), and the mixture was stirred at room temperature for 48 hr. The insoluble substance was removed by filtration, saturated aqueous ammonium chloride solution was added thereto, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (4.3 g).

$^1$H NMR (400 MHz, CDCl$_3$) δ1.33 (3H, t, J=7.2 Hz), 1.40-1.49 (9H, m), 3.02-3.20 (1H, m), 3.73 (1H, d, J=8.6 Hz), 3.82 (1H, dd, J=9.3, 5.4 Hz), 3.87 (1H, dd, J=9.4, 5.5 Hz), 4.10-4.20 (2H, m), 4.28 (2H, q, J=7.1 Hz).

B) tert-butyl 3-(4-((tert-butoxycarbonyl)amino)-2-cyano-1-ethoxy-1-oxobutan-2-yl) azetidine-1-carboxylate To a solution of tert-butyl 3-(1-cyano-2-ethoxy-2-oxoethyl)azetidine-1-carboxylate (4.3 g) obtained in Step A of Example 309, tert-butyl 1,2,3-oxathiazolidine-3-carboxylate 2,2-dioxide (4.7 g) and tetrabutylammonium bromide (520 mg) in toluene (60 mL) was added cesium carbonate (10 g), and the mixture was stirred overnight at room temperature. To the reaction mixture was added 0.5 M hydrochloric acid, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (7.0 g).

$^1$H NMR (400 MHz, CDCl$_3$) δ1.31-1.37 (3H, m), 1.40-1.52 (18H, m), 1.80-1.93 (1H, m), 2.11-2.25 (1H, m), 2.98-3.09 (1H, m), 3.26 (1H, dt, J=14.0, 7.1 Hz), 3.32-3.43 (1H, m), 3.92 (2H, dt, J=9.2, 6.2 Hz), 3.97-4.03 (1H, m), 4.03-4.08 (1H, m), 4.29 (2H, q, J=7.2 Hz), 4.69 (1H, brs).

C) tert-butyl 3-(3-cyano-2-oxopyrrolidin-3-yl)azetidine-1-carboxylate tert-Butyl 3-(4-((tert-butoxycarbonyl)amino)-2-cyano-1-ethoxy-1-oxobutan-2-yl)azetidine-1-carboxylate (7 g) obtained in Step B of Example 309 in tetrahydrofuran (80 mL) was added sodium hydride (60% in mineral oil, 816 mg) in an ice bath, and the mixture was stirred at room temperature for 1 hr. To the reaction mixture was added saturated aqueous sodium hydrogen carbonate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (1.4 g).

$^1$H NMR (400 MHz, CDCl$_3$) δ 1.46 (9H, brs), 2.27 (1H, ddd, J=13.4, 8.3, 7.0 Hz), 2.65 (1H, ddd, J=13.4, 7.6, 4.2 Hz), 2.96-3.05 (1H, m), 3.45 (1H, dddd, J=10.0, 8.5, 4.0, 1.2 Hz), 3.59 (1H, dt, J=9.9, 7.4 Hz), 3.82-3.96 (1H, m), 4.05-4.12 (2H, m), 4.13-4.18 (1H, m), 6.38 (1H, brs).

D) tert-butyl 3-(1-(2-chloropyrimidin-4-yl)-3-cyano-2-oxopyrrolidin-3-yl)azetidine-1-carboxylate To a mixture of tert-butyl 3-(3-cyano-2-oxopyrrolidin-3-yl)azetidine-1-carboxylate (1.3 g) obtained in Step C of Example 309, 2,4-dichloropyrimidine (750 mg), cesium carbonate (3.3 g) and 4,5-bis(diphenylphosphino)-9,9-dimethylxanthene (180 mg) in tetrahydrofuran (12 mL) was added tris(dibenzylideneacetone)dipalladium(0) (93 mg), and the mixture was stirred overnight at 85° C. The insoluble substance was removed by filtration through Celite, and the solvent was evaporated under reduced pressure. The residue was purified by silica gel column chromatography (hexane/ethyl acetate) to give the title compound (850 mg)

$^1$H NMR (400 MHz, DMSO-d6) 1.39 (9H, s), 2.21-2.35 (1H, m), 2.61-2.71 (1H, m), 3.25-3.31 (1H, m), 3.77-3.89 (1H, m), 3.91-4.00 (3H, m), 4.01-4.14 (2H, m), 8.19 (1H, d, J=5.6 Hz), 8.69 (1H, d, J=5.6 Hz).

E) tert-butyl 3-(3-cyano-1-(2-((4-(morpholin-4-yl)phenyl)amino)pyrimidin-4-yl)-2-oxopyrrolidin-3-yl)azetidine-1-carboxylate A solution of tert-butyl 3-(1-(2-chloropyrimidin-4-yl)-3-cyano-2-oxopyrrolidin-3-yl)azetidine-1-carboxylate (100 mg) obtained in Step D of Example 309, 4-morpholinoaniline (61 mg) and acetic acid (50 μL) in n-butanol (4.0 mL) was stirred in a microwave reactor at 150° C. for 1 hr, and the solvent was evaporated under reduced pressure. The residue was purified by silica gel column chromatography (NH, hexane/ethyl acetate), and recrystallized (diisopropyl ether/ethyl acetate) to give the title compound (35 mg).

MS(ESI+): [M+H]$^+$ 520.4.

Example 310

3-(azetidin-3-yl)-1-(2-((4-(morpholin-4-yl)phenyl)amino)pyrimidin-4-yl)-2-oxopyrrolidine-3-carbonitrile hydrochloride

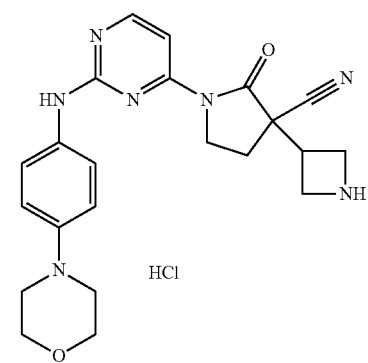 [SMILES: N#CC1(C2CNC2)CCN(c2ccnc(Nc3ccc(N4CCOCC4)cc3)n2)C1=O ; Cl]

The title compound (20 mg) was obtained from tert-butyl 3-(3-cyano-1-(2-((4-(morpholin-4-yl)phenyl)amino)pyrimidin-4-yl)-2-oxopyrrolidin-3-yl)azetidine-1-carboxylate (25 mg) obtained in Step E of Example 309 in the same manner as in Example 140.

MS(ESI+): [M+H]$^+$ 420.3.

Example 311

1-(2-((4-(morpholin-4-yl)phenyl)amino)pyrimidin-4-yl)-3-(oxetan-3-yl)-2-oxopyrrolidine-3-carbonitrile

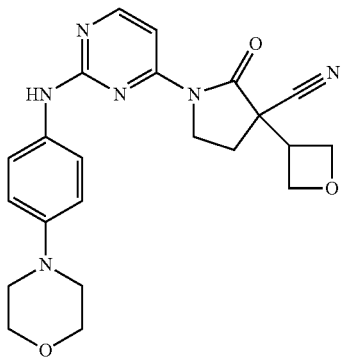 [SMILES: N#CC1(C2COC2)CCN(c2ccnc(Nc3ccc(N4CCOCC4)cc3)n2)C1=O]

A) ethyl cyano(oxetan-3-yl)acetate

The title compound (2.3 g) was obtained from oxetan-3-one (1.4 g) in the same manner as in Step A of Example 309.
$^1$H NMR (400 MHz, CDCl$_3$) δ1.33 (3H, t, J=7.1 Hz), 3.52-3.64 (1H, m), 3.89 (1H, d, J=8.8 Hz), 4.28 (2H, q, J=7.2 Hz), 4.57 (1H, t, J=6.6 Hz), 4.62 (1H, d, J=6.4 Hz), 4.88 (2H, q, J=7.7 Hz).

B) ethyl 4-((tert-butoxycarbonyl)amino)-2-cyano-2-(oxetan-3-yl)butanoate

The title compound (3.6 g) was obtained from ethyl cyano(oxetan-3-yl)acetate (2.2 g) obtained in Step A of Example 311 in the same manner as in Step B of Example 309.
$^1$H NMR (400 MHz, CDCl$_3$) δ1.34 (3H, t, J=7.1 Hz), 1.43 (9H, s), 1.85 (1H, dt, J=13.6, 6.8 Hz), 2.12-2.23 (1H, m), 3.16-3.42 (2H, m), 3.54 (1H, quin, J=7.5 Hz), 4.29 (2H, q, J=7.1 Hz), 4.63-4.76 (4H, m), 4.75-4.83 (1H, m).

C) 3-(oxetan-3-yl)-2-oxopyrrolidine-3-carbonitrile

The title compound (0.47 g) was obtained from ethyl 4-((tert-butoxycarbonyl)amino)-2-cyano-2-(oxetan-3-yl)butanoate (3.6 g) obtained in Step B of Example 311 in the same manner as in Step C of Example 309.
$^1$H NMR (400 MHz, CDCl$_3$) δ 2.31 (1H, ddd, J=13.4, 8.1, 6.8 Hz), 2.66 (1H, ddd, J=13.3, 7.8, 4.4 Hz), 3.40-3.51 (2H, m), 3.55-3.65 (1H, m), 4.66 (1H, t, J=6.7 Hz), 4.82-4.92 (3H, m), 6.95 (1H, brs).

D) 1-(2-chloropyrimidin-4-yl)-3-(oxetan-3-yl)-2-oxopyrrolidine-3-carbonitrile The title compound (0.25 g) was obtained from 3-(oxetan-3-yl)-2-oxopyrrolidine-3-carbonitrile (0.47 g) obtained in Step C of Example 311 in the same manner as in Step D of Example 309.
$^1$H NMR (400 MHz, DMSO-d$_6$) δ 2.26 (1H, ddd, J=13.1, 7.7, 4.2 Hz), 2.65 (1H, ddd, J=13.1, 8.7, 7.3 Hz), 3.69-3.79 (1H, m), 3.93-4.01 (1H, m), 4.03-4.10 (1H, m), 4.55 (1H, t, J=6.6 Hz), 4.68 (2H, d, J=7.3 Hz), 4.76 (1H, dd, J=8.1, 6.8 Hz), 8.18 (1H, d, J=5.9 Hz), 8.69 (1H, d, J=5.9 Hz).

E) 1-(2-((4-(morpholin-4-yl)phenyl)amino)pyrimidin-4-yl)-3-(oxetan-3-yl)-2-oxopyrrolidine-3-carbonitrile The title compound (59 mg) was obtained from 1-(2-chloropyrimidin-4-yl)-3-(oxetan-3-yl)-2-oxopyrrolidine-3-carbonitrile (100 mg) obtained in Step D of Example 311 in the same manner as in Step E of Example 309.
MS(ESI+): [M+H]$^+$ 421.3.

Example 312

3-cyclobutyl-1-(2-((4-(morpholin-4-yl)phenyl)amino)pyrimidin-4-yl)-2-oxopyrrolidine-3-carbonitrile

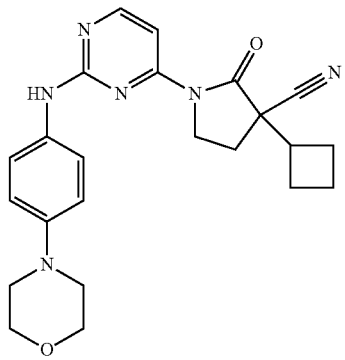 [SMILES: N#CC1(C2CCC2)CCN(c2ccnc(Nc3ccc(N4CCOCC4)cc3)n2)C1=O]

A) ethyl cyano(cyclobutyl)acetate

The title compound (1.9 g) was obtained from cyclobutanone (1.4 g) in the same manner as in Step A of Example 309.
$^1$H NMR (400 MHz, CDCl$_3$) δ 1.31 (3H, t, J=7.1 Hz), 1.87-2.08 (4H, m), 2.11-2.23 (2H, m), 2.85-2.96 (1H, m), 3.50 (1H, d, J=7.3 Hz), 4.24 (2H, q, J=7.2 Hz).

B) ethyl 4-((tert-butoxycarbonyl)amino)-2-cyano-2-cyclobutylbutanoate

The title compound (1.8 g) was obtained from ethyl cyano(cyclobutyl)acetate (1.0 g) obtained in Step A of Example 312 in the same manner as in Step B of Example 309.
$^1$H NMR (400 MHz, CDCl3) 1.32 (3H, t, J=7.1 Hz), 1.43 (9H, s), 1.74-2.00 (4H, m), 2.06-2.15 (4H, m), 2.67-2.84 (1H, m), 3.13-3.28 (1H, m), 3.30-3.43 (1H, m), 4.26 (2H, q, J=7.2 Hz), 4.66 (1H, brs).

C) 3-cyclobutyl-2-oxopyrrolidine-3-carbonitrile

The title compound (690 mg) was obtained from ethyl 4-((tert-butoxycarbonyl)amino)-2-cyano-2-cyclobutylbutanoate (1.8 g) obtained in Step B of Example 312 in the same manner as in Step C of Example 309.
$^1$H NMR (400 MHz, CDCl$_3$) δ1.84-2.00 (2H, m), 2.04-2.26 (5H, m), 2.56 (1H, ddd, J=13.2, 8.3, 6.4 Hz), 2.75 (1H, quin, J=8.6 Hz), 3.31-3.44 (1H, m), 3.44-3.54 (1H, m), 6.34 (1H, brs).

D) 1-(2-chloropyrimidin-4-yl)-3-cyclobutyl-2-oxopyrrolidine-3-carbonitrile

The title compound (0.50 g) was obtained from 3-cyclobutyl-2-oxopyrrolidine-3-carbonitrile (0.68 g) obtained in Step C of Example 312 in the same manner as in Step D of Example 309.

$^1$H NMR (400 MHz, CDCl$_3$) δ1.90-2.02 (2H, m), 2.11-2.21 (3H, m), 2.21-2.31 (2H, m), 2.58 (1H, ddd, J=13.4, 8.6, 7.3 Hz), 2.75-2.86 (1H, m), 4.04 (1H, dt, J=11.7, 7.6 Hz), 4.18 (1H, ddd, J=11.9, 8.6, 4.6 Hz), 8.27 (1H, d, J=5.9 Hz), 8.53 (1H, d, J=5.9 Hz).

E) 3-cyclobutyl-1-(2-((4-(morpholin-4-yl)phenyl)amino)pyrimidin-4-yl)-2-oxopyrrolidine-3-carbonitrile The title compound (70 mg) was obtained from 1-(2-chloropyrimidin-4-yl)-3-cyclobutyl-2-oxopyrrolidine-3-carbonitrile (100 mg) obtained in Step D of Example 312 in the same manner as in Step E of Example 309.

MS(ESI+): [M+H]$^+$ 419.4.

Examples 313 to 346

In Examples 313 to 346, the title compound was obtained from 1-(2-chloropyrimidin-4-yl)-3-ethyl-2-oxopyrrolidine-3-carbonitrile obtained in Step A of Example 2 and the aniline derivative each corresponding to the compounds of Examples 313 to 346 (these compounds can be produced according to a method known per se), in the same manner as in Step B of Example 2. MS in the tables means actual measured value.

TABLE 25-1

| Example Number | IUPAC Name | Structure | Salt | MS |
|---|---|---|---|---|
| 313 | 1-(2-anilinopyrimidin-4-yl)-3-ethyl-2-oxopyrrolidine-3-carbonitrile | 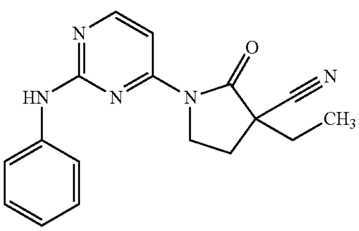 [SMILES: CCC1(C#N)CCN(c2ccnc(Nc3ccccc3)n2)C1=O] | Free | 307.9 |
| 314 | 3-ethyl-1-(2-((2-methylphenyl)amino)pyrimidin-4-yl)-2-oxopyrrolidine-3-carbonitrile | 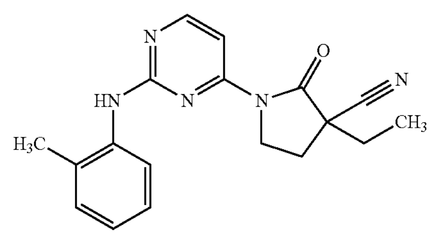 [SMILES: CCC1(C#N)CCN(c2ccnc(Nc3ccccc3C)n2)C1=O] | Free | 321.9 |
| 315 | 3-ethyl-1-(2-((4-methylphenyl)amino)pyrimidin-4-yl)-2-oxopyrrolidine-3-carbonitrile | 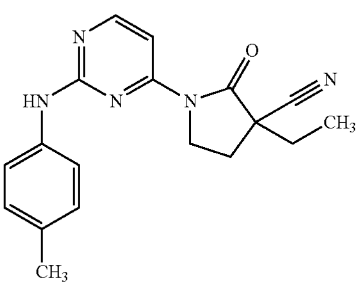 [SMILES: CCC1(C#N)CCN(c2ccnc(Nc3ccc(C)cc3)n2)C1=O] | Free | 321.9 |
| 316 | 3-ethyl-1-(2-((3-fluorophenyl)amino)pyrimidin-4-yl)-2-oxopyrrolidine-3-carbonitrile | 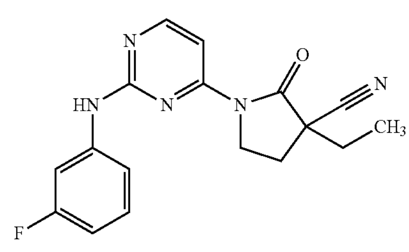 [SMILES: CCC1(C#N)CCN(c2ccnc(Nc3cccc(F)c3)n2)C1=O] | Free | 325.9 |

TABLE 25-1-continued

| Example Number | IUPAC Name | Structure | Salt | MS |
|---|---|---|---|---|
| 317 | 3-ethyl-1-(2-((4-fluorophenyl)amino)pyrimidin-4-yl)-2-oxopyrrolidine-3-carbonitrile | 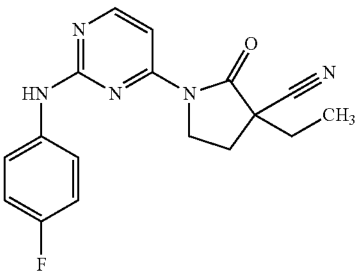 [SMILES: CCC1(C#N)CCN(c2ccnc(Nc3ccc(F)cc3)n2)C1=O] | Free | 325.9 |
| 318 | 1-(2-((2-chlorophenyl)amino)pyrimidin-4-yl)-3-ethyl-2-oxopyrrolidine-3-carbonitrile | 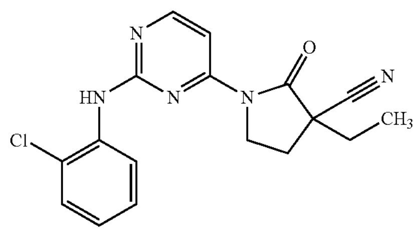 [SMILES: CCC1(C#N)CCN(c2ccnc(Nc3ccccc3Cl)n2)C1=O] | Free | 341.9 |
| 319 | 1-(2-((3-chlorophenyl)amino)pyrimidin-4-yl)-3-ethyl-2-oxopyrrolidine-3-carbonitrile | 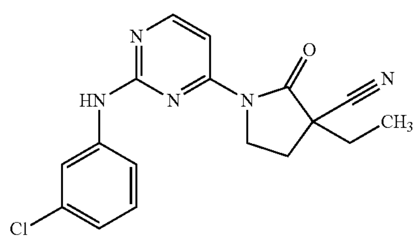 [SMILES: CCC1(C#N)CCN(c2ccnc(Nc3cccc(Cl)c3)n2)C1=O] | Free | 341.9 |
| 320 | 1-(2-((4-chlorophenyl)amino)pyrimidin-4-yl)-3-ethyl-2-oxopyrrolidine-3-carbonitrile | 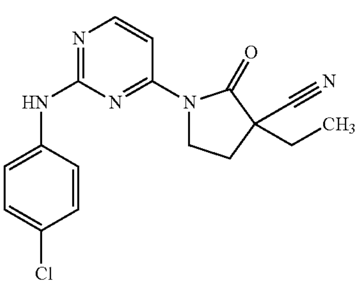 [SMILES: CCC1(C#N)CCN(c2ccnc(Nc3ccc(Cl)cc3)n2)C1=O] | Free | 341.9 |
| 321 | 3-ethyl-1-(2-((2-methoxyphenyl)amino)pyrimidin-4-yl)-2-oxopyrrolidine-3-carbonitrile | 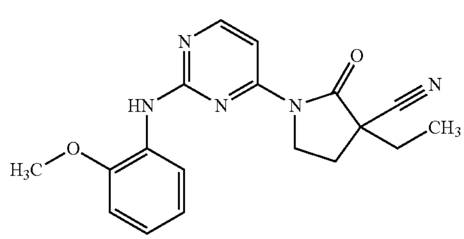 [SMILES: CCC1(C#N)CCN(c2ccnc(Nc3ccccc3OC)n2)C1=O] | Free | 337.9 |

TABLE 25-2

| Example Number | IUPAC Name | Structure | Salt | MS |
|---|---|---|---|---|
| 322 | 3-ethyl-1-(2-((3-methoxyphenyl)amino)pyrimidin-4-yl)-2-oxopyrrolidine-3-carbonitrile | 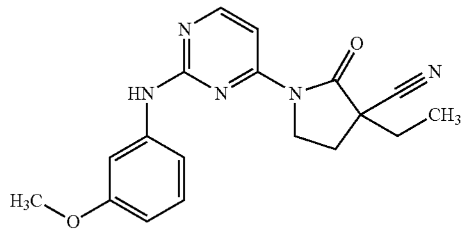 [SMILES: CCC1(C#N)CCN(c2ccnc(Nc3cccc(OC)c3)n2)C1=O] | Free | 337.9 |
| 323 | 3-ethyl-1-(2-((4-methoxyphenyl)amino)pyrimidin-4-yl)-2-oxopyrrolidine-3-carbonitrile | 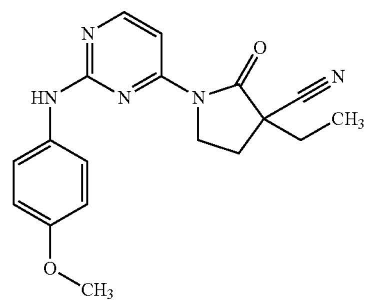 [SMILES: CCC1(C#N)CCN(c2ccnc(Nc3ccc(OC)cc3)n2)C1=O] | Free | 337.9 |
| 324 | 3-ethyl-2-oxo-1-(2-((3-(trifluoromethoxy)phenyl)amino)pyrimidin-4-yl)pyrrolidine-3-carbonitrile | 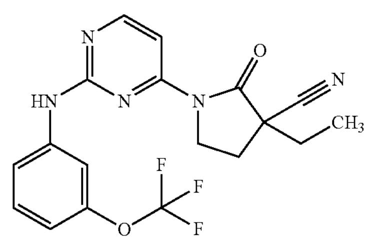 [SMILES: CCC1(C#N)CCN(c2ccnc(Nc3cccc(OC(F)(F)F)c3)n2)C1=O] | Free | 391.9 |
| 325 | 3-ethyl-2-oxo-1-(2-((4-(trifluoromethoxy)phenyl)amino)pyrimidin-4-yl)pyrrolidine-3-carbonitrile | 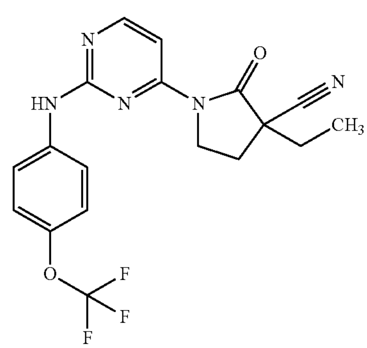 [SMILES: CCC1(C#N)CCN(c2ccnc(Nc3ccc(OC(F)(F)F)cc3)n2)C1=O] | Free | 391.9 |
| 326 | 1-(2-((3-cyanophenyl)amino)pyrimidin-4-yl)-3-ethyl-2-oxopyrrolidine-3-carbonitrile | 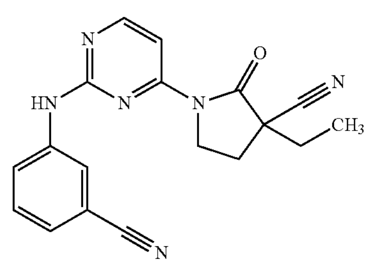 [SMILES: CCC1(C#N)CCN(c2ccnc(Nc3cccc(C#N)c3)n2)C1=O] | Free | 332.9 |

TABLE 25-2-continued

| Example Number | IUPAC Name | Structure | Salt | MS |
|---|---|---|---|---|
| 327 | 1-(2-((4-cyanophenyl)amino)pyrimidin-4-yl)-3-ethyl-2-oxopyrrolidine-3-carbonitrile | 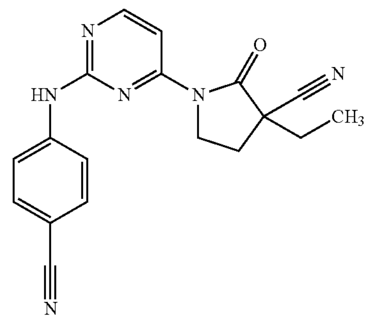 [SMILES: CCC1(C#N)CCN(c2ccnc(Nc3ccc(C#N)cc3)n2)C1=O] | Free | 332.9 |
| 328 | 3-((4-(3-cyano-3-ethyl-2-oxopyrrolidin-1-yl)pyrimidin-2-yl)amino)benzenesulfonamide | 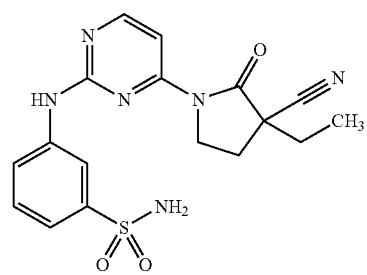 [SMILES: CCC1(C#N)CCN(c2ccnc(Nc3cccc(S(N)(=O)=O)c3)n2)C1=O] | Free | 386.9 |
| 329 | 4-((4-(3-cyano-3-ethyl-2-oxopyrrolidin-1-yl)pyrimidin-2-yl)amino)benzenesulfonamide | 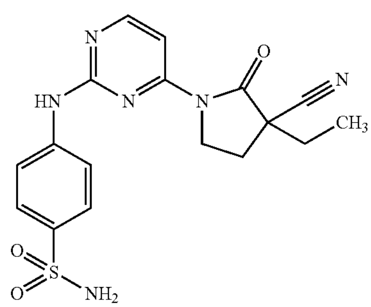 [SMILES: CCC1(C#N)CCN(c2ccnc(Nc3ccc(S(N)(=O)=O)cc3)n2)C1=O] | Free | 387 |
| 330 | 3-ethyl-1-(2-((3-(hydroxymethyl)phenyl)amino)pyrimidin-4-yl)-2-oxopyrrolidine-3-carbonitrile | 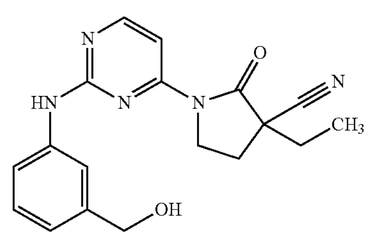 [SMILES: CCC1(C#N)CCN(c2ccnc(Nc3cccc(CO)c3)n2)C1=O] | Free | 337.9 |

TABLE 25-3

| Example Number | IUPAC Name | Structure | Salt | MS |
|---|---|---|---|---|
| 331 | 1-(2-((3-acetylphenyl)amino)pyrimidin-4-yl)-3-ethyl-2-oxopyrrolidine-3-carbonitrile | 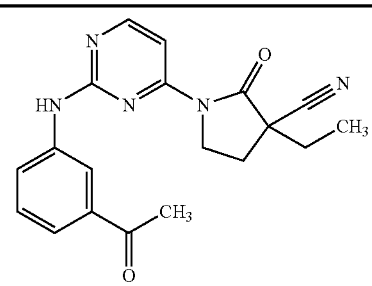 | Free | 349.9 |

TABLE 25-3-continued

| Example Number | IUPAC Name | Structure | Salt | MS |
|---|---|---|---|---|
| 332 | 1-(2-((4-tert-butylphenyl)amino)pyrimidin-4-yl)-3-ethyl-2-oxopyrrolidine-3-carbonitrile | 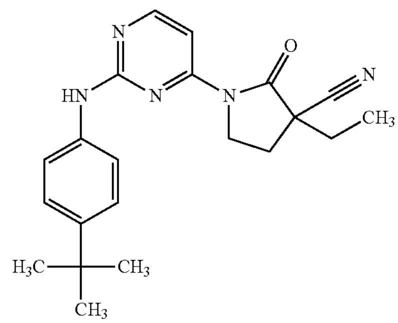 [SMILES: CCC1(C#N)CCN(c2ccnc(Nc3ccc(C(C)(C)C)cc3)n2)C1=O] | Free | 364.0 |
| 333 | 3-((4-(3-cyano-3-ethyl-2-oxopyrrolidin-1-yl)pyrimidin-2-yl)amino)benzamide | 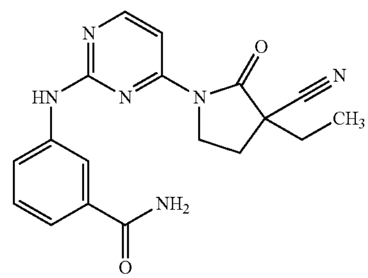 [SMILES: CCC1(C#N)CCN(c2ccnc(Nc3cccc(C(N)=O)c3)n2)C1=O] | Free | 350.9 |
| 334 | 3-ethyl-1-(2-((6-methoxypyridin-3-yl)amino)pyrimidin-4-yl)-2-oxopyrrolidine-3-carbonitrile | 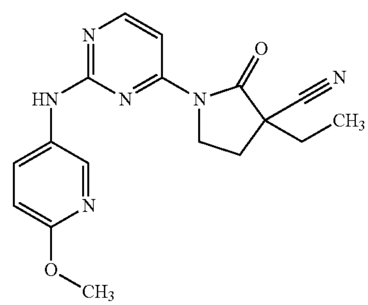 | Free | 338.9 |
| 335 | 3-ethyl-1-(2-((3-(methylsulfonyl)phenyl)amino)pyrimidin-4-yl)-2-oxopyrrolidine-3-carbonitrile | 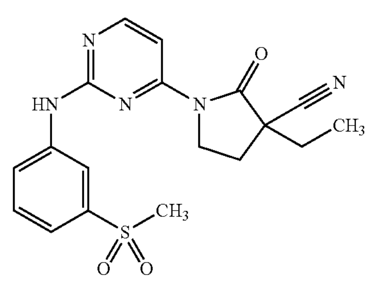 | Free | 386.0 |
| 336 | N-(3-((4-(3-cyano-3-ethyl-2-oxopyrrolidin-1-yl)pyrimidin-2-yl)amino)phenyl)acetamide | 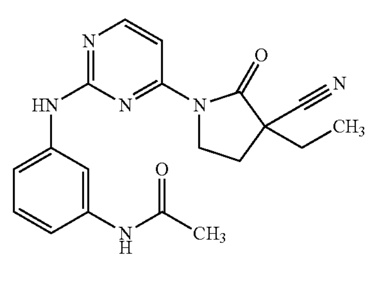 [SMILES: CCC1(C#N)CCN(c2ccnc(Nc3cccc(NC(C)=O)c3)n2)C1=O] | Free | 364.9 |

TABLE 25-3-continued

| Example Number | IUPAC Name | Structure | Salt | MS |
|---|---|---|---|---|
| 337 | 1-(2-((4-(cyanomethyl)phenyl)amino)pyrimidin-4-yl)-3-ethyl-2-oxopyrrolidine-3-carbonitrile | 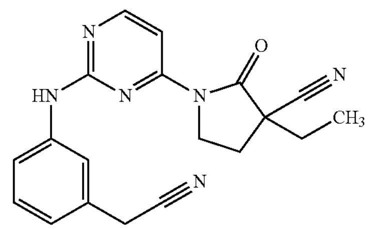 [SMILES: CCC1(C#N)CCN(c2ccnc(Nc3cccc(CC#N)c3)n2)C1=O] | Free | 364.9 |
| 338 | 3-ethyl-1-(2-((4-(2-methoxyethoxy)phenyl)amino)pyrimidin-4-yl)-2-oxopyrrolidine-3-carbonitrile | 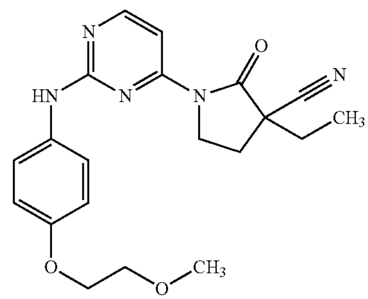 [SMILES: CCC1(C#N)CCN(c2ccnc(Nc3ccc(OCCOC)cc3)n2)C1=O] | Free | 382.0 |

TABLE 25-4

| Example Number | IUPAC Name | Structure | Salt | MS |
|---|---|---|---|---|
| 341 | 3-ethyl-1-(2-(1H-indazol-6-ylamino)pyrimidin-4-yl)-2-oxopyrrolidine-3-carbonitrile | 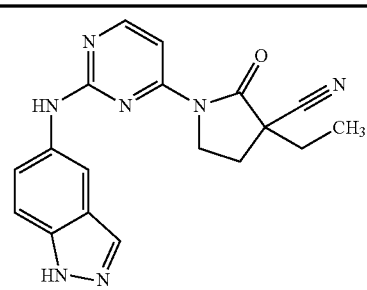 | Free | 348.0 |
| 342 | 1-(2-((1-tert-butyl-1H-pyrazol-4-yl)amino)pyrimidin-4-yl)-3-ethyl-2-oxopyrrolidine-3-carbonitrile | 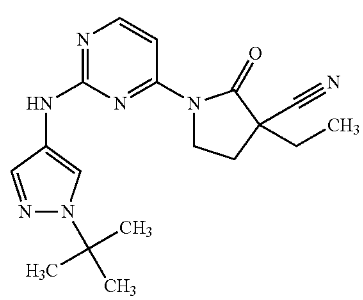 [SMILES: CCC1(C#N)CCN(c2ccnc(Nc3cnn(C(C)(C)C)c3)n2)C1=O] | Free | 353.9 |
| 343 | 4-((4-(3-cyano-3-ethyl-2-oxopyrrolidin-1-yl)pyrimidin-2-yl)amino)thiophene-2-sulfonamide | 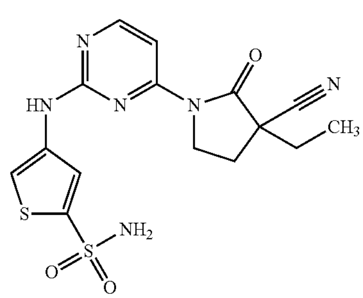 [SMILES: CCC1(C#N)CCN(c2ccnc(Nc3csc(S(N)(=O)=O)c3)n2)C1=O] | Free | 392.9 |

TABLE 25-4-continued

| Example Number | IUPAC Name | Structure | Salt | MS |
|---|---|---|---|---|
| 344 | 1-(2-(1,3-benzothiazol-6-ylamino)pyrimidin-4-yl)-3-ethyl-2-oxopyrrolidine-3-carbonitrile | 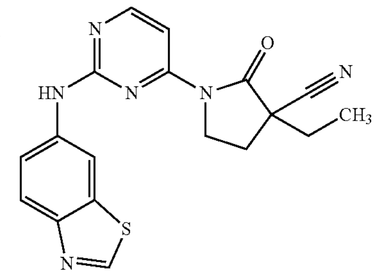 [SMILES: CCC1(C#N)CCN(c2ccnc(Nc3ccc4ncsc4c3)n2)C1=O] | Free | 364.9 |
| 345 | 3-ethyl-1-(2-((1-methyl-1H-indol-5-yl)amino)pyrimidin-4-yl)-2-oxopyrrolidine-3-carbonitrile | 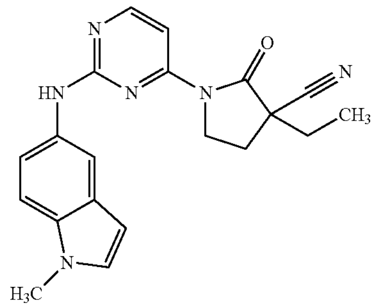 [SMILES: CCC1(C#N)CCN(c2ccnc(Nc3ccc4c(ccn4C)c3)n2)C1=O] | Free | 361.0 |

Example 347

3-cyclopropyl-1-(2-((1-(1-hydroxy-2-methylpropan-2-yl)-1H-pyrazol-4-yl)amino)pyrimidin-4-yl)-2-oxopyrrolidine-3-carbonitrile

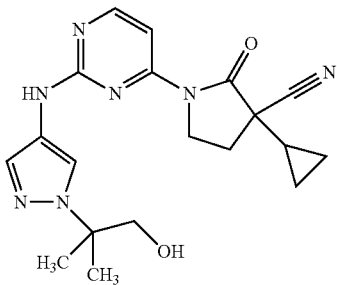 [SMILES: CC(C)(CO)n1cc(Nc2nccc(N3CCC(C#N)(C4CC4)C3=O)n2)cn1]

A) 2-(methylsulfanyl)pyrimidin-4 (3H)-one

To an aqueous solution (200 mL) of sodium hydroxide (23 g) were added 2-thioxo-2,3-dihydropyrimidin-4(1H)-one (37 g) and iodomethane (20 mL), and the mixture was stirred overnight at room temperature. To the reaction mixture was added acetic acid (17 mL), and the precipitate was collected by filtration, and washed with ice water. The residue was dried to give the title compound (28 g).
$^1$H NMR (400 MHz, DMSO-d$_6$) δ2.48 (3H, s), 6.10 (1H, d, J=6.6 Hz), 7.87 (1H, d, J=6.4 Hz), 12.69 (1H, brs).

B) ethyl 2-(4-amino-1H-pyrazol-1-yl)-2-methylpropanoate

To a solution of ethyl 2-methyl-2-(4-nitro-1H-pyrazol-1-yl)propanoate (20 g) obtained in Step F of Example 103 in ethanol (200 mL) was added 10% palladium-carbon (3.0 g), and the mixture was stirred overnight at room temperature under hydrogen atmosphere (at normal pressures). The palladium carbon was removed by filtration through Celite, and the solvent was evaporated under reduced pressure to give the title compound (17 g).
$^1$H NMR (400 MHz, DMSO-d$_6$) δ1.11 (3H, t, J=7.1 Hz), 1.65 (6H, s), 3.82 (2H, s), 4.05 (2H, q, J=7.1 Hz), 6.95 (1H, d, J=0.7 Hz), 7.12 (1H, d, J=1.0 Hz).

C) ethyl 2-methyl-2-(4-((6-oxo-1,6-dihydropyrimidin-2-yl)amino)-1H-pyrazol-1-yl)propanoate To a solution of 2-(methylsulfanyl)pyrimidin-4(3H)-one (9.1 g) obtained in Step A of Example 347 in diglyme (60 mL) was added ethyl 2-(4-amino-1H-pyrazol-1-yl)-2-methylpropanoate (13 g) obtained in Step B of Example 347, and the mixture was stirred at 140° C. for 7 hr. To the reaction mixture was added water, and the mixture was extracted with ethyl acetate. The obtained organic layer was washed with water and saturated brine, and dried over anhydrous magnesium sulfate, and the solvent was evaporated under reduced pressure. The residue was purified by silica gel column chromatography (ethyl acetate/methanol) to give the title compound (17 g).
$^1$H NMR (400 MHz, DMSO-d$_6$) δ1.08-1.14 (3H, m), 1.69-1.78 (6H, m), 4.08 (2H, q, J=7.3 Hz), 5.73 (1H, d, J=5.6 Hz), 7.53-7.61 (1H, m), 7.68-7.81 (1H, m), 8.05 (1H, s), 8.68 (1H, brs).

D) ethyl 2-(4-((4-chloropyrimidin-2-yl)amino)-1H-pyrazol-1-yl)-2-methylpropanoate To a solution of ethyl 2-methyl-2-(4-((6-oxo-1,6-dihydropyrimidin-2-yl)amino)-1H-pyrazol-1-yl)propanoate (2.0 g) obtained in Step C of Example 347 in acetonitrile (20 mL) was added phosphorus oxychloride (4.0 mL), and the mixture was stirred at 80° C. for 2 hr. To the reaction mixture was added 8 M aqueous sodium hydroxide solution (25 mL), and the mixture was extracted with ethyl acetate. The obtained organic layer was washed with water and saturated brine, and dried over anhydrous magnesium sulfate, and the solvent was evaporated under reduced pressure to give the title compound (2.0 g).

$^1$H NMR (400 MHz, DMSO-d$_6$) δ1.13 (3H, t, J=7.1 Hz), 1.75 (6H, s), 4.09 (2H, q, J=7.1 Hz), 6.85 (1H, d, J=5.1 Hz), 7.57 (1H, s), 7.98 (1H, s), 8.39 (1H, d, J=4.9 Hz), 9.92 (1H, s).

E) 2-(4-((4-chloropyrimidin-2-yl)amino)-1H-pyrazol-1-yl)-2-methylpropan-1-ol

To a solution of calcium chloride (540 mg) in a mixed solvent of tetrahydrofuran-ethanol (v/v=1/1, 5.0 mL) was added sodium borohydride (240 mg), and the mixture was stirred at room temperature for 1 hr. To the reaction mixture was added a solution of ethyl 2-(4-((4-chloropyrimidin-2-yl)amino)-1H-pyrazol-1-yl)-2-methylpropanoate (1.0 g) obtained in Step D of Example 347 in a mixed solvent of tetrahydrofuran-ethanol (v/v=1/1, 5.0 mL) in an ice bath, and the mixture was stirred overnight while it was allowed to be gradually warmed to room temperature. To the reaction mixture was added 1 M hydrochloric acid in an ice bath, and the mixture was stirred at the same temperature for 10 min. 1 M Aqueous sodium hydroxide solution was added thereto, and the solvent was evaporated under reduced pressure. To the residue was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (700 mg).
$^1$H NMR (400 MHz, DMSO-d$_6$) δ 1.45 (6H, s), 3.55 (2H, d, J=5.6 Hz), 4.96 (1H, t, J=5.6 Hz), 6.81 (1H, d, J=5.1 Hz), 7.54 (1H, s), 7.91 (1H, s), 8.37 (1H, d, J=4.2 Hz), 9.83 (1H, s).

F) 3-cyclopropyl-1-(2-((1-(1-hydroxy-2-methylpropan-2-yl)-1H-pyrazol-4-yl)amino)pyrimidin-4-yl)-2-oxopyrrolidine-3-carbonitrile To a mixture of 2-(4-((4-chloropyrimidin-2-yl)amino)-1H-pyrazol-1-yl)-2-methylpropan-1-ol (200 mg) obtained in Step E of Example 347, 3-cyclopropyl-2-oxopyrrolidine-3-carbonitrile (110 mg) obtained in Step C of Example 103, cesium carbonate (490 mg) and 4,5-bis(diphenylphosphino)-9,9-dimethylxanthene (26 mg) in toluene (2.0 mL) was added tris(dibenzylideneacetone)dipalladium(0) (14 mg), and the mixture was stirred overnight at 85° C. The insoluble substance was removed by filtration through Celite, and the solvent was evaporated under reduced pressure. The residue was purified by silica gel column chromatography (hexane/ethyl acetate) to give the title compound (130 mg).
MS(ESI+): [M+H]$^+$ 382.3.

Example 348

N-(2-(4-((4-((3S)-3-cyano-3-isopropyl-2-oxopyrrolidin-1-yl)pyrimidin-2-yl)amino)-1H-pyrazol-1-yl)ethyl)acetamide

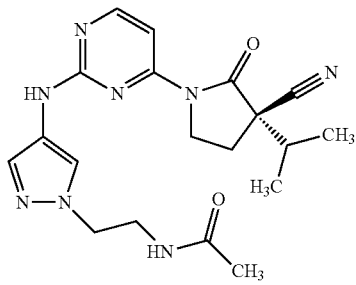 [SMILES: CC(=O)NCCn1cc(Nc2nccc(N3CC[C@@](C#N)(C(C)C)C3=O)n2)cn1]

A) tert-butyl(2-(4-nitro-1H-pyrazol-1-yl)ethyl)carbamate

To a solution of 4-nitro-1H-pyrazole (5.0 g) in N,N-dimethylformamide (100 mL) were added tert-butyl(2-bromoethyl)carbamate (12 g) and cesium carbonate (19 g), and the mixture was stirred overnight at 40° C. To the reaction mixture was added water, and the mixture was extracted with ethyl acetate. The obtained organic layer was washed with water and saturated brine, and dried over anhydrous sodium sulfate, and the solvent was evaporated under reduced pressure. The residue was purified by silica gel column chromatography (hexane/ethyl acetate) to give the title compound (13 g).
$^1$H NMR (400 MHz, DMSO-d$_6$) δ1.27-1.36 (9H, m), 3.35 (2H, q, J=5.9 Hz), 4.20 (2H, t, J=5.7 Hz), 6.96 (1H, t, J=5.6 Hz), 8.26 (1H, s), 8.79 (1H, s).

B) 2-(4-nitro-1H-pyrazol-1-yl)ethanamine hydrochloride

To a solution of tert-butyl(2-(4-nitro-1H-pyrazol-1-yl)ethyl)carbamate (8.0 g) obtained in Step A of Example 348 in ethyl acetate (30 mL) was added a solution of 4 M hydrogen chloride in ethyl acetate (4.0 mL), and the mixture was stirred at room temperature for 3 hr. The reaction mixture was concentrated under reduced pressure to give the title compound (4.7 g).
$^1$H NMR (400 MHz, DMSO-d$_6$) δ3.41 (2H, brs), 4.41-4.52 (2H, m), 8.14 (3H, brs), 8.36 (1H, s), 8.96 (1H, s).

C) N-(2-(4-nitro-1H-pyrazol-1-yl)ethyl)acetamide

To a solution of 2-(4-nitro-1H-pyrazol-1-yl)ethanamine hydrochloride (1.0 g) obtained in Step B of Example 348 in tetrahydrofuran (30 mL) were successively added triethylamine (2.2 mL) and acetyl chloride (0.44 mL) in an ice bath, and the mixture was stirred at room temperature for 2 hr. To the reaction mixture was added water, and the mixture was extracted with ethyl acetate. The obtained organic layer was washed with water and saturated brine, and dried over anhydrous sodium sulfate, and the solvent was evaporated under reduced pressure. The residue was recrystallized (hexane/ethyl acetate) to give the title compound (610 mg).
$^1$H NMR (400 MHz, DMSO-d$_6$) δ 1.71-1.83 (3H, m), 3.46 (2H, q, J=5.7 Hz), 4.21 (2H, t, J=5.9 Hz), 7.96 (1H, brs), 8.28 (1H, d, J=0.7 Hz), 8.87 (1H, s).

D) N-(2-(4-amino-1H-pyrazol-1-yl)ethyl) acetamide

To a solution of N-(2-(4-nitro-1H-pyrazol-1-yl)ethyl)acetamide (610 mg) obtained in Step C of Example 348 in ethanol (20 mL) was added 10% palladium-carbon (160 mg), and the mixture was stirred at room temperature for 3 hr under hydrogen atmosphere (at normal pressures). The palladium carbon was removed by filtration through Celite, and the solvent was evaporated under reduced pressure to give the title compound (570 mg).
$^1$H NMR (400 MHz, DMSO-d$_6$) δ 1.76-1.81 (3H, m), 3.32-3.35 (2H, m), 3.84 (2H, brs), 3.94 (2H, t, J=6.5 Hz), 6.91 (1H, d, J=0.7 Hz), 6.97-7.01 (1H, m), 7.87-7.98 (1H, m).

E) N-(2-(4-((4-((3S)-3-cyano-3-isopropyl-2-oxopyrrolidin-1-yl)pyrimidin-2-yl)amino)-1H-pyrazol-1-yl)ethyl) acetamide The title compound (28 mg) was obtained from (3S)-1-(2-chloropyrimidin-4-yl)-3-isopropyl-2-oxopyrrolidine-3-carbonitrile (55 mg) obtained in Step A of Example 9 and N-(2-(4-amino-1H-pyrazol-1-yl)ethyl)acetamide (38 mg) obtained in Step D of Example 348 in the same manner as in Step B of Example 2.

MS(ESI+): [M+H]$^+$ 397.3.

Example 349

N-(2-(4-((4-((3S)-3-cyano-3-isopropyl-2-oxopyrrolidin-1-yl)pyrimidin-2-yl)amino)-1H-pyrazol-1-yl)ethyl)methanesulfonamide

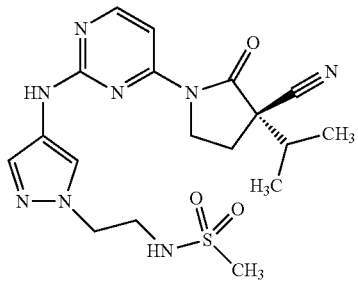 [SMILES: CC(C)[C@]1(C#N)CCN(c2ccnc(Nc3cnn(CCNS(C)(=O)=O)c3)n2)C1=O]

A) N-(2-(4-nitro-1H-pyrazol-1-yl)ethyl)methanesulfonamide

To a solution of 2-(4-nitro-1H-pyrazol-1-yl)ethanamine hydrochloride (1.0 g) obtained in Step B of Example 348 in tetrahydrofuran (30 mL) were added triethylamine (2.2 mL) and methanesulfonyl chloride (0.60 mL) in an ice bath, and the mixture was stirred at room temperature for 3 hr. To the reaction mixture was added water, and the mixture was extracted with ethyl acetate. The obtained organic layer was washed with water and saturated brine, and dried over anhydrous sodium sulfate, and the solvent was evaporated under reduced pressure. The residue was recrystallized (hexane/ethyl acetate) to give the title compound (880 mg).

$^1$H NMR (400 MHz, DMSO-d$_6$) δ 2.80-2.94 (3H, m), 3.42 (2H, q, J=6.1 Hz), 4.28 (2H, t, J=6.0 Hz), 7.24 (1H, t, J=6.1 Hz), 8.30 (1H, d, J=0.5 Hz), 8.87 (1H, s).

B) N-(2-(4-amino-1H-pyrazol-1-yl)ethyl)methanesulfonamide

To a solution of N-(2-(4-nitro-1H-pyrazol-1-yl)ethyl)methanesulfonamide (880 mg) obtained in Step A of Example 349 in ethanol (30 mL) was added 10% palladium-carbon (200 mg), and the mixture was stirred at room temperature for 3 hr under hydrogen atmosphere (at normal pressures). The palladium carbon was removed by filtration through Celite, and the solvent was evaporated under reduced pressure to give the title compound (860 mg).

$^1$H NMR (400 MHz, DMSO-d$_6$) δ 2.79 (3H, s), 3.27 (2H, t, J=6.4 Hz), 3.82 (2H, brs), 4.00 (2H, t, J=6.5 Hz), 6.93 (1H, d, J=1.0 Hz), 7.05 (1H, d, J=1.0 Hz), 7.14 (1H, brs).

C) N-(2-(4-((4-((3S)-3-cyano-3-isopropyl-2-oxopyrrolidin-1-yl)pyrimidin-2-yl)amino)-1H-pyrazol-1-yl)ethyl)methanesulfonamide The title compound (70 mg) was obtained from (3S)-1-(2-'s chloropyrimidin-4-yl)-3-isopropyl-2-oxopyrrolidine-3-carbonitrile (55 mg) obtained in Step A of Example 9 and N-(2-(4-amino-1H-pyrazol-1-yl)ethyl)acetamide (47 mg) obtained in Step B of Example 349 in the same manner as in Step B of Example 2.

MS(ESI+): [M+H]$^+$ 433.3.

Example 350

5-((4-((3R)-3-cyano-3-ethyl-2-oxopyrrolidin-1-yl)pyrimidin-2-yl)amino)pyridine-2-carboxamide

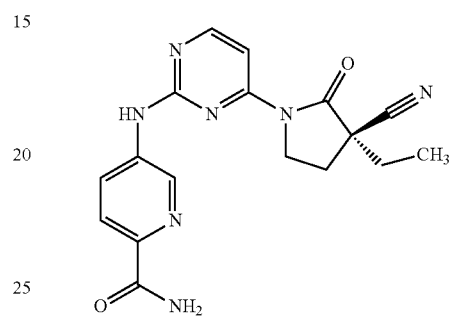

A) 5-aminopyridine-2-carboxamide

To a solution of 5-aminopyridine-2-carboxylic acid (2.0 g) in N,N-dimethylformamide (50 mL) were added ammonium chloride (3.9 g), 1-ethyl-3-(3-dimethylaminopropyl)carbodiimide (5.1 mL) and 1-hydroxybenzotriazole (4.4 g), and the mixture was stirred overnight at room temperature. To the reaction mixture was added saturated aqueous sodium hydrogen carbonate solution, and the mixture was extracted with ethyl acetate. The obtained organic layer was washed with saturated brine, and dried over anhydrous sodium sulfate, and the solvent was evaporated under reduced pressure. The residue was purified by silica gel column chromatography (NH, hexane/ethyl acetate) to give the title compound (260 mg).

MS(ESI+): [M+H]$^+$ 138.3.

B) 5-((4-((3R)-3-cyano-3-ethyl-2-oxopyrrolidin-1-yl)pyrimidin-2-yl)amino)pyridine-2-carboxamide To a solution of (3R)-1-(2-chloropyrimidin-4-yl)-3-ethyl-2-oxopyrrolidine-3-carbonitrile (200 mg) obtained in Step A of Example 8, 5-aminopyridine-2-carboxamide (130 mg) obtained in Step A of Example 350, cesium carbonate (520 mg) and 2,2'-bis(diphenylphosphino)-1,1'-binaphthyl (75 mg) in tetrahydrofuran (5.0 mL) was added tris(dibenzylideneacetone)dipalladium(0) (73 mg), and the mixture was stirred overnight at 80° C. under argon atmosphere. The insoluble substance was removed by filtration through Celite, and the solvent was evaporated under reduced pressure. The residue was purified by silica gel column chromatography (NH, hexane/ethyl acetate), and recrystallized (diisopropyl ether/ethanol) to give the title compound (25 mg).

MS(ESI+): [M+H]$^+$ 352.3.

Example 351

5-((4-((3S)-3-cyano-3-isopropyl-2-oxopyrrolidin-1-yl)pyrimidin-2-yl)amino)pyridine-2-carboxamide

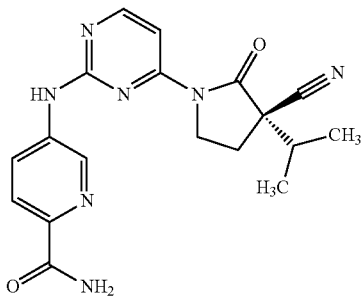 [SMILES: CC(C)[C@]1(C#N)CCN(c2ccnc(Nc3ccc(C(N)=O)nc3)n2)C1=O]

To a solution of (3S)-1-(2-chloropyrimidin-4-yl)-3-isopropyl-2-oxopyrrolidine-3-carbonitrile (200 mg) obtained in Step A of Example 9, 5-aminopyridine-2-carboxamide (120 mg) obtained in Step A of Example 350, cesium carbonate (490 mg) and 2,2'-bis(diphenylphosphino)-1,1'-binaphthyl (71 mg) in tetrahydrofuran (5.0 mL) was added tris(dibenzylideneacetone)dipalladium(0) (69 mg), and the mixture was stirred overnight at 80° C. under argon atmosphere. The insoluble substance was removed by filtration through Celite, and the solvent was evaporated under reduced pressure. The residue was purified by silica gel column chromatography (NH, hexane/ethyl acetate), and recrystallized (diisopropyl ether/ethanol) to give the title compound (54 mg).

MS(ESI+): [M+H]$^+$ 366.3.

Example 352

(3S)-3-(aminomethyl)-3-cyclopropyl-1-(2-((1-(1-hydroxy-2-methylpropan-2-yl)-1H-pyrazol-4-yl)amino)pyrimidin-4-yl)pyrrolidin-2-one

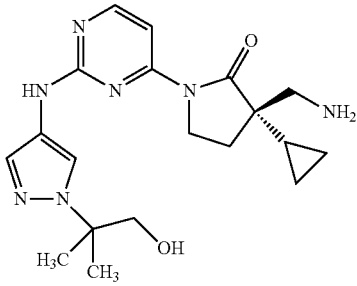 [SMILES: CC(C)(CO)n1cc(Nc2nccc(N3CC[C@@](CN)(C4CC4)C3=O)n2)cn1]

To a solution of (3S)-3-cyclopropyl-1-(2-((1-(1-hydroxy-2-methylpropan-2-yl)-1H-pyrazol-4-yl)amino)pyrimidin-4-yl)-2-oxopyrrolidine-3-carbonitrile (400 mg) obtained in Step I of Example 103 and cobalt(II) chloride hexahydrate (1.0 g) in methanol (6.0 mL) was added sodium borohydride (400 mg), and the mixture was stirred at room temperature for 4 hr. To the reaction mixture was added saturated aqueous sodium hydrogen carbonate solution in an ice bath, and the mixture was extracted with ethyl acetate. The obtained organic layer was washed with saturated brine, and dried over anhydrous sodium sulfate, and the solvent was evaporated under reduced pressure. The residue was purified by silica gel column chromatography (ethyl acetate/methanol) to give the title compound (84 mg).

MS(ESI+): [M+H]$^+$ 386.4.

Example 353

N-(((3S)-3-cyclopropyl-1-(2-((1-(1-hydroxy-2-methylpropan-2-yl)-1H-pyrazol-4-yl)amino)pyrimidin-4-yl)-2-oxopyrrolidin-3-yl)methyl)acetamide

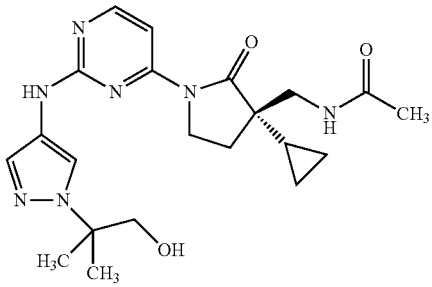 [SMILES: CC(=O)NC[C@@]1(C2CC2)CCN(c2ccnc(Nc3cnn(C(C)(C)CO)c3)n2)C1=O]

The title compound (30 mg) was obtained from (3S)-3-(aminomethyl)-3-cyclopropyl-1-(2-((1-(1-hydroxy-2-methylpropan-2-yl)-1H-pyrazol-4-yl)amino)pyrimidin-4-yl)pyrrolidin-2-one (76 mg) obtained in Example 352 in the same manner as in Step C of Example 348.

MS(ESI+): [M+H]$^+$ 428.4.

Example 354 tert-butyl(((3S)-3-cyclopropyl-1-(2-((1-(1-hydroxy-2-methylpropan-2-yl)-1H-pyrazol-4-yl)amino)pyrimidin-4-yl)-2-oxopyrrolidin-3-yl)methyl)carbamate

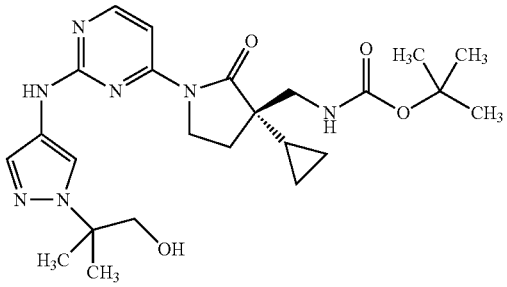 [SMILES: CC(C)(C)OC(=O)NC[C@@]1(C2CC2)CCN(c2ccnc(Nc3cnn(C(C)(C)CO)c3)n2)C1=O]

To a solution of (3S)-3-cyclopropyl-1-(2-((1-(1-hydroxy-2-methylpropan-2-yl)-1H-pyrazol-4-yl)amino)pyrimidin-4-yl)-2-oxopyrrolidine-3-carbonitrile (170 mg) obtained in Step I of Example 103 and cobalt(II) chloride hexahydrate (420 mg) in methanol (3.0 mL) was added sodium borohydride (170 mg), and the mixture was stirred at room temperature for 2 hr. To the reaction mixture were added saturated aqueous sodium hydrogen carbonate solution (5.0 mL) and di-tert-butyl dicarbonate (0.12 mL), and the mixture was stirred at room temperature for 2 hr. To the reaction mixture was added water, and the mixture was extracted with ethyl acetate. The obtained organic layer was washed with saturated aqueous ammonium chloride solution and saturated brine, and dried over anhydrous sodium sulfate, and the solvent was evaporated under reduced pressure. The residue was purified by silica gel column chromatography (hexane/ethyl acetate) to give the title compound (130 mg).

MS(ESI+): [M+H]⁺ 486.4.

Example 355

4-((4-((3S)-3-cyano-3-isopropyl-2-oxopyrrolidin-1-yl)pyrimidin-2-yl)amino)-2-fluorobenzamide

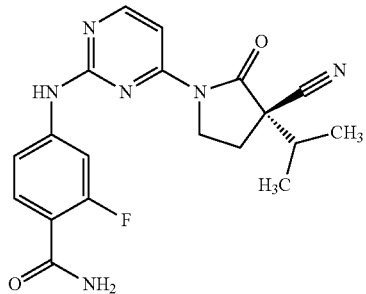 [SMILES: CC(C)[C@]1(C#N)CCN(c2ccnc(Nc3ccc(C(N)=O)c(F)c3)n2)C1=O]

A) 2-fluoro-4-nitrobenzamide

To a solution of 2-fluoro-4-nitrobenzoic acid (5.0 g) in N,N-dimethylformamide (100 mL) were added ammonium chloride (7.2 g), 1-ethyl-3-(3-dimethylaminopropyl)carbodiimide (9.5 mL), 1-hydroxybenzotriazole (8.3 g) and N,N-diisopropylethylamine (24 mL), and the mixture was stirred overnight at room temperature. To the reaction mixture was added saturated aqueous sodium hydrogen carbonate solution, and the precipitate was collected by filtration to give the title compound (3.1 g).

¹H NMR (400 MHz, DMSO-$d_6$) δ7.87 (1H, dd, J=8.3, 7.1 Hz), 7.93 (1H, brs), 8.07 (1H, brs), 8.10-8.15 (1H, m), 8.20 (1H, dd, J=9.9, 2.1 Hz).

B) 4-amino-2-fluorobenzamide

The title compound (750 mg) was obtained from 2-fluoro-4-nitrobenzamide (1.0 g) obtained in Step A of Example 355 in the same manner as in Step D of Example 348.

¹H NMR (400 MHz, DMSO-$d_6$) δ5.94 (2H, s), 6.27 (1H, dd, J=14.4, 2.0 Hz), 6.38 (1H, dd, J=8.6, 2.2 Hz), 6.89-7.24 (2H, m), 7.48 (1H, t, J=8.8 Hz).

C) 4-((4-((3S)-3-cyano-3-isopropyl-2-oxopyrrolidin-1-yl)pyrimidin-2-yl)amino)-2-fluorobenzamide The title compound (200 mg) was obtained from (3S)-1-(2-chloropyrimidin-4-yl)-3-isopropyl-2-oxopyrrolidine-3-carbonitrile (200 mg) obtained in Step A of Example 9 and 4-amino-2-fluorobenzamide (120 mg) obtained in Step B of Example 355 in the same manner as in Step B of Example 2.

MS(ESI+): [M+H]⁺ 383.3.

Example 356

4-((4-((3R)-3-cyano-3-ethyl-2-oxopyrrolidin-1-yl)pyrimidin-2-yl)amino)-2-fluorobenzamide

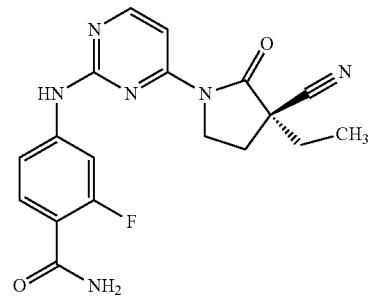 [SMILES: CC[C@]1(C#N)CCN(c2ccnc(Nc3ccc(C(N)=O)c(F)c3)n2)C1=O]

The title compound (220 mg) was obtained from (3R)-1-(2-chloropyrimidin-4-yl)-3-ethyl-2-oxopyrrolidine-3-carbonitrile (200 mg) obtained in Step A of Example 8 and 4-amino-2-fluorobenzamide (120 mg) obtained in Step B of Example 355 in the same manner as in Step B of Example 2.

MS(ESI+): [M+H]⁺ 369.2.

Example 357

3-cyclopropyl-4-methyl-1-(2-((4-(morpholin-4-yl)phenyl)amino)pyrimidin-4-yl)-2-oxopyrrolidine-3-carbonitrile

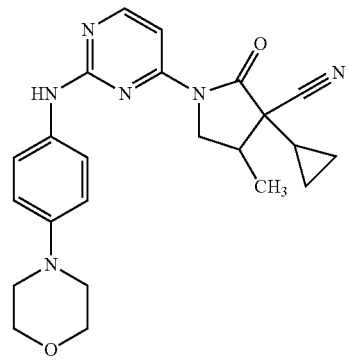 [SMILES: CC1CN(c2ccnc(Nc3ccc(N4CCOCC4)cc3)n2)C(=O)C1(C#N)C1CC1]

A) ethyl 4-((tert-butoxycarbonyl)amino)-2-cyano-2-cyclopropyl-3-methylbutanoate

The title compound (5.3 g) was obtained from tert-butyl 5-methyl-1,2,3-oxathiazolidine-3-carboxylate 2,2-dioxide (4.7 g) and ethyl cyano(cyclopropyl)acetate (3.0 g) obtained in Step A of Example 103 in the same manner as in Step B of Example 103.

MS(ESI+). found: 211.3 [M+H−(Boc)]⁺.

B) 3-cyclopropyl-4-methyl-2-oxopyrrolidine-3-carbonitrile

To ethyl 4-((tert-butoxycarbonyl)amino)-2-cyano-2-cyclopropyl-3-methylbutanoate (5.3 g) obtained in Step A of Example 357 was added 4 M hydrogen chloride in ethyl acetate (30 mL), and the mixture was stirred at room temperature for 2 hr. The reaction mixture was concentrated under reduced pressure, to a solution of the residue in acetonitrile (150 mL) was added potassium carbonate (9.4 g), and the mixture was stirred at room temperature for 5 hr. The insoluble substance was removed by filtration through Celite, and the solvent was evaporated under reduced pressure. The residue was purified by silica gel column chromatography (hexane/ethyl acetate) to give the title compound (2.2 g).
$^1$H NMR (400 MHz, DMSO-$d_6$) δ0.39-0.66 (4H, m), 1.08-1.26 (4H, m), 2.82-3.00 (1H, m), 3.26-3.46 (2H, m), 8.27 (1H, d, J=15.9 Hz).

C) 1-(2-chloropyrimidin-4-yl)-3-cyclopropyl-4-methyl-2-oxopyrrolidine-3-carbonitrile The title compound (2.6 g) was obtained from 3-cyclopropyl-4-methyl-2-oxopyrrolidine-3-carbonitrile (2.2 g) obtained in Step B of Example 357 and 2,4-dichloropyrimidine (2.0 g) in the same manner as in Step D of Example 103.
MS(ESI+): [M+H]$^+$ 277.2.

D) 3-cyclopropyl-4-methyl-1-(2-((4-(morpholin-4-yl)phenyl)amino)pyrimidin-4-yl)-2-oxopyrrolidine-3-carbonitrile The title compound (88 mg) was obtained from 1-(2-chloropyrimidin-4-yl)-3-cyclopropyl-4-methyl-2-oxopyrrolidine-3-carbonitrile (110 mg) obtained in Step C of Example 357 and 4-morpholinoaniline (68 mg) in the same manner as in Step B of Example 2.
MS(ESI+): [M+H]$^+$ 419.4.

Example 358

(3S,5S)-3-cyclopropyl-1-(2-((1-(1-hydroxy-2-methylpropan-2-yl)-1H-pyrazol-4-yl)amino)pyrimidin-4-yl)-5-methyl-2-oxopyrrolidine-3-carbonitrile hydrochloride

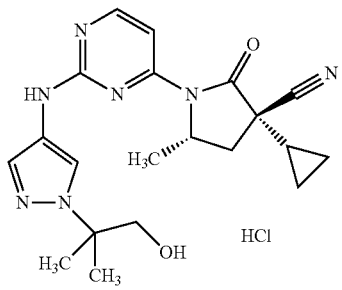 [SMILES: C[C@H]1C[C@@](C#N)(C2CC2)C(=O)N1c1ccnc(Nc2cnn(C(C)(C)CO)c2)n1 ; Cl]

A) ethyl(4S)-4-((tert-butoxycarbonyl)amino)-2-cyano-2-cyclopropylpentanoate

The title compound (5.5 g) was obtained from tert-butyl (4S)-4-methyl-1,2,3-oxathiazolidine-3-carboxylate 2,2-dioxide (4.7 g) and ethyl cyano(cyclopropyl)acetate (3.0 g) obtained in Step A of Example 103 in the same manner as in Step B of Example 103.

$^1$H NMR (400 MHz, DMSO-$d_6$) δ0.32-0.72 (4H, m), 0.96-1.11 (3H, m), 1.21-1.27 (3H, m), 1.28-1.32 (1H, m), 1.33-1.42 (9H, m), 1.84-2.27 (2H, m), 3.58-3.86 (1H, m), 4.10-4.30 (2H, m), 6.41-6.84 (1H, m).

B) (3S,5S)-3-cyclopropyl-5-methyl-2-oxopyrrolidine-3-carbonitrile (3R,5S)-3-cyclopropyl-5-methyl-2-oxopyrrolidine-3-carbonitrile (3S,5S)-3-Cyclopropyl-5-methyl-2-oxopyrrolidine-3-carbonitrile (780 mg) and (3R,5S)-3-cyclopropyl-5-methyl-2-oxopyrrolidine-3-carbonitrile (680 mg) were obtained from ethyl(4S)-4-((tert-butoxycarbonyl)amino)-2-cyano-2-cyclopropylpentanoate (5.5 g) obtained in Step A of Example 358 in the same manner as in Step B of Example 357.

(3S,5S)-3-cyclopropyl-5-methyl-2-oxopyrrolidine-3-carbonitrile $^1$H NMR (400 MHz, DMSO-$d_6$) δ0.40-0.47 (1H, m), 0.49-0.56 (2H, m), 0.60-0.69 (1H, m), 1.15 (3H, d, J=6.1 Hz), 1.23-1.33 (1H, m), 1.67 (1H, dd, J=13.3, 7.5 Hz), 2.59 (1H, dd, J=13.3, 6.7 Hz), 3.64-3.76 (1H, m), 8.46 (1H, brs).

(3R,5S)-3-cyclopropyl-5-methyl-2-oxopyrrolidine-3-carbonitrile $^1$H NMR (400 MHz, DMSO-$d_6$) δ 0.39-0.57 (3H, m), 0.58-0.67 (1H, m), 1.15 (3H, d, J=6.1 Hz), 1.32 (1H, tt, J=8.2, 5.0 Hz), 1.99-2.05 (1H, m), 2.40 (1H, dd, J=13.0, 6.4 Hz), 3.64-3.75 (1H, m), 8.39 (1H, brs).

C) (3S,5S)-3-cyclopropyl-1-(2-((1-(1-hydroxy-2-methylpropan-2-yl)-1H-pyrazol-4-yl)amino)pyrimidin-4-yl)-5-methyl-2-oxopyrrolidine-3-carbonitrile hydrochloride To a mixture of (3S,5S)-3-cyclopropyl-5-methyl-2-oxopyrrolidine-3-carbonitrile (150 mg) obtained in Step B of Example 358, 2-(4-((4-chloropyrimidin-2-yl)amino)-1H-pyrazol-1-yl)-2-methylpropan-1-ol (200 mg) obtained in Step E of Example 347, potassium carbonate (210 mg) and 4,5-bis(diphenylphosphino)-9,9-dimethylxanthene (26 mg) in toluene (2.0 mL) was added tris(dibenzylideneacetone)dipalladium(0) (14 mg), and the mixture was stirred overnight at 85° C. The insoluble substance was removed by filtration through Celite, and the solvent was evaporated under reduced pressure. The residue was purified by silica gel column chromatography (NH, hexane/ethyl acetate), and to a solution of the residue (200 mg) in ethanol (2.0 mL) was added 1 M hydrochloric acid (0.51 mL). The reaction mixture was concentrated under reduced pressure, and the residue was recrystallized (diisopropyl ether/ethyl acetate) to give the title compound (65 mg).
MS(ESI+): [M+H]$^+$ 396.4.

Example 359

(3R,5S)-3-cyclopropyl-1-(2-((1-(1-hydroxy-2-methylpropan-2-yl)-1H-pyrazol-4-yl)amino)pyrimidin-4-yl)-5-methyl-2-oxopyrrolidine-3-carbonitrile hydrochloride

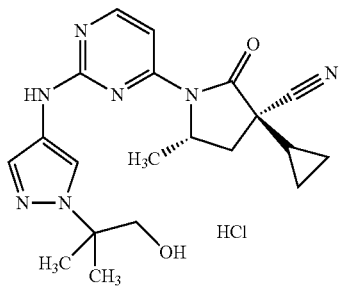 [SMILES: C[C@H]1C[C@](C#N)(C2CC2)C(=O)N1c1ccnc(Nc2cnn(C(C)(C)CO)c2)n1 ; Cl]

The title compound (110 mg) was obtained from (3R,5S)-3-cyclopropyl-5-methyl-2-oxopyrrolidine-3-carbonitrile (150 mg) obtained in Step B of Example 358 and 2-(4-((4-chloropyrimidin-2-yl)amino)-1H-pyrazol-1-yl)-2-methylpropan-1-ol (200 mg) obtained in Step E of Example 347 in the same manner as in Step C of Example 358.
MS(ESI+): [M+H]$^+$ 396.4.

Example 360

(3S,5R)-3-cyclopropyl-1-(2-((1-(1-hydroxy-2-methylpropan-2-yl)-1H-pyrazol-4-yl)amino)pyrimidin-4-yl)-5-methyl-2-oxopyrrolidine-3-carbonitrile hydrochloride

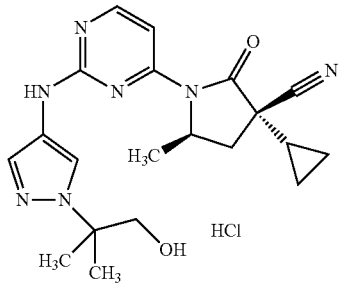 [SMILES: C[C@@H]1C[C@@](C#N)(C2CC2)C(=O)N1c1ccnc(Nc2cnn(C(C)(C)CO)c2)n1 ; Cl]

A) ethyl(4R)-4-((tert-butoxycarbonyl)amino)-2-cyano-2-cyclopropylpentanoate

The title compound (6.3 g) was obtained from tert-butyl (4R)-4-methyl-1,2,3-oxathiazolidine-3-carboxylate 2,2-dioxide (5.1 g) and ethyl cyano(cyclopropyl)acetate (3.3 g) obtained in Step A of Example 103 in the same manner as in Step B of Example 103.
$^1$H NMR (400 MHz, DMSO-d$_6$) δ0.34-0.71 (4H, m), 0.97-1.11 (3H, m), 1.22-1.27 (3H, m), 1.28-1.32 (1H, m), 1.33-1.42 (9H, m), 1.84-2.28 (2H, m), 3.53-3.84 (1H, m), 4.11-4.31 (2H, m), 6.36-6.87 (1H, m).

B) (3S,5R)-3-cyclopropyl-5-methyl-2-oxopyrrolidine-3-carbonitrile (3R,5R)-3-cyclopropyl-5-methyl-2-oxopyrrolidine-3-carbonitrile (3S,5R)-3-Cyclopropyl-5-methyl-2-oxopyrrolidine-3-carbonitrile (1.2 g) and (3R,5R)-3-cyclopropyl-5-methyl-2-oxopyrrolidine-3-carbonitrile (860 mg) were obtained from ethyl(4R)-4-((tert-butoxycarbonyl)amino)-2-cyano-2-cyclopropylpentanoate (5.0 g) obtained in Step A of Example 360 in the same manner as in Step B of Example 357.

(3S,5R)-3-cyclopropyl-5-methyl-2-oxopyrrolidine-3-carbonitrile $^1$H NMR (400 MHz, DMSO-d$_6$) δ 0.40-0.48 (1H, m), 0.48-0.56 (2H, m), 0.61-0.69 (1H, m), 1.15 (3H, d, J=6.1 Hz), 1.23-1.33 (1H, m), 1.67 (1H, dd, J=13.3, 7.5 Hz), 2.59 (1H, dd, J=13.3, 6.7 Hz), 3.64-3.76 (1H, m), 8.47 (1H, brs).

(3R,5R)-3-cyclopropyl-5-methyl-2-oxopyrrolidine-3-carbonitrile $^1$H NMR (400 MHz, DMSO-d$_6$) δ0.39-0.68 (4H, m), 1.15 (3H, d, J=6.4 Hz), 1.27-1.37 (1H, m), 2.02 (1H, dd, J=13.2, 7.8 Hz), 2.40 (1H, dd, J=13.0, 6.4 Hz), 3.64-3.75 (1H, m), 8.39 (1H, brs).

C) (3S,5R)-3-cyclopropyl-1-(2-((1-(1-hydroxy-2-methylpropan-2-yl)-1H-pyrazol-4-yl)amino)pyrimidin-4-yl)-5-methyl-2-oxopyrrolidine-3-carbonitrile hydrochloride The title compound (220 mg) was obtained from (3S,5R)-3-cyclopropyl-5-methyl-2-oxopyrrolidine-3-carbonitrile (150 mg) obtained in Step B of Example 360 and 2-(4-((4-chloropyrimidin-2-yl)amino)-1H-pyrazol-1-yl)-2-methylpropan-1-ol (200 mg) obtained in Step E of Example 347 in the same manner as in Step C of Example 358.
MS(ESI+): [M+H]$^+$ 396.4.

Example 361

(3S,5R)-3-cyclopropyl-5-methyl-1-(2-((4-(morpholin-4-yl)phenyl)amino)pyrimidin-4-yl)-2-oxopyrrolidine-3-carbonitrile hydrochloride

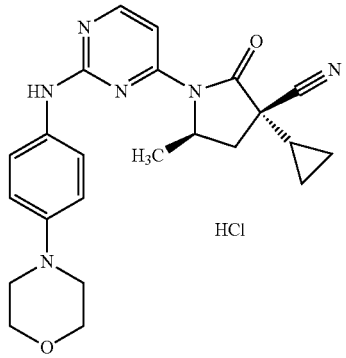 [SMILES: C[C@@H]1C[C@@](C#N)(C2CC2)C(=O)N1c1ccnc(Nc2ccc(N3CCOCC3)cc2)n1 ; Cl]

A) 2-((4-(morpholin-4-yl)phenyl)amino)pyrimidin-4(3H)-one

The title compound (3.2 g) was obtained from 2-(methylsulfanyl)pyrimidin-4(3H)-one (2.4 g) obtained in Step A of Example 347 and 4-morpholinoaniline (3.0 g) in the same manner as in Step C of Example 347.

$^1$H NMR (400 MHz, DMSO-d$_6$) δ 2.98-3.12 (4H, m), 3.64-3.79 (4H, m), 5.71 (1H, brs), 6.90 (2H, d, J=9.0 Hz), 7.41 (2H, d, J=8.3 Hz), 7.67 (1H, brs), 8.60 (1H, brs), 10.70 (1H, brs).

B) 4-chloro-N-(4-(morpholin-4-yl)phenyl)pyrimidin-2-amine

The title compound (2.6 g) was obtained from 2-((4-(morpholin-4-yl)phenyl)amino)pyrimidin-4 (3H)-one (3.2 g) obtained in Step A of Example 361 in the same manner as in Step D of Example 347.

$^1$H NMR (400 MHz, DMSO-d$_6$) δ 2.99-3.09 (4H, m), 3.67-3.78 (4H, m), 6.86 (1H, d, J=5.1 Hz), 6.89-6.94 (2H, m), 7.49-7.57 (2H, m), 8.36 (1H, d, J=5.4 Hz), 9.78 (1H, s).

C) (3S,5R)-3-cyclopropyl-5-methyl-1-(2-((4-(morpholin-4-yl)phenyl)amino)pyrimidin-4-yl)-2-oxopyrrolidine-3-carbonitrile hydrochloride The title compound (140 mg) was obtained from 4-chloro-N-(4-(morpholin-4-yl)phenyl)pyrimidin-2-amine (200 mg) obtained in Step B of Example 361 and (3S,5R)-3-cyclopropyl-5-methyl-2-oxopyrrolidine-3-carbonitrile (140 mg) obtained in Step B of Example 360 in the same manner as in Step C of Example 358.

MS(ESI+): [M+H]$^+$ 419.4.

Example 362

(3S,5S)-3-cyclopropyl-5-methyl-1-(2-((4-(morpholin-4-yl)phenyl)amino)pyrimidin-4-yl)-2-oxopyrrolidine-3-carbonitrile hydrochloride

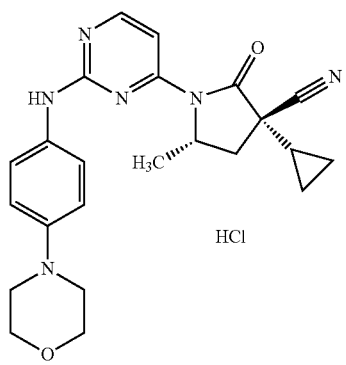 [SMILES: C[C@H]1C[C@@](C#N)(C2CC2)C(=O)N1c1ccnc(Nc2ccc(N3CCOCC3)cc2)n1 ; Cl]

The title compound (83 mg) was obtained from 4-chloro-N-(4-(morpholin-4-yl)phenyl)pyrimidin-2-amine (200 mg) obtained in Step B of Example 361 and (3S,5S)-3-cyclopropyl-5-methyl-2-oxopyrrolidine-3-carbonitrile (140 mg) obtained in Step B of Example 360 in the same manner as in Step C of Example 358.

MS(ESI+): [M+H]$^+$ 419.4.

Example 363

2-(5-((4-((3R)-3-cyano-3-ethyl-2-oxopyrrolidin-1-yl)pyrimidin-2-yl)amino)pyridin-2-yl) acetamide hydrochloride

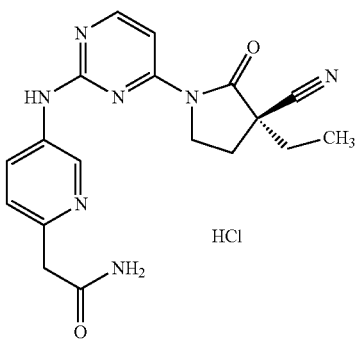 [SMILES: CC[C@]1(C#N)CCN(c2ccnc(Nc3ccc(CC(N)=O)nc3)n2)C1=O ; Cl]

A) ethyl(5-(((benzyloxy)carbonyl)amino)pyridin-2-yl)acetate

To a solution of ethyl(5-aminopyridin-2-yl)acetate (2.0 g) in tetrahydrofuran (30 mL) were successively added pyridine (2.7 mL) and benzyl chloroformate (1.9 mL) in an ice bath, and the mixture was stirred at the same temperature for 3 hr. To the reaction mixture was added water, and the mixture was extracted with ethyl acetate. The obtained organic layer was washed with water and saturated brine, and dried over anhydrous sodium sulfate, and the solvent was evaporated under reduced pressure. The residue was purified by silica gel column chromatography (hexane/ethyl acetate) to give the title compound (2.6 g).

$^1$H NMR (300 MHz, DMSO-d$_6$) δ 1.17 (3H, t, J=7.0 Hz), 3.75 (2H, s), 4.07 (2H, q, J=7.1 Hz), 4.98-5.34 (2H, m), 7.11-7.60 (6H, m), 7.85 (1H, dd, J=8.5, 2.5 Hz), 8.54 (1H, d, J=2.3 Hz), 9.95 (1H, s).

B) sodium (5-(((benzyloxy)carbonyl)amino)pyridin-2-yl)acetate

To a solution of ethyl(5-(((benzyloxy)carbonyl)amino)pyridin-2-yl)acetate (1.0 g) obtained in Step A of Example 363 in a mixed solvent of tetrahydrofuran (20 mL) and 2-propanol (5.0 mL) was added 2 M aqueous sodium hydroxide solution (6.4 mL) in an ice bath, and the mixture was stirred at the same temperature for 3 hr. The reaction mixture was collected by filtration to give the title compound (2.6 g).

$^1$H NMR (400 MHz, DMSO-d$_6$) δ 3.30 (2H, s), 5.15 (2H, s), 7.21 (1H, d, J=8.6 Hz), 7.30-7.49 (5H, m), 7.70 (1H, d, J=8.1 Hz), 8.42 (1H, s), 9.81 (1H, brs).

C) benzyl(6-(2-amino-2-oxoethyl)pyridin-3-yl)carbamate

The title compound (610 mg) was obtained from sodium (5-(((benzyloxy)carbonyl)amino)pyridin-2-yl)acetate (940 mg) obtained in Step B of Example 363 in the same manner as in Step A of Example 350.

$^1$H NMR (400 MHz, DMSO-d$_6$) δ3.50 (2H, s), 5.17 (2H, s), 6.93 (1H, brs), 7.25 (1H, d, J=8.3 Hz), 7.31-7.51 (6H, m), 7.81 (1H, dd, J=8.3, 2.2 Hz), 8.52 (1H, d, J=2.2 Hz), 9.93 (1H, brs).

D) 2-(5-aminopyridin-2-yl)acetamide

The title compound (74 mg) was obtained from benzyl(6-(2-amino-2-oxoethyl)pyridin-3-yl)carbamate (200 mg) obtained in Step C of Example 363 in the same manner as in Step D of Example 348.

$^1$H NMR (400 MHz, DMSO-d$_6$) δ3.34 (2H, s), 5.13 (2H, s), 6.75-6.89 (2H, m), 6.93-6.99 (1H, m), 7.32 (1H, brs), 7.79-7.87 (1H, m).

E) 2-(5-((4-((3R)-3-cyano-3-ethyl-2-oxopyrrolidin-1-yl)pyrimidin-2-yl)amino)pyridin-2-yl)acetamide hydrochloride To a solution of (3R)-1-(2-chloropyrimidin-4-yl)-3-ethyl-2-oxopyrrolidine-3-carbonitrile (130 mg) obtained in Step A of Example 8, 2-(5-aminopyridin-2-yl)acetamide (78 mg) obtained in Step D of Example 363, cesium carbonate (340 mg) and 2,2'-bis(diphenylphosphino)-1,1'-binaphthyl (48 mg) in tetrahydrofuran (5.0 mL) was added tris(dibenzylideneacetone)dipalladium(0) (48 mg), and the mixture was stirred overnight at 80° C. under argon atmosphere. The insoluble substance was removed by filtration through Celite, and the solvent was evaporated under reduced pressure. The residue was purified by silica gel column chromatography (NH, ethyl acetate/methanol). To a solution of the residue (200 mg) in ethanol (2.0 mL) was added 1 M hydrochloric acid (0.55 mL), the mixture was stirred at room temperature for 5 min, and the solvent was evaporated under reduced pressure. The obtained crude crystals were recrystallized (diisopropyl ether/ethanol) to give the title compound (42 mg).

MS(ESI+): [M+H]$^+$ 366.3.

Example 364

4-((4-((3R)-3-cyano-3-ethyl-2-oxopyrrolidin-1-yl)pyrimidin-2-yl)amino)benzamide

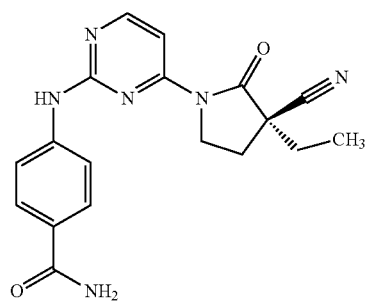

The title compound (200 mg) was obtained from (3R)-1-(2-chloropyrimidin-4-yl)-3-ethyl-2-oxopyrrolidine-3-carbonitrile (150 mg) obtained in Step A of Example 8 and 4-aminobenzamide (90 mg) in the same manner as in Step B of Example 2.

MS(ESI+): [M+H]$^+$ 351.3.

Example 365

4-((4-((3R)-3-cyano-3-ethyl-2-oxopyrrolidin-1-yl)pyrimidin-2-yl)amino)-N,N-dimethylbenzamide

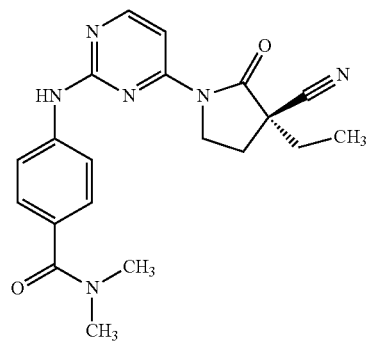 [SMILES: CC[C@]1(C#N)CCN(c2ccnc(Nc3ccc(C(=O)N(C)C)cc3)n2)C1=O]

The title compound (44 mg) was obtained from (3R)-1-(2-chloropyrimidin-4-yl)-3-ethyl-2-oxopyrrolidine-3-carbonitrile (150 mg) obtained in Step A of Example 8 and 4-amino-N,N-dimethylbenzamide (110 mg) in the same manner as in Step B of Example 2.

MS(ESI+): [M+H]$^+$ 379.4.

Example 366

(3S,5R)-3-cyclopropyl-5-methyl-1-(2-((1-methyl-1H-pyrazol-4-yl)amino)pyrimidin-4-yl)-2-oxopyrrolidine-3-carbonitrile

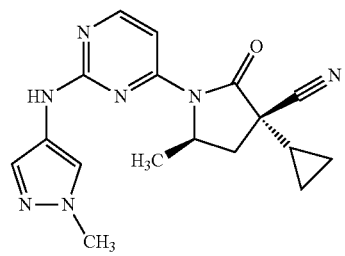 [SMILES: C[C@@H]1C[C@@](C#N)(C2CC2)C(=O)N1c1ccnc(Nc2cnn(C)c2)n1]

A) (3S,5R)-1-(2-chloropyrimidin-4-yl)-3-cyclopropyl-5-methyl-2-oxopyrrolidine-3-carbonitrile The title compound (910 mg) was obtained from (3S,5R)-3-cyclopropyl-5-methyl-2-oxopyrrolidine-3-carbonitrile (600 mg) obtained in Step B of Example 360 and 2,4-dichloropyrimidine (820 mg) in the same manner as in Step D of Example 103.

MS(ESI+): [M+H]$^+$ 277.2.

B) (3S,5R)-3-cyclopropyl-5-methyl-1-(2-((1-methyl-1H-pyrazol-4-yl)amino)pyrimidin-4-yl)-2-oxopyrrolidine-3-carbonitrile The title compound (44 mg) was obtained from (3S,5R)-1-(2-chloropyrimidin-4-yl)-3-cyclopropyl-5-methyl-2-oxopyrrolidine-3-carbonitrile (100 mg) obtained in Step A of Example 366 and 1-methyl-1H-pyrazol-4-amine (37 mg) in the same manner as in Step B of Example 2.

MS(ESI+): [M+H]+ 338.0.

Example 367

2-(4-((4-((3S,5R)-3-cyano-3-cyclopropyl-5-methyl-2-oxopyrrolidin-1-yl) pyrimidin-2-yl)amino)-1H-pyrazol-1-yl)-N-methylacetamide

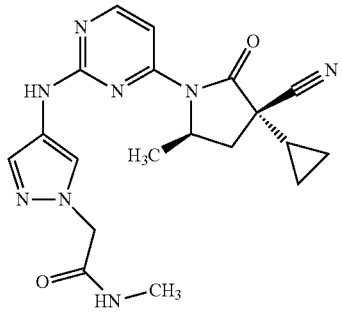 [SMILES: CNC(=O)Cn1cc(Nc2nccc(N3C(=O)[C@](C#N)(C4CC4)C[C@H]3C)n2)cn1]

The title compound (110 mg) was obtained from (3S,5R)-1-(2-chloropyrimidin-4-yl)-3-cyclopropyl-5-methyl-2-oxopyrrolidine-3-carbonitrile (100 mg) obtained in Step A of Example 366 and 2-(4-amino-1H-pyrazol-1-yl)-N-methylacetamide (59 mg) in the same manner as in Step B of Example 2.

MS(ESI+): [M+H]+ 395.1.

Example 368

(3S,5R)-3-cyclopropyl-1-(2-((1-(1,1-dioxidetetrahydro-2H-thiopyran-4-yl)-1H-pyrazol-4-yl)amino)pyrimidin-4-yl)-5-methyl-2-oxopyrrolidine-3-carbonitrile

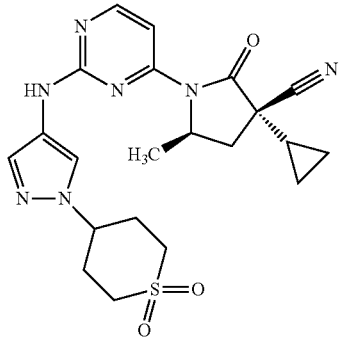 [SMILES: C[C@@H]1C[C@@](C#N)(C2CC2)C(=O)N1c1ccnc(Nc2cnn(C3CCS(=O)(=O)CC3)c2)n1]

The title compound (89 mg) was obtained from (3S,5R)-1-(2-chloropyrimidin-4-yl)-3-cyclopropyl-5-methyl-2-oxopyrrolidine-3-carbonitrile (100 mg) obtained in Step A of Example 366 and 1-(1,1-dioxidetetrahydro-2H-thiopyran-4-yl)-1H-pyrazol-4-amine (82 mg) in the same manner as in Step B of Example 2.

MS(ESI+): [M+H]+ 456.3.

Example 369

(3S,4R)-3-cyclopropyl-1-(2-((1-(1-hydroxy-2-methylpropan-2-yl)-1H-pyrazol-4-yl)amino)pyrimidin-4-yl)-4-methyl-2-oxopyrrolidine-3-carbonitrile hydrochloride

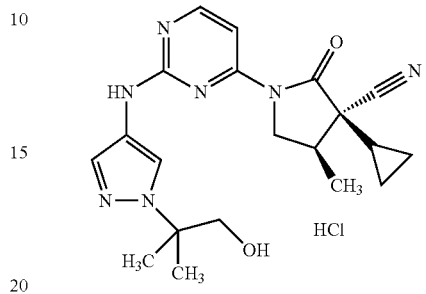

A) (3S,4R)-1-(2-chloropyrimidin-4-yl)-3-cyclopropyl-4-methyl-2-oxopyrrolidine-3-carbonitrile (3R,4S)-1-(2-chloropyrimidin-4-yl)-3-cyclopropyl-4-methyl-2-oxopyrrolidine-3-carbonitrile (3S,4S)-1-(2-chloropyrimidin-4-yl)-3-cyclopropyl-4-methyl-2-oxopyrrolidine-3-carbonitrile (3R,4R)-1-(2-chloropyrimidin-4-yl)-3-cyclopropyl-4-methyl-2-oxopyrrolidine-3-carbonitrile 1-(2-Chloropyrimidin-4-yl)-3-cyclopropyl-4-methyl-2-oxopyrrolidine-3-carbonitrile (2.6 g) obtained in Step C of Example 357 was purified by silica gel column chromatography (hexane/ethyl acetate) to give (3SR,4RS)-1-(2-chloropyrimidin-4-yl)-3-cyclopropyl-4-methyl-2-oxopyrrolidine-3-carbonitrile (820 mg) and (3SR,4SR)-1-(2-chloropyrimidin-4-yl)-3-cyclopropyl-4-methyl-2-oxopyrrolidine-3-carbonitrile (1.3 g). (3SR,4RS)-1-(2-Chloropyrimidin-4-yl)-3-cyclopropyl-4-methyl-2-oxopyrrolidine-3-carbonitrile (810 mg) was resolved by HPLC (column: CHIRALCEL OD, 50 mmID×500 mmL, manufactured by Daicel Chemical Industries, mobile phase: hexane/2-propanol=900/100) to give (3S,4R)-1-(2-chloropyrimidin-4-yl)-3-cyclopropyl-4-methyl-2-oxopyrrolidine-3-carbonitrile (400 mg) having a shorter retention time and (3R,4S)-1-(2-chloropyrimidin-4-yl)-3-cyclopropyl-4-methyl-2-oxopyrrolidine-3-carbonitrile (400 mg) having a longer retention time. (3SR,4SR)-1-(2-Chloropyrimidin-4-yl)-3-cyclopropyl-4-methyl-2-oxopyrrolidine-3-carbonitrile (1.3 g) was resolved by HPLC (column: CHIRALCEL OD, 50 mmID×500 mmL, manufactured by Daicel Chemical Industries, mobile phase: hexane/2-propanol=900/100) to give (3S,4S)-1-(2-chloropyrimidin-4-yl)-3-cyclopropyl-4-methyl-2-oxopyrrolidine-3-carbonitrile (400 mg) having a shorter retention time and (3R,4R)-1-(2-chloropyrimidin-4-yl)-3-cyclopropyl-4-methyl-2-oxopyrrolidine-3-carbonitrile (400 mg) having a longer retention time.

(3SR,4RS)-1-(2-chloropyrimidin-4-yl)-3-cyclopropyl-4-methyl-2-oxopyrrolidine-3-carbonitrile 1H NMR (400 MHz, DMSO-d6) δ0.46-0.55 (2H, m), 0.56-0.63 (1H, m), 0.69-0.81 (1H, m), 1.26 (3H, d, J=6.8 Hz), 1.35-1.54 (1H, m), 2.92-3.15 (1H, m), 3.64 (1H, t, J=10.8 Hz), 4.26 (1H, dd, J=11.0, 8.1 Hz), 8.21 (1H, d, J=5.9 Hz), 8.69 (1H, d, J=5.6 Hz).

(3SR,4SR)-1-(2-chloropyrimidin-4-yl)-3-cyclopropyl-4-methyl-2-oxopyrrolidine-3-carbonitrile $^1$H NMR (400 MHz, DMSO-$d_6$) δ0.50-0.59 (2H, m), 0.62-0.74 (2H, m), 1.26 (3H, d, J=6.8 Hz), 1.47 (1H, tt, J=8.2, 5.1 Hz), 2.65-2.80 (1H, m), 3.64 (1H, dd, J=11.5, 6.1 Hz), 4.25 (1H, dd, J=11.5, 7.1 Hz), 8.22 (1H, d, J=5.9 Hz), 8.70 (1H, d, J=5.9 Hz).

(3S,4R)-1-(2-chloropyrimidin-4-yl)-3-cyclopropyl-4-methyl-2-oxopyrrolidine-3-carbonitrile >99% ee (HPLC (column: CHIRALCEL OD, 4.6 mmID× 250 mmL, manufactured by Daicel Chemical Industries, mobile phase: hexane/2-propanol=900/100, flow rate: 1.0 mL/min, retention time: 16.37 min))

(3R,4S)-1-(2-chloropyrimidin-4-yl)-3-cyclopropyl-4-methyl-2-oxopyrrolidine-3-carbonitrile >99% ee (HPLC (column: CHIRALCEL OD, 4.6 mmID× 250 mmL, manufactured by Daicel Chemical Industries, mobile phase: hexane/2-propanol=900/100, flow rate: 1.0 mL/min, retention time: 26.87 min))

(3S,4S)-1-(2-chloropyrimidin-4-yl)-3-cyclopropyl-4-methyl-2-oxopyrrolidine-3-carbonitrile >99% ee (HPLC (column: CHIRALCEL OD, 4.6 mmID× 250 mmL, manufactured by Daicel Chemical Industries, mobile phase: hexane/2-propanol=900/100, flow rate: 1.0 mL/min, retention time: 13.64 min))

(3R,4R)-1-(2-chloropyrimidin-4-yl)-3-cyclopropyl-4-methyl-2-oxopyrrolidine-3-carbonitrile >99% ee (HPLC (column: CHIRALCEL OD, 4.6 mmID× 250 mmL, manufactured by Daicel Chemical Industries, mobile phase: hexane/2-propanol=900/100, flow rate: 1.0 mL/min, retention time: 18.47 min))

B) (3S,4R)-3-cyclopropyl-1-(2-((1-(1-hydroxy-2-methylpropan-2-yl)-1H-pyrazol-4-yl)amino)pyrimidin-4-yl)-4-methyl-2-oxopyrrolidine-3-carbonitrile hydrochloride The title compound (81 mg) was obtained from (3S,4R)-1-(2-chloropyrimidin-4-yl)-3-cyclopropyl-4-methyl-2-oxopyrrolidine-3-carbonitrile (100 mg) obtained in Step A of Example 369 and 2-(4-amino-1H-pyrazol-1-yl)-2-methylpropan-1-ol (59 mg) obtained in Step H of Example 103 in the same manner as in Step B of Example 2.

MS(ESI+): [M+H]$^+$ 396.4.

Example 370

(3R,4S)-3-cyclopropyl-1-(2-((1-(1-hydroxy-2-methylpropan-2-yl)-1H-pyrazol-4-yl)amino)pyrimidin-4-yl)-4-methyl-2-oxopyrrolidine-3-carbonitrile hydrochloride

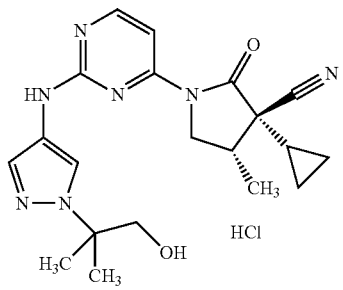 [SMILES: C[C@@H]1CN(c2ccnc(Nc3cnn(C(C)(C)CO)c3)n2)C(=O)[C@]1(C#N)C1CC1 ; Cl]

The title compound (71 mg) was obtained from (3R,4S)-1-(2-chloropyrimidin-4-yl)-3-cyclopropyl-4-methyl-2-oxopyrrolidine-3-carbonitrile (100 mg) obtained in Step A of Example 369 and 2-(4-amino-1H-pyrazol-1-yl)-2-methylpropan-1-ol (59 mg) obtained in Step H of Example 103 in the same manner as in Step B of Example 2.

MS(ESI+): [M+H]$^+$ 396.4.

Example 371

(3S,4S)-3-cyclopropyl-1-(2-((1-(1-hydroxy-2-methylpropan-2-yl)-1H-pyrazol-4-yl)amino)pyrimidin-4-yl)-4-methyl-2-oxopyrrolidine-3-carbonitrile hydrochloride

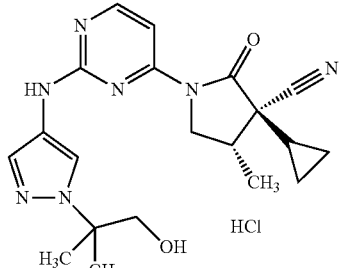

The title compound (97 mg) was obtained from (3S,4S)-1-(2-chloropyrimidin-4-yl)-3-cyclopropyl-4-methyl-2-oxopyrrolidine-3-carbonitrile (100 mg) obtained in Step A of Example 369 and 2-(4-amino-1H-pyrazol-1-yl)-2-methylpropan-1-ol (59 mg) obtained in Step H of Example 103 in the same manner as in Step B of Example 2.

MS(ESI+): [M+H]$^+$ 396.4.

Example 372

(3R,4R)-3-cyclopropyl-1-(2-((1-(1-hydroxy-2-methylpropan-2-yl)-1H-pyrazol-4-yl)amino)pyrimidin-4-yl)-4-methyl-2-oxopyrrolidine-3-carbonitrile hydrochloride

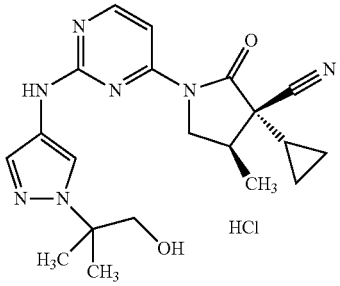 [SMILES: C[C@H]1CN(c2ccnc(Nc3cnn(C(C)(C)CO)c3)n2)C(=O)[C@]1(C#N)C1CC1 ; Cl]

The title compound (94 mg) was obtained from (3R,4R)-1-(2-chloropyrimidin-4-yl)-3-cyclopropyl-4-methyl-2-oxopyrrolidine-3-carbonitrile (100 mg) obtained in Step A of Example 369 and 2-(4-amino-1H-pyrazol-1-yl)-2-methylpropan-1-ol (59 mg) obtained in Step H of Example 103 in the same manner as in Step B of Example 2.

MS(ESI+): [M+H]$^+$ 396.4.

Example 373

4-(4-((4-((3S,5R)-3-cyano-3-cyclopropyl-5-methyl-2-oxopyrrolidin-1-yl)pyrimidin-2-yl)amino)phenyl)tetrahydro-2H-pyran-4-carboxamide

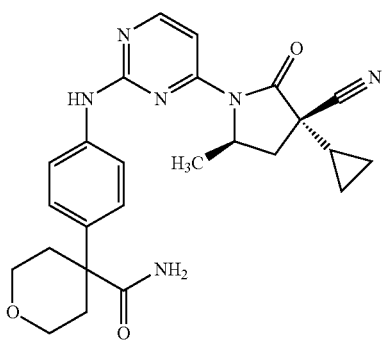 [SMILES: C[C@@H]1C[C@@](C#N)(C2CC2)C(=O)N1c1ccnc(Nc2ccc(C3(C(N)=O)CCOCC3)cc2)n1]

The title compound (110 mg) was obtained from (3S,5R)-1-(2-chloropyrimidin-4-yl)-3-cyclopropyl-5-methyl-2-oxopyrrolidine-3-carbonitrile (100 mg) obtained in Step A of Example 366 and 4-(4-aminophenyl)tetrahydro-2H-pyran-4-carboxamide (84 mg) obtained in Step C of Example 150 in the same manner as in Step B of Example 2.

MS(ESI+): [M+H]$^+$ 461.4.

Example 374

(3R,5R)-3-cyclopropyl-5-ethyl-1-(2-((4-(morpholin-4-yl)phenyl)amino)pyrimidin-4-yl)-2-oxopyrrolidine-3-carbonitrile hydrochloride

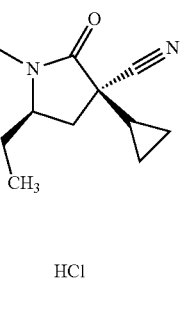

A) (3R,5R)-3-cyclopropyl-5-ethyl-2-oxopyrrolidine-3-carbonitrile (3S,5R)-3-cyclopropyl-5-ethyl-2-oxopyrrolidine-3-carbonitrile (3R,5R)-3-Cyclopropyl-5-ethyl-2-oxopyrrolidine-3-carbonitrile (990 mg) and (3S,5R)-3-cyclopropyl-5-ethyl-2-oxopyrrolidine-3-carbonitrile (590 mg) were obtained from tert-butyl(4R)-4-ethyl-1,2,3-oxathiazolidine-3-carboxylate 2,2-dioxide (4.3 g) and ethyl cyano(cyclopropyl)acetate (2.6 g) obtained in Step A of Example 103 in the same manner as in Step B of Example 103 and Step B of Example 357.

(3R,5R)-3-cyclopropyl-5-ethyl-2-oxopyrrolidine-3-carbonitrile $^1$H NMR (300 MHz, DMSO-d$_6$) δ0.38-0.57 (3H, m), 0.59-0.71 (1H, m), 0.87 (3H, t, J=7.4 Hz), 1.21-1.32 (1H, m), 1.33-1.59 (2H, m), 1.71 (1H, dd, J=13.4, 7.4 Hz), 2.57 (1H, dd, J=13.4, 6.6 Hz), 3.43-3.57 (1H, m), 8.57 (1H, brs).

(3S,5R)-3-cyclopropyl-5-ethyl-2-oxopyrrolidine-3-carbonitrile $^1$H NMR (300 MHz, DMSO-d$_6$) δ0.39-0.70 (4H, m), 0.83-0.93 (3H, m), 1.26-1.55 (3H, m), 2.05 (1H, dd, J=13.0, 7.7 Hz), 2.36 (1H, dd, J=13.2, 6.4 Hz), 3.45-3.57 (1H, m), 8.49 (1H, brs).

B) (3R,5R)-3-cyclopropyl-5-ethyl-1-(2-((4-(morpholin-4-yl)phenyl)amino)pyrimidin-4-yl)-2-oxopyrrolidine-3-carbonitrile hydrochloride The title compound (99 mg) was obtained from (3R,5R)-3-cyclopropyl-5-ethyl-2-oxopyrrolidine-3-carbonitrile (200 mg) obtained in Step A of Example 374 and 4-chloro-N-(4-(morpholin-4-yl)phenyl)pyrimidin-2-amine (270 mg) obtained in Step B of Example 361 in the same manner as in Step C of Example 358.

MS(ESI+): [M+H]$^+$ 433.4.

Example 375

(3S,5R)-3-cyclopropyl-5-ethyl-1-(2-((4-(morpholin-4-yl)phenyl)amino)pyrimidin-4-yl)-2-oxopyrrolidine-3-carbonitrile hydrochloride

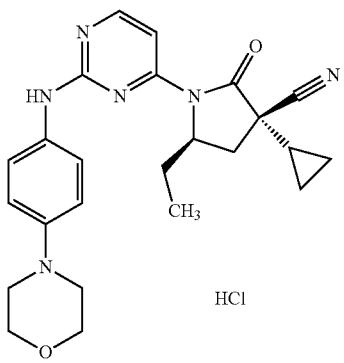 [SMILES: CC[C@@H]1C[C@@](C#N)(C2CC2)C(=O)N1c1ccnc(Nc2ccc(N3CCOCC3)cc2)n1 ; Cl]

The title compound (145 mg) was obtained from (3S,5R)-3-cyclopropyl-5-ethyl-2-oxopyrrolidine-3-carbonitrile (200 mg) obtained in Step A of Example 374 and 4-chloro-N-(4-(morpholin-4-yl)phenyl)pyrimidin-2-amine (272 mg) obtained in Step B of Example 361 in the same manner as in Step C of Example 358.

$^1$H NMR (300 MHz, DMSO-$d_6$) δ0.47-0.64 (3H, m), 0.65-0.75 (1H, m), 0.94 (3H, t, J=7.4 Hz), 1.40-1.52 (1H, m), 1.54-1.69 (1H, m), 2.00-2.16 (1H, m), 2.44 (2H, d, J=5.3 Hz), 3.37 (4H, brs), 3.92 (4H, brs), 4.56 (1H, brs), 7.39 (2H, brs), 7.58 (1H, d, J=5.7 Hz), 7.68 (2H, d, J=8.3 Hz), 8.46 (1H, d, J=5.7 Hz), 9.87 (1H, brs).

MS(ESI+): [M+H]$^+$ 433.4.

Example 376

(3S,4R)-3-cyclopropyl-4-ethyl-1-(2-((1-(1-hydroxy-2-methylpropan-2-yl)-1H-pyrazol-4-yl)amino)pyrimidin-4-yl)-2-oxopyrrolidine-3-carbonitrile hydrochloride

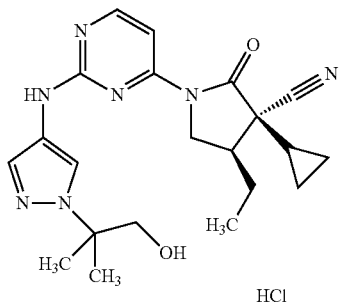 [SMILES: CC[C@H]1CN(c2ccnc(Nc3cnn(C(C)(C)CO)c3)n2)C(=O)[C@@]1(C#N)C1CC1 ; Cl]

A) ethyl 3-(((tert-butoxycarbonyl)amino)methyl)-2-cyano-2-cyclopropylpentanoate

The title compound (11 g) was obtained from tert-butyl 5-ethyl-1,2,3-oxathiazolidine-3-carboxylate 2,2-dioxide (15 g) and ethyl cyano(cyclopropyl)acetate (9.1 g) obtained in Step A of Example 103 in the same manner as in Step B of Example 103.

MS(ESI+): [M+H]$^+$ 325.3.

B) 3-cyclopropyl-4-ethyl-2-oxopyrrolidine-3-carbonitrile

The title compound (3.7 g) was obtained from ethyl 3-(((tert-butoxycarbonyl)amino)methyl)-2-cyano-2-cyclopropylpentanoate (11 g) obtained in Step A of Example 376 in the same manner as in Step B of Example 357.

$^1$H NMR (300 MHz, DMSO-$d_6$) δ0.35-0.72 (4H, m), 0.86-1.05 (3H, m), 1.20-1.25 (1H, m), 1.37-1.62 (1H, m), 1.64-1.82 (1H, m), 2.24-2.76 (1H, m), 2.84-3.05 (1H, m), 3.33-3.48 (1H, m), 8.28 (1H, d, J=14.0 Hz).

C) (3S,4R)-1-(2-chloropyrimidin-4-yl)-3-cyclopropyl-4-ethyl-2-oxopyrrolidine-3-carbonitrile (3R,4S)-1-(2-chloropyrimidin-4-yl)-3-cyclopropyl-4-ethyl-2-oxopyrrolidine-3-carbonitrile (3S,4S)-1-(2-chloropyrimidin-4-yl)-3-cyclopropyl-4-ethyl-2-oxopyrrolidine-3-carbonitrile (3R,4R)-1-(2-chloropyrimidin-4-yl)-3-cyclopropyl-4-ethyl-2-oxopyrrolidine-3-carbonitrile To a mixture of 3-cyclopropyl-4-ethyl-2-oxopyrrolidine-3-carbonitrile (3.7 g) obtained in Step B of Example 376, 2,4-dichloropyrimidine (3.1 g), cesium carbonate (13 g) and 4,5-bis(diphenylphosphino)-9,9-dimethylxanthene (0.71 g) in tetrahydrofuran (55 mL) was added tris(dibenzylideneacetone)dipalladium(0) (0.38 g), and the mixture was stirred overnight at 85° C. The insoluble substance was removed by filtration through Celite, and the solvent was evaporated under reduced pressure. The residue was purified by silica gel column chromatography (hexane/ethyl acetate) to give (3SR,4RS)-1-(2-chloropyrimidin-4-yl)-3-cyclopropyl-4-ethyl-2-oxopyrrolidine-3-carbonitrile (1.3 g) and (3SR,4SR)-1-(2-chloropyrimidin-4-yl)-3-cyclopropyl-4-ethyl-2-oxopyrrolidine-3-carbonitrile (1.6 g). (3SR,4RS)-1-(2-Chloropyrimidin-4-yl)-3-cyclopropyl-4-ethyl-2-oxopyrrolidine-3-carbonitrile (1.3 g) was resolved by HPLC (column: CHIRALCEL OD, 50 mmID×500 mmL, manufactured by Daicel Chemical Industries, mobile phase: hexane/2-propanol=700/300) to give (3S,4R)-1-(2-chloropyrimidin-4-yl)-3-cyclopropyl-4-ethyl-2-oxopyrrolidine-3-carbonitrile (500 mg) having a shorter retention time and (3R,4S)-1-(2-chloropyrimidin-4-yl)-3-cyclopropyl-4-ethyl-2-oxopyrrolidine-3-carbonitrile (510 mg) having a longer retention time. (3SR,4SR)-1-(2-Chloropyrimidin-4-yl)-3-cyclopropyl-4-ethyl-2-oxopyrrolidine-3-carbonitrile (1.6 g) was resolved by HPLC (column: CHIRALCEL OD, 50 mmID×500 mmL, manufactured by Daicel Chemical Industries, mobile phase: hexane/2-propanol=700/300) to give (3S,4S)-1-(2-chloropyrimidin-4-yl)-3-cyclopropyl-4-ethyl-2-oxopyrrolidine-3-carbonitrile (560 mg) having a shorter retention time and (3R,4R)-1-(2-chloropyrimidin-4-yl)-3-cyclopropyl-4-ethyl-2-oxopyrrolidine-3-carbonitrile (600 mg) having a longer retention time.

(3SR,4RS)-1-(2-chloropyrimidin-4-yl)-3-cyclopropyl-4-ethyl-2-oxopyrrolidine-3-carbonitrile $^1$H NMR (400 MHz, DMSO-$d_6$) δ0.45-0.53 (1H, m), 0.54-0.62 (2H, m), 0.70-0.78 (1H, m), 1.04 (3H, t, J=7.5 Hz), 1.46 (1H, tt, J=8.0, 5.2 Hz), 1.65-1.85 (2H, m), 2.83-2.97 (1H, m), 3.64 (1H, t, J=10.9 Hz), 4.26 (1H, dd, J=11.0, 8.1 Hz), 8.22 (1H, d, J=5.9 Hz), 8.69 (1H, d, J=5.9 Hz).

(3SR,4SR)-1-(2-chloropyrimidin-4-yl)-3-cyclopropyl-4-ethyl-2-oxopyrrolidine-3-carbonitrile $^1$H NMR (400 MHz, DMSO-d$_6$) δ0.50-0.61 (2H, m), 0.63-0.77 (2H, m), 1.01 (3H, t, J=7.5 Hz), 1.41-1.50 (1H, m), 1.57 (1H, ddd, J=13.6, 9.8, 7.3 Hz), 1.78 (1H, ddd, J=13.6, 7.5, 4.4 Hz), 2.52-2.62 (1H, m), 3.69 (1H, dd, J=11.5, 6.6 Hz), 4.25 (1H, dd, J=11.4, 7.5 Hz), 8.22 (1H, d, J=5.9 Hz), 8.70 (1H, d, J=5.9 Hz).

(3S,4R)-1-(2-chloropyrimidin-4-yl)-3-cyclopropyl-4-ethyl-2-oxopyrrolidine-3-carbonitrile >99% ee (HPLC (column: CHIRALCEL OD, 4.6 mmID× 250 mmL, manufactured by Daicel Chemical Industries, mobile phase: hexane/2-propanol=700/300, flow rate: 1.0 mL/min, retention time: 8.02 min))

(3R,4S)-1-(2-chloropyrimidin-4-yl)-3-cyclopropyl-4-ethyl-2-oxopyrrolidine-3-carbonitrile >99% ee (HPLC (column: CHIRALCEL OD, 4.6 mmID× 250 mmL, manufactured by Daicel Chemical Industries, mobile phase: hexane/2-propanol=700/300, flow rate: 1.0 mL/min, retention time: 12.48 min))

(3S,4S)-1-(2-chloropyrimidin-4-yl)-3-cyclopropyl-4-ethyl-2-oxopyrrolidine-3-carbonitrile >99% ee (HPLC (column: CHIRALCEL OD, 4.6 mmID× 250 mmL, manufactured by Daicel Chemical Industries, mobile phase: hexane/2-propanol=700/300, flow rate: 1.0 mL/min, retention time: 7.14 min))

(3R,4R)-1-(2-chloropyrimidin-4-yl)-3-cyclopropyl-4-ethyl-2-oxopyrrolidine-3-carbonitrile >99% ee (HPLC (column: CHIRALCEL OD, 4.6 mmID× 250 mmL, manufactured by Daicel Chemical Industries, mobile phase: hexane/2-propanol=700/300, flow rate: 1.0 mL/min, retention time: 9.07 min))

D) (3S,4R)-3-cyclopropyl-4-ethyl-1-(2-((1-(1-hydroxy-2-methylpropan-2-yl)-1H-pyrazol-4-yl)amino)pyrimidin-4-yl)-2-oxopyrrolidine-3-carbonitrile hydrochloride The title compound (87 mg) was obtained from (3S,4R)-1-(2-chloropyrimidin-4-yl)-3-cyclopropyl-4-ethyl-2-oxopyrrolidine-3-carbonitrile (100 mg) obtained in Step C of Example 376 and 2-(4-amino-1H-pyrazol-1-yl)-2-methylpropan-1-ol (56 mg) obtained in Step H of Example 103 in the same manner as in Step B of Example 2.

MS(ESI+): [M+H]$^+$ 410.4.

Example 377

(3R,4S)-3-cyclopropyl-4-ethyl-1-(2-((1-(1-hydroxy-2-methylpropan-2-yl)-1H-pyrazol-4-yl)amino)pyrimidin-4-yl)-2-oxopyrrolidine-3-carbonitrile hydrochloride

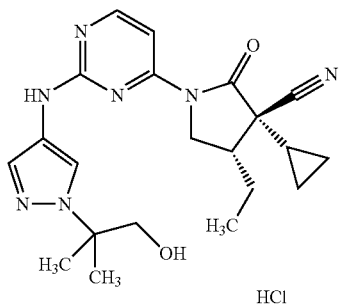 [SMILES: CC[C@@H]1CN(c2ccnc(Nc3cnn(C(C)(C)CO)c3)n2)C(=O)[C@]1(C#N)C1CC1 ; Cl]

The title compound (87 mg) was obtained from (3R,4S)-1-(2-chloropyrimidin-4-yl)-3-cyclopropyl-4-ethyl-2-oxopyrrolidine-3-carbonitrile (100 mg) obtained in Step C of Example 376 and 2-(4-amino-1H-pyrazol-1-yl)-2-methylpropan-1-ol (56 mg) obtained in Step H of Example 103 in the same manner as in Step B of Example 2.

MS(ESI+): [M+H]$^+$ 410.4.

Example 378

(3S,4S)-3-cyclopropyl-4-ethyl-1-(2-((1-(1-hydroxy-2-methylpropan-2-yl)-1H-pyrazol-4-yl)amino)pyrimidin-4-yl)-2-oxopyrrolidine-3-carbonitrile hydrochloride

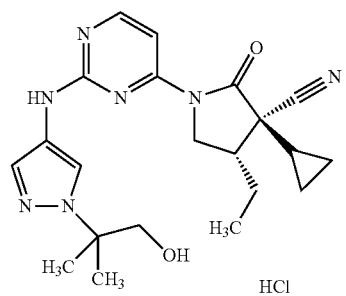 [SMILES: CC[C@@H]1CN(c2ccnc(Nc3cnn(C(C)(C)CO)c3)n2)C(=O)[C@@]1(C#N)C1CC1 ; Cl]

The title compound (70 mg) was obtained from (3S,4S)-1-(2-chloropyrimidin-4-yl)-3-cyclopropyl-4-ethyl-2-oxopyrrolidine-3-carbonitrile (100 mg) obtained in Step C of Example 376 and 2-(4-amino-1H-pyrazol-1-yl)-2-methylpropan-1-ol (56 mg) obtained in Step H of Example 103 in the same manner as in Step B of Example 2.

MS(ESI+): [M+H]$^+$ 410.4.

Example 379

(3R,4R)-3-cyclopropyl-4-ethyl-1-(2-((1-(1-hydroxy-2-methylpropan-2-yl)-1H-pyrazol-4-yl)amino)pyrimidin-4-yl)-2-oxopyrrolidine-3-carbonitrile hydrochloride

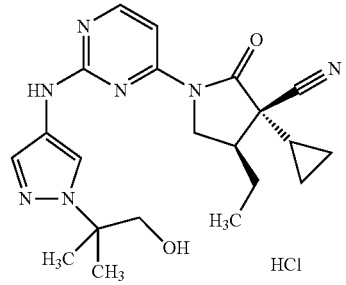 [SMILES: CC[C@H]1CN(c2ccnc(Nc3cnn(C(C)(C)CO)c3)n2)C(=O)[C@]1(C#N)C1CC1 ; Cl]

The title compound (63 mg) was obtained from (3R,4R)-1-(2-chloropyrimidin-4-yl)-3-cyclopropyl-4-ethyl-2-oxopyrrolidine-3-carbonitrile (100 mg) obtained in Step C of Example 376 and 2-(4-amino-1H-pyrazol-1-yl)-2-methylpropan-1-ol (56 mg) obtained in Step H of Example 103 in the same manner as in Step B of Example 2.

MS(ESI+): [M+H]$^+$ 410.4.

Example 380 tert-butyl 4-(5-((4-((3S,5R)-3-cyano-3-cyclopropyl-5-methyl-2-oxopyrrolidin-1-yl) pyrimidin-2-yl)amino)pyridin-2-yl)piperidine-1-carboxylate

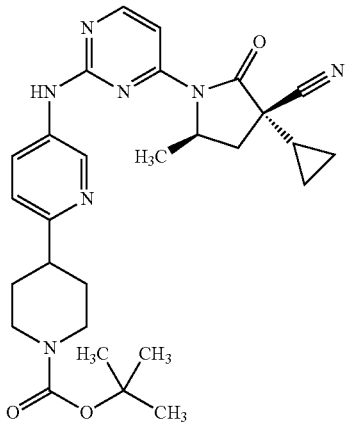 [SMILES: C[C@@H]1C[C@@](C#N)(C2CC2)C(=O)N1c1ccnc(Nc2ccc(C3CCN(C(=O)OC(C)(C)C)CC3)nc2)n1]

The title compound (280 mg) was obtained from (3S,5R)-1-(2-chloropyrimidin-4-yl)-3-cyclopropyl-5-methyl-2-oxopyrrolidine-3-carbonitrile (100 mg) obtained in Step A of Example 366 and tert-butyl 4-(5-aminopyridin-2-yl)piperidine-1-carboxylate (300 mg) in the same manner as in Example 56.

MS(ESI+): [M+H]$^+$ 518.5.

Example 381

4-(4-((4-((3R,4S)-3-cyano-3-cyclopropyl-4-methyl-2-oxopyrrolidin-1-yl)pyrimidin-2-yl)amino)phenyl)tetrahydro-2H-pyran-4-carboxamide hydrochloride

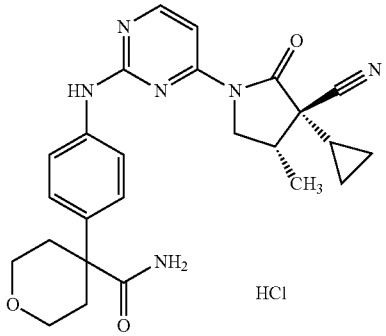 [SMILES: C[C@@H]1CN(c2ccnc(Nc3ccc(C4(C(N)=O)CCOCC4)cc3)n2)C(=O)[C@]1(C#N)C1CC1 ; Cl]

The title compound (110 mg) was obtained from (3R,4S)-1-(2-chloropyrimidin-4-yl)-3-cyclopropyl-4-methyl-2-oxopyrrolidine-3-carbonitrile (92 mg) obtained in Step A of Example 369 and 4-(4-aminophenyl)tetrahydro-2H-pyran-4-carboxamide (77 mg) obtained in Step C of Example 150 in the same manner as in Step B of Example 2.

MS(ESI+): [M+H]$^+$ 461.4.

Example 382

(3S,5R)-3-cyclopropyl-5-methyl-2-oxo-1-(2-((6-(piperidin-4-yl)pyridin-3-yl)amino)pyrimidin-4-yl)pyrrolidine-3-carbonitrile hydrochloride

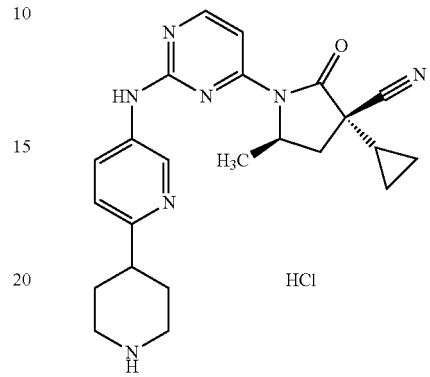

The title compound (290 mg) was obtained from tert-butyl 4-(5-((4-((3S,5R)-3-cyano-3-cyclopropyl-5-methyl-2-oxopyrrolidin-1-yl)pyrimidin-2-yl)amino)pyridin-2-yl)piperidine-1-carboxylate (280 mg) obtained in Example 380 in the same manner as in Step B of Example 348.

MS(ESI+): [M+H]$^+$ 418.4.

Example 383

(3S,5R)-1-(2-((6-(1-acetylpiperidin-4-yl)pyridin-3-yl)amino)pyrimidin-4-yl)-3-cyclopropyl-5-methyl-2-oxopyrrolidine-3-carbonitrile

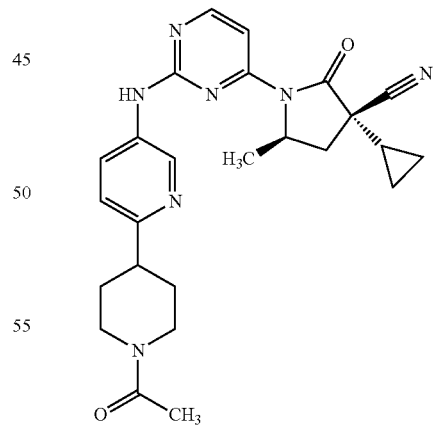

The title compound (48 mg) was obtained from (3S,5R)-3-cyclopropyl-5-methyl-2-oxo-1-(2-((6-(piperidin-4-yl)pyridin-3-yl)amino)pyrimidin-4-yl)pyrrolidine-3-carbonitrile hydrochloride (100 mg) obtained in Example 382 in the same manner as in Step C of Example 348.

MS(ESI+): [M+H]$^+$ 460.2.

Example 384

(3S,5R)-3-cyclopropyl-5-ethyl-1-(2-((1-(1-hydroxy-2-methylpropan-2-yl)-1H-pyrazol-4-yl)amino)pyrimidin-4-yl)-2-oxopyrrolidine-3-carbonitrile hydrochloride

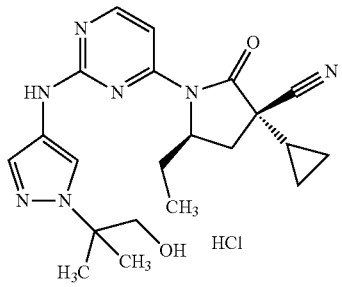 [SMILES: CC[C@@H]1C[C@@](C#N)(C2CC2)C(=O)N1c1ccnc(Nc2cnn(C(C)(C)CO)c2)n1 ; Cl]

The title compound (47 mg) was obtained from 2-(4-((4-chloropyrimidin-2-yl)amino)-1H-pyrazol-1-yl)-2-methyl-propan-1-ol (250 mg) obtained in Step E of Example 347 and (3S,5R)-3-cyclopropyl-5-ethyl-2-oxopyrrolidine-3-carbonitrile (200 mg) obtained in Step A of Example 374 in the same manner as in Step F of Example 347.

MS(ESI+): [M+H]⁺ 410.4.

Example 385

(3S,5R)-3-cyclopropyl-1-(2-((6-(1-(methoxyacetyl)piperidin-4-yl)pyridin-3-yl)amino)pyrimidin-4-yl)-5-methyl-2-oxopyrrolidine-3-carbonitrile

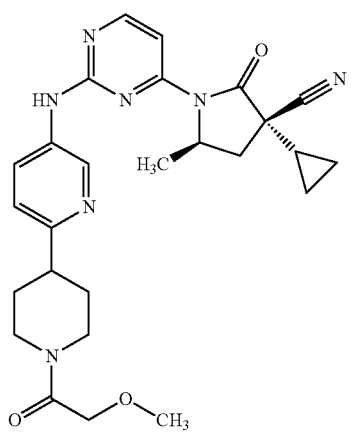 [SMILES: COCC(=O)N1CCC(c2ccc(Nc3nccc(N4C(=O)[C@](C#N)(C5CC5)C[C@H]4C)n3)cn2)CC1]

The title compound (30 mg) was obtained from (3S,5R)-3-cyclopropyl-5-methyl-2-oxo-1-(2-((6-(piperidin-4-yl)pyridin-3-yl)amino)pyrimidin-4-yl)pyrrolidine-3-carbonitrile hydrochloride (100 mg) obtained in Example 382 and meth- oxyacetyl chloride (18 μL) in the same manner as in Step C of Example 348.

MS(ESI+): [M+H]⁺ 490.5.

Example 386

2-(4-((4-((3R,4S)-3-cyano-3-cyclopropyl-4-methyl-2-oxopyrrolidin-1-yl)pyrimidin-2-yl)amino)-1H-pyrazol-1-yl)-2-methylpropanamide

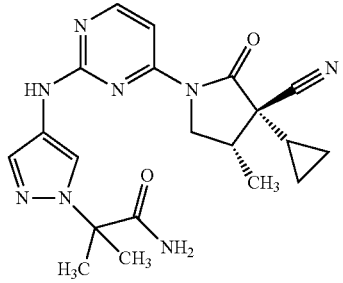 [SMILES: C[C@@H]1CN(c2ccnc(Nc3cnn(C(C)(C)C(N)=O)c3)n2)C(=O)[C@]1(C#N)C1CC1]

The title compound (78 mg) was obtained from (3R,4S)-1-(2-chloropyrimidin-4-yl)-3-cyclopropyl-4-methyl-2-oxopyrrolidine-3-carbonitrile (100 mg) obtained in Step A of Example 369 and 2-(4-amino-1H-pyrazol-1-yl)-2-methylpropanamide (61 mg) obtained in Step C of Example 109 in the same manner as in Step B of Example 2.

MS(ESI+): [M+H]⁺ 409.4.

Example 387

5-((4-((3S,5R)-3-cyano-3-cyclopropyl-5-methyl-2-oxopyrrolidin-1-yl)pyrimidin-2-yl)amino)-N,N-dimethylpyridine-2-carboxamide hydrochloride

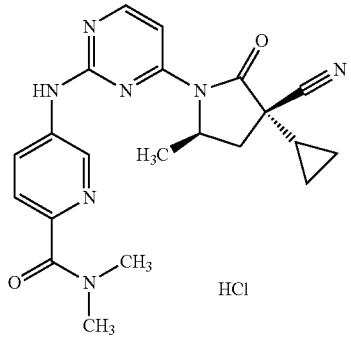 [SMILES: C[C@@H]1C[C@@](C#N)(C2CC2)C(=O)N1c1ccnc(Nc2ccc(C(=O)N(C)C)nc2)n1 ; Cl]

The title compound (25 mg) was obtained from (3S,5R)-1-(2-chloropyrimidin-4-yl)-3-cyclopropyl-5-methyl-2-oxopyrrolidine-3-carbonitrile (250 mg) obtained in Step A of Example 366 and 5-amino-N,N-dimethylpicolinamide (150 mg) in the same manner as in Example 56.

MS(ESI+): [M+H]⁺ 406.3.

Example 388 ethyl 3-cyclopropyl-1-(2-((4-(morpholin-4-yl)phenyl)amino)pyrimidin-4-yl)-2-oxopyrrolidine-3-carboxylate

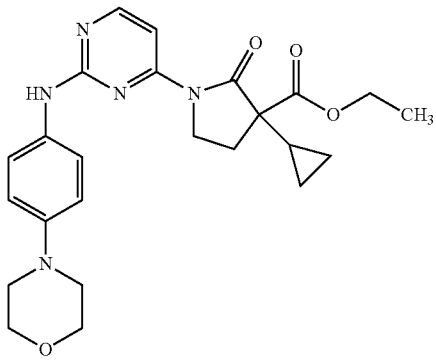 [SMILES: CCOC(=O)C1(C2CC2)CCN(c2ccnc(Nc3ccc(N4CCOCC4)cc3)n2)C1=O]

A) diethyl cyclopropylmalonate

To a solution of ethyl cyano(cyclopropyl)acetate (17 g) obtained in Step A of Example 103 in ethanol (150 mL) was added conc. hydrochloric acid (150 mL) at room temperature, and the mixture was stirred at 100° C. for 2 hr. The reaction mixture was concentrated under reduced pressure, to the obtained residue was added water, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (10 g).
$^1$H NMR (300 MHz, DMSO-$d_6$) δ 0.21-0.33 (2H, m), 0.49-0.60 (2H, m), 1.14-1.23 (7H, m), 2.84 (1H, d, J=9.8 Hz), 4.13 (4H, q, J=7.2 Hz).

B) diethyl(2-((tert-butoxycarbonyl)amino)ethyl)(cyclopropyl)malonate

To a solution of diethyl cyclopropylmalonate (7.7 g) obtained in Step A of Example 388 in N,N-dimethylformamide (90 mL) was added sodium hydride (60% in mineral oil, 1.8 g), and the mixture was stirred at 0° C. for 30 min. To the reaction mixture was added tert-butyl 1,2,3-oxathiazolidine-3-carboxylate 2,2-dioxide (9.4 g) at the same temperature, and the mixture was stirred at 0° C. for 2 hr. To the reaction mixture was added 1M hydrochloric acid, and the mixture was extracted with ethyl acetate. The obtained organic layer was washed with water and saturated brine, and dried over anhydrous magnesium sulfate, and the solvent was evaporated under reduced pressure. The residue was purified by silica gel column chromatography (hexane/ethyl acetate) to give the title compound (6.7 g).
$^1$H NMR (300 MHz, DMSO-$d_6$) δ0.21-0.33 (2H, m), 0.43-0.58 (2H, m), 1.11-1.21 (6H, m), 1.29-1.42 (10H, m), 1.79-1.91 (2H, m), 2.96 (2H, dt, J=10.7, 5.4 Hz), 4.10 (4H, q, J=6.9 Hz), 6.80 (1H, t, J=5.3 Hz).

C) ethyl 3-cyclopropyl-2-oxopyrrolidine-3-carboxylate

The title compound (3.6 g) was obtained from diethyl(2-((tert-butoxycarbonyl)amino)ethyl)(cyclopropyl)malonate (6.7 g) obtained in Step B of Example 388 in the same manner as in Step B of Example 357.
$^1$H NMR (300 MHz, DMSO-$d_6$) δ0.05-0.22 (1H, m), 0.31-0.41 (1H, m), 0.43-0.53 (2H, m), 1.18 (3H, t, J=7.2 Hz), 1.25-1.37 (1H, m), 1.66-1.82 (1H, m), 2.25 (1H, ddd, J=13.1, 8.0, 5.3 Hz), 3.07-3.29 (2H, m), 4.02-4.18 (2H, m), 7.87 (1H, brs).

D) ethyl 3-cyclopropyl-1-(2-((4-(morpholin-4-yl)phenyl)amino)pyrimidin-4-yl)-2-oxopyrrolidine-3-carboxylate The title compound (23 mg) was obtained from ethyl 3-cyclopropyl-2-oxopyrrolidine-3-carboxylate (48 mg) obtained in Step C of Example 388 and 4-chloro-N-(4-(morpholin-4-yl)phenyl)pyrimidin-2-amine (71 mg) obtained in Step B of Example 361 in the same manner as in Step C of Example 361.
MS(ESI+): [M+H]$^+$ 452.4.

Example 389

2-(4-((4-((3S,5R)-3-cyano-3-cyclopropyl-5-methyl-2-oxopyrrolidin-1-yl)pyrimidin-2-yl)amino)phenyl)-2-methylpropanoic acid

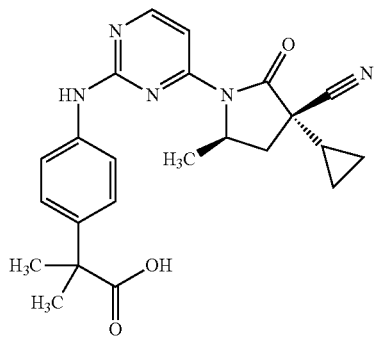 [SMILES: C[C@@H]1C[C@@](C#N)(C2CC2)C(=O)N1c1ccnc(Nc2ccc(C(C)(C)C(=O)O)cc2)n1]

The title compound (220 mg) was obtained from (3S,5R)-1-(2-chloropyrimidin-4-yl)-3-cyclopropyl-5-methyl-2-oxopyrrolidine-3-carbonitrile (200 mg) obtained in Step A of Example 366 and 2-(4-aminophenyl)-2-methylpropanoic acid (140 mg) in the same manner as in Step B of Example 2.
MS(ESI+): [M+H]$^+$ 420.3.

Example 390

4-((4-((3S,5R)-3-cyano-3-cyclopropyl-5-methyl-2-oxopyrrolidin-1-yl)pyrimidin-2-yl)amino)benzamide hydrochloride

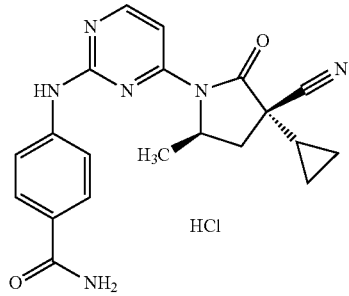 [SMILES: C[C@@H]1C[C@@](C#N)(C2CC2)C(=O)N1c1ccnc(Nc2ccc(C(N)=O)cc2)n1 ; Cl]

The title compound (120 mg) was obtained from (3S,5R)-1-(2-chloropyrimidin-4-yl)-3-cyclopropyl-5-methyl-2-oxopyrrolidine-3-carbonitrile (150 mg) obtained in Step A of Example 366 and 4-aminobenzamide (89 mg) in the same manner as in Step B of Example 2.
MS(ESI+): [M+H]+ 377.3.

Example 391

4-((4-((3S,5R)-3-cyano-3-cyclopropyl-5-methyl-2-oxopyrrolidin-1-yl) pyrimidin-2-yl)amino)-N-methylbenzamide hydrochloride

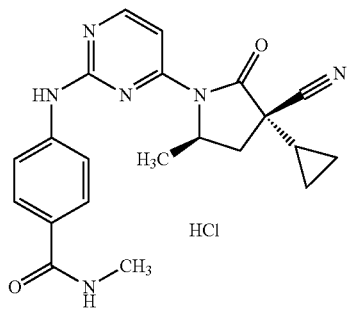 [SMILES: CNC(=O)c1ccc(Nc2nccc(N3C(=O)[C@](C#N)(C4CC4)C[C@H]3C)n2)cc1 ; Cl]

The title compound (170 mg) was obtained from (3S,5R)-1-(2-chloropyrimidin-4-yl)-3-cyclopropyl-5-methyl-2-oxopyrrolidine-3-carbonitrile (150 mg) obtained in Step A of Example 366 and 4-amino-N-methylbenzamide (98 mg) in the same manner as in Step B of Example 2.
MS(ESI+): [M+H]+ 391.4.

Example 392 ethyl 3-cyclopropyl-1-(2-((1-methyl-1H-pyrazol-4-yl)amino)pyrimidin-4-yl)-2-oxopyrrolidine-3-carboxylate

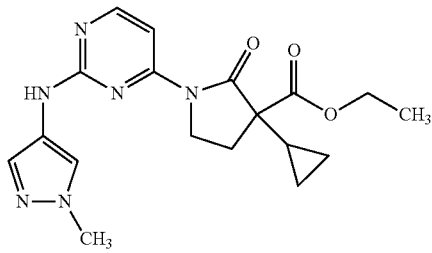 [SMILES: CCOC(=O)C1(C2CC2)CCN(c2ccnc(Nc3cnn(C)c3)n2)C1=O]

A) 2-((1-methyl-1H-pyrazol-4-yl)amino)pyrimidin-4(3H)-one

The title compound (5.4 g) was obtained from 2-(methylsulfanyl)pyrimidin-4(3H)-one (5.2 g) obtained in Step A of Example 347 and 1-methyl-1H-pyrazol-4-amine (4.1 g) in the same manner as in Step C of Example 347.
$^1$H NMR (400 MHz, DMSO-$d_6$) δ ppm 3.79 (3H, s), 5.62-5.78 (1H, m), 7.45 (1H, s), 7.63-7.78 (1H, m), 7.89 (1H, s), 8.47-8.75 (1H, m), 10.77 (1H, dd, J=15.5, 8.7 Hz).

B) 4-chloro-N-(1-methyl-1H-pyrazol-4-yl)pyrimidin-2-amine

The title compound (3.3 g) was obtained from 2-((1-methyl-1H-pyrazol-4-yl)amino)pyrimidin-4(3H)-one (3.4 g) obtained in Step A of Example 392 in the same manner as in Step D of Example 347.
$^1$H NMR (400 MHz, DMSO-$d_6$) δ ppm 3.81 (3H, s), 6.83 (1H, d, J=5.3 Hz), 7.46 (1H, s), 7.85 (1H, s), 8.37 (1H, d, J=5.3 Hz), 9.87 (1H, s).

C) ethyl 3-cyclopropyl-1-(2-((1-methyl-1H-pyrazol-4-yl)amino)pyrimidin-4-yl)-2-oxopyrrolidine-3-carboxylate The title compound (346 mg) was obtained from 4-chloro-N-(1-methyl-1H-pyrazol-4-yl)pyrimidin-2-amine (260 mg) obtained in Step B of Example 392 and ethyl 3-cyclopropyl-2-oxopyrrolidine-3-carboxylate (240 mg) obtained in Step C of Example 388 in the same manner as in Step F of Example 347.
MS (ESI+): [M+H]+ 371.3.

Example 393

3-cyclopropyl-3-(hydroxymethyl)-1-(2-((1-methyl-1H-pyrazol-4-yl)amino)pyrimidin-4-yl)pyrrolidin-2-one

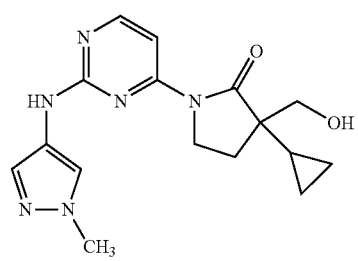 [SMILES: Cn1cc(Nc2nccc(N3CCC(CO)(C4CC4)C3=O)n2)cn1]

The title compound (50 mg) was obtained from ethyl 3-cyclopropyl-1-(2-((1-methyl-1H-pyrazol-4-yl)amino)pyrimidin-4-yl)-2-oxopyrrolidine-3-carboxylate (330 mg) obtained in Step C of Example 392 in the same manner as in Step E of Example 347.
MS(ESI+): [M+H]+ 329.3.

Example 394

(3S)-3-cyclopropyl-1-(2-((1-(1,1-dioxidetetrahydro-2H-thiopyran-4-yl)-1H-pyrazol-4-yl)amino)pyrimidin-4-yl)-2-oxopyrrolidine-3-carbonitrile

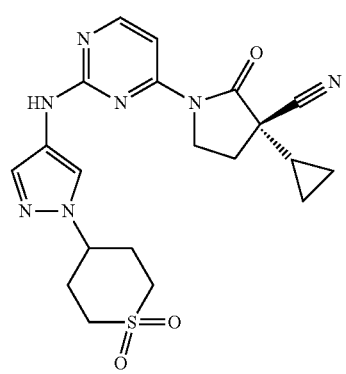

The title compound (72 mg) was obtained from (3S)-1-(2-chloropyrimidin-4-yl)-3-cyclopropyl-2-oxopyrrolidine-3- carbonitrile (100 mg) obtained in Step E of Example 103 and 1-(1,1-dioxidetetrahydro-2H-thiopyran-4-yl)-1H-pyrazol-4-amine (86 mg) in the same manner as in Step B of Example 2.

MS(ESI+): [M+H]$^+$ 442.1.

Example 395

(3R,4S)-3-cyclopropyl-1-(2-((1-(1,1-dioxidetetrahydro-2H-thiopyran-4-yl)-1H-pyrazol-4-yl)amino)pyrimidin-4-yl)-4-methyl-2-oxopyrrolidine-3-carbonitrile

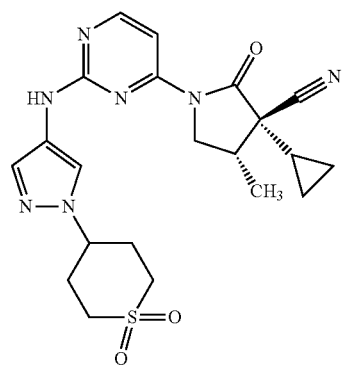

The title compound (72 mg) was obtained from (3R,4S)-1-(2-chloropyrimidin-4-yl)-3-cyclopropyl-4-methyl-2-oxopyrrolidine-3-carbonitrile (100 mg) obtained in Step A of Example 369 and 1-(1,1-dioxidetetrahydro-2H-thiopyran-4-yl)-1H-pyrazol-4-amine (82 mg) in the same manner as in Step B of Example 2.

MS(ESI+): [M+H]$^+$ 456.1.

Example 396

(3-cyclopropyl-1-(2-((1-methyl-1H-pyrazol-4-yl)amino)pyrimidin-4-yl)-2-oxopyrrolidin-3-yl)acetonitrile

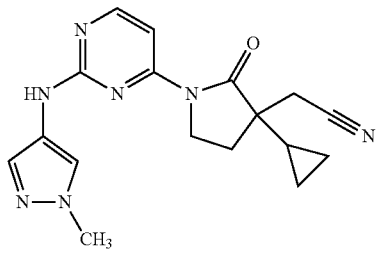 [SMILES: Cn1cc(Nc2nccc(N3CCC(CC#N)(C4CC4)C3=O)n2)cn1]

To a solution of 3-cyclopropyl-3-(hydroxymethyl)-1-(2-((1-methyl-1H-pyrazol-4-yl)amino)pyrimidin-4-yl)pyrrolidin-2-one (45 mg) obtained in Example 393 in tetrahydrofuran (1.0 mL) were added methanesulfonyl chloride (15 μL) and triethylamine (29 μL) at 0° C., and the mixture was stirred at 0° C. for 1 hr. To the reaction mixture was added saturated aqueous sodium hydrogen carbonate solution, and the mixture was extracted with ethyl acetate. The obtained organic layer was washed with saturated brine, and dried over anhydrous magnesium sulfate, and the solvent was evaporated under reduced pressure. To a solution of the residue in N,N-dimethylformamide (1.0 mL) were added potassium cyanide (36 mg) and sodium iodide (82 mg) at room temperature, and the mixture was stirred overnight at 120° C. To the reaction mixture was added saturated aqueous sodium hydrogen carbonate solution, and the mixture was extracted with ethyl acetate. The obtained organic layer was washed with saturated brine, and dried over anhydrous magnesium sulfate, and the solvent was evaporated under reduced pressure. The residue was purified by silica gel column chromatography (hexane/ethyl acetate) to give the title compound (17 mg).

MS(ESI+): [M+H]$^+$ 338.0.

Example 397

2-(4-((4-((3S,5R)-3-cyano-3-cyclopropyl-5-methyl-2-oxopyrrolidin-1-yl)pyrimidin-2-yl)amino)phenyl)-2-methylpropanamide hydrochloride

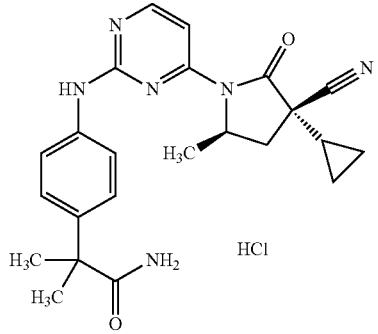 [SMILES: C[C@@H]1C[C@@](C#N)(C2CC2)C(=O)N1c1ccnc(Nc2ccc(C(C)(C)C(N)=O)cc2)n1 ; Cl]

The title compound (35 mg) was obtained from 2-(4-((4-((3S,5R)-3-cyano-3-cyclopropyl-5-methyl-2-oxopyrrolidin-1-yl)pyrimidin-2-yl)amino)phenyl)-2-methylpropanoic acid (100 mg) obtained in Example 389 in the same manner as in Example 350.

MS(ESI+): [M+H]$^+$ 419.4.

Example 398

4-((4-((3S,5R)-3-cyano-3-cyclopropyl-5-methyl-2-oxopyrrolidin-1-yl)pyrimidin-2-yl)amino)-N,N-dimethylbenzamide hydrochloride

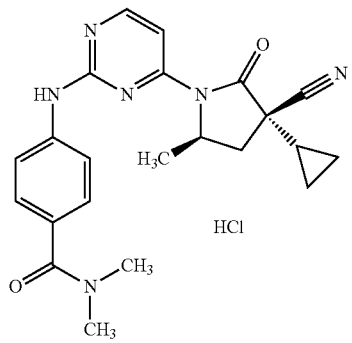 [SMILES: C[C@@H]1C[C@@](C#N)(C2CC2)C(=O)N1c1ccnc(Nc2ccc(C(=O)N(C)C)cc2)n1 ; Cl]

The title compound (82 mg) was obtained from (3S,5R)-1-(2-chloropyrimidin-4-yl)-3-cyclopropyl-5-methyl-2-oxopyrrolidine-3-carbonitrile (150 mg) obtained in Step A of Example 366 and 4-amino-N,N-dimethylbenzamide (89 mg) in the same manner as in Step B of Example 2.

MS(ESI+): [M+H]$^+$ 405.3.

Experimental Example

Tyk2 Enzyme Inhibition Test

Tyk2 enzyme inhibitory activity of test compounds was measured by LANCE method (PerkinElmer). First, a test compound diluted with assay buffer (50 mM HEPES (pH=7.5), mM MgCl$_2$, 1 mM EGTA, 2 mM DTT, 0.01% Tween20, 0.01% BSA) was added to 384-well plate at 2 μL each. Then, a Tyk2 (Invitrogen) solution and a fluorescence-labeled peptide substrate (ULight-JAK1, PerkinElmer) solution diluted with assay buffer at 375 ng/mL and 300 nM, respectively were added at 2 μL each. Then, enzyme reaction was started by adding 2 μL each of ATP solution prepared with assay buffer at 30 μM. After the reaction at room temperature for 1 hr, Detection Buffer (PerkinElmer) prepared to be 20 mM EDTA, 4 nM europium-labeled anti-phosphotyrosine antibody (PerkinElmer) was added at 6 μL each. After standing at room temperature for 1 hr, fluorescence intensity (excitation wavelength 340 nm, fluorescence wavelength 665 nm, delay time 100 microsecond) was measured by a plate reader, Envision (PerkinElmer). The inhibitory activity of each compound was calculated as relative value where fluorescence intensity of a well without enzyme is considered as 100% inhibition.

TABLE 26

| Ex. No. | Tyk2 enzyme inhibitory activity (%, 1 μM) | Ex. No. | Tyk2 enzyme inhibitory activity (%, 1 μM) |
|---|---|---|---|
| 1 | 99 | 33 | 97 |
| 4 | 100 | 61 | 14 |
| 7 | 100 | 72 | 20 |
| 10 | 97 | 77 | 22 |
| 12 | 51 | 85 | 100 |
| 15 | 89 | 86 | 100 |
| 29 | 91 | 87 | 100 |
| 31 | 98 | 101 | 88 |

TABLE 27

| Ex. No. | Tyk2 enzyme inhibitory activity (%, 1 μM) | Ex. No. | Tyk2 enzyme inhibitory activity (%, 1 μM) |
|---|---|---|---|
| 103 | 100 | 109 | 99 |
| 128 | 100 | 133 | 24 |
| 134 | 99 | 265 | 99 |

Experimental Example 2

Recombinant mouse IL-23 (1 μg/20 μL/site) was intradermally administered into the right auricle of 7-8-week-old LEWEIS male rat. As control, phosphate buffered saline (PBS) which is a solvent was administered instead of IL-23. Then, a drug (the compound of Example 103) suspended in 0.5% methyl cellulose (MC) was orally administered 30 min before IL-23 administration, respectively. 0.5% MC was used as vehicle. The auricle tissues of 6 mm diameter were collected about 24 hr after IL-23 administration. Lysis buffer was added thereto, the tissues were crushed using beads, and centrifugalized, and the supernatant was collected. IL-22 in the tissues was measured using ELISA kit (R & D Systems). The result is shown below as a IL-23 inhibitory rate relative to vehicle. (mean of n=6)

The compound of Example 103 (10 mg/kg, q.d.): inhibitory rate 79%

Formulation Example 1

Production of Capsule

| 1) compound of Example 1 | 30 mg |
|---|---|
| 2) fine powder cellulose | 10 mg |
| 3) lactose | 19 mg |
| 4) magnesium stearate | 1 mg |
| Total | 60 mg |

1), 2), 3) and 4) are mixed and filled in a gelatin capsule.

Formulation Example 2

Production of Tablet

| 1) compound of Example 1 | 30 g |
|---|---|
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, and the mixture is vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

The compound of the present invention has a superior Tyk2 inhibitory action, which is useful as an agent for the prophylaxis or treatment of autoimmune diseases (e.g., psoriasis, rheumatoid arthritis, inflammatory bowel disease, Sjogren's syndrome, Behcet's disease, multiple sclerosis, systemic lupus erythematosus etc.) and the like.

This application is based on patent application No. 2012-075166 filed on Mar. 28, 2012 in Japan, the contents of which are encompassed in full herein.

The invention claimed is:
1. A compound represented by the formula (I):

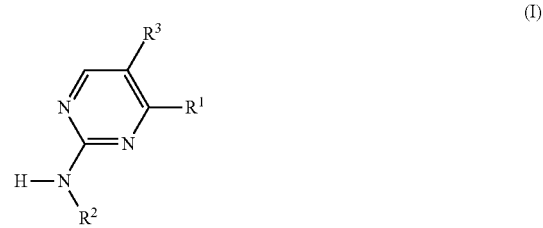

wherein
R¹ is a group represented by the following formula:

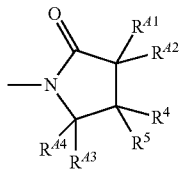

wherein
$R^{41}$ and $R^{42}$ are the same or different and each is
(1) a cyano group,
(2) a carbamoyl group,
(3) a $C_{1-6}$ alkyl group optionally substituted by 1 to 3 substituents selected from
  (I) a carboxy group,
  (II) a cyano group,
  (III) a halogen atom,
  (IV) a $C_{1-6}$ alkoxy group,
  (V) a $C_{3-6}$ cycloalkyl group,
  (VI) an amino group optionally mono- or di-substituted by substituent(s) selected from
    (i) a $C_{1-6}$ alkyl-carbonyl group, and
    (ii) a $C_{1-6}$ alkoxy-carbonyl group, and
  (VII) a hydroxy group,
(4) a $C_{3-6}$ cycloalkyl group,
(5) a 3- to 8-membered monocyclic non-aromatic heterocyclic group optionally substituted by 1 to 3 $C_{1-6}$ alkoxy-carbonyl groups, or
(6) a $C_{1-6}$ alkoxy-carbonyl group;
$R^{43}$ is a hydrogen atom or a $C_{1-3}$ alkyl group;
$R^{44}$ is a hydrogen atom;
$R^4$ is a hydrogen atom or a $C_{1-3}$ alkyl group; and
$R^5$ is a hydrogen atom;
$R^2$ is a hydrogen atom, an optionally substituted $C_{1-6}$ alkyl group, an optionally substituted aromatic ring group, or an acyl group; and
$R^3$ is a hydrogen atom, a halogen atom, a cyano group, or an optionally substituted $C_{1-6}$ alkyl group,
or a salt thereof.

2. The compound or salt of claim 1, wherein $R^2$ is
(1) a 5- or 6-membered monocyclic aromatic heterocyclic group, a $C_{6-14}$ aryl group or a 8- to 12-membered fused aromatic heterocyclic group, each of which is optionally substituted by 1 to 3 substituents selected from
  (a) a cyano group,
  (b) a carboxy group,
  (c) a halogen atom,
  (d) a $C_{1-6}$ alkyl group optionally substituted by 1 to 3 substituents selected from
    (I) a hydroxy group,
    (II) a cyano group,
    (III) a carboxy group,
    (IV) a carbamoyl group optionally mono- or di-substituted by $C_{1-6}$ alkyl group(s) optionally substituted by 1 to 3 substituents selected from
      (i) a $C_{1-6}$ alkoxy group,
      (ii) a hydroxy group,
      (iii) a halogen atom, and
      (iv) a $C_{1-6}$ alkylsulfonyl group,
    (V) an amino group optionally mono- or di-substituted by substituent(s) selected from
      (i) a $C_{1-6}$ alkyl-carbonyl group optionally substituted by 1 to 3 substituents selected from (A) a $C_{1-6}$ alkoxy group and (B) a hydroxy group,
      (ii) a $C_{1-6}$ alkylsulfonyl group,
      (iii) a sulfamoyl group optionally mono- or di-substituted by $C_{1-6}$ alkyl group(s), and
      (iv) a $C_{1-6}$ alkyl group,
    (VI) a $C_{1-6}$ alkoxy-carbonyl group,
    (VII) a $C_{6-14}$ aryl group optionally substituted by 1 to 3 $C_{1-6}$ alkoxy groups,
    (VIII) a 3- to 8-membered monocyclic non-aromatic heterocyclic group,
    (IX) a 3- to 8-membered monocyclic non-aromatic heterocyclylcarbonyl group optionally substituted by 1 to 3 substituents selected from
      (i) a hydroxy group,
      (ii) a carbamoyl group, and
      (iii) a $C_{1-6}$ alkyl group,
    (X) a halogen atom, and
    (XI) a $C_{1-6}$ alkylsulfonyl group,
  (e) a $C_{1-6}$ alkyl-carbonyl group,
  (f) a $C_{1-6}$ alkylsulfonyl group,
  (g) an amino group optionally mono- or di-substituted by substituent(s) selected from
    (I) a $C_{1-6}$ alkyl group,
    (II) a $C_{1-6}$ alkyl-carbonyl group optionally substituted by 1 to 3 $C_{1-6}$ alkoxy groups, and
    (III) a $C_{1-6}$ alkylsulfonyl group,
  (h) a carbamoyl group optionally mono- or di-substituted by substituent(s) selected from
    (I) a $C_{1-6}$ alkyl group optionally substituted by 1 to 3 substituents selected from
      (i) a hydroxy group,
      (ii) a 3- to 8-membered monocyclic non-aromatic heterocyclic group optionally substituted by 1 to 3 $C_{1-6}$ alkyl groups, and
      (iii) a $C_{1-6}$ alkylsulfonyl group,
    (II) a $C_{3-6}$ cycloalkyl group optionally substituted by 1 to 3 substituents selected from
      (i) a cyano group, and
      (ii) a hydroxy group, and
    (III) a 3- to 8-membered monocyclic non-aromatic heterocyclic group,
  (i) a sulfamoyl group optionally mono- or di-substituted by $C_{1-6}$ alkyl group(s),
  (j) a 3- to 8-membered monocyclic non-aromatic heterocyclic group optionally substituted by 1 to 3 substituents selected from
    (I) a $C_{1-6}$ alkyl group optionally substituted by 1 to 3 hydroxy groups,
    (II) a $C_{1-6}$ alkyl-carbonyl group optionally substituted by 1 to 3 substituents selected from
      (i) a $C_{1-6}$ alkoxy group, and
      (ii) a cyano group,
    (III) a $C_{1-6}$ alkoxy-carbonyl group,
    (IV) an oxo group,
    (V) a $C_{1-6}$ alkylsulfonyl group,
    (VI) a carbamoyl group optionally mono- or di-substituted by $C_{1-6}$ alkyl group(s),
    (VII) a cyano group,
    (VIII) a hydroxy group, and
    (IX) a carboxy group, (k) a $C_{3-6}$ cycloalkyl group optionally substituted by 1 to 3 substituents selected from
  (I) a carbamoyl group optionally mono- or di-substituted by $C_{1-6}$ alkyl group(s),
  (II) a carboxy group, and
  (III) a $C_{1-6}$ alkyl group optionally substituted by 1 to 3 hydroxy groups,
(l) a $C_{1-6}$ alkoxy group optionally substituted by 1 to 3 substituents selected from
  (I) a halogen atom,
  (II) a $C_{1-6}$ alkoxy group, and
  (III) a $C_{3-6}$ cycloalkyl group,
(m) a $C_{1-6}$ alkoxy-carbonyl group,
(n) a 3- to 8-membered monocyclic non-aromatic heterocyclylcarbonyl group optionally substituted by 1 to 3 substituents selected from
  (I) a hydroxy group,
  (II) an oxo group,
  (III) a halogen atom,
  (IV) a $C_{1-6}$ alkoxy group, and
  (V) a $C_{1-6}$ alkyl group,
(o) a $C_{1-6}$ alkylsulfanyl group, and
(p) a 5- or 6-membered monocyclic aromatic heterocyclic group.

3. (3S)-3-Cyclopropyl-1-(2-((1-(1-hydroxy-2-methylpropan-2-yl)-1H-pyrazol-4-yl)amino)pyrimidin-4-yl)-2-oxopyrrolidine-3-carbonitrile or a salt thereof.

4. (3S)-3-Cyclopropyl-1-(2-((1-(1-(hydroxymethyl)cyclopropyl)-1H-pyrazol-4-yl)amino)pyrimidin-4-yl)-2-oxopyrrolidine-3-carbonitrile or a salt thereof.

5. (3R)-3-Ethyl-1-(2-((4-(4-(hydroxymethyl)tetrahydro-2H-pyran-4-yl)phenyl)amino)pyrimidin-4-yl)-2-oxopyrrolidine-3-carbonitrile or a salt thereof.

6. A medicament comprising the compound or salt of claim 1.

* * * * *